(12) United States Patent
Hakonarson et al.

(10) Patent No.: US 11,173,153 B2
(45) Date of Patent: *Nov. 16, 2021

(54) METHODS OF DIAGNOSING AND TREATING ANXIETY DISORDER

(71) Applicant: THE CHILDREN'S HOSPITAL OF PHILADELPHIA, Philadelphia, PA (US)

(72) Inventors: Hakon Hakonarson, Malvern, PA (US); Charlly Kao, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/258,977

(22) Filed: Sep. 7, 2016

(65) Prior Publication Data

US 2017/0087141 A1    Mar. 30, 2017

Related U.S. Application Data

(60) Provisional application No. 62/215,628, filed on Sep. 8, 2015, provisional application No. 62/215,633, filed on Sep. 8, 2015, provisional application No. 62/215,636, filed on Sep. 8, 2015, provisional application No. 62/215,673, filed on Sep. 8, 2015.

(51) Int. Cl.
| | |
|---|---|
| *A61K 31/454* | (2006.01) |
| *A61K 45/06* | (2006.01) |
| *C12Q 1/6883* | (2018.01) |

(52) U.S. Cl.
CPC ............ *A61K 31/454* (2013.01); *A61K 45/06* (2013.01); *C12Q 1/6883* (2013.01); *C12Q 2600/156* (2013.01); *C12Q 2600/158* (2013.01)

(58) Field of Classification Search
CPC .................................................... A61K 31/454
USPC ........................................................ 514/326
See application file for complete search history.

(56) References Cited

U.S. PATENT DOCUMENTS

| | | | |
|---|---|---|---|
| 9,884,057 B2 | 2/2018 | Hakonarson et al. | |
| 2004/0116505 A1* | 6/2004 | Krauss ............... | A61K 31/4015 514/424 |
| 2005/0233321 A1 | 10/2005 | Hess et al. | |
| 2007/0244152 A1 | 10/2007 | Lowy | |
| 2007/0299113 A1 | 12/2007 | Kalvinsh et al. | |
| 2009/0176740 A1 | 7/2009 | Phillips, II | |
| 2010/0120628 A1 | 5/2010 | Belouchi et al. | |
| 2010/0143921 A1 | 6/2010 | Sadee et al. | |
| 2010/0216734 A1 | 8/2010 | Barlow et al. | |
| 2011/0269688 A1 | 11/2011 | Hakonarson et al. | |
| 2012/0149677 A1 | 6/2012 | Dudkin et al. | |
| 2013/0143867 A1 | 6/2013 | Fogel et al. | |
| 2013/0203814 A1 | 8/2013 | Glessner et al. | |
| 2013/0225623 A1 | 8/2013 | Buxbaum et al. | |
| 2014/0303243 A1 | 10/2014 | Hakonarson et al. | |
| 2014/0315992 A1 | 10/2014 | Hakonarson et al. | |
| 2016/0032390 A1 | 2/2016 | Hakonarson et al. | |
| 2017/0083664 A1 | 3/2017 | Hakonarson et al. | |
| 2017/0087139 A1 | 3/2017 | Hakonarson et al. | |
| 2017/0087140 A1 | 3/2017 | Hakonarson et al. | |
| 2018/0110767 A1 | 4/2018 | Hakonarson et al. | |

FOREIGN PATENT DOCUMENTS

| | | |
|---|---|---|
| WO | 2003054167 A2 | 7/2003 |
| WO | 2005094801 A1 | 10/2005 |
| WO | 2007104035 A1 | 9/2007 |
| WO | 2008136995 A1 | 11/2008 |
| WO | 2009105718 A1 | 8/2009 |
| WO | 2010057112 A2 | 5/2010 |
| WO | 2012027491 A1 | 1/2012 |
| WO | 2013006857 A1 | 1/2013 |
| WO | 2016022324 A1 | 2/2016 |
| WO | 2016205348 A1 | 12/2016 |

OTHER PUBLICATIONS

Michael et al., CPA-Bull, de l'APC (2003), pp. 9-13.*
Niswender er al., Ann. Rev. Pharmacol. Toxicol. (2010), vol. 50, pp. 295-322.*
Ella et al., Nat. Genet. (2012), vol. 44(1), pp. 78-84 (online Dec. 4, 2011).*
Clarke et al., Case Report in Med. (2009), vol. ID 361518, pp. 1-5. submitted in U.S. Appl. No. 15/258,924.*
Addington et al., J. Child Psychol. Psychiast. (2012), vol. 53(5), pp. 510-518. submitted in U.S. Appl. No. 15/258,924.*
Jarrett et al., Clin. Psychol. Rev. (2008) vol. 28 pp. 1266-1280.*
Clinical Trial, NTC02286817, Nov. 7, 2014.*
Braaten et al., Soc. Biol. Psych. (2003) 53:93-99.*
Caporino et al., J. Am. Acad. Child Adolescent Psych. (2013), vol. 52(1), pp. 57-67.*
Clinical Trial, NTC02286817, Nov. 7, 2014. Previously mailed Aug. 6, 2020.*
Braaten et al., Soc. Biol. Psych. (2003) 53:93-99. Previously mailed Aug. 6, 2020.*
Caporino et al., J. Am. Acad. Child Adolescent Psych. (2013), vol. 52(1), pp. 57-67. Previously mailed Aug. 6, 2020.*
Caporino, et al. "Defining Treatment Response and Remission in Child Anxiety: Signal Detection Analysis Using Pediatric Anxiety Rating Scale" J Am Acad Child Adolesc Psychiatry, 52(1):57-67 (2013).
Ebell, M. H. "Diagnosis of Anxiety Disorders in Primary Care" Am Fam Physician, 78(4):501-502 (2008).

(Continued)

*Primary Examiner* — Taofiq A Solola
(74) *Attorney, Agent, or Firm* — Kathleen D. Rigaut; Howson & Howson LLP

(57) ABSTRACT

Methods and uses for diagnosing and treating anxiety disorders are encompassed, wherein diagnosis and treatment may be based upon an assessment of genetic alterations in metabotropic glutamate receptor (mGluR) network genes and wherein treatment is with nonspecific activators of mGluRs such as fasoracetam.

16 Claims, 45 Drawing Sheets

(56) References Cited

OTHER PUBLICATIONS

Elia, et al. "Genome-wide copy number variation study associates metabotropic glutamate receptor gene networks with attention deficit hyperactivity disorder" Nat Genet., 44(1):78 84 (2011).
Gasparini et al. "Allosteric Modulaators for mGlu Receptors" Current Neuropharmacology, 5:187-194 (2007).
Ghelardini, et al. "DM235 (Sunifiram): a Novel Nootropic with Potential as a Cognitive Enhancer," Naunyn-Schmiedeberg's Archives of Pharmacology, 365:419-426 (2002).
Hadley et al. "The impact of metabotropic glutamate receptor and other gene family interaction networks on autism" Nature Communications, 5:4074 (2014).
Henrichsen, et al. "Copy number variants, diseases and gene expression" Human Molecular Genetics 18(1):R1-R8 (2009).
Leigh, M.J.S. et al. "A Randomized Double-Blind, Placebo-Controlled Trial of Minocycline in Children and Adolescents with Fragile X Syndrome" J. Dev. Behav Pediatr 34(3): 147-155 (2013).
Malykh et al. "Piracetam and Piracetam-Like Drugs: From Basic Science to Novel Clinical Applications to CNS Disorders" Drugs 70(30):287-312 (2010).
National Institute of Mental Health "Anxiety Disorder" NIH Publication No. 09 3879 (2009).
Baker, K. and Voorstman, J.A.S. "Is there a core neuropsychiatric phenotype in 22q11.2 deletion syndrome?" Curr. Op. Neurol. 25: 131-137 (2012).
Shannon P, et al. "Cytoscape: A Software Environment for Integrated Models of Biomolecular Interaction Networks" Genome Res. 13(11):2498-504 (2003).
Kelleher, R.J. et al. "High-Throughput Sequencing of mGluR Signaling Pathway Genes Reveals Enrichment of Rare Variants in Autism" PLoS One 7(4): e35003 (2012).
Wang K, et al. "PennCNV: An integrated hidden Markov model designed for high-resolution copy number variation detection in whole-genome SNP genotyping data" Genome Res. 17(11):1665-74 (2007).
Wang, K, et al. "Copy Number Variation Detection via High-Density SNP Genotyping" Cold Spring Harb Protoc. (2008).
Halperin, J. M., et al. "Reliability, Validity, and Preliminary Normative Data for the Children's Aggression Scale-Teacher Version" J. Am. Acad. Child Adolesc. Psychiatry 42(8): 965-971 (2003).
Waschbusch, D.A., and Elgar, F. J. "Development and Validation of the Conduct Disorder Rating Scale" Assessment 14(1): 65-74 (2007).
Hellings, J. A. et al. "The Overt Aggression Scale for Rating Aggression in Outpatient Youth with Autistic Disorder: Preliminary Findings" J. Neuropsychiatry Clin. Neurosci. 17: 29-35 (2005).
Akutagava-Martins, C. et al. "Glutamatergic Copy Number Variants and Their Roe in Attention-Deficit/Hyperactivity Disorder" Am. J. Med. Genet. Part B 165B: 502-509 (2014).
Park, S. et al. "The Metabotropic Glutamate Receptor Subtype 7 rw 3792452 Polymorphism is Associated with the Response to Methylphenidate in Children with Attention-Deficit/Hyperactivity Disorder" J. Child Adolesc. Phychopharmacoloty 24(4): 223-227 (2014).
Park, S. et al. "Association between the GRM7 rs3792452 polymorphism and attention deficit hyperactivity disorder in a Korean sample" Behavioral and Brain Functions 9: 1-8 (2013).
Goodman, D. et al. "Interpreting ADHD Rating Scale Scores: Linking ADHD Rating Scale Scores and CGI Levels in Two Randomized Controlled Trials of Lisdexamfetamine Dimesylate in ADHD" Primary Psychiatry 17(3): 44-52 (2010).
Hidalgo, et al. "An effect-size analysis of pharmacologic treatments for generalized anxiety disorder" Journal of Psychopharmacology, 21(8):864-872 (2007).
Research Unit on Pediatric Phychopharmacology Anxiety Study Group "Fluvoxamine for the treatment of anxiety disorders in children and adolescents" New Engl. J. Med. 344: 1279-85 (2001).
Murck, H. et al. "Taking Personalized Medicine Seriously: Biomarker Approaches in Phase IIb/III Studies in Major Depression and Schizophrenia" Innov. Clin. Neurosci. 12(3-4 Suppl. A): 26S-40S (2015).
Jonas,R.K. et al. "The 22q11.2 Deletion Syndrome as a Window into Complex Neuropsychiatric Disorders Over the Lifespan" Biol. Psychiatry 75(5): 351-360 (2014).
Prosecution History of U.S. Appl. No. 13/776,662.
Nagamitsu, S. et al. "Upregulated GABA inhibitory function in ADHD children with child behavior checklist-dysregulation profile: 123I-iomazenil SPECT study" Frontiers in Psychiatry 6: 84 (Jun. 2015).
Gregory, Karen J. et al: "Pharmacology of metabotropic glutamate receptor allosteric modulators: structural basis and therapeutics potential for CNS disorders", Progress in Molecular Biology and Translational Science, 115: 61-121 (2013).
Malykh, Andrei G. et al: "Piracetam and piracetam-like drugs: from basic science to novel clinical application to CNS disorders" Drugs, 70(3): 287-312 (2010).
Palucha, et al.: "Metabotropic glutamate receptor ligands as possible anxiolytic and antidepressant drug", Pharmacology and Therapeutics, 115(1):116-147 (2007).
International Search Report and Written Opinion issued in PCT/US2016/050581 dated Dec. 21, 2016.
Akutagava-Martins, et al. "Glutamatergic Copy Number Variants and Their Role in Attention-Deficit/Hyperactivity Disorder" Am J Med Genet Part B. 1656:502-509 (2014).
"Fasoracetam: LAM 105, NS 105" Drugs R&D, 2(2): 135-136 (1999).
Fistova, et al. "Study specific effects of nootropic drugs on glutamate receptors in the rat brain" Eksp Klin Farmakol. 74(1):abstract(2011).
Gualtieri, et al. "Design and Study of Piracetam-like Nootropics, Controversial Members of the Problematic Class of Cognition-Enhancing Drugs" Current Pharmaceutical Design, 8:125-138 (2002).
Hamelin and Lehmann Effects of putative cognition enhancers on the NMDA receptor by [3H]MK801 binding, European Journal of Pharmacology 281: R11-R13 (1995).
Hirouchi et al. "Role of metabotropic glutamate receptor subclasses in modulation of adenylyl cyclase activity by a notropic NS-105" European Journal of Pharmacology, 387:9-17 (2000).
Kelleher III et al. "High-Throughput Sequencing of mGluR Signaling Pathway Genes Reveals Enrichment of Rare Variants in Autism" PLos ONE, 7(4):e35003 (2012).
Nomura and Nishizaki, "Nefiracetam facilitates hippocampa neurotransmission by a mechanism independent of the piracetam and aniracetam action" Brain Research, 870: 157-162 (2000).
Ogasawara, et al. "Involvement of Cholinergic and GABAergic Systems in the Reversal of Memory Disruption by NS-105, a Cognition Enhancer" Pharmacology Biochemistry and Behavior, 64(1):41-52 (1999).
Oka, et al. "A novel cognition enhancer NS-105 modulates adenylate cyclase activity through metabotropic glutamate receptors in primary neuronal culture" Nauny-Schmiedeberg's Arch Pharmacol, 356:189-196 (1997).
Shimidzu et al."Effect of a novel cognition enhancer NS-105 on learned helplessness in rats: Possible invlvement of GABA B receptor up-regulation after repeated treatement" European Journal of Pharmacology 338:225-232 (1997).
Winblad, "Piracetam: A Review of Pharmacological Properties and Clinical Uses" CNS Drug Reviews, 11(2):169-182 (2005).
Winnicka, et al. "Piracetam—An Old Drug with Novel Properties?" Acta Poloniae Pharmaceutica—Drug Research, 62(5):405-409 (2005).
Zavadenko et al. "Atomoxetine and piracetam in the treatment of attention deficit hyperactivity disorder in children" ZH Nevrol Psikhiatr IM S S Korsakova, 108(7):abstract (2008).
Declaration of Hakon Hakonarson, MD, PhD dated Mar. 8, 2017.
Elia, J. et al. "Genome-wide copy number variation study associates metabotropic glutamate receptor gene netwarks with attention deficit hyperactivity disorder" Nat Genet., 44(1):78-84 (2015).
Hodgins et al., "Adolescents with conduct disorder: does anxiety make a difference?" The J. of Forensic Psychiatric and Psychology (2011 ), vol. 22(5), pp. 669-691.
Miller, Caroline, "How Anxiety Leads to Disruptive Behavior: kids who seem oppositional are often severely anxious" Child Mind

(56) References Cited

OTHER PUBLICATIONS

Institute: Anxiety and Disruptive Behavior in Children, pp. 1-3. https://childmind.org/article/how-anxiety-leads-to-disruptive-behavior/) visited Nov. 27, 2017.
Oka, M. et al. "Involvement of metabotropic glutamate receptors in Gi- and Gs-dependent modulation of adenylate cyclase activity induced by a novel cognition enhancer NS-105 in rat brain" Brain Research, 754: 121-130 (1997).
Bloch, Michael et al: "Recent advances in Tourette syndrome," Current Opinion in Neurology, 24(2):119-125 (2011).
Cohen, S., et al. "Clinical Assessment of Tourette Syndrome and Tic Disorders" Neurosci Biobehavb Rev., 37(6):997-1007 (2013).
Dietrich, Andrea et al: "The Tourette International Collaborative Genetics (TIC Genetics) study, finding the genes causing Tourette syndrome: objectives and methods", European Child and Adolescent Psychiatry, 24(2):141-151 (2014).
Ercan, E. S., et al. "Risperidone in the treatment of conduct disorder in preschool children without intellectual disability" Child and Adolescent Psychiatry and Mental Health, 5:10 (2011).
Gerevich, J., et al. "The generalizability of the Buss-Perry Aggression Questionnaire" Int J Methods Psychiatr. Res., 16(3):124-136 (2007).
Halperin, J., et al. "Reliability, Validity, and Preliminary Normative Data for the Children's Aggression Scale-Teacher Version" J Am Acad Child Adolesc Psychiatry, 42(8):965-971 (2003).
Hellings, et al. "The Overt Aggression Scale for Rating Aggression in Outpatient Youth with Autistic Disorder: Preliminary Findings" J of Neuropsychiatry and Clinical Neurosciences, 17:29-35 (2005).
International Search Report and Written Opinion issued in PCT/US2016/050573 dated Dec. 21, 2016.
International Search Report and Written Opinion issued in PCT/US2016/050580 dated Dec. 20, 2016.
James, A. C. "Prescribing antiphsychotics for children and adolescents" Advances in psychiatric treatment, 16:63-75 (2010).
Kendler, Kenneth S. et al: "Familial Influences on Conduct Disorder Reflect 2 Genetic Factors and 1 Shared Environmental Factor", JAMA Psychiatry, 70(1): 78.
Navarro, J.F. et al. "P.1.d.006 Effects of LY379268, a selective agonist of mGlu2/3 receptors, on isolation-induced aggression in male mice" European Neuropsychopharmacology, 18: S252 (2008).
Sansone, S., et al. "Psychometric Study of the Aberrant BEhavior Checklist in Fragile X Syndrome and Implications for Targeted Treatment" J Autism Dev Disord, 42(7):1377-1392 (2012).
Nock, M. K., et la. "Prevalence, Subtypes, and Correlates of DSM-IV Conduct Disorder in the National Comorbidity Survey Replication" Psychol Med., 36(5):699-710 (2006).
Shimidzu, Takako et al: "Effect of a novel cognition enhancer NS-105 on learned helplessness in rats: Possible involvement of GABAB receptor up-regulation after repeated treatment" European Journal of Pharmacology, 338(3):225-232 (1997).
Singer, H.S. et al: "Baclofen treatment in Tourette syndrome: A double-blind placebo-controlled, crossover trial" Neurology, 56(5):599-604 (2001).
Toteja, N., et al. "Prevalence and correlates of antipsychotic polypharmacy in children and adolescents receiving antipsychotic treatment" Int J Neuropsychopharmacol., 17(7):1095-1105 (2014).
US Dept of Health and Human Services: Public Health Service "Tourette Syndrome" NIH Publication No. 12-2163 (2012).
Waschbusch, D. A., et al. "Development and Validation of the Conduct Disorder Rating Scale" Assessment, 14(1):65-74 (2007).
Wittmann, Marion et al: "Activation of Group III mGluRs Inhibits GABAergic and Glutamatergic Transmission in Substantia Nigra Pars Reticulata" Journal of Neurophysiology, 1960-1968 (2001).
Declaration of Hakon Hakonarson, MD, PhD dated Apr. 12, 2018, filed Apr. 16, 2018 in U.S. Appl. No. 15/258,969.
Declaration of Hakon Hakonarson, MD, PhD dated Apr. 12, 2018, filed Apr. 16, 2018 in U.S. Appl. No. 15/258,977 (the present application).

Akhundian, J., "Effect of Piracetam on attention deficit and hyperactivity disorder" Iranian Journal of Pediatrics, 2001, 11(2): 32-36; abstract only.
Aman, M.G. "Annotated Biography on the Aberrant Behavior Checklist (ABC)." Unpublished Manuscript. Columbus, OH: The Ohio State University (2010).
Lo-Castro, A., et al. "ADHD and genetic syndromes." Brain and Development. (2011), vol. 33, pp. 456-461 (Year: 2011).
Corkum, P. "Actigraphy and Parental Ratings of Sleep in Children with Attention-Deficit/Hyperactivity Disorder (ADHD)" Sleep, 24(3):303-312 (2001).
Database Geo [online] NCBI Accession No. GPL6433, "Illumina HumanHap550 Genotyping Beadchip v1," Feb. 5, 2008, XP002717448.
Elia, J. et al., "Rare Structural Variants Found in Attention-Deficit Hyperactivity Disorder are Preferentially Associated with Neurodevelopmental Genes," Molecular Psychiatry, 2010, 15(6): 637-646, and supplementary table s1 (p. 1-7).
Elia, J., et al. "Fasoracetam in adolescents with ADHD and glutamatergic gene network variants disrupting mGluR neurotransmitter signaling." Nature Communications. (2018), vol. 9, Issue 4, pp. 1-9.
Extended European Search Report in copending European Patent Application No. 11820610.1, dated Jan. 2, 2014.
File history for U.S. Appl. No. 13/776,662, filed Feb. 25, 2013.
Firth, H. V. "22q11.2 Duplication" Gene Reviews—NCBI Bookshelf (2013).
Forero, D. et al. "Candidate Genes Involved in Neural Plasticity and the Risk for Attention-Deficit Hyperactivity Disorder: a Meta-Analysis of 8 Common Variants," Journal of Psychiatry and Neuroscience, 2009, 34(5): 361-366.
Forkmann, T., et al. "The clinical global impression scale and the influence of patient or staff perspective on outcome" BMC Psychiatry, 11:83 (2011).
Gerevich, J. et al. "The generalizability of the Buss-Perry Aggression Questionnaire" Int. J. Meth. Psychiatr. Res. 16(3): 124-136 (2007).
Harty, S.C. et a. "Adolescents with Childhood ADHD and Comorbid Disruptive Behavior Disorders: Aggression, Anger, and Hostility" Child Psychiatry Hum. Dev. 40(1): 85-97 (2009).
International Search Report and Written Opinion issued in PCT/US2016/050559 dated Feb. 16, 2017.
International Search Report for PCT/US2011/048993, dated Jan. 27, 2012.
Kam, H.J., et al. "High-Resolution Actigraphic Analysis of ADHD: A Wide Range of Movement Variability Observation in Three School Courses—A Pilot Study" Healthc Inform Res, 17(1):29-37 (2011).
Klopocki et al., "Copy-Number Variations, Noncoding Sequences, and Human Phenotypes" Annual Review Genomics Human Genetics, 2011, 12:53-72.
Krom, M. et al., "A Common Variant in DRD3 Receptor is Associated with Autism Spectrum Disorder," Biological Psychiatry, 2009, 65(7): 625-630.
Leigh, M. et al. "A Randomized Double-Blind, Placebo-Controlled Trial of Minocycline in Children and Adolescents with Fragile X Syndrome" J. Dev Behav Pediatr, 34(3):147-155 (2013).
Manning, M. et al. "Array-based technology and recommendations for utilization in medical genetics practice for detection of chromosomal abnormalities" Genetics in Medicine, 12(11):742-745 (2010).
Neale, B. et al., "Genome-Wide Association Scan of Attention Deficit Hyperactivity Disorder," American Journal of Medical Genetics Part B: Neuropsychiatric Genetics, 2008, vol. 147B, pp. 1337-1344.
O'Connor et al., "Metabotropic Glutamate Receptor 7: At the Interface of Cognition and Emotion," Eur J Pharacol. Apr. 2, 2010 (online); 639:123-131 [Abstract].
Office Action issued in Canadian Application No. 2,807,505 dated May 7, 2018.
Park, S. et al. "Associatation between the GRM7 rs3792452 polymorphism and attention deficit hyperactiveity disorder in a Korean sample" Behavioral and Brain Functions, 9:1 (2013).
Prosecution History of U.S. Appl. No. 13/108,652.
Prosecution History of U.S. Appl. No. 14/131,359.

(56) References Cited

OTHER PUBLICATIONS

Prosecution History of U.S. Appl. No. 14/292,480.
Rizzo et al. "Clinical Pharmacology of Comorbid Attention Deficit Hyperactivity Disorder in Tourette Syndrome" Int. Rev. Neurobiol, Chapter 14, 415-444 (2013).
Schneider, M. et al. "Psychiatric Disorders From Childhood to Adulthood in 22q11.2 Deletion Syndrome: Results from the International Consortium on Brain Behavior in 22q11.2 Deletion Syndrom" Am J. Psychiatry 171(6):627-639 (2014).
Semenova et al., "The Effects of the mGluR5 Antagonist MPEP and the mGluR2/3 Antagonist LY341495 on Rats' Performance in the 5-choice Serial Reaction Time Task," Neuropharmacology, 2007, 52(3):863-872.
Shaffer, L. et al. "American College of Medical Genetics guideline on the cytogenetic evaluation of the individual with the developmental delay or mental retardation" Genetics in Medicine, 7(9):650-654 (2005).
Steele, et al. "Remission Versus Response as the Goal of Therapy in ADHD: A New Standard for the Field?" Clinical Therapeutics, 28(11):1892-1908 (2006).
Stofanko, M., et al. "Simple, Rapid and Inexpensive Quantitative Fluorescent PCR Method for Detection of Microdeletion and Microduplication Syndromes" PLOS ONE, 8(4): e61328 (2013).
Tarver, J. et al.: "Attention-deficit hyperactivity disorder (ADHD): an updated review of the essential facts" Child: Care, Health and Development, 40(6):762-774 (2014).
The Research Unit on Pediatric Psychopharmacology Anxiety Study Group "Fluvoxamine for the Treatment of Anxiety Disorders in Children and Adolescents" N Engl J Med, vol. 344 (17):1279-1285 (2001).
U.S. National Library of Medicine. "Phase I Single Dose, Open-Label Pharmacokinetic Study and Single-Blind, Placebo-Controlled Dose Escalation Study of NFC-1 in Adolescents With Attention Deficit Hyperactivity Disorder (NFC1-GREAT)." Clinical Trials. gov Identifier: NCT02286817. Nov. 10, 2014. (Year: 2014).
Wigal, S. B., et al. "NWP06, an Extended-Release Oral Suspension of Methylphenidate, Improved Attention-Deficit/Hyperactivity Disorder Symptoms Compared with Placebo in a Labratory Classroom Study" Journal of Child and Adolescent Psychopharmacology, 23(1):3-10 (2013).
Clarke, R. A. et al. "Tourette Syndrome and Klippel-Feil Anomaly in a Child with Chromosome 22q11 Duplication" Case Reports in Medicine vol. ID 361518 pp. 1-5 (2009).
Addington, A. et al. "Annual Research Review: Impact of advances in genetics in understanding developmental psychopathology" J. Child Psychol. Psychiatry vol. 53(5) 510-518 (2012).
Jones, G. et al. "Exploratory dose-escalation study of NFC-1 in ADHD adolescents with glutamatergic gene network variants" 62nd Annual Meeting AACAP, 2015, poster.
Auerbach, B. D. et al. "Mutations causing syndromic autism define an axis of synaptic pathophysiology" Nature, 480(7375):63-8 (2011).
Aevi Genomic Medicine, Aevi Genomic Medicine Announces Top-Line Results from Placebo-Controlled ASCEND Trial (Parts A & B) of AEVI-001 in Children with ADHD, News Release, https://aevigenomicmedicine.gcs-web.com/news-releases/news-release-details/aevi-genomic-medicine-announces-top-line-results-placebo, Jan. 2, 2019.
Childress, A. et al. "Current Investigational Drugs for the Treatment of Attention-Deficit/Hyperactivity Disorder" Expert Opinion in Investigational Drugs, 2016, vol. 25(4):463-474.
Cooper, G. M. et al. "Systematic assessment of copy number variant detection via genome-wide SNP genotyping" nature genetics 2008, 40(10):1199-1203.
Fewtrell, MS, et al. Hirschsprung's disease associated with a deletion of chromosome 10 (q11.2q21.2): a further link with the neurocristopathies? J Med Genet 1994: 31:325-327.
Karayiorgou, M. et al. "22q11.2 microdeletions: linking DNA structural variation to brain dysfunction and schizophrenia" Nature Reviews—Neuroscience, 2010, vol. 11:402-416.
Turgay, A. "Treatment of Comorbidity in Conduct Disorder with Attention-Deficit Hyperactivity Disorder (ADHD)" Essent. Psychopharmacol., 6(5):277-290 (2005).

\* cited by examiner

| Condition | Number of patient samples | Number of patient samples fully genotyped |
|---|---|---|
| Anxiety | 1708 | 925 |
| Depression | 164 | 95 |
| OCD | 262 | 150 |
| Phobias | 93 | 55 |

*Fig. 1*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| ACAT1 | chr11:107992257-108018891 | chr11:107492257-108518891 | chr11:107497467-107523485 | rs7925970 | kgp3957860 |
| ACCN1 | chr17:31340105-32483825 | chr17:30840105-32983825 | chr17:28364218-29507938 | rs2519865 | kgp10854156 |
| ACTR2 | chr2:65454828-65498390 | chr2:64954828-65998390 | chr2:65308405-65351891 | rs1477043 | kgp4266233 |
| ADCY1 | chr7:45614124-45762714 | chr7:45114124-46262714 | chr7:45580649-45729239 | rs2289367 | kgp13398740 |
| ADRBK1 | chr11:67033904-67054029 | chr11:66533904-67554029 | chr11:66790480-66810605 | kgp7862175 | kgp2126040 |
| ALDOA | chr16:30064410-30081741 | chr16:29564410-30581741 | chr16:29971972-29989236 | kgp733881 | kgp6386467,rs33997546 |
| APP | chr21:27252860-27543446 | chr21:26752860-28043446 | chr21:26174731-26465003 | rs7281883 | kgp2004872 |
| ARL15 | chr5:53180613-53606403 | chr5:52680613-54106403 | chr5:53216370-53642160 | kgp10474479 | rs10058571 |
| ATXN7L3 | chr17:42269172-42275529 | chr17:41769172-42775529 | chr17:39624698-39631055 | rs11650560 | rs6503398 |
| BDKRB2 | chr14:96671134-96710666 | chr14:96171134-97210666 | chr14:95740887-95780419 | kgp19731302 | kgp1905230 |
| CA8 | chr8:61101422-61193954 | chr8:60601422-61693954 | chr8:61263976-61356508 | kgp9568230 | kgp1623935 |
| CACNA1B | chr9:140772240-141019076 | chr9:140272240-141519076 | chr9:139892061-140136452 | kgp18327422 | kgp12374930 |
| CACYBP | chr1:174968570-174981163 | chr1:174468570-175481163 | chr1:173235193-173247786 | rs1013769 | kgp15391194 |
| CALM1 | chr14:90863326-90874619 | chr14:90363326-91374619 | chr14:89933125-89944363 | kgp828819 | kgp22766175 |
| CHRM3 | chr1:239549864-240049896 | chr1:239049864-240549896 | chr1:237616487-238116519 | kgp1999037 | rs1537850 |
| CIC | chr19:42788816-42799949 | chr19:42288816-43299949 | chr19:47480656-47491789 | kgp21495548 | kgp22794755 |
| CNP | chr17:40118758-40129754 | chr17:39618758-40629754 | chr17:37372284-37383280 | kgp4988562 | kgp1573374 |

*Fig. 2-1*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| CNTN4 | chr3:2140549-3099645 | chr3:1640549-3599645 | chr3:2117246-3074645 | kgp7465125 | kgp11488181,rs9811783 |
| CRHR1 | chr17:954314-1170453 | chr17:454314-1670453 | chr17:41217448-41268973 | kgp12243700 | kgp2967880 |
| CTNNA2 | chr2:79412356-80875988 | chr2:78912356-81375988 | chr2:79265864-80729416 | kgp2692843 | kgp6161954 |
| DISC1 | chr1:231664398-232177019 | chr1:231164398-232677019 | chr1:229829183-230243641 | kgp15830047 | kgp10247084 |
| DPP6 | chr7:153584418-154685995 | chr7:153084418-155185995 | chr7:153215351-154316928 | rs1822707 | rs7781545 |
| DYNLL1 | chr12:120907659-120936298 | chr12:120407659-121436298 | chr12:119392042-119420681 | rs2393569 | rs1169303 |
| FPR1 | chr19:52249022-52255150 | chr19:51749022-52755150 | chr19:56940837-56946962 | rs11084062 | kgp21351572 |
| GAPDH | chr12:6643656-6647536 | chr12:6143656-7147536 | chr12:6513917-6517797 | kgp12277967 | kgp3951989 |
| GNA15 | chr19:3136190-3163766 | chr19:2636190-3663766 | chr19:3087190-3114766 | kgp9441497 | rs8109485 |
| GNAI2 | chr3:50263723-50296786 | chr3:49763723-50796786 | chr3:50238727-50271790 | rs1049256 | kgp1163947 |
| GNAO1 | chr16:56225250-56391356 | chr16:55725250-56891356 | chr16:54782751-54948857 | rs36013 | kgp16402238 |
| GNAQ | chr9:80335190-80646219 | chr9:79835190-81146219 | chr9:79525010-79836012 | rs3802497 | kgp478959 |
| GRIK1 | chr21:30909253-31312282 | chr21:30409253-31812282 | chr21:29831124-30234153 | kgp6759057 | kgp13183414 |
| GRIK3 | chr1:37261127-37499844 | chr1:36761127-37999844 | chr1:37033714-37272431 | kgp15160339 | kgp6185747 |
| GRM1 | chr6:146348781-146758731 | chr6:145848781-147258731 | chr6:146390474-146800424 | kgp17333275 | rs17076442 |
| GRM3 | chr7:86273229-86494192 | chr7:85773229-86994192 | chr7:86111165-86332128 | rs7809507 | rs6950721 |
| GRM5 | chr11:88237743-88796816 | chr11:87737743-89296816 | chr11:87881005-88436464 | kgp11022062 | rs7123374 |
| GRM7 | chr3:6902801-7783218 | chr3:6402801-8283218 | chr3:6877926-7758217 | rs17288121 | kgp10770379 |
| GRM8 | chr7:126078651-126893147 | chr7:125578651-127393147 | chr7:125865887-126680383 | rs11767202 | kgp13721602 |

Fig. 2-2

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| GSN | chr9:123963760-124095120 | chr9:123463760-124595120 | chr9:123003581-123134941 | rs10984984 | kgp10246924 |
| HOMER1 | chr5:78669785-78809700 | chr5:78169785-79309700 | chr5:78705541-78845456 | kgp22480767 | rs2438612 |
| HTR2A | chr13:47407512-47471169 | chr13:46907512-47971169 | chr13:46305513-46368995 | rs4942513 | rs2185411 |
| LARP7 | chr4:113558119-113578742 | chr4:113058119-114078742 | chr4:113777568-113798191 | kgp20778198 | rs10516593 |
| MAPK1 | chr22:22113946-22221970 | chr22:21613946-22721970 | chr22:20443946-20551970 | rs2019503 | rs5758017 |
| MTHFD1 | chr14:64854758-64926725 | chr14:64354758-65426725 | chr14:63924845-63996474 | kgp8236539 | kgp19721535 |
| MX1 | chr21:42792519-42831141 | chr21:42292519-43331141 | chr21:41714311-41753008 | rs7280789 | kgp9356591 |
| NARG1 | chr4:140222675-140311935 | chr4:139722675-140811935 | chr4:140442125-140531385 | kgp951257 | kgp22761518 |
| NEGR1 | chr1:71868624-72748405 | chr1:71368624-73248405 | chr1:71641212-72520993 | kgp15840593 | kgp15187386 |
| NLN | chr5:65018022-65125111 | chr5:64518022-65625111 | chr5:65053840-65155145 | kgp8540617 | kgp6780911 |
| NMI | chr2:152126981-152146430 | chr2:151626981-152646430 | chr2:151835227-151854676 | rs9789673 | rs4303715 |
| PCBP3 | chr21:47063682-47355618 | chr21:46563682-47855618 | chr21:45888110-46180046 | rs13047590 | rs17371795 |
| PDE1C | chr7:31792631-32338383 | chr7:31292631-32838383 | chr7:31759156-32305466 | rs960434 | rs10264489 |
| PPP2R1A | chr19:52693054-52729678 | chr19:52193054-53229678 | chr19:57385045-57421483 | kgp3827878 | kgp21490256 |
| PRPSAP1 | chr17:74306867-74350279 | chr17:73806867-74850279 | chr17:71818609-71861526 | kgp13936725 | kgp5222426 |
| PSMD11 | chr17:30771501-30808042 | chr17:30271501-31308042 | chr17:27795614-27832155 | kgp12010810 | rs8065019 |
| PSMD13 | chr11:236807-252984 | chr11:1-752984 | chr11:226807-242984 | kgp9815230 | kgp7252222 |
| PXN | chr12:120648241-120703574 | chr12:120148241-121203574 | chr12:119132632-119187946 | kgp9790305 | kgp10851563 |
| QRICH2 | chr17:74270129-74303761 | chr17:73770129-74803761 | chr17:71781724-71815356 | kgp9494493 | kgp13978344 |
| RANBP1 | chr22:20105023-20114706 | chr22:19605023-20614706 | chr22:18485023-18494704 | kgp15081773 | kgp240898 |
| RAP2A | chr13:98086474-98120252 | chr13:97586474-98620252 | chr13:96884476-96918245 | kgp1964422 | kgp12456635 |

*Fig. 2-3*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| RCC1 | chr1:28832454-28865708 | chr1:28332454-29365708 | chr1:28717331-28738194 | kgp4972332 | kgp10549261 |
| RGS12 | chr4:3315873-3441640 | chr4:2815873-3941640 | chr4:3285671-3411438 | kgp6603457 | kgp12100218 |
| RIF1 | chr2:152266396-152333860 | chr2:151766396-152833860 | chr2:151974645-152040665 | rs13010870 | kgp14366130 |
| RUVBL2 | chr19:49497155-49519182 | chr19:48997155-50019182 | chr19:54188967-54210994 | kgp2866116 | rs6509434 |
| RYR1 | chr19:38924339-39078204 | chr19:38424339-39578204 | chr19:43616179-43770044 | kgp21463042 | kgp10827233 |
| RYR2 | chr1:237205701-237997288 | chr1:236705701-238497288 | chr1:235272324-236063911 | kgp15265824 | kgp855991 |
| SDC3 | chr1:31342312-31381480 | chr1:30842312-31881480 | chr1:31114899-31154067 | kgp3545961 | rs1039630 |
| SELE | chr1:169691780-169703220 | chr1:169191780-170203220 | chr1:167958404-167969844 | kgp11738441 | kgp5736867 |
| SERPINB9 | chr6:2887503-2903545 | chr6:2387503-3403545 | chr6:2832502-2848506 | rs4959652 | kgp9198993 |
| SETD4 | chr21:37415981-37451687 | chr21:36915981-37951687 | chr21:36337851-36373557 | rs8131794 | kgp10193814 |
| SGTB | chr5:64961754-65017941 | chr5:64461754-65517941 | chr5:64997510-65053697 | rs2367239 | rs253229 |
| SHANK1 | chr19:51165083-51220195 | chr19:50665083-51720195 | chr19:55856895-55912007 | kgp8880890 | kgp5265049 |
| SLC7A10 | chr19:33699569-33716756 | chr19:33199569-34216756 | chr19:38391410-38408548 | kgp3880561 | kgp21532613 |
| SORD | chr15:45315301-45367287 | chr15:44815301-45867287 | chr15:43102632-43154331 | rs3752691 | rs17627219 |
| STRAP | chr12:16035287-16056410 | chr12:15535287-16556410 | chr12:15926554-15947677 | kgp9763258 | kgp18858589 |
| TK1 | chr17:76170159-76183285 | chr17:75670159-76683285 | chr17:73681754-73694880 | kgp13960604 | kgp4569268 |
| TNIK | chr3:170780291-171178197 | chr3:170280291-171678197 | chr3:172264363-172660546 | kgp17660929 | kgp3100328 |
| USP24 | chr1:55532031-55681039 | chr1:55032031-56181039 | chr1:55304619-55453350 | kgp3052862 | kgp5594096 |
| VHL | chr3:10183318-10195354 | chr3:9683318-10695354 | chr3:10158318-10168746 | kgp6652387 | rs9942062 |

*Fig. 2-4*

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| ACAT2 | chr6:160182988-160200087 | chr6:159682988-160700087 | chr12:51783540-51804590 | kgp17016252 | rs3119312 |
| ACCN2 | chr12:50451486-50477394 | chr12:49951486-50977394 | chr12:48737753-48763661 | kgp6083801 | kgp2326833 |
| ACP1 | chr2:264868-278282 | chr2:1-778282 | chr2:254871-268282 | kgp14878812 | kgp6217001 |
| ACTB | chr7:5566778-5570232 | chr7:5066778-6070232 | chr7:5533304-5536758 | kgp10503129 | rs17136342 |
| ADA | chr20:43248162-43280376 | chr20:42748162-43780376 | chr20:42681576-42713790 | kgp505723 | rs2207199 |
| ADD1 | chr4:2845583-2931802 | chr4:2345583-3431802 | chr4:2815381-2901587 | kgp5601859 | kgp5383382 |
| ADD2 | chr2:70834749-70995375 | chr2:70334749-71495375 | chr2:70688257-70848837 | kgp14188216 | kgp4077094 |
| ADORA1 | chr1:203096835-203136533 | chr1:202596835-203636533 | chr1:201363458-201403156 | rs16850143 | rs12568960 |
| ADRA1B | chr5:159343739-159400017 | chr5:158843739-159900017 | chr5:159276317-159332595 | rs17056747 | kgp2774549 |
| ADRA2A | chr10:112836789-112840662 | chr10:112336789-113340662 | chr10:112826910-112830560 | kgp3219023 | rs10787379 |
| ADRA2C | chr4:3768295-3770253 | chr4:3268295-4270253 | chr4:3737872-3740016 | kgp21189210 | kgp21320659 |
| ADRB2 | chr5:148206155-148208197 | chr5:147706155-148708197 | chr5:148186348-148188381 | kgp6738042 | rs352336 |
| ANXA2 | chr15:60639349-60690185 | chr15:60139349-61190185 | chr15:58426641-58477477 | kgp19904124 | kgp1248561 |
| APTX | chr9:32972603-33001639 | chr9:32472603-33501639 | chr9:32962607-33015110 | kgp8123814 | kgp22778750 |
| AQP1 | chr7:30893009-30965131 | chr7:30393009-31465131 | chr7:30917992-30931656 | kgp13347683 | rs11983505 |
| ARHGAP24 | chr4:86396283-86923823 | chr4:85896283-87423823 | chr4:86615307-87142847 | kgp12192788 | kgp20991115 |
| ARRB1 | chr11:74971165-75062875 | chr11:74471165-75562875 | chr11:74654129-74740521 | kgp13077708 | kgp12867051 |
| ARRB2 | chr17:4613788-4624795 | chr17:4113788-5124795 | chr17:4560537-4571544 | kgp10630047 | rs2304905 |

Fig. 3-1

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| BDKRB1 | chr14:96722546-96731100 | chr14:96222546-97231100 | chr14:95792311-95800853 | rs10146784 | kgp10194056 |
| BTBD2 | chr19:1985446-2015702 | chr19:1485446-2515702 | chr19:1936446-1966702 | kgp9698924 | rs12985186 |
| BTG2 | chr1:203274663-203278729 | chr1:202774663-203778729 | chr1:201541286-201545352 | kgp11073362 | kgp22834576 |
| C17orf44 | chr17:8123966-8127361 | chr17:7623966-8627361 | chr17:8064691-8068086 | kgp14083005 | kgp8066962 |
| C1orf116 | chr1:207191865-207206101 | chr1:206691865-207706101 | chr1:205258488-205272724 | kgp15208593 | rs12094477 |
| C7orf25 | chr7:42948871-42971805 | chr7:42448871-43471805 | chr7:42915396-42938330 | kgp13766903 | kgp8523923 |
| CALB2 | chr16:71392615-71424342 | chr16:70892615-71924342 | chr16:69950126-69981843 | rs1774414 | kgp16319275 |
| CALM2 | chr2:47387220-47403740 | chr2:46887220-47903740 | chr2:47146583-47257154 | kgp12094177 | kgp4237241 |
| CALM3 | chr14:90863326-90874619 | chr14:90363326-91374619 | chr19:51796351-51805879 | kgp828819 | kgp22766175 |
| CAMK1 | chr3:9799028-9811668 | chr3:9299028-10311668 | chr3:9774030-9786661 | kgp4340327 | kgp1318661 |
| CAMK2B | chr7:44256748-44365230 | chr7:43756748-44865230 | chr7:44223273-44331749 | rs10245456 | kgp10338229 |
| CAMK4 | chr5:110559946-110820748 | chr5:110059946-111320748 | chr5:110587980-110848647 | kgp11981357 | kgp22673631 |
| CCNB1 | chr5:68462836-68474070 | chr5:67962836-68974070 | chr5:68498668-68509826 | kgp5100830 | rs28529133 |
| CDC42 | chr1:22379119-22419436 | chr1:21879119-22919436 | chr1:22251706-22292023 | kgp15282552 | rs209696 |
| CENTG1 | chr12:58118076-58135944 | chr12:57618076-58635944 | chr12:56404343-56422211 | kgp22774357 | rs12825103 |
| CHGB | chr20:5891973-5906005 | chr20:5391973-6406005 | chr20:5840167-5854003 | kgp19217529 | kgp5406173 |
| CHP | chr15:41523436-41574083 | chr15:41023436-42074083 | chr15:39310728-39361375 | kgp9389002 | kgp10815429 |
| CHRM2 | chr7:136553398-136701771 | chr7:136053398-137201771 | chr7:136203938-136352311 | rs2882248 | kgp11051162 |
| CMPK | chr2:6988440-7005950 | chr2:6488440-7505950 | chr2:6905891-6923401 | rs16865056 | kgp6717309 |
| CNR1 | chr6:88849584-88875767 | chr6:88349584-89375767 | chr6:88910155-88932281 | kgp11366911 | kgp5424340 |

Fig. 3-2

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| COPB2 | chr3:139076432-139108522 | chr3:138576432-139608522 | chr3:140559122-140591212 | kgp17652827 | rs2554152 |
| CYCS | chr7:25158269-25164980 | chr7:24658269-25664980 | chr7:25124799-25131480 | kgp22782658 | kgp9259047 |
| DCN | chr12:91539034-91576806 | chr12:91039034-92076806 | chr12:90063165-90100937 | rs11105720 | rs1602946 |
| DHCR7 | chr11:71145456-71159477 | chr11:70645456-71659477 | chr11:70823104-70837125 | rs2016495 | kgp4157665 |
| DLST | chr14:75348593-75370450 | chr14:74848593-75870450 | chr14:74418371-74440198 | kgp6099186 | rs11621369 |
| DRD2 | chr11:113280316-113346001 | chr11:112780316-113846001 | chr11:112785526-112851211 | kgp12732525 | rs1062613 |
| DRD3 | chr3:113847556-113918254 | chr3:113347556-114418254 | chr3:115330246-115400944 | kgp18078164 | kgp7361746 |
| DSTN | chr20:17550598-17588652 | chr20:17050598-18088652 | chr20:17498598-17536652 | kgp19350858 | rs1581925 |
| ECHS1 | chr10:135175986-135186908 | chr10:134675986-135686908 | chr10:135025979-135036898 | kgp21664075 | kgp22837031 |
| EGFR | chr7:55086724-55275031 | chr7:54586724-55775031 | chr7:55054218-55242525 | kgp12053718 | kgp3314724 |
| EIF3S3 | chr8:117657055-117768062 | chr8:117157055-118268062 | chr8:117726236-117837243 | kgp10576753 | rs1793723 |
| ERBB2 | chr17:37844392-37884915 | chr17:37344392-38384915 | chr17:35097918-35138441 | kgp11528115 | kgp670921 |
| F2R | chr5:76011867-76031595 | chr5:75511867-76531595 | chr5:76047623-76067351 | kgp22518836 | kgp1549629 |
| F2RL2 | chr5:75911306-75919240 | chr5:75411306-76419240 | chr5:75947062-75954996 | kgp10188048 | kgp8041699 |
| F2RL3 | chr19:16999825-17002830 | chr19:16499825-17502830 | chr19:16860825-16863830 | kgp9756004 | kgp12567834 |
| F3 | chr1:94994731-95007413 | chr1:94494731-95507413 | chr1:94767460-94779903 | kgp22732356 | kgp5203715 |
| FKBP3 | chr14:45584801-45604009 | chr14:45084801-46104009 | chr14:44654858-44674272 | kgp8973198 | kgp19724486 |
| FSCN1 | chr7:5632435-5646287 | chr7:5132435-6146287 | chr7:5598979-5612812 | kgp11535801 | kgp22733484 |
| FURIN | chr15:91411884-91426687 | chr15:90911884-91926687 | chr15:89212888-89227691 | kgp19755110 | kgp7570879 |
| FYN | chr6:111981534-112194655 | chr6:111481534-112694655 | chr6:112089177-112301320 | kgp9553033 | kgp10843976 |

*Fig. 3-3*

| Tier 2 Gene | GeneRange (hg19) | GeneRange +500kb(hg19) | GeneRange (hg18) | StartSNP (GeneRange + 500kb) | EndSNP (GeneRange + 500kb) |
|---|---|---|---|---|---|
| GLP1R | chr6:39016556-39055520 | chr6:38516556-39555520 | chr6:39124534-39163498 | kgp11427391 | kgp8067157 |
| GLP2R | chr17:9729380-9793022 | chr17:9229380-10293022 | chr17:9670105-9733747 | kgp13857921 | kgp14095302 |
| GNAI1 | chr7:79764139-79848725 | chr7:79264139-80348725 | chr7:79602075-79686661 | kgp3340161 | kgp96572 |
| GNAI3 | chr1:110091185-110138452 | chr1:109591185-110638452 | chr1:109892708-109939975 | rs28503409 | kgp2138201 |
| GNB2L1 | chr5:180663927-180670906 | chr5:180163927-181170906 | chr5:180596533-180603512 | kgp9825803 | kgp22785368 |
| GOT1 | chr10:101156626-101190530 | chr10:100656626-101690530 | chr10:101146617-101180336 | kgp21656902 | kgp21815940 |
| GP1BA | chr17:4835591-4838325 | chr17:4335591-5338325 | chr17:4776371-4779067 | kgp13949132 | kgp11186643 |
| GPR26 | chr10:125425870-125456913 | chr10:124925870-125956913 | chr10:125415860-125444113 | kgp7582662 | kgp21578542 |
| GRB2 | chr17:73314156-73401790 | chr17:72814156-73901790 | chr17:70825751-70913385 | kgp13841089 | kgp14035219 |
| GRB7 | chr17:37894161-37903538 | chr17:37394161-38403538 | chr17:35147712-35157064 | kgp14102913 | kgp13833584 |
| GRIA1 | chr5:152870083-153193429 | chr5:152370083-153693429 | chr5:152850276-153173622 | rs1438937 | rs10057369 |
| GRM2 | chr3:51741080-51752625 | chr3:51241080-52252625 | chr3:51716127-51727665 | rs4367100 | rs13060808 |
| GRM4 | chr6:33989627-34113869 | chr6:33489627-34613869 | chr6:34097605-34231377 | kgp17076142 | rs6909637 |
| GRM6 | chr5:178405329-178422124 | chr5:177905329-178922124 | chr5:178337935-178354730 | rs603852 | rs11249632 |
| HBXIP | chr1:110943876-110950546 | chr1:110443876-111450546 | chr1:110745399-110752069 | kgp8686658 | rs1936942 |
| HD | chr6:125596496-125623282 | chr6:125096496-126123282 | chr6:125638195-125664981 | rs11154263 | rs11967627 |
| HNRPA3 | chr2:178077422-178088685 | chr2:177577422-178588685 | chr2:177785668-177796931 | kgp14203861 | rs1344924 |
| HOMER3 | chr19:19017768-19045219 | chr19:18517768-19545219 | chr19:18901011-18912983 | rs13344313 | rs4808199 |
| HRPT2 | chr1:193091088-193223942 | chr1:192591088-193723942 | chr1:191357711-191490565 | kgp2473538 | kgp12065536 |
| HSP90AB1 | chr6:44214848-44221614 | chr6:43714848-44721614 | chr6:44322826-44329592 | kgp5836209 | kgp8706663 |

*Fig. 3-4*

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| IL8RB | chr2:218989997-219001975 | chr2:218489997-219501975 | chr2:218698242-218710220 | kgp22730583 | rs1055816 |
| IMPDH2 | chr3:49061761-49066875 | chr3:48561761-49566875 | chr3:49036765-49041879 | kgp22731595 | kgp5626213 |
| IQGAP2 | chr5:75699148-76003957 | chr5:75199148-76503957 | chr5:75734904-76039713 | kgp22490664 | rs11739698 |
| ITGB1 | chr10:33189245-33247293 | chr10:32689245-33747293 | chr10:33229251-33287299 | kgp12034252 | rs11009395 |
| ITGB7 | chr12:53585106-53601000 | chr12:53085106-54101000 | chr12:51871373-51887267 | kgp19011413 | kgp3313746 |
| ITPR1 | chr3:4535031-4889524 | chr3:4035031-5389524 | chr3:4510033-4864286 | kgp17889944 | kgp1749057 |
| KIAA0090 | chr1:19544583-19578046 | chr1:19044583-20078046 | chr1:19417170-19450633 | rs624761 | rs1009631 |
| KIAA1683 | chr19:18367905-18385319 | chr19:17867905-18885319 | chr19:18228907-18246235 | kgp6435620 | rs10412356 |
| LAMA4 | chr6:112429133-112575828 | chr6:111929133-113075828 | chr6:112535826-112682521 | kgp16962466 | kgp17024247 |
| LRP2BP | chr4:186285031-186300172 | chr4:185785031-186800172 | chr4:186522026-186537166 | kgp7238414 | rs9994907 |
| LRRC59 | chr17:48458593-48474914 | chr17:47958593-48974914 | chr17:45813597-45829831 | kgp1609816 | kgp13856216 |
| LTA | chr6:2825414-2827639 | chr6:2825414-2827639 | chr6:2787675-2789683 | kgp11675228 | rs6912537 |
| LYAR | chr4:4269428-4291896 | chr4:3769428-4791896 | chr4:4320337-4342744 | kgp22780996 | kgp7317116 |
| LYN | chr8:56792385-56925006 | chr8:56292385-57425006 | chr8:56954939-57086494 | kgp8836202 | rs2670027 |
| MAP4 | chr3:47892179-48130769 | chr3:47392179-48630769 | chr3:47867188-48105715 | kgp17741397 | rs35623035 |
| MAPT | chr17:43971747-44105699 | chr17:43471747-44605699 | chr17:41327543-41461546 | kgp22730329 | kgp13941400 |
| MARK4 | chr19:45754515-45808541 | chr19:45254515-46308541 | chr19:50446681-50500381 | kgp10230030 | kgp21456098 |
| MC4R | chr18:58038563-58040001 | chr18:57538563-58540001 | chr18:56189543-56190981 | kgp7049183 | kgp1258536 |
| MGC11082 | chr18:3602998-3604385 | chr18:3102998-4104385 | chr18:3592998-3594385 | kgp15965827 | kgp12318627 |
| MRPL14 | chr6:44081372-44095191 | chr6:43581372-44595191 | chr6:44189349-44203169 | kgp17035193 | rs527322 |

*Fig. 3-5*

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| MRPS16 | chr10:75006445-75012451 | chr10:74506445-75512451 | chr10:74678606-74682457 | kgp21628722 | rs12243089 |
| MTNR1A | chr4:187454808-187476537 | chr4:186954808-187976537 | chr4:187691802-187713531 | rs12648771 | rs4476657 |
| MTNR1B | chr11:92702788-92715948 | chr11:92202788-93215948 | chr11:92342436-92355596 | kgp10063029 | rs2658801 |
| MYC | chr8:128748314-128753680 | chr8:128248314-129253680 | chr8:128817497-128822855 | kgp3177285 | kgp1944877 |
| MYO6 | chr6:76458908-76629254 | chr6:75958908-77129254 | chr6:76515628-76685974 | kgp17262775 | kgp17183304 |
| NANS | chr9:100818958-100845365 | chr9:100318958-101345365 | chr9:99847709-99885178 | rs10817759 | rs2778908 |
| NCK1 | chr3:136581049-136667968 | chr3:136081049-137167968 | chr3:138063762-138150658 | kgp117446 | kgp10600232 |
| NFKBIA | chr14:35870715-35873960 | chr14:35370715-36373960 | chr14:34940466-34943711 | kgp19552677 | kgp19707730 |
| NPY2R | chr4:156129780-156138228 | chr4:155629780-156638228 | chr4:156349230-156357678 | kgp3956236 | kgp20850236 |
| NUDC | chr1:27248223-27272887 | chr1:26748223-27772887 | chr1:27120810-27145474 | rs11247955 | kgp15594139 |
| OPRD1 | chr1:29138653-29190208 | chr1:28638653-29690208 | chr1:29011240-29062795 | kgp9104521 | kgp15855740 |
| PAFAH1B3 | chr19:42801184-42806952 | chr19:42301184-43306952 | chr19:47493024-47498563 | kgp21540635 | kgp22735078 |
| PCBP1 | chr2:70314584-70316334 | chr2:69814584-70816334 | chr2:70168204-70169836 | kgp14596264 | kgp6568959 |
| PCDHA4 | chr5:140186671-140391929 | chr5:139686671-140891929 | chr5:140166855-140372115 | kgp6468526 | kgp10727572 |
| PCID1 | chr11:32605313-32624037 | chr11:32105313-33124037 | chr11:32561889-32580613 | kgp13035948 | rs10836023 |
| PCMT1 | chr6:150070830-150132557 | chr6:149570830-150632557 | chr6:150112657-150174249 | kgp17277449 | kgp10169289 |
| PDCD5 | chr19:33072093-33078358 | chr19:32572093-33578358 | chr19:37763943-37770169 | kgp21531284 | rs7259333 |
| PDE1B | chr12:54943176-54973023 | chr12:54443176-55473023 | chr12:53229670-53259290 | kgp18962385 | rs11171250 |
| PDE6G | chr17:79617488-79623607 | chr17:79117488-80123607 | chr17:77227893-77234038 | kgp317116 | kgp13898509 |
| PGM1 | chr1:64058946-64125916 | chr1:63558946-64625916 | chr1:63831534-63898505 | kgp175729 | kgp15416792 |

*Fig. 3-6*

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| PHKB | chr16:47495209-47735434 | chr16:46995209-48235434 | chr16:46052710-46292935 | kgp8481371 | rs16945930 |
| PHKG2 | chr16:30759619-30772497 | chr16:30259619-31272497 | chr16:30667237-30676183 | kgp16316196 | kgp22773724 |
| PICK1 | chr22:38453261-38471708 | chr22:37953261-38971708 | chr22:36783207-36801654 | kgp5170623 | kgp1759680 |
| PIK3CA | chr3:178866310-178952497 | chr3:178366310-179452497 | chr3:180349004-180435191 | rs7615444 | rs1025864 |
| PIK3R1 | chr5:67511583-67597649 | chr5:67011583-68097649 | chr5:67547359-67633405 | kgp7844449 | rs7737296 |
| PLA2G7 | chr6:46672052-46703430 | chr6:46172052-47203430 | chr6:46780011-46811110 | kgp4678268 | kgp9155835 |
| PLCB1 | chr20:8113295-8865547 | chr20:7613295-9365547 | chr20:8061295-8813547 | kgp19226483 | rs2076234 |
| PLCB3 | chr11:64018994-64036924 | chr11:63518994-64536924 | chr11:63775697-63793195 | kgp9427286 | rs484886 |
| PLCG2 | chr16:81812898-81991899 | chr16:81312898-82491899 | chr16:80370430-80549400 | kgp4622733 | kgp3230988 |
| PPIH | chr1:43124047-43142429 | chr1:42624047-43642429 | chr1:42896634-42915016 | kgp1870818 | rs11210802 |
| PRDX1 | chr1:45976706-45988562 | chr1:45476706-46488562 | chr1:45749293-45760196 | rs3806405 | kgp15560310 |
| PRKCA | chr17:64298925-64806862 | chr17:63798925-65306862 | chr17:61729387-62237324 | kgp13847618 | kgp13994829 |
| PRLHR | chr10:120352915-120355160 | chr10:119852915-120855160 | chr10:120342905-120345150 | rs853584 | kgp21690663 |
| PRMT1 | chr19:50180408-50191707 | chr19:49680408-50691707 | chr19:54872307-54883516 | kgp1460116 | kgp5315133 |
| PSAT1 | chr9:80912058-80945009 | chr9:80412058-81445009 | chr9:80101878-80134829 | kgp2581728 | kgp9769053 |
| PSEN1 | chr14:73603142-73690399 | chr14:73103142-74190399 | chr14:72672931-72756862 | kgp8405661 | kgp19611371 |
| PSMA1 | chr11:14526421-14665180 | chr11:14026421-15165180 | chr11:14482997-14621739 | kgp12643195 | kgp13010596 |
| PSMC1 | chr14:90722893-90738966 | chr14:90222893-91238966 | chr14:89792646-89808719 | rs10140098 | kgp19595798 |
| PSMD1 | chr2:231921577-232037540 | chr2:231421577-232537540 | chr2:231629852-231745717 | rs1678155 | kgp11602861 |
| PSMD6 | chr3:63996230-64009658 | chr3:63496230-64509658 | chr3:63971270-63984698 | kgp9706776 | kgp17718198 |

*Fig. 3-7*

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| PSME1 | chr14:24605377-24608176 | chr14:24105377-25108176 | chr14:23675217-23678016 | kgp11494860 | kgp2234181 |
| PTHR2 | chr2:209353736-209704818 | chr2:208853736-210204818 | chr2:209061981-209413063 | kgp14652386 | rs1020407 |
| PYGL | chr14:51371934-51411248 | chr14:50871934-51911248 | chr14:50441686-50480984 | kgp10991856 | rs7146882 |
| PYGM | chr11:64513860-64528187 | chr11:64013860-65028187 | chr11:64270436-64284763 | kgp12876954 | rs675671 |
| RAB2 | chr8:61429469-61536203 | chr8:60929469-62036203 | chr8:61592023-61698757 | kgp7067636 | rs3864667 |
| RALA | chr7:39663151-39747723 | chr7:39163151-40247723 | chr7:39629686-39714242 | kgp22733616 | rs11768838 |
| RCC2 | chr1:17733250-17766250 | chr1:17233250-18266250 | chr1:17605865-17638807 | kgp15535308 | kgp7647703 |
| RGS2 | chr1:192778168-192781407 | chr1:192278168-193281407 | chr1:191044793-191048026 | rs10921130 | kgp11065785 |
| RHOA | chr3:49396578-49449526 | chr3:48896578-49949526 | chr3:49371582-49424530 | kgp11466037 | rs868891 |
| RPA2 | chr1:28218048-28241236 | chr1:27718048-28741236 | chr1:28090635-28113823 | rs12033326 | kgp15705538 |
| RPLP2 | chr11:809935-812876 | chr11:309935-1312876 | chr11:799935-802876 | kgp11473410 | kgp7750669 |
| RPN2 | chr20:35807455-35870025 | chr20:35307455-36370025 | chr20:35240887-35303439 | kgp9846122 | kgp19260650 |
| RPS14 | chr5:149823791-149829319 | chr5:149323791-150329319 | chr5:149803984-149809512 | kgp22444746 | kgp22218062 |
| RRM1 | chr11:4137307-4223759 | chr11:3637307-4723759 | chr11:4072499-4116682 | rs6578398 | kgp4491491 |
| S100A6 | chr1:153507075-153508717 | chr1:153007075-154008717 | chr1:151773699-151775341 | kgp15193014 | rs10908627 |
| SACS | chr13:23902964-24007841 | chr13:23402964-24507841 | chr13:22800964-22905841 | kgp16818396 | rs2765089 |
| SARS | chr1:109756514-109780804 | chr1:109256514-110280804 | chr1:109558062-109582308 | kgp5910329 | rs1803687 |
| SCTR | chr2:120197418-120282028 | chr2:119697418-120782028 | chr2:119913888-119998498 | kgp12364473 | kgp22762988 |
| SET | chr9:131445933-131458675 | chr9:130945933-131958675 | chr9:130485754-130498496 | kgp11282765 | kgp18608937 |
| SF3B14 | chr2:24290453-24299314 | chr2:23790453-24799314 | chr2:24143957-24152818 | kgp14521970 | rs12474894 |

*Fig. 3-8*

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| SHBG | chr17:7517381-7536700 | chr17:7017381-8036700 | chr17:7458106-7477395 | kgp7760759 | rs6503086 |
| SIAH1 | chr16:48390274-48482309 | chr16:47890274-48982309 | chr16:46947777-47039810 | kgp4639784 | kgp7644930 |
| SLC2A1 | chr1:43391045-43424847 | chr1:42891045-43924847 | chr1:43163632-43197434 | kgp2036523 | rs2782652 |
| SLC6A3 | chr5:1392904-1445543 | chr5:892904-1945543 | chr5:1445909-1498538 | kgp22585075 | kgp9690399 |
| SNCA | chr4:90645249-90759447 | chr4:90145249-91259447 | chr4:90865727-90978470 | kgp11552673 | kgp8195783 |
| SNRPB2 | chr20:16710608-16722417 | chr20:16210608-17222417 | chr20:16658628-16670037 | kgp19326624 | kgp19208923 |
| SOCS6 | chr18:67956136-67997434 | chr18:67456136-68497434 | chr18:66107116-66148414 | kgp10928836 | rs4243325 |
| SOCS7 | chr17:36508006-36561846 | chr17:36008006-37061846 | chr17:33761530-33809545 | rs12936144 | rs4794796 |
| SRC | chr20:35973087-36033821 | chr20:35473087-36533821 | chr20:35406501-35467235 | kgp19359278 | kgp9150551 |
| STAU1 | chr20:47729875-47805288 | chr20:47229875-48305288 | chr20:47163282-47238695 | rs11905650 | kgp19233876 |
| STX12 | chr1:28099693-28150963 | chr1:27599693-28650963 | chr1:27972280-28023550 | kgp22731625 | kgp15287949 |
| SYK | chr9:93564011-93660842 | chr9:93064011-94160842 | chr9:92603890-92698304 | kgp12394293 | rs894962 |
| TBCA | chr5:76986994-77072185 | chr5:76486994-77572185 | chr5:77022750-77107941 | rs2928164 | rs10059285 |
| TBXA2R | chr19:3594503-3606831 | chr19:3094503-4106831 | chr19:3545503-3557658 | kgp21472781 | kgp1760692 |
| TCP1 | chr6:160199529-160210735 | chr6:159699529-160710735 | chr6:160119519-160130725 | kgp16923201 | kgp10518192 |
| TEAD3 | chr6:35441373-35464861 | chr6:34941373-35964861 | chr6:35549351-35572839 | rs847861 | kgp3339 |
| TFAM | chr10:60145175-60155897 | chr10:59645175-60655897 | chr10:59815181-59825903 | kgp9406331 | kgp6514369 |
| TGM2 | chr20:36756863-36793700 | chr20:36256863-37293700 | chr20:36190277-36227114 | rs6067098 | kgp9992037 |
| TJP1 | chr15:29992356-30114706 | chr15:29492356-30614706 | chr15:27779648-27901998 | kgp19895791 | rs2604694 |
| TLR10 | chr4:38773859-38784611 | chr4:38273859-39284611 | chr4:38450646-38460984 | kgp9612652 | rs6531705 |

*Fig. 3-9*

| Tier 2 Gene | GeneRange (hg19) | GeneRange +500kb(hg19) | GeneRange (hg18) | StartSNP (GeneRange + 500kb) | EndSNP (GeneRange +500kb) |
|---|---|---|---|---|---|
| TMEM4 | chr12:56704213-56710128 | chr12:56204213-57210128 | chr12:54990480-54996395 | kgp6718939 | kgp6565807 |
| TPI1 | chr12:6976583-6980110 | chr12:6476583-7480110 | chr12:6846966-6850253 | kgp3883976 | kgp18849054 |
| TRAF2 | chr9:139776384-139821067 | chr9:139276384-140321067 | chr9:138896205-138940888 | rs3812570 | kgp9465784 |
| TRMT112 | chr11:64084164-64085033 | chr11:63584164-64585033 | chr11:63840740-63841609 | kgp1242205 | rs2957154 |
| TUBA1 | chr12:49521565-49525304 | chr12:49021565-50025304 | chr12:47807832-47811571 | kgp4948752 | kgp18737983 |
| TUBA1A | chr12:49578582-49582861 | chr12:49078582-50082861 | chr12:47864849-47869128 | kgp5373125 | kgp1407179 |
| TUBA1B | chr12:49521566-49525304 | chr12:49021566-50025304 | chr12:47807832-47866883 | kgp4948752 | kgp18737983 |
| TUBA2 | chr12:49578793-49580616 | chr12:49078793-50080616 | chr12:47865060-47866883 | kgp18983720 | kgp75177 |
| TUBB | chr6:1981087-1986127 | chr6:1981087-1986127 | chr6:1935034-1940074 | kgp17000846 | kgp16908954 |
| TUBG1 | chr17:40761357-40767256 | chr17:40261357-41267256 | chr17:38015219-38020777 | rs12600570 | kgp3534380 |
| TXN | chr9:113006091-113018920 | chr9:112506091-113518920 | chr9:112046130-112058599 | kgp18601393 | kgp652846 |
| TXNDC4 | chr9:102741463-102861330 | chr9:102241463-103361330 | chr9:101781284-101901151 | kgp22740558 | rs10989168 |
| TXNL2 | chr10:131934639-131977932 | chr10:131434639-132477932 | chr10:131824629-131867922 | kgp21587397 | rs2921907 |
| TYMS | chr18:657603-673499 | chr18:157603-1173499 | chr18:647603-663499 | kgp1671520 | kgp5560925 |
| UBQLN4 | chr1:156005091-156023516 | chr1:155505091-156523516 | chr1:154271715-154290140 | rs12746592 | kgp204451 |
| UCHL1 | chr4:41258897-41270446 | chr4:40758897-41770446 | chr4:40953685-40965203 | rs10029833 | kgp21157719 |
| VIPR1 | chr3:42530790-42579065 | chr3:42030790-43079065 | chr3:42519120-42554064 | rs794894 | kgp10771397 |
| YWHAQ | chr2:9724105-9771106 | chr2:9224105-10271106 | chr2:9641556-9688557 | kgp7327726 | rs1138729 |
| ZAP70 | chr2:98330030-98356323 | chr2:97830030-98856323 | chr2:97696462-97722755 | kgp10723114 | kgp14308801 |

*Fig. 3-10*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| ABI3 | chr17:47287588-47300587 | chr17:46787588-47800587 | chr17:44642587-44655586 | rs7211412 | kgp13987803 |
| ACTA1 | chr1:229566992-229569843 | chr1:229066992-230069843 | chr1:227633615-227636466 | kgp706951 | kgp9594907 |
| ACTN2 | chr1:236849769-236927558 | chr1:236349769-237427558 | chr1:234916392-234994181 | kgp12139182 | kgp9945691 |
| ADCY5 | chr3:123001142-123167392 | chr3:122501142-123667392 | chr3:124486088-124650082 | kgp5729470 | kgp18234294 |
| ADCY8 | chr8:131792546-132052835 | chr8:131292546-132552835 | chr8:131861728-132122017 | rs11778881 | kgp4563992 |
| ADCYAP1R1 | chr7:31092075-31151093 | chr7:30592075-31651093 | chr7:31058666-31112836 | kgp6410265 | kgp5976045 |
| ADD3 | chr10:111756107-111895323 | chr10:111256107-112395323 | chr10:111746097-111885313 | kgp2922347 | kgp21705322 |
| AFAP1 | chr4:7760439-7941653 | chr4:7260439-8441653 | chr4:7811339-7992553 | kgp10066670 | kgp2565038 |
| AGTR1 | chr3:148415657-148460790 | chr3:147915657-148960790 | chr3:149898347-149943480 | kgp17969929 | rs9827666 |
| AHCYL1 | chr1:110527386-110566364 | chr1:110027386-111066364 | chr1:110328830-110367887 | kgp15280262 | kgp8467474 |
| AKAP12 | chr6:151561133-151679694 | chr6:151061133-152179694 | chr6:151603201-151719602 | kgp17415975 | kgp17180004 |
| AKAP13 | chr15:85923870-86292586 | chr15:85423870-86792586 | chr15:83724874-84093590 | rs11073778 | kgp10945265 |
| AKAP5 | chr14:64932216-64941221 | chr14:64432216-65441221 | chr14:64001969-64010974 | rs945029 | rs4499147 |
| AKAP9 | chr7:91570188-91739987 | chr7:91070188-92239987 | chr7:91408127-91577925 | kgp7513665 | kgp8102448 |
| AKR1C3 | chr10:5005453-5149878 | chr10:4505453-5649878 | chr10:4995453-5139878 | rs1679414 | kgp8379007 |
| AKT1 | chr14:105235686-105262080 | chr14:104735686-105762080 | chr14:104306731-104333125 | kgp10896929 | kgp7260890 |
| ANK2 | chr4:113739238-114304896 | chr4:113239238-114804896 | chr4:113958687-114524345 | kgp8454825 | kgp10144793 |
| ANKRD24 | chr19:4183350-4224811 | chr19:3683350-4724811 | chr19:4134350-4175811 | kgp3226366 | rs7255543 |

*Fig. 4-1*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| ANXA6 | chr5:150480266-150537443 | chr5:149980266-151037443 | chr5:150460460-150517560 | kgp22603058 | rs11747938 |
| ANXA7 | chr10:75135188-75173841 | chr10:74635188-75673841 | chr10:74805194-74843847 | kgp21588521 | kgp5026768,rs2227568 |
| APLP2 | chr11:129939715-130014706 | chr11:129439715-130514706 | chr11:129445010-129519910 | kgp22802171 | rs7116475 |
| AR | chrX:66763873-66950461 | chrX:66263873-67450461 | chrX:66680598-66860844 | rs478505 | kgp22776402 |
| ARF1 | chr1:228270360-228286913 | chr1:227770360-228786913 | chr1:226336983-226353536 | kgp7035482 | kgp5092378 |
| ARF3 | chr12:49329991-49351252 | chr12:48829991-49851252 | chr12:47616258-47637519 | kgp9963537 | kgp19162961 |
| ARHGAP1 | chr11:46698631-46722120 | chr11:46198631-47222120 | chr11:46655207-46678696 | rs11038804 | kgp12872953 |
| ARHGEF1 | chr19:42399421-42434296 | chr19:41899421-42934296 | chr19:47079106-47103444 | kgp21546138 | kgp9753873 |
| ARL3 | chr10:104433483-104474190 | chr10:103933483-104974190 | chr10:104423477-104464180 | rs4919614 | kgp2065500 |
| ARL8B | chr3:5163929-5222601 | chr3:4663929-5722601 | chr3:5138929-5197601 | kgp5083934 | kgp17728482 |
| ASCL2 | chr11:2289727-2292182 | chr11:1789727-2792182 | chr11:2246303-2248758 | kgp12845252 | kgp7129584 |
| ATF3 | chr1:212738675-212794119 | chr1:212238675-213294119 | chr1:210805319-210860739 | rs10863936 | kgp12569686 |
| ATN1 | chr12:7033625-7053815 | chr12:6533625-7553815 | chr12:6903886-6924076 | kgp18714644 | kgp19128481 |
| ATP1B1 | chr1:169075946-169101960 | chr1:168575946-169601960 | chr1:167342570-167368584 | rs10800363 | kgp305361 |
| ATP2B1 | chr12:89981825-90049844 | chr12:89481825-90549844 | chr12:88505956-88573975 | kgp4237218 | kgp19117315 |
| ATP2B2 | chr3:10365706-10749716 | chr3:9865706-11249716 | chr3:10342743-10724716 | kgp7774534 | rs7625756 |
| ATXN1 | chr6:16299342-16761721 | chr6:15799342-17261721 | chr6:16407321-16869700 | kgp2173519 | rs6921352 |
| ATXN3 | chr14:92524895-92572965 | chr14:92024895-93072965 | chr14:91594648-91642718 | kgp11986238 | rs2146498 |
| ATXN7 | chr3:63850232-63989136 | chr3:63350232-64489136 | chr3:63825272-63964176 | rs9311874 | kgp797614 |
| AVPR1A | chr12:63540215-63546590 | chr12:63040215-64046590 | chr12:61826482-61832857 | rs952865 | kgp3671976 |
| B4GALT1 | chr9:33110638-33167356 | chr9:32610638-33667356 | chr9:33100638-33157356 | kgp18539535 | kgp18370584 |

*Fig. 4-2*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| BANK1 | chr4:102341117-102995969 | chr4:101841117-103495969 | chr4:102560140-103214992 | rs6851921 | kgp20796561 |
| BCAP31 | chrX:152965946-152990201 | chrX:152465946-153490201 | chrX:152619145-152643081 | rs6627302 | kgp22764947 |
| BCAR1 | chr16:75262927-75301951 | chr16:74762927-75801951 | chr16:73820428-73859452 | kgp7158675 | kgp16367309 |
| BCL2 | chr18:60790578-60986657 | chr18:60290578-61486657 | chr18:58941558-59137637 | rs435439 | rs1720898 |
| BMI1 | chr10:22610138-22620414 | chr10:22110138-23120414 | chr10:22645304-22660192 | kgp3019331 | rs12775513 |
| BMPR2 | chr2:203241049-203432474 | chr2:202741049-203932474 | chr2:202949294-203140719 | rs2072504 | kgp3183288 |
| BOC | chr3:112930411-113006305 | chr3:112430411-113506305 | chr3:114413101-114488995 | kgp12164746 | kgp3299668 |
| BPGM | chr7:134331530-134364567 | chr7:133831530-134864567 | chr7:133982094-134015107 | kgp13720725 | kgp8542611 |
| BRCA1 | chr17:41196311-41322420 | chr17:40696311-41822420 | chr17:38449839-38530994 | kgp1014784 | kgp13921789 |
| BRCA2 | chr13:32889616-32973809 | chr13:32389616-33473809 | chr13:31787616-31871809 | rs2146284 | rs9596502 |
| BRD7 | chr16:50352928-50402845 | chr16:49852928-50902845 | chr16:48910441-48960330 | kgp3843480 | kgp6018549 |
| BRF2 | chr8:37701397-37707431 | chr8:37201397-38207431 | chr8:37820560-37826569 | rs7818467 | kgp22772561 |
| BRMS1 | chr11:66104803-66112582 | chr11:65604803-66612582 | chr11:65861379-65869158 | kgp22746103 | kgp12809093 |
| BTK | chrX:100604434-100645770 | chrX:100104434-101145770 | chrX:100491097-100532426 | kgp22759057 | kgp22747202 |
| C1orf128 | chr1:24104887-24114722 | chr1:23604887-24614722 | chr1:23977474-23987309 | kgp283495 | kgp2701674 |
| C1orf42 | chr1:152486978-152488481 | chr1:151986978-152988481 | chr1:150753602-150755105 | kgp15694971 | rs4363385 |
| C1QBP | chr17:5336098-5342471 | chr17:4836098-5842471 | chr17:5276822-5283195 | kgp14047547 | rs17825455 |
| C20orf20 | chr20:61427804-61431945 | chr20:60927804-61931945 | chr20:60898282-60902390 | kgp9228388 | kgp19363625 |
| C20orf24 | chr20:35234136-35240960 | chr20:34734136-35740960 | chr20:34636369-34674374 | rs6060820 | rs1744760 |
| C4orf14 | chr4:57829515-57843826 | chr4:57329515-58343826 | chr4:57524272-57538583 | kgp22756132 | kgp1831456 |
| C4orf17 | chr4:100432160-100463460 | chr4:99932160-100963460 | chr4:100651222-100682483 | kgp20878925 | kgp21204347 |

*Fig. 4-3*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| C5orf25 | chr5:175665369-175772990 | chr5:175165369-176272990 | chr5:175598008-175705596 | kgp7679859 | rs480782 |
| C9orf25 | chr9:34398181-34458568 | chr9:33898181-34958568 | chr9:34388181-34448568 | kgp22772722 | rs7031962 |
| CABIN1 | chr22:24407764-24574596 | chr22:23907764-25074596 | chr22:22737764-22904596 | kgp5637302 | kgp5793536 |
| CABP1 | chr12:121078421-121105127 | chr12:120578421-121605127 | chr12:119562804-119589510 | kgp18737891 | rs503720 |
| CACNA1C | chr12:2162415-2807115 | chr12:1662415-3307115 | chr12:2032676-2677376 | kgp9477564 | kgp1276729 |
| CALCR | chr7:93053798-93204042 | chr7:92553798-93704042 | chr7:92891734-93041978 | kgp3815436 | kgp10249142 |
| CALD1 | chr7:134464163-134655480 | chr7:133964163-135155480 | chr7:134114710-134306012 | rs16874469 | kgp22829820 |
| CAMK2A | chr5:149599053-149669403 | chr5:149099053-150169403 | chr5:149579247-149649529 | kgp9269229 | kgp22536863 |
| CAMK2G | chr10:75572258-75634349 | chr10:75072258-76134349 | chr10:75242264-75304349 | kgp5617603 | kgp4007437 |
| CAMKK1 | chr17:3763616-3796337 | chr17:3263616-4296337 | chr17:3710365-3743086 | kgp4927794 | kgp13998561 |
| CAMKK2 | chr12:121675494-121736111 | chr12:121175494-122236111 | chr12:120159877-120220494 | kgp3636283,rs1800556 | kgp3169612 |
| CAPN2 | chr1:223889294-223963720 | chr1:223389294-224463720 | chr1:221966741-222030343 | rs2430408 | kgp15138476 |
| CASP3 | chr4:185548849-185570629 | chr4:185048849-186070629 | chr4:185785843-185807623 | kgp8529169 | rs2046535 |
| CASP6 | chr4:110609784-110624629 | chr4:110109784-111124629 | chr4:110829233-110844078 | kgp20840443 | kgp20817413 |
| CASP7 | chr10:115438934-115490664 | chr10:114938934-115990664 | chr10:115428924-115480654 | kgp12503193 | rs12266538 |
| CASP8 | chr2:202098165-202152434 | chr2:201598165-202652434 | chr2:201806410-201860679 | kgp6115041 | rs12468196 |
| CASR | chr3:121902529-122005344 | chr3:121402529-122505344 | chr3:123385219-123488034 | kgp18115887 | rs13095775 |
| CAV1 | chr7:115929905-116201239 | chr7:115429905-116701239 | chr7:115717141-115988466 | kgp13705413 | kgp1550529,rs13222576 |
| CBL | chr11:119076989-119178859 | chr11:118576989-119678859 | chr11:118582199-118684069 | kgp4184476 | rs10892470 |
| CBX1 | chr17:46147413-46178883 | chr17:45647413-46678883 | chr17:43502412-43533882 | kgp4510682 | kgp14007862 |
| CCDC106 | chr19:56158953-56164526 | chr19:55658953-56664526 | chr19:60850765-60856338 | kgp2072564 | rs901476 |

*Fig. 4-4*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| CCND1 | chr11:69455872-69469242 | chr11:68955872-69969242 | chr11:69165053-69178423 | kgp12357966 | rs1893085 |
| CCNE1 | chr19:30302900-30315215 | chr19:29802900-30815215 | chr19:34994740-35007059 | kgp21358604 | kgp21349680 |
| CCR4 | chr3:32993065-32996403 | chr3:32493065-33496403 | chr3:32968069-32971407 | rs4955290 | kgp3855989 |
| CCR5 | chr3:46411632-46417697 | chr3:45911632-46917697 | chr3:46386636-46392701 | kgp17737690 | rs936173 |
| CD163 | chr12:7623411-7656414 | chr12:7123411-8156414 | chr12:7514676-7547681 | rs9668071 | kgp3219786 |
| CD5 | chr11:60869929-60895323 | chr11:60369929-61395323 | chr11:60626505-60651899 | rs7927817 | kgp13056421 |
| CD9 | chr12:6309481-6347437 | chr12:5809481-6847437 | chr12:6179133-6217688 | rs9669580 | kgp1124940 |
| CDC2 | chr10:62538235-62553924 | chr10:62038235-63053924 | chr10:62208241-62223930 | kgp21922934 | rs3125326 |
| CDKN2C | chr1:51433607-51440309 | chr1:50933607-51940309 | chr1:51206195-51212897 | rs17106219 | kgp15324656 |
| CENTA1 | chr7:937537-994306 | chr7:437537-1494306 | chr7:904063-960832 | kgp4856315,rs3924019 | kgp11391801 |
| CETN3 | chr5:89689528-89705603 | chr5:89189528-90205603 | chr5:89725284-89741359 | rs277054 | kgp22368793 |
| CFTR | chr7:117120016-117308718 | chr7:116620016-117808718 | chr7:116907252-117095954 | kgp13265715 | kgp13590397 |
| CHAT | chr10:50822349-50901939 | chr10:50322349-51401939 | chr10:50487146-50543156 | kgp8189482 | kgp8898453 |
| CHD3 | chr17:7788122-7816075 | chr17:7288122-8316075 | chr17:7728847-7756800 | rs7208523 | kgp11776706 |
| CHUK | chr10:101948123-101989344 | chr10:101448123-102489344 | chr10:101938113-101979334 | kgp6141810 | kgp9150190 |
| CISH | chr3:50643884-50649262 | chr3:50143884-51149262 | chr3:50618929-50624207 | kgp5610191 | rs6783700 |
| CKAP1 | chr19:36605888-36616849 | chr19:36105888-37116849 | chr19:41297728-41308689 | rs7249516 | rs3108171 |
| CKMT2 | chr5:80529138-80562217 | chr5:80029138-81062217 | chr5:80564894-80597973 | kgp9822295 | kgp7416171 |
| CLTB | chr5:175819455-175843540 | chr5:175319455-176343540 | chr5:175752061-175776146 | rs4867811 | kgp1551194 |
| CLU | chr8:27454433-27472328 | chr8:26954433-27972328 | chr8:27510367-27528244 | kgp886026 | rs4732823 |
| CMIP | chr16:81478774-81745367 | chr16:80978774-82245367 | chr16:80036394-80302866 | rs11150329 | kgp16425289 |

*Fig. 4-5*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| CNGA2 | chrX:150903217-150914036 | chrX:150403217-151414036 | chrX:150653873-150664692 | rs1202896 | kgp22766776 |
| CNKSR2 | chrX:21392535-21672813 | chrX:20892535-22172813 | chrX:21302900-21580700 | kgp22768242 | kgp22744096 |
| CNN1 | chr19:11649578-11661138 | chr19:11149578-12161138 | chr19:11510578-11522138 | kgp11148982 | rs8100428 |
| CNR2 | chr1:24200459-24239817 | chr1:23700459-24739817 | chr1:24073046-24112404 | rs9887921 | kgp7256331 |
| COIL | chr17:55015560-55038411 | chr17:54515560-55538411 | chr17:52370559-52393410 | rs7219528 | kgp13879956 |
| CORO1B | chr11:67205517-67211292 | chr11:66705517-67711292 | chr11:66962093-66967839 | kgp8733070 | kgp12910446 |
| COX17 | chr3:119388371-119396243 | chr3:118888371-119896243 | chr3:120871061-120878933 | rs2903301 | rs7634938 |
| CPE | chr4:166300096-166419482 | chr4:165800096-166919482 | chr4:166519546-166638932 | rs4541465 | kgp20841166 |
| CRADD | chr12:94071150-94288616 | chr12:93571150-94788616 | chr12:92595281-92768662 | kgp18995270 | rs10859694 |
| CREM | chr10:35415768-35501886 | chr10:34915768-36001886 | chr10:35455806-35541892 | kgp21684668 | rs654221 |
| CRIPT | chr2:46844324-46852881 | chr2:46344324-47352881 | chr2:46697811-46705687 | kgp11216746 | kgp5110136 |
| CSNK2A1 | chr20:463337-524482 | chr20:1-1024482 | chr20:411337-472482 | kgp19358001 | kgp2852236 |
| CSNK2A2 | chr16:58191811-58231782 | chr16:57691811-58731782 | chr16:56749312-56789283 | kgp3607479 | kgp9299300 |
| CSNK2B | chr6:2919235-2923423 | chr6:2919235-2923423 | chr6:31741635-31748206 | kgp7558035 | kgp17052091 |
| CTNNB1 | chr3:41236400-41280845 | chr3:40736400-41780845 | chr3:41211404-41255849 | kgp17791054 | kgp17873276 |
| DAPK3 | chr19:3958451-3971038 | chr19:3458451-4471038 | chr19:3909451-3922038 | kgp9392695 | kgp6448823 |
| DBN1 | chr5:176883613-176900694 | chr5:176383613-177400694 | chr5:176816219-176833300 | rs3733876 | kgp6700800 |
| DDIT4 | chr10:74033676-74035797 | chr10:73533676-74535797 | chr10:73703682-73705803 | kgp21593001 | kgp10561095 |
| DDX5 | chr17:62494373-62502484 | chr17:61994373-63002484 | chr17:59926199-59932869 | kgp14113893 | rs4239089 |
| DEFB1 | chr8:6728096-6735529 | chr8:6228096-7235529 | chr8:6715508-6722939 | kgp20078124 | rs12680482 |
| DGKD | chr2:234263152-234380743 | chr2:233763152-234880743 | chr2:233927891-234045482 | rs12477794 | rs28902188 |

*Fig. 4-6*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| DGKZ | chr11:46354454-46402104 | chr11:45854454-46902104 | chr11:46311314-46358680 | rs2090602 | kgp22737291 |
| DIRAS2 | chr9:93372113-93405108 | chr9:92872113-93905108 | chr9:92411933-92444928 | rs7860989 | kgp10944799 |
| DLG1 | chr3:196769430-197026143 | chr3:196269430-197526143 | chr3:198253827-198510540 | kgp18074003 | rs841672 |
| DLG3 | chrX:69664704-69725339 | chrX:69164704-70225339 | chrX:69581448-69642062 | kgp22756738 | kgp22752290 |
| DLG4 | chr17:7093209-7123369 | chr17:6593209-7623369 | chr17:7033933-7063781 | kgp10999626 | rs3744258 |
| DNM1 | chr9:130965662-131017527 | chr9:130465662-131517527 | chr9:130005483-130057348 | kgp1183767 | rs4836625 |
| DNM3 | chr1:171810620-172381857 | chr1:171310620-172881857 | chr1:170077260-170648480 | kgp15671556 | rs2213746 |
| DNMT2 | chr10:17184981-17243681 | chr10:16684981-17743681 | chr10:17224987-17283687 | kgp1566842 | kgp21855354 |
| DPYSL2 | chr8:26371708-26515693 | chr8:25871708-27015693 | chr8:26427707-26571610 | rs11998023 | rs12544814 |
| DRD1 | chr5:174867674-174871163 | chr5:174367674-175371163 | chr5:174800280-174803769 | kgp4432341 | kgp8293487 |
| DRD1IP | chr5:174867675-174871163 | chr5:174367675-175371163 | chr5:174800281-174803769 | kgp4432341 | kgp8293487 |
| DST | chr6:56479153-56716714 | chr6:55979153-57216714 | chr6:56430743-56816422 | kgp1980963 | rs12209200 |
| DVL1 | chr1:1270657-1284492 | chr1:770657-1784492 | chr1:1260520-1274355 | kgp4076808 | kgp15201879 |
| DVL2 | chr17:7128660-7137863 | chr17:6628660-7637863 | chr17:7069384-7078587 | kgp1788685 | kgp2456831,rs3744255 |
| DVL3 | chr3:183873283-183891314 | chr3:183373283-184391314 | chr3:185355977-185374008 | kgp10156744 | kgp4088221 |
| EDF1 | chr9:139756570-139760738 | chr9:139256570-140260738 | chr9:138876391-138880559 | rs3829109 | kgp4292076 |
| EDG3 | chr9:91606324-91620069 | chr9:91106324-92120069 | chr9:90796144-90809889 | kgp18366537 | kgp113389 |
| EDG5 | chr19:10332109-10341948 | chr19:9832109-10841948 | chr19:10193109-10202948 | kgp21505357 | kgp12277401 |
| EDG8 | chr19:10623418-10628668 | chr19:10123418-11128668 | chr19:10484418-10489668 | rs4804478 | kgp9055694 |
| EEF1D | chr8:144661866-144679845 | chr8:144161866-145179845 | chr8:144733040-144750726 | kgp20077380 | kgp4311396 |
| EEF2 | chr19:3976053-3985461 | chr19:3476053-4485461 | chr19:3927053-3936461 | kgp21334437 | rs10406730 |

Fig. 4-7

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| EFNB1 | chrX:68048839-68066029 | chrX:67548839-68566029 | chrX:67965564-67982754 | rs7879567 | kgp22774708 |
| EFNB2 | chr13:107142078-107187388 | chr13:106642078-107687388 | chr13:105940096-105985338 | rs9587049 | kgp1472981 |
| EIF1B | chr3:40351172-40353915 | chr3:39851172-40853915 | chr3:40326176-40328919 | kgp17543799 | kgp724180 |
| ENO2 | chr12:7023613-7032859 | chr12:6523613-7532859 | chr12:6893874-6903120 | kgp6644683 | kgp18788179 |
| EPB41 | chr1:29213602-29446558 | chr1:28713602-29946558 | chr1:29086214-29319545 | kgp15837735 | kgp8194212 |
| EPB41L1 | chr20:34679425-34820721 | chr20:34179425-35320721 | chr20:34142839-34284135 | rs1886695 | kgp10646202 |
| EPB41L2 | chr6:131160487-131384462 | chr6:130660487-131884462 | chr6:131202180-131426058 | kgp3398782 | kgp16921144 |
| EPHB2 | chr1:23037330-23241823 | chr1:22537330-23741823 | chr1:22909917-23114410 | rs2473249 | kgp22776625 |
| ESR1 | chr6:152011630-152424408 | chr6:151511630-152924408 | chr6:152053323-152466101 | rs9478984 | rs818451 |
| ESR2 | chr14:64693750-64805268 | chr14:64193750-65305268 | chr14:63763503-63875021 | kgp3039416 | kgp8515773 |
| ESRRG | chr1:216676587-217311097 | chr1:216176587-217811097 | chr1:214743210-215377720 | kgp2104463 | kgp3054869 |
| ETHE1 | chr19:44010870-44031396 | chr19:43510870-44531396 | chr19:48702710-48723236 | rs11668932 | kgp561363 |
| EWSR1 | chr22:29663997-29696515 | chr22:29163997-30196515 | chr22:27994016-28026515 | rs6005868 | rs4823054 |
| F11R | chr1:160965000-161008774 | chr1:160465000-161508774 | chr1:159231624-159275404 | rs678456 | kgp10744728 |
| FADD | chr11:70049268-70053508 | chr11:69549268-70553508 | chr11:69726916-69731134 | kgp12619639 | kgp12640488 |
| FAS | chr10:90729552-90775542 | chr10:90229552-91275542 | chr10:90740267-90765522 | kgp6970830 | kgp1640747 |
| FBLIM1 | chr1:16083153-16113084 | chr1:15583153-16613084 | chr1:15955740-15985671 | rs16851480 | kgp15648830 |
| FER | chr5:108083522-108523373 | chr5:107583522-109023373 | chr5:108111421-108551272 | rs11958626 | rs845734 |
| FEZ1 | chr11:125315640-125366206 | chr11:124815640-125866206 | chr11:124820857-124871333 | rs10160591 | kgp12966369 |
| FEZ2 | chr2:36779403-36825332 | chr2:36279403-37325332 | chr2:36632904-36678836 | kgp10246319 | kgp9712350 |
| FFAR1 | chr19:35842444-35843367 | chr19:35342444-36343367 | chr19:40534294-40535197 | rs8106116 | kgp21511691 |

*Fig. 4-8*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| FFAR2 | chr19:35939202-35941865 | chr19:35439202-36441865 | chr19:40631042-40633705 | rs2112502 | rs7247246 |
| FKBP1A | chr20:1349620-1373816 | chr20:849620-1873816 | chr20:1297621-1321745 | kgp4567229 | kgp10348674 |
| FLJ31945 | chr13:50699952-50702599 | chr13:50199952-51202599 | chr13:49597953-49600600 | kgp9786864 | kgp16621897 |
| FLJ41278 | chr12:65277553-65371302 | chr12:64777553-65871302 | chr12:63563820-63657569 | rs6581555 | kgp1662303 |
| FLNA | chrX:153576899-153603006 | chrX:153076899-154103006 | chrX:153230093-153256200 | rs7049293 | rs28412378 |
| FLNB | chr3:57994126-58157982 | chr3:57494126-58657982 | chr3:57969166-58133017 | rs7629743 | rs11130670 |
| FREQ | chr9:132934856-132999583 | chr9:132434856-133499583 | chr9:131974677-132039404 | kgp12208188 | kgp18380808 |
| FRS2 | chr12:69864128-69973562 | chr12:69364128-70473562 | chr12:68150395-68259829 | kgp19095191 | kgp12534834 |
| FSHR | chr2:49189295-49381666 | chr2:48689295-49881666 | chr2:49043155-49235134 | kgp297164 | kgp11229604 |
| FXN | chr9:71650478-71715094 | chr9:71150478-72215094 | chr9:70840163-70878772 | rs265076 | kgp213209 |
| FXR1 | chr3:180630233-180700539 | chr3:180130233-181200539 | chr3:182113145-182177647 | kgp22773686 | kgp3235523 |
| G6PD | chrX:153759605-153775787 | chrX:153259605-154275787 | chrX:153412799-153428981 | rs2239471 | kgp22745531 |
| GABRR1 | chr6:89887222-89927496 | chr6:89387222-90427496 | chr6:89944690-89983779 | kgp3728710 | kgp17056993 |
| GABRR2 | chr6:89967238-90024967 | chr6:89467238-90524967 | chr6:90023957-90081686 | kgp16994883 | kgp9012178 |
| GALR2 | chr17:74070891-74073573 | chr17:73570891-74573573 | chr17:71582486-71585168 | rs1042861 | rs16967307 |
| GAP43 | chr3:115342150-115440334 | chr3:114842150-115940334 | chr3:116825141-116922842 | rs10511341 | kgp18168870 |
| GC | chr4:72607410-72671237 | chr4:72107410-73171237 | chr4:72826274-72888622 | rs10013437 | kgp12025264 |
| GFAP | chr17:42982993-42992920 | chr17:42482993-43492920 | chr17:40338518-40348394 | rs8066197 | rs12947718 |
| GFI1 | chr1:92940317-92952433 | chr1:92440317-93452433 | chr1:92712905-92725021 | kgp80379 | kgp15436210 |
| GFI1B | chr9:135853893-135867084 | chr9:135353893-136367084 | chr9:134843714-134856903 | kgp1227599 | kgp22817803 |
| GFPT1 | chr2:69546900-69614386 | chr2:69046900-70114386 | chr2:69405910-69467829 | kgp7360674 | kgp14824626 |

*Fig. 4-9*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| GH1 | chr17:61994562-61996198 | chr17:61494562-62496198 | chr17:59348294-59349930 | kgp6455446 | kgp10132757 |
| GIT1 | chr17:27900486-27916610 | chr17:27400486-28416610 | chr17:24924612-24940736 | kgp14082001 | rs8065059 |
| GIT2 | chr12:110367606-110434194 | chr12:109867606-110934194 | chr12:108851991-108918483 | kgp8064273 | kgp556710 |
| GJA1 | chr6:121756744-121770873 | chr6:121256744-122270873 | chr6:121798443-121812572 | kgp5203283 | kgp1494786 |
| GJB1 | chrX:70435061-70445065 | chrX:69935061-70945065 | chrX:70351786-70361777 | kgp22820938 | rs35542412 |
| GMFB | chr14:54941208-54955744 | chr14:54441208-55455744 | chr14:54010958-54025494 | kgp5212952 | kgp7377769 |
| GNA12 | chr7:2767740-2883959 | chr7:2267740-3383959 | chr7:2734266-2850485 | kgp9177535 | kgp13694655 |
| GNAS | chr20:57414794-57486250 | chr20:56914794-57986250 | chr20:56848189-56919645 | rs471661 | rs729997 |
| GNAZ | chr22:23412668-23467221 | chr22:22912668-23967221 | chr22:21742668-21797221 | kgp15075658 | rs9680742 |
| GPM6A | chr4:176554087-176923648 | chr4:176054087-177423648 | chr4:176791081-177160642 | rs6849435 | kgp8852764 |
| GPSM2 | chr1:109419602-109476957 | chr1:108919602-109976957 | chr1:109221125-109274567 | kgp15175401 | kgp15178378 |
| GRB14 | chr2:165349322-165478360 | chr2:164849322-165978360 | chr2:165057568-165186606 | kgp8982508 | kgp14153450 |
| GRIA2 | chr4:158141294-158287226 | chr4:157641294-158787226 | chr4:158361185-158506676 | kgp22818527 | rs6836401 |
| GRIA3 | chrX:122318095-122624766 | chrX:121818095-123124766 | chrX:122145776-122452447 | rs7057244 | rs12559968 |
| GRIA4 | chr11:105480799-105852819 | chr11:104980799-106352819 | chr11:104986009-105358029 | kgp12888967 | kgp2959570 |
| GRIN1 | chr9:140033608-140063214 | chr9:139533608-140563214 | chr9:139153429-139183029 | kgp18425565 | kgp18521447 |
| GRIN2A | chr16:9847264-10276611 | chr16:9347264-10776611 | chr16:9762922-10184112 | kgp16441783 | rs9932893 |
| GRIN2B | chr12:13714409-14133022 | chr12:13214409-14633022 | chr12:13605676-14024289 | rs3741818 | kgp7391296 |
| GRK1 | chr13:114321596-114438637 | chr13:113821596-114938637 | chr13:113369597-113373973 | kgp16671784 | rs11147317 |
| GRK4 | chr4:2965342-3042474 | chr4:2465342-3542474 | chr4:2935140-3012272 | rs846252 | rs6821202 |
| GSK3A | chr19:42734337-42746736 | chr19:42234337-43246736 | chr19:47426177-47438576 | kgp21481263 | kgp10870487 |

*Fig. 4-10*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| GSK3B | chr3:119540801-119813264 | chr3:119040801-120313264 | chr3:121028235-121295203 | kgp17616951 | kgp4570827 |
| GSTM4 | chr1:110198697-110208123 | chr1:109698697-110708123 | chr1:110000225-110009648 | rs595635 | kgp15760598 |
| HABP4 | chr9:99212413-99253618 | chr9:98712413-99753618 | chr9:98252234-98293439 | kgp18578220 | kgp18630342 |
| HAND1 | chr5:153854531-153857824 | chr5:153354531-154357824 | chr5:153834724-153838017 | kgp7530958 | rs2431184 |
| HAND2 | chr4:174447651-174451378 | chr4:173947651-174951378 | chr4:174684226-174687953 | kgp20847640 | kgp20778226 |
| HARS | chr5:140053489-140070971 | chr5:139553489-140570971 | chr5:140033673-140051155 | rs6874491 | rs12654953 |
| HDAC6 | chrX:48660286-48683380 | chrX:48160286-49183380 | chrX:48545430-48568324 | kgp22835768 | rs2015487 |
| HES1 | chr3:193853930-193856401 | chr3:193353930-194356401 | chr3:195336627-195339090 | kgp11414670 | rs7649259 |
| HLA-A | chr6:1150035-1295564 | chr6:1150035-1295564 | chr6:30018304-30085130 | rs9392258 | rs9391920 |
| HLA-C | chr6:2585738-2671188 | chr6:2585738-2671188 | chr6:2486041-2572197 | rs9392400 | kgp1905253 |
| HLA-DQA2 | chr6:4166320-4171833 | chr6:4166320-4171833 | chr6:3895192-3901275 | kgp17451336 | kgp17218419 |
| HMGB1 | chr13:31032878-31191510 | chr13:30532878-31691510 | chr13:29930878-30089510 | rs1557088 | kgp8054835 |
| HMGN1 | chr21:40714240-40721047 | chr21:40214240-41221047 | chr21:39636110-39643140 | kgp4524272 | kgp8317624 |
| HMGN2 | chr1:26798901-26803133 | chr1:26298901-27303133 | chr1:26671488-26675720 | rs1429936 | kgp8260087 |
| HMMR | chr5:162887516-162918953 | chr5:162387516-163418953 | chr5:162820240-162851525 | kgp9548441 | rs1363073 |
| HMOX2 | chr16:4524718-4560348 | chr16:4024718-5060348 | chr16:4464719-4500349 | kgp16414002 | kgp7117794 |
| HMP19 | chr5:173472723-173536182 | chr5:172972723-174036182 | chr5:173405329-173468788 | kgp22404239 | rs12186684 |
| HOMER2 | chr15:83517728-83621476 | chr15:83017728-84121476 | chr15:81314789-81412477 | rs1267659 | kgp4123064 |
| HRH4 | chr18:22040592-22059921 | chr18:21540592-22559921 | chr18:20294590-20313919 | rs7235445 | kgp7887799 |
| HSP90AA1 | chr14:102547074-102606086 | chr14:102047074-103106086 | chr14:101616827-101675839 | kgp3260354 | kgp19714004 |
| HSPA1A | chr6:31783290-31785719 | chr6:31283290-32285719 | chr6:31891315-31893698 | kgp4709627 | rs9296020 |

*Fig. 4-11*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| HSPA1B | chr6:3089162-3091686 | chr6:3089162-3091686 | chr6:3043109-3045633 | kgp6503147 | kgp5869121 |
| HSPA4 | chr5:132387661-132440709 | chr5:131887661-132940709 | chr5:132415560-132468608 | kgp22352512 | kgp7658141 |
| HSPB1 | chr7:75931874-75933614 | chr7:75431874-76433614 | chr7:75769858-75771546 | kgp4195218 | kgp10852432 |
| HSPB3 | chr5:53751430-53752214 | chr5:53251430-54252214 | chr5:53787201-53787964 | rs16881895 | rs3815916 |
| HSPB8 | chr12:119616594-119632551 | chr12:119116594-120132551 | chr12:118100977-118116934 | kgp18981306 | kgp18823622 |
| HSPBP1 | chr19:55773590-55791751 | chr19:55273590-56291751 | chr19:60465518-60483540 | kgp3134010 | kgp21533588 |
| HSPE1 | chr2:198364720-198368187 | chr2:197864720-198868187 | chr2:198073364-198076416 | kgp9884304 | kgp12004769 |
| HSPH1 | chr13:31710762-31736502 | chr13:31210762-32236502 | chr13:30608762-30634502 | kgp16548529 | kgp16811501 |
| HTATIP | chr11:20385289-20405329 | chr11:19885289-20905329 | chr11:20341865-20361905 | rs2707094 | kgp309631 |
| HTR2B | chr2:231972949-231989824 | chr2:231472949-232489824 | chr2:231681198-231698068 | rs6761068 | rs4973459 |
| HTR2C | chrX:113818550-114144624 | chrX:113318550-114644624 | chrX:113724806-114050880 | rs7055827 | kgp22830072 |
| HTR6 | chr1:19991779-20006055 | chr1:19491779-20506055 | chr1:19864366-19878642 | kgp15912015 | kgp10523409 |
| IGSF4 | chr11:115044345-115375241 | chr11:114544345-115875241 | chr11:114549555-114880451 | rs1607260 | rs7928212 |
| IKBKB | chr8:42128819-42190171 | chr8:41628819-42690171 | chr8:42247985-42309122 | kgp9748756 | kgp3164559 |
| IKBKE | chr1:206643585-206670223 | chr1:206143585-207170223 | chr1:204710418-204736845 | kgp15543770 | kgp6359437 |
| IKBKG | chrX:153770458-153793261 | chrX:153270458-154293261 | chrX:153423652-153446455 | rs633 | kgp22831959 |
| IL4R | chr16:27325250-27376099 | chr16:26825250-27876099 | chr16:27232751-27283600 | kgp11144142 | kgp16489203 |
| IL5RA | chr3:3108007-3152058 | chr3:2608007-3652058 | chr3:3086420-3127031 | kgp10211459 | kgp22835987 |
| IL8RA | chr2:219027567-219031716 | chr2:218527567-219531716 | chr2:218735812-218739961 | kgp14521358 | rs16859170 |
| INSR | chr19:7112265-7294011 | chr19:6612265-7794011 | chr19:7063265-7245011 | kgp5914741 | kgp21453659 |
| IQCB1 | chr3:121488609-121553926 | chr3:120988609-122053926 | chr3:122971299-123036616 | rs11921531 | rs6438722 |

*Fig. 4-12*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| IQGAP1 | chr15:90931472-91045475 | chr15:90431472-91545475 | chr15:88732476-88846479 | kgp1876985 | kgp20028694 |
| IRAK1 | chrX:153275956-153285342 | chrX:152775956-153785342 | chrX:152929150-152938536 | kgp22756383 | rs6643680 |
| IRS1 | chr2:227596032-227663506 | chr2:227096032-228163506 | chr2:227304276-227371750 | kgp12414080 | kgp9391097 |
| IRS4 | chrX:107975726-107979607 | chrX:107475726-108479607 | chrX:107862367-107866295 | kgp22794644 | rs5985712 |
| ITGB2 | chr21:46305867-46348753 | chr21:45805867-46848753 | chr21:45130296-45173181 | kgp13225366 | rs11702782 |
| ITGB3BP | chr1:63906440-63988944 | chr1:63406440-64488944 | chr1:63679049-63761423 | rs1572109 | kgp5171315 |
| ITGB4 | chr17:73717515-73753899 | chr17:73217515-74253899 | chr17:71229110-71265494 | kgp2663142 | kgp4575494 |
| ITGB5 | chr3:124481794-124606144 | chr3:123981794-125106144 | chr3:125964484-126088834 | kgp5281659 | kgp17765518 |
| ITPKA | chr15:41786055-41795757 | chr15:41286055-42295757 | chr15:39573413-39583039 | kgp22747722 | kgp10507061 |
| ITPKB | chr1:226819390-226926876 | chr1:226319390-227426876 | chr1:224886013-224991987 | rs1219671 | rs7519099 |
| ITPR3 | chr6:33589155-33664348 | chr6:33089155-34164348 | chr6:33697138-33772326 | rs3117030 | kgp4515850 |
| IXL | chr19:39881963-39891203 | chr19:39381963-40391203 | chr19:44573803-44583043 | kgp986483 | kgp6117029 |
| JAK1 | chr1:65298905-65432619 | chr1:64798905-65932619 | chr1:65071493-65205207 | kgp8976721 | kgp9745392 |
| KCNE1 | chr21:35818987-35884573 | chr21:35318987-36384573 | chr21:34740857-34806443 | kgp13187567 | kgp5041106 |
| KCNE4 | chr2:223916861-223920355 | chr2:223416861-224420355 | chr2:223625105-223628599 | kgp14948218 | kgp14631899 |
| KCNH2 | chr7:150642043-150675402 | chr7:150142043-151175402 | chr7:150272981-150305947 | kgp13542655 | kgp7948285 |
| KCNJ2 | chr17:68164813-68176183 | chr17:67664813-68676183 | chr17:65676408-65687778 | rs6501341 | kgp2814913 |
| KCNN2 | chr5:113698015-113832197 | chr5:113198015-114332197 | chr5:113725914-113860096 | kgp9619904 | rs10056549 |
| KCNN4 | chr19:44270684-44285409 | chr19:43770684-44785409 | chr19:48962524-48977249 | rs6509074 | kgp21388839 |
| KCNQ2 | chr20:62037541-62103993 | chr20:61537541-62603993 | chr20:61507985-61574437 | rs16983364 | kgp19265466 |
| KCNQ3 | chr8:133133104-133493004 | chr8:132633104-133993004 | chr8:133210437-133562186 | kgp20244043 | rs4074676 |

*Fig. 4-13*

| Tier 3 Gene | GeneRange(hg19) | GeneRange+500kb(hg19) | GeneRange(hg18) | StartSNP (GeneRange+500kb) | EndSNP (GeneRange+500 kb) |
|---|---|---|---|---|---|
| KCNQ5 | chr6:73331570-73908573 | chr6:72831570-74408573 | chr6:73388555-73962301 | kgp7790415 | rs9446983 |
| KDR | chr4:55944425-55991762 | chr4:55444425-56491762 | chr4:55639405-55686519 | kgp11624145 | rs10022874 |
| KIAA1377 | chr11:101785745-101871793 | chr11:101285745-102371793 | chr11:101290955-101377003 | kgp12804311 | rs9667864 |
| KIAA1549 | chr7:138516126-138666064 | chr7:138016126-139166064 | chr7:138166666-138255110 | rs11769851 | kgp10209774 |
| KIF3A | chr5:132028322-132073265 | chr5:131528322-132573265 | chr5:132056221-132101164 | rs3805685 | rs4958109 |
| KIT | chr4:55524094-55606881 | chr4:55024094-56106881 | chr4:55218851-55301638 | kgp4467115 | kgp9403472 |
| KLHL20 | chr1:173684079-173755840 | chr1:173184079-174255840 | chr1:171950702-172022463 | rs13374515 | kgp5594942 |
| KLHL3 | chr5:136953188-137071779 | chr5:136453188-137571779 | chr5:136981087-137099678 | rs2966736 | rs10040989 |
| KLK10 | chr19:51515999-51523431 | chr19:51015999-52023431 | chr19:56207811-56215243 | kgp9495392 | kgp21503250 |
| KRAS | chr12:25358179-25403854 | chr12:24858179-25903854 | chr12:25249446-25295121 | kgp19038229 | kgp1316534 |
| KRT10 | chr17:38974368-38978863 | chr17:38474368-39478863 | chr17:36227894-36232373 | kgp7164026 | kgp6621387 |
| KRT18 | chr12:53342654-53346685 | chr12:52842654-53846685 | chr12:51628921-51632952 | rs406857 | rs11834179 |
| LCK | chr1:32716839-32751766 | chr1:32216839-33251766 | chr1:32489426-32524353 | rs12037400 | kgp6229337 |
| LGALS2 | chr22:37966252-37976024 | chr22:37466252-38476024 | chr22:36296198-36305970 | kgp14999686 | rs8135665 |
| LMNA | chr1:156052368-156108548 | chr1:155552368-156608548 | chr1:154318992-154375172 | kgp11675488 | rs12408758 |
| LMNB1 | chr5:126112314-126172712 | chr5:125612314-126672712 | chr5:126140731-126200608 | kgp5014465 | kgp22418220 |
| LOC100133669 | chr8:144063447-144099807 | chr8:143563447-144599807 | chr8:144134822-144171182 | rs10875483 | kgp10850793 |
| LOC154092 | chr6:134758853-134825158 | chr6:134258853-135325158 | chr6:134800546-134866851 | kgp11630779 | kgp22793805 |
| LOC339290 | chr18:5238098-5246505 | chr18:4738098-5746505 | chr18:5222874-5228525 | kgp5290787 | kgp989326 |
| LOC340357 | chr8:12623570-12668910 | chr8:12123570-13168910 | chr8:12667941-12713281 | kgp22754906 | kgp20305069 |
| LOC400604 | chr17:48944039-48945732 | chr17:48444039-49445732 | chr17:46299038-46300731 | kgp11815481 | kgp10163248 |

*Fig. 4-14*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| LOC613126 | chr7:91763906-91771854 | chr7:91263906-92271854 | chr7:91601842-91609790 | kgp13774218 | rs3731343 |
| LTB4R | chr14:24780704-24787242 | chr14:24280704-25287242 | chr14:23850544-23855992 | kgp19673807 | rs8007336 |
| LTF | chr3:46477495-46526724 | chr3:45977495-47026724 | chr3:46452499-46501728 | kgp17788490 | kgp1176589 |
| LXN | chr3:158384202-158390482 | chr3:157884202-158890482 | chr3:159866899-159873176 | rs6764092 | kgp7955381 |
| LYST | chr1:235824344-236030220 | chr1:235324344-236530220 | chr1:233890968-234096843 | rs2295815 | kgp9270301 |
| MAD2L1BP | chr6:43597278-43608688 | chr6:43097278-44108688 | chr6:43705256-43716666 | rs1537638 | kgp1522302 |
| MAGED1 | chrX:51546154-51645450 | chrX:51046154-52145450 | chrX:51562894-51662190 | kgp22779908 | kgp22784919 |
| MAP1A | chr15:43809805-43823818 | chr15:43309805-44323818 | chr15:41597097-41611110 | kgp12180163 | kgp10318377 |
| MAP1LC3A | chr20:33134691-33148149 | chr20:32634691-33648149 | chr20:32598352-32611810 | kgp19388199 | kgp5639543 |
| MAP2K1 | chr15:66679210-66783882 | chr15:66179210-67283882 | chr15:64466264-64570936 | kgp19795142 | kgp382480 |
| MAP2K4 | chr17:11924134-12047051 | chr17:11424134-12547051 | chr17:11864859-11987776 | rs16944942 | rs9915536 |
| MAP2K5 | chr15:67835020-68099455 | chr15:67335020-68599455 | chr15:65622074-65886506 | kgp19854650 | kgp20006731 |
| MAP3K10 | chr19:40697650-40721482 | chr19:40197650-41221482 | chr19:45389490-45413314 | kgp6290284 | rs2561531 |
| MAP3K3 | chr17:61699774-61773670 | chr17:61199774-62273670 | chr17:59053506-59127402 | kgp14048701 | kgp5230870 |
| MAP3K7 | chr6:91225352-91296907 | chr6:90725352-91796907 | chr6:91282073-91353628 | rs9451316 | rs9451576 |
| MAP3K7IP1 | chr22:39745953-39827887 | chr22:39245953-40327887 | chr22:38075899-38157833 | kgp10431646 | rs137981 |
| MAP3K7IP2 | chr6:149639062-149732747 | chr6:149139062-150232747 | chr6:149680755-149774440 | kgp9485571 | kgp9110056 |
| MAP3K8 | chr10:30722949-30750762 | chr10:30222949-31250762 | chr10:30762871-30790767 | kgp22034763 | kgp11496819 |
| MAP6 | chr11:75297962-75379479 | chr11:74797962-75879479 | chr11:74975610-75057127 | rs11236323 | kgp695651 |
| MAPK14 | chr6:35995453-36079013 | chr6:35495453-36579013 | chr6:36103550-36186513 | rs4711420 | kgp10854130 |
| MAPK3 | chr16:30125425-30134630 | chr16:29625425-30634630 | chr16:30032926-30042131 | kgp11463254 | kgp2105557 |

*Fig. 4-15*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| MARCKS | chr6:114178526-114184652 | chr6:113678526-114684652 | chr6:114285219-114291345 | kgp17187839 | kgp1113238 |
| MBP | chr18:74690788-74844774 | chr18:74190788-75344774 | chr18:72819776-72973762 | kgp5208536 | rs12960102 |
| MCC | chr5:112357795-112824527 | chr5:111857795-113324527 | chr5:112385694-112852426 | kgp22530369 | kgp22589538 |
| MGMT | chr10:131265453-131565783 | chr10:130765453-132065783 | chr10:131155455-131455358 | kgp11264334 | kgp1514587 |
| MIP | chr12:56843285-56848435 | chr12:56343285-57348435 | chr12:55130150-55134696 | kgp19052399,rs11834873 | kgp18750923 |
| MLF2 | chr12:6857935-6876641 | chr12:6357935-7376641 | chr12:6728196-6746902 | kgp18998724 | rs1001653 |
| MLLT3 | chr9:20344967-20622514 | chr9:19844967-21122514 | chr9:20334967-20612514 | kgp18504776 | rs1016129 |
| MNAT1 | chr14:61201458-61435398 | chr14:60701458-61935398 | chr14:60271222-60505151 | kgp5293246 | rs7142051 |
| MPHOSPH6 | chr16:82181766-82203829 | chr16:81681766-82703829 | chr16:80739267-80761330 | kgp406017 | rs3852734 |
| MRPS12 | chr19:39421347-39423659 | chr19:38921347-39923659 | chr19:44113187-44115499 | kgp21348524 | kgp21366907 |
| MRPS6 | chr21:35445822-35515334 | chr21:34945822-36015334 | chr21:34367692-34437204 | kgp11037760 | rs2834555 |
| MRVI1 | chr11:10594637-10715535 | chr11:10094637-11215535 | chr11:10551213-10672111 | rs7946995 | kgp11739225 |
| MSN | chrX:64887510-64961793 | chrX:64387510-65461793 | chrX:64804235-64878518 | rs7887705 | kgp22760405 |
| MYF5 | chr12:81110707-81113447 | chr12:80610707-81613447 | chr12:79634838-79637578 | rs12313692 | kgp5599463 |
| MYF6 | chr12:81101407-81103256 | chr12:80601407-81603256 | chr12:79625576-79627382 | rs7954738 | rs7972054 |
| MYLK | chr3:123331142-123603149 | chr3:122831142-124103149 | chr3:124813832-125085839 | kgp9270532 | rs510324 |
| MYO10 | chr5:16662015-16936385 | chr5:16162015-17436385 | chr5:16715015-16989385 | kgp22359577 | kgp12241403 |
| MYO7A | chr11:76839309-76926286 | chr11:76339309-77426286 | chr11:76516957-76603934 | rs2186677 | kgp304899 |
| MYO9B | chr19:17186590-17324104 | chr19:16686590-17824104 | chr19:17047595-17185104 | kgp21430919 | kgp4164870 |
| MYOC | chr1:171604556-171621823 | chr1:171104556-172121823 | chr1:169871179-169888396 | rs1736563 | kgp1482992 |
| MYOD1 | chr11:17741109-17743678 | chr11:17241109-18243678 | chr11:17697685-17700254 | kgp10809253 | rs12285714 |

*Fig. 4-16*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| MYOG | chr1:203052256-203055377 | chr1:202552256-203555377 | chr1:201318879-201322000 | rs4950858 | rs2798625 |
| MYOT | chr5:137022409-137223540 | chr5:136522409-137723540 | chr5:137231472-137251440 | kgp22294838 | kgp5559791 |
| MYT1L | chr2:1792884-2335045 | chr2:1292884-2835045 | chr2:1771891-2314052 | kgp356515 | kgp7720594 |
| NACA | chr12:57106210-57119326 | chr12:56606210-57619326 | chr12:55392477-55405593 | rs4759218 | kgp11483848 |
| NCALD | chr8:102698769-103137135 | chr8:102198769-103637135 | chr8:102767945-103206311 | kgp11277997 | rs16869664 |
| NCF1C | chr7:74572383-74587816 | chr7:74072383-75087816 | chr7:74210380-74225695 | kgp7635479 | kgp954065 |
| NCL | chr2:232319458-232329205 | chr2:231819458-232829205 | chr2:232027702-232037449 | rs13415867 | kgp12447433 |
| NCOR2 | chr12:124808956-125052010 | chr12:124308956-125552010 | chr12:123397062-123617963 | rs11057368 | kgp12274490 |
| NEUROD1 | chr2:182540832-182545392 | chr2:182040832-183045392 | chr2:182249438-182253626 | kgp7038037 | rs12612546 |
| NF2 | chr22:29999544-30094589 | chr22:29499544-30594589 | chr22:28329544-28424589 | kgp15024372 | kgp10478391 |
| NFASC | chr1:204797781-204991950 | chr1:204297781-205491950 | chr1:203064445-203258572 | rs12044614 | kgp11817505 |
| NFATC1 | chr18:77155771-77289323 | chr18:76655771-77789323 | chr18:75256759-75390311 | rs12150804 | kgp11226294 |
| NFATC2 | chr20:50007764-50179168 | chr20:49507764-50679168 | chr20:49441171-49612777 | rs761240 | kgp19325060 |
| NFKB2 | chr10:104154228-104162281 | chr10:103654228-104662281 | chr10:104144218-104152271 | kgp11777223 | rs7897654 |
| NFKBIB | chr19:39390339-39399534 | chr19:38890339-39899534 | chr19:44082454-44091374 | kgp21403480 | kgp4374047 |
| NFKBIE | chr6:44225902-44233525 | chr6:43725902-44733525 | chr6:44333880-44341503 | rs866236 | kgp11221406 |
| NGB | chr14:77731833-77737655 | chr14:77231833-78237655 | chr14:76801586-76807408 | kgp4649405 | rs11622713 |
| NHP2L1 | chr22:42069936-42084913 | chr22:41569936-42584913 | chr22:40399882-40414859 | kgp22806642 | kgp282841 |
| NOS1 | chr12:117645946-117799607 | chr12:117145946-118299607 | chr12:116135361-116283965 | rs11068156 | kgp763518 |
| NP | chr14:20937541-20945248 | chr14:20437541-21445248 | chr14:20007381-20015088 | kgp8768601 | kgp19427360 |
| NPHP1 | chr2:110880913-110962639 | chr2:110380913-111462639 | chr2:110238202-110319928 | rs10496434 | kgp3845148 |

*Fig. 4-17*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| NRBP1 | chr2:27650656-27665124 | chr2:27150656-28165124 | chr2:27504160-27518628 | kgp14600002 | kgp14258181 |
| NRGN | chr11:124609828-124617102 | chr11:124109828-125117102 | chr11:124115038-124122312 | kgp483624 | kgp5783287 |
| NUCB1 | chr19:49403306-49426540 | chr19:48903306-49926540 | chr19:54095380-54118339 | kgp282275 | kgp9015400 |
| OBSCN | chr1:228395860-228566575 | chr1:227895860-229066575 | chr1:226462483-226633198 | kgp22809391 | kgp706951 |
| OGG1 | chr3:9791627-9808353 | chr3:9291627-10308353 | chr3:9765704-9783342 | rs17744749 | rs1642974 |
| OPRK1 | chr8:54138275-54164194 | chr8:53638275-54664194 | chr8:54300828-54326747 | kgp11808605 | kgp7186378 |
| OPRM1 | chr6:154360442-154568001 | chr6:153860442-155068001 | chr6:154402135-154609693 | kgp22790919 | kgp7491549 |
| P2RY1 | chr3:152552735-152555843 | chr3:152052735-153055843 | chr3:154035425-154038533 | rs4472028 | kgp1812100 |
| PA2G4 | chr12:56498102-56507694 | chr12:55998102-57007694 | chr12:54784369-54793961 | kgp18842835 | rs12308290 |
| PABPC4 | chr1:40026484-40042521 | chr1:39526484-40542521 | chr1:39799074-39815003 | rs6692557 | rs6681804 |
| PAEP | chr9:138453603-138458622 | chr9:137953603-138958622 | chr9:137593424-137598443 | kgp4360258 | rs11103302 |
| PAFAH1B1 | chr17:2496922-2588909 | chr17:1996922-3088909 | chr17:2443672-2535659 | kgp13951566 | kgp4861640 |
| PAM | chr5:102201526-102366808 | chr5:101701526-102866808 | chr5:102229425-102393316 | rs10075318 | kgp4660412 |
| PARD6A | chr16:67694850-67696681 | chr16:67194850-68196681 | chr16:66252351-66254182 | kgp16268099,rs1106304 | kgp16328412 |
| PARD6B | chr20:49348080-49370278 | chr20:48848080-49870278 | chr20:48781487-48803685 | kgp19335956 | kgp19356310 |
| PARD6G | chr18:77915116-78005397 | chr18:77415116-78505397 | chr18:76016105-76106388 | kgp15973881 | rs12960632 |
| PAWR | chr12:79985744-80084790 | chr12:79485744-80584790 | chr12:78509875-78608921 | rs2950386 | kgp19124809 |
| PCNT | chr21:47744035-47865682 | chr21:47244035-48365682 | chr21:46568463-46690110 | kgp13165624 | rs10483083 |
| PCP4 | chr21:41239346-41301322 | chr21:40739346-41801322 | chr21:40161216-40223192 | kgp5198475 | rs2837624 |
| PDC | chr1:186412697-186430239 | chr1:185912697-186930239 | chr1:184679337-184696862 | kgp15446019 | kgp15206197 |
| PDCD8 | chrX:129263338-129299861 | chrX:128763338-129799861 | chrX:129091019-129127542 | rs3131260 | kgp22747824 |

*Fig. 4-18*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PDCL | chr9:125580375-125590935 | chr9:125080375-126090935 | chr9:124620443-124630661 | kgp11050939 | rs7341862 |
| PDE1A | chr2:183007182-183387507 | chr2:182507182-183887507 | chr2:182715427-183095498 | kgp205462 | kgp14271078 |
| PDE4DIP | chr1:144676436-145076186 | chr1:144176436-145576186 | chr1:143388229-143787436 | rs7548928 | kgp15506281 |
| PDE6D | chr2:232597146-232645974 | chr2:232097146-233145974 | chr2:232305390-232354218 | kgp448503 | rs11686328 |
| PDIA2 | chr16:330605-337209 | chr16:1-837209 | chr16:270606-277210 | kgp4861413 | rs3817833 |
| PDLIM7 | chr5:176910394-176924602 | chr5:176410394-177424602 | chr5:176843000-176857208 | kgp10474318 | kgp9286031 |
| PDPK1 | chr16:2587969-2653189 | chr16:2087969-3153189 | chr16:2527970-2593190 | rs11876 | rs2741932 |
| PEA15 | chr1:160175124-160185162 | chr1:159675124-160685162 | chr1:158441750-158451786 | kgp15388960 | kgp4800109 |
| PELO | chr5:52083773-52098452 | chr5:51583773-52598452 | chr5:52119530-52134209 | kgp7417119 | kgp22419632 |
| PFDN1 | chr5:139624634-139682689 | chr5:139124634-140182689 | chr5:139604818-139662873 | kgp2976589 | rs3733707 |
| PFDN4 | chr20:52824501-52836492 | chr20:52324501-53336492 | chr20:52257908-52269899 | kgp2671049 | kgp19401284 |
| PFDN5 | chr12:53689234-53693234 | chr12:53189234-54193234 | chr12:51975501-51979501 | kgp9320945 | kgp18934893 |
| PFKFB2 | chr1:207207760-207254368 | chr1:206707760-207754368 | chr1:205293242-205320991 | rs6666087 | kgp15524399 |
| PFN1 | chr17:4848946-4851825 | chr17:4348946-5351825 | chr17:4789691-4792570 | kgp459103 | rs11869909 |
| PGK1 | chrX:77359665-77382324 | chrX:76859665-77882324 | chrX:77246321-77268980 | kgp22784498 | kgp22747606 |
| PHKA1 | chrX:71798663-71934029 | chrX:71298663-72434029 | chrX:71715388-71850754 | kgp22784635 | kgp22830838,rs5982097 |
| PHKA2 | chrX:18910415-19002480 | chrX:18410415-19502480 | chrX:18820336-18912401 | kgp22820040 | kgp22735291 |
| PHKG1 | chr7:56148674-56160689 | chr7:55648674-56660689 | chr7:56116168-56128183 | rs4947514 | kgp13251786 |
| PIAS4 | chr19:4007748-4038067 | chr19:3507748-4538067 | chr19:3958748-3989067 | kgp21496330 | rs966384 |
| PIK3C3 | chr18:39535198-39661446 | chr18:39035198-40161446 | chr18:37789196-37915444 | kgp16093917 | kgp16001617 |
| PIK3CG | chr7:106505722-106547592 | chr7:106005722-107047592 | chr7:106292958-106334828 | kgp13830163 | kgp58259 |

*Fig. 4-19*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| PLCB2 | chr15:40580097-40600174 | chr15:40080097-41100174 | chr15:38367389-38387466 | rs594863 | kgp19835274 |
| PLCD1 | chr3:38048986-38071154 | chr3:37548986-38571154 | chr3:38023990-38046137 | rs155528 | kgp8999289 |
| PLD1 | chr3:171318194-171528504 | chr3:170818194-172028504 | chr3:172801338-173011198 | kgp17613784 | kgp17918658 |
| PLD2 | chr17:4710395-4726727 | chr17:4210395-5226727 | chr17:4657377-4673694 | rs9915202 | kgp10024037 |
| PLEKHA4 | chr19:49340353-49371884 | chr19:48840353-49871884 | chr19:54032166-54063670 | kgp21466232 | kgp7036888 |
| PLK1 | chr16:23690200-23701688 | chr16:23190200-24201688 | chr16:23597701-23609189 | kgp6012631 | kgp22747639 |
| POLA2 | chr11:65029431-65065088 | chr11:64529431-65565088 | chr11:64786007-64821664 | rs637332 | rs12800057 |
| POLB | chr8:42195972-42229331 | chr8:41695972-42729331 | chr8:42315186-42348470 | kgp20057794 | kgp20541648 |
| POLR2C | chr16:57496550-57505921 | chr16:56996550-58005921 | chr16:56054051-56063422 | kgp12245826 | rs3888264 |
| POLR3F | chr20:18448032-18465286 | chr20:17948032-18965286 | chr20:18396032-18413286 | kgp4834782 | kgp4034265 |
| PPARA | chr22:46546498-46639653 | chr22:46046498-47139653 | chr22:44925162-45018317 | kgp1216941 | kgp15069036 |
| PPEF1 | chrX:18709044-18846034 | chrX:18209044-19346034 | chrX:18618965-18755955 | kgp22764965 | kgp22802655 |
| PPEF2 | chr4:76781025-76823681 | chr4:76281025-77323681 | chr4:77000049-77042705 | kgp3982074 | kgp4693685 |
| PPM1A | chr14:60712469-60765805 | chr14:60212469-61265805 | chr14:59782222-59835559 | kgp19716116 | kgp5849461 |
| PPP1R13B | chr14:104200087-104313927 | chr14:103700087-104813927 | chr14:103269840-103383680 | kgp19713395 | kgp19494408 |
| PPP1R14A | chr19:38741876-38747231 | chr19:38241876-39247231 | chr19:43433716-43439012 | kgp7541975 | kgp4659188 |
| PPP3CA | chr4:101944586-102268628 | chr4:101444586-102768628 | chr4:102163609-102487376 | kgp4575683 | kgp7268908 |
| PPYR1 | chr10:47083533-47088320 | chr10:46583533-47588320 | chr10:46503539-46508326 | kgp507194 | rs11259820 |
| PQBP1 | chrX:48755194-48760422 | chrX:48255194-49260422 | chrX:48640138-48645364 | rs28833838 | rs2015487 |
| PREI3 | chr2:198364721-198418423 | chr2:197864721-198918423 | chr2:198072966-198126668 | kgp9884304 | kgp9480848 |
| PRG2 | chr11:57154833-57191532 | chr11:56654833-57691532 | chr19:763517-772952 | kgp13043879 | kgp12981403 |

*Fig. 4-20*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PRKACA | chr19:14202506-14228559 | chr19:13702506-14728559 | chr19:14063506-14089559 | kgp6577295 | kgp559477 |
| PRKCB1 | chr16:23847300-24231932 | chr16:23347300-24731932 | chr16:23754801-24139433 | rs7190829 | rs2343354 |
| PRKCD | chr3:53195222-53226733 | chr3:52695222-53726733 | chr3:53170262-53201773 | rs11715796 | kgp8788109 |
| PRKCG | chr19:54385466-54410901 | chr19:53885466-54910901 | chr19:59077278-59102713 | kgp1393848 | kgp11043930 |
| PRKCI | chr3:169940219-170023770 | chr3:169440219-170523770 | chr3:171422913-171506464 | kgp17942550 | rs12485248 |
| PRKCZ | chr1:1981908-2116834 | chr1:1481908-2616834 | chr1:1971768-2106694 | kgp15756715 | kgp907107 |
| PRKG1 | chr10:52750910-54058110 | chr10:52250910-54558110 | chr10:52420950-53725280 | kgp22035660 | rs7923443 |
| PSCD2 | chr19:48972465-48985571 | chr19:48472465-49485571 | chr19:53664277-53677383 | rs16981057 | rs5464 |
| PSEN2 | chr1:227058272-227083804 | chr1:226558272-227583804 | chr1:225124895-225150427 | rs3219110 | kgp1301981,rs3014274 |
| PSG9 | chr19:43757434-43773682 | chr19:43257434-44273682 | chr19:48449274-48465522 | kgp21418993 | kgp7929858 |
| PSMA2 | chr7:42956461-42971805 | chr7:42456461-43471805 | chr7:42922986-42938330 | kgp13636285 | kgp8523923 |
| PSMD2 | chr3:184017021-184026840 | chr3:183517021-184526840 | chr3:185499715-185509534 | kgp4284536 | rs11711955 |
| PSPC1 | chr13:20277008-20357159 | chr13:19777008-20857159 | chr13:19146895-19255083 | kgp249471 | kgp2992302 |
| PTGIR | chr19:47123724-47128354 | chr19:46623724-47628354 | chr19:51815564-51820194 | kgp21532737 | rs184290 |
| PTMAP7 | chr2:232573235-232578250 | chr2:232073235-233078250 | chr2:232281479-232286494 | kgp6878597 | kgp14464906 |
| PTP4A1 | chr6:64231650-64293489 | chr6:63731650-64793489 | chr6:64289609-64351448 | rs4710239 | kgp357802 |
| PTP4A3 | chr8:142432006-142441620 | chr8:141932006-142941620 | chr8:142501188-142510802 | rs12678285 | kgp3296894 |
| PTPN11 | chr12:112856535-112947717 | chr12:112356535-113447717 | chr12:111340918-111432100 | kgp22816522 | rs1293743 |
| PTPN12 | chr7:77166772-77269388 | chr7:76666772-77769388 | chr7:77004770-77107322 | kgp4690058 | rs3807707 |
| PTPN6 | chr12:7055739-7070479 | chr12:6555739-7570479 | chr12:6926000-6940740 | kgp18831609 | kgp18845056 |
| PTPRA | chr20:2844824-3019315 | chr20:2344824-3519315 | chr20:2792824-2967315 | kgp725112 | rs2853218 |

*Fig. 4-21*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PTPRJ | chr11:48002109-48192394 | chr11:47502109-48692394 | chr11:47958685-48148970 | kgp11833163 | kgp12755942 |
| PTPRS | chr19:5158505-5340814 | chr19:4658505-5840814 | chr19:5109505-5291814 | kgp6271833 | kgp4407357 |
| PTPRU | chr1:29563027-29653325 | chr1:29063027-30153325 | chr1:29435633-29525903 | rs12068075 | kgp9719744 |
| RAB27A | chr15:55495163-55582013 | chr15:54995163-56082013 | chr15:53283091-53369293 | kgp19829554 | rs11631355 |
| RAB3B | chr1:52373627-52456436 | chr1:51873627-52956436 | chr1:52157422-52228936 | kgp22830492 | rs10493168 |
| RAB5A | chr3:19988571-20026667 | chr3:19488571-20526667 | chr3:19963762-20001647 | rs1348231 | kgp8738867 |
| RAB8B | chr15:63481727-63559973 | chr15:62981727-64059973 | chr15:61268780-61347026 | kgp20037308 | rs17773778 |
| RABAC1 | chr19:42460832-42463528 | chr19:41960832-42963528 | chr19:47152675-47155311 | kgp22776019 | kgp2186225 |
| RAC1 | chr7:6414125-6443598 | chr7:5914125-6943598 | chr7:6380650-6410123 | kgp13594313 | kgp2338008 |
| RACGAP1 | chr12:50382944-50419307 | chr12:49882944-50919307 | chr12:48669211-48705574 | rs12317050 | kgp2525417 |
| RAF1 | chr3:12625099-12705700 | chr3:12125099-13205700 | chr3:12600099-12680700 | kgp17997932 | kgp3531880 |
| RALB | chr2:120997639-121052286 | chr2:120497639-121552286 | chr2:120726883-120768756 | rs17661862 | kgp5177758 |
| RASSF1 | chr3:50367216-50378367 | chr3:49867216-50878367 | chr3:50342220-50353371 | kgp8151957 | kgp7341826 |
| RBM23 | chr14:23369853-23388396 | chr14:22869853-23888396 | chr14:22439693-22458236 | rs3811239 | kgp128686 |
| RBM5 | chr3:50126340-50156397 | chr3:49626340-50656397 | chr3:49952595-50112488 | kgp22823256 | rs375544 |
| RCVRN | chr17:9801026-9808684 | chr17:9301026-10308684 | chr17:9741751-9749409 | rs8082538 | kgp2141837 |
| REL | chr2:61108751-61150178 | chr2:60608751-61650178 | chr2:60962255-61003682 | kgp8245960 | kgp14294452 |
| RELA | chr11:65421066-65430443 | chr11:64921066-65930443 | chr11:65177647-65186951 | kgp6667058 | kgp4478491 |
| RELB | chr19:45504706-45541456 | chr19:45004706-46041456 | chr19:50196551-50233292 | kgp9280266 | kgp9663255 |
| RFC5 | chr12:118454505-118470042 | chr12:117954505-118970042 | chr12:116938892-116954422 | rs11068526 | kgp19024344 |
| RGS10 | chr10:121259338-121302222 | chr10:120759338-121802222 | chr10:121249328-121292212 | kgp21619652 | kgp5105745 |

*Fig. 4-22*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| RGS13 | chr1:192605267-192629440 | chr1:192105267-193129440 | chr1:190871904-190896012 | rs11806786 | kgp1816960 |
| RGS14 | chr5:176784843-176799599 | chr5:176284843-177299599 | chr5:176717449-176732205 | rs1000144 | kgp11311419 |
| RGS16 | chr1:182567757-182573548 | chr1:182067757-183073548 | chr1:180834380-180840171 | kgp15787070 | kgp4798391 |
| RGS18 | chr1:192127591-192154945 | chr1:191627591-192654945 | chr1:190394214-190421568 | rs1338034 | kgp6525246 |
| RGS19 | chr20:62704534-62711324 | chr20:62204534-63211324 | chr20:62174978-62181768 | rs1630157 | kgp19264714 |
| RGS4 | chr1:163038395-163046592 | chr1:162538395-163546592 | chr1:161305019-161313216 | kgp15623644 | kgp15384575 |
| RGS5 | chr1:163112088-163291581 | chr1:162612088-163791581 | chr1:161378720-161439496 | kgp15331781 | kgp2554099 |
| RGS7 | chr1:240938816-241520478 | chr1:240438816-242020478 | chr1:239005439-239587101 | rs16839692 | kgp15345284 |
| RHO | chr3:129247481-129254187 | chr3:128747481-129754187 | chr3:130730171-130736877 | kgp12236862 | kgp11280524 |
| RHOH | chr4:40198526-40246281 | chr4:39698526-40746281 | chr4:39874921-39922676 | rs3912392 | rs17513557 |
| RIC8A | chr11:208529-215110 | chr11:1-715110 | chr11:198529-205110 | kgp9815230 | rs11246286 |
| RIC8B | chr12:107168398-107283094 | chr12:106668398-107783094 | chr12:105692528-105807224 | kgp7665070 | kgp2084662 |
| RIOK3 | chr18:21032786-21063099 | chr18:20532786-21563099 | chr18:19286784-19317097 | kgp4053645 | kgp16177785 |
| RIPK1 | chr6:3064121-3115421 | chr6:2564121-3615421 | chr6:3009120-3060420 | rs17208835 | kgp17120238 |
| RIPK2 | chr8:90769974-90803292 | chr8:90269974-91303292 | chr8:90839109-90872433 | rs7813237 | rs2214416 |
| RIT1 | chr1:155867600-155881177 | chr1:155367600-156381177 | chr1:154134224-154147801 | kgp10974682 | rs12022607 |
| RIT2 | chr18:40323191-40695657 | chr18:39823191-41195657 | chr18:38577189-38949655 | rs6507465 | kgp3440940 |
| RNF10 | chr12:120972131-121015397 | chr12:120472131-121515397 | chr12:119456514-119499780 | kgp19140786 | kgp19017203 |
| RNF11 | chr1:51701944-51739119 | chr1:51201944-52239119 | chr1:51474532-51511707 | kgp4558813 | kgp7772065 |
| RPL10 | chrX:153627678-153632038 | chrX:153127678-154132038 | chrX:153279911-153283874 | rs2071127 | rs4074307 |
| RPL12 | chr9:130209952-130213711 | chr9:129709952-130713711 | chr9:129249775-129253505 | kgp11622632 | rs3802355 |

*Fig. 4-23*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| RPL37A | chr2:217363519-217366188 | chr2:216863519-217866188 | chr2:217071764-217074433 | kgp2247391 | kgp7636371 |
| RRAD | chr16:66955581-66959439 | chr16:66455581-67459439 | chr16:65513082-65516940 | kgp16522328 | kgp16305055 |
| RTN4 | chr2:55199326-55277734 | chr2:54699326-55777734 | chr2:55052830-55131238 | kgp3749465 | rs3748945 |
| S100A8 | chr1:153362507-153363664 | chr1:152862507-153863664 | chr1:151629131-151630173 | rs6587709 | kgp4686042 |
| SAT1 | chrX:23801274-23804327 | chrX:23301274-24304327 | chrX:23711224-23714248 | kgp22758306 | kgp22759648 |
| SCN8A | chr12:51985019-52202299 | chr12:51485019-52702299 | chr12:50271286-50488566 | rs7979705 | kgp7295633 |
| SDC1 | chr2:20400557-20425194 | chr2:19900557-20925194 | chr2:20264038-20288675 | kgp14253812 | kgp8380770 |
| SDC2 | chr8:97505881-97624037 | chr8:97005881-98124037 | chr8:97575057-97693213 | rs1421221 | kgp1305908 |
| SDC4 | chr20:43953928-43977064 | chr20:43453928-44477064 | chr20:43387342-43410478 | rs8116486 | kgp19276986 |
| SDCBP | chr8:59465727-59495419 | chr8:58965727-59995419 | chr8:59628281-59657973 | rs954172 | kgp20217944 |
| SDCBP2 | chr20:1290554-1373816 | chr20:790554-1873816 | chr20:1238620-1257838 | kgp9852208 | kgp10348674 |
| SDPR | chr2:192699031-192712006 | chr2:192199031-193212006 | chr2:192407280-192420226 | kgp6263901 | kgp14266860 |
| SELENBP1 | chr1:151336779-151345164 | chr1:150836779-151845164 | chr1:149603403-149611788 | rs12406660 | rs6684312 |
| SEMG1 | chr20:43835637-43838414 | chr20:43335637-44338414 | chr20:43269087-43271823 | rs6094023 | rs6094202 |
| SEMG2 | chr20:43835637-43853099 | chr20:43335637-44353099 | chr20:43269087-43286513 | rs6094023 | rs6017667 |
| SEPT4 | chr17:56597610-56618179 | chr17:56097610-57118179 | chr17:53952614-53964410 | kgp1250021 | rs34058624 |
| SETDB1 | chr1:150898814-150937220 | chr1:150398814-151437220 | chr1:149165511-149203837 | rs12759551 | kgp1978717 |
| SGOL1 | chr3:20202084-20227724 | chr3:19702084-20727724 | chr3:20177088-20202687 | kgp9539943 | kgp18040639 |
| SGOL2 | chr2:201390864-201448818 | chr2:200890864-201948818 | chr2:201099186-201156750 | kgp9074393 | kgp14634946 |
| SH2B3 | chr12:111843751-111889427 | chr12:111343751-112389427 | chr12:110328134-110373810 | kgp7682395 | kgp10017505 |
| SHC1 | chr1:154934773-154946959 | chr1:154434773-155446959 | chr1:153201397-153213464 | kgp11196367 | kgp15752431 |

*Fig. 4-24*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| SIRT2 | chr19:39369194-39390502 | chr19:38869194-39890502 | chr19:44061039-44082201 | kgp21526327 | kgp9511717 |
| SLC1A1 | chr9:4490426-4587469 | chr9:3990426-5087469 | chr9:4480443-4577469 | kgp7074545 | kgp9946842 |
| SLC6A9 | chr1:44457171-44497134 | chr1:43957171-44997134 | chr1:44234741-44269721 | rs6687571 | rs6672462 |
| SLC9A3R1 | chr17:72744762-72765499 | chr17:72244762-73265499 | chr17:70256378-70277089 | kgp14032523 | kgp14006779 |
| SMAD3 | chr15:67358194-67487533 | chr15:66858194-67987533 | chr15:65145248-65274587 | kgp1676807 | kgp19813377 |
| SMAD5 | chr5:135468535-135518422 | chr5:134968535-136018422 | chr5:135496434-135546321 | kgp5717445 | kgp8569495 |
| SMN2 | chr5:70220767-70248842 | chr5:69720767-70748842 | chr5:70256523-70284594 | rs28591114 | kgp22633148 |
| SMPD3 | chr16:68392229-68482409 | chr16:67892229-68982409 | chr16:66949730-67039905 | kgp2756941 | kgp16310484 |
| SNAP23 | chr15:42787503-42825259 | chr15:42287503-43325259 | chr15:40575126-40612548 | rs1668586 | kgp19741111 |
| SNAP25 | chr20:10199476-10288066 | chr20:9699476-10788066 | chr20:10147476-10236065 | kgp4923784 | kgp19370207 |
| SNAP91 | chr6:84262604-84419127 | chr6:83762604-84919127 | chr6:84319331-84475831 | kgp17413387 | kgp16958869 |
| SNTA1 | chr20:31995762-32031698 | chr20:31495762-32531698 | chr20:31459423-31495359 | kgp994844 | kgp22753335 |
| SNURF | chr15:25200069-25244225 | chr15:24700069-25744225 | chr15:22751162-22795318 | kgp20028287 | kgp5644000 |
| SOX4 | chr6:21593971-21598849 | chr6:21093971-22098849 | chr6:21701950-21706828 | kgp3609791 | rs9466264 |
| SPAG1 | chr8:101170262-101254132 | chr8:100670262-101754132 | chr8:101239438-101323306 | kgp5198147 | kgp20550876 |
| SPG7 | chr16:89574804-89624174 | chr16:89074804-90124174 | chr16:88102305-88151675 | kgp3688149 | rs3809643 |
| SPP1 | chr4:88896801-88904563 | chr4:88396801-89404563 | chr4:89115825-89123587 | kgp20744622 | kgp20764098 |
| SPTBN1 | chr2:54683453-54898583 | chr2:54183453-55398583 | chr2:54536957-54752087 | kgp14832324 | kgp12300457 |
| SQSTM1 | chr5:179233387-179265077 | chr5:178733387-179765077 | chr5:179170503-179197683 | kgp10101186 | kgp2553327 |
| SRGAP3 | chr3:9022277-9291311 | chr3:8522277-9791311 | chr3:8997277-9266311 | kgp5324812 | kgp18088153 |
| STARD13 | chr13:33677271-34250932 | chr13:33177271-34750932 | chr13:32575306-33148932 | kgp1217969 | kgp9105015 |

*Fig. 4-25*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| STC2 | chr5:172741725-172756506 | chr5:172241725-173256506 | chr5:172674331-172689112 | kgp22378380 | kgp10706002 |
| STRN | chr2:37064840-37193615 | chr2:36564840-37693615 | chr2:36928975-37047119 | kgp3533593 | kgp9369923 |
| STRN4 | chr19:47222767-47250251 | chr19:46722767-47750251 | chr19:51914607-51941560 | kgp21470253 | rs4804031 |
| STX4 | chr16:31044415-31051485 | chr16:30544415-31551485 | chr16:30951916-30958986 | kgp16259387 | kgp7678241 |
| STX5 | chr11:62574331-62599563 | chr11:62074331-63099563 | chr11:62330944-62356136 | kgp10937693 | kgp568990 |
| STXBP1 | chr9:130374485-130454995 | chr9:129874485-130954995 | chr9:129414388-129494816 | rs1768374 | kgp4399986 |
| STXBP3 | chr1:109289284-109352148 | chr1:108789284-109852148 | chr1:109090807-109153671 | rs6583070 | rs17036360 |
| SULT1E1 | chr4:70706929-70725870 | chr4:70206929-71225870 | chr4:70741518-70760459 | kgp22798798 | kgp5241292 |
| SUMO4 | chr6:149721494-149722182 | chr6:149221494-150222182 | chr6:149763187-149763875 | rs1871921 | kgp17155476 |
| SYT1 | chr12:79257772-79845788 | chr12:78757772-80345788 | chr12:77781903-78367834 | kgp11848377 | kgp18913198 |
| SYT9 | chr11:7273180-7490276 | chr11:6773180-7990276 | chr11:7229756-7446846 | rs7928685 | kgp8567849 |
| TANC1 | chr2:159825145-160089170 | chr2:159325145-160589170 | chr2:159533391-159797416 | rs4664962 | kgp22743229 |
| TANK | chr2:161993465-162092683 | chr2:161493465-162592683 | chr2:161701711-161800928 | kgp7233899 | rs1006427 |
| TAOK2 | chr16:29985187-30003582 | chr16:29485187-30503582 | chr16:29892722-29911082 | rs257868 | kgp2310172 |
| TBCD | chr17:80709939-80901062 | chr17:80209939-81401062 | chr17:78303228-78494351 | rs11653735 | kgp10867492 |
| TBCE | chr1:235530727-235612280 | chr1:235030727-236112280 | chr1:233597350-233678903 | rs2673969 | kgp15284682 |
| TBK1 | chr12:64845839-64895899 | chr12:64345839-65395899 | chr12:63132203-63182158 | kgp18934034 | kgp19122002 |
| TCF1 | chr5:134240810-134298336 | chr5:133740810-134798336 | chr5:134268709-134326235 | kgp22161149 | kgp4823163 |
| TCF3 | chr19:1609288-1652328 | chr19:1109288-2152328 | chr19:1560294-1603328 | rs2302109 | kgp2427498 |
| TCF4 | chr18:52889561-53303188 | chr18:52389561-53803188 | chr18:51040559-51454183 | kgp10409423 | rs1792746 |
| TDGF1 | chr3:46616044-46623952 | chr3:46116044-47123952 | chr3:46594216-46598956 | kgp980076 | kgp18003873 |

*Fig. 4-26*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| TEP1 | chr14:20833825-20881579 | chr14:20333825-21381579 | chr14:19905765-19951420 | rs1780944 | rs12435821 |
| TERT | chr5:1253286-1295162 | chr5:753286-1795162 | chr5:1306286-1348162 | kgp22831882 | rs4975846 |
| TGFA | chr2:70674411-70781147 | chr2:70174411-71281147 | chr2:70527924-70634613 | kgp14279885 | kgp4236793 |
| TIAM1 | chr21:32490735-32931290 | chr21:31990735-33431290 | chr21:31412606-31853161 | rs1702403 | rs1892577 |
| TM4SF1 | chr3:149086804-149095568 | chr3:148586804-149595568 | chr3:150569494-150578258 | kgp18120845 | kgp17746361 |
| TMSB4X | chrX:12993225-12995346 | chrX:12493225-13495346 | chrX:12903145-12905267 | kgp22760889 | kgp22772999 |
| TNFRSF14 | chr1:2487804-2495267 | chr1:1987804-2995267 | chr1:2479150-2486613 | rs2803309 | kgp11439882 |
| TNFRSF1A | chr12:6437922-6451283 | chr12:5937922-6951283 | chr12:6308183-6321522 | kgp6731378,rs4764519 | kgp19158534 |
| TNFRSF1B | chr1:12227059-12269277 | chr1:11727059-12769277 | chr1:12149646-12191864 | kgp15495881 | rs3010872 |
| TNIP2 | chr4:2743386-2758103 | chr4:2243386-3258103 | chr4:2713184-2727859 | kgp20948263 | kgp5432833 |
| TNNI2 | chr11:1860232-1862910 | chr11:1360232-2362910 | chr11:1817480-1819484 | kgp11231095 | rs800123 |
| TNNI3 | chr19:55663135-55669100 | chr19:55163135-56169100 | chr19:60354947-60360912 | rs13382124 | kgp21397937 |
| TNNT2 | chr1:201328141-201346805 | chr1:200828141-201846805 | chr1:199594764-199613428 | rs12733378 | rs10920269 |
| TOMM20 | chr1:235272657-235292256 | chr1:234772657-235792256 | chr1:233339282-233358754 | kgp8358331 | kgp15139309 |
| TOP2A | chr17:38544772-38574202 | chr17:38044772-39074202 | chr17:35798321-35827695 | kgp7375263 | kgp10420460 |
| TP53 | chr17:7571719-7590863 | chr17:7071719-8090863 | chr17:7512444-7531588 | kgp12029669 | kgp11286494 |
| TRADD | chr16:67188088-67193812 | chr16:66688088-67693812 | chr16:65745589-65751313 | kgp16482196 | kgp16510307,rs28521023 |
| TRAF1 | chr9:123664670-123691451 | chr9:123164670-124191451 | chr9:122704492-122731300 | kgp6551598 | rs306777 |
| TRAF6 | chr11:36505316-36531863 | chr11:36005316-37031863 | chr11:36467298-36488398 | kgp12764289 | rs333778 |
| TRBV21-1 | chr7:142344427-142344887 | chr7:141844427-142844887 | chr7:142025416-142025876 | kgp2155197 | kgp9570297 |
| TRIM2 | chr4:154074269-154260474 | chr4:153574269-154760474 | chr4:154293719-154479918 | rs6849505 | rs6843172 |

*Fig. 4-27*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| TRIM29 | chr11:119981993-120008863 | chr11:119481993-120508863 | chr11:119487203-119514073 | kgp12998914 | rs7122702 |
| TRIO | chr5:14143828-14509458 | chr5:13643828-15009458 | chr5:14196828-14562458 | rs1445678 | kgp8041369 |
| TRPC1 | chr3:142443265-142526729 | chr3:141943265-143026729 | chr3:143925955-144009419 | rs9842771 | rs7641069 |
| TRPC3 | chr4:122800182-122872909 | chr4:122300182-123372909 | chr4:123019881-123092359 | kgp21231448 | kgp5789583 |
| TRPC4 | chr13:38210772-38443939 | chr13:37710772-38943939 | chr13:37108794-37341935 | kgp22792521 | rs7338958 |
| TRPV1 | chr17:3468739-3512705 | chr17:2968739-4012705 | chr17:3415489-3459454 | kgp8654960 | rs9890881 |
| TRPV4 | chr12:110220891-110271212 | chr12:109720891-110771212 | chr12:108705276-108755595 | kgp11365980 | kgp19139284 |
| TRPV6 | chr7:142568959-142583490 | chr7:142068959-143083490 | chr7:142279081-142293599 | kgp9647465 | kgp2837315 |
| TSC22D4 | chr7:100064141-100076902 | chr7:99564141-100576902 | chr7:99902077-99914838 | kgp5759639 | kgp10599319 |
| TSHR | chr14:81421868-81612646 | chr14:80921868-82112646 | chr14:80491621-80682399 | kgp19546597 | rs10134565 |
| TSPAN6 | chrX:99883794-99891794 | chrX:99383794-100391794 | chrX:99770450-99778450 | kgp22794008 | rs7059563 |
| TTBK1 | chr6:43211221-43255997 | chr6:42711221-43755997 | chr6:43319199-43363975 | kgp17369454 | kgp17498760 |
| TTC1 | chr5:159436179-159492550 | chr5:158936179-159992550 | chr5:159368757-159425128 | kgp5018309 | kgp22489460 |
| TTK | chr6:80714321-80752244 | chr6:80214321-81252244 | chr6:80771077-80808958 | kgp949561 | kgp12311980 |
| TTN | chr2:179390717-179672150 | chr2:178890717-180172150 | chr2:179098963-179380395 | rs959775 | rs6433773 |
| TUB | chr11:8040790-8127654 | chr11:7540790-8627654 | chr11:8016755-8084228 | kgp12365126 | kgp1066384 |
| TUBA8 | chr22:18593452-18614498 | chr22:18093452-19114498 | chr22:16940685-16994498 | rs1034470 | kgp9877961 |
| UBE2V2 | chr8:48920994-48974454 | chr8:48420994-49474454 | chr8:49083547-49137007 | kgp3293751 | kgp20374954 |
| ULK1 | chr12:132379278-132407707 | chr12:131879278-132907707 | chr12:130945231-130973649 | kgp7696078 | kgp11815104 |
| USP7 | chr16:8985950-9057341 | chr16:8485950-9557341 | chr16:8893451-8964842 | kgp79060 | rs1035944 |
| VAV1 | chr19:6772721-6857371 | chr19:6272721-7357371 | chr19:6723721-6808371 | kgp21410647 | kgp21471951 |

*Fig. 4-28*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| VCL | chr10:75754950-75879914 | chr10:75254950-76379914 | chr10:75424956-75549920 | rs7099640 | kgp21840278 |
| VDAC1 | chr5:133307565-133340824 | chr5:132807565-133840824 | chr5:133335505-133368723 | kgp22321002 | kgp9499928 |
| VIL2 | chr6:159186773-159239340 | chr6:158686773-159739340 | chr6:159106761-159159328 | rs9366083 | kgp10633571 |
| VIM | chr10:17270257-17279592 | chr10:16770257-17779592 | chr10:17310475-17319598 | kgp1974218 | kgp8572563 |
| VTN | chr17:26694298-26697373 | chr17:26194298-27197373 | chr17:23718425-23721500 | rs12602762 | kgp2208161 |
| WDR62 | chr19:36545782-36596012 | chr19:36045782-37096012 | chr19:41237622-41287852 | kgp5818871 | kgp7464156 |
| WDR91 | chr7:134868589-134896316 | chr7:134368589-135396316 | chr7:134520524-134546811 | kgp7394785 | kgp4752834 |
| WWC1 | chr5:167719064-167899308 | chr5:167219064-168399308 | chr5:167651669-167829342 | rs10454965 | rs7724207 |
| XK | chrX:37545132-37591383 | chrX:37045132-38091383 | chrX:37430051-37476322 | kgp22781551 | kgp22821350 |
| YWHAB | chr20:43514343-43537161 | chr20:43014343-44037161 | chr20:42947757-42970575 | rs4364072 | rs2247619 |
| YWHAE | chr17:1247833-1303556 | chr17:747833-1803556 | chr17:1194592-1250267 | rs4968122 | kgp1552188 |
| YWHAG | chr7:75956107-75988342 | chr7:75456107-76488342 | chr7:75794051-75826252 | kgp13357645 | kgp7952605 |
| YWHAZ | chr8:101930803-101965623 | chr8:101430803-102465623 | chr8:102000089-102034745 | rs4075553 | kgp4135753 |
| ZNF24 | chr18:32912177-32924426 | chr18:32412177-33424426 | chr18:31166175-31178424 | kgp5227729 | kgp15931312 |

*Fig. 4-29*

| Gene set | Number of CNV calls in gene set for patients with anxiety | Number of CNV calls in gene set for patients with depression | Number of CNV calls in gene set for patients with OCD | Number of CNV calls in gene set for patients with phobias |
|---|---|---|---|---|
| Tier 1 | 162 | 16 | 32 | 9 |
| Tiers 1 + 2 | 250 | 24 | 44 | 11 |
| Tiers 1 + 2 + 3 | 546 | 53 | 86 | 25 |

*Fig. 5*

| Gene set | % of patients with anxiety who had a CNV call within gene set | % of patients with depression who had a CNV call within gene set | % of patients with OCD who had a CNV call within gene set | % of patients with phobia who had a CNV call within gene set |
|---|---|---|---|---|
| Tier 1 | 7.91 | 0.78 | 1.56 | 0.44 |
| Tiers 1 + 2 | 12.20 | 1.17 | 2.15 | 0.54 |
| Tiers 1 + 2 + 3 | 26.65 | 2.59 | 4.20 | 1.22 |

*Fig. 6*

METHODS OF DIAGNOSING AND TREATING ANXIETY DISORDER

CROSS-REFERENCE TO RELATED APPLICATIONS

This application claims priority to the following four United States Provisional Patent Applications, each filed on Sep. 8, 2015: 62/215,628; 62/215,633; 62/215,636; and 62/215,673, each of which is incorporated herein by reference in its entirety.

FIELD

This application relates to the treatment of anxiety disorders with nonselective activators of metabotropic glutamate receptors (mGluRs) and of diagnosis and treatment of anxiety disorders in subjects having genetic alterations, such as copy number variations (CNVs), in one or more mGluR network genes.

BACKGROUND

Anxiety is a group of disorders characterized by excessive, irrational fear and dread. Anxiety disorders include panic disorder, obsessive-compulsive disorder (OCD), post-traumatic stress disorder (PTSD), social anxiety disorder/social phobia, separation anxiety disorder, phobias, and generalized anxiety disorder.

Anxiety disorders are often classified by having a duration of at least 6 months. The stress and fearfulness triggered by a stressful event may develop into an anxiety disorder over time if not treated.

Anxiety disorders affect approximately 40 million Americans each year, which is equivalent to about 18% of the population (see National Institutes of Health (2009): Anxiety Disorders, Publication No. 09 3879). In many patients, anxiety disorders occur along with other mental or physical illnesses or with alcohol or substance abuse. Anxiety disorders, such as panic disorder, can become disabling, with patients developing such intense fears of everyday situations that they become housebound.

Anxiety disorders can also result in exaggerated worry and tension that interferes with sleep and concentration and that leads to physical symptoms such as headaches, nausea, difficulty swallowing, and lightheadedness. Anxiety disorders can also lead to difficulty in performing simple, everyday tasks and are often accompanied by substance abuse or depression.

Presently, anxiety disorders may be diagnosed using a patient history, which may include a variety of rating scales (Ebell M H (2008) Am Fam Physician. 78(4):501-502). Standard scales may be used to evaluate the efficacy of treatment response and remission in pediatric anxiety, such as the Pediatric Anxiety Rating Scale (PARS), which is a validated clinician-rated measure of symptom severity and associated impairment that has been used for evaluation of therapies for generalized anxiety disorder, social phobia, and separation anxiety disorder (see Caporino N E (2013) J Am Acad Child Adolesc Psychiatry 52(1): 57-67). Rating scales that may be used in pediatric patients for associated or comorbid conditions include the Children's Depressive Rating Scale and Children's Yale-Brown Obsessive Compulsive Scale.

People with anxiety disorders may be treated with medications and/or psychotherapy. However, medications to treat anxiety disorders, such as antidepressants, anti-anxiety medications, and beta-blockers, cannot cure the disorders, although they can be helpful in controlling some physical symptoms.

Antidepressants have a long onset, so patients must be willing to continue medications until symptoms begin to improve.

Benzodiazepines are anti-anxiety medications that can work quickly, but often patients develop tolerance to these medications and need to escalate dosing to see an effect. Beta-blockers can provide some relief from physical symptoms of anxiety and may be helpful for patients who know that they are going to do an activity that generates anxiety, but they do not necessarily impact the underlying anxiety disorder. Because of the high prevalence of anxiety disorders and the limits of present pharmacotherapy, new treatment options are needed.

Precision or personalized medicine is a concept relating to prevention and treatment strategies that take individual variability into account. Recently, a precision-medicine-based clinical trial was completed reporting successful treatment of ADHD in subjects having at least one genetic alteration in a metabotropic glutamate receptor (mGluR) network gene. In that study, subjects having a genetic alteration in an mGluR network gene were successfully treated with fasoracetam (NFC-1), which has been shown in vitro to be a nonselective activator against all classes of mGluRs (See Hirouchi M, et al. (2000) European Journal of Pharmacology 387:9-17). We herein describe that patients with anxiety disorders, including those patients that are characterized by genetic alterations in mGluR network genes, may also benefit from treatment with nonselective mGluR activators such as NFC-1.

SUMMARY

The inventors have studied the genotypes of over 900 patients diagnosed with anxiety disorder and have found that these patients possess genetic alterations in one or more metabotropic glutamate receptor (mGluR) network genes at a significantly higher frequency than patients diagnosed with phobia, obsessive compulsive disorder (OCD), or depression. The frequency of genetic alterations in mGluR network genes was also substantially higher in this anxiety population than in control populations that do not have other neuropsychological disorders.

Thus, provided herein are methods of treating anxiety disorder in a subject comprising administering an effective amount of a nonselective activator of metabotropic glutamate receptors (mGluRs) to a subject, thereby treating anxiety disorder. In some embodiments the subject has at least one genetic alteration in an mGluR network gene, such as a copy number variation (CNV).

In some embodiments, a method of treating anxiety disorder in a subject is provided comprising administering an effective amount of a nonselective activator of metabotropic glutamate receptors (mGluRs) to a subject that has one symptom of anxiety and at least one genetic alteration in an mGluR network gene, thereby treating anxiety disorder. In another embodiment, a method of treating anxiety disorder in a subject is provided comprising administering an effective amount of a nonselective activator of metabotropic glutamate receptors (mGluRs) to a subject that has one symptom of anxiety, thereby treating anxiety disorder. The symptom may be any symptom known to those of skill in the art, including the symptoms provided in the Diagnostic and Statistical Manual of Mental Disorders, Fifth Edition (DSM-5 2013), including, but not limited to, fear and anxiety.

Also provided herein are methods of treating anxiety disorder comprising administering an effective amount of a nonselective activator of metabotropic glutamate receptors (mGluRs) to a subject that has at least one genetic alteration in an mGluR network gene, such as a CNV, thereby treating anxiety disorder. In some embodiments, where the subject has a CNV in an mGluR network gene, the CNV is a duplication or deletion.

Also provided are methods of treating anxiety disorder in a subject comprising obtaining results from a genetic screen that determines whether a subject has a genetic alteration in an mGluR network gene, and, if the results show that the subject has at least one genetic alteration in an mGluR network gene, treating the subject by administering an effective amount of a nonselective activator of mGluRs.

In some embodiments of the above methods, the nonselective activator of mGluRs is fasoracetam, such as fasoracetam monohydrate (NS-105 or NFC-1). In some embodiments the fasoracetam is administered at a dose of 50 mg, 100 mg, 150 mg, 200 mg, 250 mg, 300 mg, 350 mg, or 400 mg, wherein the dose is administered once, twice, or three times daily. In some embodiments, fasoracetam is administered at a dose of 50-400 mg, 100-400 mg, or 200-400 mg, and administered once, twice, or three times daily. In some embodiments, the fasoracetam is administered at a dose of 200-400 mg, such as 200 mg, 300 mg, or 400 mg, and administered twice daily.

In some embodiments the method comprises considering results of a screen to determine whether the subject has a genetic alteration such as a CNV in an mGluR network gene. In some embodiments of the above methods, the subject has a CNV in at least 1, 2, 3, 4, 5, 6, 7, 8, 9, or 10 mGluR network genes. In some embodiments a CNV in an mGluR network gene is determined by obtaining a nucleic acid-comprising sample from the subject and subjecting the sample to a screen that assesses CNVs in at least 5, 6, 7, 8, 9, 10, 15, 20, 30, 40, 50, 60, 70, or all of Tier 1 mGluR network genes. In some embodiments a CNV in an mGluR network gene is determined by obtaining a nucleic acid-comprising sample from the subject and subjecting the sample to a screen that assesses CNVs in at least 50, at least 100, at least 150, at least 175, or all of Tier 2 mGluR network genes. In some embodiments a CNV in an mGluR network gene is determined by obtaining a nucleic acid sample from the subject and subjecting the sample to a screen that assesses CNVs in at least 50, at least 100, at least 200, at least 300, at least 400, at least 500, or all of Tier 3 mGluR network genes. In some embodiments the screen does not assess CNVs in one or more of GRM1, GRM2, GRM3, GRM4, GRM5, GRM6, GRM7, or GRM8. In certain embodiments the subject does not have a CNV in one or more of GRM1, GRM2, GRM3, GRM4, GRM5, GRM6, GRM7, or GRM8.

In some embodiments of the above methods, the anxiety disorder is one or more of generalized anxiety disorder, phobia, social anxiety disorder, social phobia, panic disorder, panic attack, post-traumatic stress disorders, separation anxiety disorder, selective mutism, agoraphobia, or an anxiety disorder induced by a substance/medication or due to another medical condition. In some embodiments, the methods reduce at least one symptom of anxiety disorder in the subject, such as fear, anxiety, separation anxiety, and/or panic attacks (e.g. frequency and severity of attacks). In some embodiments, the methods reduce other behavioral symptoms such as inattentiveness, hyperactivity, and/or impulsiveness. In some embodiments, the methods also comprise assessing symptoms such as fear, anxiety, separation anxiety, panic attacks and their frequency or severity, as well as inattentiveness, hyperactivity, and/or impulsiveness during or after administration, for example, to determine if one or more of those symptoms have been reduced in the subject. In some methods, such assessment may be performed based on the Pediatric Anxiety Rating Scale (PARS). In some embodiments, the methods further comprise obtaining a clinical global impression of severity or improvement for the subject during or after administration. In some embodiments, the methods may improve clinical global improvement scores in the subject.

In some embodiments the subject is a pediatric or adolescent subject, such as between the ages of 5 and 17, 5 and 8, 8 and 17, 8 and 12, 12 and 18, 13 and 18, or 12 and 17. In other embodiments the subject is an adult. In some embodiments, the subject has experienced symptoms of anxiety for at least six months, while in other embodiments, anxiety symptoms have endured for less than six months yet anxiety disorder has been diagnosed in the subject.

In some embodiments of the above methods, the nonselective activator of mGluRs is administered in combination with another pharmaceutical or non-pharmaceutical therapy. In some embodiments, the non-pharmaceutical therapy comprises brain stimulation, such as vagus nerve stimulation, repetitive transcranial magnetic stimulation, magnetic seizure therapy, or deep brain stimulation. In some embodiments, the activator is administered in combination with an anxiolytic agent such as benzodiazepine, an antidepressant, a pregabalin, or a beta-blocker.

Also provided herein are methods for diagnosing anxiety disorder in a subject comprising isolating a nucleic-acid comprising sample from a subject, analyzing the sample for the presence or absence of a genetic alteration in at least one mGluR network genes, and diagnosing anxiety disorder if the subject has at least one genetic alteration in a mGluR network gene. Also provided are methods for diagnosing anxiety disorder in a subject comprising isolating a nucleic-acid comprising sample from a subject, isolating nucleic acid from the sample, analyzing the nucleic acid for the presence or absence of a genetic alteration in at least one mGluR network genes, and diagnosing anxiety disorder if the subject has at least one genetic alteration in a mGluR network gene. Provided as well are methods for identifying a subject as having anxiety disorder comprising obtaining a sample from a patient, optionally isolating nucleic acid from the sample, optionally amplifying the nucleic acid, and analyzing the nucleic acid in the sample for the presence or absence of a genetic alteration, such as a CNV, in at least one mGluR network gene, wherein the subject is identified as having anxiety disorder if at least one genetic alteration, such as a CNV, in an mGluR network gene is detected. The invention also provides methods for diagnosing anxiety disorder in a subject comprising analyzing genetic information about one or more mGluR network genes, comparing the subject's information to a control subject that does not have anxiety disorder, and diagnosing anxiety disorder if the genetic information suggests that the subject has at least one genetic alteration in a mGluR network gene.

Provided herein also are methods of confirming a diagnosis of anxiety disorder in a subject comprising: obtaining a nucleic acid-comprising sample from a subject diagnosed with anxiety disorder by a method that does not comprise detecting or analyzing genetic alterations in mGluR network genes; optionally amplifying the nucleic acid in the sample;

and determining whether the subject has at least one genetic alteration, such as a CNV, in an mGluR network gene, and confirming a diagnosis of anxiety disorder if the subject has at least one genetic alteration in a mGluR network gene.

In any of the above methods, the analysis for the presence or absence of at least one genetic alteration in a mGluR network gene may comprise microarrays, whole genome sequencing, exome sequencing, targeted sequencing, FISH, comparative genomic hybridization, genome mapping, or other methods using next-generation sequencing, Sanger sequencing, PCR, or TaqMan technologies.

In some embodiments, the subject has CNVs in one, two, or more mGluR network genes. In some embodiments, the methods comprise detecting CNVs in mGluR network genes by subjecting the sample to a screen that assesses CNVs in at least 2, 3, 4, 5, 6, 7, 8, 9, or 10 mGluR network genes. In some embodiments, CNVs in mGluR network genes are determined by subjecting the sample to a screen that assesses CNVs in at least 5, 6, 7, 8, 9, 10, 15, 20, 30, 40, 50, 60, 70, or all of Tier 1 mGluR network genes. In some embodiments, CNVs in mGluR network genes are determined by subjecting the sample to a screen that assesses CNVs in at least 50, at least 100, at least 150, at least 175, or all of Tier 2 mGluR network genes. In some embodiments, CNVs in mGluR network genes are determined by subjecting the sample to a screen that assesses CNVs in at least 50, at least 100, at least 200, at least 300, at least 400, at least 500, or all of Tier 3 mGluR network genes.

In some embodiments of the above methods, the anxiety disorder is one or more of generalized anxiety disorder, phobia, social anxiety disorder, social phobia, panic disorder, panic attack, post-traumatic stress disorders, separation anxiety disorder, selective mutism, agoraphobia, or an anxiety disorder induced by a substance/medication or due to another medical condition. In some embodiments, the subject is a pediatric or adolescent subject, such as a subject between the ages of 5 and 17, 5 and 8, 8 and 17, 8 and 12, 12 and 18, 13 and 18, or 12 and 17. In other embodiments, the subject is an adult subject. In some embodiments, the subject has experienced symptoms of anxiety for at least six months.

In some embodiments, the screening method for determining the presence or absence of at least one mGluR network gene genetic alteration comprises microarrays, whole genome sequencing, exome sequencing, targeted sequencing, FISH, comparative genomic hybridization, genome mapping, or other methods using next-generation sequencing, Sanger sequencing, PCR, or TaqMan technologies.

In some embodiments, the subject is not assessed for genetic alterations or CNVs in one or more of GRM1, GRM2, GRM3, GRM4, GRM5, GRM6, GRM7, and GRM8. In some embodiments, the subject does not have CNVs in one or more of GRM1, GRM2, GRM3, GRM4, GRM5, GRM6, GRM7, and GRM8. In some embodiments, the subject does not have CNVs in any of GRM1, GRM2, GRM3, GRM4, GRM5, GRM6, GRM7, and GRM8.

In any of the methods and embodiments described in the preceding paragraphs of this Summary, in the claims, or in the Detailed Description, the subject may have anxiety disorder as well as one or more comorbid conditions such as attention-deficit hyperactivity disorder (ADHD), oppositional defiant disorder (ODD), conduct disorder, Tourette's syndrome, phobia, obsessive compulsive disorder (OCD), difficulty controlling anger, disruptive behavior symptoms, dermatillomania, a developmental disorder, a movement disorder, a mood disorder, or depression. In other cases, the subject does not have one or more of ADHD, ODD, conduct disorder, Tourette's syndrome, phobia, obsessive compulsive disorder (OCD), difficulty controlling anger, disruptive behavior symptoms, dermatillomania, a developmental disorder, a movement disorder, a mood disorder, or depression. In yet other cases, the subject does not have any of ADHD, ODD, conduct disorder, Tourette's syndrome, phobia, obsessive compulsive disorder (OCD), difficult controlling anger, disruptive behavior symptoms, dermatillomania, a developmental disorder, a mood disorder, a movement disorder, or depression. In some embodiments, the anxiety subject does not have OCD, phobia, or depression.

In any of the methods and embodiments described herein, symptoms of inattentiveness, hyperactivity, and/or impulsiveness may be reduced in the subject. For example, these symptoms may be lessened after 1 week of treatment with the activator, such as after 2 weeks, after 3 weeks, or after 4 weeks of treatment.

In some embodiments, the subject has co-morbid symptoms of ADHD and in some cases, the method reduces ADHD symptoms. In some embodiments, the subject has OCD and in some cases, the method reduces OCD symptoms. In some cases, the subject has co-morbid symptoms of dermatillomania, such as excessive skin picking, and the method reduces those symptoms. In some embodiments, the subject has one or more co-morbid developmental disorders, and in some cases, the method reduces the severity of symptoms related to the developmental disorders. For example, these symptoms may be lessened after 1 week of treatment with the activator, such as after 2 weeks, after 3 weeks, or after 4 weeks of treatment.

In some embodiments, the subject may have one or more of the following changes in symptoms after at least one, two, three, or four weeks of treatment with the activator: (a) the subject has symptoms of anger control and the anger control symptoms are reduced; (b) the subject has symptoms of disruptive behavior and the disruptive behavior symptoms are reduced; (c) the subject's CGI-I is reduced by at least 1 or by at least 2; (d) the subject's CGI-I score after one, two, three, or four weeks of treatment is 1 or 2; (e) the subject's CGI-S score after one, two, three, or four weeks of treatment is 1; (f) the subject has ADHD and the subject's ADHD Rating Scale score is reduced by at least 25%, such as at least 30%, at least 35%, or at least 40%; (g) the subject has symptoms of inattentiveness and the inattentiveness symptoms are reduced; (h) the subject has symptoms of hyperactivity and the hyperactivity symptoms are reduced; (i) the subject has symptoms of impulsiveness and the impulsiveness symptoms are reduced; (j) the subject has symptoms of ODD such as anger and irritability, argumentation and defiance, and/or vindictiveness and the ODD symptoms are reduced; (k) the subject has symptoms of conduct disorder and the conduct disorder symptoms are reduced; (l) the subject has a movement disorder and the associated symptoms are reduced; (m) the subject has symptoms of OCD, and the OCD symptoms are reduced; (n) the subject has symptoms of autism, and the autism symptoms are reduced; and (o) the subject has symptoms of Tourette's syndrome and the Tourette's syndrome symptoms are reduced. In any of the methods and embodiments described herein, a subject may be treated when a clinician notes that the subject is more interested in doing things and/or becomes socially proactive.

In one embodiment, a method for diagnosing an mGluR-associated disorder is provided, wherein a subject is diagnosed with an mGluR-associated disorder if at least one genetic alteration in an mGluR network gene is detected.

BRIEF DESCRIPTION OF THE DRAWINGS

FIG. 1 shows the number of samples from patients with anxiety, depression, obsessive-compulsive disorder (OCD), and phobias included in a genotyping study designed to assess genetic alterations in mGluR network genes. Only those patient samples that were fully genotyped are included in the data analysis.

FIGS. 2-1 to 2-4 show the mGluR network genes included in the Tier 1 gene set. These genes have 2 degrees of protein-protein interaction with mGluR genes (GRM1-8) based on the Cytoscape Human Interactome, which is software for integrating biomolecular interaction networks with high-throughput data (as described in Shannon P (2003) Genome Research 13:2498-2504). The Tier 1 gene set includes 76 genes. The exact location for each gene in Tier 1 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The start single nucleotide polymorphism (StartSNP) (i.e., the SNP located 500 kilobases before the gene of interest) and the EndSNP (i.e., the SNP located 500 kilobases after the gene of interest) are also listed. Genes of the mGluRs themselves are noted as "GRM." The expanded regions (i.e., 500 kg up and down stream) frequently harbor regulatory elements and if impacted by a CNV, can have the same impact on the gene expression and function as a CNV residing in the gene sequence itself.

FIGS. 3-1 to 3-10 show the mGluR network genes included in the Tier 2 gene set. These genes have 2 degrees of protein-protein interaction with mGluR genes (GRM1-8) based on the Cytoscape Human Interactome but exclude genes from Tier 1. The Tier 2 gene set includes 197 genes. The exact location for each gene in Tier 2 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The start single nucleotide polymorphism (StartSNP) (i.e., the SNP located 500 kilobases before the gene of interest) and the EndSNP (i.e., the SNP located 500 kilobases after the gene of interest) in hg19 are also listed.

FIGS. 4-1 to 4-29 show genes within the Tier 3 gene set. Genes with reciprocal gene querying with 2 degrees of protein-protein interaction with mGluR genes based on Cytoscape Human Interactome are included. Genes contained within Tiers 1 and 2 are excluded from Tier 3. The Tier 3 gene set includes 599 genes. The exact location for each gene in Tier 3 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The StartSNP (i.e., the SNP located 500 kilobases before the gene of interest) and the EndSNP (i.e., the SNP located 500 kilobases after the gene of interest) in hg19 are also listed.

FIG. 5 shows the number of copy number variation (CNV) calls containing Tier gene (mGluR network gene) within the samples from the 925 anxiety patients who were fully genotyped; the 95 depression patients who were fully genotyped; the 150 OCD patients that were fully genotyped; and the 55 phobia patients that were fully genotyped. Note that some patients had more than one CNV call that contained a mGluR network genes in a Tier gene.

FIG. 6 shows the percentage of fully-genotyped patients with anxiety, depression, OCD, or phobia who had a CNV within Tier 1, Tiers 1+2, or Tiers 1+2+3 mGluR network gene sets.

DESCRIPTION OF THE EMBODIMENTS

I. Definitions

A "mGluR" or metabotropic glutamate receptor refers to one of eight glutamate receptors expressed in neural tissue named mGluR1, mGluR2, mGluR3, mGluR4, mGluR5, mGluR6, mGluR7, and mGluR8. Their genes are abbreviated GRM1 to GRM8. The mGluR proteins are G-protein-coupled receptors. They are typically placed into three sub-groups, Group I receptors including mGluR1 and mGluR5 are classed as slow excitatory receptors. Group II includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

A "mGluR network gene," for purposes of this invention, comprises not only the mGluR genes GRM1, GRM2, GRM3, GRM4, GRM5, GRM6, GRM7, and GRM8, but also each of the other genes listed herein in FIGS. 2-4 as well as the regions of DNA that regulate the genes listed in FIGS. 2-4. In addition, "mGluR network proteins" are the proteins encoded by the mGluR network genes.

The mGluR network genes are grouped into three subsets: Tier 1, Tier2, and Tier 3. (See FIGS. 2-4.) Tier 1 mGluR network genes, shown in FIG. 2, comprise 76 genes, including some GRM genes themselves as well as a number of other genes. The Tier 2 mGluR network genes, shown in FIG. 3, comprise 197 genes, and exclude the Tier 1 genes.

Tiers 1 and 2 together are included in the "primary mGluR network." The "primary network" of mGluR genes also includes the genes 4-Sep, LOC642393, and LOC653098, for a total of 276 genes. There are presently technical difficulties in assessing the 4-Sep, LOC642393, and LOC653098 genes. Thus, they are not included in the genes of Tiers 1 and 2, although they are included in the primary network of genes of the present invention. The genes of Tier 1 and Tier 2 differ in that alterations in Tier 1 genes had been documented in previous genotyping studies of subjects suffering from mental disorders.

Tier 3 mGluR network genes, shown in FIG. 4, comprise 599 genes that are in the distal part of the mGluR network based on the merged human interactome provided by the Cytoscape Software (Shannon P et al. (2003) Genome Research 13:2498-2504), and exclude the Tier 1 and Tier 2 genes. The Tier 3 genes are thus part of the "distal mGluR network." In addition to the Tier 3 genes, the genes LOC285147, LOC147004, and LOC93444 are included in the "distal mGluR network," although they were not assessed in the present study and are not included in Tier 3 due to technical difficulties in assessing genetic alterations in these genes.

A "genetic alteration" as used herein means any alteration in the DNA of a gene, or in the DNA regulating a gene, that, for example, may result in a gene product that is functionally changed as compared to a gene product produced from a non-altered DNA. A functional change may be differing expression levels (up-regulation or down-regulation) or loss or change in one or more biological activities, for example. A genetic alteration includes without limitation, copy number variations (CNVs), single nucleotide variants (SNVs), also called single nucleotide polymorphisms (SNPs) herein, frame shift mutations, or any other base pair substitutions, insertions, and deletions or duplications.

A "copy number variation" or "CNV" is a duplication or deletion of a DNA segment encompassing a gene, genes, segment of a gene, or DNA region regulating a gene, as compared to a reference genome. In some embodiments, a CNV is determined based on variation from a normal diploid state. In some embodiments, a CNV represents a copy number change involving a DNA fragment that is 1 kilobase (kb) or larger. CNVs described herein do not include those variants that arise from the insertion/deletion of transposable elements (e.g., 6-kb KpnI repeats). The term CNV therefore encompasses terms such as large-scale copy number variants (LCVs; Iafrate et al. 2004), copy number polymorphisms (CNPs; Sebat et al. 2004), and intermediate-sized variants (ISVs; Tuzun et al. 2005), but not retrotransposon insertions.

A "CNV deletion" or "deletion CNV" or similar terms refer to a CNV in which a gene, DNA segment regulating a gene, or gene segment is deleted. A "CNV duplication" or "duplication CNV" or similar terms refer to a CNV in which a gene, DNA segment regulating a gene, or gene segment is present in at least two, and possibly more than two, copies in comparison with the single copy found in a normal reference genome.

A "sample" refers to a sample from a subject that may be tested, for example, for presence of a CNV in one or more mGluR network proteins, as described herein. The sample may comprise cells, and it may comprise body fluids, such as blood, serum, plasma, cerebral spinal fluid, urine, saliva, tears, pleural fluid, and the like.

"Anxiety disorders" are defined in the Diagnostic and Statistical Manual of Mental Disorders, Fifth Edition (DSM-5 2013) as a group of disorders that share features of persistent, excessive fear and anxiety. Anxiety disorders typically have a duration of at least 6 months, although, in some embodiments herein the anxiety disorder is diagnosed after less than 6 months of duration. In children, anxiety disorders are typically diagnosed using one or more rating scales, such as, the Pediatric Anxiety Rating Scale (PARS), the Children's Depressive Rating Scale, and the Children's Yale-Brown Obsessive Compulsive Scale. We herein describe new methods for diagnosing and treating anxiety disorders.

Anxiety disorders include, but are not limited to, "generalized anxiety disorder," "social anxiety disorder," "social phobia," "panic attack," "panic disorder," "post-traumatic stress disorder," "agoraphobia," "separation anxiety disorder," "separation anxiety disorder," "anxiety disorder induced by a substance/medication or due to another medical condition," and "selective mutism," among others.

"Generalized anxiety disorder" is excessive worry about a variety of everyday problems occurring more days than not for at least 6 months. "Social anxiety disorder" is a marked fear or anxiety about one or more social situations and is interchangeable with "social phobia". "Panic attacks" are the abrupt onset of intense fear or discomfort associated with symptoms such as heart palpitations, sweating, dizziness, or nausea. "Panic disorder" is diagnosed in patients with recurrent unexpected panic attacks. "Post-traumatic stress disorder" (or "PTSD") is a condition that can occur in people who have been exposed to an actual or threatened death, serious injury, or sexual violence, wherein the individual experiences recurrent distressing memories, flashbacks, psychological distress, and/or physiological reactions to cues following the event. "Agoraphobia" is a condition wherein an individual has marked fear about situations such as being in public spaces, standing in crowds, or being outside of their home alone. "Separation anxiety disorder" is developmentally inappropriate and excessive fear or anxiety concerning separation from those to whom the individual is attached. "Selective mutism" is a condition characterized by consistent failure to speak in specific social situations in which there is an expectation to speak (e.g., in school), despite having the ability to speak in other situations.

Patients with an anxiety disorder may also have inattention, hyperactivity, anxiety, mood, and sleep disturbances.

The terms "subject" and "patient" are used interchangeably to refer to a human. The terms "pediatric subject" or "pediatric patient" are used interchangeably to refer to a human less than 18 years of age. An "adult patient" refers to a human 18 years of age or older. An "adolescent patient" or "adolescent subject" is a subject typically about 12 to 18, such as 12 to 17 or 13 to 18, years old.

In addition to definitions included in this sub-section, further definitions of terms are interspersed throughout the text.

II. Methods of Diagnosing Anxiety Disorders

In some embodiments, the invention comprises methods of diagnosing anxiety disorder in a subject comprising analyzing the genetic information of the subject to determine whether the subject has a genetic variation in at least one mGluR network gene, and diagnosing the subject as having anxiety disorder if a genetic variation is found. In some embodiments, a screen for the presence of mGluR network gene variations is one of two or more tests or evaluations that are performed to diagnose a subject. In some embodiments, the subject has anxiety disorder but does not have ADHD, ODD, conduct disorder, autism, Tourette's syndrome, phobia, obsessive compulsive disorder (OCD), difficulty controlling anger, disruptive behaviors, dermatillomania, a developmental disorder, a mood disorder, a movement disorder, or depression. In some embodiments, the subject has anxiety disorder and also one or more of ADHD, oppositional-defiant disorder (ODD), conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, and depression. In some embodiments, the subject does not have any of ADHD, oppositional-defiant disorder (ODD), conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression. In some embodiments, the subject does not have any of OCD, phobia, or depression. A subject has anxiety rather than anxiety disorder if the symptoms of the disorder have been present for less than six months.

In other embodiments, the invention encompasses confirming a diagnosis of anxiety disorder in a subject. As used herein, "confirming a diagnosis of anxiety disorder" means re-diagnosing a subject who has already been diagnosed with anxiety disorder. In this one embodiment, the method of confirming a diagnosis of anxiety disorder comprises analyzing the genetic information of a subject that has been diagnosed as having anxiety disorder by a method that does not comprise analyzing mGluR network genes, to determine whether the subject has a genetic variation in at least one mGluR network gene, and confirming the diagnosis of anxiety disorder if a genetic variation in at least one mGluR network gene is found. In some embodiments, a screen for the presence of mGluR network gene variations is one of two or more tests or evaluations that are performed to confirm a diagnosis in a subject. In some embodiments, the subject has anxiety disorder but does not have any of ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression. In some embodiments, the subject has anxiety disorder and also one or more of ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, and depression. A subject has anxiety rather than anxiety disorder if the symptoms of the disorder have been present for less than six months.

In another embodiment, the invention comprises confirming a diagnosis of anxiety disorder in a subject who does not have ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression, comprising analyzing the genetic information of a subject that has been diagnosed as having anxiety disorder by a method that does not comprise analyzing mGluR network genes, to determine whether the subject has a genetic variation in at least one mGluR network gene, and confirming the diagnosis of anxiety disorder if a genetic variation in at least one mGluR network gene is found.

In one embodiment, anxiety disorder is diagnosed and/or confirmed if at least one CNV, SNV, frameshift mutation, or any other base pair substitution, insertion, deletion or duplication in an mGluR network gene is detected. In other embodiments, anxiety disorder is diagnosed and/or confirmed if at least one CNV, SNV, frameshift mutation, or any other base pair substitution, insertion, deletion, or duplication in a Tier 1 mGluR network gene is detected. In another embodiment, anxiety disorder is diagnosed and/or confirmed if at least one CNV, SNV, frameshift mutation, or any other base pair substitution, insertion, deletion, or duplication in a Tier 2 mGluR network gene is detected. In still other embodiments, anxiety disorder is diagnosed and/or confirmed if at least one CNV, SNV, frameshift mutation, or any other base pair substitution, insertion, deletion, or duplication in a Tier 3 mGluR network gene is detected.

A diagnosis or confirmation of diagnosis of anxiety disorder may be based or confirmed on finding a genetic alteration in a Tier 1, Tier 2, and/or Tier 3 mGluR network gene. The genetic alteration may be a CNV. The CNV may be a duplication or deletion of a region of DNA that contains some or all of the DNA encoding and controlling/regulating an mGluR network gene. In some embodiments, the diagnosis or confirmation of diagnosis of anxiety disorder is made in a patient who does not have any of ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression. In some embodiments, the diagnosis or confirmation of diagnosis of anxiety disorder is made in a patient who has anxiety disorder and also one or more of ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, and depression.

In some embodiments, the diagnosis or confirmation of diagnosis of anxiety disorder is based on a finding that the copy number of an mGluR network gene deviates from the normal diploid state. In some embodiments, the diagnosis or confirmation of diagnosis of anxiety disorder is based on a copy number of zero or one, which indicates a CNV deletion. In some embodiments, the diagnosis or confirmation of diagnosis of anxiety disorder is based on a copy number of three or greater, which indicates a CNV duplication. In some embodiments, the diagnosis or confirmation of diagnosis of an anxiety disorder is made in a patient who does not have ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression by the presence of a copy number of zero or one, or by a copy number of three or greater, or by any deviation from the diploid state.

In some embodiments, a more severe form of anxiety disorder is diagnosed or confirmed if at least two CNVs in mGluR network genes are detected. In one embodiment, a more severe form of anxiety disorder in a patient who does not have ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression is diagnosed or confirmed if at least two CNVs in mGluR network genes are detected. In one embodiment, a more severe form of anxiety disorder in a patient who also has at least one of ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression is diagnosed or confirmed if at least two CNVs in mGluR network genes are detected.

In one embodiment, a method of diagnosing and/or confirming anxiety disorder comprises obtaining a nucleic acid-containing sample from a subject; optionally amplifying the nucleic acid; optionally labeling the nucleic acid sample; applying the nucleic acid to a solid support that comprises one or more nucleic acids of mGluR network genes, wherein the nucleic acids optionally comprise SNVs of mGluR network genes; removing any unbound nucleic acid sample; and detecting any nucleic acid that has bound to the nucleic acid on the solid support, wherein the subject is diagnosed or confirmed as having anxiety disorder if bound nucleic acids are detected. In one embodiment the method further comprises comparing any bound nucleic acids to a standard or control and diagnosing or confirming anxiety disorder if the analysis finds that the test sample is different from the control or standard. In another embodiment of this method, the patient with anxiety disorder does not have ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression. In another embodiment, the patient with anxiety disorder also has at least one of ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression.

In each diagnostic, confirming, and treatment method of the invention, the anxiety disorder may be generalized anxiety disorder, phobia, social anxiety disorder, social phobia, panic disorder, panic attack, post-traumatic stress disorders, separation anxiety disorder, selective mutism, agoraphobia, or an anxiety disorder induced by a substance/medication or due to another medical condition. In each diagnostic, confirming, and treatment method of the invention, the subject may have an anxiety disorder but not have ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression. In other diagnostic, confirming, and treatment methods of the invention, the subject has anxiety disorder and one or more additional disorders such as ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression.

III. Methods and Uses for Treating Anxiety Disorder

Encompassed herein are methods of treating anxiety disorder in a subject comprising administering an effective amount of a nonselective mGluR activator. The term "treatment," as used herein, includes any administration or application of a therapeutic for a disease or disorder in a subject, and includes inhibiting the disease, arresting its development, relieving the symptoms of the disease, or preventing occurrence or reoccurrence of the disease or symptoms of the disease.

The mGluR proteins are typically placed into three subgroups, group I receptors including mGluR1 and mGluR5 are classed as slow excitatory receptors.

Group II includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

A "nonselective activator of mGluRs" refers to a molecule that activates mGluRs from more than one of the group I, II, and III categories. Thus, a nonselective activator of mGluRs may provide for a general stimulation of the mGluR networks. This is in contrast to specific mGluR activators that may only significantly activate a single mGluR, such as mGluR5, for example. Nonselective mGluR activators also include nonselective mGluR agonists.

In some embodiments, the nonselective mGluR activator is fasoracetam. Fasoracetam is a nootropic (i.e., cognitive-enhancing) drug that can stimulate both group I and group II/III mGluRs in in vitro studies. (See Hirouchi M, et al. (2000) European Journal of Pharmacology 387:9-17.) Fasoracetam may stimulate adenylate cyclase activity through activation of group I mGluRs, while it may also inhibit adenylate cyclase activity by stimulating group II and III mGluRs. (Oka M, et al (1997) Brain Research 754:121-130.) Fasoracetam has been observed to be highly bioavailable (79%-97%) with a half-life of 5-6.5 hours in prior human studies (see Malykh A G, et al. (2010) Drugs 70(3): 287-312). Fasoracetam is a member of the racetam family of chemicals that share a five-carbon oxopyrrolidone ring.

The structure of fasoracetam is:

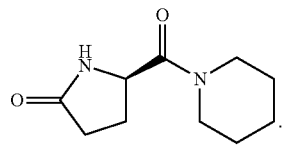 [SMILES: O=C1CC[C@H](C(=O)N2CCCCC2)N1]

The term "fasoracetam" as used herein encompasses pharmaceutically acceptable hydrates and any solid state, amorphous, or crystalline forms of the fasoracetam molecule. For example, the term fasoracetam herein includes forms such as NFC-1: fasoracetam monohydrate. In addition to NFC-1, fasoracetam is also known as C-NS-105, NS105, and LAM-105.

NFC-1 has been previously studied in Phase I-III clinical trials in dementia-related cognitive impairment but did not show sufficient efficacy in dementia in Phase III trials. These trials demonstrated that NFC-1 was generally safe and well tolerated for those indications. Phase III data indicated that NFC-1 showed beneficial effects on psychiatric symptoms in cerebral infarct patients and adult dementia patients with cerebrovascular diseases.

In each of the method of treatment embodiments, a metabotropic glutamate receptor positive allosteric modulator, a metabotropic glutamate receptor negative allosteric modulator, or a tachykinin-3/neurokinin-3 receptor (TACR-3/NK3R) antagonist may be administered alone or in combination with a nonselective activator of mGluRs, for example, to subjects having an alteration in a mGluR network gene. In some embodiments, the treatment agent comprises ADX63365, ADX50938, ADX71149, AMN082, a 1-(hetero)aryl-3-amino-pyrrolidine derivative, LY341495, ADX48621, GSK1144814, or SB223412.

Also encompassed herein are methods of treating anxiety disorder comprising administering fasoracetam to a subject that has a genetic alteration in at least one mGluR network gene. In some embodiments, this subject has anxiety disorder but does not have ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression, while in other embodiments, the subject has anxiety disorder as well as at least one of ADHD, ODD, autism, conduct disorder, Tourette's syndrome, phobia, obsessive compulsive disorder (OCD), difficulty controlling anger, disruptive behavior symptoms, dermatillomania, a developmental disorder, a mood disorder, a movement disorder, or depression.

In some embodiments, the treatment methods comprise identifying or diagnosing a subject as having a genetic alteration in at least one mGluR network gene, and administering a nonselective mGluR activator such as fasoracetam to the identified or diagnosed subject. In some of the embodiments, the subject has anxiety disorder, but does not have ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression. In other embodiments, the subject has anxiety disorder, as well as one or more neuropsychological disorders such as ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, and depression.

In each method of treating embodiment of the invention, the anxiety disorder may be generalized anxiety disorder, phobia, social anxiety disorder, social phobia, panic disorder, panic attack, post-traumatic stress disorders, separation anxiety disorder, selective mutism, agoraphobia, or an anxiety disorder induced by a substance/medication or due to another medical condition. In each method of treating embodiment of the invention, the subject may have an anxiety disorder, but not one or more neuropsychological disorders such as ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, and depression.

In each method of treating embodiment of the invention, the nonselective mGluR activator may improve symptoms of inattention, hyperactivity, anxiety, mood, and sleep disturbances that may be seen in patients with an anxiety disorder.

In one embodiment, the nonselective mGluR activator is administered to a subject that has anxiety disorder and has been confirmed as having at least one genetic alteration in an mGluR network gene. The genetic alteration may be in a Tier 1 mGluR network gene. The genetic alteration may be in a Tier 2 mGluR network gene. The genetic alteration may be in a Tier 3 mGluR network gene. The genetic alteration may be more than one genetic alteration, and the more than one alteration may be in one of Tiers 1, 2, or 3, or in any combination of Tiers.

Some embodiments include a method of treating anxiety disorder comprising obtaining genetic information about a subject's mGluR network genes, and administering a nonselective mGluR activator if the subject has at least one genetic alteration, such as a CNV, in an mGluR network gene. Other embodiments encompass a method of treating anxiety disorder comprising obtaining genetic information about a subject's mGluR network genes, and administering a nonselective mGluR activator if the subject has least one genetic alteration, such as a CNV, in a Tier 1 mGluR network gene.

Other embodiments include a method of treating anxiety disorder comprising obtaining genetic information about a subject's mGluR network genes, and administering a nonselective mGluR activator if the subject has at least one genetic alteration, such as a CNV, in a Tier 2 mGluR network gene. Still other embodiments encompass a method of treating anxiety disorder comprising obtaining genetic information about a subject's mGluR network genes, and administering a nonselective mGluR activator if the subject has at least one genetic alteration, such as a CNV, in a Tier 3 mGluR network gene. Subjects having more than one CNV in any one Tier, or in a combination of any of the three Tiers, may be treated by administering a nonselective mGluR activator. In some embodiments, subjects having anxiety disorder, but not having ADHD, ODD, conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, or depression, may be treated. In other method of treatment embodiments of the invention, the subject has one or more neuropsychological disorders such as ADHD, ODD conduct disorder, autism, Tourette's syndrome, phobia, obsessive compulsive disorder (OCD), difficulty controlling anger, disruptive behavior symptoms, dermatillomania, a developmental disorder, a mood disorder, a movement disorder, and depression in addition to anxiety disorder.

IV. Methods for Determining the Presence or Absence of Genetic Alterations

Any biological sample may be used to determine the presence or absence of mGluR network gene alterations, including, but not limited to, blood, urine, serum, gastric lavage, CNS fluid, any type of cell (such as brain cells, white blood cells, mononuclear cells) or body tissue. Any biological sample whereby DNA can be extracted may be used to determine the presence or absence of mGluR network gene alterations. Samples may be freshly collected, or samples may have been previously collected for any use/purpose and stored until the time of testing for genetic alterations. DNA that was previously purified for a different purpose may also be used.

Various methods for determining genetic alterations are known, including the following:

A. Single Nucleotide Variant (SNV)/Single Nucleotide Polymorphism (SNP) Genotyping Determining whether a patient has a genetic alteration, such as a CNV, in an mGluR network gene may be done by SNP/SNV Genotyping. A "single nucleotide variant (SNV)," also called a "single nucleotide polymorphism (SNP)" herein, refers to a change in which a single base in the DNA differs from the usual base at that position. Millions of SNVs have been cataloged in the human genome. Some SNVs are normal variations in the genome, while others are associated with disease. While specific SNVs may be associated with disease states or susceptibility, high-density SNV genotyping can also be undertaken, whereby sequencing information on SNVs is used to determine the unique genetic makeup of an individual.

In SNV genotyping, SNVs can be determined by hybridizing complementary DNA probes to the SNV site. A wide range of platforms can be used with SNV genotyping tools to accommodate varying sample throughputs, multiplexing capabilities, and chemistries. In high-density SNV arrays, hundreds of thousands of probes are arrayed on a small chip, such that many SNVs can be interrogated simultaneously when target DNA is processed on the chip. By determining the amount of hybridization of target DNA in a sample to a probe (or redundant probes) on the array, specific SNV alleles can be determined. Use of arrays for SNV genotyping allows the large-scale interrogation of SNVs.

When analyzing CNVs, after SNVs have been analyzed, a computer program can be used to manipulate the SNV data to arrive at CNV data. PennCNV or a similar program, can then be used to detect signal patterns across the genome and identify consecutive genetic markers with copy number changes. (See Wang K, et al. (June 2008) Cold Spring Harb Protoc). PennCNV allows for kilobase-resolution detection of CNVs. (See Wang K, et al. (November 2007) Genome Res. 17(11):1665-74).

In CNV analysis, the SNV genotyping data is compared with the behavior of normal diploid DNA. The software uses SNV genotyping data to determine the signal intensity data and SNV allelic ratio distribution and to then use these data to determine when there is deviation from the normal diploid condition of DNA that indicates a CNV. This is done in part by using the log R Ratio (LRR), which is a normalized measure of the total signal intensity for the two alleles of the SNV (Wang 2008). If the software detects regions of contiguous SNVs with intensity (LRR) trending below 0, this indicates a CNV deletion. If the software instead detects regions of contiguous SNVs with intensity (LRR) trending above 0, this indicates a CNV duplication. If no change in LRR is observed compared to the behavior of diploid DNA, the sequence is in the normal diploid state with no CNV present. The software also uses B allele frequency (BAF), a normalized measure of the allelic intensity ratio of two alleles that changes when alleles are lost or gained as with a CNV deletion or duplication. For example, a CNV deletion is indicated by both a decrease in LRR values and a lack of heterozygotes in BAF values. In contrast, a CNV duplication is indicated by both an increase in LRR values and a splitting of the heterozygous genotype BAF clusters into two distinct clusters. The software automates the calculation of LRR and BAF to detect CNV deletions and duplications for whole-genome SNV data. The simultaneous analysis of intensity and genotype data accurately defines the normal diploid state and determines CNVs.

Array platforms such as those from Illumina, Affymetrix, and Agilent may be used in SNV Genotyping. Custom arrays may also be designed and used based on the data described herein.

B. Comparative Genomic Hybridization

Comparative genomic hybridization (CGH) is another method that may be used to evaluate genetic alterations such as CNVs. CGH is a molecular cytogenetic method for analyzing genetic alterations such as CNVs in comparison to a reference sample using competitive fluorescence in situ hybridization (FISH). DNA is isolated from a patient and a reference source and independently labeled with fluorescent molecules (i.e., fluorophores) after denaturation of the DNA. Hybridization of the fluorophores to the resultant samples are compared along the length of each chromosome to identify chromosomal differences between the two sources. A mismatch of colors indicates a gain or loss of material in the test sample in a specific region, while a match of the colors indicates no difference in genetic alterations such as copy number between the test and reference samples at a particular region.

C. Comparative Genomic Hybridization

Whole genome sequencing, whole exome sequencing, or targeted sequencing may also be used to analyze genetic alterations such as CNVs. Whole genome sequencing (also known as full genome sequencing, complete genome sequencing, or entire genome sequencing) involves sequencing of the full genome of a species, including genes that do or do not code for proteins. Whole exome sequencing, in contrast, is sequencing of only the protein-coding genes in the genome (approximately 1% of the genome). Targeted sequencing involves sequencing of only selected parts of the genome.

A wide range of techniques would be known to those skilled in the art to perform whole genome, whole exome, or targeted sequencing with DNA purified from a subject. Similar techniques could be used for different types of sequencing.

Techniques used for whole genome sequencing include nanopore technology, fluorophore technology, DNA nanoball technology, and pyrosequencing (i.e., sequencing by synthesis). In particular, next-generation sequencing (NGS) involves sequencing of millions of small fragments of DNA in parallel followed by use of bioinformatics analyses to piece together sequencing data from the fragments.

As whole exome sequencing does not need to sequence as large an amount of DNA as whole genome sequencing, a wider range of techniques are may be used. Methods for whole exome sequencing include polymerase chain reaction methods, NGS methods, molecular inversion probes, hybrid capture using microarrays, in-solution capture, and classical Sanger sequencing. Targeted sequencing allows for providing sequence data for specific genes rather than whole genomes and can use any of the techniques used for other types of sequencing, including specialized microarrays containing materials for sequencing genes of interest.

D. Other Methods for Determining Genetic Alterations

Proprietary methodologies, such as those from BioNano or OpGen, using genome mapping technology can also be used to evaluate genetic alterations such as CNVs.

Standard molecular biology methodologies such as quantitative polymerase chain reaction (PCR), droplet PCR, and TaqMan probes (i.e., hydrolysis probes designed to increase the specificity of quantitative PCR) can be used to assess genetic alterations such as CNVs. Fluorescent in situ hybridization (FISH) probes may also be used to evaluate genetic alterations such as CNVs. The analysis of genetic alterations such as CNVs present in patients with anxiety is not limited by the precise methods whereby the genetic alterations such as CNVs are determined.

V. Methods for Diagnosing Anxiety Based on CNV Data

In some embodiments, the genetic alteration is a SNV or CNV. The SNV(s) or CNV(s) associated with anxiety disorder are found in an mGluR network gene, such as a gene listed in Tier1, Tier2, or Tier3 as shown in FIGS. 2-4 or a set or panel of such genes.

In some embodiments, gene sets of mGluR network genes are used for analyzing samples from patients with or suspected of having anxiety disorder. In some embodiments, the presence of CNV duplications or deletions within these gene sets or panels is determined. In some embodiments, CNVs in the Tier 1 genes shown in FIG. 2 are determined. In some embodiments a panel of at least 10, at least 20, at least 30, at least 40, at least 50, at least 60, at least 70, or all 76 of the Tier 1 genes is evaluated for the presence of CNVs. Within any such panel of genes, individual, specific Tier 1 genes may be excluded from the analysis set. Any or all of GRM1-8 may be excluded from the panel, for example.

In some embodiments, the Tier 2 genes as shown in FIG. 3 are analyzed for the presence of genetic alterations such as CNVs. Tier 2 genes are those that are tightly associated with mGluRs, but which are not contained within Tier 1.

In some embodiments, the Tier 2 genes are evaluated together with Tier 1 genes. In some embodiments, at least 100 Tier 2 genes are evaluated, while in some embodiments, at least 150, or 197 of the Tier 2 genes are evaluated. Individual, specific Tier 2 genes may be excluded from the gene set for evaluation in some embodiments.

In some embodiments, the 599 Tier 3 genes shown in FIG. 4 are evaluated for genetic alterations such as CNVs. In some embodiments, the Tier 3 genes are evaluated together with Tier 1 and/or Tier 2 genes. In some embodiments, at least 100 Tier 3 genes are evaluated, while in some embodiments, at least 150, 200, 250, 300, 350, 400, 450, or 599 of the Tier 3 genes are evaluated. Individual, specific Tier 3 genes may be excluded from the gene set for evaluation in some embodiments.

VI. Methods of Administration and Combination Therapy

In some embodiments, the agent that modulates mGluR signaling is fasoracetam or fasoracetam monohydrate (also known as C-NS-105, NFC1, NS105, or LAM-105).

A. Dosing

In some embodiments, fasoracetam may be administered as fasoracetam monohydrate (NFC-1). In some embodiments, fasoracetam may be administered by mouth (i.e., per os). In some embodiments, fasoracetam may be administered as capsules. In some embodiments, fasoracetam capsules may contain 50, 60, 70, 80, 90, 100, 110, 120, 125, 130, 135, 140, 145, 150, 155, 160, 165, 170, 175, 180, 185, 190, 195, or 200 mg of fasoracetam monohydrate. In some embodiments, fasoracetam may be dosed once daily or twice daily. In some embodiments, the daily dose of fasoracetam may be 50 mg once-daily, 100 mg once-daily, 200 mg once-daily, 400 mg once-daily, 50 mg twice-daily, 100 mg twice-daily, 200 mg twice-daily, or 400 mg twice-daily. In some embodiments, fasoracetam dosing may be adjusted using a series of dose escalations. In some embodiments, pharmacokinetic data on drug level or clinical response is used to determine changes in dosing. In some embodiments, dose escalation of fasoracetam is not used. In some embodiments, subjects are treated at a dose of fasoracetam expected to be clinically efficacious without a dose-escalation protocol.

B. Combination Therapies

In some embodiments, fasoracetam is used in combination with other agents for the treatment of anxiety disorder. The other agent used in combination with fasoracetam may be an anxiolytic (such as barbiturates, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam), antidepressant (such as fluoxetine, escitalopram, bupropion, mirtazapine, amitriptyline, imipramine, venlafaxine, sertraline, paroxetine, or other compounds in the classes of tricyclic antidepressants, selective serotonin reuptake inhibitors, serotonin and norepinephrine reuptake inhibitors, norepinephrine and dopamine reuptake inhibitors, monoamine oxidase inhibitors, or other drugs approved for the use of depression), or beta-blocker (such as acebutolol, atenolol, betaxolol, bisoprolol, esmolol, nebivolol, metoprolol, cartelol, penbutolol, pindolol, carvedilol, labetalol, levobunolol, metipranolol, nadolol, propranolol, sotalol, timolol, or other selective or nonselective blockers of beta-adrenergic receptors).

In some embodiments, fasoracetam may be used in combination with a non-pharmacologic treatment, such as psychotherapy or brain stimulation therapies. In some embodiments, fasoracetam is used in combination with brain stimulation, which may be vagus nerve stimulation, repetitive transcranial magnetic stimulation, magnetic seizure therapy, deep brain stimulation, or any other therapies involving modulation of brain function by electricity, magnets, or implants.

VII. Articles of Manufacture

In some embodiments, the invention comprises articles of manufacture that may be used in the methods and treatments described herein. In one embodiment, the manufacture is a solid support or microarray for use in detecting genetic alterations in some or all of the mGluR network genes listed in FIGS. 1-3 (i.e., Tiers 1-3). (See also Tables 1-3 herein providing start and stop locations for different mGluR network-related SNPs. This information may be useful in constructing a microarray.) In some embodiments, genes contained in multiple Tiers are assessed within the same solid support or microarray. In some embodiments, certain mGluR network genes are excluded. In some embodiments, the GRM genes are excluded.

Thus, for example, in some embodiments in which mGluR network genes are assayed to determine if there is a genetic alteration in one or more of the genes, such as a CNV, a solid support or microarray, such as on a chip, is used that contains appropriate probes for determining the presence of genetic alterations in 10, 20, 30, 40, 50, 60, 70 or all of the Tier 1 genes. In certain embodiments, the detectable labels are not naturally occurring. In some embodiments, the solid support or microarray may also include appropriate probes for determining the presence of genetic alterations in at least 10, 20, 30, 50, 100, 150, or all of the Tier 2 genes. In some embodiments, it may further include appropriate probes for determining the presence of genetic alterations in at least 10, 20, 50, 100, 200, 300, 400, 500 or all of the Tier 3 genes. For example, such a solid support, microarray, or chip may be used to determine the presence of genetic alterations such as CNVs or SNVs in the Tier 1, Tier 1+2, or Tier 1+2+3 mGluR gene networks as part of a method of treating an ADHD or 22q deletion and/or duplication patient.

In some embodiments, the manufacture is a set of probes for mGluR network genes of interest from Tiers 1, 2, and/or 3. In some embodiments the probes are labelled. Similarly, sets of probes may be manufactured for determining the presence of genetic alterations in 10, 20, 30, 40, 50, 60, 70 or all of the Tier 1 genes. In some embodiments, probes may be manufactured for determining the presence of genetic alterations in at least 10, 20, 30, 50, 100, 150, or all of the Tier 2 genes. In some embodiments, probes may further include those for determining the presence of genetic alterations in at least 10, 20, 50, 100, 200, 300, 400, 500 or all of the Tier 3 genes. These various probe sets may be used in methods of determining the presence of genetic alterations, such as CNVs and SNVs in the Tier 1, Tier 1+2, or Tier 1+2+3 mGluR gene networks as part of a method of treating an ADHD or 22q deletion and/or duplication patient.

EXAMPLE

Example 1

Enrichment of CNV Calls Containing mGluR Network Genes in Samples from Patients with Anxiety Disorders A study of potential enrichment of mGluR network genes was undertaken in patients who had anxiety, phobias, depression, and obsessive-compulsive disorders (OCD). Given the critical role of mGluRs and their signaling networks, changes in copy number of mGluR network genes may provide new approaches for diagnostics or treatments for psychiatric disorders.

Previously, a large-scale genome association study for copy-number variations enriched in patients with ADHD was performed as described in Elia et al., Nature Genetics, 44(1): 78-84 (2012)). Elia's study included about 2,493 patients with ADHD and about 9,222 controls, all of whom were of European ancestry and were between the ages of 6 and 18 years of age. This study noted that the rate of CNVs that contained a mGluR network gene was 1.2% in the control group, and that this rate increased to 11.3% in ADHD patients.

Samples for the present study were selected based on ICP-9 codes for diagnoses of children and adolescents from electronic health records that were treated at the Children's Hospital of Philadelphia (CHOP). All subjects had been evaluated by a pediatric psychiatrist who had entered a diagnosis of anxiety, depression, obsessive-compulsive disorder (OCD), or phobia. FIG. 1 shows the number of patient samples analyzed in each of the anxiety, depression, OCD and phobia groups. Certain patients for each group were fully genotyped as shown in FIG. 1. Data from fully genotyped patients were used for analysis.

Single nucleotide variant (SNV)/single nucleotide polymorphism (SNP) genotype data were used to determine CNVs. SNV genotyping provides a genetic fingerprint of an individual using a large number of SNV markers to provide high-density SNV genotyping data (see Wang K, et al. (November 2007) Genome Res. 17(11):1665-74). Human-Hap550 Genotyping BeadChip™ (Illumina) or Human610-Quad v1.0 BeadChip™ (Illumina) were used in this study. For both chips, the same 520 SNVs were analyzed; therefore, data from these two chips are interchangeable. Standard manufacturer protocols were used for all genotyping assays. Illumina readers were used for all experiments.

SNV genotyping data from each fully genotyped patient sample were analyzed with the PennCNV software to determine the signal intensity data and SNV allelic ratio distribution. These data were then used to determine CNVs via simultaneous analysis of intensity and genotype data (as previously described in Wang 2008). Using this analysis, data indicating a region of loss of contiguous SNVs lead to a call of a CNV deletion. Data indicating a region of gain of contiguous SNVs lead to a call of a CNV duplication. A single individual may have multiple CNV deletions/duplications or may not have any CNVs.

As discussed previously, three tiers of mGluR network genes were developed. FIGS. 2-4 show the genes that are included in the three gene sets—Tier 1 (76 genes) in FIG. 2, Tier 2 (197 genes) in FIG. 3, and Tier 3 (599 genes) in FIG. 4. Note that these gene sets were non-inclusive, so a single gene was only contained in a single Tier.

FIG. 5 shows data on the number of CNV calls in each mGluR gene Tier for the different patient groups. CNVs are either a duplication or deletion. The data indicate that a larger number of CNV calls were seen for each gene set of mGluR network genes in the samples from patients with anxiety as compared to patients with depression, OCD, and phobia.

The percentage of patients who had a CNV call (either duplication or deletion) in each gene set of mGluR network genes is shown in FIG. 6. These data indicate that a substantially higher percentage of patients with anxiety had a CNV call within each of the mGluR network gene sets compared with patients with depression, phobia, or OCD. The control frequency of patients with CNVs in mGluR network genes has previously been estimated in a large study of over 9,000 controls of European ancestry to be 1.2% (see Elia), supporting the specificity of the enrichment of mGluR network genes within CNVs in patients with anxiety disorders. Based on data in the present study, the frequency of patients with OCD, phobia, or depression for CNVs was less than 1.6% for the Tier 1 gene set, while the frequency of patients with CNVs in patients with anxiety was 7.91% for Tier 1, 12.20% for Tier 1 and 2, and 26.65% for Tiers 1, 2, and 3. See FIG. 6.

As indicated in FIGS. 5-6, there was a significant enrichment of mGluR network gene alterations in the patients with anxiety. Therefore, diagnostics and treatments focused on modulation of mGluR gene networks may be of particular use in patients with anxiety disorders.

Example 2

Analysis of mGluR Network Genes Contained within CNVs from Samples of Patients with Anxiety Disorder We next analyzed genotyping data from the 925 fully genotyped patients with anxiety disorder to identify the genes associated with the CNVs. The mGluR network genes that are contained within CNVs from this group of 925 patients are presented as examples of genes within the mGluR network that are contained within CNVs either as duplications or deletions.

Table 1 shows data of representative CNVs from patients with anxiety wherein a Tier 1 mGluR network gene was located within, or in the vicinity of, a CNV in the patient's sample. CNVs can lead to structural changes that affect the transcription of genes located outside of, but in the vicinity of, the CNV. As such, mGluR network genes within one of the Tiers that were located within 500,000 base pairs of a CNV were also included in the analysis. When an mGluR network gene is contained within the listed CNV, this is noted with a "distance from gene" value of 0. When an mGluR network gene is contained in close proximity to a CNV but not within it, this is presented with a "distance from gene" value of greater than 0.

Table 1 lists the chromosome wherein the CNV was located, with its start and stop location in relation to the Human Genome version 19 (hg19). The number of SNVs located within the CNV is noted as "Num SNP," and the length of the CNV is noted in base pairs. The StartSNP and EndSNP of the CNV are also provided.

The "State, CN" column indicates the copy number resulting from the CNV. As normal human DNA (i.e. with no CNV) should be diploid and would have a "State, CN" of 2. CNVs with a "State, CN" of 0 or 1 indicate a copy number deletion. In contrast, CNVs with a "State, CN" of three or greater indicate a copy number duplication.

The confidence value indicates the relative confidence that the call of the CNV is correct. All CNVs included in this analysis had a positive confidence value, indicating a high likelihood that the CNV call is correct. A value of 15 or greater was seen for most CNVs and is considered extremely high confidence in the CNV call based on qPCR and Taqman genotyping validation.

In Table 1, the "mGluR gene" column lists the specific mGluR network gene within Tier 1 contained within the listed CNV. Table 1 is sorted to show all of the CNVs that included a given Tier 1 mGluR network gene. Some Tier 1 genes may be represented in multiple CNVs from different patients in the study, leading to multiple rows for those particular mGluR network genes. Some Tier 1 genes may not have been represented in a CNV from this particular patient population.

Table 2 shows data from specific CNVs that contained a Tier 1 or Tier 2 mGluR network gene. The organization of Table 2 follows that of Table 1. The "mGluR gene" column lists the specific mGluR network gene within Tier 1 or Tier 2 contained within the listed CNV. Table 2 is sorted to show all of the CNVs that included a given Tier 1 or Tier 2 mGluR network gene. Some Tier 1 or Tier 2 genes may be represented in multiple CNVs from different patients in the study, leading to multiple rows for those particular genes. Some Tier 1 or Tier 2 genes may not have been represented in a CNV from this particular patient population.

Table 3 shows data from specific CNVs that contained a Tier 1, 2, or 3 mGluR network gene. The organization of Table 3 follows that of Tables 1 and 2. The "mGluR gene" column lists the specific mGluR network gene within Tier 1, Tier 2, or Tier 3 contained within the listed CNV. Table 3 is sorted to show all the CNVs that included a given Tier 1, 2, or 3 mGluR network gene. Some Tier 1, 2, or 3 genes may be represented in multiple CNVs from different patients in the study, leading to multiple rows for those particular mGluR network genes. Some Tier 1, 2, or 3 genes may not have been represented in a CNV from this particular patient population.

Together, the data in Tables 1-3 indicate that a wide variety of mGluR network genes contained within each Tier are present in CNVs from patients with anxiety. If a larger patient cohort with anxiety phenotype was genotyped, all the genes in Tier-1, Tier-2, and Tier-3 would show enrichment for CNVs in patients with anxiety.

Example 3

Improvements in Anxiety/Mood in ADHD Patients Given Fasoracetam Monohydrate (NFC-1)

An open-label Phase Ib clinical trial was conducted to investigate the safety, pharmacokinetics and efficacy of NFC-1 (fasoracetam monohydrate) in adolescent subjects between the ages of 12 and 17 previously diagnosed with ADHD who also had at least one genetic alteration in an mGluR network gene.

The study included 30 ADHD subjects who were between ages 12 and 17, of any ancestry or race, and of weight within the 5th to 95th percentile for their age, and otherwise judged to be in good medical health. Subjects were genotyped and included in the trial if they possess at least one genetic alteration in the form of at least one copy number variation (deletion or duplication) in an mGluR network gene that potentially disrupts the function of the gene. Seventeen of the 30 subjects have a CNV in a tier 1 mGluR network gene, while 7 subjects have a CNV in a Tier 2 gene and 6 in a Tier 3 gene. At enrollment, several trial subjects showed evidence of co-morbid phenotypes such as anxiety and mood disorders, based on the results of items 19-47 of a parent-conducted Vanderbilt Scale.

Exclusion criteria comprised subjects suffering from a clinically significant illness, either mental or physical, that, in the investigator's opinion, might confound the results of the study or that might prevent them from completing the study, subjects that are pregnant or nursing, subjects that test positive for illicit drugs of that have a history of drug abuse, subjects that consume alcoholic beverages, or subjects for which the investigator is otherwise concerned regarding their compliance or suitability.

NFC-1 capsules of either 50 mg or 200 mg comprising fasoracetam monohydrate as active ingredient and placebo capsules comprising microcellulose were used for the study. The design of the trial was a phone screening (1 day), enrollment phase (1 to 2 days), a wash-out phase for subjects currently on ADHD medications (1-14 days), pharmacokinetic (PK) assessment (2 days), followed by a dose-escalation phase (35 days) and a follow-up phone visit approximately four weeks after the last dose, for a maximum of 127 days. All ADHD medications were discontinued during the wash-out phase prior to the study. The wash-out period for stimulants was 2-3 days and that for atomoxetine or noradrenergic agonists was 10-12 days. No new ADHD medications were started during the study.

A dose-escalation phase of the trial ran over a 5-week period, after the initial wash-out period and the PK and initial safety assessments. During week 1, all subjects were administered placebo capsules twice daily. After one week of placebo treatment, patients were started on 50 mg bid NFC-1 for 1 week. If safety and responsiveness data from prior dose level of fasoracetam indicated it was appropriate, subjects were then escalated to the next higher dose (100, 200, or 400 mg). Subjects who showed tolerance to the 50 mg bid dose as well as response to the drug were to be maintained at that level for the remaining 3 weeks of the trial. Subjects who showed tolerance but lack of response or partial response to the 50 mg bid dose were to be moved up to the next higher dose of 100 mg during the following week. Subjects who showed tolerance at 100 mg but lack of response or partial response were to be moved up to the 200 mg dose the following week while those who showed both tolerance and response at 100 mg were to be kept at 100 mg bid for the remainder of the trial. Similarly, subjects moved up to the 200 mg dose who showed both tolerance and response were to be kept at 200 mg for the final week of the trial while those showing tolerance but lack of response or partial response were moved to a 400 mg dose for the final week. Of the 30 trial subjects, 3 received a maximum dose of 100 mg, 9 received a maximum dose of 200 mg, and the remaining 18 received a maximum dose of 400 mg.

Certain subjects in the study also displayed other co-morbid phenotypes such as anxiety, depression, mood disorders, and sleep disturbances such as insomnia, according to the information recorded in the enrollment and week 1. At enrollment, two subjects had maximum scores of 3 on 2 of the 3 Vanderbilt Scale items (nos. 41, 42, and 47) that are related to anxiety. At week 5, these subjects scored 3 on all 3 items.

Results of a BRIEF scale were also analyzed for changes in anxiety/mood scores in all 30 subjects. The BRIEF scale, performed by parents, requests information on the frequency of the following behaviors:
 1. Over-reacts to small problems;
 6. Upset with new situations;
 7. Explosive-angry outbursts;
 12. Upset by changes in plans;
 13. Disturbed by change of teacher/class;
 20. Easily tearful;
 23. Resists change of routine, foods, plans;
 25. Outbursts for little reason;
 26. Mood changes frequently;
 30. Trouble getting used to new situations;
 45. Reacts more strongly to situations than other children;
 50. Mood easily influenced by situation;
 62. Angry or tearful outbursts are intense but end suddenly;
 64. Small events trigger big reactions; and
 70. Becomes upset too easily.

The answers to these questions are scored as "never," "sometimes," or "often." The BRIEF test was administered at enrollment and again after each week of the dose escalation treatment from placebo week to week 5. All scores for all 30 subjects for each question above were added up for enrollment and week 5, giving 1 point for each "never" or "often" score. It was found that the total "never" score for all questions for all subjects at enrollment was 125 and at week 5 was 191, showing a trend toward improvement. Similarly, the total "often" score at enrollment was 154 while the total "often" score at week 5 was 77, again showing a trend toward improvement in anxiety and mood symptoms in the ADHD subjects.

Example 4

Treatment with Fasoracetam Monohydrate (NFC-1) of ADHD Patients with CNVs in mGluR Network Genes and Impact on Obsessive Compulsive Symptoms Among the 30 ADHD subjects tested in the open-label Phase Ib clinical trial described in Example 2, eight had symptoms of obsessive compulsive-disorder (OCD). One of the subjects with tics also had symptoms of OCD. In all eight subjects, OCD symptoms improved during therapy with NFC-1.

One subject with OCD also had a history of ear scratching (i.e dermatillomania), leading to a bleeding ulcer. The bleeding ulcer healed during therapy with NFC-1, indicating that the subject's dermatillomania symptoms had reduced during NFC-1 therapy.

Example 5

Study of Phenotypes Associated with mGluR Network CNVs

A total of 1,000 ADHD patients aged 6-17 years were enrolled in a trial to consider phenotypes that may be associated with CNVs in Tier 1 or 2 mGluR network genes. Study sites collected saliva for a DNA sample. Each DNA sample was then subjected to DNA extraction, genetic sequencing, and biobanking of DNA.

Genetic sequencing results together with medical history were used to evaluate genotype (based on genetic sequencing) and phenotype (based on interviews conducted by a clinician with the subject's parent(s)/guardian(s)). Subjects had ADHD as defined by the Diagnostic and Statistical Manual of Mental Disorders, 5th Edition (DSM-V).

A single clinician posed a series of questions related to potential behavioral or health phenotypes to the parent(s) or legal guardian(s) of the subjects. For each individual phenotype, the parent/guardian was asked: "Is this a current concern" and a Yes or No answer was collected. The clinician determined the frequency of Yes and No responses to generate phenotype data.

The study found that prevalence of anger control as a current concern for parents was 58.9% in ADHD subjects with a Tier 1 or 2 mGluR network gene CNV but only 47.4% in ADHD subjects without such an mGluR network gene CNV. This difference was statistically significant (odds ratio of 1.59, P=0.003). This odds ratio of greater than 1 implies a higher prevalence of current anger control concerns in parents in ADHD subjects who had a Tier 1 or 2 mGluR network gene CNV versus those without such a CNV.

The prevalence of disruptive behavior as a current concern for parents was 57.1% in ADHD subjects with a Tier 1 or 2 mGluR network gene CNV and 43.9% in ADHD subjects without such an mGluR network gene CNV. This difference was also statistically significant (odds ratio of 1.70, P<0.001), indicating a higher prevalence of current disruptive behavior concerns in parents in ADHD subjects who also had an mGluR network gene mutation versus those without a mutation.

Example 6

Copy Number Variation in mGluR Network Genes in ADHD Subjects with Co-Morbid Disorders Samples from 2707 known ADHD pediatric subjects (mean age of about 10-10.5 years) were genotyped on 550/610 Illumina chips to determine if they have one or more CNVs in Tier 1 or Tier 2 genes. The 2707 subjects included 759 females and 1778 males of African American or white ethnicity (1063 and 1483, respectively). 430 of the 2707 subjects (16.9%) had at least one CNV in an mGluR Tier 1 or Tier 2 gene.

The 2707 subjects' records were also checked to determine if they had co-morbid diagnoses according to the World Health Organization International Classification of Diseases 9th Edition (ICD-9). Of the 2707 subjects, 1902 (about 70%) had comorbidities while 805 did not. Of those 1902 subjects with comorbidities, about 30% had more than one comorbidity, and about 20% had two or more, while smaller percentages had larger numbers of comorbidities.

The most prevalent comorbidities, each occurring in more than 100 of the subjects, are listed in Table 4. The table lists the comorbidities by ICD-9 code and provides the number of cases among the 2707 subjects (column titled "N") and name for each co-morbid condition or disorder.

TABLE 4

| ICD-9 Code | N | Name |
|---|---|---|
| N_299.00 | 342 | Autistic disorder, current or active state |
| N_299.80 | 267 | Other specified pervasive developmental disorders, current or active state |
| N_299.90 | 179 | Unspecified pervasive developmental disorder, current or active state |
| N_300.00 | 407 | Anxiety state unspecified |
| N_311 | 244 | Depressive disorder not elsewhere classified |
| N_312.9 | 568 | Unspecified disturbance of conduct |
| N_313.81 | 313 | Oppositional defiant disorder (ODD) |
| N_314.9 | 120 | Unspecified hyperkinetic syndrome of childhood |
| N_315.2 | 320 | Other specific developmental learning difficulties |
| N_315.31 | 189 | Expressive language disorder |
| N_315.32 | 157 | Mixed receptive-expressive language disorder |
| N_315.39 | 327 | Other developmental speech disorder |
| N_315.4 | 116 | Developmental coordination disorder |
| N_315.5 | 160 | Mixed development disorder |
| N_315.8 | 398 | Other specified delays in development |
| N_315.9 | 479 | Unspecified delay in development |
| N_319 | 110 | Unspecified intellectual disabilities |

The comorbidies in Table 4 tend to cluster into a few different groups: disorders related to anxiety, depression, or mood; prevalent developmental disorders; less prevalent developmental disorders; and autism and related disorders.

The genotype data and the comorbidity data were then combined to determine how many of the subjects with CNVs in Tier 1 or 2 mGluR network genes also had comorbidities. It was found that 316 of the subjects with such a CNV also had at least one comorbidity (about 18% of the CNV-positive subjects or about 12% of the total subjects) while 114 of the subjects without a Tier 1 or 2 mGluR network gene CNV had at least one comorbidity (about 15% of the CNV-negative subjects or about 4% of the total subjects). This difference showed a P value of 0.118. Thus, comorbidities tended to be more common in CNV-positive than in CNV-negative subjects overall. When only subjects identifying as white ethnicity are considered, there was a highly significant correlation between mGluR CNVs and ADHD comorbidities. Specifically, 218 of 1483 subjects had at least one CNV in a Tier 1 or 2 mGluR network gene, and, of those 218 subjects, 169 also had a comorbidity whereas 49 did not. That difference showed a P value of 0.004.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

TABLE 1

| Chr: Start-Stop(hg19) | NumSNP | Length | State, CN | StartSNP | EndSNP | Confidence | Distance From Gene | mGluR Gene |
|---|---|---|---|---|---|---|---|---|
| chr11: 84128537-120941583 | 7678 | 36813047 | 1 | rs488925 | rs4643089 | 29.271 | 0 | ACAT1 |
| chr11: 98062720-121890280 | 5422 | 23827561 | 1 | rs6589308 | rs1944465 | 29.075 | 0 | ACAT1 |
| chr11: 21723471-131521797 | 20508 | 109798327 | 1 | rs11828478 | rs2512898 | 27.565 | 0 | ACAT1 |
| chr11: 42185849-126756938 | 15451 | 84571090 | 1 | rs4375424 | rs10750356 | 36.99 | 0 | ACAT1 |
| chr11: 74545378-134940416 | 14496 | 60395039 | 3 | rs512780 | rs11224228 | 527.758 | 0 | ACAT1 |
| chr17: 21685812-67308196 | 12365 | 45622385 | 1 | rs34864328 | rs17686852 | 50.018 | 0 | ACCN1 |
| chr17: 32104675-32822032 | 239 | 717358 | 4 | rs6505377 | rs213135 | 113.523 | 0 | ACCN1 |
| chr17: 26648492-58955084 | 5831 | 32306593 | 3 | rs1981512 | rs8068776 | 15.642 | 0 | ACCN1 |
| chr2: 34870277-241929621 | 37755 | 207059345 | 3 | rs13422005 | rs10205276 | 46.946 | 0 | ACTR2 |
| chr2: 38101137-241482099 | 36812 | 203380963 | 1 | rs879321 | rs7576043 | 52.099 | 0 | ACTR2 |
| chr2: 12056323-227979775 | 39094 | 215923453 | 1 | rs966391 | rs1922020 | 31.384 | 0 | ACTR2 |
| chr2: 41212010-82396211 | 9721 | 41184202 | 3 | rs12614285 | rs934310 | 396.396 | 0 | ACTR2 |
| chr7: 8794418-119068130 | 23484 | 110273713 | 1 | rs2189621 | rs6977904 | 70.867 | 0 | ADCY1 |
| chr7: 7724805-53845684 | 11772 | 46120880 | 3 | rs10263415 | rs6948633 | 42.007 | 0 | ADCY1 |
| chr7: 8872727-156383359 | 27773 | 147510633 | 1 | rs917038 | rs878717 | 32.336 | 0 | ADCY1 |
| chr7: 11855636-156148608 | 26852 | 144292973 | 1 | rs6947930 | rs6945016 | 36.446 | 0 | ADCY1 |
| chr7: 60392-84158180 | 19095 | 84097789 | 3 | rs12670102 | rs2715048 | 208.308 | 0 | ADCY1 |
| chr11: 23168804-106781292 | 16332 | 83612489 | 1 | rs11027007 | rs7103285 | 49.747 | 0 | ADRBK1 |
| chr11: 66898492-67136981 | 22 | 238490 | 1 | rs11227699 | rs3781941 | 17.955 | 0 | ADRBK1 |
| chr11: 21723471-131521797 | 20508 | 109798327 | 1 | rs11828478 | rs2512898 | 27.565 | 0 | ADRBK1 |
| chr11: 42185849-126756938 | 15451 | 84571090 | 1 | rs4375424 | rs10750356 | 36.99 | 0 | ADRBK1 |
| chr11: 66933410-67046501 | 14 | 113092 | 1 | rs1253784 | rs12274774 | 5.288 | 0 | ADRBK1 |
| chr16: 29441284-33923125 | 585 | 4481842 | 3 | rs7206789 | rs4043755 | 42.437 | 0 | ALDOA |
| chr16: 176743-50013967 | 8328 | 49837225 | 3 | rs2562164 | rs12597023 | 174.392 | 0 | ALDOA |
| chr21: 14601415-48084989 | 8249 | 33483575 | 3 | rs2775537 | rs2839378 | 41.154 | 0 | APP |
| chr21: 14601415-48084989 | 8249 | 33483575 | 3 | rs2775537 | rs2839378 | 12047.211 | 0 | APP |
| chr21: 14595264-48084989 | 8781 | 33489726 | 3 | rs2847443 | rs2839378 | 1871.363 | 0 | APP |
| chr21: 14601415-48084989 | 8249 | 33483575 | 3 | rs2775537 | rs2839378 | 4787.438 | 0 | APP |
| chr21: 14768343-48084989 | 8193 | 33316647 | 3 | rs2257224 | rs2839378 | 5021.076 | 0 | APP |
| chr21: 10708231-47970581 | 8807 | 37262351 | 3 | rs4044122 | rs2255397 | 73.188 | 0 | APP |
| chr5: 49952847-89853069 | 7268 | 39900223 | 3 | rs12188654 | rs42467 | 26.225 | 0 | ARL15 |
| chr5: 39526068-67275356 | 4441 | 27749289 | 1 | rs16869031 | rs999826 | 77.848 | 0 | ARL15 |
| chr5: 52884614-53418318 | 145 | 533705 | 1 | rs524289 | rs9292039 | 31.471 | 0 | ARL15 |
| chr5: 4872310-180709915 | 35876 | 175837606 | 3 | rs816467 | rs10071993 | 179.394 | 0 | ARL15 |
| chr17: 21685812-67308196 | 12365 | 45622385 | 1 | rs34864328 | rs17686852 | 50.018 | 0 | ATXN7L3 |
| chr17: 26648492-58955084 | 5831 | 32306593 | 3 | rs1981512 | rs8068776 | 15.642 | 0 | ATXN7L3 |
| chr14: 26898958-104436931 | 17396 | 77537974 | 1 | rs1245195 | rs11851097 | 57.233 | 0 | BDKRB2 |
| chr14: 80818058-105348552 | 5492 | 24530495 | 3 | rs6574553 | rs2028416 | 15.874 | 0 | BDKRB2 |
| chr14: 65405722-103799039 | 8979 | 38393318 | 3 | rs11623705 | rs11628472 | 266.153 | 0 | BDKRB2 |
| chr8: 60424884-145286483 | 17030 | 84861600 | 3 | rs1401422 | rs9720889 | 8.858 | 0 | CA8 |
| chr8: 60494752-60667231 | 25 | 172480 | 1 | rs12674637 | rs6471803 | 14.25 | 434192 | CA8 |
| chr8: 23218101-146274708 | 23020 | 123056608 | 1 | rs7010362 | rs7822726 | 38.828 | 0 | CA8 |
| chr8: 30757798-142750969 | 20699 | 111993172 | 1 | rs10101203 | rs6421025 | 34.223 | 0 | CA8 |
| chr8: 43235525-66712108 | 3632 | 23476584 | 3 | rs10091311 | rs7001138 | 58.838 | 0 | CA8 |
| chr9: 139492789-140913833 | 196 | 1421045 | 1 | rs28485548 | cnvi0002661 | 28.211 | 0 | CACNA1B |
| chr9: 139821068-141105225 | 163 | 1284158 | 3 | rs3750512 | rs11559363 | 55.611 | 0 | CACNA1B |
| chr1: 79710545-188898319 | 17303 | 109187775 | 1 | rs417181 | rs16829637 | 45.89 | 0 | CACYBP |
| chr1: 75098453-243531649 | 27360 | 168433197 | 1 | rs12117493 | rs10927002 | 32.113 | 0 | CACYBP |
| chr1: 64114301-245591329 | 29842 | 181477029 | 1 | rs11208257 | rs1173850 | 37.504 | 0 | CACYBP |
| chr1: 174219398-247422297 | 15986 | 73202900 | 1 | rs16846809 | rs4642922 | 35.258 | 0 | CACYBP |
| chr1: 109645793-194560463 | 12025 | 84914671 | 3 | cnvi0008281 | rs10921616 | 63.121 | 0 | CACYBP |
| chr14: 26898958-104436931 | 17396 | 77537974 | 1 | rs1245195 | rs11851097 | 57.233 | 0 | CALM1 |
| chr14: 80818058-105348552 | 5492 | 24530495 | 3 | rs6574553 | rs2028416 | 15.874 | 0 | CALM1 |
| chr14: 65405722-103799039 | 8979 | 38393318 | 3 | rs11623705 | rs11628472 | 266.153 | 0 | CALM1 |
| chr1: 178626526-244159143 | 13064 | 65532618 | 3 | rs2761477 | rs479338 | 11.373 | 0 | CHRM3 |
| chr1: 238655362-242087644 | 1078 | 3432283 | 3 | rs2392861 | rs4658565 | 806.215 | 0 | CHRM3 |
| chr1: 75098453-243531649 | 27360 | 168433197 | 1 | rs12117493 | rs10927002 | 32.113 | 0 | CHRM3 |
| chr1: 64114301-245591329 | 29842 | 181477029 | 1 | rs11208257 | rs1173850 | 37.504 | 0 | CHRM3 |
| chr1: 174219398-247422297 | 15986 | 73202900 | 1 | rs16846809 | rs4642922 | 35.258 | 0 | CHRM3 |
| chr1: 236848751-249219320 | 3293 | 12370570 | 3 | rs819666 | cnvi0018731 | 920.725 | 0 | CHRM3 |
| chr19: 31569338-53780966 | 3788 | 22211629 | 1 | rs2867544 | rs10407424 | 33.9 | 0 | CIC |
| chr19: 288246-59110628 | 11009 | 58822383 | 3 | rs10409452 | cnvi0009466 | 100.582 | 0 | CIC |
| chr17: 21685812-67308196 | 12365 | 45622385 | 1 | rs34864328 | rs17686852 | 50.018 | 0 | CNP |
| chr17: 26648492-58955084 | 5831 | 32306593 | 3 | rs1981512 | rs8068776 | 15.642 | 0 | CNP |
| chr3: 1850547-2114929 | 103 | 264383 | 3 | rs4543005 | rs9880266 | 402.844 | 25621 | CNTN4 |
| chr3: 1819843-1962536 | 66 | 142694 | 1 | rs9875417 | rs4685465 | 225.117 | 178014 | CNTN4 |
| chr3: 234726-6328031 | 2293 | 6093356 | 3 | rs7632811 | rs1595039 | 106.207 | 0 | CNTN4 |
| chr3: 179527-114630641 | 23879 | 114451115 | 3 | rs4684741 | rs1587972 | 207.852 | 0 | CNTN4 |
| chr3: 1818056-1981567 | 55 | 163512 | 1 | rs7624354 | rs1488757 | 186.651 | 158983 | CNTN4 |
| chr17: 21685812-67308196 | 12365 | 45622385 | 1 | rs34864328 | rs17686852 | 50.018 | 0 | CRHR1 |
| chr17: 43657921-44064851 | 65 | 406870 | 3 | rs9898857 | rs8079215 | 86.447 | 0 | CRHR1 |
| chr17: 43657921-44354796 | 88 | 696876 | 3 | rs9898857 | rs2732700 | 21.196 | 0 | CRHR1 |
| chr17: 26648492-58955084 | 5831 | 32306593 | 3 | rs1981512 | rs8068776 | 15.642 | 0 | CRHR1 |
| chr2: 34870277-241929621 | 37755 | 207059345 | 3 | rs13422005 | rs10205276 | 46.946 | 0 | CTNNA2 |
| chr2: 77041264-194763754 | 21140 | 117722491 | 1 | rs2102827 | rs16835406 | 94.091 | 0 | CTNNA2 |
| chr2: 38101137-241482099 | 36812 | 203380963 | 1 | rs879321 | rs7576043 | 52.099 | 0 | CTNNA2 |

TABLE 1-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr2: 12056323-227979775 | 39094 | 215923453 | 1 | rs966391 | rs1922020 | 31.384 | 0 | CTNNA2 |
| chr2: 41212010-82396211 | 9721 | 41184202 | 3 | rs12614285 | rs934310 | 396.396 | 0 | CTNNA2 |
| chr1: 178626526-244159143 | 13064 | 65532618 | 3 | rs2761477 | rs479338 | 11.373 | 0 | DISC1 |
| chr1: 188850774-235423607 | 10060 | 46572834 | 1 | rs16824466 | rs12409696 | 43.25 | 0 | DISC1 |
| chr1: 191875752-235423607 | 9517 | 43547856 | 1 | rs9427811 | rs12409696 | 62.01 | 0 | DISC1 |
| chr1: 231711489-231813134 | 28 | 101646 | 3 | rs1765782 | rs6541281 | 70.39 | 0 | DISC1 |
| chr1: 231711489-231813134 | 22 | 101646 | 3 | rs1765782 | rs6541281 | 42.561 | 0 | DISC1 |
| chr1: 75098453-243531649 | 27360 | 168433197 | 1 | rs12117493 | rs10927002 | 32.113 | 0 | DISC1 |
| chr1: 64114301-245591329 | 29842 | 181477029 | 1 | rs11208257 | rs1173850 | 37.504 | 0 | DISC1 |
| chr1: 174219398-247422297 | 15986 | 73202900 | 1 | rs16846809 | rs4642922 | 35.258 | 0 | DISC1 |
| chr1: 226536645-236803753 | 2600 | 10267109 | 3 | rs874583 | rs10925178 | 100.109 | 0 | DISC1 |
| chr7: 78621315-155831817 | 13678 | 77210503 | 3 | rs1006818 | rs6969015 | 123.319 | 0 | DPP6 |
| chr7: 153503148-153662151 | 40 | 159004 | 3 | rs2622200 | rs4726357 | 86.109 | 0 | DPP6 |
| chr7: 153843805-153946551 | 29 | 102747 | 3 | rs9690764 | rs9640345 | 36.97 | 0 | DPP6 |
| chr7: 153694399-153811655 | 11 | 117257 | 3 | rs10235799 | rs3115192 | 13.736 | 0 | DPP6 |
| chr7: 8872727-156383359 | 27773 | 147510633 | 1 | rs917038 | rs878717 | 32.336 | 0 | DPP6 |
| chr7: 11855636-156148608 | 26852 | 144292973 | 1 | rs6947930 | rs6945016 | 36.446 | 0 | DPP6 |
| chr7: 143807304-158827326 | 3603 | 15020023 | 1 | rs10252253 | rs2071624 | 54.584 | 0 | DPP6 |
| chr12: 59512781-127744939 | 13469 | 68232159 | 3 | rs908394 | rs7966946 | 20.62 | 0 | DYNLL1 |
| chr12: 10020267-129866293 | 23654 | 119846027 | 1 | rs1597097 | rs2170504 | 45.428 | 0 | DYNLL1 |
| chr12: 112610714-133708729 | 5366 | 21098016 | 3 | rs11066306 | rs11147249 | 695.45 | 0 | DYNLL1 |
| chr12: 50855195-133778796 | 17748 | 82923602 | 3 | rs4351895 | rs7975069 | 159.589 | 0 | DYNLL1 |
| chr19: 43257015-55294329 | −7309 | 12037315 | 3 | rs7246152 | rs2569676 | 21.402 | 0 | FPR1 |
| chr19: 31569338-53780966 | 3788 | 22211629 | 1 | rs2867544 | rs10407424 | 33.9 | 0 | FPR1 |
| chr19: 288246-59110628 | 11009 | 58822383 | 3 | rs10409452 | cnvi0009466 | 100.582 | 0 | FPR1 |
| chr12: 6562293-6711147 | 27 | 148855 | 1 | rs2041385 | rs1639122 | 19.307 | 0 | GAPDH |
| chr12: 6485661-6711147 | 48 | 225487 | 1 | rs3759324 | rs1639122 | 18.66 | 0 | GAPDH |
| chr12: 207886-50770291 | 11565 | 50562406 | 3 | rs868249 | rs4477515 | 43.892 | 0 | GAPDH |
| chr19: 266034-18063908 | 3100 | 17795476 | 3 | rs2312724 | rs7250332 | 19.51 | 0 | GNA15 |
| chr19: 629303-4119012 | 709 | 3489710 | 1 | rs2283575 | rs350887 | 26.758 | 0 | GNA15 |
| chr19: 288246-59110628 | 11009 | 58822383 | 3 | rs10409452 | cnvi0009466 | 100.582 | 0 | GNA15 |
| chr3: 33409611-170735099 | 23775 | 137325489 | 1 | rs3915062 | rs11924032 | 26.867 | 0 | GNAI2 |
| chr3: 13878889-149737330 | 24723 | 135858442 | 1 | rs12634112 | rs2007869 | 55.663 | 0 | GNAI2 |
| chr3: 179527-114630641 | 23879 | 114451115 | 3 | rs4684741 | rs1587972 | 207.852 | 0 | GNAI2 |
| chr16: 50219449-89544756 | 10324 | 39325308 | 3 | rs6500298 | rs3803681 | 108.108 | 0 | GNAO1 |
| chr9: 2522475-140068342 | 25719 | 137545868 | 3 | rs10966757 | rs4074426 | 93.386 | 0 | GNAQ |
| chr9: 33180228-132003792 | 14691 | 98823565 | 1 | rs7854765 | rs9408988 | 28.69 | 0 | GNAQ |
| chr9: 1989033-107532317 | 18263 | 105543285 | 1 | rs7864828 | rs10820726 | 39.824 | 0 | GNAQ |
| chr9: 46587-94335290 | 17484 | 94288704 | 3 | rs10814410 | rs9409606 | 762.393 | 0 | GNAQ |
| chr21: 14601415-48084989 | 8249 | 33483575 | 3 | rs2775537 | rs2839378 | 41.154 | 0 | GRIK1 |
| chr21: 30057145-31992864 | 372 | 1935720 | 1 | rs6516861 | rs1702405 | 41.668 | 0 | GRIK1 |
| chr21: 14601415-48084989 | 8249 | 33483575 | 3 | rs2775537 | rs2839378 | 12047.211 | 0 | GRIK1 |
| chr21: 14595264-48084989 | 8781 | 33489726 | 3 | rs2847443 | rs2839378 | 1871.363 | 0 | GRIK1 |
| chr21: 14601415-48084989 | 8249 | 33483575 | 3 | rs2775537 | rs2839378 | 4787.438 | 0 | GRIK1 |
| chr21: 14768343-48084989 | 8193 | 33316647 | 3 | rs2257224 | rs2839378 | 5021.076 | 0 | GRIK1 |
| chr21: 10708231-47970581 | 8807 | 37262351 | 3 | rs4044122 | rs2255397 | 73.188 | 0 | GRIK1 |
| chr1: 1005806-105612342 | 19173 | 104606537 | 3 | rs3934834 | rs1584633 | 44.152 | 0 | GRIK3 |
| chr1: 2006108-109527861 | 22130 | 107521754 | 3 | rs2254669 | rs839879 | 162.269 | 0 | GRIK3 |
| chr6: 73120320-165130872 | 18715 | 92010553 | 1 | rs9442780 | rs10946016 | 76.383 | 0 | GRM1 |
| chr6: 73120320-165130872 | 18715 | 92010553 | 1 | rs9442780 | rs10946016 | 76.383 | 0 | GRM1 |
| chr6: 94117546-165103679 | 15579 | 70986134 | 1 | rs3799792 | rs9347902 | 34.066 | 0 | GRM1 |
| chr6: 94117546-165103679 | 15579 | 70986134 | 1 | rs3799792 | rs9347902 | 34.066 | 0 | GRM1 |
| chr6: 66609532-147053632 | 15315 | 80444101 | 3 | rs9354335 | rs4896886 | 44.941 | 0 | GRM1 |
| chr6: 66609532-147053632 | 15315 | 80444101 | 3 | rs9354335 | rs4896886 | 44.941 | 0 | GRM1 |
| chr6: 66541198-162520133 | 19344 | 95978936 | 1 | rs2000382 | rs6901071 | 27.509 | 0 | GRM1 |
| chr6: 66541198-162520133 | 19344 | 95978936 | 1 | rs2000382 | rs6901071 | 27.509 | 0 | GRM1 |
| chr6: 64844594-169078546 | 21567 | 104233953 | 1 | rs4710465 | rs601639 | 46.524 | 0 | GRM1 |
| chr6: 64844594-169078546 | 21567 | 104233953 | 1 | rs4710465 | rs601639 | 46.524 | 0 | GRM1 |
| chr6: 67621368-147709180 | 16188 | 80087813 | 1 | rs6919455 | rs7739314 | 52.498 | 0 | GRM1 |
| chr6: 67621368-147709180 | 16188 | 80087813 | 1 | rs6919455 | rs7739314 | 52.498 | 0 | GRM1 |
| chr6: 100082983-170909002 | 16393 | 70826020 | 3 | rs594231 | rs12213906 | 261.313 | 0 | GRM1 |
| chr6: 100082983-170909002 | 16393 | 70826020 | 3 | rs594231 | rs12213906 | 261.313 | 0 | GRM1 |
| chr7: 78621315-155831817 | 13678 | 77210503 | 3 | rs1006818 | rs6969015 | 123.319 | 0 | GRM3 |
| chr7: 8794418-119068130 | 23484 | 110273713 | 3 | rs2189621 | rs6977904 | 70.867 | 0 | GRM3 |
| chr7: 85117732-86026526 | 122 | 908795 | 1 | rs4728584 | rs10242995 | 65.094 | 246704 | GRM3 |
| chr7: 8872727-156383359 | 27773 | 147510633 | 1 | rs917038 | rs878717 | 32.336 | 0 | GRM3 |
| chr7: 11855636-156148608 | 26852 | 144292973 | 1 | rs6947930 | rs6945016 | 36.446 | 0 | GRM3 |
| chr7: 84302877-110993169 | 5183 | 26690293 | 3 | rs4338048 | rs10254893 | 203.09 | 0 | GRM3 |
| chr11: 23168804-106781292 | 16332 | 83612489 | 1 | rs11027007 | rs7103285 | 49.747 | 0 | GRM5 |
| chr11: 23168804-106781292 | 16332 | 83612489 | 1 | rs11027007 | rs7103285 | 49.747 | 0 | GRM5 |
| chr11: 84128537-120941583 | 7678 | 36813047 | 1 | rs488925 | rs4643089 | 29.271 | 0 | GRM5 |
| chr11: 84128537-120941583 | 7678 | 36813047 | 1 | rs488925 | rs4643089 | 29.271 | 0 | GRM5 |
| chr11: 81251505-103234729 | 4842 | 21983225 | 3 | rs7935238 | rs1913462 | 26.176 | 0 | GRM5 |
| chr11: 81251505-103234729 | 4842 | 21983225 | 3 | rs7935238 | rs1913462 | 26.176 | 0 | GRM5 |
| chr11: 21723471-131521797 | 20508 | 109798327 | 1 | rs11828478 | rs2512898 | 27.565 | 0 | GRM5 |
| chr11: 21723471-131521797 | 20508 | 109798327 | 1 | rs11828478 | rs2512898 | 27.565 | 0 | GRM5 |

TABLE 1-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr11: 42185849-126756938 | 15451 | 84571090 | 1 | rs4375424 | rs10750356 | 36.99 | 0 | GRM5 |
| chr11: 42185849-126756938 | 15451 | 84571090 | 1 | rs4375424 | rs10750356 | 36.99 | 0 | GRM5 |
| chr11: 74545378-134940416 | 14496 | 60395039 | 3 | rs512780 | rs11224228 | 527.758 | 0 | GRM5 |
| chr11: 74545378-134940416 | 14496 | 60395039 | 3 | rs512780 | rs11224228 | 527.758 | 0 | GRM5 |
| chr3: 5824878-8781331 | 952 | 2956454 | 3 | rs2470628 | rs11916022 | 924.891 | 0 | GRM7 |
| chr3: 5824878-8781331 | 952 | 2956454 | 3 | rs2470628 | rs11916022 | 924.891 | 0 | GRM7 |
| chr3: 179527-114630641 | 23879 | 114451115 | 3 | rs4684741 | rs1587972 | 207.852 | 0 | GRM7 |
| chr3: 179527-114630641 | 23879 | 114451115 | 3 | rs4684741 | rs1587972 | 207.852 | 0 | GRM7 |
| chr7: 78621315-155831817 | 13678 | 77210503 | 3 | rs1006818 | rs6969015 | 123.319 | 0 | GRM8 |
| chr7: 78621315-155831817 | 13678 | 77210503 | 3 | rs1006818 | rs6969015 | 123.319 | 0 | GRM8 |
| chr7: 8872727-156383359 | 27773 | 147510633 | 1 | rs917038 | rs878717 | 32.336 | 0 | GRM8 |
| chr7: 8872727-156383359 | 27773 | 147510633 | 1 | rs917038 | rs878717 | 32.336 | 0 | GRM8 |
| chr7: 11855636-156148608 | 26852 | 144292973 | 1 | rs6947930 | rs6945016 | 36.446 | 0 | GRM8 |
| chr7: 11855636-156148608 | 26852 | 144292973 | 1 | rs6947930 | rs6945016 | 36.446 | 0 | GRM8 |
| chr7: 125676925-125780682 | 24 | 103758 | 1 | rs1419535 | rs10267757 | 26.358 | 297970 | GRM8 |
| chr7: 125676925-125780682 | 24 | 103758 | 1 | rs1419535 | rs10267757 | 26.358 | 297970 | GRM8 |
| chr7: 120061880-143606234 | 4616 | 23544355 | 3 | rs12531689 | rs10247493 | 18.96 | 0 | GRM8 |
| chr7: 120061880-143606234 | 4616 | 23544355 | 3 | rs12531689 | rs10247493 | 18.96 | 0 | GRM8 |
| chr9: 2522475-140068342 | 25719 | 137545868 | 3 | rs10966757 | rs4074426 | 93.386 | 0 | GSN |
| chr9: 33180228-132003792 | 14691 | 98823565 | 1 | rs7854765 | rs9408988 | 28.69 | 0 | GSN |
| chr9: 100158052-139077343 | 9815 | 38919292 | 3 | rs1020884 | rs4842126 | 470.601 | 0 | GSN |
| chr5: 49952847-89853069 | 7268 | 39900223 | 3 | rs12188654 | rs42467 | 26.225 | 0 | HOMER1 |
| chr5: 57343495-171903310 | 21683 | 114559816 | 1 | rs10940593 | rs10042482 | 61.169 | 0 | HOMER1 |
| chr5: 78520731-78765405 | 35 | 244675 | 1 | rs4704546 | rs7710089 | 12.78 | 0 | HOMER1 |
| chr5: 78542290-79057477 | 95 | 515188 | 1 | rs10474578 | rs259126 | 38.26 | 0 | HOMER1 |
| chr5: 4872310-180709915 | 35876 | 175837606 | 3 | rs816467 | rs10071993 | 179.394 | 0 | HOMER1 |
| chr13: 19584477-81204088 | 13265 | 61619612 | 3 | rs1334954 | rs1176297 | 22.162 | 0 | HTR2A |
| chr13: 23742931-115064482 | 19829 | 91321552 | 1 | rs4770401 | rs7999630 | 44.074 | 0 | HTR2A |
| chr13: 36707502-103656104 | 13622 | 66948603 | 1 | rs3827890 | rs1952590 | 38.726 | 0 | HTR2A |
| chr13: 47300055-47409034 | 48 | 108980 | 1 | rs1539177 | rs6314 | 25.525 | 0 | HTR2A |
| chr13: 19121741-63373781 | 10326 | 44252041 | 3 | rs9578050 | rs9539575 | 82.761 | 0 | HTR2A |
| chr4: 68173959-185767176 | 20235 | 117593218 | 1 | rs6552083 | rs4862428 | 61.893 | 0 | LARP7 |
| chr4: 63726348-173015421 | 19871 | 109289074 | 1 | rs17082970 | rs2131002 | 30.251 | 0 | LARP7 |
| chr4: 29179713-117038307 | 15513 | 87858595 | 1 | rs1507441 | rs1068807 | 71.6 | 0 | LARP7 |
| chr4: 89603085-113991140 | 4018 | 24388056 | 3 | rs2972038 | rs2279892 | 28.405 | 0 | LARP7 |
| chr4: 22401728-188608857 | 28456 | 166207130 | 1 | rs4697297 | rs7687115 | 35.717 | 0 | LARP7 |
| chr4: 31222833-180548076 | 24457 | 149325244 | 1 | rs7662351 | rs3849606 | 36.162 | 0 | LARP7 |
| chr4: 113385223-113578609 | 25 | 193387 | 1 | cnvi0012240 | rs1129065 | 19.233 | 0 | LARP7 |
| chr4: 69590353-190872778 | 23145 | 121282426 | 3 | rs293433 | rs12646565 | 315.633 | 0 | LARP7 |
| chr22: 16871137-51184393 | 9245 | 34313257 | 3 | rs131538 | rs7284680 | 209.79 | 0 | MAPK1 |
| chr14: 26898958-104436931 | 17396 | 77537974 | 1 | rs1245195 | rs11851097 | 57.233 | 0 | MTHFD1 |
| chr14: 64926097-65063315 | 19 | 137219 | 1 | rs2281603 | rs10134770 | 14.377 | 0 | MTHFD1 |
| chr14: 19917123-65327288 | 10286 | 45410166 | 3 | rs2495197 | rs9323455 | 270.291 | 0 | MTHFD1 |
| chr21: 14601415-48084989 | 8249 | 33483575 | 3 | rs2775537 | rs2839378 | 41.154 | 0 | MX1 |
| chr21: 14601415-48084989 | 8249 | 33483575 | 3 | rs2775537 | rs2839378 | 12047.211 | 0 | MX1 |
| chr21: 14595264-48084989 | 8781 | 33489726 | 3 | rs2847443 | rs2839378 | 1871.363 | 0 | MX1 |
| chr21: 14601415-48084989 | 8249 | 33483575 | 3 | rs2775537 | rs2839378 | 4787.438 | 0 | MX1 |
| chr21: 14768343-48084989 | 8193 | 33316647 | 3 | rs2257224 | rs2839378 | 5021.076 | 0 | MX1 |
| chr21: 10708231-47970581 | 8807 | 37262351 | 3 | rs4044122 | rs2255397 | 73.188 | 0 | MX1 |
| chr1: 1005806-105612342 | 19173 | 104606537 | 3 | rs3934834 | rs1584633 | 44.152 | 0 | NEGR1 |
| chr1: 64114301-245591329 | 29842 | 181477029 | 1 | rs11208257 | rs1173850 | 37.504 | 0 | NEGR1 |
| chr1: 72606418-72717743 | 14 | 111326 | 1 | rs1385919 | rs1776012 | 17.335 | 0 | NEGR1 |
| chr1: 2006108-109527861 | 22130 | 107521754 | 3 | rs2254669 | rs839879 | 162.269 | 0 | NEGR1 |
| chr5: 49952847-89853069 | 7268 | 39900223 | 3 | rs12188654 | rs42467 | 26.225 | 0 | NLN |
| chr5: 57343495-171903310 | 21683 | 114559816 | 1 | rs10940593 | rs10042482 | 61.169 | 0 | NLN |
| chr5: 39526068-67275356 | 4441 | 27749289 | 1 | rs16869031 | rs999826 | 77.848 | 0 | NLN |
| chr5: 4872310-180709915 | 35876 | 175837606 | 3 | rs816467 | rs10071993 | 179.394 | 0 | NLN |
| chr2: 34870277-241929621 | 37755 | 207059345 | 3 | rs13422005 | rs10205276 | 46.946 | 0 | NMI |
| chr2: 77041264-194762754 | 21140 | 117722491 | 1 | rs2102827 | rs16835406 | 94.091 | 0 | NMI |
| chr2: 38101137-241482099 | 36812 | 203380963 | 1 | rs879321 | rs7576043 | 52.099 | 0 | NMI |
| chr2: 12056323-227979775 | 39094 | 215923453 | 1 | rs966391 | rs1922020 | 31.384 | 0 | NMI |
| chr2: 83383702-175194550 | 16291 | 91810849 | 3 | rs12469609 | rs11891208 | 154.4 | 0 | NMI |
| chr21: 14601415-48084989 | 8249 | 33483575 | 3 | rs2775537 | rs2839378 | 41.154 | 0 | PCBP3 |
| chr21: 44839153-47856106 | 674 | 3016954 | 1 | rs2838302 | rs2236616 | 38.158 | 0 | PCBP3 |
| chr21: 47091361-47226895 | 18 | 135535 | 1 | rs2838973 | rs2839002 | 14.709 | 0 | PCBP3 |
| chr21: 14601415-48084989 | 8249 | 33483575 | 3 | rs2775537 | rs2839378 | 12047.211 | 0 | PCBP3 |
| chr21: 14595264-48084989 | 8781 | 33489726 | 3 | rs2847443 | rs2839378 | 1871.363 | 0 | PCBP3 |
| chr21: 14601415-48084989 | 8249 | 33483575 | 3 | rs2775537 | rs2839378 | 4787.438 | 0 | PCBP3 |
| chr21: 46381900-48098560 | 448 | 1716661 | 1 | rs8132265 | cnvi0019195 | 712.68 | 0 | PCBP3 |
| chr21: 14768343-48084989 | 8193 | 33316647 | 3 | rs2257224 | rs2839378 | 5021.076 | 0 | PCBP3 |
| chr21: 10708231-47970581 | 8807 | 37262351 | 3 | rs4044122 | rs2255397 | 73.188 | 0 | PCBP3 |
| chr7: 8794418-119068130 | 23484 | 110273713 | 1 | rs2189621 | rs6977904 | 70.867 | 0 | PDE1C |
| chr7: 7724805-53845684 | 11772 | 46120880 | 3 | rs10263415 | rs6948633 | 42.007 | 0 | PDE1C |
| chr7: 8872727-156383359 | 27773 | 147510633 | 1 | rs917038 | rs878717 | 32.336 | 0 | PDE1C |
| chr7: 11855636-156148608 | 26852 | 144292973 | 1 | rs6947930 | rs6945016 | 36.446 | 0 | PDE1C |
| chr7: 60392-84158180 | 19095 | 84097789 | 3 | rs12670102 | rs2715048 | 208.308 | 0 | PDE1C |

TABLE 1-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr19: 43257015-55294329 | −7309 | 12037315 | 3 | rs7246152 | rs2569676 | 21.402 | 0 | PPP2R1A |
| chr19: 52365654-54612628 | 524 | 2246975 | 3 | rs4514789 | rs254262 | 59.657 | 0 | PPP2R1A |
| chr19: 31569338-53780966 | 3788 | 22211629 | 1 | rs2867544 | rs10407424 | 33.9 | 0 | PPP2R1A |
| chr19: 288246-59110628 | 11009 | 58822383 | 3 | rs10409452 | cnvi0009466 | 100.582 | 0 | PPP2R1A |
| chr17: 44458950-81047708 | −8195 | 36588759 | 1 | cnvi0016818 | rs35680231 | 35.591 | 0 | PRPSAP1 |
| chr17: 62662507-81047708 | −11496 | 18385202 | 3 | rs6504246 | rs35680231 | 56.048 | 0 | PRPSAP1 |
| chr17: 21685812-67308196 | 12365 | 45622385 | 1 | rs34864328 | rs17686852 | 50.018 | 0 | PSMD11 |
| chr17: 26648492-58955084 | 5831 | 32306593 | 3 | rs1981512 | rs8068776 | 15.642 | 0 | PSMD11 |
| chr11: 211482-66910826 | 13813 | 66699345 | 3 | rs2293168 | rs4375446 | 30.249 | 0 | PSMD13 |
| chr12: 59512781-127744939 | 13469 | 68232159 | 3 | rs908394 | rs7966946 | 20.62 | 0 | PXN |
| chr12: 10020267-129866293 | 23654 | 119846027 | 1 | rs1597097 | rs2170504 | 45.428 | 0 | PXN |
| chr12: 112610714-133708729 | 5366 | 21098016 | 3 | rs11066188 | rs11147249 | 695.45 | 0 | PXN |
| chr12: 50855195-133778796 | 17748 | 82923602 | 3 | rs4351895 | rs7975069 | 159.589 | 0 | PXN |
| chr17: 44458950-81047708 | −8195 | 36588759 | 1 | cnvi0016818 | rs35680231 | 35.591 | 0 | QRICH2 |
| chr17: 62662507-81047708 | −11496 | 18385202 | 3 | rs6504246 | rs35680231 | 56.048 | 0 | QRICH2 |
| chr22: 18907405-21465780 | 610 | 2558376 | 3 | rs9618419 | rs11703181 | 1799.961 | 0 | RANBP1 |
| chr22: 19601238-20241160 | 201 | 639923 | 3 | rs8135473 | rs1567871 | 11.687 | 0 | RANBP1 |
| chr22: 18877787-21462353 | 613 | 2584567 | 1 | rs2543958 | rs140392 | 772.063 | 0 | RANBP1 |
| chr22: 18877787-21462353 | 512 | 2584567 | 1 | rs2543958 | rs140392 | 1596.687 | 0 | RANBP1 |
| chr22: 16871137-51184393 | 9245 | 34313257 | 3 | rs131538 | rs7284680 | 209.79 | 0 | RANBP1 |
| chr13: 87746779-104646511 | 3908 | 16899733 | 3 | rs9301986 | rs17414312 | 27.724 | 0 | RAP2A |
| chr13: 90018392-105190802 | 4136 | 15172411 | 1 | rs7335222 | rs11841281 | 42.954 | 0 | RAP2A |
| chr13: 23742931-115064482 | 19829 | 91321552 | 1 | rs4770401 | rs7999630 | 44.074 | 0 | RAP2A |
| chr13: 36707502-103656104 | 13622 | 66948603 | 1 | rs3827890 | rs1952590 | 38.726 | 0 | RAP2A |
| chr13: 65193124-115053155 | 12025 | 49860032 | 3 | rs9598811 | rs7327124 | 78.057 | 0 | RAP2A |
| chr1: 1005806-105612342 | 19173 | 104606537 | 3 | rs3934834 | rs1584633 | 44.152 | 0 | RCC1 |
| chr1: 2006108-109527861 | 22130 | 107521754 | 3 | rs2254669 | rs839879 | 162.269 | 0 | RCC1 |
| chr4: 179131-68998153 | 13495 | 68819023 | 3 | rs7686948 | rs7687396 | 625.133 | 0 | RGS12 |
| chr2: 34870277-241929621 | 37755 | 207059345 | 3 | rs13422005 | rs10205276 | 46.946 | 0 | RIF1 |
| chr2: 77041264-194763754 | 21140 | 117722491 | 1 | rs2102827 | rs16835406 | 94.091 | 0 | RIF1 |
| chr2: 38101137-241482099 | 36812 | 203380963 | 1 | rs879321 | rs7576043 | 52.099 | 0 | RIF1 |
| chr2: 12056323-227979775 | 39094 | 215923453 | 1 | rs966391 | rs1922020 | 31.384 | 0 | RIF1 |
| chr2: 83383702-175194550 | 16291 | 91810849 | 3 | rs12469609 | rs11891208 | 154.4 | 0 | RIF1 |
| chr19: 43257015-55294329 | −7309 | 12037315 | 3 | rs7246152 | rs2569676 | 21.402 | 0 | RUVBL2 |
| chr19: 31569338-53780966 | 3788 | 22211629 | 1 | rs2867544 | rs10407424 | 33.9 | 0 | RUVBL2 |
| chr19: 288246-59110628 | 11009 | 58822383 | 3 | rs10409452 | cnvi0009466 | 100.582 | 0 | RUVBL2 |
| chr19: 31569338-53780966 | 3788 | 22211629 | 1 | rs2867544 | rs10407424 | 33.9 | 0 | RYR1 |
| chr19: 288246-59110628 | 11009 | 58822383 | 3 | rs10409452 | cnvi0009466 | 100.582 | 0 | RYR1 |
| chr1: 178626526-244159143 | 13064 | 65532618 | 3 | rs2761477 | rs479338 | 11.373 | 0 | RYR2 |
| chr1: 237570457-237675464 | 37 | 105008 | 1 | rs4659495 | rs2618721 | 15.007 | 0 | RYR2 |
| chr1: 75098453-243531649 | 27360 | 168433197 | 1 | rs12117493 | rs10927002 | 32.113 | 0 | RYR2 |
| chr1: 64114301-245591329 | 29842 | 181477029 | 1 | rs11208257 | rs1173850 | 37.504 | 0 | RYR2 |
| chr1: 174219398-247422297 | 15986 | 73202900 | 1 | rs16846809 | rs4642922 | 35.258 | 0 | RYR2 |
| chr1: 237584925-237904870 | 86 | 319946 | 1 | rs4593814 | rs10925504 | 31.95 | 0 | RYR2 |
| chr1: 236848751-249219320 | 3293 | 12370570 | 3 | rs819666 | cnvi0018731 | 920.725 | 0 | RYR2 |
| chr1: 1005806-105612342 | 19173 | 104606537 | 3 | rs3934834 | rs1584633 | 44.152 | 0 | SDC3 |
| chr1: 2006108-109527861 | 22130 | 107521754 | 3 | rs2254669 | rs839879 | 162.269 | 0 | SDC3 |
| chr1: 79710545-188898319 | 17303 | 109187775 | 1 | rs417181 | rs16829637 | 45.89 | 0 | SELE |
| chr1: 169556446-171300348 | 340 | 1743903 | 1 | rs9332480 | rs7541160 | 32.81 | 0 | SELE |
| chr1: 75098453-243531649 | 27360 | 168433197 | 1 | rs12117493 | rs10927002 | 32.113 | 0 | SELE |
| chr1: 64114301-245591329 | 29842 | 181477029 | 1 | rs11208257 | rs1173850 | 37.504 | 0 | SELE |
| chr1: 109645793-194560463 | 12025 | 84914671 | 3 | cnvi0008281 | rs10921616 | 63.121 | 0 | SELE |
| chr6: 2681610-31453618 | 81 | 28772009 | 3 | rs1131896 | rs9267212 | 428.177 | 0 | SERPINB9 |
| chr6: 2585208-31281876 | −2 | 28696669 | 1 | rs1634748 | rs1634747 | 31.615 | 0 | SERPINB9 |
| chr6: 1171596-29899147 | 47 | 28727552 | 0 | rs3128994 | rs2394704 | 63.572 | 0 | SERPINB9 |
| chr6: 1175965-29899147 | 43 | 28723183 | 0 | rs1611522 | rs2394704 | 52.089 | 0 | SERPINB9 |
| chr6: 1171596-29895228 | 43 | 28723633 | 0 | rs3128994 | rs9259831 | 53.123 | 0 | SERPINB9 |
| chr6: 1171596-29899147 | 47 | 28727552 | 0 | rs3128994 | rs2394704 | 80.695 | 0 | SERPINB9 |
| chr6: 1177990-29899147 | 39 | 28721158 | 0 | rs2428530 | rs2394704 | 44.381 | 0 | SERPINB9 |
| chr6: 2681610-31453618 | 81 | 28772009 | 3 | rs1131896 | rs9267212 | 390.234 | 0 | SERPINB9 |
| chr6: 2584569-31286381 | 8 | 28701813 | 1 | rs9391764 | rs9265057 | 34.598 | 0 | SERPINB9 |
| chr6: 1171596-29892436 | 39 | 28720841 | 1 | rs3128994 | rs9259806 | 31.699 | 0 | SERPINB9 |
| chr6: 1171596-29895228 | 43 | 28723633 | 0 | rs3128994 | rs9259831 | 43.568 | 0 | SERPINB9 |
| chr6: 181089-30430875 | 1806 | 30249787 | 3 | rs1535053 | rs35792611 | 80.394 | 0 | SERPINB9 |
| chr21: 14601415-48084989 | 8249 | 33483575 | 3 | rs2775537 | rs2839378 | 41.154 | 0 | SETD4 |
| chr21: 36927793-37647438 | 142 | 719646 | 3 | rs2205031 | rs9980084 | 187.28 | 0 | SETD4 |
| chr21: 14601415-48084989 | 8249 | 33483575 | 3 | rs2775537 | rs2839378 | 12047.211 | 0 | SETD4 |
| chr21: 14595264-48084989 | 8781 | 33489726 | 3 | rs2847443 | rs2839378 | 1871.363 | 0 | SETD4 |
| chr21: 14601415-48084989 | 8249 | 33483575 | 3 | rs2775537 | rs2839378 | 4787.438 | 0 | SETD4 |
| chr21: 14768343-48084989 | 8193 | 33316647 | 3 | rs2257224 | rs2839378 | 5021.076 | 0 | SETD4 |
| chr21: 10708231-47970581 | 8807 | 37262351 | 3 | rs4044122 | rs2255397 | 73.188 | 0 | SETD4 |
| chr5: 49952847-89853069 | 7268 | 39900223 | 3 | rs12188654 | rs42467 | 26.225 | 0 | SGTB |
| chr5: 57343495-171903310 | 21683 | 114559816 | 1 | rs10940593 | rs10042482 | 61.169 | 0 | SGTB |
| chr5: 39526068-67275356 | 4441 | 27749289 | 1 | rs16869031 | rs999826 | 77.848 | 0 | SGTB |
| chr5: 4872310-180709915 | 35876 | 175837606 | 3 | rs816467 | rs10071993 | 179.394 | 0 | SGTB |
| chr19: 43257015-55294329 | −7309 | 12037315 | 3 | rs7246152 | rs2569676 | 21.402 | 0 | SHANK1 |

TABLE 1-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr19: 31569338-53780966 | 3788 | 22211629 | 1 | rs2867544 | rs10407424 | 33.9 | 0 | SHANK1 |
| chr19: 288246-59110628 | 11009 | 58822383 | 3 | rs10409452 | cnvi0009466 | 100.582 | 0 | SHANK1 |
| chr19: 31569338-53780966 | 3788 | 22211629 | 1 | rs2867544 | rs10407424 | 33.9 | 0 | SLC7A10 |
| chr19: 288246-59110628 | 11009 | 58822383 | 3 | rs10409452 | cnvi0009466 | 100.582 | 0 | SLC7A10 |
| chr15: 29325866-56044189 | 5303 | 26718324 | 3 | rs4779705 | rs2414433 | 21.732 | 0 | SORD |
| chr15: 44763598-47394943 | 502 | 2631346 | 3 | rs7172106 | rs4095484 | 142.088 | 0 | SORD |
| chr15: 43392075-66051345 | 4963 | 22659271 | 3 | rs8028608 | rs6494537 | 59.842 | 0 | SORD |
| chr2: 8171838-32535863 | 5853 | 24364026 | 3 | rs11609309 | rs7963182 | 23.697 | 0 | STRAP |
| chr12: 10020267-129866293 | 23654 | 119846027 | 1 | rs1597097 | rs2170504 | 45.428 | 0 | STRAP |
| chr12: 10113083-116370432 | 20594 | 106257350 | 1 | rs2012504 | rs7958254 | 35.157 | 0 | STRAP |
| chr12: 207886-50770291 | 11565 | 50562406 | 3 | rs868249 | rs4477515 | 43.892 | 0 | STRAP |
| chr17: 75730493-79302149 | 880 | 3571657 | 3 | rs7210773 | rs2864474 | 14.319 | 0 | TK1 |
| chr17: 44458950-81047708 | −8195 | 36588759 | 1 | cnvi0016818 | rs35680231 | 35.591 | 0 | TK1 |
| chr17: 62662507-81047708 | −11496 | 18385202 | 1 | rs6504246 | rs35680231 | 56.048 | 0 | TK1 |
| chr3: 145967173-173899890 | 4912 | 27932718 | 3 | rs9863647 | rs7618997 | 46.396 | 0 | TNIK |
| chr3: 164955741-191742104 | 5741 | 26786364 | 1 | rs2218152 | rs9835019 | 52.438 | 0 | TNIK |
| chr3: 83075971-196935657 | 21465 | 113859687 | 1 | rs9872858 | rs34729751 | 44.35 | 0 | TNIK |
| chr3: 102240202-195550366 | 17318 | 93310165 | 1 | rs1620217 | rs11711870 | 41.031 | 0 | TNIK |
| chr3: 166503411-190576461 | 4854 | 24073051 | 1 | rs11925936 | rs1393054 | 31.414 | 0 | TNIK |
| chr3: 114889454-177826047 | 12700 | 62936594 | 3 | rs6795297 | rs7628308 | 102.526 | 0 | TNIK |
| chr1: 1005806-105612342 | 19173 | 104606537 | 3 | rs3934834 | rs1584633 | 44.152 | 0 | USP24 |
| chr1: 2006108-109527861 | 22130 | 107521754 | 3 | rs2254669 | rs839879 | 162.269 | 0 | USP24 |
| chr3: 179527-114630641 | 23879 | 114451115 | 3 | rs4684741 | rs1587972 | 207.852 | 0 | VHL |

TABLE 2

| Chr: Start-Stop(hg19) | NumSNP | Length | State, CN | StartSNP | EndSNP | Confidence | Distance From Gene | mGluR Gene |
|---|---|---|---|---|---|---|---|---|
| chr11: 42185849-126756938 | 15451 | 84571090 | 1 | rs4375424 | rs10750356 | 36.99 | 0 | ACAT1 |
| chr11: 21723471-131521797 | 20508 | 109798327 | 1 | rs11828478 | rs2512898 | 27.565 | 0 | ACAT1 |
| chr11: 84128537-120941583 | 7678 | 36813047 | 1 | rs488925 | rs4643089 | 29.271 | 0 | ACAT1 |
| chr11: 98062720-121890280 | 5422 | 23827561 | 1 | rs6589308 | rs1944465 | 29.075 | 0 | ACAT1 |
| chr11: 74545378-134940416 | 14496 | 60395039 | 3 | rs512780 | rs11224228 | 527.758 | 0 | ACAT1 |
| chr6: 64844594-169078546 | 21567 | 104233953 | 1 | rs4710465 | rs601639 | 46.524 | 0 | ACAT2 |
| chr6: 66541198-162520133 | 19344 | 95978936 | 1 | rs2000382 | rs6901071 | 27.509 | 0 | ACAT2 |
| chr6: 73120320-165130872 | 18715 | 92010553 | 1 | rs9442780 | rs10946016 | 76.383 | 0 | ACAT2 |
| chr6: 94117546-165103679 | 15579 | 70986134 | 1 | rs3799792 | rs9347902 | 34.066 | 0 | ACAT2 |
| chr6: 151495383-165969396 | 3761 | 14474010 | 3 | rs9322304 | rs1022180 | 22.826 | 0 | ACAT2 |
| chr6: 100082983-170909002 | 16393 | 70826020 | 3 | rs594231 | rs12213906 | 261.313 | 0 | ACAT2 |
| chr17: 32104675-32822032 | 239 | 717358 | 4 | rs6505377 | rs213135 | 113.523 | 0 | ACCN1 |
| chr17: 21685812-67308196 | 12365 | 45622385 | 1 | rs34864328 | rs17686852 | 50.018 | 0 | ACCN1 |
| chr17: 26648492-58955084 | 5831 | 32306593 | 3 | rs1981921 | rs8068776 | 15.642 | 0 | ACCN1 |
| chr12: 10113083-116370432 | 20594 | 106257350 | 1 | rs2012504 | rs7958254 | 35.157 | 0 | ACCN2 |
| chr12: 10020267-129866293 | 23654 | 119846027 | 1 | rs1597097 | rs2170504 | 45.428 | 0 | ACCN2 |
| chr12: 39967134-84174413 | 8879 | 44207280 | 1 | rs11172661 | rs11116039 | 39.568 | 0 | ACCN2 |
| chr12: 207886-50770291 | 11565 | 50562406 | 3 | rs868249 | rs4477515 | 43.892 | 0 | ACCN2 |
| chr2: 18856-41136833 | 9721 | 41117978 | 3 | rs11901199 | rs10187704 | 191.638 | 0 | ACP1 |
| chr7: 60392-84158180 | 19095 | 84097789 | 3 | rs12670102 | rs2715048 | 208.308 | 0 | ACTB |
| chr2: 12056323-227979775 | 39094 | 215923453 | 1 | rs966391 | rs1922020 | 31.384 | 0 | ACTR2 |
| chr2: 38101137-241482099 | 36812 | 203380963 | 1 | rs879321 | rs7576043 | 52.099 | 0 | ACTR2 |
| chr2: 34870277-241929621 | 37755 | 207059345 | 3 | rs13422005 | rs10205276 | 46.946 | 0 | ACTR2 |
| chr2: 41212010-82396211 | 9721 | 41184202 | 3 | rs12614285 | rs934310 | 396.396 | 0 | ACTR2 |
| chr20: 13712393-55093901 | 8218 | 41381509 | 1 | rs6033810 | rs6999 | 41.237 | 0 | ADA |
| chr20: 4591715-58420336 | 11753 | 53828622 | 1 | rs6139494 | rs1416388 | 40.922 | 0 | ADA |
| chr20: 7869205-62424661 | 11941 | 54555637 | 3 | rs2294306 | rs6010672 | 9.732 | 0 | ADA |
| chr20: 236802-54845796 | 12646 | 54608995 | 3 | rs448294 | rs6064362 | 286.151 | 0 | ADA |
| chr7: 11855636-156148608 | 26852 | 144292973 | 1 | rs6947930 | rs6945016 | 36.446 | 0 | ADCY1 |
| chr7: 8872727-156383359 | 27773 | 147510633 | 1 | rs917038 | rs878717 | 32.336 | 0 | ADCY1 |
| chr7: 8794418-119068130 | 23484 | 110273713 | 1 | rs2189621 | rs6977904 | 70.867 | 0 | ADCY1 |
| chr7: 7724805-53845684 | 11772 | 46120880 | 3 | rs10263415 | rs6948633 | 42.007 | 0 | ADCY1 |
| chr7: 60392-84158180 | 19095 | 84097789 | 3 | rs12670102 | rs2715048 | 208.308 | 0 | ADCY1 |
| chr4: 179131-68998153 | 13495 | 68819023 | 3 | rs7686948 | rs7687396 | 625.133 | 0 | ADD1 |
| chr2: 12056323-227979775 | 39094 | 215923453 | 1 | rs966391 | rs1922020 | 31.384 | 0 | ADD2 |
| chr2: 38101137-241482099 | 36812 | 203380963 | 1 | rs879321 | rs7576043 | 52.099 | 0 | ADD2 |
| chr2: 34870277-241929621 | 37755 | 207059345 | 3 | rs13422005 | rs10205276 | 46.946 | 0 | ADD2 |
| chr2: 41212010-82396211 | 9721 | 41184202 | 3 | rs12614285 | rs934310 | 396.396 | 0 | ADD2 |
| chr1: 64114290-245591329 | 29842 | 181477029 | 1 | rs11208257 | rs1173805 | 37.504 | 0 | ADORA1 |
| chr1: 75098453-243531649 | 27360 | 168433197 | 1 | rs12117493 | rs10927002 | 32.113 | 0 | ADORA1 |
| chr1: 189128124-227340790 | 7927 | 38212667 | 1 | rs7515205 | rs12752546 | 167.428 | 0 | ADORA1 |
| chr1: 178626526-244159143 | 13064 | 65532618 | 3 | rs2761477 | rs479338 | 11.373 | 0 | ADORA1 |
| chr1: 188850774-235423607 | 10060 | 46572834 | 1 | rs16829466 | rs12409696 | 43.25 | 0 | ADORA1 |
| chr1: 191875752-235423607 | 9517 | 43547856 | 1 | rs9427811 | rs12409696 | 62.01 | 0 | ADORA1 |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr1: 174219398-247422297 | 15986 | 73202900 | 1 | rs16846809 | rs4642922 | 35.258 | 0 | ADORA1 |
| chr1: 197187605-226404457 | 6316 | 29216853 | 3 | rs10922187 | rs3008192 | 130.989 | 0 | ADORA1 |
| chr5: 84830796-171903310 | 16642 | 87072515 | 1 | rs300657 | rs10042482 | 42.208 | 0 | ADRA1B |
| chr5: 57343495-171903310 | 21683 | 114559816 | 1 | rs10940593 | rs10042482 | 61.169 | 0 | ADRA1B |
| chr5: 4872310-180709915 | 35876 | 175837606 | 3 | rs816467 | rs10071993 | 179.394 | 0 | ADRA1B |
| chr10: 7188484-134205354 | 26672 | 127016871 | 1 | rs1977295 | rs3923858 | 50.772 | 0 | ADRA2A |
| chr10: 57671424-133349223 | 16243 | 75677800 | 1 | rs11005106 | rs4301710 | 37.114 | 0 | ADRA2A |
| chr10: 58385643-124973104 | 13625 | 66587462 | 1 | rs7920235 | rs17663304 | 36.18 | 0 | ADRA2A |
| chr10: 55492162-117205017 | 13465 | 61712856 | 1 | rs6481032 | rs1933664 | 62.56 | 0 | ADRA2A |
| chr10: 53602190-135522754 | 19167 | 81920565 | 3 | rs12247820 | rs10909028 | 139.373 | 0 | ADRA2A |
| chr4: 179131-68998153 | 13495 | 68819023 | 3 | rs7686948 | rs7687396 | 625.133 | 0 | ADRA2C |
| chr5: 84830796-171903310 | 16642 | 87072515 | 1 | rs300657 | rs10042482 | 42.208 | 0 | ADRB2 |
| chr5: 57343495-171903310 | 21683 | 114559816 | 1 | rs10940593 | rs10042482 | 61.169 | 0 | ADRB2 |
| chr5: 98442871-150317237 | 9828 | 51874367 | 1 | rs1447379 | rs7710790 | 38.687 | 0 | ADRB2 |
| chr5: 4872310-180709915 | 35876 | 175837606 | 3 | rs816467 | rs10071993 | 179.394 | 0 | ADRB2 |
| chr11: 42185849-126756938 | 15451 | 84571090 | 1 | rs4375424 | rs10750356 | 36.99 | 0 | ADRBK1 |
| chr11: 21723471-131521797 | 20508 | 109798327 | 1 | rs11828478 | rs2512898 | 27.565 | 0 | ADRBK1 |
| chr11: 23168804-106781292 | 16332 | 83612489 | 1 | rs11027007 | rs7103285 | 49.747 | 0 | ADRBK1 |
| chr11: 66898492-67136981 | 22 | 238490 | 1 | rs11227699 | rs3781941 | 17.955 | 0 | ADRBK1 |
| chr11: 66933410-67046501 | 14 | 113092 | 1 | rs1253784 | rs12274774 | 5.288 | 0 | ADRBK1 |
| chr16: 29441284-33923125 | 585 | 4481842 | 3 | rs7206789 | rs4043755 | 42.437 | 0 | ALDOA |
| chr16: 176743-50013967 | 8328 | 49837225 | 3 | rs2562326 | rs12597023 | 174.392 | 0 | ALDOA |
| chr9: 1989033-107532317 | 18263 | 105543285 | 1 | rs7864828 | rs10820726 | 39.824 | 0 | ANXA2 |
| chr9: 33180228-132003792 | 14691 | 98823565 | 1 | rs7854765 | rs9408988 | 28.69 | 0 | ANXA2 |
| chr15: 51688996-102398060 | 11030 | 50709065 | 1 | rs2459396 | rs7181527 | 36.939 | 0 | ANXA2 |
| chr9: 2522475-140068342 | 25719 | 137545868 | 3 | rs10966757 | rs4074426 | 93.386 | 0 | ANXA2 |
| chr15: 53775670-96810867 | 9973 | 43035198 | 1 | rs657495 | rs2589238 | 49.204 | 0 | ANXA2 |
| chr9: 46587-94335290 | 17484 | 94288704 | 3 | rs10814410 | rs9409606 | 762.393 | 0 | ANXA2 |
| chr15: 43392075-66051345 | 4963 | 22659271 | 3 | rs8028608 | rs6494537 | 59.842 | 0 | ANXA2 |
| chr21: 14601415-48084989 | 8249 | 33483575 | 3 | rs2775537 | rs2839378 | 12047.211 | 0 | APP |
| chr21: 14601415-48084989 | 8249 | 33483575 | 3 | rs2775537 | rs2839378 | 41.154 | 0 | APP |
| chr21: 14595264-48084989 | 8781 | 33489726 | 3 | rs2847443 | rs2839378 | 1871.363 | 0 | APP |
| chr21: 14601415-48084989 | 8249 | 33483575 | 3 | rs2775537 | rs2839378 | 4787.438 | 0 | APP |
| chr21: 14768343-48084989 | 8193 | 33316647 | 3 | rs2257224 | rs2839378 | 5021.076 | 0 | APP |
| chr21: 10708231-47970581 | 8807 | 37262351 | 3 | rs4044122 | rs2255397 | 73.188 | 0 | APP |
| chr9: 1989033-107532317 | 18263 | 105543285 | 1 | rs7864828 | rs10820726 | 39.824 | 0 | APTX |
| chr9: 2522475-140068342 | 25719 | 137545868 | 3 | rs10966757 | rs4074426 | 93.386 | 0 | APTX |
| chr9: 46587-94335290 | 17484 | 94288704 | 3 | rs10814410 | rs9409606 | 762.393 | 0 | APTX |
| chr7: 11855636-156148608 | 26852 | 144292973 | 1 | rs6947930 | rs6945016 | 36.446 | 0 | AQP1 |
| chr7: 8872727-156383359 | 27773 | 147510633 | 1 | rs917038 | rs878717 | 32.336 | 0 | AQP1 |
| chr7: 8794418-119068130 | 23484 | 110273713 | 1 | rs2189621 | rs6977904 | 70.867 | 0 | AQP1 |
| chr7: 7724805-53845684 | 11772 | 46120880 | 3 | rs10263415 | rs6948633 | 42.007 | 0 | AQP1 |
| chr7: 60392-84158180 | 19095 | 84097789 | 3 | rs12670102 | rs2715048 | 208.308 | 0 | AQP1 |
| chr4: 31222833-180548076 | 24457 | 149325244 | 1 | rs7662351 | rs3849606 | 36.162 | 0 | ARHGAP24 |
| chr4: 22401728-188608857 | 28456 | 166207130 | 1 | rs4697297 | rs7687115 | 35.717 | 0 | ARHGAP24 |
| chr4: 68173959-185767176 | 20235 | 117593218 | 1 | rs6552083 | rs4862428 | 61.893 | 0 | ARHGAP24 |
| chr4: 63726348-173015421 | 19817 | 109289074 | 1 | rs17082970 | rs2131002 | 30.251 | 0 | ARHGAP24 |
| chr4: 29179713-117038307 | 15513 | 87858595 | 1 | rs1507441 | rs1068807 | 71.6 | 0 | ARHGAP24 |
| chr4: 69590353-190872778 | 23145 | 121282426 | 3 | rs293433 | rs12646565 | 315.633 | 0 | ARHGAP24 |
| chr5: 39526068-67275356 | 4441 | 27749289 | 1 | rs16869031 | rs999826 | 77.848 | 0 | ARL15 |
| chr5: 49952247-89853069 | 7268 | 39900223 | 3 | rs12188654 | rs42467 | 26.225 | 0 | ARL15 |
| chr5: 52884614-53418318 | 145 | 533705 | 1 | rs524289 | rs9292039 | 31.471 | 0 | ARL15 |
| chr5: 4872310-180709915 | 35876 | 175837606 | 3 | rs816467 | rs10071993 | 179.394 | 0 | ARL15 |
| chr11: 42185849-126756938 | 15451 | 84571090 | 1 | rs4375424 | rs10750356 | 36.99 | 0 | ARRB1 |
| chr11: 21723471-131521797 | 20508 | 109798327 | 1 | rs11828478 | rs2512898 | 27.565 | 0 | ARRB1 |
| chr11: 23168804-106781292 | 16332 | 83612489 | 1 | rs11027007 | rs7103285 | 49.747 | 0 | ARRB1 |
| chr11: 74545378-134940416 | 14496 | 60395039 | 1 | rs512780 | rs11224228 | 527.758 | 0 | ARRB1 |
| chr17: 108420-26610769 | 5548 | 26502350 | 3 | rs12452527 | rs658591 | 82.699 | 0 | ARRB2 |
| chr17: 21685812-67308196 | 12365 | 45622385 | 1 | rs34864328 | rs17686852 | 50.018 | 0 | ATXN7L3 |
| chr17: 26648492-58955084 | 5831 | 32306593 | 3 | rs1981512 | rs8068776 | 15.642 | 0 | ATXN7L3 |
| chr14: 26898958-104436931 | 17396 | 77537974 | 1 | rs1245195 | rs11851097 | 57.233 | 0 | BDKRB1 |
| chr14: 80818058-105348552 | 5492 | 24530495 | 1 | rs6574553 | rs2028416 | 15.874 | 0 | BDKRB1 |
| chr14: 65405722-103799039 | 8979 | 38393318 | 1 | rs11623705 | rs11628472 | 266.153 | 0 | BDKRB1 |
| chr14: 26898958-104436931 | 17396 | 77537974 | 1 | rs1245195 | rs11851097 | 57.233 | 0 | BDKRB2 |
| chr14: 80818058-105348552 | 5492 | 24530495 | 1 | rs6574553 | rs2028416 | 15.874 | 0 | BDKRB2 |
| chr14: 65405722-103799039 | 8979 | 38393318 | 1 | rs11623705 | rs11628472 | 266.153 | 0 | BDKRB2 |
| chr19: 629303-4119012 | 709 | 3489710 | 1 | rs2283575 | rs350887 | 26.758 | 0 | BTBD2 |
| chr19: 266034-18061509 | 3100 | 17795476 | 3 | rs2312724 | rs7250332 | 19.51 | 0 | BTBD2 |
| chr19: 1130986-2128054 | 143 | 997069 | 1 | rs10413074 | rs1017084 | 25.799 | 0 | BTBD2 |
| chr19: 288246-59110628 | 11009 | 58822383 | 3 | rs10409452 | cnvi0009466 | 100.582 | 0 | BTBD2 |
| chr1: 64114301-245591329 | 29842 | 181477029 | 1 | rs11208257 | rs1173850 | 37.504 | 0 | BTG2 |
| chr1: 75098524-243531649 | 27360 | 168433197 | 1 | rs12117493 | rs10927002 | 32.113 | 0 | BTG2 |
| chr1: 189128124-227340790 | 7927 | 38212667 | 1 | rs7515205 | rs12752546 | 167.428 | 0 | BTG2 |
| chr1: 178626526-244159143 | 13064 | 65532618 | 3 | rs2761477 | rs479338 | 11.373 | 0 | BTG2 |
| chr1: 188850774-235423607 | 10060 | 46572834 | 1 | rs16829466 | rs12409696 | 43.25 | 0 | BTG2 |
| chr1: 191875752-235423607 | 9517 | 43547856 | 1 | rs9427811 | rs12409696 | 62.01 | 0 | BTG2 |
| chr1: 174219398-247422297 | 15986 | 73202900 | 1 | rs16846809 | rs4642922 | 35.258 | 0 | BTG2 |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr1: 197187605-226404457 | 6316 | 29216853 | 3 | rs10922187 | rs3008192 | 130.989 | 0 | BTG2 |
| chr1: 64114301-245591329 | 29842 | 181477029 | 1 | rs11208257 | rs1173850 | 37.504 | 0 | C1orf116 |
| chr1: 75098453-243531649 | 27360 | 168433197 | 1 | rs12117493 | rs10927002 | 32.113 | 0 | C1orf116 |
| chr1: 189128124-227340790 | 7927 | 38212667 | 1 | rs7515205 | rs12752546 | 167.428 | 0 | C1orf116 |
| chr1: 178626526-244159143 | 13064 | 65532618 | 3 | rs2761477 | rs479338 | 11.373 | 0 | C1orf116 |
| chr1: 188850774-235423607 | 10060 | 46572834 | 1 | rs16829466 | rs12409696 | 43.25 | 0 | C1orf116 |
| chr1: 191875752-235423607 | 9517 | 43547856 | 1 | rs9427811 | rs12409696 | 62.01 | 0 | C1orf116 |
| chr1: 174219398-247422297 | 15986 | 73202900 | 1 | rs16846809 | rs4642922 | 35.258 | 0 | C1orf116 |
| chr1: 197187605-226404457 | 6316 | 29216853 | 3 | rs10922187 | rs3008192 | 130.989 | 0 | C1orf116 |
| chr7: 11855636-156148608 | 26852 | 144292973 | 1 | rs6947930 | rs6945016 | 36.446 | 0 | C7orf25 |
| chr7: 8872727-156383359 | 27773 | 147510633 | 1 | rs917038 | rs878717 | 32.336 | 0 | C7orf25 |
| chr7: 8794418-119068130 | 23484 | 110273713 | 1 | rs2189621 | rs6977904 | 70.867 | 0 | C7orf25 |
| chr7: 7724805-53845684 | 11772 | 46120880 | 3 | rs10263415 | rs6948633 | 42.007 | 0 | C7orf25 |
| chr7: 60392-84158180 | 19095 | 84097789 | 3 | rs12670102 | rs2715048 | 208.308 | 0 | C7orf25 |
| chr8: 30757798-142750969 | 20699 | 111993172 | 1 | rs10101203 | rs6421025 | 34.223 | 0 | CA8 |
| chr8: 23218101-146274708 | 23020 | 123056608 | 1 | rs7010362 | rs7822726 | 38.828 | 0 | CA8 |
| chr8: 60424884-145286483 | 17030 | 84861600 | 3 | rs1401422 | rs9720889 | 8.858 | 0 | CA8 |
| chr8: 60494757-60667231 | 25 | 172480 | 1 | rs12674637 | rs6471803 | 14.25 | 434192 | CA8 |
| chr8: 43235525-66712108 | 3632 | 23476584 | 3 | rs10091311 | rs7001138 | 58.838 | 0 | CA8 |
| chr9: 139492789-140913833 | 196 | 1421045 | 1 | rs28485548 | cnvi0002661 | 28.211 | 0 | CACNA1B |
| chr9: 139821068-141105225 | 163 | 1284158 | 3 | rs3750512 | rs11559363 | 55.611 | 0 | CACNA1B |
| chr1: 64114301-245591329 | 29842 | 181477029 | 1 | rs11208257 | rs1173850 | 37.504 | 0 | CACYBP |
| chr1: 75098453-243531649 | 27360 | 168433197 | 1 | rs12117493 | rs10927002 | 32.113 | 0 | CACYBP |
| chr1: 79710545-188898319 | 17303 | 109187775 | 1 | rs417181 | rs16829637 | 45.89 | 0 | CACYBP |
| chr1: 174219398-247422297 | 15986 | 73202900 | 1 | rs16846809 | rs4642922 | 35.258 | 0 | CACYBP |
| chr1: 109645793-194560463 | 12025 | 84914671 | 3 | cnvi0008281 | rs10921616 | 63.121 | 0 | CACYBP |
| chr16: 64107047-82920737 | 4544 | 18813691 | 3 | rs2319723 | rs918661 | 28.887 | 0 | CALB2 |
| chr16: 59854720-89273883 | 7609 | 29419164 | 3 | rs1373880 | rs8046156 | 31.884 | 0 | CALB2 |
| chr16: 50219449-89544756 | 10324 | 39325308 | 3 | rs6500298 | rs3803681 | 108.108 | 0 | CALB2 |
| chr14: 26898958-104436931 | 17396 | 77537974 | 1 | rs1245195 | rs11851097 | 57.233 | 0 | CALM1 |
| chr14: 80818058-105348552 | 5492 | 24530495 | 3 | rs6574553 | rs2028416 | 15.874 | 0 | CALM1 |
| chr14: 65405722-103799039 | 8979 | 38393318 | 3 | rs11623705 | rs11628472 | 266.153 | 0 | CALM1 |
| chr2: 12056323-227979775 | 39094 | 215923453 | 1 | rs966391 | rs1922020 | 31.384 | 0 | CALM2 |
| chr2: 38101137-241482099 | 36812 | 203380963 | 1 | rs879321 | rs7576043 | 52.099 | 0 | CALM2 |
| chr2: 34870277-241929621 | 37755 | 207059345 | 3 | rs13422005 | rs10205276 | 46.946 | 0 | CALM2 |
| chr2: 41212010-82396211 | 9721 | 41184202 | 3 | rs12614285 | rs934310 | 396.396 | 0 | CALM2 |
| chr19: 31569338-53780966 | 3788 | 22211629 | 1 | rs2867544 | rs10407424 | 33.9 | 0 | CALM3 |
| chr14: 26898958-104436931 | 17396 | 77537974 | 1 | rs1245195 | rs11851097 | 57.233 | 0 | CALM3 |
| chr14: 80818058-105348552 | 5492 | 24530495 | 3 | rs6574553 | rs2028416 | 15.874 | 0 | CALM3 |
| chr19: 43257015-55294329 | -7309 | 12037315 | 3 | rs7246152 | rs2569676 | 21.402 | 0 | CALM3 |
| chr19: 288246-59110628 | 11009 | 58822383 | 3 | rs10409452 | cnvi0009466 | 100.582 | 0 | CALM3 |
| chr14: 65405722-103799039 | 8979 | 38393318 | 3 | rs11623705 | rs11628472 | 266.153 | 0 | CALM3 |
| chr3: 179527-114630641 | 23879 | 114451115 | 3 | rs4684741 | rs1587972 | 207.852 | 0 | CAMK1 |
| chr7: 11855636-156148608 | 26852 | 144292973 | 1 | rs6947930 | rs6945016 | 36.446 | 0 | CAMK2B |
| chr7: 8872727-156383359 | 27773 | 147510633 | 1 | rs917038 | rs878717 | 32.336 | 0 | CAMK2B |
| chr7: 8794418-119068130 | 23484 | 110273713 | 1 | rs2189621 | rs6977904 | 70.867 | 0 | CAMK2B |
| chr7: 7724805-53845684 | 11772 | 46120880 | 3 | rs10263415 | rs6948633 | 42.007 | 0 | CAMK2B |
| chr7: 60392-84158180 | 19095 | 84097789 | 3 | rs12670102 | rs2715048 | 208.308 | 0 | CAMK2B |
| chr5: 84830796-171903310 | 16642 | 87072515 | 1 | rs300657 | rs10042482 | 42.208 | 0 | CAMK4 |
| chr5: 57343495-171903310 | 21683 | 114559816 | 1 | rs10940593 | rs10042482 | 61.169 | 0 | CAMK4 |
| chr5: 80735161-125293366 | 8499 | 44558206 | 1 | rs1541830 | rs327816 | 52.167 | 0 | CAMK4 |
| chr5: 98442871-150317237 | 9828 | 51874367 | 1 | rs1447379 | rs7710790 | 38.687 | 0 | CAMK4 |
| chr5: 108979318-132114847 | 4575 | 23135530 | 1 | rs31595 | rs30514 | 35.063 | 0 | CAMK4 |
| chr5: 108284342-111242002 | 627 | 2957661 | 1 | rs3797817 | rs17133870 | 44.164 | 0 | CAMK4 |
| chr5: 4872310-180709915 | 35876 | 175837606 | 3 | rs816467 | rs10071993 | 179.394 | 0 | CAMK4 |
| chr5: 57343495-171903310 | 21683 | 114559816 | 1 | rs10940593 | rs10042482 | 61.169 | 0 | CCNB1 |
| chr5: 49952847-89853069 | 7268 | 39900223 | 1 | rs12188654 | rs42467 | 26.225 | 0 | CCNB1 |
| chr5: 4872310-180709915 | 35876 | 175837606 | 3 | rs816467 | rs10071993 | 179.394 | 0 | CCNB1 |
| chr1: 1005806-105612342 | 19173 | 104606537 | 3 | rs3934834 | rs1584633 | 44.152 | 0 | CDC42 |
| chr1: 2006108-109527861 | 22130 | 107521754 | 3 | rs2254669 | rs839873 | 162.269 | 0 | CDC42 |
| chr20: 4591715-58420336 | 11753 | 53828622 | 1 | rs6139494 | rs1416388 | 40.922 | 0 | CHGB |
| chr20: 236802-54845796 | 12646 | 54608995 | 3 | rs448294 | rs6064362 | 286.151 | 0 | CHGB |
| chr15: 29325866-56044189 | 5303 | 26718324 | 3 | rs4779705 | rs2414433 | 21.732 | 0 | CHP |
| chr15: 32939946-43104406 | 2544 | 10164461 | 3 | rs12594777 | rs13380301 | 32.942 | 0 | CHP |
| chr7: 11855636-156148608 | 26852 | 144292973 | 1 | rs6947930 | rs6945016 | 36.446 | 0 | CHRM2 |
| chr7: 8872727-156383359 | 27773 | 147510633 | 1 | rs917038 | rs878717 | 32.336 | 0 | CHRM2 |
| chr7: 78621315-155831817 | 13678 | 77210503 | 3 | rs1006818 | rs6969015 | 123.319 | 0 | CHRM2 |
| chr7: 120061880-143606234 | 4616 | 23544355 | 3 | rs12531689 | rs10247493 | 18.96 | 0 | CHRM2 |
| chr1: 64114301-245591329 | 29842 | 181477029 | 1 | rs11208257 | rs1173850 | 37.504 | 0 | CHRM3 |
| chr1: 75098453-243531649 | 27360 | 168433197 | 1 | rs12117493 | rs10927002 | 32.113 | 0 | CHRM3 |
| chr1: 178626526-244159143 | 13064 | 65532618 | 3 | rs2761477 | rs479338 | 11.373 | 0 | CHRM3 |
| chr1: 238655362-242087644 | 1078 | 3432283 | 3 | rs2392861 | rs4658565 | 806.215 | 0 | CHRM3 |
| chr1: 174219398-247422297 | 15986 | 73202900 | 1 | rs16846809 | rs4642922 | 35.258 | 0 | CHRM3 |
| chr1: 236848751-249219320 | 3293 | 12370570 | 3 | rs819666 | cnvi0018731 | 920.725 | 0 | CHRM3 |
| chr19: 31569338-53780966 | 3788 | 22211629 | 1 | rs2867544 | rs10407424 | 33.9 | 0 | CIC |
| chr19: 288246-59110628 | 11009 | 58822383 | 3 | rs10409452 | cnvi0009466 | 100.582 | 0 | CIC |
| chr17: 21685812-67308196 | 12365 | 45622385 | 1 | rs34864328 | rs17686852 | 50.018 | 0 | CNP |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr17: 26648492-58955084 | 5831 | 32306593 | 3 | rs1981512 | rs8068776 | 15.642 | 0 | CNP |
| chr6: 64844594-169078546 | 21567 | 104233953 | 1 | rs4710465 | rs601639 | 46.524 | 0 | CNR1 |
| chr6: 66541198-162520133 | 19344 | 95978936 | 1 | rs2000382 | rs6901071 | 27.509 | 0 | CNR1 |
| chr6: 73120320-165130872 | 18715 | 92010553 | 1 | rs9442780 | rs10946016 | 76.383 | 0 | CNR1 |
| chr6: 66609532-147053632 | 15315 | 80444101 | 3 | rs9354335 | rs4896886 | 44.941 | 0 | CNR1 |
| chr6: 26922906-93578359 | 19746 | 66655454 | 1 | rs9348738 | rs9363009 | 27.061 | 0 | CNR1 |
| chr6: 62697746-94090076 | 6391 | 31392331 | 1 | rs6455128 | rs3799807 | 108.85 | 0 | CNR1 |
| chr6: 67621368-147709180 | 16188 | 80087813 | 1 | rs6919455 | rs7739314 | 52.498 | 0 | CNR1 |
| chr6: 79198069-99893938 | 4062 | 20695870 | 3 | rs1321584 | rs4504482 | 200.961 | 0 | CNR1 |
| chr3: 13878889-149737330 | 24723 | 135858442 | 1 | rs12634112 | rs2007869 | 55.663 | 0 | COPB2 |
| chr3: 102240202-195550366 | 17318 | 93310165 | 1 | rs1620217 | rs11711870 | 41.031 | 0 | COPB2 |
| chr3: 83075971-196935657 | 21465 | 113859687 | 1 | rs9872858 | rs34729751 | 44.35 | 0 | COPB2 |
| chr3: 33409611-170735099 | 23775 | 137325489 | 1 | rs3915062 | rs11924032 | 26.867 | 0 | COPB2 |
| chr3: 103140700-144883172 | 8539 | 41742473 | 1 | rs4314176 | rs6797159 | 44.122 | 0 | COPB2 |
| chr3: 114889454-177826047 | 12700 | 62936594 | 3 | rs6795297 | rs7628308 | 102.526 | 0 | COPB2 |
| chr17: 43657921-44354796 | 88 | 696876 | 3 | rs9898857 | rs2732700 | 21.196 | 0 | CRHR1 |
| chr17: 21685812-67308196 | 12365 | 45622385 | 1 | rs34864328 | rs17686852 | 50.018 | 0 | CRHR1 |
| chr17: 43657921-44064851 | 65 | 406931 | 3 | rs9898857 | rs8079215 | 86.447 | 0 | CRHR1 |
| chr17: 26648492-58955084 | 5831 | 32306593 | 3 | rs1981512 | rs8068776 | 15.642 | 0 | CRHR1 |
| chr7: 11855636-156148608 | 26852 | 144292973 | 1 | rs6947930 | rs6945016 | 36.446 | 0 | CYCS |
| chr8: 8872727-156383359 | 27773 | 147510633 | 1 | rs917038 | rs878717 | 32.336 | 0 | CYCS |
| chr7: 8794418-119068130 | 23484 | 110273713 | 1 | rs2189621 | rs6977904 | 70.867 | 0 | CYCS |
| chr7: 7724805-53845684 | 11772 | 46120880 | 3 | rs10263415 | rs6948633 | 42.007 | 0 | CYCS |
| chr7: 60392-84158180 | 19095 | 84097789 | 3 | rs12670102 | rs2715048 | 208.308 | 0 | CYCS |
| chr12: 10113083-116370432 | 20594 | 106257350 | 1 | rs2012504 | rs7958254 | 35.157 | 0 | DCN |
| chr12: 10020267-129866293 | 23654 | 119846027 | 1 | rs1597097 | rs2170504 | 45.428 | 0 | DCN |
| chr12: 59512781-127744939 | 13469 | 68232159 | 3 | rs908394 | rs7966946 | 20.62 | 0 | DCN |
| chr12: 84589672-93258498 | 1292 | 8668827 | 1 | rs1482434 | rs11106721 | 43.425 | 0 | DCN |
| chr12: 50855195-133778796 | 17748 | 82923602 | 3 | rs4351895 | rs7975069 | 159.589 | 0 | DCN |
| chr11: 42185849-126756938 | 15451 | 84571090 | 1 | rs4375424 | rs10750356 | 36.99 | 0 | DHCR7 |
| chr11: 21723471-131521797 | 20508 | 109798327 | 1 | rs11828478 | rs2512898 | 27.565 | 0 | DHCR7 |
| chr11: 23168804-106781292 | 16332 | 83612489 | 1 | rs11027007 | rs7103285 | 49.747 | 0 | DHCR7 |
| chr11: 67086298-74446791 | 1348 | 7360494 | 3 | rs1944096 | rs7103136 | 173.017 | 0 | DHCR7 |
| chr1: 64114301-245591329 | 29842 | 181477029 | 1 | rs11208257 | rs11173850 | 37.504 | 0 | DISC1 |
| chr1: 75098453-243531649 | 27360 | 168433197 | 1 | rs12117493 | rs10927002 | 32.113 | 0 | DISC1 |
| chr1: 231711489-231813134 | 28 | 101646 | 3 | rs1765782 | rs6541281 | 70.39 | 0 | DISC1 |
| chr1: 231711489-231813134 | 22 | 101646 | 3 | rs1765782 | rs6541281 | 42.561 | 0 | DISC1 |
| chr1: 178626526-244159143 | 13064 | 65532618 | 3 | rs2761477 | rs479338 | 11.373 | 0 | DISC1 |
| chr1: 188850774-235423607 | 10060 | 46572834 | 1 | rs16829466 | rs12409696 | 43.25 | 0 | DISC1 |
| chr1: 191875752-235423607 | 9517 | 43547856 | 1 | rs9427811 | rs12409696 | 62.01 | 0 | DISC1 |
| chr1: 174219398-247422297 | 15986 | 73202900 | 1 | rs16846809 | rs4642922 | 35.258 | 0 | DISC1 |
| chr1: 226536645-236803753 | 2600 | 10267109 | 3 | rs874583 | rs10925178 | 100.109 | 0 | DISC1 |
| chr14: 26898958-104436931 | 17396 | 77537974 | 1 | rs1245276 | rs11851097 | 57.233 | 0 | DLST |
| chr14: 65405722-103799039 | 8979 | 38393318 | 3 | rs11623705 | rs11628472 | 266.153 | 0 | DLST |
| chr11: 42185849-126756938 | 15451 | 84571090 | 1 | rs4375424 | rs10750356 | 36.99 | 0 | DRD2 |
| chr11: 21723471-131521797 | 20508 | 109798327 | 1 | rs11828478 | rs2512898 | 27.565 | 0 | DRD2 |
| chr11: 84128925-120941589 | 7678 | 36813047 | 1 | rs488925 | rs4643089 | 29.271 | 0 | DRD2 |
| chr11: 98062720-121890280 | 5422 | 23827561 | 1 | rs6589308 | rs1944465 | 29.075 | 0 | DRD2 |
| chr11: 74545378-134940416 | 14496 | 60395039 | 3 | rs512780 | rs11224228 | 527.758 | 0 | DRD2 |
| chr3: 13878889-149737330 | 24723 | 135858442 | 1 | rs12634112 | rs2007869 | 55.663 | 0 | DRD3 |
| chr3: 102240202-195550366 | 17318 | 93310165 | 1 | rs1620217 | rs11711870 | 41.031 | 0 | DRD3 |
| chr3: 83075971-196935657 | 21465 | 113859687 | 1 | rs9872858 | rs34729751 | 44.35 | 0 | DRD3 |
| chr3: 33409611-170735099 | 23775 | 137325489 | 1 | rs3915062 | rs11924032 | 26.867 | 0 | DRD3 |
| chr3: 103140700-144883172 | 8539 | 41742473 | 1 | rs4314176 | rs6797159 | 44.122 | 0 | DRD3 |
| chr3: 179527-114630641 | 23879 | 114451115 | 3 | rs4684741 | rs1587972 | 207.852 | 0 | DRD3 |
| chr20: 13712393-55093901 | 8218 | 41381509 | 1 | rs6033810 | rs6999 | 41.237 | 0 | DSTN |
| chr20: 4591715-58420336 | 11753 | 53828622 | 1 | rs6139494 | rs1416388 | 40.922 | 0 | DSTN |
| chr20: 7869025-62424661 | 11941 | 54555637 | 3 | rs2294306 | rs6010652 | 9.732 | 0 | DSTN |
| chr20: 236802-54845796 | 12646 | 54608995 | 3 | rs448294 | rs6064362 | 286.151 | 0 | DSTN |
| chr12: 10020267-129866293 | 23654 | 119846027 | 1 | rs1597097 | rs2170504 | 45.428 | 0 | DYNLL1 |
| chr12: 59512781-127744939 | 13469 | 68232159 | 3 | rs908394 | rs7966946 | 20.62 | 0 | DYNLL1 |
| chr12: 112610714-133708729 | 5366 | 21098016 | 3 | rs11066188 | rs11147249 | 695.45 | 0 | DYNLL1 |
| chr12: 50855195-133778796 | 17748 | 82923602 | 3 | rs4351895 | rs7975069 | 159.589 | 0 | DYNLL1 |
| chr10: 53602190-135522754 | 19167 | 81920565 | 3 | rs12247820 | rs10909028 | 139.373 | 0 | ECHS1 |
| chr7: 11855636-156148608 | 26852 | 144292973 | 1 | rs6947930 | rs6945016 | 36.446 | 0 | EGFR |
| chr8: 8872727-156383359 | 27773 | 147510633 | 1 | rs917038 | rs878717 | 32.336 | 0 | EGFR |
| chr7: 8794418-119068130 | 23484 | 110273713 | 1 | rs2189621 | rs6977904 | 70.867 | 0 | EGFR |
| chr7: 60392-84158180 | 19095 | 84097789 | 3 | rs12670102 | rs2715048 | 208.308 | 0 | EGFR |
| chr17: 21685812-67308196 | 12365 | 45622385 | 1 | rs34864328 | rs17686852 | 50.018 | 0 | ERBB2 |
| chr17: 26648492-58955084 | 5831 | 32306593 | 3 | rs1981512 | rs8068776 | 15.642 | 0 | ERBB2 |
| chr5: 57343495-171903310 | 21683 | 114559816 | 1 | rs10940593 | rs10042482 | 61.169 | 0 | F2R |
| chr5: 49952847-89853069 | 7268 | 39900223 | 3 | rs12188654 | rs42467 | 26.225 | 0 | F2R |
| chr5: 4872310-180709915 | 35876 | 175837606 | 3 | rs816467 | rs10071993 | 179.394 | 0 | F2R |
| chr5: 57343495-171903310 | 21683 | 114559816 | 1 | rs10940593 | rs10042482 | 61.169 | 0 | F2RL2 |
| chr5: 49952847-89853069 | 7268 | 39900223 | 3 | rs12188654 | rs42467 | 26.225 | 0 | F2RL2 |
| chr5: 4872310-180709915 | 35876 | 175837606 | 3 | rs816467 | rs10071993 | 179.394 | 0 | F2RL2 |
| chr19: 266034-18061509 | 3100 | 17795476 | 3 | rs2312724 | rs7250332 | 19.51 | 0 | F2RL3 |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr19: 288246-59110628 | 11009 | 58822383 | 3 | rs10409452 | cnvi0009466 | 100.582 | 0 | F2RL3 |
| chr1: 64114301-245591329 | 29842 | 181477029 | 1 | rs11208257 | rs1173850 | 37.504 | 0 | F3 |
| chr1: 75098453-243531649 | 27360 | 168433197 | 1 | rs12117493 | rs10927002 | 32.113 | 0 | F3 |
| chr1: 79710545-188898319 | 17303 | 109187775 | 1 | rs417181 | rs16829637 | 45.89 | 0 | F3 |
| chr1: 1005806-105612342 | 19173 | 104606537 | 3 | rs3934834 | rs1584633 | 44.152 | 0 | F3 |
| chr1: 2006108-109527861 | 22130 | 107521754 | 3 | rs2254669 | rs839879 | 162.269 | 0 | F3 |
| chr14: 26898958-104436931 | 17396 | 77537974 | 1 | rs1245195 | rs11851097 | 57.233 | 0 | FKBP3 |
| chr14: 19917123-65327288 | 10286 | 45410166 | 3 | rs2495197 | rs9323455 | 270.291 | 0 | FKBP3 |
| chr19: 31569338-53780966 | 3788 | 22211629 | 1 | rs2867544 | rs10407424 | 33.9 | 0 | FPR1 |
| chr19: 43257015-55294329 | −7309 | 12037315 | 3 | rs7246152 | rs2569676 | 21.402 | 0 | FPR1 |
| chr19: 288246-59110628 | 11009 | 58822383 | 3 | rs10409452 | cnvi0009466 | 100.582 | 0 | FPR1 |
| chr7: 60392-84158180 | 19095 | 84097789 | 3 | rs12670102 | rs2715048 | 208.308 | 0 | FSCN1 |
| chr15: 51688996-102398060 | 11030 | 50709065 | 1 | rs2459396 | rs7181527 | 36.939 | 0 | FURIN |
| chr15: 53775670-96810867 | 9973 | 43035198 | 1 | rs657495 | rs2589238 | 49.204 | 0 | FURIN |
| chr15: 91345348-91492877 | 34 | 147530 | 3 | rs16944840 | rs749938 | 0 | 0 | FURIN |
| chr15: 66108544-102427006 | 8615 | 36318463 | 3 | cnvi0007613 | rs11632620 | 159.164 | 0 | FURIN |
| chr6: 64844594-169078546 | 21567 | 104233953 | 1 | rs4710465 | rs601639 | 46.524 | 0 | FYN |
| chr6: 66541198-162520133 | 19344 | 95978936 | 1 | rs2000384 | rs6901071 | 27.509 | 0 | FYN |
| chr6: 73120320-165130872 | 18715 | 92010553 | 1 | rs9442780 | rs10946016 | 76.383 | 0 | FYN |
| chr6: 66609532-147053632 | 15315 | 80444101 | 3 | rs9354335 | rs4896886 | 44.941 | 0 | FYN |
| chr6: 94117546-165103679 | 15579 | 70986134 | 1 | rs3799792 | rs9347902 | 34.066 | 0 | FYN |
| chr6: 67621368-147709180 | 16188 | 80087813 | 1 | rs6919465 | rs7739314 | 52.498 | 0 | FYN |
| chr6: 100082983-170909002 | 16393 | 70826020 | 3 | rs594231 | rs12213906 | 261.313 | 0 | FYN |
| chr12: 6485661-6711147 | 48 | 225487 | 1 | rs3759324 | rs1639122 | 18.66 | 0 | GAPDH |
| chr12: 6562293-6711147 | 27 | 148855 | 1 | rs2041385 | rs1639122 | 19.307 | 0 | GAPDH |
| chr12: 207886-50770291 | 11565 | 50562406 | 3 | rs868249 | rs4477515 | 43.892 | 0 | GAPDH |
| chr6: 26922906-93578359 | 19746 | 66655454 | 1 | rs9348738 | rs9363009 | 27.061 | 0 | GLP1R |
| chr6: 31289284-56929863 | 15402 | 25640580 | 3 | rs9265170 | cnvi0015437 | 25.647 | 0 | GLP1R |
| chr6: 32968276-73449742 | 15442 | 40481467 | 3 | rs2395300 | rs4235869 | 415.87 | 0 | GLP1R |
| chr17: 108420-26610769 | 5548 | 26502350 | 3 | rs12452527 | rs658591 | 82.699 | 0 | GLP2R |
| chr19: 629303-4119012 | 709 | 3489710 | 1 | rs2283575 | rs350887 | 26.758 | 0 | GNA15 |
| chr19: 266034-18061509 | 3100 | 17795476 | 3 | rs2312724 | rs7250332 | 19.51 | 0 | GNA15 |
| chr19: 288246-59110628 | 11009 | 58822383 | 3 | rs10409452 | cnvi0009466 | 100.582 | 0 | GNA15 |
| chr7: 11855826-156148608 | 26852 | 144292973 | 1 | rs6947930 | rs6945016 | 36.446 | 0 | GNAI1 |
| chr7: 8872727-156383359 | 27773 | 147510633 | 1 | rs917038 | rs878717 | 32.336 | 0 | GNAI1 |
| chr7: 8794418-119068130 | 23484 | 110273713 | 1 | rs2189621 | rs6977904 | 70.867 | 0 | GNAI1 |
| chr7: 78621315-155831817 | 13678 | 77210503 | 3 | rs1006818 | rs6969015 | 123.319 | 0 | GNAI1 |
| chr7: 60392-84158180 | 19095 | 84097789 | 3 | rs12670102 | rs2715048 | 208.308 | 0 | GNAI1 |
| chr3: 13878624-149737330 | 24723 | 135858442 | 1 | rs12634112 | rs2007869 | 55.663 | 0 | GNAI2 |
| chr3: 33409611-170735099 | 23775 | 137325489 | 1 | rs3915062 | rs11924032 | 26.867 | 0 | GNAI2 |
| chr3: 179527-114630641 | 23879 | 114451115 | 3 | rs4684741 | rs1587972 | 207.852 | 0 | GNAI2 |
| chr1: 64114301-245591329 | 29842 | 181477029 | 1 | rs11208257 | rs1173850 | 37.504 | 0 | GNAI3 |
| chr1: 75098453-243531649 | 27360 | 168433197 | 1 | rs12117493 | rs10927002 | 32.113 | 0 | GNAI3 |
| chr1: 79710545-188898319 | 17303 | 109187775 | 1 | rs417181 | rs16829637 | 45.89 | 0 | GNAI3 |
| chr1: 109645793-194560463 | 12025 | 84914671 | 3 | cnvi0008281 | rs10921616 | 63.121 | 0 | GNAI3 |
| chr16: 50219449-89544756 | 10324 | 39325308 | 3 | rs6500298 | rs3803681 | 108.108 | 0 | GNAO1 |
| chr9: 1989033-107532317 | 18263 | 105543285 | 1 | rs7864820 | rs10820712 | 39.824 | 0 | GNAQ |
| chr9: 33180228-132003792 | 14691 | 98823565 | 1 | rs7854765 | rs9408988 | 28.69 | 0 | GNAQ |
| chr9: 2522475-140068342 | 25719 | 137545868 | 3 | rs10966757 | rs4074426 | 93.386 | 0 | GNAQ |
| chr9: 46587-94335290 | 17484 | 94288704 | 3 | rs10814410 | rs9409606 | 762.393 | 0 | GNAQ |
| chr5: 4872310-180709915 | 35876 | 175837606 | 1 | rs816467 | rs10071993 | 179.394 | 0 | GNB2L1 |
| chr10: 7188484-134205354 | 26672 | 127016871 | 1 | rs1977295 | rs3923858 | 50.772 | 0 | GOT1 |
| chr10: 57671424-133349223 | 16243 | 75677800 | 1 | rs11005106 | rs4301710 | 37.114 | 0 | GOT1 |
| chr10: 58385643-124973104 | 13625 | 66587462 | 1 | rs7920235 | rs17663304 | 36.18 | 0 | GOT1 |
| chr10: 55492106-117205017 | 13465 | 61712856 | 1 | rs6481032 | rs1933664 | 62.56 | 0 | GOT1 |
| chr10: 53602190-135522754 | 19167 | 81920565 | 3 | rs12247820 | rs10909028 | 139.373 | 0 | GOT1 |
| chr17: 108420-26610769 | 5548 | 26502350 | 3 | rs12452527 | rs658591 | 82.699 | 0 | GP1BA |
| chr10: 7188484-134205354 | 26672 | 127016871 | 1 | rs1977295 | rs3923858 | 50.772 | 0 | GPR26 |
| chr10: 57671424-133349223 | 16243 | 75677800 | 1 | rs11005106 | rs4301710 | 37.114 | 0 | GPR26 |
| chr10: 124668629-135157955 | 2949 | 10489327 | 3 | rs11248331 | rs10776672 | 23.553 | 0 | GPR26 |
| chr10: 53602190-135522754 | 19167 | 81920565 | 3 | rs12247820 | rs10909028 | 139.373 | 0 | GPR26 |
| chr17: 44458950-81047708 | −8195 | 36588759 | 1 | cnvi0016818 | rs35680231 | 35.591 | 0 | GRB2 |
| chr17: 62662507-81047708 | −11496 | 18385202 | 3 | rs6504246 | rs35680231 | 56.048 | 0 | GRB2 |
| chr17: 21685812-67308196 | 12365 | 45622385 | 1 | rs34864328 | rs17686852 | 50.018 | 0 | GRB7 |
| chr17: 26648492-58955084 | 5831 | 32306593 | 3 | rs1981512 | rs8068776 | 15.642 | 0 | GRB7 |
| chr5: 84830796-171903310 | 16642 | 87072515 | 1 | rs300657 | rs10042482 | 42.208 | 0 | GRIA1 |
| chr5: 57343495-171903310 | 21683 | 114559816 | 1 | rs10940593 | rs10042482 | 61.169 | 0 | GRIA1 |
| chr5: 4872310-180709915 | 35876 | 175837606 | 3 | rs816467 | rs10071993 | 179.394 | 0 | GRIA1 |
| chr21: 14601415-48084989 | 8249 | 33483575 | 1 | rs2775537 | rs2839378 | 12047.211 | 0 | GRIK1 |
| chr21: 14601415-48084989 | 8249 | 33483575 | 1 | rs2775537 | rs2839378 | 41.154 | 0 | GRIK1 |
| chr21: 30057145-31992864 | 372 | 1935720 | 1 | rs6516861 | rs1702405 | 41.668 | 0 | GRIK1 |
| chr21: 14595264-48084989 | 8781 | 33489726 | 3 | rs2847443 | rs2839378 | 1871.363 | 0 | GRIK1 |
| chr21: 14601415-48084989 | 8249 | 33483575 | 3 | rs2775537 | rs2839378 | 4787.438 | 0 | GRIK1 |
| chr21: 14768343-48084989 | 8193 | 33316647 | 3 | rs2257224 | rs2839378 | 5021.076 | 0 | GRIK1 |
| chr21: 10708231-47970581 | 8807 | 37262351 | 3 | rs4044122 | rs2255397 | 73.188 | 0 | GRIK1 |
| chr1: 1005806-105612342 | 19173 | 104606537 | 3 | rs3934834 | rs1584633 | 44.152 | 0 | GRIK3 |
| chr1: 2006108-109527861 | 22130 | 107521754 | 3 | rs2254669 | rs839879 | 162.269 | 0 | GRIK3 |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr6: 64844594-169078546 | 21567 | 104233953 | 1 | rs4710465 | rs601639 | 46.524 | 0 | GRM1 |
| chr6: 66541198-162520133 | 19344 | 95978936 | 1 | rs2000382 | rs6901071 | 27.509 | 0 | GRM1 |
| chr6: 73120320-165130872 | 18715 | 92010553 | 1 | rs9442780 | rs10946016 | 76.383 | 0 | GRM1 |
| chr6: 66609532-147053632 | 15315 | 80444101 | 3 | rs9354335 | rs4896886 | 44.941 | 0 | GRM1 |
| chr6: 94117546-165103679 | 15579 | 70986134 | 1 | rs3799792 | rs9347902 | 34.066 | 0 | GRM1 |
| chr6: 67621368-147709180 | 16188 | 80087813 | 1 | rs6919455 | rs7739314 | 52.498 | 0 | GRM1 |
| chr6: 100082983-170909002 | 16393 | 70826020 | 3 | rs594231 | rs12213906 | 261.313 | 0 | GRM1 |
| chr3: 13878889-149737330 | 24723 | 135858442 | 1 | rs12634112 | rs2007869 | 55.663 | 0 | GRM2 |
| chr3: 33409611-170735099 | 23775 | 137325489 | 1 | rs3915062 | rs11924032 | 26.867 | 0 | GRM2 |
| chr3: 179527-114630641 | 23879 | 114451115 | 3 | rs4684741 | rs1587972 | 207.852 | 0 | GRM2 |
| chr7: 11855636-156148608 | 26852 | 144292973 | 1 | rs6947930 | rs6945016 | 36.446 | 0 | GRM3 |
| chr7: 8872727-156383359 | 27773 | 147510633 | 1 | rs917038 | rs878717 | 32.336 | 0 | GRM3 |
| chr7: 85117732-86026526 | 122 | 908795 | 1 | rs4728584 | rs10242995 | 65.094 | 246704 | GRM3 |
| chr7: 8794418-119068130 | 23484 | 110273713 | 1 | rs2189621 | rs6977904 | 70.867 | 0 | GRM3 |
| chr7: 78621315-155831817 | 13678 | 77210503 | 3 | rs1006818 | rs6969015 | 123.319 | 0 | GRM3 |
| chr7: 84302877-110993169 | 5183 | 26690293 | 3 | rs4338048 | rs10254893 | 203.09 | 0 | GRM3 |
| chr6: 26922906-93578359 | 19746 | 66655454 | 1 | rs9348738 | rs9363009 | 27.061 | 0 | GRM4 |
| chr6: 31289284-56929863 | 15402 | 25640580 | 3 | rs9265170 | cnvi0015437 | 25.647 | 0 | GRM4 |
| chr6: 32968276-73449742 | 15442 | 40481467 | 3 | rs2395300 | rs4235869 | 415.87 | 0 | GRM4 |
| chr11: 42185849-126756938 | 15451 | 84571090 | 1 | rs4375424 | rs10750356 | 36.99 | 0 | GRM5 |
| chr11: 21723471-131521797 | 20508 | 109798327 | 1 | rs11828478 | rs2512898 | 27.565 | 0 | GRM5 |
| chr11: 23168804-106781292 | 16332 | 83612489 | 1 | rs11027007 | rs7103285 | 49.747 | 0 | GRM5 |
| chr11: 84128537-120941583 | 7678 | 36813047 | 1 | rs488925 | rs4643089 | 29.271 | 0 | GRM5 |
| chr11: 81251505-103234729 | 4842 | 21983225 | 3 | rs7935238 | rs1913462 | 26.176 | 0 | GRM5 |
| chr11: 74545378-134940416 | 14496 | 60395039 | 3 | rs512780 | rs11224228 | 527.758 | 0 | GRM5 |
| chr5: 161172541-179954615 | 4271 | 18782075 | 3 | rs4921415 | rs10059433 | 6.291 | 0 | GRM6 |
| chr5: 4872310-180709915 | 35876 | 175837606 | 3 | rs816467 | rs10071993 | 179.394 | 0 | GRM6 |
| chr3: 5824878-8781331 | 952 | 2956454 | 3 | rs2470628 | rs11916022 | 924.891 | 0 | GRM7 |
| chr3: 179527-114630641 | 23879 | 114451115 | 3 | rs4684741 | rs1587972 | 207.852 | 0 | GRM7 |
| chr7: 11855636-156148608 | 26852 | 144292973 | 1 | rs6947930 | rs6945016 | 36.446 | 0 | GRM8 |
| chr7: 8872727-156383359 | 27773 | 147510633 | 1 | rs917038 | rs878717 | 32.336 | 0 | GRM8 |
| chr7: 78621315-155831817 | 13678 | 77210503 | 3 | rs1006818 | rs6969015 | 123.319 | 0 | GRM8 |
| chr7: 125676925-125780682 | 24 | 103758 | 1 | rs1419535 | rs10267757 | 26.358 | 297970 | GRM8 |
| chr7: 120061880-143606234 | 4616 | 23544355 | 3 | rs12531689 | rs10247493 | 18.96 | 0 | GRM8 |
| chr9: 33180228-132003792 | 14691 | 98823565 | 1 | rs7854765 | rs9408988 | 28.69 | 0 | GSN |
| chr9: 2522475-140068342 | 25719 | 137545868 | 3 | rs10966757 | rs4074426 | 93.386 | 0 | GSN |
| chr9: 100158052-139077343 | 9815 | 38919292 | 3 | rs1020884 | rs4842126 | 470.601 | 0 | GSN |
| chr1: 64114301-245591329 | 29842 | 181477029 | 1 | rs11208257 | rs1173850 | 37.504 | 0 | HBXIP |
| chr1: 75098253-243551649 | 27360 | 168433197 | 1 | rs12117493 | rs10927002 | 32.113 | 0 | HBXIP |
| chr1: 79710545-188898319 | 17303 | 109187775 | 1 | rs417181 | rs16829637 | 45.89 | 0 | HBXIP |
| chr1: 109645793-194560463 | 12025 | 84914671 | 3 | cnvi0008281 | rs10921616 | 63.121 | 0 | HBXIP |
| chr5: 78520731-78765405 | 35 | 244675 | 1 | rs4704546 | rs7710089 | 12.78 | 0 | HOMER1 |
| chr5: 57343495-171903310 | 21683 | 114559816 | 1 | rs10940593 | rs10042482 | 61.169 | 0 | HOMER1 |
| chr5: 49952847-89853069 | 7268 | 39900223 | 3 | rs12188654 | rs42467 | 26.225 | 0 | HOMER1 |
| chr5: 78542290-79057477 | 95 | 515188 | 1 | rs10474578 | rs259126 | 38.26 | 0 | HOMER1 |
| chr5: 4872310-180709915 | 35876 | 175837606 | 3 | rs816467 | rs10071993 | 179.394 | 0 | HOMER1 |
| chr19: 18622443-22202166 | 372 | 3579724 | 3 | rs4808912 | rs10412244 | 11.197 | 0 | HOMER3 |
| chr19: 288246-59110628 | 11009 | 58822383 | 3 | rs10409452 | cnvi0009466 | 100.582 | 0 | HOMER3 |
| chr6: 26922906-93578359 | 19746 | 66655454 | 1 | rs9348738 | rs9363009 | 27.061 | 0 | HSP90AB1 |
| chr6: 31289284-56929863 | 15402 | 25640580 | 3 | rs9265170 | cnvi0015437 | 25.647 | 0 | HSP90AB1 |
| chr6: 32968276-73449742 | 15442 | 40481467 | 3 | rs2395300 | rs4235869 | 415.87 | 0 | HSP90AB1 |
| chr13: 36707502-103656104 | 13622 | 66948603 | 1 | rs3827890 | rs1952590 | 38.726 | 0 | HTR2A |
| chr13: 23742931-115064482 | 19829 | 91321552 | 1 | rs4770401 | rs7999630 | 44.074 | 0 | HTR2A |
| chr13: 19584477-81204088 | 13265 | 61619612 | 3 | rs1334954 | rs1176297 | 22.162 | 0 | HTR2A |
| chr13: 47300055-47409034 | 48 | 108980 | 1 | rs1539197 | rs6314 | 25.525 | 0 | HTR2A |
| chr13: 19121741-63373781 | 10326 | 44252041 | 3 | rs9578050 | rs9539575 | 82.761 | 0 | HTR2A |
| chr3: 13878889-149737330 | 24723 | 135858442 | 1 | rs12634112 | rs2007869 | 55.663 | 0 | IMPDH2 |
| chr3: 33409611-170735099 | 23775 | 137325489 | 1 | rs3915062 | rs11924032 | 26.867 | 0 | IMPDH2 |
| chr3: 48801929-49362892 | 29 | 560964 | 1 | rs6766238 | rs1865741 | 15.852 | 0 | IMPDH2 |
| chr3: 179527-114630641 | 23879 | 114451115 | 3 | rs4684741 | rs1587972 | 207.852 | 0 | IMPDH2 |
| chr5: 57343495-171903310 | 21683 | 114559816 | 1 | rs10940593 | rs10042482 | 61.169 | 0 | IQGAP2 |
| chr5: 49952847-89853069 | 7268 | 39900223 | 3 | rs12188654 | rs42467 | 26.225 | 0 | IQGAP2 |
| chr5: 4872310-180709915 | 35876 | 175837606 | 3 | rs816467 | rs10071993 | 179.394 | 0 | IQGAP2 |
| chr10: 7188484-134205354 | 26672 | 127016871 | 1 | rs1977295 | rs3923858 | 50.772 | 0 | ITGB1 |
| chr10: 734229-69155636 | 14859 | 68421408 | 1 | rs1769236 | rs2394375 | 72.104 | 0 | ITGB1 |
| chr10: 88874-53366180 | 12853 | 53277307 | 3 | cnvi0015449 | rs10998465 | 319.021 | 0 | ITGB1 |
| chr12: 10113083-116370432 | 20594 | 106257350 | 1 | rs2012504 | rs7958254 | 35.157 | 0 | ITGB7 |
| chr12: 10020267-129866293 | 23654 | 119846027 | 1 | rs1597097 | rs2170504 | 45.428 | 0 | ITGB7 |
| chr12: 39967134-84174413 | 8879 | 44207280 | 1 | rs11172661 | rs11116039 | 39.568 | 0 | ITGB7 |
| chr12: 50855195-133778796 | 17748 | 82923602 | 3 | rs4351895 | rs7975069 | 159.589 | 0 | ITGB7 |
| chr3: 3748218-4590681 | 268 | 842464 | 1 | rs901050 | rs6802929 | 33.083 | 0 | ITPR1 |
| chr3: 234726-6328081 | 2293 | 6093356 | 3 | rs7632811 | rs1595039 | 106.207 | 0 | ITPR1 |
| chr3: 179527-114630641 | 23879 | 114451115 | 3 | rs4684741 | rs1587972 | 207.852 | 0 | ITPR1 |
| chr1: 1005806-105612342 | 19173 | 104606537 | 3 | rs3934834 | rs1584633 | 44.152 | 0 | KIAA0090 |
| chr1: 2006108-109527861 | 22130 | 107521754 | 3 | rs2254669 | rs839879 | 162.269 | 0 | KIAA0090 |
| chr19: 288246-59110628 | 11009 | 58822383 | 3 | rs10409452 | cnvi0009466 | 100.582 | 0 | KIAA1683 |
| chr6: 64844594-169078546 | 21567 | 104233953 | 1 | rs4710465 | rs601639 | 46.524 | 0 | LAMA4 |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr6: 66541198-162520133 | 19344 | 95978936 | 1 | rs2000382 | rs6901071 | 27.509 | 0 | LAMA4 |
| chr6: 73120320-165130872 | 18715 | 92010553 | 1 | rs9442780 | rs10946016 | 76.383 | 0 | LAMA4 |
| chr6: 66609532-147053632 | 15315 | 80444101 | 3 | rs9354335 | rs4896886 | 44.941 | 0 | LAMA4 |
| chr6: 94117546-165103679 | 15579 | 70986134 | 1 | rs3799792 | rs9347902 | 34.066 | 0 | LAMA4 |
| chr6: 67621368-147709180 | 16188 | 80087813 | 1 | rs6919045 | rs7739314 | 52.498 | 0 | LAMA4 |
| chr6: 100082983-170909002 | 16393 | 70826020 | 3 | rs594231 | rs12213906 | 261.313 | 0 | LAMA4 |
| chr4: 22401728-188608857 | 28456 | 166207130 | 1 | rs4697297 | rs7687115 | 35.717 | 0 | LRP2BP |
| chr4: 162592024-189861553 | 6129 | 27269530 | 1 | rs5005966 | rs6853039 | 63.501 | 0 | LRP2BP |
| chr4: 163766726-189931630 | 5627 | 26164905 | 3 | rs10033012 | rs10018868 | 25.326 | 0 | LRP2BP |
| chr4: 69590353-190872778 | 23145 | 121282426 | 3 | rs293433 | rs12646565 | 315.633 | 0 | LRP2BP |
| chr17: 44458950-81047708 | −8195 | 36588759 | 1 | cnvi0016818 | rs35680231 | 35.591 | 0 | LRRC59 |
| chr17: 21685812-67308196 | 12365 | 45622385 | 1 | rs34864328 | rs17686852 | 50.018 | 0 | LRRC59 |
| chr17: 26648492-58955084 | 5831 | 32306593 | 3 | rs1981512 | rs8068776 | 15.642 | 0 | LRRC59 |
| chr6: 31337633-32449411 | 1650 | 1111779 | 1 | rs9266433 | rs1964995 | 124.395 | 0 | LTA |
| chr6: 31281438-32874796 | −7311 | 1593359 | 1 | cnvi0006173 | rs9469310 | 36.913 | 0 | LTA |
| chr6: 26922906-93578359 | 19746 | 66655454 | 1 | rs9348738 | rs9363009 | 27.061 | 0 | LTA |
| chr6: 3760708-31957364 | 8062 | 28196657 | 3 | rs2187825 | cnvi0006380 | 39.016 | 0 | LTA |
| chr6: 31289284-32512613 | 10001 | 1223330 | 3 | rs9265170 | rs35571839 | 45.035 | 0 | LTA |
| chr6: 31281438-32449411 | −7879 | 1167974 | 1 | cnvi0006173 | rs1964995 | 24.023 | 0 | LTA |
| chr6: 31281438-32354428 | −8033 | 1072991 | 1 | cnvi0006173 | rs4424066 | 37.329 | 0 | LTA |
| chr6: 31289284-31960770 | 9811 | 671487 | 3 | rs9265170 | cnvi0006385 | 29.628 | 0 | LTA |
| chr6: 26430946-31878433 | −8001 | 5447453 | 1 | rs2893848 | rs519417 | 55.651 | 0 | LTA |
| chr6: 29253756-32671521 | 2267 | 3417766 | 1 | rs9468508 | rs9275439 | 51.553 | 0 | LTA |
| chr6: 31289284-56929863 | 15402 | 25640580 | 3 | rs9265170 | cnvi0015437 | 25.647 | 0 | LTA |
| chr6: 30475431-32449411 | −7687 | 1973981 | 3 | cnvi0005997 | rs1964995 | 153.275 | 0 | LTA |
| chr4: 179131-68998153 | 13495 | 68819023 | 3 | rs7686948 | rs7687396 | 625.133 | 0 | LYAR |
| chr8: 30757798-142750969 | 20699 | 111993172 | 1 | rs10101203 | rs6421025 | 34.223 | 0 | LYN |
| chr8: 56843930-57035027 | 38 | 191098 | 1 | rs10091244 | rs4386955 | 14.478 | 0 | LYN |
| chr8: 23218101-146274708 | 23020 | 123056608 | 1 | rs7010362 | rs7822726 | 38.828 | 0 | LYN |
| chr8: 56706994-56851419 | 31 | 144426 | 1 | rs2316972 | rs1126327 | 1.58 | 0 | LYN |
| chr8: 43235525-66712108 | 3632 | 23476584 | 3 | rs10091311 | rs7001138 | 58.838 | 0 | LYN |
| chr3: 13878889-149737330 | 24723 | 135858442 | 1 | rs12634112 | rs2007869 | 55.663 | 0 | MAP4 |
| chr3: 33409611-170735099 | 23775 | 137325489 | 1 | rs3915062 | rs11924032 | 26.867 | 0 | MAP4 |
| chr3: 179527-114630641 | 23879 | 114451115 | 3 | rs4684741 | rs1587972 | 207.852 | 0 | MAP4 |
| chr22: 16871137-51184393 | 9245 | 34313257 | 3 | rs131538 | rs7284680 | 209.79 | 0 | MAPK1 |
| chr17: 43657921-44354796 | 88 | 696876 | 3 | rs9898857 | rs2732700 | 21.196 | 0 | MAPT |
| chr17: 21685812-67308196 | 12365 | 45622385 | 1 | rs34864328 | rs17686852 | 50.018 | 0 | MAPT |
| chr17: 43657921-44064851 | 65 | 406931 | 3 | rs9898857 | rs8079215 | 86.447 | 0 | MAPT |
| chr17: 26648492-58955084 | 5831 | 32306593 | 3 | rs1981512 | rs8068776 | 15.642 | 0 | MAPT |
| chr19: 31569338-53780966 | 3788 | 22211629 | 1 | rs2867544 | rs10407424 | 33.9 | 0 | MARK4 |
| chr19: 43257015-55294329 | −7309 | 12037315 | 3 | rs7246152 | rs2569676 | 21.402 | 0 | MARK4 |
| chr19: 288246-59110628 | 11009 | 58822383 | 3 | rs10409452 | cnvi0009466 | 100.582 | 0 | MARK4 |
| chr18: 25388300-75954881 | 11539 | 50566582 | 1 | rs11083228 | rs1876021 | 39.235 | 0 | MC4R |
| chr18: 26162481-67193217 | 9255 | 41030737 | 1 | rs12458903 | rs9961907 | 31.327 | 0 | MC4R |
| chr18: 1583633-58142042 | 11490 | 56558410 | 3 | rs9945988 | rs1560399 | 3.736 | 0 | MC4R |
| chr18: 26550830-63713914 | 8241 | 37163085 | 1 | rs16945738 | rs2715304 | 17.922 | 0 | MC4R |
| chr18: 46516210-68441007 | 5088 | 21924798 | 1 | rs7229153 | rs1282652 | 51.891 | 0 | MC4R |
| chr18: 44788908-78015180 | 8492 | 33226273 | 3 | rs9944807 | rs12960632 | 579.2 | 0 | MC4R |
| chr6: 26922906-93578359 | 19746 | 66655454 | 1 | rs9348738 | rs9363009 | 27.061 | 0 | MRPL14 |
| chr6: 31289284-56929863 | 15402 | 25640580 | 3 | rs9265170 | cnvi0015437 | 25.647 | 0 | MRPL14 |
| chr6: 32968276-73449742 | 15442 | 40481467 | 3 | rs2395300 | rs4235869 | 415.87 | 0 | MRPL14 |
| chr10: 7188484-134205354 | 26672 | 127016871 | 1 | rs1977295 | rs3923858 | 50.772 | 0 | MRPS16 |
| chr10: 57671424-133349223 | 16243 | 75677800 | 1 | rs11005106 | rs4301710 | 37.114 | 0 | MRPS16 |
| chr10: 58385643-124973104 | 13625 | 66587462 | 1 | rs7920235 | rs17663304 | 36.18 | 0 | MRPS16 |
| chr10: 55492192-117205017 | 13465 | 61712856 | 1 | rs6481032 | rs1933664 | 62.56 | 0 | MRPS16 |
| chr10: 53602190-135522754 | 19167 | 81920565 | 3 | rs12247820 | rs10909028 | 139.373 | 0 | MRPS16 |
| chr14: 26898958-104436931 | 17396 | 77537974 | 1 | rs1245195 | rs11851097 | 57.233 | 0 | MTHFD1 |
| chr14: 64926097-65063315 | 19 | 137219 | 1 | rs2281603 | rs10134770 | 14.377 | 0 | MTHFD1 |
| chr14: 19917123-65327288 | 10286 | 45410166 | 3 | rs2495197 | rs9323455 | 270.291 | 0 | MTHFD1 |
| chr4: 22401728-188608857 | 28456 | 166207130 | 1 | rs4697297 | rs7687115 | 35.717 | 0 | MTNR1A |
| chr4: 162592024-189861553 | 6129 | 27269530 | 1 | rs5005966 | rs6853039 | 63.501 | 0 | MTNR1A |
| chr4: 163766726-189931630 | 5627 | 26164905 | 3 | rs10033012 | rs10018868 | 25.326 | 0 | MTNR1A |
| chr4: 69590353-190872778 | 23145 | 121282426 | 3 | rs293433 | rs12646565 | 315.633 | 0 | MTNR1A |
| chr11: 42185849-126756938 | 15451 | 84571090 | 1 | rs4375424 | rs10750356 | 36.99 | 0 | MTNR1B |
| chr11: 21723471-131521797 | 20508 | 109798327 | 1 | rs11828478 | rs2512898 | 27.565 | 0 | MTNR1B |
| chr11: 23168804-106781292 | 16332 | 83612489 | 1 | rs11027007 | rs7103285 | 49.747 | 0 | MTNR1B |
| chr11: 84128537-120941583 | 7678 | 36813047 | 1 | rs488925 | rs4643089 | 29.271 | 0 | MTNR1B |
| chr11: 81251505-103234729 | 4842 | 21983225 | 3 | rs7935238 | rs1913462 | 26.176 | 0 | MTNR1B |
| chr11: 74545378-134940416 | 14496 | 60395039 | 3 | rs512780 | rs11224228 | 527.758 | 0 | MTNR1B |
| chr21: 14601415-48084989 | 8249 | 33483575 | 3 | rs2775537 | rs2839378 | 12047.211 | 0 | MX1 |
| chr21: 14601415-48084989 | 8249 | 33483575 | 3 | rs2775537 | rs2839378 | 41.154 | 0 | MX1 |
| chr21: 14595264-48084989 | 8781 | 33489726 | 3 | rs2847443 | rs2839378 | 1871.363 | 0 | MX1 |
| chr21: 14601415-48084989 | 8249 | 33483575 | 3 | rs2775537 | rs2839378 | 4787.438 | 0 | MX1 |
| chr21: 14768343-48084989 | 8193 | 33316647 | 3 | rs2257224 | rs2839378 | 5021.076 | 0 | MX1 |
| chr21: 10708231-47970581 | 8807 | 37262351 | 3 | rs4044122 | rs2255397 | 73.188 | 0 | MX1 |
| chr8: 30757798-142750969 | 20699 | 111993172 | 1 | rs10101203 | rs6421025 | 34.223 | 0 | MYC |
| chr8: 23218101-146274708 | 23020 | 123056608 | 1 | rs7010362 | rs7822726 | 38.828 | 0 | MYC |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr8: 60424884-145286483 | 17030 | 84861600 | 3 | rs1401422 | rs9720889 | 8.858 | 0 | MYC |
| chr8: 66822030-144791126 | 16557 | 77969097 | 3 | rs6472235 | rs10100154 | 251.068 | 0 | MYC |
| chr6: 64844594-169078546 | 21567 | 104233953 | 1 | rs4710465 | rs601639 | 46.524 | 0 | MYO6 |
| chr6: 66541198-162520133 | 19344 | 95978936 | 1 | rs2000382 | rs6901071 | 27.509 | 0 | MYO6 |
| chr6: 73120320-165130872 | 18715 | 92010553 | 1 | rs9442780 | rs10946016 | 76.383 | 0 | MYO6 |
| chr6: 66609532-147053632 | 15315 | 80444101 | 3 | rs9354335 | rs4896886 | 44.941 | 0 | MYO6 |
| chr6: 26922906-93578359 | 19746 | 66655454 | 1 | rs9348738 | rs9363009 | 27.061 | 0 | MYO6 |
| chr6: 62697746-94090076 | 6391 | 31392331 | 1 | rs6455128 | rs3799807 | 108.85 | 0 | MYO6 |
| chr6: 67621368-147709180 | 16188 | 80087813 | 1 | rs6919455 | rs7739314 | 52.498 | 0 | MYO6 |
| chr6: 75600804-78928379 | 602 | 3327576 | 3 | rs7743423 | rs1416055 | 49.19 | 0 | MYO6 |
| chr9: 1989033-107532317 | 18263 | 105543285 | 1 | rs7864828 | rs10820726 | 39.824 | 0 | NANS |
| chr9: 33180228-132003792 | 14691 | 98823565 | 1 | rs7854765 | rs9408988 | 28.69 | 0 | NANS |
| chr2: 2522475-140068342 | 25719 | 137545868 | 3 | rs10966757 | rs4074426 | 93.386 | 0 | NANS |
| chr9: 100158052-139077343 | 9815 | 38919292 | 3 | rs1020884 | rs4842126 | 470.601 | 0 | NANS |
| chr3: 13878889-149737330 | 24723 | 135858442 | 1 | rs12634112 | rs2007869 | 55.663 | 0 | NCK1 |
| chr3: 102240202-195550366 | 17318 | 93310165 | 1 | rs1620217 | rs11711870 | 41.031 | 0 | NCK1 |
| chr3: 83075971-196935657 | 21465 | 113859687 | 1 | rs9872858 | rs34729751 | 44.35 | 0 | NCK1 |
| chr3: 33409611-170735099 | 23775 | 137325489 | 1 | rs3915062 | rs11924032 | 26.867 | 0 | NCK1 |
| chr3: 103140700-144883172 | 8539 | 41742473 | 1 | rs4314176 | rs6797159 | 44.122 | 0 | NCK1 |
| chr3: 114889454-177826047 | 12700 | 62936594 | 3 | rs6795297 | rs7628308 | 102.526 | 0 | NCK1 |
| chr14: 26898958-104436931 | 17396 | 77537974 | 1 | rs1245195 | rs11851097 | 57.233 | 0 | NFKBIA |
| chr14: 26018408-44486343 | 3682 | 18467936 | 3 | rs10138404 | rs9323093 | 17.669 | 0 | NFKBIA |
| chr14: 35433187-35884639 | 78 | 451453 | 3 | rs2273154 | rs1012919 | 170.85 | 0 | NFKBIA |
| chr14: 35760062-35886955 | 27 | 126894 | 4 | rs17536892 | rs2415290 | 5.425 | 0 | NFKBIA |
| chr14: 19917123-65327288 | 10286 | 45410166 | 3 | rs2495197 | rs9323455 | 270.291 | 0 | NFKBIA |
| chr2: 12056323-227979775 | 39094 | 215923453 | 1 | rs966391 | rs1922020 | 31.384 | 0 | NMI |
| chr2: 38101137-241482099 | 36812 | 203380963 | 1 | rs879321 | rs7576043 | 52.099 | 0 | NMI |
| chr2: 34870277-241929621 | 37755 | 207059345 | 3 | rs13422005 | rs10205276 | 46.946 | 0 | NMI |
| chr2: 77041264-194763754 | 21140 | 117722491 | 1 | rs2102827 | rs16835406 | 94.091 | 0 | NMI |
| chr2: 83383707-175194550 | 16291 | 91810849 | 3 | rs12469076 | rs11891208 | 154.4 | 0 | NMI |
| chr4: 31222833-180548076 | 24457 | 149325244 | 1 | rs7662351 | rs3849606 | 36.162 | 0 | NPY2R |
| chr4: 22401728-188608857 | 28456 | 166207130 | 1 | rs4697297 | rs7687115 | 35.717 | 0 | NPY2R |
| chr4: 68173959-185767176 | 20235 | 117593218 | 1 | rs6552083 | rs4862428 | 61.893 | 0 | NPY2R |
| chr4: 63726348-173015421 | 19817 | 109289074 | 1 | rs17082970 | rs2131002 | 30.251 | 0 | NPY2R |
| chr4: 126374899-162380016 | 6166 | 36005118 | 1 | rs4834042 | rs17041092 | 33.404 | 0 | NPY2R |
| chr4: 137206602-158430547 | 3577 | 21223946 | 3 | rs1597600 | rs12507865 | 83.533 | 0 | NPY2R |
| chr4: 155739051-165849854 | 1997 | 10110804 | 1 | rs7691720 | rs10005938 | 26.215 | 0 | NPY2R |
| chr4: 69590353-190872778 | 23145 | 121282426 | 3 | rs293433 | rs12646565 | 315.633 | 0 | NPY2R |
| chr1: 1005806-105612342 | 19173 | 104606537 | 3 | rs3934834 | rs1584633 | 44.152 | 0 | NUDC |
| chr1: 2006108-109527861 | 22130 | 107521754 | 3 | rs2254669 | rs839879 | 162.269 | 0 | NUDC |
| chr1: 1005806-105612342 | 19173 | 104606537 | 3 | rs3934834 | rs1584633 | 44.152 | 0 | OPRD1 |
| chr1: 2006108-109527861 | 22130 | 107521754 | 3 | rs2254669 | rs839879 | 162.269 | 0 | OPRD1 |
| chr19: 31569338-53780966 | 3788 | 22211629 | 1 | rs2867544 | rs10407424 | 33.9 | 0 | PAFAH1B3 |
| chr19: 288246-59110628 | 11009 | 58822383 | 3 | rs10409452 | cnvi0009466 | 100.582 | 0 | PAFAH1B3 |
| chr2: 12056323-227979775 | 39094 | 215923453 | 1 | rs966391 | rs1922020 | 31.384 | 0 | PCBP1 |
| chr2: 38101137-241482099 | 36812 | 203380963 | 1 | rs879321 | rs7576043 | 52.099 | 0 | PCBP1 |
| chr2: 34870277-241929621 | 37755 | 207059345 | 3 | rs13422005 | rs10205276 | 46.946 | 0 | PCBP1 |
| chr2: 69979290-70389900 | 49 | 410611 | 3 | rs10177224 | rs11677137 | 16.309 | 0 | PCBP1 |
| chr2: 41212010-82396211 | 9721 | 41184202 | 3 | rs12614285 | rs934310 | 396.396 | 0 | PCBP1 |
| chr21: 14601415-48084989 | 8249 | 33483575 | 3 | rs2775537 | rs2839378 | 12047.211 | 0 | PCBP3 |
| chr21: 47091361-47226895 | 18 | 135535 | 1 | rs2838973 | rs2839002 | 14.709 | 0 | PCBP3 |
| chr21: 14601415-48084989 | 8249 | 33483575 | 3 | rs2775537 | rs2839378 | 41.154 | 0 | PCBP3 |
| chr21: 44839153-47856106 | 674 | 3016954 | 1 | rs2838302 | rs2236616 | 38.158 | 0 | PCBP3 |
| chr21: 14595264-48084989 | 8781 | 33489726 | 3 | rs2847443 | rs2839378 | 1871.363 | 0 | PCBP3 |
| chr21: 14601415-48084989 | 8249 | 33483575 | 3 | rs2775537 | rs2839378 | 4787.438 | 0 | PCBP3 |
| chr21: 46381900-48098560 | 448 | 1716661 | 1 | rs8132265 | cnvi0019195 | 712.68 | 0 | PCBP3 |
| chr21: 14768343-48084989 | 8193 | 33316647 | 3 | rs2257224 | rs2839378 | 5021.076 | 0 | PCBP3 |
| chr21: 10708231-47970581 | 8807 | 37262351 | 3 | rs4044122 | rs2255397 | 73.188 | 0 | PCBP3 |
| chr5: 84830796-171903310 | 16642 | 87072515 | 1 | rs300657 | rs10042482 | 42.208 | 0 | PCDHA4 |
| chr5: 57343495-171903310 | 21683 | 114559816 | 1 | rs10940593 | rs10042482 | 61.169 | 0 | PCDHA4 |
| chr5: 98442871-150317237 | 9828 | 51874367 | 1 | rs1447379 | rs7710790 | 38.687 | 0 | PCDHA4 |
| chr5: 4872310-180709915 | 35876 | 175837606 | 3 | rs816467 | rs10071993 | 179.394 | 0 | PCDHA4 |
| chr6: 64844594-169078546 | 21567 | 104233953 | 1 | rs4710465 | rs601639 | 46.524 | 0 | PCMT1 |
| chr6: 66541198-162520133 | 19344 | 95978936 | 1 | rs2000382 | rs6901071 | 27.509 | 0 | PCMT1 |
| chr6: 73120320-165130872 | 18715 | 92010553 | 1 | rs9442780 | rs10946016 | 76.383 | 0 | PCMT1 |
| chr6: 94117546-165103679 | 15579 | 70986134 | 1 | rs3799792 | rs9347902 | 34.066 | 0 | PCMT1 |
| chr6: 100082983-170909002 | 16393 | 70826020 | 3 | rs594231 | rs12213906 | 261.313 | 0 | PCMT1 |
| chr19: 31569338-53780966 | 3788 | 22211629 | 1 | rs2867544 | rs10407424 | 33.9 | 0 | PDCD5 |
| chr19: 288246-59110628 | 11009 | 58822383 | 3 | rs10409452 | cnvi0009466 | 100.582 | 0 | PDCD5 |
| chr12: 10113083-116370432 | 20594 | 106257350 | 1 | rs2012504 | rs7958254 | 35.157 | 0 | PDE1B |
| chr12: 10020267-129866293 | 23654 | 119846027 | 1 | rs1597097 | rs2170504 | 45.428 | 0 | PDE1B |
| chr12: 39967134-84174413 | 8879 | 44207280 | 1 | rs11172661 | rs11116039 | 39.568 | 0 | PDE1B |
| chr12: 50855195-133778796 | 17748 | 82923602 | 3 | rs4351895 | rs7975069 | 159.589 | 0 | PDE1B |
| chr7: 11855636-156148608 | 26852 | 144292973 | 1 | rs6947930 | rs6945016 | 36.446 | 0 | PDE1C |
| chr7: 8872727-156383359 | 27773 | 147510633 | 1 | rs917038 | rs878717 | 32.336 | 0 | PDE1C |
| chr7: 8794418-119068130 | 23484 | 110273713 | 1 | rs2189621 | rs6977904 | 70.867 | 0 | PDE1C |
| chr7: 7724805-53845684 | 11772 | 46120880 | 3 | rs10263415 | rs6948633 | 42.007 | 0 | PDE1C |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr7: 60392-84158180 | 19095 | 84097789 | 3 | rs12670102 | rs2715048 | 208.308 | 0 | PDE1C |
| chr17: 44458950-81047708 | -8195 | 36588759 | 1 | cnvi0016818 | rs35680231 | 35.591 | 0 | PDE6G |
| chr17: 62662507-81047708 | -11496 | 18385202 | 3 | rs6504246 | rs35680231 | 56.048 | 0 | PDE6G |
| chr1: 64114301-245591329 | 29842 | 181477029 | 1 | rs11208257 | rs1173850 | 37.504 | 0 | PGM1 |
| chr1: 1005806-105612342 | 19173 | 104606537 | 3 | rs3934834 | rs1584633 | 44.152 | 0 | PGM1 |
| chr1: 2006108-109527861 | 22130 | 107521754 | 3 | rs2254669 | rs839879 | 162.269 | 0 | PGM1 |
| chr16: 176743-50013967 | 8328 | 49837225 | 3 | rs2562164 | rs12597023 | 174.392 | 0 | PHKB |
| chr16: 29441284-33923125 | 585 | 4481842 | 3 | rs7206789 | rs4043755 | 42.437 | 0 | PHKG2 |
| chr16: 176743-50013967 | 8328 | 49837225 | 3 | rs2562164 | rs12597023 | 174.392 | 0 | PHKG2 |
| chr22: 16871137-51184393 | 9245 | 34313257 | 3 | rs131538 | rs7284680 | 209.79 | 0 | PICK1 |
| chr3: 166503411-190576461 | 4854 | 24073051 | 1 | rs11925936 | rs1393054 | 31.414 | 0 | PIK3CA |
| chr3: 102240202-195550366 | 17318 | 93310165 | 1 | rs1620217 | rs11711870 | 41.031 | 0 | PIK3CA |
| chr3: 83075971-196935657 | 21465 | 113859687 | 1 | rs9872858 | rs34729751 | 44.35 | 0 | PIK3CA |
| chr3: 164955741-191742104 | 5741 | 26786364 | 1 | rs2218152 | rs9835019 | 52.438 | 0 | PIK3CA |
| chr3: 177912894-197551411 | 4129 | 19638518 | 3 | rs9290640 | rs1273562 | 185.507 | 0 | PIK3CA |
| chr5: 57343495-171903310 | 21683 | 114559816 | 1 | rs10940593 | rs10042482 | 61.169 | 0 | PIK3R1 |
| chr5: 49952847-89853069 | 7268 | 39900223 | 3 | rs12188654 | rs42467 | 26.225 | 0 | PIK3R1 |
| chr5: 4872310-180709915 | 35876 | 175837606 | 3 | rs816467 | rs10071993 | 179.394 | 0 | PIK3R1 |
| chr6: 26922906-93578359 | 19746 | 66655454 | 1 | rs9348738 | rs9363009 | 27.061 | 0 | PLA2G7 |
| chr6: 31289284-56929863 | 15402 | 25640580 | 3 | rs9265170 | cnvi0015437 | 25.647 | 0 | PLA2G7 |
| chr6: 32968276-73449742 | 15442 | 40481467 | 3 | rs2395300 | rs4235869 | 415.87 | 0 | PLA2G7 |
| chr20: 4591715-58420336 | 11753 | 53828622 | 1 | rs6139494 | rs1416388 | 40.922 | 0 | PLCB1 |
| chr20: 7869025-62424661 | 11941 | 54555637 | 3 | rs2294306 | rs6010652 | 9.732 | 0 | PLCB1 |
| chr20: 236802-54845796 | 12646 | 54608995 | 3 | rs448294 | rs6064362 | 286.151 | 0 | PLCB1 |
| chr11: 42185849-126756938 | 15451 | 84571090 | 1 | rs4375424 | rs10750356 | 36.99 | 0 | PLCB3 |
| chr11: 21723471-131521797 | 20508 | 109798327 | 1 | rs11828454 | rs2512898 | 27.565 | 0 | PLCB3 |
| chr11: 23168804-106781292 | 16332 | 83612489 | 1 | rs11027007 | rs7103285 | 49.747 | 0 | PLCB3 |
| chr11: 211482-66910826 | 13813 | 66699345 | 3 | rs2293168 | rs4375446 | 30.249 | 0 | PLCB3 |
| chr16: 64107047-82920737 | 4544 | 18813691 | 1 | rs2319723 | rs918661 | 28.887 | 0 | PLCG2 |
| chr16: 59854730-89273883 | 7609 | 29419164 | 3 | rs1373880 | rs8046156 | 31.884 | 0 | PLCG2 |
| chr16: 50219449-89544756 | 10324 | 39325308 | 3 | rs6500298 | rs3803681 | 108.108 | 0 | PLCG2 |
| chr1: 1005806-105612342 | 19173 | 104606537 | 3 | rs3934834 | rs1584633 | 44.152 | 0 | PPIH |
| chr1: 2006108-109527861 | 22130 | 107521754 | 3 | rs2254669 | rs839879 | 162.269 | 0 | PPIH |
| chr19: 31569338-53780966 | 3788 | 22211629 | 1 | rs2867544 | rs10407424 | 33.9 | 0 | PPP2R1A |
| chr19: 43257015-55294329 | -7309 | 12037315 | 3 | rs7246152 | rs2569676 | 21.402 | 0 | PPP2R1A |
| chr19: 52365654-54612628 | 524 | 2246975 | 1 | rs4514789 | rs254262 | 59.657 | 0 | PPP2R1A |
| chr19: 288246-59110628 | 11009 | 58822383 | 3 | rs10409452 | cnvi0009466 | 100.582 | 0 | PPP2R1A |
| chr1: 1005806-105612342 | 19173 | 104606537 | 3 | rs3934834 | rs1584633 | 44.152 | 0 | PRDX1 |
| chr1: 2006108-109527861 | 22130 | 107521754 | 3 | rs2254669 | rs839879 | 162.269 | 0 | PRDX1 |
| chr17: 44458950-81047708 | -8195 | 36588759 | 1 | cnvi0016818 | rs35680231 | 35.591 | 0 | PRKCA |
| chr17: 21685812-67308196 | 12365 | 45622385 | 1 | rs34864328 | rs17686852 | 50.018 | 0 | PRKCA |
| chr17: 59314257-66170047 | 1135 | 6855791 | 1 | rs758467 | rs4558468 | 71.379 | 0 | PRKCA |
| chr17: 61016209-66240093 | 890 | 5223885 | 1 | rs1588368 | rs11658645 | 37.309 | 0 | PRKCA |
| chr17: 62662507-81047708 | -11496 | 18385202 | 3 | rs6504246 | rs35680231 | 56.048 | 0 | PRKCA |
| chr10: 7188484-134205354 | 26672 | 127016871 | 1 | rs1977295 | rs3923858 | 50.772 | 0 | PRLHR |
| chr10: 57671424-133349223 | 16243 | 75677800 | 1 | rs11005106 | rs4301710 | 37.114 | 0 | PRLHR |
| chr10: 58385643-124973104 | 13625 | 66587462 | 1 | rs7920235 | rs17663304 | 36.18 | 0 | PRLHR |
| chr10: 53602190-135522754 | 19167 | 81920565 | 3 | rs12247820 | rs10909028 | 139.373 | 0 | PRLHR |
| chr19: 31569338-53780966 | 3788 | 22211629 | 1 | rs2867544 | rs10407424 | 33.9 | 0 | PRMT1 |
| chr19: 43257015-55294329 | -7309 | 12037315 | 3 | rs7246152 | rs2569676 | 21.402 | 0 | PRMT1 |
| chr19: 288246-59110628 | 11009 | 58822383 | 3 | rs10409452 | cnvi0009466 | 100.582 | 0 | PRMT1 |
| chr17: 44458950-81047708 | -8195 | 36588759 | 1 | cnvi0016818 | rs35680231 | 35.591 | 0 | PRPSAP1 |
| chr17: 62662507-81047708 | -11496 | 18385202 | 3 | rs6504246 | rs35680231 | 56.048 | 0 | PRPSAP1 |
| chr9: 1989033-107532317 | 18263 | 105543285 | 1 | rs7864828 | rs10820726 | 39.824 | 0 | PSAT1 |
| chr9: 33180228-132003792 | 14691 | 98823565 | 1 | rs7854765 | rs9408988 | 28.69 | 0 | PSAT1 |
| chr9: 2522475-140068342 | 25719 | 137545868 | 3 | rs10966757 | rs4074426 | 93.386 | 0 | PSAT1 |
| chr9: 46587-94335290 | 17484 | 94288704 | 3 | rs10814410 | rs9409606 | 762.393 | 0 | PSAT1 |
| chr14: 26898958-104436931 | 17396 | 77537974 | 1 | rs1245195 | rs11851097 | 57.233 | 0 | PSEN1 |
| chr14: 65405722-103799039 | 8979 | 38393318 | 3 | rs11623705 | rs11628472 | 266.153 | 0 | PSEN1 |
| chr11: 345515-17408630 | 4247 | 17063116 | 3 | rs11246094 | rs5215 | 30.474 | 0 | PSMA1 |
| chr11: 211482-66910826 | 13813 | 66699345 | 3 | rs2293168 | rs4375446 | 30.249 | 0 | PSMA1 |
| chr14: 90716051-90836365 | 22 | 120315 | 1 | rs11159958 | rs11626241 | 15.241 | 0 | PSMC1 |
| chr14: 26898958-104436931 | 17396 | 77537974 | 1 | rs1245195 | rs11851097 | 57.233 | 0 | PSMC1 |
| chr14: 80818058-105348552 | 5492 | 24530495 | 3 | rs6574553 | rs2028416 | 15.874 | 0 | PSMC1 |
| chr14: 65405722-103799039 | 8979 | 38393318 | 3 | rs11623705 | rs11628472 | 266.153 | 0 | PSMC1 |
| chr2: 38101137-241482099 | 36812 | 203380963 | 1 | rs879321 | rs7576043 | 52.099 | 0 | PSMD1 |
| chr2: 34870277-241929621 | 37755 | 207059345 | 3 | rs13422005 | rs10205276 | 46.946 | 0 | PSMD1 |
| chr2: 231927569-232035793 | 10 | 108225 | 1 | rs3815844 | rs2032953 | 14.229 | 0 | PSMD1 |
| chr2: 193255360-242529978 | 10289 | 49274619 | 3 | rs1351905 | cnvi0010399 | 93.244 | 0 | PSMD1 |
| chr17: 21685812-67308196 | 12365 | 45622385 | 1 | rs34864328 | rs17686852 | 50.018 | 0 | PSMD11 |
| chr17: 26648492-58955084 | 5831 | 32306593 | 3 | rs1981512 | rs8068776 | 15.642 | 0 | PSMD11 |
| chr11: 211482-66910826 | 13813 | 66699345 | 3 | rs2293168 | rs4375446 | 30.249 | 0 | PSMD13 |
| chr3: 13878889-149737330 | 24723 | 135858442 | 1 | rs12634112 | rs2007869 | 55.663 | 0 | PSMD6 |
| chr3: 33409611-170735099 | 23775 | 137325489 | 1 | rs3915062 | rs11924032 | 26.867 | 0 | PSMD6 |
| chr3: 179527-114630641 | 23879 | 114451115 | 3 | rs4684741 | rs1587972 | 207.852 | 0 | PSMD6 |
| chr14: 22513116-32242747 | 1997 | 9729632 | 1 | rs4982546 | rs17098165 | 31.673 | 0 | PSME1 |
| chr14: 22349686-25012115 | 755 | 2662430 | 1 | rs994827 | rs7142675 | 27.602 | 0 | PSME1 |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr14: 19917123-65327288 | 10286 | 45410166 | 3 | rs2495197 | rs9323455 | 270.291 | 0 | PSME1 |
| chr12: 10020267-129866293 | 23654 | 119846027 | 1 | rs1597097 | rs2170504 | 45.428 | 0 | PXN |
| chr12: 59512781-127744939 | 13469 | 68232159 | 3 | rs908394 | rs7966946 | 20.62 | 0 | PXN |
| chr12: 112610714-133708729 | 5366 | 21098016 | 3 | rs11066188 | rs11147249 | 695.45 | 0 | PXN |
| chr12: 50855195-133778769 | 17748 | 82923602 | 3 | rs4351895 | rs7975069 | 159.589 | 0 | PXN |
| chr14: 26898958-104436931 | 17396 | 77537974 | 1 | rs1245195 | rs11851097 | 57.233 | 0 | PYGL |
| chr14: 19917123-65327288 | 10286 | 45410166 | 3 | rs2495197 | rs9323455 | 270.291 | 0 | PYGL |
| chr11: 42185849-126756938 | 15451 | 84571090 | 1 | rs4375424 | rs10750356 | 36.99 | 0 | PYGM |
| chr11: 21723471-131521797 | 20508 | 109798327 | 1 | rs11828478 | rs2512898 | 27.565 | 0 | PYGM |
| chr11: 23168804-106781292 | 16332 | 83612489 | 1 | rs11027007 | rs7103285 | 49.747 | 0 | PYGM |
| chr11: 211482-66910826 | 13813 | 66699345 | 3 | rs2293168 | rs4375446 | 30.249 | 0 | PYGM |
| chr17: 44458950-81047708 | -8195 | 36588759 | 1 | cnvi0016818 | rs35680231 | 35.591 | 0 | QRICH2 |
| chr17: 62662507-81047708 | -11496 | 18385202 | 3 | rs6504246 | rs35680231 | 56.048 | 0 | QRICH2 |
| chr7: 11855636-156148608 | 26852 | 144292973 | 1 | rs6947930 | rs6945016 | 36.446 | 0 | RALA |
| chr7: 8872727-156383359 | 27773 | 147510633 | 1 | rs917038 | rs878717 | 32.336 | 0 | RALA |
| chr7: 8794418-119068130 | 23484 | 110273713 | 1 | rs2189621 | rs6977904 | 70.867 | 0 | RALA |
| chr7: 7724805-53845684 | 11772 | 46120880 | 3 | rs10263415 | rs6948633 | 42.007 | 0 | RALA |
| chr7: 60392-84158180 | 19095 | 84097789 | 3 | rs12670102 | rs2715048 | 208.308 | 0 | RALA |
| chr22: 18877787-21462353 | 613 | 2584567 | 3 | rs2543958 | rs140392 | 772.063 | 0 | RANBP1 |
| chr22: 18907405-21465780 | 610 | 2558376 | 3 | rs9618419 | rs11703181 | 1799.961 | 0 | RANBP1 |
| chr22: 19601238-20241160 | 201 | 639923 | 3 | rs8135473 | rs1567871 | 11.687 | 0 | RANBP1 |
| chr22: 19613784-21462353 | 380 | 1848570 | 3 | rs5993743 | rs140392 | 153.49 | 0 | RANBP1 |
| chr22: 18877787-21462353 | 512 | 2584567 | 1 | rs2543958 | rs140392 | 1596.687 | 0 | RANBP1 |
| chr22: 16871137-51184393 | 9245 | 34313257 | 3 | rs131538 | rs7284680 | 209.79 | 0 | RANBP1 |
| chr13: 36707502-103656104 | 13622 | 66948603 | 1 | rs3827890 | rs1952590 | 38.726 | 0 | RAP2A |
| chr13: 23742931-115064482 | 19829 | 91321552 | 1 | rs4770401 | rs7999630 | 44.074 | 0 | RAP2A |
| chr13: 87746779-104646511 | 3908 | 16899733 | 3 | rs9301986 | rs17414312 | 27.724 | 0 | RAP2A |
| chr13: 90018392-105190802 | 4136 | 15172411 | 1 | rs7335222 | rs11841281 | 42.954 | 0 | RAP2A |
| chr13: 65193124-115053155 | 12025 | 49860032 | 3 | rs9598811 | rs7327124 | 78.057 | 0 | RAP2A |
| chr1: 1005806-105612342 | 19173 | 104606537 | 3 | rs3934834 | rs1584633 | 44.152 | 0 | RCC1 |
| chr1: 2006108-109527861 | 22130 | 107521754 | 3 | rs2254669 | rs839879 | 162.269 | 0 | RCC1 |
| chr1: 1005806-105612342 | 19173 | 104606537 | 3 | rs3934834 | rs1584633 | 44.152 | 0 | RCC2 |
| chr1: 2006108-109527861 | 22130 | 107521754 | 3 | rs2254669 | rs839879 | 162.269 | 0 | RCC2 |
| chr4: 179131-68819153 | 13495 | 68819023 | 3 | rs7686919 | rs7687396 | 625.133 | 0 | RGS12 |
| chr1: 64114301-245591329 | 29842 | 181477029 | 1 | rs11208257 | rs1173850 | 37.504 | 0 | RGS2 |
| chr1: 75098453-243531649 | 27360 | 168433197 | 1 | rs12117493 | rs10927002 | 32.113 | 0 | RGS2 |
| chr1: 189128124-227340790 | 7927 | 38212667 | 1 | rs7515205 | rs12752546 | 167.428 | 0 | RGS2 |
| chr1: 178626526-244159143 | 13064 | 65532618 | 3 | rs2761477 | rs479338 | 11.373 | 0 | RGS2 |
| chr1: 188850774-235423607 | 10060 | 46572834 | 1 | rs16829466 | rs12409696 | 43.25 | 0 | RGS2 |
| chr1: 191875752-235423607 | 9517 | 43547856 | 1 | rs9427811 | rs12409696 | 62.01 | 0 | RGS2 |
| chr1: 174219398-247422297 | 15986 | 73202900 | 1 | rs16846809 | rs4642922 | 35.258 | 0 | RGS2 |
| chr1: 109645793-194560463 | 12025 | 84914671 | 3 | cnvi0008281 | rs10921616 | 63.121 | 0 | RGS2 |
| chr3: 13878864-149737330 | 24723 | 135858442 | 1 | rs12634112 | rs2007869 | 55.663 | 0 | RHOA |
| chr3: 33409611-170735099 | 23775 | 137325489 | 1 | rs3915062 | rs11924032 | 26.867 | 0 | RHOA |
| chr3: 179527-114630641 | 23879 | 114451115 | 3 | rs4684741 | rs1587972 | 207.852 | 0 | RHOA |
| chr2: 12056323-227979775 | 39094 | 215923453 | 1 | rs966391 | rs1922020 | 31.384 | 0 | RIF1 |
| chr2: 38101137-241482099 | 36812 | 203380963 | 1 | rs879321 | rs7576043 | 52.099 | 0 | RIF1 |
| chr2: 34870277-241929621 | 37755 | 207059345 | 3 | rs13422005 | rs10205276 | 46.946 | 0 | RIF1 |
| chr2: 77041264-194763754 | 21140 | 117722491 | 1 | rs2102827 | rs16835406 | 94.091 | 0 | RIF1 |
| chr2: 83383702-175194550 | 16291 | 91810849 | 3 | rs12469609 | rs11891208 | 154.4 | 0 | RIF1 |
| chr1: 1005806-105612342 | 19173 | 104606537 | 3 | rs3934834 | rs1584633 | 44.152 | 0 | RPA2 |
| chr1: 2006108-109527861 | 22130 | 107521754 | 3 | rs2254669 | rs839879 | 162.269 | 0 | RPA2 |
| chr11: 345515-17408630 | 4247 | 17063116 | 3 | rs11246094 | rs5215 | 30.474 | 0 | RPLP2 |
| chr11: 211482-66910826 | 13813 | 66699345 | 3 | rs2293168 | rs4375446 | 30.249 | 0 | RPLP2 |
| chr20: 13712769-55093901 | 8218 | 41381509 | 1 | rs6033810 | rs6999 | 41.237 | 0 | RPN2 |
| chr20: 4591715-58420336 | 11753 | 53828622 | 1 | rs6139494 | rs1416388 | 40.922 | 0 | RPN2 |
| chr20: 7869025-62424661 | 11941 | 54555637 | 1 | rs2294306 | rs6010652 | 9.732 | 0 | RPN2 |
| chr20: 236802-54845796 | 12646 | 54608995 | 3 | rs448294 | rs6064362 | 286.151 | 0 | RPN2 |
| chr5: 84830796-171903310 | 16642 | 87072515 | 1 | rs300657 | rs10042482 | 42.208 | 0 | RPS14 |
| chr5: 57343495-171903310 | 21683 | 114559816 | 1 | rs10940593 | rs10042482 | 61.169 | 0 | RPS14 |
| chr5: 98442871-150317237 | 9828 | 51874367 | 1 | rs1447379 | rs7710790 | 38.687 | 0 | RPS14 |
| chr5: 4872310-180709915 | 35876 | 175837606 | 3 | rs816467 | rs10071993 | 179.394 | 0 | RPS14 |
| chr11: 3906740-4201641 | 55 | 294902 | 1 | rs11600857 | rs2044138 | 27.361 | 0 | RRM1 |
| chr11: 345515-17408630 | 4247 | 17063116 | 3 | rs11246094 | rs5215 | 30.474 | 0 | RRM1 |
| chr11: 211482-66910826 | 13813 | 66699345 | 3 | rs2293168 | rs4375446 | 30.249 | 0 | RRM1 |
| chr19: 31569338-53780966 | 3788 | 22211629 | 1 | rs2867544 | rs10407424 | 33.9 | 0 | RUVBL2 |
| chr19: 43257015-55294329 | -7309 | 12037315 | 3 | rs7246152 | rs2569676 | 21.402 | 0 | RUVBL2 |
| chr19: 288246-59110628 | 11009 | 58822383 | 3 | rs10409452 | cnvi0009466 | 100.582 | 0 | RUVBL2 |
| chr19: 31569338-53780966 | 3788 | 22211629 | 1 | rs2867544 | rs10407424 | 33.9 | 0 | RYR1 |
| chr19: 288246-59110628 | 11009 | 58822383 | 3 | rs10409452 | cnvi0009466 | 100.582 | 0 | RYR1 |
| chr1: 64114301-245591329 | 29842 | 181477029 | 1 | rs11208257 | rs1173850 | 37.504 | 0 | RYR2 |
| chr1: 75098453-243531649 | 27360 | 168433197 | 1 | rs12117493 | rs10927002 | 32.113 | 0 | RYR2 |
| chr1: 178626526-244159143 | 13064 | 65532618 | 3 | rs2761477 | rs479338 | 11.373 | 0 | RYR2 |
| chr1: 237570457-237675464 | 37 | 105008 | 1 | rs4659495 | rs2618721 | 15.007 | 0 | RYR2 |
| chr1: 174219398-247422297 | 15986 | 73202900 | 1 | rs16846809 | rs4642922 | 35.258 | 0 | RYR2 |
| chr1: 237584925-237904870 | 86 | 319946 | 1 | rs4593814 | rs10925504 | 31.95 | 0 | RYR2 |
| chr1: 236848751-249219320 | 3293 | 12370570 | 3 | rs819666 | cnvi0018731 | 920.725 | 0 | RYR2 |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr1: 64114301-245591329 | 29842 | 181477029 | 1 | rs11208257 | rs1173850 | 37.504 | 0 | S100A6 |
| chr1: 75098453-243531649 | 27360 | 168433197 | 1 | rs12117493 | rs10927002 | 32.113 | 0 | S100A6 |
| chr1: 79710545-188898319 | 17303 | 109187775 | 1 | rs417181 | rs16829637 | 45.89 | 0 | S100A6 |
| chr1: 109645793-194560463 | 12025 | 84914671 | 3 | cnvi0008281 | rs10921616 | 63.121 | 0 | S100A6 |
| chr13: 23742931-115064482 | 19829 | 91321552 | 1 | rs4770401 | rs7999630 | 44.074 | 0 | SACS |
| chr13: 19584477-81204088 | 13265 | 61619612 | 3 | rs1334954 | rs1176297 | 22.162 | 0 | SACS |
| chr13: 19121741-63373781 | 10326 | 44252041 | 3 | rs9578050 | rs9539575 | 82.761 | 0 | SACS |
| chr1: 64114301-245591329 | 29842 | 181477029 | 1 | rs11208257 | rs1173850 | 37.504 | 0 | SARS |
| chr1: 75098453-243531649 | 27360 | 168433197 | 1 | rs12117493 | rs10927002 | 32.113 | 0 | SARS |
| chr1: 79710545-188898319 | 17303 | 109187775 | 1 | rs417181 | rs16829637 | 45.89 | 0 | SARS |
| chr1: 109645793-194560463 | 12025 | 84914671 | 3 | cnvi0008281 | rs10921616 | 63.121 | 0 | SARS |
| chr2: 12056323-227979775 | 39094 | 215923453 | 1 | rs966391 | rs1922020 | 31.384 | 0 | SCTR |
| chr2: 38101137-241482099 | 36812 | 203380963 | 1 | rs879321 | rs7576043 | 52.099 | 0 | SCTR |
| chr2: 34870277-241929621 | 37755 | 207059345 | 3 | rs13422005 | rs10205276 | 46.946 | 0 | SCTR |
| chr2: 77041264-194763754 | 21140 | 117722491 | 3 | rs2102827 | rs16835406 | 94.091 | 0 | SCTR |
| chr2: 83383702-175194550 | 16291 | 91810849 | 3 | rs12469609 | rs11891208 | 154.4 | 0 | SCTR |
| chr1: 1005806-105612342 | 19173 | 104606537 | 3 | rs3934834 | rs1584633 | 44.152 | 0 | SDC3 |
| chr1: 2006108-109527861 | 22130 | 107521754 | 3 | rs2254669 | rs839879 | 162.269 | 0 | SDC3 |
| chr1: 64114301-245591329 | 29842 | 181477029 | 1 | rs11208257 | rs1173850 | 37.504 | 0 | SELE |
| chr1: 75098453-243531649 | 27360 | 168433197 | 1 | rs12117493 | rs10927002 | 32.113 | 0 | SELE |
| chr1: 79710545-188898319 | 17303 | 109187775 | 1 | rs417181 | rs16829637 | 45.89 | 0 | SELE |
| chr1: 169556446-171300348 | 340 | 1743903 | 1 | rs9332480 | rs7541160 | 32.81 | 0 | SELE |
| chr1: 109645793-194560463 | 12025 | 84914671 | 3 | cnvi0008281 | rs10921616 | 63.121 | 0 | SELE |
| chr6: 2681610-31453618 | 81 | 28772009 | 3 | rs1131896 | rs9267212 | 428.177 | 0 | SERPINB9 |
| chr6: 1171596-29899147 | 47 | 28727552 | 0 | rs3128994 | rs2394704 | 80.695 | 0 | SERPINB9 |
| chr6: 1171596-29899147 | 47 | 28727552 | 0 | rs3128994 | rs2394704 | 63.572 | 0 | SERPINB9 |
| chr6: 1171596-29895228 | 43 | 28723633 | 0 | rs3128994 | rs9259831 | 53.123 | 0 | SERPINB9 |
| chr6: 1175965-29899147 | 43 | 28723183 | 0 | rs1611522 | rs2394704 | 52.089 | 0 | SERPINB9 |
| chr6: 1177990-29899147 | 39 | 28721158 | 0 | rs2428530 | rs2394704 | 44.381 | 0 | SERPINB9 |
| chr6: 2585208-31281876 | -2 | 28696669 | 1 | rs1634746 | rs1634747 | 31.615 | 0 | SERPINB9 |
| chr6: 2681610-31453618 | 81 | 28772009 | 3 | rs1131896 | rs9267212 | 390.234 | 0 | SERPINB9 |
| chr6: 2584569-31286381 | 8 | 28701813 | 1 | rs9391764 | rs9265057 | 34.598 | 0 | SERPINB9 |
| chr6: 1171596-29892436 | 39 | 28720841 | 1 | rs3128994 | rs9259806 | 31.699 | 0 | SERPINB9 |
| chr6: 1171596-29895228 | 43 | 28723633 | 0 | rs3128994 | rs9259831 | 43.568 | 0 | SERPINB9 |
| chr6: 181089-30430875 | 1806 | 30249787 | 3 | rs1535053 | rs35792611 | 80.394 | 0 | SERPINB9 |
| chr9: 33180228-132003792 | 14691 | 98823565 | 1 | rs7854765 | rs9408988 | 28.69 | 0 | SET |
| chr9: 2522475-140068342 | 25719 | 137545868 | 3 | rs10966757 | rs4074426 | 93.386 | 0 | SET |
| chr9: 100158052-139077343 | 9815 | 38919292 | 3 | rs1020884 | rs4842126 | 470.601 | 0 | SET |
| chr21: 14601415-48084989 | 8249 | 33483575 | 3 | rs2775537 | rs2839378 | 12047.211 | 0 | SETD4 |
| chr21: 14601415-48084989 | 8249 | 33483575 | 3 | rs2775537 | rs2839378 | 41.154 | 0 | SETD4 |
| chr21: 36927793-37647438 | 142 | 719646 | 3 | rs2205031 | rs9980084 | 187.28 | 0 | SETD4 |
| chr21: 14595264-48084989 | 8781 | 33489726 | 3 | rs2847443 | rs2839378 | 1871.363 | 0 | SETD4 |
| chr21: 14601415-48084989 | 8249 | 33483575 | 3 | rs2775537 | rs2839378 | 4787.438 | 0 | SETD4 |
| chr21: 14768343-48084989 | 8193 | 33316647 | 3 | rs2257224 | rs2839378 | 5021.076 | 0 | SETD4 |
| chr21: 10708231-47970581 | 8807 | 37262351 | 3 | rs4044122 | rs2255397 | 73.188 | 0 | SETD4 |
| chr2: 12056323-227979775 | 39094 | 215923453 | 1 | rs966391 | rs1922020 | 31.384 | 0 | SF3B14 |
| chr2: 18856-41136833 | 9721 | 41117978 | 3 | rs11901199 | rs10187704 | 191.638 | 0 | SF3B14 |
| chr19: 31569338-53780966 | 3788 | 22211629 | 1 | rs2867544 | rs10407424 | 33.9 | 0 | SHANK1 |
| chr19: 43257015-55294329 | -7309 | 12037315 | 3 | rs7246152 | rs2569676 | 21.402 | 0 | SHANK1 |
| chr19: 288246-59110628 | 11009 | 58822383 | 3 | rs10409452 | cnvi0009466 | 100.582 | 0 | SHANK1 |
| chr17: 108420-26610769 | 5548 | 26502350 | 3 | rs12452527 | rs658591 | 82.699 | 0 | SHBG |
| chr16: 176743-50013967 | 8328 | 49837225 | 3 | rs2562164 | rs12597023 | 174.392 | 0 | SIAH1 |
| chr1: 1005806-105612342 | 19173 | 104606537 | 3 | rs3934834 | rs1584633 | 44.152 | 0 | SLC2A1 |
| chr1: 2006108-109527861 | 22130 | 107521754 | 3 | rs2254669 | rs839879 | 162.269 | 0 | SLC2A1 |
| chr5: 141659-19410008 | 4662 | 18868350 | 3 | rs11741126 | rs4642370 | 50.124 | 0 | SLC6A3 |
| chr5: 506051-4746181 | 1345 | 4240131 | 3 | rs6864158 | rs7716294 | 447.942 | 0 | SLC6A3 |
| chr4: 31222833-180548076 | 24457 | 149325244 | 1 | rs7662351 | rs3849606 | 36.162 | 0 | SNCA |
| chr4: 22401728-188608857 | 28456 | 166207130 | 1 | rs4697297 | rs7687115 | 35.717 | 0 | SNCA |
| chr4: 68173959-185767176 | 20235 | 117593218 | 1 | rs6552083 | rs4862428 | 61.893 | 0 | SNCA |
| chr4: 63726348-173015421 | 19817 | 109289074 | 1 | rs17082970 | rs2131002 | 30.251 | 0 | SNCA |
| chr4: 29179713-117038307 | 15513 | 87858595 | 1 | rs1507441 | rs1068807 | 71.6 | 0 | SNCA |
| chr4: 89603085-113991140 | 4018 | 24388056 | 3 | rs2972038 | rs2279892 | 28.405 | 0 | SNCA |
| chr4: 90618264-90784528 | 33 | 166265 | 1 | rs17286290 | rs2736994 | 16.242 | 0 | SNCA |
| chr4: 69590253-190872778 | 23415 | 121282426 | 3 | rs9293433 | rs12646565 | 315.633 | 0 | SNCA |
| chr20: 13712393-55093901 | 8218 | 41381509 | 1 | rs6033810 | rs6999 | 41.237 | 0 | SNRPB2 |
| chr20: 4591715-58420336 | 11753 | 53828622 | 1 | rs6139494 | rs1416388 | 40.922 | 0 | SNRPB2 |
| chr20: 7869025-62424661 | 11941 | 54555637 | 3 | rs2294306 | rs6010652 | 9.732 | 0 | SNRPB2 |
| chr20: 236802-54845796 | 12646 | 54608995 | 3 | rs448294 | rs6064362 | 286.151 | 0 | SNRPB2 |
| chr18: 25388300-75954881 | 11539 | 50566582 | 1 | rs11083228 | rs1876021 | 39.235 | 0 | SOCS6 |
| chr18: 46516210-68441007 | 5088 | 21924798 | 1 | rs7229153 | rs1282652 | 51.891 | 0 | SOCS6 |
| chr18: 64480206-70125971 | 1534 | 5645766 | 3 | rs10516001 | rs1347013 | 65.248 | 0 | SOCS6 |
| chr18: 65585580-69281510 | 1074 | 3695931 | 1 | rs11875790 | rs8090683 | 111.579 | 0 | SOCS6 |
| chr18: 62041997-76047493 | 3846 | 14005497 | 1 | rs1421538 | rs8085865 | 33.212 | 0 | SOCS6 |
| chr18: 44788908-78015180 | 8492 | 33226273 | 3 | rs9944807 | rs12960632 | 579.2 | 0 | SOCS6 |
| chr17: 21685812-67308196 | 12365 | 45622385 | 1 | rs34864328 | rs17686852 | 50.018 | 0 | SOCS7 |
| chr17: 26648492-58955084 | 5831 | 32306593 | 3 | rs1981512 | rs8068776 | 15.642 | 0 | SOCS7 |
| chr15: 44763598-47394943 | 502 | 2631346 | 3 | rs7172106 | rs4095484 | 142.088 | 0 | SORD |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr15: 29325866-56044189 | 5303 | 26718324 | 3 | rs4779705 | rs2414433 | 21.732 | 0 | SORD |
| chr15: 43392075-66051345 | 4963 | 22659271 | 3 | rs8028608 | rs6494537 | 59.842 | 0 | SORD |
| chr20: 13712393-55093901 | 8218 | 41381509 | 1 | rs6033810 | rs6999 | 41.237 | 0 | SRC |
| chr20: 4591715-58420336 | 11753 | 53828622 | 1 | rs6139494 | rs1416388 | 40.922 | 0 | SRC |
| chr20: 7869025-62424661 | 11941 | 54555637 | 3 | rs2294306 | rs6010652 | 9.732 | 0 | SRC |
| chr20: 35942718-36175566 | 43 | 232849 | 3 | rs6104528 | rs4810841 | 2.708 | 0 | SRC |
| chr20: 236802-54845796 | 12646 | 54608995 | 3 | rs448294 | rs6064362 | 286.151 | 0 | SRC |
| chr20: 13712393-55093901 | 8218 | 41381509 | 1 | rs6033810 | rs6999 | 41.237 | 0 | STAU1 |
| chr20: 4591715-58420336 | 11753 | 53828622 | 1 | rs6139494 | rs1416388 | 40.922 | 0 | STAU1 |
| chr20: 7869025-62424661 | 11941 | 54555637 | 3 | rs2294306 | rs6010652 | 9.732 | 0 | STAU1 |
| chr20: 236802-54845796 | 12646 | 54608995 | 3 | rs448294 | rs6064362 | 286.151 | 0 | STAU1 |
| chr12: 10113083-116370432 | 20594 | 106257350 | 1 | rs2012504 | rs7958254 | 35.157 | 0 | STRAP |
| chr12: 10020267-129866293 | 23654 | 119846027 | 1 | rs1597097 | rs2170504 | 45.428 | 0 | STRAP |
| chr12: 8171838-32535863 | 5853 | 24364026 | 3 | rs11609309 | rs7963182 | 23.697 | 0 | STRAP |
| chr12: 207886-50770291 | 11565 | 50562406 | 3 | rs868249 | rs4477515 | 43.892 | 0 | STRAP |
| chr1: 1005806-105612342 | 19173 | 104606537 | 3 | rs3934834 | rs1584633 | 44.152 | 0 | STX12 |
| chr1: 2006108-109527861 | 22130 | 107521754 | 1 | rs2254669 | rs839879 | 162.269 | 0 | STX12 |
| chr9: 1989033-107532317 | 18263 | 105543285 | 1 | rs7854628 | rs10820726 | 39.824 | 0 | SYK |
| chr9: 33180228-132003792 | 14691 | 98823565 | 1 | rs7854765 | rs9408988 | 28.69 | 0 | SYK |
| chr9: 2522475-140068342 | 25719 | 137545868 | 3 | rs10966757 | rs4074426 | 93.386 | 0 | SYK |
| chr9: 46587-94335290 | 17484 | 94288704 | 3 | rs10814410 | rs9409606 | 762.393 | 0 | SYK |
| chr5: 57343495-171903310 | 21683 | 114559816 | 1 | rs10940593 | rs10042482 | 61.169 | 0 | TBCA |
| chr5: 49952847-89853069 | 7268 | 39900223 | 3 | rs12188654 | rs42467 | 26.225 | 0 | TBCA |
| chr5: 4872310-180709915 | 35876 | 175837606 | 3 | rs816467 | rs10071993 | 179.394 | 0 | TBCA |
| chr19: 629303-4119012 | 709 | 3489710 | 1 | rs2283575 | rs350887 | 26.758 | 0 | TBXA2R |
| chr19: 266034-18061509 | 3100 | 17795476 | 3 | rs2312724 | rs7250332 | 19.51 | 0 | TBXA2R |
| chr19: 288246-59110628 | 11009 | 58822383 | 3 | rs10409452 | cnvi0009466 | 100.582 | 0 | TBXA2R |
| chr6: 64844594-169078546 | 21567 | 104233953 | 1 | rs4710465 | rs601639 | 46.524 | 0 | TCP1 |
| chr6: 66541198-162520133 | 19344 | 95978936 | 1 | rs2000382 | rs6901071 | 27.509 | 0 | TCP1 |
| chr6: 73120320-165130872 | 18715 | 92010553 | 1 | rs9442780 | rs10946016 | 76.383 | 0 | TCP1 |
| chr6: 94117546-165103679 | 15579 | 70986134 | 1 | rs3799792 | rs9347902 | 34.066 | 0 | TCP1 |
| chr6: 151495387-165969396 | 3761 | 14474010 | 3 | rs9322304 | rs1022180 | 22.826 | 0 | TCP1 |
| chr6: 100082983-170909002 | 16393 | 70826020 | 3 | rs594231 | rs12213906 | 261.313 | 0 | TCP1 |
| chr6: 26922926-93578359 | 19746 | 66655454 | 1 | rs9348738 | rs9363009 | 27.061 | 0 | TEAD3 |
| chr6: 31289284-56929863 | 15402 | 25640580 | 3 | rs9265170 | cnvi0015437 | 25.647 | 0 | TEAD3 |
| chr6: 32968276-73449742 | 15442 | 40481467 | 3 | rs2395300 | rs4235869 | 415.87 | 0 | TEAD3 |
| chr10: 7188484-134205354 | 26672 | 127016871 | 1 | rs1977295 | rs3923858 | 50.772 | 0 | TFAM |
| chr10: 57671424-133349223 | 16243 | 75677800 | 1 | rs11005106 | rs4301710 | 37.114 | 0 | TFAM |
| chr10: 734229-69155636 | 14859 | 68421408 | 3 | rs1769236 | rs2394375 | 72.104 | 0 | TFAM |
| chr10: 58385643-124973104 | 13625 | 66587462 | 3 | rs7920235 | rs17663304 | 36.18 | 0 | TFAM |
| chr10: 55492162-117205017 | 13465 | 61712856 | 1 | rs6481032 | rs1933664 | 62.56 | 0 | TFAM |
| chr10: 53602190-135522754 | 19167 | 81920565 | 3 | rs12247820 | rs10909028 | 139.373 | 0 | TFAM |
| chr20: 13712393-55093901 | 8218 | 41381509 | 1 | rs6033810 | rs6999 | 41.237 | 0 | TGM2 |
| chr20: 4591715-58420336 | 11753 | 53828622 | 1 | rs6139494 | rs1416388 | 40.922 | 0 | TGM2 |
| chr20: 7869025-62424661 | 11941 | 54555637 | 3 | rs2294306 | rs6010652 | 9.732 | 0 | TGM2 |
| chr20: 236802-54845796 | 12646 | 54608995 | 3 | rs448294 | rs6064362 | 286.151 | 0 | TGM2 |
| chr15: 29325866-56044189 | 5303 | 26718324 | 3 | rs4779705 | rs2414433 | 21.732 | 0 | TJP1 |
| chr15: 29659013-30239328 | 126 | 580316 | 1 | rs4779618 | rs12905328 | 41.602 | 0 | TJP1 |
| chr15: 20058438-32544679 | 2394 | 12486242 | 3 | rs12591240 | cnvi0018163 | 296.82 | 0 | TJP1 |
| chr15: 22267462-32461463 | 2232 | 10194002 | 3 | rs4123826 | rs286103 | 218.215 | 0 | TJP1 |
| chr17: 44458950-81047708 | −8195 | 36588759 | 1 | cnvi0016818 | rs35680231 | 35.591 | 0 | TK1 |
| chr17: 75730493-79302149 | 880 | 3571657 | 1 | rs7210773 | rs2864474 | 14.319 | 0 | TK1 |
| chr17: 62662507-81047708 | −11496 | 18385202 | 3 | rs6504246 | rs35680231 | 56.048 | 0 | TK1 |
| chr4: 31222833-180548076 | 24457 | 149325244 | 1 | rs7662351 | rs3849606 | 36.162 | 0 | TLR10 |
| chr4: 22401728-188608857 | 28456 | 166207130 | 1 | rs4697728 | rs7687115 | 35.717 | 0 | TLR10 |
| chr4: 29179713-117038307 | 15513 | 87858595 | 1 | rs1507441 | rs1068807 | 71.6 | 0 | TLR10 |
| chr4: 179131-68998153 | 13495 | 68819023 | 3 | rs7686948 | rs7687396 | 625.133 | 0 | TLR10 |
| chr3: 166503411-190576461 | 4854 | 24073051 | 1 | rs11925936 | rs1393054 | 31.414 | 0 | TNIK |
| chr3: 102240202-195550366 | 17318 | 93310165 | 1 | rs1620217 | rs11711870 | 41.031 | 0 | TNIK |
| chr3: 83075971-196935657 | 21465 | 113859687 | 1 | rs9872856 | rs34729751 | 44.35 | 0 | TNIK |
| chr3: 145967173-173899890 | 4912 | 27932718 | 3 | rs9863647 | rs7618997 | 46.396 | 0 | TNIK |
| chr3: 164955741-191742104 | 5741 | 26786364 | 3 | rs2218152 | rs9835019 | 52.438 | 0 | TNIK |
| chr3: 114889454-177826047 | 12700 | 62936594 | 3 | rs6795297 | rs7628308 | 102.526 | 0 | TNIK |
| chr12: 207886-50770291 | 11565 | 50562406 | 3 | rs868249 | rs4477515 | 43.892 | 0 | TPI1 |
| chr9: 139492789-140913833 | 196 | 1421045 | 1 | rs28485548 | cnvi0002661 | 28.211 | 0 | TRAF2 |
| chr9: 139492789-140212642 | 109 | 719854 | 3 | rs28485548 | rs13295516 | 12.464 | 0 | TRAF2 |
| chr9: 2522475-140068342 | 25719 | 137545868 | 3 | rs10966757 | rs4074426 | 93.386 | 0 | TRAF2 |
| chr9: 139725120-140176250 | 50 | 451131 | 1 | rs2811750 | rs28576426 | 24.435 | 0 | TRAF2 |
| chr11: 42185849-126756938 | 15451 | 84571090 | 1 | rs4375424 | rs10750356 | 36.99 | 0 | TRMT112 |
| chr11: 21723471-131521797 | 20508 | 109798327 | 1 | rs11828478 | rs2512898 | 27.565 | 0 | TRMT112 |
| chr11: 23168804-106781292 | 16332 | 83612489 | 1 | rs11027007 | rs7103285 | 49.747 | 0 | TRMT112 |
| chr11: 211482-66910826 | 13813 | 66699345 | 3 | rs2293168 | rs4375224 | 30.249 | 0 | TRMT112 |
| chr12: 10113083-116370432 | 20594 | 106257350 | 1 | rs2012504 | rs7958254 | 35.157 | 0 | TUBA1A |
| chr12: 10020267-129866293 | 23654 | 119846027 | 1 | rs1597097 | rs2170504 | 45.428 | 0 | TUBA1A |
| chr12: 39967134-84174413 | 8879 | 44207280 | 1 | rs11172661 | rs11116039 | 39.568 | 0 | TUBA1A |
| chr12: 207886-50770291 | 11565 | 50562406 | 3 | rs868249 | rs4477515 | 43.892 | 0 | TUBA1A |
| chr12: 10113083-116370432 | 20594 | 106257350 | 1 | rs2012504 | rs7958254 | 35.157 | 0 | TUBA1B |

TABLE 2-continued

| Chr: Start-Stop(hg19) | NumSNP | Length | State, CN | StartSNP | EndSNP | Confidence | Distance From Gene | mGluR Gene |
|---|---|---|---|---|---|---|---|---|
| chr12: 10020267-129866293 | 23654 | 119846027 | 1 | rs1597097 | rs2170504 | 45.428 | 0 | TUBA1B |
| chr12: 39967134-84174413 | 8879 | 44207280 | 1 | rs11172661 | rs11116039 | 39.568 | 0 | TUBA1B |
| chr12: 207886-50770291 | 11565 | 50562406 | 3 | rs868249 | rs4477515 | 43.892 | 0 | TUBA1B |
| chr6: 10123365-31221039 | −3135 | 21097675 | 1 | rs2181334 | rs4416711 | 318.459 | 0 | TUBB |
| chr6: 26922906-93578359 | 19746 | 66655454 | 1 | rs9348738 | rs9363009 | 27.061 | 0 | TUBB |
| chr6: 2681610-31453618 | 81 | 28772009 | 3 | rs1131896 | rs9267212 | 428.177 | 0 | TUBB |
| chr6: 2585208-31281876 | −2 | 28696669 | 1 | rs1634746 | rs1634747 | 31.615 | 0 | TUBB |
| chr6: 3760708-31957364 | 8062 | 28196657 | 3 | rs2187825 | cnvi0006380 | 39.016 | 0 | TUBB |
| chr6: 19044000-31286381 | −6774 | 12242382 | 1 | rs6922929 | rs9265057 | 31.384 | 0 | TUBB |
| chr6: 24697388-31341340 | −8293 | 6643953 | 1 | rs2092404 | rs9266515 | 38.794 | 0 | TUBB |
| chr6: 26430981-31878433 | −8001 | 5447453 | 1 | rs2893848 | rs519417 | 55.651 | 0 | TUBB |
| chr6: 2681610-31453618 | 81 | 28772009 | 3 | rs1131896 | rs9267212 | 390.234 | 0 | TUBB |
| chr6: 2584569-31286381 | 8 | 28701813 | 1 | rs9391764 | rs9265057 | 34.598 | 0 | TUBB |
| chr6: 29253756-32671521 | 2267 | 3417766 | 1 | rs9468508 | rs9275439 | 51.553 | 0 | TUBB |
| chr6: 19044000-31286381 | −6774 | 12242382 | 0 | rs6922929 | rs9265057 | 33.119 | 0 | TUBB |
| chr6: 30475431-32449411 | −7687 | 1973981 | 3 | cnvi0005997 | rs1964995 | 153.275 | 0 | TUBB |
| chr17: 21685812-67308196 | 12365 | 45622385 | 1 | rs34864328 | rs17686852 | 50.018 | 0 | TUBG1 |
| chr17: 26648492-58955084 | 5831 | 32306593 | 3 | rs1981512 | rs8068776 | 15.642 | 0 | TUBG1 |
| chr9: 33180228-132003792 | 14691 | 98823565 | 1 | rs7854765 | rs9408988 | 28.69 | 0 | TXN |
| chr9: 2522475-140068342 | 25719 | 137545868 | 3 | rs10966757 | rs4074426 | 93.386 | 0 | TXN |
| chr9: 100158052-139077343 | 9815 | 38919292 | 3 | rs1020884 | rs4842126 | 470.601 | 0 | TXN |
| chr18: 10274-30780701 | 6393 | 30770428 | 3 | cnvi0008694 | rs271534 | 338.777 | 0 | TYMS |
| chr1: 64114301-245591329 | 29842 | 181477029 | 1 | rs11208257 | rs1173850 | 37.504 | 0 | UBQLN4 |
| chr1: 75098453-243531649 | 27360 | 168433197 | 1 | rs12117493 | rs10927002 | 32.113 | 0 | UBQLN4 |
| chr1: 79710545-188898319 | 17303 | 109187775 | 1 | rs417181 | rs16829637 | 45.89 | 0 | UBQLN4 |
| chr1: 109645793-194560463 | 12025 | 84914671 | 3 | cnvi0008281 | rs10921616 | 63.121 | 0 | UBQLN4 |
| chr4: 31222833-180548076 | 24457 | 149325244 | 1 | rs7662351 | rs3849606 | 36.162 | 0 | UCHL1 |
| chr4: 22401728-188608857 | 28456 | 166207130 | 1 | rs4697297 | rs7687115 | 35.717 | 0 | UCHL1 |
| chr4: 29179713-117038307 | 15513 | 87858595 | 1 | rs1507441 | rs1068807 | 71.6 | 0 | UCHL1 |
| chr4: 39472311-63464732 | 3456 | 23992422 | 3 | rs2687975 | rs4403080 | 120.672 | 0 | UCHL1 |
| chr4: 179131-68998153 | 13495 | 68819023 | 3 | rs7686406 | rs7687396 | 625.133 | 0 | UCHL1 |
| chr3: 179527-114630641 | 23879 | 114451115 | 3 | rs4684741 | rs1587972 | 207.852 | 0 | VHL |
| chr3: 13878889-149737330 | 24723 | 135858442 | 1 | rs12634112 | rs2007869 | 55.663 | 0 | VIPR1 |
| chr3: 33409611-170735099 | 23775 | 137325489 | 1 | rs3915062 | rs11924032 | 26.867 | 0 | VIPR1 |
| chr3: 179527-114630641 | 23879 | 114451115 | 3 | rs4684741 | rs1587972 | 207.852 | 0 | VIPR1 |
| chr2: 18856-41136833 | 9721 | 41117978 | 3 | rs11901199 | rs10187704 | 191.638 | 0 | YWHAQ |
| chr2: 12056323-227979775 | 39094 | 215923453 | 1 | rs966391 | rs1922020 | 31.384 | 0 | ZAP70 |
| chr2: 38101137-241482099 | 36812 | 203380963 | 1 | rs879321 | rs7576043 | 52.099 | 0 | ZAP70 |
| chr2: 34870277-241929621 | 37755 | 207059345 | 3 | rs13422005 | rs10205276 | 46.946 | 0 | ZAP70 |
| chr2: 77041264-194763754 | 21140 | 117722491 | 1 | rs2102827 | rs16835406 | 94.091 | 0 | ZAP70 |
| chr2: 83383702-175194550 | 16291 | 91810849 | 3 | rs12469609 | rs11891208 | 154.4 | 0 | ZAP70 |

TABLE 3

| Chr:Start-Stop(hg19) | NumSNP | Length | State, CN | StartSNP | EndSNP | Confidence | Distance From Gene | mGluR Gene |
|---|---|---|---|---|---|---|---|---|
| chr17:44458950-81047708 | −8195 | 36588759 | 1 | cnvi0016818 | rs35680231 | 35.591 | 0 | ABI3 |
| chr17:21685812-67308196 | 12365 | 45622385 | 1 | rs34864328 | rs17686852 | 50.018 | 0 | ABI3 |
| chr17:26648492-58955084 | 5831 | 32306593 | 3 | rs1981512 | rs8068776 | 15.642 | 0 | ABI3 |
| chr11:42185849-126756938 | 15451 | 84571090 | 1 | rs4375424 | rs10750356 | 36.99 | 0 | ACAT1 |
| chr11:84128537-120941583 | 7678 | 36813047 | 1 | rs488925 | rs4643089 | 29.271 | 0 | ACAT1 |
| chr11:21723471-131531787 | 20508 | 109798327 | 1 | rs11828478 | rs2512898 | 27.565 | 0 | ACAT1 |
| chr11:98062720-121890280 | 5422 | 23827561 | 1 | rs6589308 | rs1944465 | 29.075 | 0 | ACAT1 |
| chr11:74545378-134940416 | 14496 | 60395039 | 3 | rs512780 | rs11224228 | 527.758 | 0 | ACAT1 |
| chr6:64844594-169078546 | 21567 | 104233953 | 1 | rs4710465 | rs601639 | 46.524 | 0 | ACAT2 |
| chr6:151495387-165969396 | 3761 | 14474010 | 3 | rs9322304 | rs1022304 | 22.826 | 0 | ACAT2 |
| chr6:73120320-165130872 | 18715 | 92010553 | 1 | rs9442780 | rs10946016 | 76.383 | 0 | ACAT2 |
| chr6:66541198-162520133 | 19344 | 95978936 | 1 | rs2000382 | rs6901071 | 27.509 | 0 | ACAT2 |
| chr6:94117546-165103679 | 15579 | 70986134 | 1 | rs3799792 | rs9347902 | 34.066 | 0 | ACAT2 |
| chr6:100082983-170909002 | 16393 | 70826020 | 3 | rs594231 | rs12213906 | 261.313 | 0 | ACAT2 |
| chr17:32104675-32822032 | 239 | 717358 | 4 | rs6505377 | rs213135 | 113.523 | 0 | ACCN1 |
| chr17:21685812-67308196 | 12365 | 45622385 | 1 | rs34864328 | rs17686852 | 50.018 | 0 | ACCN1 |
| chr17:26648492-58955084 | 5831 | 32306593 | 3 | rs1981512 | rs8068776 | 15.642 | 0 | ACCN1 |
| chr12:10113083-116370432 | 20594 | 106257350 | 1 | rs2012504 | rs7958254 | 35.157 | 0 | ACCN2 |
| chr12:10020267-129866293 | 23654 | 119846027 | 1 | rs1597097 | rs2170504 | 45.428 | 0 | ACCN2 |
| chr12:39967134-84174413 | 8879 | 44207280 | 1 | rs11172661 | rs11116039 | 39.568 | 0 | ACCN2 |
| chr12:207886-50770291 | 11565 | 50562406 | 3 | rs868249 | rs4477515 | 43.892 | 0 | ACCN2 |
| chr2:18856-41136833 | 9721 | 41117978 | 3 | rs11901199 | rs10187704 | 191.638 | 0 | ACP1 |
| chr1:64114301-245591329 | 29842 | 181477029 | 1 | rs11208257 | rs1173850 | 37.504 | 0 | ACTA1 |
| chr1:178626526-244159143 | 13064 | 65532618 | 3 | rs2761477 | rs479338 | 11.373 | 0 | ACTA1 |
| chr1:75098453-243531649 | 27360 | 168433197 | 1 | rs12117493 | rs10927002 | 32.113 | 0 | ACTA1 |
| chr1:188850774-235423607 | 10060 | 46572834 | 1 | rs16829466 | rs12409696 | 43.25 | 0 | ACTA1 |
| chr1:191875752-235423607 | 9517 | 43547856 | 1 | rs9427811 | rs12409696 | 62.01 | 0 | ACTA1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr1:174219398-247422297 | 15986 | 73202900 | 1 | rs16846809 | rs4642922 | 35.258 | 0 | ACTA1 |
| chr1:226536645-236803753 | 2600 | 10267109 | 3 | rs874583 | rs10925178 | 100.109 | 0 | ACTA1 |
| chr7:60392-84158180 | 19095 | 84097789 | 3 | rs12670102 | rs2715048 | 208.308 | 0 | ACTB |
| chr1:64114301-245591329 | 29842 | 181477029 | 1 | rs11208257 | rs1173850 | 37.504 | 0 | ACTN2 |
| chr1:178626526-244159143 | 13064 | 65532618 | 3 | rs2761477 | rs479338 | 11.373 | 0 | ACTN2 |
| chr1:75098453-243531649 | 27360 | 168433197 | 1 | rs12117493 | rs10927002 | 32.113 | 0 | ACTN2 |
| chr1:174219398-247422297 | 15986 | 73202900 | 1 | rs16846809 | rs4642922 | 35.258 | 0 | ACTN2 |
| chr1:236848751-249219320 | 3293 | 12370570 | 3 | rs819666 | cnvi0018731 | 920.725 | 0 | ACTN2 |
| chr2:12056323-227979775 | 39094 | 215923453 | 1 | rs966391 | rs1922020 | 31.384 | 0 | ACTR2 |
| chr2:34870277-241929621 | 37755 | 207059345 | 3 | rs13422005 | rs10205276 | 46.946 | 0 | ACTR2 |
| chr2:38101137-241482099 | 36812 | 203380963 | 1 | rs879321 | rs7576043 | 52.099 | 0 | ACTR2 |
| chr2:41212010-82396211 | 9721 | 41184202 | 3 | rs12614285 | rs934310 | 396.396 | 0 | ACTR2 |
| chr20:13712393-55093901 | 8218 | 41381509 | 1 | rs6033810 | rs6999 | 41.237 | 0 | ADA |
| chr20:7869025-62424661 | 11941 | 54555637 | 3 | rs2294306 | rs6010652 | 9.732 | 0 | ADA |
| chr20:4591715-58420336 | 11753 | 53828622 | 1 | rs6139494 | rs1416388 | 40.922 | 0 | ADA |
| chr20:236802-54845796 | 12646 | 54608995 | 3 | rs448294 | rs60064362 | 286.151 | 0 | ADA |
| chr7:11855636-156148608 | 26852 | 144292973 | 1 | rs6947930 | rs6945016 | 36.446 | 0 | ADCY1 |
| chr7:7724805-53845684 | 11772 | 46120880 | 3 | rs10263415 | rs6948633 | 42.007 | 0 | ADCY1 |
| chr7:8872727-156383359 | 27773 | 147510633 | 1 | rs917038 | rs878717 | 32.336 | 0 | ADCY1 |
| chr7:8794418-119068130 | 23484 | 110273713 | 1 | rs2189621 | rs6977904 | 70.867 | 0 | ADCY1 |
| chr7:60392-84158180 | 19095 | 84097789 | 3 | rs12670102 | rs2715048 | 208.308 | 0 | ADCY1 |
| chr3:13878889-149737330 | 24723 | 135858442 | 1 | rs12634112 | rs2007869 | 55.663 | 0 | ADCY5 |
| chr3:33409611-170735099 | 23775 | 137325489 | 1 | rs3915062 | rs11924032 | 26.867 | 0 | ADCY5 |
| chr3:102240202-195550366 | 17318 | 93310165 | 1 | rs1620217 | rs11711870 | 41.031 | 0 | ADCY5 |
| chr3:103140700-144883172 | 8539 | 41742473 | 1 | rs4314176 | rs6797159 | 44.122 | 0 | ADCY5 |
| chr3:83075971-196935657 | 21465 | 113859687 | 1 | rs9872658 | rs34729751 | 44.35 | 0 | ADCY5 |
| chr3:114889454-177826047 | 12700 | 62936594 | 3 | rs6795297 | rs7628308 | 102.526 | 0 | ADCY5 |
| chr8:30757798-142750969 | 20699 | 111993172 | 1 | rs10101203 | rs6421025 | 34.223 | 0 | ADCY8 |
| chr8:60424884-145286483 | 17030 | 84861600 | 3 | rs1401422 | rs9720889 | 8.858 | 0 | ADCY8 |
| chr8:130808973-134279601 | 923 | 3470092 | 3 | rs7823788 | rs2976574 | 37.758 | 0 | ADCY8 |
| chr8:23218101-146274708 | 23020 | 123056608 | 1 | rs7010362 | rs7822726 | 38.828 | 0 | ADCY8 |
| chr8:66822030-144791126 | 16557 | 77969097 | 3 | rs6472235 | rs10100154 | 251.068 | 0 | ADCY8 |
| chr7:11855636-156148608 | 26852 | 144292973 | 1 | rs6947930 | rs6945016 | 36.446 | 0 | ADCYAP1R1 |
| chr7:7724805-53845684 | 11772 | 46120880 | 3 | rs10263415 | rs6948633 | 42.007 | 0 | ADCYAP1R1 |
| chr7:8872727-156383359 | 27773 | 147510633 | 1 | rs917038 | rs878717 | 32.336 | 0 | ADCYAP1R1 |
| chr7:8794418-119068130 | 23484 | 110273713 | 1 | rs2189621 | rs6977904 | 70.867 | 0 | ADCYAP1R1 |
| chr7:60392-84158180 | 19095 | 84097789 | 3 | rs12670102 | rs2715048 | 208.308 | 0 | ADCYAP1R1 |
| chr4:179131-68998153 | 13495 | 68819023 | 3 | rs7686948 | rs7687396 | 625.133 | 0 | ADD1 |
| chr2:12056323-227979775 | 39094 | 215923453 | 1 | rs966391 | rs1922020 | 31.384 | 0 | ADD2 |
| chr2:34870277-241929621 | 37755 | 207059345 | 3 | rs13422005 | rs10205276 | 46.946 | 0 | ADD2 |
| chr2:38101137-241482099 | 36812 | 203380963 | 1 | rs879321 | rs7576043 | 52.099 | 0 | ADD2 |
| chr2:41212010-82396211 | 9721 | 41184202 | 3 | rs12614285 | rs934310 | 396.396 | 0 | ADD2 |
| chr10:7188484-134205354 | 26672 | 127016871 | 1 | rs1977295 | rs3923858 | 50.772 | 0 | ADD3 |
| chr10:58385643-124973104 | 13625 | 66587462 | 1 | rs7920235 | rs17663304 | 36.18 | 0 | ADD3 |
| chr10:57671424-133349223 | 16243 | 75677800 | 1 | rs11005106 | rs4301710 | 37.114 | 0 | ADD3 |
| chr10:55492162-117205017 | 13465 | 61712856 | 1 | rs6481032 | rs1933664 | 62.56 | 0 | ADD3 |
| chr10:53602190-135522754 | 19167 | 81920565 | 3 | rs12247820 | rs10909028 | 139.373 | 0 | ADD3 |
| chr1:64114301-245591329 | 29842 | 181477029 | 1 | rs11208257 | rs1173850 | 37.504 | 0 | ADORA1 |
| chr1:178626526-244159143 | 13064 | 65532618 | 3 | rs2761477 | rs479338 | 11.373 | 0 | ADORA1 |
| chr1:75098453-243531649 | 27360 | 168433197 | 1 | rs12117493 | rs10927002 | 32.113 | 0 | ADORA1 |
| chr1:188850774-235423607 | 10060 | 46572834 | 1 | rs16829466 | rs12409696 | 43.25 | 0 | ADORA1 |
| chr1:191875752-235423607 | 9517 | 43547856 | 1 | rs9427811 | rs12409696 | 62.01 | 0 | ADORA1 |
| chr1:189128124-227340790 | 7927 | 38212667 | 1 | rs7515205 | rs12752546 | 167.428 | 0 | ADORA1 |
| chr1:174219398-247422297 | 15986 | 73202900 | 1 | rs16846809 | rs4642922 | 35.258 | 0 | ADORA1 |
| chr1:197187605-226404425 | 6316 | 29216853 | 3 | rs10922187 | rs3008192 | 130.989 | 0 | ADORA1 |
| chr5:84830796-171903310 | 16642 | 87072515 | 1 | rs300657 | rs10042482 | 42.208 | 0 | ADRA1B |
| chr5:57343495-171903310 | 21683 | 114559816 | 1 | rs10940593 | rs10042482 | 61.169 | 0 | ADRA1B |
| chr5:4872310-180709915 | 35876 | 175837606 | 3 | rs816467 | rs10071993 | 179.394 | 0 | ADRA1B |
| chr10:7188484-134205354 | 26672 | 127016871 | 1 | rs1977295 | rs3923858 | 50.772 | 0 | ADRA2A |
| chr10:58385643-124973104 | 13625 | 66587462 | 1 | rs7920235 | rs17663304 | 36.18 | 0 | ADRA2A |
| chr10:57671424-133349223 | 16243 | 75677800 | 1 | rs11005106 | rs4301710 | 37.114 | 0 | ADRA2A |
| chr10:55492162-117205017 | 13465 | 61712856 | 1 | rs6481032 | rs1933664 | 62.56 | 0 | ADRA2A |
| chr10:53602190-135522754 | 19167 | 81920565 | 3 | rs12247820 | rs10909028 | 139.373 | 0 | ADRA2A |
| chr4:179131-68998153 | 13495 | 68819023 | 3 | rs7686948 | rs7687396 | 625.133 | 0 | ADRA2C |
| chr5:84830796-171903310 | 16642 | 87072515 | 1 | rs300657 | rs10042482 | 42.208 | 0 | ADRB2 |
| chr5:57343495-171903310 | 21683 | 114559816 | 1 | rs10940593 | rs10042482 | 61.169 | 0 | ADRB2 |
| chr5:98442871-150317237 | 9828 | 51874367 | 1 | rs1447379 | rs7710790 | 38.687 | 0 | ADRB2 |
| chr5:4872310-180709915 | 35876 | 175837606 | 3 | rs816467 | rs10071993 | 179.394 | 0 | ADRB2 |
| chr11:42185849-126756938 | 15451 | 84571090 | 1 | rs4375424 | rs10750356 | 36.99 | 0 | ADRBK1 |
| chr11:66898492-67136981 | 22 | 238490 | 1 | rs11227699 | rs3781941 | 17.955 | 0 | ADRBK1 |
| chr11:21723471-131521797 | 20508 | 109798327 | 1 | rs11828478 | rs2512898 | 27.565 | 0 | ADRBK1 |
| chr11:23168804-106781292 | 16332 | 83612489 | 1 | rs11027007 | rs7103285 | 49.747 | 0 | ADRBK1 |
| chr11:66933410-67046501 | 14 | 113092 | 1 | rs1253784 | rs12274774 | 5.288 | 0 | ADRBK1 |
| chr4:6487726-29802167 | 5076 | 23314442 | 3 | rs13117055 | rs16882325 | 48.087 | 0 | AFAP1 |
| chr4:179131-68998153 | 13495 | 68819023 | 3 | rs7686948 | rs7687396 | 625.133 | 0 | AFAP1 |
| chr3:13878889-149737330 | 24723 | 135858442 | 1 | rs12634112 | rs2007869 | 55.663 | 0 | AGTR1 |
| chr3:145967173-173899890 | 4912 | 27932718 | 3 | rs9863647 | rs7618997 | 46.396 | 0 | AGTR1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr3:33409611-170735099 | 23775 | 137325489 | 1 | rs3915062 | rs11924032 | 26.867 | 0 | AGTR1 |
| chr3:102240202-195550366 | 17318 | 93310165 | 1 | rs1620217 | rs11711870 | 41.031 | 0 | AGTR1 |
| chr3:83075971-196935657 | 21465 | 113859687 | 1 | rs9872858 | rs34729751 | 44.35 | 0 | AGTR1 |
| chr3:148403438-148598058 | 101 | 194621 | 1 | rs201944 | rs6762776 | 28.127 | 0 | AGTR1 |
| chr3:114889454-177826047 | 12700 | 62936594 | 3 | rs6795027 | rs7628308 | 102.526 | 0 | AGTR1 |
| chr1:64114301-245591329 | 29842 | 181477029 | 1 | rs11208257 | rs1173850 | 37.504 | 0 | AHCYL1 |
| chr1:75098453-243531649 | 27360 | 168433197 | 1 | rs12117493 | rs10927002 | 32.113 | 0 | AHCYL1 |
| chr1:79710545-188898319 | 17303 | 109187775 | 1 | rs417181 | rs16829637 | 45.89 | 0 | AHCYL1 |
| chr1:109645793-194560463 | 12025 | 84914671 | 3 | cnvi0008281 | rs10921616 | 63.121 | 0 | AHCYL1 |
| chr6:64844594-169078546 | 21567 | 104233953 | 1 | rs4710465 | rs601639 | 46.524 | 0 | AKAP12 |
| chr6:151495387-165969396 | 3761 | 14474010 | 3 | rs9322304 | rs1022180 | 22.826 | 0 | AKAP12 |
| chr6:73120320-165130872 | 18715 | 92010553 | 1 | rs9442780 | rs10946016 | 76.383 | 0 | AKAP12 |
| chr6:66541198-162520133 | 19344 | 95978936 | 1 | rs2000382 | rs6901071 | 27.509 | 0 | AKAP12 |
| chr6:94117546-165103509 | 15579 | 70986134 | 1 | rs3799792 | rs9347902 | 34.066 | 0 | AKAP12 |
| chr6:100082983-170909002 | 16393 | 70826020 | 3 | rs594231 | rs12213906 | 261.313 | 0 | AKAP12 |
| chr15:86103176-86282934 | 60 | 179759 | 1 | rs16941432 | rs11630179 | 16.029 | 0 | AKAP13 |
| chr15:51688996-102398060 | 11030 | 50709065 | 1 | rs2459396 | rs7181527 | 36.939 | 0 | AKAP13 |
| chr15:53775670-96810867 | 9973 | 43035198 | 1 | rs657495 | rs2589238 | 49.204 | 0 | AKAP13 |
| chr15:85877017-86143504 | 76 | 266488 | 3 | rs6497007 | rs1551971 | 67.92 | 0 | AKAP13 |
| chr15:85607670-86109582 | 80 | 501913 | 1 | rs11073917 | rs8034125 | 17.186 | 0 | AKAP13 |
| chr15:66108544-102427006 | 8615 | 36318463 | 3 | cnvi0007613 | rs11632620 | 159.164 | 0 | AKAP13 |
| chr14:26898958-104436931 | 17396 | 77537974 | 1 | rs1245695 | rs11851063 | 57.233 | 0 | AKAP5 |
| chr14:64926097-65063315 | 19 | 137219 | 1 | rs2281603 | rs10134770 | 14.377 | 0 | AKAP5 |
| chr14:19917123-65327288 | 10286 | 45410166 | 3 | rs2495197 | rs9323455 | 270.291 | 0 | AKAP5 |
| chr7:11855636-156148608 | 26852 | 144292973 | 1 | rs6947930 | rs6945016 | 36.446 | 0 | AKAP9 |
| chr7:78621315-155831817 | 13678 | 77210503 | 3 | rs1006818 | rs6969015 | 123.319 | 0 | AKAP9 |
| chr7:8872727-156383359 | 27773 | 147510633 | 1 | rs917038 | rs878717 | 32.336 | 0 | AKAP9 |
| chr7:8794418-119068130 | 23484 | 110273713 | 1 | rs2189621 | rs6977904 | 70.867 | 0 | AKAP9 |
| chr7:84302877-110993169 | 5183 | 26690293 | 3 | rs4338048 | rs10254893 | 203.09 | 0 | AKAP9 |
| chr10:734229-69155636 | 14859 | 68421408 | 3 | rs1769236 | rs2394375 | 72.104 | 0 | AKR1C3 |
| chr10:88874-53366180 | 12853 | 53277307 | 3 | cnvi0015449 | rs10998465 | 319.021 | 0 | AKR1C3 |
| chr14:105154105-105277209 | 16 | 123105 | 1 | rs3809456 | rs4983559 | 17.771 | 0 | AKT1 |
| chr14:105163532-105277209 | 15 | 113678 | 1 | rs7140154 | rs4983559 | 13.231 | 0 | AKT1 |
| chr14:80818058-105348552 | 5492 | 24530495 | 3 | rs6574553 | rs2028416 | 15.874 | 0 | AKT1 |
| chr14:104921616-105268228 | 55 | 346613 | 1 | rs11622864 | rs4983387 | 29.892 | 0 | AKT1 |
| chr14:105163532-106766841 | 179 | 1603310 | 3 | rs7140154 | rs8010546 | 35.65 | 0 | AKT1 |
| chr14:103847274-107188715 | 464 | 3341442 | 3 | rs8020912 | rs4280141 | 104.64 | 0 | AKT1 |
| chr16:29441284-33923125 | 585 | 4481842 | 3 | rs7206789 | rs4043755 | 42.437 | 0 | ALDOA |
| chr16:176743-50013967 | 8328 | 49837225 | 3 | rs2562164 | rs12597023 | 174.392 | 0 | ALDOA |
| chr4:31222833-180548076 | 24457 | 149325244 | 1 | rs7662351 | rs3849606 | 36.162 | 0 | ANK2 |
| chr4:89603085-113991140 | 4018 | 24388056 | 3 | rs2972038 | rs2279892 | 28.405 | 0 | ANK2 |
| chr4:68173959-185767176 | 20235 | 117593218 | 1 | rs6552083 | rs4862428 | 61.893 | 0 | ANK2 |
| chr4:22401728-188608857 | 28456 | 166207130 | 1 | rs4697297 | rs7687115 | 35.717 | 0 | ANK2 |
| chr4:63726348-173015421 | 19817 | 109289074 | 1 | rs17082970 | rs2131002 | 30.251 | 0 | ANK2 |
| chr4:29179713-117038307 | 15513 | 87858595 | 1 | rs1507441 | rs1068807 | 71.6 | 0 | ANK2 |
| chr4:69590353-190872778 | 23145 | 121282426 | 3 | rs293433 | rs12646565 | 315.633 | 0 | ANK2 |
| chr19:266034-18061509 | 3100 | 17795476 | 3 | rs2312724 | rs7250332 | 19.51 | 0 | ANKRD24 |
| chr19:288246-59110628 | 11009 | 58822383 | 3 | rs10409452 | cnvi0009466 | 100.582 | 0 | ANKRD24 |
| chr9:1989033-107532317 | 18263 | 105543285 | 1 | rs7864828 | rs10820726 | 39.824 | 0 | ANXA2 |
| chr9:2522475-140068342 | 25719 | 137545868 | 3 | rs10966757 | rs4074426 | 93.386 | 0 | ANXA2 |
| chr9:33180228-132003792 | 14691 | 98823565 | 1 | rs7854765 | rs9408938 | 28.69 | 0 | ANXA2 |
| chr15:51688996-102398060 | 11030 | 50709065 | 1 | rs2459396 | rs7181527 | 36.939 | 0 | ANXA2 |
| chr15:53775670-96810867 | 9973 | 43035198 | 1 | rs657495 | rs2589238 | 49.204 | 0 | ANXA2 |
| chr9:46587-94335290 | 17484 | 94288704 | 3 | rs10814410 | rs9409606 | 762.393 | 0 | ANXA2 |
| chr15:43392075-66051345 | 4963 | 22659271 | 3 | rs8028608 | rs6494357 | 59.842 | 0 | ANXA2 |
| chr5:84830796-171903310 | 16642 | 87072515 | 1 | rs300657 | rs10042482 | 42.208 | 0 | ANXA6 |
| chr5:57343495-171903310 | 21683 | 114559816 | 1 | rs10940593 | rs10042482 | 61.169 | 0 | ANXA6 |
| chr5:4872310-180709915 | 35876 | 175837606 | 3 | rs816467 | rs10071993 | 179.394 | 0 | ANXA6 |
| chr10:7188484-134205354 | 26672 | 127016871 | 1 | rs1977295 | rs3923858 | 50.772 | 0 | ANXA7 |
| chr10:58385643-124973104 | 13625 | 66587462 | 1 | rs7920235 | rs17663304 | 36.18 | 0 | ANXA7 |
| chr10:57671424-133349223 | 16243 | 75677800 | 1 | rs11005106 | rs4301710 | 37.114 | 0 | ANXA7 |
| chr10:55492162-117205017 | 13465 | 61712856 | 1 | rs6481032 | rs1933664 | 62.56 | 0 | ANXA7 |
| chr10:53602190-135522754 | 19167 | 81920565 | 3 | rs12247820 | rs10909028 | 139.373 | 0 | ANXA7 |
| chr11:21723471-131521797 | 20508 | 109798327 | 1 | rs11828478 | rs2512898 | 27.565 | 0 | APLP2 |
| chr11:74545378-134940416 | 14496 | 60395039 | 3 | rs512780 | rs11224228 | 527.758 | 0 | APLP2 |
| chr21:14601415-48084989 | 8249 | 33483575 | 3 | rs2775537 | rs2839378 | 12047.211 | 0 | APP |
| chr21:14601415-48084989 | 8249 | 33483575 | 3 | rs2775537 | rs2839378 | 41.154 | 0 | APP |
| chr21:14768343-48084989 | 8193 | 33316647 | 3 | rs2257224 | rs2839378 | 5021.076 | 0 | APP |
| chr21:14601415-48084989 | 8249 | 33483575 | 3 | rs2775537 | rs2839378 | 4787.438 | 0 | APP |
| chr21:14595264-48084989 | 8781 | 33489726 | 3 | rs2847443 | rs2839378 | 1871.363 | 0 | APP |
| chr21:10708231-47970581 | 8807 | 37262351 | 3 | rs4044122 | rs2255397 | 73.188 | 0 | APP |
| chr9:1989033-107532317 | 18263 | 105543285 | 1 | rs7864828 | rs10820726 | 39.824 | 0 | APTX |
| chr9:2522475-140068342 | 25719 | 137545868 | 3 | rs10966757 | rs4074426 | 93.386 | 0 | APTX |
| chr9:46587-94335290 | 17484 | 94288704 | 3 | rs10814410 | rs9409606 | 762.393 | 0 | APTX |
| chr7:11855636-156148608 | 26852 | 144292973 | 1 | rs6947930 | rs6945016 | 36.446 | 0 | AQP1 |
| chr7:7724805-53845684 | 11772 | 46120880 | 3 | rs10263415 | rs6948633 | 42.007 | 0 | AQP1 |
| chr7:8872727-156383359 | 27773 | 147510633 | 1 | rs917038 | rs878717 | 32.336 | 0 | AQP1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr7:8794418-119068130 | 23484 | 110273713 | 1 | rs2189621 | rs6977904 | 70.867 | 0 | AQP1 |
| chr7:60392-84158180 | 19095 | 84097789 | 3 | rs12670102 | rs2715048 | 208.308 | 0 | AQP1 |
| chr1:64114301-245591329 | 29842 | 181477029 | 1 | rs11208257 | rs1173850 | 37.504 | 0 | ARF1 |
| chr1:178626526-244159143 | 13064 | 65532618 | 3 | rs2761477 | rs479338 | 11.373 | 0 | ARF1 |
| chr1:75098453-243531699 | 27360 | 168433197 | 1 | rs12117493 | rs10927002 | 32.113 | 0 | ARF1 |
| chr1:188850774-235423607 | 10060 | 46572834 | 1 | rs16829466 | rs12409696 | 43.25 | 0 | ARF1 |
| chr1:191875752-235423607 | 9517 | 43547856 | 1 | rs9427811 | rs12409696 | 62.01 | 0 | ARF1 |
| chr1:174219398-247422297 | 15986 | 73202900 | 1 | rs16846809 | rs4642922 | 35.258 | 0 | ARF1 |
| chr1:226536645-236803753 | 2600 | 10267109 | 3 | rs874583 | rs10925178 | 100.109 | 0 | ARF1 |
| chr2:10113083-116370432 | 20594 | 106257350 | 1 | rs2012504 | rs7958254 | 35.157 | 0 | ARF3 |
| chr2:10020267-129866293 | 23654 | 119846027 | 1 | rs1597097 | rs2170504 | 45.428 | 0 | ARF3 |
| chr2:39967134-84174413 | 8879 | 44207280 | 1 | rs11172661 | rs11116039 | 39.568 | 0 | ARF3 |
| chr2:207886-50770291 | 11565 | 50562406 | 3 | rs868249 | rs4477515 | 43.892 | 0 | ARF3 |
| chr11:42185849-126756938 | 15451 | 84571090 | 1 | rs4375424 | rs10750356 | 36.99 | 0 | ARHGAP1 |
| chr11:21723471-131521797 | 20508 | 109798327 | 1 | rs11828478 | rs2512898 | 27.565 | 0 | ARHGAP1 |
| chr11:23168804-106781292 | 16332 | 83612489 | 1 | rs11027007 | rs7103285 | 49.747 | 0 | ARHGAP1 |
| chr11:46370767-47132132 | 68 | 761366 | 1 | rs876701 | rs7108434 | 27.248 | 0 | ARHGAP1 |
| chr11:211482-66910826 | 13813 | 66699345 | 3 | rs2293168 | rs4375446 | 30.249 | 0 | ARHGAP1 |
| chr4:31222833-180548076 | 24457 | 149325244 | 1 | rs7662351 | rs3849606 | 36.162 | 0 | ARHGAP24 |
| chr4:68173959-185767176 | 20235 | 117593218 | 1 | rs6552083 | rs4862428 | 61.893 | 0 | ARHGAP24 |
| chr4:22401728-188608857 | 28456 | 166207130 | 1 | rs4697297 | rs7687115 | 35.717 | 0 | ARHGAP24 |
| chr4:63726348-173015421 | 19817 | 109289074 | 1 | rs17082970 | rs2131002 | 30.251 | 0 | ARHGAP24 |
| chr4:29179713-117038307 | 15513 | 87858595 | 1 | rs1507441 | rs1068807 | 71.6 | 0 | ARHGAP24 |
| chr4:69590353-190872778 | 23145 | 121282426 | 3 | rs293433 | rs12646565 | 315.633 | 0 | ARHGAP24 |
| chr19:31569338-53780966 | 3788 | 22211629 | 1 | rs2867544 | rs10407424 | 33.9 | 0 | ARHGEF1 |
| chr19:288246-59110628 | 11009 | 58822383 | 3 | rs10409452 | cnvi0009466 | 100.582 | 0 | ARHGEF1 |
| chr5:39526068-67275356 | 4441 | 27749289 | 1 | rs16869031 | rs999826 | 77.848 | 0 | ARL15 |
| chr5:49952847-89853069 | 7268 | 39900223 | 3 | rs12188654 | rs42467 | 26.225 | 0 | ARL15 |
| chr5:52884614-53418318 | 145 | 533705 | 1 | rs524289 | rs9292039 | 31.471 | 0 | ARL15 |
| chr5:4872310-180709915 | 35876 | 175837606 | 3 | rs816467 | rs10071993 | 179.394 | 0 | ARL15 |
| chr10:7188484-134205354 | 26672 | 127016871 | 1 | rs1977295 | rs3923858 | 50.772 | 0 | ARL3 |
| chr10:58385643-124973104 | 13625 | 66587462 | 1 | rs7920235 | rs17663304 | 36.18 | 0 | ARL3 |
| chr10:57671424-133349223 | 16243 | 75677800 | 1 | rs11005106 | rs4301710 | 37.114 | 0 | ARL3 |
| chr10:55492162-117205017 | 13465 | 61712856 | 1 | rs6481032 | rs1933664 | 62.56 | 0 | ARL3 |
| chr10:53602190-135522754 | 19167 | 81920565 | 3 | rs12247820 | rs10909028 | 139.373 | 0 | ARL3 |
| chr3:234726-6328081 | 2293 | 6093356 | 3 | rs7632811 | rs1595039 | 106.207 | 0 | ARL8B |
| chr3:179527-114630641 | 23879 | 114451115 | 3 | rs4684741 | rs1587972 | 207.852 | 0 | ARL8B |
| chr11:42185849-126756938 | 15451 | 84571090 | 1 | rs4375424 | rs10750356 | 36.99 | 0 | ARRB1 |
| chr11:21723471-131521797 | 20508 | 109798327 | 1 | rs11828478 | rs2512898 | 27.565 | 0 | ARRB1 |
| chr11:23168804-106781292 | 16332 | 83612489 | 1 | rs11027007 | rs7103285 | 49.747 | 0 | ARRB1 |
| chr11:74545378-134940416 | 14496 | 60395039 | 3 | rs512780 | rs11224228 | 527.758 | 0 | ARRB1 |
| chr17:108420-26610769 | 5548 | 26502350 | 3 | rs12452527 | rs658591 | 82.699 | 0 | ARRB2 |
| chr1:345515-17408630 | 4247 | 17063116 | 3 | rs11246094 | rs5215 | 30.474 | 0 | ASCL2 |
| chr11:211482-66910826 | 13813 | 66699345 | 3 | rs2293168 | rs4375446 | 30.249 | 0 | ASCL2 |
| chr1:64114301-245591329 | 29842 | 181477029 | 1 | rs11208257 | rs1173850 | 37.504 | 0 | ATF3 |
| chr1:178626526-244159143 | 13064 | 65532618 | 3 | rs2761477 | rs479338 | 11.373 | 0 | ATF3 |
| chr1:75098453-243531699 | 27360 | 168433197 | 1 | rs12117493 | rs10927002 | 32.113 | 0 | ATF3 |
| chr1:188850774-235423607 | 10060 | 46572834 | 1 | rs16829466 | rs12409696 | 43.25 | 0 | ATF3 |
| chr1:191875752-235423607 | 9517 | 43547856 | 1 | rs9427811 | rs12409696 | 62.01 | 0 | ATF3 |
| chr1:189128124-227340790 | 7927 | 38212667 | 1 | rs7515205 | rs12752546 | 167.428 | 0 | ATF3 |
| chr1:174219398-247422297 | 15986 | 73202900 | 1 | rs16846809 | rs4642922 | 35.258 | 0 | ATF3 |
| chr1:197187605-226404457 | 6316 | 29216853 | 3 | rs10922187 | rs3008192 | 130.989 | 0 | ATF3 |
| chr2:207886-50770291 | 11565 | 50562406 | 3 | rs868249 | rs4477515 | 43.892 | 0 | ATN1 |
| chr1:64114301-245591329 | 29842 | 181477029 | 1 | rs11208257 | rs1173850 | 37.504 | 0 | ATP1B1 |
| chr1:75098453-243531699 | 27360 | 168433197 | 1 | rs12117493 | rs10927002 | 32.113 | 0 | ATP1B1 |
| chr1:79710545-188898319 | 17303 | 109187775 | 1 | rs417181 | rs16829637 | 45.89 | 0 | ATP1B1 |
| chr1:109645793-194560463 | 12025 | 84914671 | 3 | cnvi0008281 | rs10921616 | 63.121 | 0 | ATP1B1 |
| chr2:10113083-116370432 | 20594 | 106257350 | 1 | rs2012504 | rs7958254 | 35.157 | 0 | ATP2B1 |
| chr2:59512781-127744939 | 13469 | 68232159 | 3 | rs908394 | rs7966946 | 20.62 | 0 | ATP2B1 |
| chr2:10020267-129866293 | 23654 | 119846027 | 1 | rs1597097 | rs2170504 | 45.428 | 0 | ATP2B1 |
| chr2:84589672-93258498 | 1292 | 8668827 | 1 | rs1482434 | rs11106721 | 43.425 | 0 | ATP2B1 |
| chr2:50855195-133778796 | 17748 | 82923602 | 3 | rs4351895 | rs7975069 | 159.589 | 0 | ATP2B1 |
| chr3:179527-114630641 | 23879 | 114451115 | 3 | rs4684741 | rs1587972 | 207.852 | 0 | ATP2B2 |
| chr6:10123365-31221039 | -3135 | 21097675 | 1 | rs2181334 | rs4416711 | 318.459 | 0 | ATXN1 |
| chr6:2681610-31453618 | 81 | 28772009 | 3 | rs1131896 | rs9267212 | 428.177 | 0 | ATXN1 |
| chr6:3760708-31957364 | 8062 | 28196657 | 3 | rs2187825 | cnvi0006380 | 39.016 | 0 | ATXN1 |
| chr6:1171596-29895228 | 43 | 28723633 | 0 | rs3128994 | rs9259831 | 53.123 | 0 | ATXN1 |
| chr6:1171596-29899147 | 47 | 28727552 | 0 | rs3128994 | rs2394704 | 80.695 | 0 | ATXN1 |
| chr6:1177990-29899147 | 39 | 28721158 | 0 | rs2428530 | rs2394704 | 44.381 | 0 | ATXN1 |
| chr6:1175965-29899147 | 43 | 28723183 | 0 | rs1611522 | rs2394704 | 52.089 | 0 | ATXN1 |
| chr6:2585208-31281876 | -2 | 28696669 | 1 | rs1634746 | rs1634747 | 31.615 | 0 | ATXN1 |
| chr6:1171596-29899147 | 47 | 28727552 | 0 | rs3128994 | rs2394704 | 63.572 | 0 | ATXN1 |
| chr6:2584569-31286381 | 8 | 28701813 | 1 | rs9391764 | rs9265057 | 34.598 | 0 | ATXN1 |
| chr6:2681610-31453618 | 81 | 28772009 | 3 | rs1131896 | rs9267212 | 390.234 | 0 | ATXN1 |
| chr6:1171596-29892436 | 39 | 28720841 | 1 | rs3128994 | rs9259806 | 31.699 | 0 | ATXN1 |
| chr6:1171596-29895228 | 43 | 28723633 | 0 | rs3128994 | rs9259831 | 43.568 | 0 | ATXN1 |
| chr6:181089-30430875 | 1806 | 30249787 | 3 | rs1535053 | rs35792611 | 80.394 | 0 | ATXN1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr14:80818058-105348552 | 5492 | 24530495 | 3 | rs6574553 | rs2028416 | 15.874 | 0 | ATXN3 |
| chr14:92416364-92538953 | 29 | 122590 | 1 | rs2498852 | rs7144492 | 16.714 | 0 | ATXN3 |
| chr14:26898958-104436931 | 17396 | 77537974 | 1 | rs1245195 | rs11851097 | 57.233 | 0 | ATXN3 |
| chr14:65405722-103799039 | 8979 | 38393318 | 3 | rs11623705 | rs11628472 | 266.153 | 0 | ATXN3 |
| chr3:13878889-149737330 | 24723 | 135858442 | 1 | rs12634112 | rs2007869 | 55.663 | 0 | ATXN7 |
| chr3:33409611-170735099 | 23775 | 137325489 | 1 | rs3915062 | rs11924032 | 26.867 | 0 | ATXN7 |
| chr3:179527-114630641 | 23879 | 114451115 | 3 | rs4684741 | rs1587972 | 207.852 | 0 | ATXN7 |
| chr17:21685812-67308196 | 12365 | 45622385 | 1 | rs34864328 | rs17686852 | 50.018 | 0 | ATXN7L3 |
| chr17:26648492-58955084 | 5831 | 32306593 | 3 | rs1981512 | rs8068776 | 15.642 | 0 | ATXN7L3 |
| chr12:63576379-63675857 | 23 | 99479 | 1 | rs7302283 | rs4763075 | 12.637 | 29789 | AVPR1A |
| chr12:10113083-116370432 | 20594 | 106257350 | 1 | rs2012504 | rs7958254 | 35.157 | 0 | AVPR1A |
| chr12:59512781-127744939 | 13469 | 68232159 | 3 | rs908394 | rs7966946 | 20.62 | 0 | AVPR1A |
| chr12:10020267-129866293 | 23654 | 119846027 | 1 | rs1597097 | rs2170504 | 45.428 | 0 | AVPR1A |
| chr12:39967134-84174413 | 8879 | 44207280 | 1 | rs11172661 | rs11116039 | 39.568 | 0 | AVPR1A |
| chr12:50855195-133778796 | 17748 | 82923602 | 3 | rs4351895 | rs7975069 | 159.589 | 0 | AVPR1A |
| chr9:33141752-33260632 | 23 | 118881 | 3 | rs2770807 | rs706121 | 26.37 | 0 | B4GALT1 |
| chr9:1989033-107532317 | 18263 | 105543285 | 1 | rs7864828 | rs10820726 | 39.824 | 0 | B4GALT1 |
| chr9:2522475-140068342 | 25719 | 137545868 | 3 | rs10966757 | rs4074426 | 93.386 | 0 | B4GALT1 |
| chr9:46587-94335290 | 17484 | 94288704 | 3 | rs10814410 | rs9409606 | 762.393 | 0 | B4GALT1 |
| chr4:31222833-180548076 | 24457 | 149325244 | 1 | rs7662351 | rs3849606 | 36.162 | 0 | BANK1 |
| chr4:89603085-113991140 | 4018 | 24388056 | 3 | rs2972038 | rs2279892 | 28.405 | 0 | BANK1 |
| chr4:68173959-185769115 | 20235 | 117593218 | 1 | rs6552083 | rs4862428 | 61.893 | 0 | BANK1 |
| chr4:102178963-102407109 | 19 | 228147 | 1 | rs2850965 | rs1863575 | 20.006 | 0 | BANK1 |
| chr4:22401728-188608857 | 28456 | 166207130 | 1 | rs4697297 | rs7687115 | 35.717 | 0 | BANK1 |
| chr4:102974061-104493370 | 290 | 1519310 | 3 | rs10516490 | rs2588907 | 29.673 | 0 | BANK1 |
| chr4:102715888-102961880 | 45 | 245993 | 1 | rs4522806 | rs6821429 | 17.305 | 0 | BANK1 |
| chr4:63726348-173015421 | 19817 | 109289074 | 1 | rs17082970 | rs2131002 | 30.251 | 0 | BANK1 |
| chr4:29179713-117038307 | 15513 | 87858595 | 1 | rs1507441 | rs1068807 | 71.6 | 0 | BANK1 |
| chr4:69590353-190872778 | 23145 | 121282426 | 3 | rs293433 | rs12646565 | 315.633 | 0 | BANK1 |
| chr16:59854720-89273883 | 7609 | 29419164 | 3 | rs1373880 | rs8046156 | 31.884 | 0 | BCAR1 |
| chr16:64107047-82920737 | 4544 | 18813691 | 1 | rs2319723 | rs918661 | 28.887 | 0 | BCAR1 |
| chr16:50219449-89544756 | 10324 | 39325308 | 3 | rs6500298 | rs3803681 | 108.108 | 0 | BCAR1 |
| chr18:25388300-75954881 | 11539 | 50566582 | 1 | rs11083228 | rs1876021 | 39.235 | 0 | BCL2 |
| chr18:46516210-68441007 | 5088 | 21924798 | 1 | rs7229153 | rs1282652 | 51.891 | 0 | BCL2 |
| chr18:26550830-63713914 | 8241 | 37163085 | 1 | rs16945738 | rs2715304 | 17.922 | 0 | BCL2 |
| chr18:26162481-67193217 | 9255 | 41030737 | 1 | rs12458903 | rs9961907 | 31.327 | 0 | BCL2 |
| chr18:44789908-78015180 | 8492 | 33226273 | 3 | rs9944807 | rs12960632 | 579.2 | 0 | BCL2 |
| chr14:80818058-105348552 | 5492 | 24530495 | 3 | rs6574553 | rs2028416 | 15.874 | 0 | BDKRB1 |
| chr14:26898958-104436931 | 17396 | 77537974 | 1 | rs1245195 | rs11851097 | 57.233 | 0 | BDKRB1 |
| chr14:65405722-103799039 | 8979 | 38393318 | 3 | rs11623705 | rs11628472 | 266.153 | 0 | BDKRB1 |
| chr14:80818058-105348552 | 5492 | 24530495 | 3 | rs6574553 | rs2028416 | 15.874 | 0 | BDKRB2 |
| chr14:26898958-104436931 | 17396 | 77537974 | 1 | rs1245195 | rs11851097 | 57.233 | 0 | BDKRB2 |
| chr14:65405722-103799039 | 8979 | 38393318 | 3 | rs11623705 | rs11628472 | 266.153 | 0 | BDKRB2 |
| chr10:7188484-134205354 | 26672 | 127016871 | 1 | rs1977295 | rs3923858 | 50.772 | 0 | BMI1 |
| chr10:734229-69155636 | 14859 | 68421408 | 3 | rs1769236 | rs2394375 | 72.104 | 0 | BMI1 |
| chr10:88874-53366180 | 12853 | 53277307 | 3 | cnvi0015449 | rs10998465 | 319.021 | 0 | BMI1 |
| chr2:12056323-227969775 | 39094 | 215923453 | 1 | rs966391 | rs1922020 | 31.384 | 0 | BMPR2 |
| chr2:34870277-241929621 | 37755 | 207059345 | 3 | rs13422005 | rs10205276 | 46.946 | 0 | BMPR2 |
| chr2:203285157-203545198 | 26 | 260042 | 1 | rs6747299 | rs6709463 | 22.241 | 0 | BMPR2 |
| chr2:38101137-241482099 | 36812 | 203380963 | 1 | rs879321 | rs7576043 | 52.099 | 0 | BMPR2 |
| chr2:185050218-212752193 | 4583 | 27701972 | 1 | rs1526196 | rs6727171 | 45.31 | 0 | BMPR2 |
| chr2:193255360-242529978 | 10289 | 49274619 | 3 | rs1351905 | cnvi0010399 | 93.244 | 0 | BMPR2 |
| chr3:13878889-149737330 | 24723 | 135858442 | 1 | rs12634112 | rs2007869 | 55.663 | 0 | BOC |
| chr3:33409611-170735099 | 23775 | 137325489 | 1 | rs3915062 | rs11924032 | 26.867 | 0 | BOC |
| chr3:102240202-195550366 | 17318 | 93310165 | 1 | rs1620217 | rs11711870 | 41.031 | 0 | BOC |
| chr3:103140700-144883172 | 8539 | 41742473 | 1 | rs4314176 | rs6797159 | 44.122 | 0 | BOC |
| chr3:83075971-196935657 | 21465 | 113859687 | 1 | rs9872858 | rs34729751 | 44.35 | 0 | BOC |
| chr3:179527-114630641 | 23879 | 114451115 | 3 | rs4684741 | rs1587972 | 207.852 | 0 | BOC |
| chr7:11855636-156148608 | 26852 | 144292973 | 1 | rs6947930 | rs6945016 | 36.446 | 0 | BPGM |
| chr7:78621315-155831817 | 13678 | 77210503 | 3 | rs1006818 | rs6969015 | 123.319 | 0 | BPGM |
| chr7:8872727-156383359 | 27773 | 147510633 | 1 | rs917038 | rs878717 | 32.336 | 0 | BPGM |
| chr7:120061880-143606234 | 4616 | 23544355 | 3 | rs12531689 | rs10247493 | 18.96 | 0 | BPGM |
| chr17:21685812-67308196 | 12365 | 45622385 | 1 | rs34864328 | rs17686852 | 50.018 | 0 | BRCA1 |
| chr17:26648492-58955084 | 5831 | 32306593 | 3 | rs1981512 | rs8068776 | 15.642 | 0 | BRCA1 |
| chr13:19584477-81204088 | 13265 | 61619612 | 3 | rs1334954 | rs1176297 | 22.162 | 0 | BRCA2 |
| chr13:23742931-115064482 | 19829 | 91321552 | 1 | rs4770401 | rs7999630 | 44.074 | 0 | BRCA2 |
| chr13:19121741-63373781 | 10326 | 44252041 | 3 | rs9578050 | rs9539575 | 82.761 | 0 | BRCA2 |
| chr16:50219449-89544756 | 10324 | 39325308 | 3 | rs6500298 | rs3803681 | 108.108 | 0 | BRD7 |
| chr8:30757798-142750969 | 20699 | 111993172 | 1 | rs10101203 | rs6421025 | 34.223 | 0 | BRF2 |
| chr8:23218101-146274708 | 23020 | 123056608 | 1 | rs7010362 | rs7822726 | 38.828 | 0 | BRF2 |
| chr8:25304020-43159151 | 3371 | 17855132 | 3 | rs10503771 | cnvi0018779 | 263.504 | 0 | BRF2 |
| chr11:42185849-126756938 | 15451 | 84571090 | 1 | rs10750356 | rs4375424 | 36.99 | 0 | BRMS1 |
| chr11:21723471-131521797 | 20508 | 109798327 | 1 | rs11828478 | rs2512898 | 27.565 | 0 | BRMS1 |
| chr11:23168804-106781292 | 16332 | 83612489 | 1 | rs11027007 | rs7103285 | 49.747 | 0 | BRMS1 |
| chr11:211482-66910826 | 13813 | 66699345 | 1 | rs2293168 | rs4375446 | 30.249 | 0 | BRMS1 |
| chr19:1130986-2128054 | 143 | 997069 | 1 | rs10413074 | rs1017084 | 25.799 | 0 | BTBD2 |
| chr19:266034-18061509 | 3100 | 17795476 | 3 | rs2312724 | rs7250332 | 19.51 | 0 | BTBD2 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr19:629303-4119012 | 709 | 3489710 | 1 | rs2283575 | rs350887 | 26.758 | 0 | BTBD2 |
| chr19:288246-59110628 | 11009 | 58822383 | 3 | rs10409452 | cnvi0009466 | 100.582 | 0 | BTBD2 |
| chr1:64114301-245591329 | 29842 | 181477029 | 1 | rs11208257 | rs1173850 | 37.504 | 0 | BTG2 |
| chr1:178626526-244159143 | 13064 | 65532618 | 3 | rs2761477 | rs479338 | 11.373 | 0 | BTG2 |
| chr1:75098453-243531649 | 27360 | 168433197 | 1 | rs12117493 | rs10927002 | 32.113 | 0 | BTG2 |
| chr1:188850774-235423607 | 10060 | 46572834 | 1 | rs16829466 | rs12409696 | 43.25 | 0 | BTG2 |
| chr1:191875752-235423607 | 9517 | 43547856 | 1 | rs9427811 | rs12409696 | 62.01 | 0 | BTG2 |
| chr1:189128124-227340790 | 7927 | 38212667 | 1 | rs7515205 | rs12752546 | 167.428 | 0 | BTG2 |
| chr1:174219398-247422297 | 15986 | 73202900 | 1 | rs16846809 | rs4642922 | 35.258 | 0 | BTG2 |
| chr1:197187605-226404457 | 6316 | 29216853 | 3 | rs10922187 | rs3008192 | 130.989 | 0 | BTG2 |
| chr1:64114301-245591329 | 29842 | 181477029 | 1 | rs11208257 | rs1173850 | 37.504 | 0 | C1orf116 |
| chr1:178626526-244159143 | 13064 | 65532618 | 3 | rs2761477 | rs479338 | 11.373 | 0 | C1orf116 |
| chr1:75098453-243531649 | 27360 | 168433197 | 1 | rs12117493 | rs10927002 | 32.113 | 0 | C1orf116 |
| chr1:188850774-235423607 | 10060 | 46572834 | 1 | rs16829466 | rs12409696 | 43.25 | 0 | C1orf116 |
| chr1:191875752-235423607 | 9517 | 43547856 | 1 | rs9427811 | rs12409696 | 62.01 | 0 | C1orf116 |
| chr1:189128124-227340790 | 7927 | 38212667 | 1 | rs7515205 | rs12752546 | 167.428 | 0 | C1orf116 |
| chr1:174219398-247422297 | 15986 | 73202900 | 1 | rs16846809 | rs4642922 | 35.258 | 0 | C1orf116 |
| chr1:197187605-226404457 | 6316 | 29216853 | 3 | rs10922187 | rs3008192 | 130.989 | 0 | C1orf116 |
| chr17:5233817-5398033 | 30 | 164217 | 1 | rs12600505 | rs9913432 | 15.632 | 0 | C1QBP |
| chr17:108420-26610769 | 5548 | 26502350 | 3 | rs12452527 | rs658591 | 82.699 | 0 | C1QBP |
| chr20:7869025-62424661 | 11941 | 54555637 | 3 | rs2294306 | rs6010652 | 9.732 | 0 | C20orf20 |
| chr20:54870769-62912466 | 2390 | 8041695 | 3 | rs6069696 | rs6062363 | 249.708 | 0 | C20orf20 |
| chr20:13712393-55093901 | 8218 | 41381509 | 1 | rs6033810 | rs6999 | 41.237 | 0 | C20orf24 |
| chr20:7869025-62424661 | 11941 | 54555637 | 3 | rs2294306 | rs6010652 | 9.732 | 0 | C20orf24 |
| chr20:4591715-58420336 | 11753 | 53828622 | 1 | rs6139494 | rs1416388 | 40.922 | 0 | C20orf24 |
| chr20:236802-54845796 | 12646 | 54608995 | 3 | rs448294 | rs6064362 | 286.151 | 0 | C20orf24 |
| chr4:31222833-180548076 | 24457 | 149325244 | 1 | rs7662351 | rs3849606 | 36.162 | 0 | C4orf17 |
| chr4:89603085-113991140 | 4018 | 24388056 | 3 | rs2972038 | rs2279892 | 28.405 | 0 | C4orf17 |
| chr4:68173959-185767176 | 20235 | 117593218 | 1 | rs6552083 | rs4862428 | 61.893 | 0 | C4orf17 |
| chr4:22401728-188668857 | 28456 | 166207130 | 1 | rs4697297 | rs7687115 | 35.717 | 0 | C4orf17 |
| chr4:63726348-173015421 | 19817 | 109289074 | 1 | rs17082970 | rs2131002 | 30.251 | 0 | C4orf17 |
| chr4:29179713-117038307 | 15513 | 87858595 | 1 | rs1507441 | rs1068807 | 71.6 | 0 | C4orf17 |
| chr4:69590353-190872778 | 23145 | 121282426 | 3 | rs293433 | rs12646565 | 315.633 | 0 | C4orf17 |
| chr5:161172541-179954615 | 4271 | 18782075 | 3 | rs4921415 | rs10059433 | 6.291 | 0 | C5orf25 |
| chr5:4872310-180759915 | 35876 | 175837606 | 3 | rs816467 | rs10071993 | 179.394 | 0 | C5orf25 |
| chr7:11855636-156148608 | 26852 | 144292973 | 1 | rs6947930 | rs6945016 | 36.446 | 0 | C7orf25 |
| chr7:7724805-53845684 | 11772 | 46120880 | 3 | rs10263415 | rs6948633 | 42.007 | 0 | C7orf25 |
| chr7:8872727-156383359 | 27773 | 147510633 | 1 | rs917038 | rs878717 | 32.336 | 0 | C7orf25 |
| chr7:8794418-119068130 | 23484 | 110273713 | 1 | rs2189621 | rs6977904 | 70.867 | 0 | C7orf25 |
| chr7:60392-84158180 | 19095 | 84097789 | 3 | rs12670102 | rs2715048 | 208.308 | 0 | C7orf25 |
| chr9:1989033-107532317 | 18263 | 105543285 | 1 | rs7864828 | rs10820726 | 39.824 | 0 | C9orf25 |
| chr9:2522475-140068342 | 25719 | 137545868 | 3 | rs10966757 | rs4074426 | 93.386 | 0 | C9orf25 |
| chr9:33180228-132003792 | 14691 | 98823565 | 1 | rs7854765 | rs9408988 | 28.69 | 0 | C9orf25 |
| chr9:46587-94335290 | 17484 | 94288704 | 3 | rs10814410 | rs9409606 | 762.393 | 0 | C9orf25 |
| chr8:30757798-142750969 | 20699 | 111993172 | 1 | rs10101203 | rs6421025 | 34.223 | 0 | CA8 |
| chr8:60424884-145286483 | 17030 | 84861600 | 3 | rs1401422 | rs9720889 | 8.858 | 0 | CA8 |
| chr8:23218101-146274708 | 23020 | 123056608 | 1 | rs7010362 | rs7822726 | 38.828 | 0 | CA8 |
| chr8:60494752-60667231 | 25 | 172480 | 1 | rs12674637 | rs6471803 | 14.25 | 434192 | CA8 |
| chr8:43235525-66712108 | 3632 | 23476584 | 3 | rs10091311 | rs7001138 | 58.838 | 0 | CA8 |
| chr22:16871137-51184393 | 9245 | 34313257 | 3 | rs131538 | rs7284680 | 209.79 | 0 | CABIN1 |
| chr12:59512781-127744959 | 13469 | 68232159 | 3 | rs908394 | rs7966946 | 20.62 | 0 | CABP1 |
| chr12:10020267-129866293 | 23654 | 119846027 | 1 | rs1597097 | rs2170504 | 45.428 | 0 | CABP1 |
| chr12:112610714-133708729 | 5366 | 21098016 | 3 | rs11066188 | rs11147249 | 695.45 | 0 | CABP1 |
| chr12:50855195-133778796 | 17748 | 82923602 | 3 | rs4351895 | rs7975069 | 159.589 | 0 | CABP1 |
| chr9:139492789-140913833 | 196 | 1421045 | 1 | rs28485548 | cnvi0002661 | 28.211 | 0 | CACNA1B |
| chr9:139821068-141105225 | 163 | 1284158 | 3 | rs3750512 | rs11559363 | 55.611 | 0 | CACNA1B |
| chr12:207886-50770291 | 11565 | 50562406 | 3 | rs868249 | rs4477515 | 43.892 | 0 | CACNA1C |
| chr1:64114301-245591329 | 29842 | 181477029 | 1 | rs11208257 | rs1173850 | 37.504 | 0 | CACYBP |
| chr1:75098453-243531649 | 27360 | 168433197 | 1 | rs12117493 | rs10927002 | 32.113 | 0 | CACYBP |
| chr1:79710545-188898319 | 17303 | 109187775 | 1 | rs417181 | rs16829637 | 45.89 | 0 | CACYBP |
| chr1:174219398-247422297 | 15986 | 73202900 | 1 | rs16846809 | rs4642922 | 35.258 | 0 | CACYBP |
| chr1:109645793-194560463 | 12025 | 84914671 | 3 | cnvi0008281 | rs10921616 | 63.121 | 0 | CACYBP |
| chr16:59854720-89273883 | 7609 | 29419164 | 3 | rs1373880 | rs8046156 | 31.884 | 0 | CALB2 |
| chr16:64107047-82920793 | 4544 | 18813691 | 1 | rs2319723 | rs918661 | 28.887 | 0 | CALB2 |
| chr16:50219449-89544756 | 10324 | 39325308 | 3 | rs6500298 | rs3803681 | 108.108 | 0 | CALB2 |
| chr7:11855636-156148608 | 26852 | 144292973 | 1 | rs6947930 | rs6945016 | 36.446 | 0 | CALCR |
| chr7:78621315-155831817 | 13678 | 77210503 | 3 | rs1006818 | rs6969015 | 123.319 | 0 | CALCR |
| chr7:8872727-156383359 | 27773 | 147510633 | 1 | rs917038 | rs878717 | 32.336 | 0 | CALCR |
| chr7:8794418-119068130 | 23484 | 110273713 | 1 | rs2189621 | rs6977904 | 70.867 | 0 | CALCR |
| chr7:84302877-110993169 | 5183 | 26690293 | 3 | rs4338048 | rs10254893 | 203.09 | 0 | CALCR |
| chr7:11855636-156148608 | 26852 | 144292973 | 1 | rs6947930 | rs6945016 | 36.446 | 0 | CALD1 |
| chr7:78621315-155831817 | 13678 | 77210503 | 3 | rs1006818 | rs6969015 | 123.319 | 0 | CALD1 |
| chr7:8872727-156383359 | 27773 | 147510633 | 1 | rs917038 | rs878717 | 32.336 | 0 | CALD1 |
| chr7:120061880-143606234 | 4616 | 23544355 | 3 | rs12531689 | rs10247493 | 18.96 | 0 | CALD1 |
| chr14:80818058-105348552 | 5492 | 24530495 | 3 | rs6574553 | rs2028416 | 15.874 | 0 | CALM1 |
| chr14:26898958-104436931 | 17396 | 77537974 | 1 | rs1245195 | rs11851097 | 57.233 | 0 | CALM1 |
| chr14:65405722-103799039 | 8979 | 38393318 | 3 | rs11623705 | rs11628472 | 266.153 | 0 | CALM1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr2:12056323-227979775 | 39094 | 215923453 | 1 | rs966391 | rs1922020 | 31.384 | 0 | CALM2 |
| chr2:34870277-241929621 | 37755 | 207059345 | 3 | rs13422005 | rs10205276 | 46.946 | 0 | CALM2 |
| chr2:38101137-241482099 | 36812 | 203380963 | 1 | rs879321 | rs7576043 | 52.099 | 0 | CALM2 |
| chr2:41212010-82396211 | 9721 | 41184202 | 3 | rs12614285 | rs934310 | 396.396 | 0 | CALM2 |
| chr19:31569338-53780966 | 3788 | 22211629 | 1 | rs2867544 | rs10407424 | 33.9 | 0 | CALM3 |
| chr14:80818058-105348552 | 5492 | 24530495 | 3 | rs6574553 | rs2028416 | 15.874 | 0 | CALM3 |
| chr19:43257015-55294329 | −7309 | 12037315 | 3 | rs7246152 | rs2569676 | 21.402 | 0 | CALM3 |
| chr14:26898958-104436931 | 17396 | 77537974 | 1 | rs1245195 | rs11851097 | 57.233 | 0 | CALM3 |
| chr19:288246-59110628 | 11009 | 58822383 | 3 | rs10409452 | cnvi0009466 | 100.582 | 0 | CALM3 |
| chr14:65405722-103799039 | 8979 | 38393318 | 3 | rs11623705 | rs11628472 | 266.153 | 0 | CALM3 |
| chr3:179527-114630641 | 23879 | 114451115 | 3 | rs4684741 | rs1587972 | 207.852 | 0 | CAMK1 |
| chr5:84830796-171903310 | 16642 | 87072515 | 1 | rs300657 | rs10042482 | 42.208 | 0 | CAMK2A |
| chr5:149480879-149638360 | 72 | 157482 | 3 | rs13362413 | rs4958445 | 6.487 | 0 | CAMK2A |
| chr5:57343495-171903310 | 21683 | 114559816 | 1 | rs10940593 | rs10042482 | 61.169 | 0 | CAMK2A |
| chr5:98442871-150317237 | 9828 | 51874367 | 1 | rs1447379 | rs7710790 | 38.687 | 0 | CAMK2A |
| chr5:4872310-180709915 | 35876 | 175837606 | 3 | rs816467 | rs10071993 | 179.394 | 0 | CAMK2A |
| chr7:11855636-156148608 | 26852 | 144292973 | 1 | rs6947930 | rs6945016 | 36.446 | 0 | CAMK2B |
| chr7:7724805-53845684 | 11772 | 46120880 | 3 | rs10263415 | rs6948633 | 42.007 | 0 | CAMK2B |
| chr7:8872727-156383359 | 27773 | 147510633 | 1 | rs917038 | rs878717 | 32.336 | 0 | CAMK2B |
| chr7:8794418-119068130 | 23484 | 110273713 | 1 | rs2189621 | rs6977904 | 70.867 | 0 | CAMK2B |
| chr7:60392-84158180 | 19095 | 84097789 | 3 | rs12670102 | rs2715048 | 208.308 | 0 | CAMK2B |
| chr10:7188484-134205354 | 26672 | 127016871 | 1 | rs1977295 | rs3923858 | 50.772 | 0 | CAMK2G |
| chr10:58385643-124973104 | 13625 | 66587462 | 1 | rs7920235 | rs17663304 | 36.18 | 0 | CAMK2G |
| chr10:57671424-133349223 | 16243 | 75677800 | 1 | rs11005106 | rs4301710 | 37.114 | 0 | CAMK2G |
| chr10:55492162-117205017 | 13465 | 61712856 | 1 | rs6481032 | rs1933664 | 62.56 | 0 | CAMK2G |
| chr10:53602190-135522754 | 19167 | 81920565 | 3 | rs12247820 | rs10909028 | 139.373 | 0 | CAMK2G |
| chr5:84830796-171903310 | 16642 | 87072515 | 1 | rs300657 | rs10042482 | 42.208 | 0 | CAMK4 |
| chr5:108979318-132114847 | 4575 | 23135530 | 1 | rs31595 | rs30514 | 35.063 | 0 | CAMK4 |
| chr5:57343495-171903310 | 21683 | 114559816 | 1 | rs10940593 | rs10042482 | 61.169 | 0 | CAMK4 |
| chr5:98442871-150317237 | 9828 | 51874367 | 1 | rs1447379 | rs7710790 | 38.687 | 0 | CAMK4 |
| chr5:80735161-125293366 | 8499 | 44558206 | 1 | rs1541830 | rs327816 | 52.167 | 0 | CAMK4 |
| chr5:108284342-111242002 | 627 | 2957661 | 1 | rs3797817 | rs17133870 | 44.164 | 0 | CAMK4 |
| chr5:4872310-180709915 | 35876 | 175837606 | 3 | rs816467 | rs10071993 | 179.394 | 0 | CAMK4 |
| chr17:3760621-3910613 | 44 | 149993 | 3 | rs218722 | rs1105936 | 4.306 | 0 | CAMKK1 |
| chr7:108420-26610769 | 5548 | 26502350 | 3 | rs12452527 | rs658591 | 82.699 | 0 | CAMKK1 |
| chr12:59512781-127744939 | 13469 | 68232159 | 3 | rs908394 | rs7966946 | 20.62 | 0 | CAMKK2 |
| chr12:10020267-129866293 | 23654 | 119846027 | 1 | rs1597097 | rs2170504 | 45.428 | 0 | CAMKK2 |
| chr12:112610714-133708729 | 5366 | 21098016 | 3 | rs11066188 | rs11147249 | 695.45 | 0 | CAMKK2 |
| chr12:50855195-133778796 | 17748 | 82923602 | 3 | rs4351891 | rs7975069 | 159.589 | 0 | CAMKK2 |
| chr1:64114301-245591329 | 29842 | 181477029 | 1 | rs11208257 | rs1173850 | 37.504 | 0 | CAPN2 |
| chr1:178626526-244159143 | 13064 | 65532618 | 3 | rs2761477 | rs479338 | 11.373 | 0 | CAPN2 |
| chr1:75098453-243531649 | 27360 | 168433197 | 1 | rs12117493 | rs10927002 | 32.113 | 0 | CAPN2 |
| chr1:188850774-235423607 | 10060 | 46572834 | 1 | rs16829466 | rs12409696 | 43.25 | 0 | CAPN2 |
| chr1:191875752-235423607 | 9517 | 43547856 | 1 | rs9427811 | rs12409696 | 62.01 | 0 | CAPN2 |
| chr1:189128124-227340790 | 7927 | 38212667 | 1 | rs7515205 | rs12752546 | 167.428 | 0 | CAPN2 |
| chr1:174219398-247422297 | 15986 | 73202900 | 1 | rs16846809 | rs4642922 | 35.258 | 0 | CAPN2 |
| chr1:197187605-226404457 | 6316 | 29216853 | 3 | rs10922187 | rs3008291 | 130.989 | 0 | CAPN2 |
| chr4:163766726-189931630 | 5627 | 26164905 | 3 | rs10033012 | rs10018868 | 25.326 | 0 | CASP3 |
| chr4:68173959-185767176 | 20235 | 117593218 | 1 | rs6552083 | rs4862428 | 61.893 | 0 | CASP3 |
| chr4:22401728-188608857 | 28456 | 166207130 | 1 | rs4697297 | rs7687115 | 35.717 | 0 | CASP3 |
| chr4:162592024-189861553 | 6129 | 27269530 | 1 | rs5005964 | rs6853039 | 63.501 | 0 | CASP3 |
| chr4:69590353-190872778 | 23145 | 121282426 | 3 | rs293433 | rs12646565 | 315.633 | 0 | CASP3 |
| chr4:31222833-180548076 | 24457 | 149325244 | 1 | rs7662351 | rs3849606 | 36.162 | 0 | CASP6 |
| chr4:89603085-113991140 | 4018 | 24388056 | 3 | rs2972038 | rs2279892 | 28.405 | 0 | CASP6 |
| chr4:68173959-185767176 | 20235 | 117593218 | 1 | rs6552083 | rs4862428 | 61.893 | 0 | CASP6 |
| chr4:22401728-188608857 | 28456 | 166207130 | 1 | rs4697297 | rs7687115 | 35.717 | 0 | CASP6 |
| chr4:63726348-173015421 | 19817 | 109289074 | 1 | rs17082970 | rs2131002 | 30.251 | 0 | CASP6 |
| chr4:29179713-117038307 | 15513 | 87858595 | 1 | rs1507441 | rs1068807 | 71.6 | 0 | CASP6 |
| chr4:69590353-190872778 | 23145 | 121282426 | 3 | rs293433 | rs12646565 | 315.633 | 0 | CASP6 |
| chr10:7188484-134205354 | 26672 | 127016871 | 1 | rs1977295 | rs3923858 | 50.772 | 0 | CASP7 |
| chr10:58385643-124973104 | 13625 | 66587462 | 1 | rs7920235 | rs17663304 | 36.18 | 0 | CASP7 |
| chr10:57671424-133349223 | 16243 | 75677800 | 1 | rs11005106 | rs4301710 | 37.114 | 0 | CASP7 |
| chr10:55492162-117205017 | 13465 | 61712856 | 1 | rs6481032 | rs1933664 | 62.56 | 0 | CASP7 |
| chr10:53602190-135522754 | 19167 | 81920565 | 3 | rs12247820 | rs10909028 | 139.373 | 0 | CASP7 |
| chr2:12056323-227979775 | 39094 | 215923453 | 1 | rs966391 | rs1922020 | 31.384 | 0 | CASP8 |
| chr2:34870277-241929621 | 37755 | 207059345 | 3 | rs13422005 | rs10205276 | 46.946 | 0 | CASP8 |
| chr2:201924078-202178089 | 27 | 254012 | 3 | rs6737556 | rs12986657 | 7.613 | 0 | CASP8 |
| chr2:38101137-241482099 | 36812 | 203380963 | 1 | rs879321 | rs7576043 | 52.099 | 0 | CASP8 |
| chr2:185050218-212752193 | 4583 | 27701976 | 1 | rs1526196 | rs6727114 | 45.31 | 0 | CASP8 |
| chr2:201988238-202111380 | 11 | 123143 | 1 | rs7583529 | rs3769825 | 18.612 | 0 | CASP8 |
| chr2:193255360-242529978 | 10289 | 49274619 | 3 | rs1351905 | cnvi0010399 | 93.244 | 0 | CASP8 |
| chr3:13878889-149737330 | 24723 | 135858442 | 1 | rs12634112 | rs2007869 | 55.663 | 0 | CASR |
| chr3:33409611-170735099 | 23775 | 137325489 | 1 | rs3915062 | rs11924032 | 26.867 | 0 | CASR |
| chr3:102240202-195550366 | 17318 | 93310165 | 1 | rs1620217 | rs11711870 | 41.031 | 0 | CASR |
| chr3:103140700-144883172 | 8539 | 41742473 | 1 | rs4314176 | rs6797159 | 44.122 | 0 | CASR |
| chr3:83075971-196935657 | 21465 | 113859687 | 1 | rs9872858 | rs34729751 | 44.35 | 0 | CASR |
| chr3:114889454-177826047 | 12700 | 62936594 | 3 | rs6795297 | rs7628308 | 102.526 | 0 | CASR |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr7:11855636-156148608 | 26852 | 144292973 | 1 | rs6947930 | rs6945016 | 36.446 | 0 | CAV1 |
| chr7:78621315-155831817 | 13678 | 77210503 | 3 | rs1006818 | rs6969015 | 123.319 | 0 | CAV1 |
| chr7:8872727-156383359 | 27773 | 147510633 | 1 | rs917038 | rs878717 | 32.336 | 0 | CAV1 |
| chr7:8794418-119068130 | 23484 | 110273713 | 1 | rs2189621 | rs6977904 | 70.867 | 0 | CAV1 |
| chr7:109628488-125717914 | 2698 | 16089427 | 1 | cnvi0014315 | rs1582264 | 33.443 | 0 | CAV1 |
| chr7:111385084-118923413 | 1217 | 7538330 | 3 | rs718845 | rs11978545 | 371.267 | 0 | CAV1 |
| chr11:42185849-126756938 | 15451 | 84571090 | 1 | rs4375424 | rs10750356 | 36.99 | 0 | CBL |
| chr11:84128537-120941583 | 7678 | 36813047 | 1 | rs488925 | rs4643089 | 29.271 | 0 | CBL |
| chr11:21723471-131521797 | 20508 | 109798327 | 1 | rs11828478 | rs2512898 | 27.565 | 0 | CBL |
| chr11:98062720-121890280 | 5422 | 23827561 | 1 | rs6589308 | rs1944465 | 29.075 | 0 | CBL |
| chr11:74545378-134940416 | 14496 | 60395039 | 3 | rs512780 | rs11224228 | 527.758 | 0 | CBL |
| chr17:44458950-81047708 | −8195 | 36588759 | 1 | cnvi0016818 | rs35680231 | 35.591 | 0 | CBX1 |
| chr17:21685812-67308196 | 12365 | 45622385 | 1 | rs34864328 | rs17686852 | 50.018 | 0 | CBX1 |
| chr17:26648492-58955084 | 5831 | 32306593 | 3 | rs1981512 | rs8068776 | 15.642 | 0 | CBX1 |
| chr19:288246-59110628 | 11009 | 58822383 | 3 | rs10409452 | cnvi0009466 | 100.582 | 0 | CCDC106 |
| chr5:49952847-89853069 | 7268 | 39900223 | 3 | rs12188654 | rs42467 | 26.225 | 0 | CCNB1 |
| chr5:57343495-171903310 | 21683 | 114559816 | 1 | rs10940593 | rs10042482 | 61.169 | 0 | CCNB1 |
| chr5:4872310-180709915 | 35876 | 175837606 | 3 | rs816467 | rs10071993 | 179.394 | 0 | CCNB1 |
| chr11:42185849-126756938 | 15451 | 84571090 | 1 | rs4375424 | rs10750356 | 36.99 | 0 | CCND1 |
| chr11:21723471-131521797 | 20508 | 109798327 | 1 | rs11828478 | rs2512898 | 27.565 | 0 | CCND1 |
| chr11:23168804-106781292 | 16332 | 83612489 | 1 | rs11027007 | rs7103285 | 49.747 | 0 | CCND1 |
| chr11:67086298-74446791 | 1348 | 7360494 | 3 | rs1944096 | rs7103285 | 173.017 | 0 | CCND1 |
| chr19:288246-59110628 | 11009 | 58822383 | 3 | rs10409452 | cnvi0009466 | 100.582 | 0 | CCNE1 |
| chr3:13878889-149737330 | 24723 | 135858442 | 1 | rs12634112 | rs2007869 | 55.663 | 0 | CCR4 |
| chr3:179527-114630641 | 23879 | 114451115 | 3 | rs4684741 | rs1587972 | 207.852 | 0 | CCR4 |
| chr3:13878889-149737330 | 24723 | 135858442 | 1 | rs12634112 | rs2007869 | 55.663 | 0 | CCR5 |
| chr3:33409611-170735099 | 23775 | 137325489 | 1 | rs3915062 | rs11924032 | 26.867 | 0 | CCR5 |
| chr3:179527-114630641 | 23879 | 114451115 | 3 | rs4684741 | rs1587972 | 207.852 | 0 | CCR5 |
| chr12:7383187-8099302 | 149 | 716116 | 1 | rs7962099 | rs1473164 | 74.227 | 0 | CD163 |
| chr12:7631883-8692843 | 157 | 1060961 | 1 | rs6488336 | rs10841656 | 50.943 | 0 | CD163 |
| chr12:207886-50770291 | 11565 | 50562406 | 3 | rs868249 | rs4477515 | 43.892 | 0 | CD163 |
| chr11:42185849-126756938 | 15451 | 84571090 | 1 | rs4375424 | rs10750356 | 36.99 | 0 | CD5 |
| chr11:21723471-131521797 | 20508 | 109798327 | 1 | rs11828478 | rs2512898 | 27.565 | 0 | CD5 |
| chr11:23168804-106781292 | 16332 | 83612489 | 1 | rs11027007 | rs7103285 | 49.747 | 0 | CD5 |
| chr11:211482-66910826 | 13813 | 66699345 | 3 | rs2293168 | rs4375446 | 30.249 | 0 | CD5 |
| chr12:207886-50770291 | 11565 | 50562406 | 3 | rs868249 | rs4477515 | 43.892 | 0 | CD9 |
| chr1:1005806-105612342 | 19173 | 104606537 | 3 | rs3934834 | rs1584633 | 44.152 | 0 | CDC42 |
| chr1:2006108-109527861 | 22130 | 107521754 | 3 | rs2254669 | rs839879 | 162.269 | 0 | CDC42 |
| chr1:1005806-105612342 | 19173 | 104606537 | 3 | rs3934834 | rs1584633 | 44.152 | 0 | CDKN2C |
| chr1:2006108-109527861 | 22130 | 107521754 | 3 | rs2254669 | rs839879 | 162.269 | 0 | CDKN2C |
| chr5:84830796-171903310 | 16642 | 87072515 | 1 | rs300657 | rs10042482 | 42.208 | 0 | CETN3 |
| chr5:49952847-89853069 | 7268 | 39900223 | 3 | rs12188654 | rs42467 | 26.225 | 0 | CETN3 |
| chr5:57343495-171903310 | 21683 | 114559816 | 1 | rs10940593 | rs10042482 | 61.169 | 0 | CETN3 |
| chr5:84160703-104650005 | 3339 | 20489303 | 1 | rs6860783 | rs560688 | 92.914 | 0 | CETN3 |
| chr5:80735161-125293366 | 8499 | 44558206 | 1 | rs1541830 | rs327816 | 52.167 | 0 | CETN3 |
| chr5:4872310-180709915 | 35876 | 175837606 | 3 | rs816467 | rs10071993 | 179.394 | 0 | CETN3 |
| chr7:11855636-156148608 | 26852 | 144292973 | 1 | rs6947930 | rs6945016 | 36.446 | 0 | CFTR |
| chr7:78621315-155831817 | 13678 | 77210503 | 3 | rs1006818 | rs6969015 | 123.319 | 0 | CFTR |
| chr7:8872727-156383359 | 27773 | 147510633 | 1 | rs917038 | rs878717 | 32.336 | 0 | CFTR |
| chr7:8794418-119068130 | 23484 | 110273713 | 1 | rs2189621 | rs6977904 | 70.867 | 0 | CFTR |
| chr7:109628488-125717914 | 2698 | 16089427 | 1 | cnvi0014315 | rs1582264 | 33.443 | 0 | CFTR |
| chr7:117170774-118611141 | 254 | 1440368 | 1 | rs1429566 | rs12531411 | 29.859 | 0 | CFTR |
| chr7:111385084-118923413 | 1217 | 7538330 | 3 | rs718845 | rs11978545 | 371.267 | 0 | CFTR |
| chr10:7188484-134205354 | 26672 | 127016871 | 1 | rs1977295 | rs3923858 | 50.772 | 0 | CHAT |
| chr10:734229-69155636 | 14859 | 68421408 | 3 | rs1769236 | rs2394375 | 72.104 | 0 | CHAT |
| chr10:46928388-52437780 | 1060 | 5509393 | 3 | rs7915055 | rs3001866 | 425.826 | 0 | CHAT |
| chr10:88874-53366180 | 12853 | 53277307 | 3 | cnvi0015449 | rs10998465 | 319.021 | 0 | CHAT |
| chr17:108420-26610769 | 5548 | 26502350 | 3 | rs12452527 | rs658591 | 82.699 | 0 | CHD3 |
| chr20:4591715-58420336 | 11753 | 53828622 | 1 | rs6139494 | rs1416388 | 40.922 | 0 | CHGB |
| chr20:236802-54845796 | 12646 | 54608995 | 3 | rs448294 | rs6064362 | 286.151 | 0 | CHGB |
| chr15:29325866-56044189 | 5303 | 26718324 | 3 | rs4779705 | rs2414433 | 21.732 | 0 | CHP |
| chr15:32939946-43104406 | 2544 | 10164461 | 3 | rs12594777 | rs13380301 | 32.942 | 0 | CHP |
| chr7:11855636-156148608 | 26852 | 144292973 | 1 | rs6947930 | rs6945016 | 36.446 | 0 | CHRM2 |
| chr7:78621315-155831817 | 13678 | 77210503 | 3 | rs1006818 | rs6969015 | 123.319 | 0 | CHRM2 |
| chr7:8872727-156383359 | 27773 | 147510633 | 1 | rs917038 | rs878717 | 32.336 | 0 | CHRM2 |
| chr7:120061880-143606234 | 4616 | 23544355 | 3 | rs12531689 | rs10247493 | 18.96 | 0 | CHRM2 |
| chr1:64114301-245591329 | 29842 | 181477029 | 1 | rs11208257 | rs1173850 | 37.504 | 0 | CHRM3 |
| chr1:178626526-244159143 | 13064 | 65532618 | 3 | rs2761477 | rs479338 | 11.373 | 0 | CHRM3 |
| chr1:75098453-243531649 | 27360 | 168433197 | 1 | rs12117493 | rs10927002 | 32.113 | 0 | CHRM3 |
| chr1:238655362-242087644 | 1078 | 3432283 | 3 | rs2392861 | rs4658565 | 806.215 | 0 | CHRM3 |
| chr1:174219398-247422297 | 15986 | 73202900 | 1 | rs16846809 | rs4642922 | 35.258 | 0 | CHRM3 |
| chr1:236848751-249212342 | 3293 | 12370570 | 3 | rs819666 | cnvi0018731 | 920.725 | 0 | CHRM3 |
| chr10:7188484-134205354 | 26672 | 127016871 | 1 | rs1977295 | rs3923858 | 50.772 | 0 | CHUK |
| chr10:58385643-124973104 | 13625 | 66587462 | 1 | rs7920235 | rs17663304 | 36.18 | 0 | CHUK |
| chr10:57671424-133349223 | 16243 | 75677800 | 1 | rs11005106 | rs4301710 | 37.114 | 0 | CHUK |
| chr10:55492162-117205017 | 13465 | 61712856 | 1 | rs6481032 | rs1933664 | 62.56 | 0 | CHUK |
| chr10:53602190-135522754 | 19167 | 81920565 | 3 | rs12247820 | rs10909028 | 139.373 | 0 | CHUK |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr19:31569338-53780966 | 3788 | 22211629 | 1 | rs2867544 | rs10407424 | 33.9 | 0 | CIC |
| chr19:288246-59110628 | 11009 | 58822383 | 3 | rs10409452 | cnvi0009466 | 100.582 | 0 | CIC |
| chr3:13878889-149737330 | 24723 | 135858442 | 1 | rs12634112 | rs2007869 | 55.663 | 0 | CISH |
| chr3:33409611-170735099 | 23775 | 137325489 | 1 | rs3915062 | rs11924032 | 26.867 | 0 | CISH |
| chr3:179527-114630641 | 23879 | 114451115 | 3 | rs4684741 | rs1587972 | 207.852 | 0 | CISH |
| chr5:49952847-89853069 | 7268 | 39900223 | 3 | rs12188654 | rs42467 | 26.225 | 0 | CKMT2 |
| chr5:57343495-171903310 | 21683 | 114559816 | 1 | rs10940593 | rs10042482 | 61.169 | 0 | CKMT2 |
| chr5:4872310-180709915 | 35876 | 175837606 | 3 | rs816467 | rs10071993 | 179.394 | 0 | CKMT2 |
| chr5:161172541-179954615 | 4271 | 18782075 | 3 | rs4921415 | rs10059433 | 6.291 | 0 | CLTB |
| chr5:4872310-180709915 | 35876 | 175837606 | 3 | rs816467 | rs10071993 | 179.394 | 0 | CLTB |
| chr8:2365648-32608792 | 10334 | 30243145 | 3 | rs2100623 | rs3757934 | 31.188 | 0 | CLU |
| chr8:23218101-146274708 | 23020 | 123056608 | 1 | rs7010362 | rs7822726 | 38.828 | 0 | CLU |
| chr8:25304020-43159151 | 3371 | 17855132 | 3 | rs10503771 | cnvi0018779 | 263.504 | 0 | CLU |
| chr16:59854720-89273883 | 7609 | 29419046 | 3 | rs1373880 | rs8046156 | 31.884 | 0 | CMIP |
| chr16:64107047-82920737 | 4544 | 18813691 | 1 | rs2319723 | rs918661 | 28.887 | 0 | CMIP |
| chr16:50219449-89544756 | 10324 | 39325308 | 3 | rs6500298 | rs3803681 | 108.108 | 0 | CMIP |
| chr19:266034-18061509 | 3100 | 17795476 | 3 | rs2312724 | rs7250332 | 19.51 | 0 | CNN1 |
| chr19:288246-59110628 | 11009 | 58822383 | 3 | rs10409452 | cnvi0009466 | 100.582 | 0 | CNN1 |
| chr17:21685812-67308196 | 12365 | 45622385 | 1 | rs34864328 | rs17686852 | 50.018 | 0 | CNP |
| chr17:26648492-58955084 | 5831 | 32306593 | 3 | rs1981512 | rs8068776 | 15.642 | 0 | CNP |
| chr6:64844594-169078546 | 21567 | 104233953 | 1 | rs4710465 | rs601639 | 46.524 | 0 | CNR1 |
| chr6:66609532-147053633 | 15315 | 80444101 | 3 | rs9354335 | rs4896886 | 44.941 | 0 | CNR1 |
| chr6:73120320-165130872 | 18715 | 92010553 | 1 | rs9442780 | rs10946016 | 76.383 | 0 | CNR1 |
| chr6:26922906-93578359 | 19746 | 66655454 | 1 | rs9348738 | rs9363009 | 27.061 | 0 | CNR1 |
| chr6:66541198-162520133 | 19344 | 95978936 | 1 | rs2000382 | rs6901071 | 27.509 | 0 | CNR1 |
| chr6:62697746-94090036 | 6391 | 31392331 | 1 | rs6455128 | rs3799807 | 108.85 | 0 | CNR1 |
| chr6:67621368-147709180 | 16188 | 80087813 | 1 | rs6919455 | rs7739314 | 52.498 | 0 | CNR1 |
| chr6:79198069-99893938 | 4062 | 20695870 | 3 | rs1321584 | rs4504482 | 200.961 | 0 | CNR1 |
| chr1:1005806-105612342 | 19173 | 104606537 | 3 | rs3934834 | rs1584633 | 44.152 | 0 | CNR2 |
| chr1:2006108-109527861 | 22130 | 107521754 | 3 | rs2254026 | rs839879 | 162.269 | 0 | CNR2 |
| chr17:54276856-55773806 | 409 | 1496951 | 1 | rs9911321 | rs1544508 | 34.437 | 0 | COIL |
| chr17:44458950-81047708 | −8195 | 36588759 | 1 | cnvi0016818 | rs35680231 | 35.591 | 0 | COIL |
| chr17:21685812-67308196 | 12365 | 45622385 | 1 | rs34864328 | rs17686852 | 50.018 | 0 | COIL |
| chr17:26648492-58955084 | 5831 | 32306593 | 3 | rs1981512 | rs8068776 | 15.642 | 0 | COIL |
| chr3:13878889-149737330 | 24723 | 135858442 | 1 | rs12634112 | rs2007869 | 55.663 | 0 | COPB2 |
| chr3:33409611-170735099 | 23775 | 137325489 | 1 | rs3915062 | rs11924032 | 26.867 | 0 | COPB2 |
| chr3:102240202-195550366 | 17318 | 93310165 | 1 | rs1620217 | rs11711870 | 41.031 | 0 | COPB2 |
| chr3:103140700-144883172 | 8539 | 41742473 | 1 | rs4314176 | rs6797159 | 44.122 | 0 | COPB2 |
| chr3:83075971-196935657 | 21465 | 113859687 | 1 | rs9872858 | rs34729751 | 44.35 | 0 | COPB2 |
| chr3:114889454-177826047 | 12700 | 62936594 | 3 | rs6795297 | rs7628308 | 102.526 | 0 | COPB2 |
| chr11:42185849-126756938 | 15451 | 84571090 | 1 | rs4375424 | rs10750356 | 36.99 | 0 | CORO1B |
| chr11:21723471-131521797 | 20508 | 109798327 | 1 | rs11828478 | rs2512898 | 27.565 | 0 | CORO1B |
| chr11:23168804-106781292 | 16332 | 83612489 | 1 | rs11027007 | rs7103285 | 49.747 | 0 | CORO1B |
| chr11:67186000-67288594 | 13 | 102595 | 1 | rs1790733 | rs2276118 | 16.171 | 0 | CORO1B |
| chr11:67086298-74446791 | 1348 | 7360494 | 3 | rs1944096 | rs7103136 | 173.017 | 0 | CORO1B |
| chr3:13878889-149737330 | 24723 | 135858442 | 1 | rs12634112 | rs2007869 | 55.663 | 0 | COX17 |
| chr3:33409611-170735099 | 23775 | 137325489 | 1 | rs3915062 | rs11924032 | 26.867 | 0 | COX17 |
| chr3:102240202-195550366 | 17318 | 93310165 | 1 | rs1620217 | rs11711870 | 41.031 | 0 | COX17 |
| chr3:103140700-144883172 | 8539 | 41742473 | 1 | rs4314176 | rs6797159 | 44.122 | 0 | COX17 |
| chr3:83075971-196935657 | 21465 | 113859687 | 1 | rs9872858 | rs34729751 | 44.35 | 0 | COX17 |
| chr3:114889454-177826047 | 12700 | 62936594 | 3 | rs6795297 | rs7628308 | 102.526 | 0 | COX17 |
| chr4:31222833-180548076 | 24457 | 149325244 | 1 | rs7662351 | rs3849606 | 36.162 | 0 | CPE |
| chr4:163766726-189931630 | 5627 | 26164905 | 3 | rs10033012 | rs10018868 | 25.326 | 0 | CPE |
| chr4:68173959-185767176 | 20235 | 117593218 | 1 | rs6552083 | rs4862428 | 61.893 | 0 | CPE |
| chr4:22401728-188660853 | 28456 | 166207130 | 1 | rs4697297 | rs7687115 | 35.717 | 0 | CPE |
| chr4:63726348-173015421 | 19817 | 109289074 | 1 | rs17082970 | rs2131002 | 30.251 | 0 | CPE |
| chr4:162592024-189861553 | 6129 | 27269530 | 1 | rs5005966 | rs6853039 | 63.501 | 0 | CPE |
| chr4:69590353-190872778 | 23145 | 121282426 | 3 | rs293433 | rs12646565 | 315.633 | 0 | CPE |
| chr2:10113083-116370432 | 20594 | 106257350 | 1 | rs2012504 | rs7958254 | 35.157 | 0 | CRADD |
| chr2:59512781-127744899 | 13469 | 68232159 | 3 | rs908394 | rs7966946 | 20.62 | 0 | CRADD |
| chr2:10020267-129866293 | 23654 | 119846027 | 1 | rs1597097 | rs2170504 | 45.428 | 0 | CRADD |
| chr2:50855195-133778796 | 17748 | 82923602 | 3 | rs4351895 | rs7975069 | 159.589 | 0 | CRADD |
| chr10:7188484-134205354 | 26672 | 127016871 | 1 | rs1977295 | rs3923858 | 50.772 | 0 | CREM |
| chr10:734229-69155636 | 14859 | 68421408 | 3 | rs1769230 | rs2394379 | 72.104 | 0 | CREM |
| chr10:88874-53366180 | 12853 | 53277307 | 3 | cnvi0015449 | rs10998465 | 319.021 | 0 | CREM |
| chr17:43657921-44354796 | 88 | 696876 | 3 | rs9898857 | rs2732700 | 21.196 | 0 | CRHR1 |
| chr17:43657921-44064851 | 65 | 406931 | 3 | rs9898857 | rs8079215 | 86.447 | 0 | CRHR1 |
| chr17:21685812-67308196 | 12365 | 45622385 | 1 | rs34864328 | rs17686852 | 50.018 | 0 | CRHR1 |
| chr17:26648492-58955084 | 5831 | 32306593 | 3 | rs1981512 | rs8068776 | 15.642 | 0 | CRHR1 |
| chr2:46812338-46995893 | 51 | 183556 | 1 | rs1376406 | rs13424717 | 14.574 | 0 | CRIPT |
| chr2:12056323-227979775 | 39094 | 215923453 | 1 | rs966391 | rs1922020 | 31.384 | 0 | CRIPT |
| chr2:34870277-241929657 | 37755 | 207059345 | 3 | rs13422005 | rs10205276 | 46.946 | 0 | CRIPT |
| chr2:38101137-241482099 | 36812 | 203380963 | 1 | rs879321 | rs7576043 | 52.099 | 0 | CRIPT |
| chr2:41212010-82396211 | 9721 | 41184202 | 3 | rs12614285 | rs934310 | 396.396 | 0 | CRIPT |
| chr11:345515-17408630 | 4247 | 17063116 | 3 | rs11246094 | rs5215 | 30.474 | 0 | CSNK2A1 |
| chr11:211482-66910826 | 13813 | 66699345 | 3 | rs2293168 | rs4375446 | 30.249 | 0 | CSNK2A1 |
| chr20:236802-54845796 | 12646 | 54608995 | 3 | rs448294 | rs6064362 | 286.151 | 0 | CSNK2A1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr16:50219449-89544756 | 10324 | 39325308 | 3 | rs6500298 | rs3803681 | 108.108 | 0 | CSNK2A2 |
| chr6:26922906-93578359 | 19746 | 66655454 | 1 | rs9348738 | rs9363009 | 27.061 | 0 | CSNK2B |
| chr6:31289284-32512613 | 10001 | 1223330 | 3 | rs9265170 | rs35571839 | 45.035 | 0 | CSNK2B |
| chr6:3760708-31957364 | 8062 | 28196657 | 3 | rs2187825 | cnvi0006380 | 39.016 | 0 | CSNK2B |
| chr6:31281438-32449411 | -7879 | 1167974 | 1 | cnvi0006173 | rs1964995 | 24.023 | 0 | CSNK2B |
| chr6:31337633-32449411 | 1650 | 1111779 | 1 | rs9266433 | rs1964995 | 124.395 | 0 | CSNK2B |
| chr6:31281438-32354428 | -8033 | 1072991 | 1 | cnvi0006173 | rs4424066 | 37.329 | 0 | CSNK2B |
| chr6:31289284-31960770 | 9811 | 671487 | 3 | rs9265170 | cnvi0006385 | 29.628 | 0 | CSNK2B |
| chr6:31281438-32874796 | -7311 | 1593359 | 1 | cnvi0006173 | rs9469310 | 36.913 | 0 | CSNK2B |
| chr6:26430981-31878433 | -8001 | 5447453 | 1 | rs2893848 | rs519417 | 55.653 | 0 | CSNK2B |
| chr6:29253756-32671521 | 2267 | 3417766 | 1 | rs9468508 | rs9275439 | 51.553 | 0 | CSNK2B |
| chr6:31289284-56929863 | 15402 | 25640580 | 3 | rs9265170 | cnvi0015437 | 25.647 | 0 | CSNK2B |
| chr6:30475431-32449411 | -7687 | 1973981 | 3 | cnvi0005997 | rs1964995 | 153.275 | 0 | CSNK2B |
| chr3:13878889-149737330 | 24723 | 135858442 | 1 | rs12634112 | rs2007869 | 55.663 | 0 | CTNNB1 |
| chr3:33409611-170735099 | 23775 | 137325489 | 1 | rs3915062 | rs11924032 | 26.867 | 0 | CTNNB1 |
| chr3:179527-114630641 | 23879 | 114451115 | 3 | rs4684741 | rs1587972 | 207.852 | 0 | CTNNB1 |
| chr7:11855636-156148608 | 26852 | 144292973 | 1 | rs6947930 | rs6945016 | 36.446 | 0 | CYCS |
| chr7:7724805-53845684 | 11772 | 46120880 | 3 | rs10263415 | rs6948633 | 42.007 | 0 | CYCS |
| chr7:8872727-156383359 | 27773 | 147510633 | 1 | rs917038 | rs878717 | 32.336 | 0 | CYCS |
| chr7:8794418-119068130 | 23484 | 110273713 | 1 | rs2189621 | rs6977904 | 70.867 | 0 | CYCS |
| chr7:60392-84158180 | 19095 | 84097789 | 3 | rs12670102 | rs2715048 | 208.308 | 0 | CYCS |
| chr19:266034-18061509 | 3100 | 17795406 | 3 | rs2312724 | rs7250332 | 19.51 | 0 | DAPK3 |
| chr19:629303-4119012 | 709 | 3489710 | 1 | rs2283575 | rs350887 | 26.758 | 0 | DAPK3 |
| chr19:288246-59110628 | 11009 | 58822383 | 3 | rs10409452 | cnvi0009466 | 100.582 | 0 | DAPK3 |
| chr5:161172541-179954615 | 4271 | 18782075 | 3 | rs4921415 | rs10059433 | 6.291 | 0 | DBN1 |
| chr5:4872310-180709599 | 35876 | 175837606 | 3 | rs816467 | rs10071993 | 179.394 | 0 | DBN1 |
| chr12:10113083-116370432 | 20594 | 106257350 | 1 | rs2012504 | rs7958254 | 35.157 | 0 | DCN |
| chr12:59512781-127744939 | 13469 | 68232159 | 3 | rs908394 | rs7966946 | 20.62 | 0 | DCN |
| chr12:10020267-129866293 | 23654 | 119846027 | 1 | rs1597097 | rs2170504 | 45.428 | 0 | DCN |
| chr12:84589672-93258498 | 1292 | 8668827 | 1 | rs1482434 | rs11106721 | 43.425 | 0 | DCN |
| chr12:50855195-133778796 | 17748 | 82923602 | 3 | rs4351895 | rs7975069 | 159.589 | 0 | DCN |
| chr10:7188484-134205354 | 26672 | 127016871 | 1 | rs1977295 | rs3923858 | 50.772 | 0 | DDIT4 |
| chr10:58385643-124973104 | 13625 | 66587462 | 1 | rs7920235 | rs17663304 | 36.18 | 0 | DDIT4 |
| chr10:57671424-133349223 | 16243 | 75677800 | 1 | rs11005106 | rs4301710 | 37.114 | 0 | DDIT4 |
| chr10:55492162-117205017 | 13465 | 61712856 | 1 | rs6481032 | rs1933664 | 62.56 | 0 | DDIT4 |
| chr10:53602190-135522754 | 19167 | 81920565 | 3 | rs12247820 | rs10909028 | 139.373 | 0 | DDIT4 |
| chr17:44458950-81047708 | -8195 | 36588759 | 1 | cnvi0016818 | rs35680231 | 35.591 | 0 | DDX5 |
| chr17:21685812-67308196 | 12365 | 45622385 | 1 | rs34864328 | rs17686852 | 50.018 | 0 | DDX5 |
| chr17:61016209-66240093 | 890 | 5223885 | 1 | rs1588368 | rs11658645 | 37.309 | 0 | DDX5 |
| chr17:59314257-66170047 | 1135 | 6855791 | 1 | rs758467 | rs4558468 | 71.379 | 0 | DDX5 |
| chr17:59205829-62530143 | 453 | 3324315 | 3 | rs7222210 | rs9897203 | 107.455 | 0 | DDX5 |
| chr8:2365648-32608792 | 10334 | 30243145 | 3 | rs2100623 | rs3757934 | 31.188 | 0 | DEFB1 |
| chr8:6721326-6829085 | 67 | 107760 | 3 | rs2738050 | rs2738113 | 19.653 | 0 | DEFB1 |
| chr8:62041-25061807 | 9818 | 24999767 | 1 | rs4710857 | rs1510758 | 96.736 | 0 | DEFB1 |
| chr2:34870277-241929621 | 37755 | 207059345 | 3 | rs13422005 | rs10205276 | 46.946 | 0 | DGKD |
| chr2:38101137-241482099 | 36812 | 203380963 | 1 | rs879321 | rs7576043 | 52.099 | 0 | DGKD |
| chr2:193255360-242559193 | 10289 | 49274619 | 3 | rs1351905 | cnvi0010399 | 93.244 | 0 | DGKD |
| chr11:42185849-126756938 | 15451 | 84571090 | 1 | rs4375424 | rs10750356 | 36.99 | 0 | DGKZ |
| chr11:21723471-131521797 | 20508 | 109798327 | 1 | rs11828478 | rs2512898 | 27.565 | 0 | DGKZ |
| chr11:23168804-106781292 | 16332 | 83612489 | 1 | rs11027007 | rs7103285 | 49.747 | 0 | DGKZ |
| chr11:46370767-47132132 | 68 | 761366 | 1 | rs876701 | rs7108434 | 27.248 | 0 | DGKZ |
| chr11:211482-66910826 | 13813 | 66699345 | 3 | rs2293168 | rs4375446 | 30.249 | 0 | DGKZ |
| chr11:42185849-126756938 | 15451 | 84571090 | 1 | rs4375424 | rs10750356 | 36.99 | 0 | DHCR7 |
| chr11:21723471-131521797 | 20508 | 109798327 | 1 | rs11828478 | rs2512898 | 27.565 | 0 | DHCR7 |
| chr11:23168804-106781292 | 16332 | 83612489 | 1 | rs11027007 | rs7103285 | 49.747 | 0 | DHCR7 |
| chr11:67086298-74446791 | 1348 | 7360494 | 3 | rs1944096 | rs7103136 | 173.017 | 0 | DHCR7 |
| chr9:1989033-107532317 | 18263 | 105543285 | 1 | rs7864828 | rs10820726 | 39.824 | 0 | DIRAS2 |
| chr9:2522475-140068342 | 25719 | 137545868 | 3 | rs10966757 | rs4074426 | 93.386 | 0 | DIRAS2 |
| chr9:33180228-132003792 | 14691 | 98823565 | 1 | rs7854765 | rs9408988 | 28.69 | 0 | DIRAS2 |
| chr9:46587-94335290 | 17484 | 94288704 | 3 | rs10814410 | rs9409606 | 762.393 | 0 | DIRAS2 |
| chr1:231711489-231813134 | 22 | 101646 | 3 | rs1765782 | rs6541281 | 42.561 | 0 | DISC1 |
| chr1:64114301-245591329 | 29842 | 181477029 | 1 | rs11208257 | rs1173850 | 37.504 | 0 | DISC1 |
| chr1:178626526-244159143 | 13064 | 65532618 | 3 | rs2761477 | rs479338 | 11.373 | 0 | DISC1 |
| chr1:75098453-243531682 | 27360 | 168433197 | 1 | rs12117493 | rs10927002 | 32.113 | 0 | DISC1 |
| chr1:231711489-231813134 | 28 | 101646 | 3 | rs1765782 | rs6541281 | 70.39 | 0 | DISC1 |
| chr1:188850774-235423607 | 10060 | 46572834 | 1 | rs16829466 | rs12409696 | 43.25 | 0 | DISC1 |
| chr1:191875752-235423607 | 9517 | 43547856 | 1 | rs9427811 | rs12409696 | 62.01 | 0 | DISC1 |
| chr1:174219398-247422297 | 15986 | 73202900 | 1 | rs16846809 | rs4642922 | 35.258 | 0 | DISC1 |
| chr1:226536645-236803753 | 2600 | 10267109 | 3 | rs874583 | rs10925178 | 100.109 | 0 | DISC1 |
| chr3:196793858-196910082 | 10 | 116225 | 1 | rs6795358 | rs9861658 | 12.924 | 0 | DLG1 |
| chr3:196793858-196993693 | 16 | 199836 | 1 | rs6795358 | rs406284 | 14.667 | 0 | DLG1 |
| chr3:196910082-197026932 | 10 | 116850 | 1 | rs9861658 | rs338217 | 12.736 | 0 | DLG1 |
| chr3:196793858-196963612 | 17 | 169755 | 1 | rs6795358 | rs338186 | 23.577 | 0 | DLG1 |
| chr3:196793858-196935657 | 12 | 141800 | 1 | rs6795358 | rs34729751 | 16.088 | 0 | DLG1 |
| chr3:83075971-196935657 | 21465 | 113859687 | 1 | rs9872858 | rs34729751 | 44.35 | 0 | DLG1 |
| chr3:196793858-196935657 | 12 | 141800 | 1 | rs6795358 | rs34729751 | 14.018 | 0 | DLG1 |
| chr3:196838486-197019935 | 12 | 181450 | 1 | rs1356612 | rs1741949 | 16.796 | 0 | DLG1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr3:196793858-196963612 | 17 | 169755 | 1 | rs6795358 | rs338186 | 15.023 | 0 | DLG1 |
| chr3:177912894-197551411 | 4129 | 19638518 | 3 | rs9290640 | rs1273562 | 185.507 | 0 | DLG1 |
| chr17:108420-26610769 | 5548 | 26502350 | 3 | rs12452527 | rs658591 | 82.699 | 0 | DLG4 |
| chr14:26898958-104436931 | 17396 | 77537974 | 1 | rs1245195 | rs11851097 | 57.233 | 0 | DLST |
| chr14:65405722-103799039 | 8979 | 38393318 | 3 | rs11623705 | rs11628472 | 266.153 | 0 | DLST |
| chr9:2522475-140068342 | 25719 | 137545868 | 3 | rs10966757 | rs4074426 | 93.386 | 0 | DNM1 |
| chr9:33180228-132003792 | 14691 | 98823565 | 1 | rs7854765 | rs9408988 | 28.69 | 0 | DNM1 |
| chr9:100158052-139077343 | 9815 | 38919292 | 3 | rs1020884 | rs4842126 | 470.601 | 0 | DNM1 |
| chr1:64114301-245591329 | 29842 | 181477029 | 1 | rs11208257 | rs1173850 | 37.504 | 0 | DNM3 |
| chr1:172367677-172511969 | 31 | 144293 | 4 | rs10911684 | rs12087284 | 11.699 | 0 | DNM3 |
| chr1:75098453-243531649 | 27360 | 168433197 | 1 | rs12117493 | rs10927002 | 32.113 | 0 | DNM3 |
| chr1:79710545-188898319 | 17303 | 109187775 | 1 | rs417181 | rs16829637 | 45.89 | 0 | DNM3 |
| chr1:109645793-194560463 | 12025 | 84914671 | 3 | cnvi0008281 | rs10921616 | 63.121 | 0 | DNM3 |
| chr2:2365648-32608792 | 10334 | 30243145 | 3 | rs2100623 | rs3757934 | 31.188 | 0 | DPYSL2 |
| chr8:23218101-146274708 | 23020 | 123056608 | 1 | rs7010362 | rs7822726 | 38.828 | 0 | DPYSL2 |
| chr8:25304020-43159151 | 3371 | 17855132 | 3 | rs10503771 | cnvi0018779 | 263.504 | 0 | DPYSL2 |
| chr5:161172541-179954615 | 4271 | 18782075 | 3 | rs4921415 | rs10059433 | 6.291 | 0 | DRD1 |
| chr5:4872310-180709915 | 35876 | 175837606 | 3 | rs816467 | rs10071993 | 179.394 | 0 | DRD1 |
| chr11:42185849-126756938 | 15451 | 84571090 | 1 | rs4375424 | rs10750356 | 36.99 | 0 | DRD2 |
| chr11:84128537-120941583 | 7678 | 36813047 | 1 | rs488925 | rs4643089 | 29.271 | 0 | DRD2 |
| chr11:21723471-131521797 | 20508 | 109798327 | 1 | rs11828478 | rs2512898 | 27.565 | 0 | DRD2 |
| chr11:98062720-121890280 | 5422 | 23827561 | 1 | rs6589308 | rs1944465 | 29.075 | 0 | DRD2 |
| chr11:74545378-134940416 | 14496 | 60395039 | 3 | rs512780 | rs11224228 | 527.758 | 0 | DRD2 |
| chr3:13878889-149737330 | 24723 | 135858442 | 1 | rs12634112 | rs2007869 | 55.663 | 0 | DRD3 |
| chr3:33409611-170735099 | 23775 | 137325489 | 1 | rs3915062 | rs11924032 | 26.867 | 0 | DRD3 |
| chr3:102240202-195550366 | 17318 | 93310165 | 1 | rs1620217 | rs11711870 | 41.031 | 0 | DRD3 |
| chr3:103140700-144883172 | 8539 | 41742473 | 1 | rs4314176 | rs6797159 | 44.122 | 0 | DRD3 |
| chr3:83075971-196935657 | 21465 | 113859687 | 1 | rs9872858 | rs34729751 | 44.35 | 0 | DRD3 |
| chr3:179527-114630641 | 23879 | 114451115 | 3 | rs4684741 | rs1587972 | 207.852 | 0 | DRD3 |
| chr6:49184770-63747049 | 1854 | 14562280 | 3 | rs2496363 | rs1539022 | 8.974 | 0 | DST |
| chr6:26922906-93578359 | 19746 | 66655454 | 1 | rs9348738 | rs9363009 | 27.061 | 0 | DST |
| chr6:31289284-56929863 | 15402 | 25640580 | 3 | rs9265170 | cnvi0015437 | 25.647 | 0 | DST |
| chr6:32968276-73449742 | 15442 | 40481467 | 3 | rs2395300 | rs4235869 | 415.87 | 0 | DST |
| chr20:13712393-55093901 | 8218 | 41381509 | 1 | rs6033810 | rs6999 | 41.237 | 0 | DSTN |
| chr20:7869025-62424661 | 11941 | 54555637 | 3 | rs2294306 | rs6010652 | 9.732 | 0 | DSTN |
| chr20:4591715-58420336 | 11753 | 53828622 | 1 | rs6139494 | rs1416388 | 40.922 | 0 | DSTN |
| chr20:236802-54845796 | 12646 | 54608995 | 3 | rs448294 | rs6064362 | 286.151 | 0 | DSTN |
| chr1:1005806-105612342 | 19173 | 104606537 | 3 | rs3934834 | rs1584633 | 44.152 | 0 | DVL1 |
| chr1:536794-1682374 | 159 | 1145581 | 3 | rs4649701 | rs4648812 | 64.942 | 0 | DVL1 |
| chr1:1229770-2378046 | 167 | 1148277 | 1 | rs6669227 | rs34241773 | 44.903 | 0 | DVL1 |
| chr1:1201632-2182470 | 109 | 980839 | 1 | rs12402622 | rs260512 | 27.748 | 0 | DVL1 |
| chr1:1254841-3342804 | 386 | 2087964 | 1 | rs10907179 | rs870171 | 39.259 | 0 | DVL1 |
| chr1:1162435-1277903 | 19 | 115468 | 3 | rs3766186 | rs34411680 | 14.65 | 0 | DVL1 |
| chr17:108420-26610769 | 5548 | 26502350 | 3 | rs12452527 | rs658591 | 82.699 | 0 | DVL2 |
| chr3:166503411-190576461 | 4854 | 24073051 | 1 | rs11925936 | rs1393054 | 31.414 | 0 | DVL3 |
| chr3:102240202-195550366 | 17318 | 93310165 | 1 | rs1620217 | rs11711870 | 41.031 | 0 | DVL3 |
| chr3:164955741-191791204 | 5741 | 26786264 | 1 | rs2218152 | rs9835019 | 52.438 | 0 | DVL3 |
| chr3:83075971-196935657 | 21465 | 113859687 | 1 | rs9872858 | rs34729751 | 44.35 | 0 | DVL3 |
| chr3:177912894-197551411 | 4129 | 19638518 | 3 | rs9290640 | rs1273562 | 185.507 | 0 | DVL3 |
| chr12:59512781-127744939 | 13469 | 68232159 | 3 | rs908394 | rs7966946 | 20.62 | 0 | DYNLL1 |
| chr12:10020267-129866293 | 23654 | 119846027 | 1 | rs1597097 | rs2170920 | 45.428 | 0 | DYNLL1 |
| chr12:112610714-133708729 | 5366 | 21098016 | 3 | rs11066188 | rs11147249 | 695.45 | 0 | DYNLL1 |
| chr12:50855195-133778796 | 17748 | 82923602 | 3 | rs4351895 | rs7975069 | 159.589 | 0 | DYNLL1 |
| chr10:53602190-135522754 | 19167 | 81920565 | 3 | rs12247820 | rs10909028 | 139.373 | 0 | ECHS1 |
| chr9:2522475-140068342 | 25719 | 137545868 | 3 | rs10966757 | rs4074426 | 93.386 | 0 | EDF1 |
| chr9:139492789-140913833 | 196 | 1421045 | 1 | rs28485548 | cnvi0002661 | 28.211 | 0 | EDF1 |
| chr9:139492789-140212642 | 109 | 719854 | 3 | rs28485548 | rs13295516 | 12.464 | 0 | EDF1 |
| chr9:139725120-140176250 | 50 | 451131 | 1 | rs2811750 | rs28576426 | 24.435 | 0 | EDF1 |
| chr8:144656754-145255867 | 71 | 599114 | 1 | rs4606077 | rs7015323 | 34.761 | 0 | EEF1D |
| chr8:60424884-145268483 | 17030 | 84861600 | 3 | rs1401422 | rs9720889 | 8.858 | 0 | EEF1D |
| chr8:23218101-146274708 | 23020 | 123056608 | 1 | rs7010362 | rs7822726 | 38.828 | 0 | EEF1D |
| chr8:66822030-144791126 | 16557 | 77969097 | 3 | rs6472235 | rs10100154 | 251.068 | 0 | EEF1D |
| chr19:266034-18061509 | 3100 | 17795476 | 3 | rs2312724 | rs7250332 | 19.51 | 0 | EEF2 |
| chr19:629303-4119012 | 709 | 3489710 | 1 | rs2283575 | rs350887 | 26.758 | 0 | EEF2 |
| chr19:288246-59110628 | 11009 | 58822383 | 3 | rs10409452 | cnvi0009466 | 100.582 | 0 | EEF2 |
| chr13:23742931-115064482 | 19829 | 91321552 | 1 | rs4770401 | rs7999630 | 44.074 | 0 | EFNB2 |
| chr13:65193124-115053155 | 12025 | 49860032 | 3 | rs9598811 | rs7327124 | 78.057 | 0 | EFNB2 |
| chr7:11855636-156148608 | 26852 | 144292973 | 1 | rs6947930 | rs6945016 | 36.446 | 0 | EGFR |
| chr7:8872727-156383359 | 27773 | 147510633 | 1 | rs917038 | rs878717 | 32.336 | 0 | EGFR |
| chr7:8794418-119068130 | 23484 | 110273713 | 1 | rs2189621 | rs6977904 | 70.867 | 0 | EGFR |
| chr7:60392-84158180 | 19095 | 84097789 | 3 | rs12670102 | rs2715048 | 208.308 | 0 | EGFR |
| chr3:13878889-149737330 | 24723 | 135858442 | 1 | rs12634112 | rs2007869 | 55.663 | 0 | EIF1B |
| chr3:33409611-170735099 | 23775 | 137325489 | 1 | rs3915062 | rs11924032 | 26.867 | 0 | EIF1B |
| chr3:179527-114630641 | 23879 | 114451115 | 3 | rs4684741 | rs1587972 | 207.852 | 0 | EIF1B |
| chr12:207886-50770291 | 11565 | 50562406 | 3 | rs868249 | rs4477515 | 43.892 | 0 | ENO2 |
| chr1:1005806-105612342 | 19173 | 104606537 | 3 | rs3934834 | rs1584633 | 44.152 | 0 | EPB41 |
| chr1:2006108-109527861 | 22130 | 107521754 | 3 | rs2254669 | rs839879 | 162.269 | 0 | EPB41 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr20:13712393-55093901 | 8218 | 41381509 | 1 | rs6033810 | rs6999 | 41.237 | 0 | EPB41L1 |
| chr20:7869025-62424661 | 11941 | 54555637 | 3 | rs2294306 | rs6010652 | 9.732 | 0 | EPB41L1 |
| chr20:4591715-58420336 | 11753 | 53828622 | 1 | rs6139494 | rs1416388 | 40.922 | 0 | EPB41L1 |
| chr20:236802-54845796 | 12646 | 54608995 | 3 | rs448294 | rs6064362 | 286.151 | 0 | EPB41L1 |
| chr6:64844594-169078546 | 21567 | 104233953 | 1 | rs4710465 | rs601639 | 46.524 | 0 | EPB41L2 |
| chr6:66609532-147053632 | 15315 | 80444101 | 3 | rs9354335 | rs4896886 | 44.941 | 0 | EPB41L2 |
| chr6:73120320-165130872 | 18715 | 92010553 | 1 | rs9442780 | rs10946016 | 76.383 | 0 | EPB41L2 |
| chr6:66541198-162520133 | 19344 | 95978936 | 1 | rs2000382 | rs6901071 | 27.509 | 0 | EPB41L2 |
| chr6:94117546-165103679 | 15579 | 70986134 | 1 | rs3799792 | rs9347902 | 34.066 | 0 | EPB41L2 |
| chr6:67621368-147709180 | 16188 | 80087813 | 1 | rs6919455 | rs7739314 | 52.498 | 0 | EPB41L2 |
| chr6:100082983-170909002 | 16393 | 70826020 | 3 | rs594231 | rs12213906 | 261.313 | 0 | EPB41L2 |
| chr1:1005806-105612342 | 19173 | 104606537 | 3 | rs3934834 | rs1584633 | 44.152 | 0 | EPHB2 |
| chr1:2006108-109527861 | 22130 | 107521754 | 3 | rs2254669 | rs839879 | 162.269 | 0 | EPHB2 |
| chr17:21685812-67308196 | 12365 | 45622385 | 1 | rs34864328 | rs17686852 | 50.018 | 0 | ERBB2 |
| chr17:26648492-58955084 | 5831 | 32306593 | 3 | rs1981512 | rs8068776 | 15.642 | 0 | ERBB2 |
| chr6:64844594-169078546 | 21567 | 104233953 | 1 | rs4710465 | rs601639 | 46.524 | 0 | ESR1 |
| chr6:151495387-165969396 | 3761 | 14474010 | 3 | rs9322304 | rs1022180 | 22.826 | 0 | ESR1 |
| chr6:73120320-165130872 | 18715 | 92010553 | 1 | rs9442780 | rs10946016 | 76.383 | 0 | ESR1 |
| chr6:66541198-162520133 | 19344 | 95978936 | 1 | rs2000382 | rs6901071 | 27.509 | 0 | ESR1 |
| chr6:94117546-165103679 | 15579 | 70986134 | 1 | rs3799792 | rs9347902 | 34.066 | 0 | ESR1 |
| chr6:100082983-170909002 | 16393 | 70826020 | 3 | rs594231 | rs12213906 | 261.313 | 0 | ESR1 |
| chr14:64655161-64792340 | 27 | 137180 | 1 | rs1255986 | rs3020443 | 16.892 | 0 | ESR2 |
| chr14:26898958-104436931 | 17396 | 77537974 | 1 | rs1245195 | rs11851097 | 57.233 | 0 | ESR2 |
| chr14:19917123-65327288 | 10286 | 45410166 | 3 | rs2495197 | rs9323455 | 270.291 | 0 | ESR2 |
| chr1:64114301-245591329 | 29842 | 181477029 | 1 | rs11208257 | rs1173850 | 37.504 | 0 | ESRRG |
| chr1:178626526-244159143 | 13064 | 65532618 | 3 | rs2761477 | rs479338 | 11.373 | 0 | ESRRG |
| chr1:75098453-243531649 | 27360 | 168433197 | 1 | rs12117493 | rs10927002 | 32.113 | 0 | ESRRG |
| chr1:188850774-235423607 | 10060 | 46572834 | 1 | rs16829466 | rs12409696 | 43.25 | 0 | ESRRG |
| chr1:191875752-235423607 | 9517 | 43547856 | 1 | rs9427811 | rs12409696 | 62.01 | 0 | ESRRG |
| chr1:189128124-227340790 | 7927 | 38212670 | 1 | rs7515205 | rs12752546 | 167.428 | 0 | ESRRG |
| chr1:174219398-247422297 | 15986 | 73202900 | 1 | rs16846809 | rs4642922 | 35.258 | 0 | ESRRG |
| chr1:197187605-226404457 | 6316 | 29216853 | 3 | rs10922187 | rs3008192 | 130.989 | 0 | ESRRG |
| chr19:31569338-53780966 | 3788 | 22211629 | 1 | rs2867544 | rs10407424 | 33.9 | 0 | ETHE1 |
| chr19:43257015-55294329 | −7309 | 12037315 | 3 | rs7246152 | rs2569676 | 21.402 | 0 | ETHE1 |
| chr19:288246-59110628 | 11009 | 58822383 | 3 | rs10409452 | cnvi0009466 | 100.582 | 0 | ETHE1 |
| chr22:16871137-51184393 | 9245 | 34313257 | 3 | rs131538 | rs7284680 | 209.79 | 0 | EWSR1 |
| chr1:64114301-245591329 | 29842 | 181477029 | 1 | rs11208257 | rs1173850 | 37.504 | 0 | F11R |
| chr1:75098453-243531649 | 27360 | 168433197 | 1 | rs12117493 | rs10927002 | 32.113 | 0 | F11R |
| chr1:79710545-188898319 | 17303 | 109187775 | 1 | rs417181 | rs16829637 | 45.89 | 0 | F11R |
| chr1:109645793-194560463 | 12025 | 84914671 | 3 | cnvi0008281 | rs10921616 | 63.121 | 0 | F11R |
| chr5:49952847-89853069 | 7268 | 39900223 | 3 | rs12188654 | rs42467 | 26.225 | 0 | F2R |
| chr5:57343495-171903310 | 21683 | 114559816 | 1 | rs10940593 | rs10042482 | 61.169 | 0 | F2R |
| chr5:4872310-180709915 | 35876 | 175837606 | 3 | rs816467 | rs10071993 | 179.394 | 0 | F2R |
| chr5:49952847-89853069 | 7268 | 39900223 | 3 | rs12188654 | rs42467 | 26.225 | 0 | F2RL2 |
| chr5:57343495-171903310 | 21683 | 114559816 | 1 | rs10940593 | rs10042482 | 61.169 | 0 | F2RL2 |
| chr5:4872310-180709915 | 35876 | 175837606 | 3 | rs816467 | rs10071993 | 179.394 | 0 | F2RL2 |
| chr19:266034-18061509 | 3100 | 17795476 | 3 | rs2312724 | rs7250332 | 19.51 | 0 | F2RL3 |
| chr19:288246-59110628 | 11009 | 58822383 | 3 | rs10409452 | cnvi0009466 | 100.582 | 0 | F2RL3 |
| chr1:64114301-245591329 | 29842 | 181477029 | 1 | rs11208257 | rs1173850 | 37.504 | 0 | F3 |
| chr1:1005806-105612342 | 19173 | 104606537 | 3 | rs3934834 | rs1584633 | 44.152 | 0 | F3 |
| chr1:75098453-243531649 | 27360 | 168433197 | 1 | rs12117493 | rs10927002 | 32.113 | 0 | F3 |
| chr1:79710545-188898319 | 17303 | 109187775 | 1 | rs417181 | rs16829637 | 45.89 | 0 | F3 |
| chr1:2006108-109527861 | 22130 | 107521754 | 3 | rs2254669 | rs839879 | 162.269 | 0 | F3 |
| chr11:42185849-126756938 | 15451 | 84571090 | 1 | rs4375424 | rs10750356 | 36.99 | 0 | FADD |
| chr11:21723471-131521797 | 20508 | 109798327 | 1 | rs11828478 | rs2512898 | 27.565 | 0 | FADD |
| chr11:23168804-106781292 | 16332 | 83612489 | 1 | rs11027007 | rs7103285 | 49.747 | 0 | FADD |
| chr11:67086298-74446791 | 1348 | 7360494 | 3 | rs1944096 | rs7103136 | 173.017 | 0 | FADD |
| chr10:7188484-134205354 | 26672 | 127016871 | 1 | rs1977295 | rs3923858 | 50.772 | 0 | FAS |
| chr10:58385643-124973104 | 13625 | 66587462 | 3 | rs7920235 | rs17663304 | 36.18 | 0 | FAS |
| chr10:57671424-133349223 | 16243 | 75677800 | 1 | rs11005106 | rs4301710 | 37.114 | 0 | FAS |
| chr10:55492162-117205017 | 13465 | 61712856 | 1 | rs6481032 | rs1933664 | 62.56 | 0 | FAS |
| chr10:53602190-135522754 | 19167 | 81920565 | 3 | rs12247820 | rs10909028 | 139.373 | 0 | FAS |
| chr1:1005806-105612342 | 19173 | 104606537 | 3 | rs3934834 | rs1584633 | 44.152 | 0 | FBLIM1 |
| chr1:2006108-109527861 | 22130 | 107521754 | 3 | rs2254669 | rs839879 | 162.269 | 0 | FBLIM1 |
| chr5:84830796-171903310 | 16642 | 87072515 | 1 | rs300657 | rs10042482 | 42.208 | 0 | FER |
| chr5:108343438-108490168 | 32 | 146731 | 1 | rs11958129 | rs11952637 | 17.906 | 0 | FER |
| chr5:57343495-171903310 | 21683 | 114559816 | 1 | rs10940593 | rs10042482 | 61.169 | 0 | FER |
| chr5:98442871-150354329 | 9828 | 51874367 | 1 | rs1447379 | rs7710790 | 38.687 | 0 | FER |
| chr5:108410880-108517282 | 20 | 106403 | 1 | rs17161593 | rs7715602 | 19.545 | 0 | FER |
| chr5:108295480-108436014 | 26 | 140535 | 1 | rs7734092 | rs3816024 | 16.128 | 0 | FER |
| chr5:80735161-125293366 | 8499 | 44558206 | 1 | rs1541830 | rs327816 | 52.167 | 0 | FER |
| chr5:108284342-111242002 | 627 | 2957792 | 1 | rs3797817 | rs17133870 | 44.164 | 0 | FER |
| chr5:108029900-108145817 | 30 | 115918 | 1 | rs10050689 | rs2900037 | 16.489 | 0 | FER |
| chr5:104968250-109596993 | 929 | 4628744 | 3 | rs10079505 | rs4367336 | 15.741 | 0 | FER |
| chr5:4872310-180709915 | 35876 | 175837606 | 3 | rs816467 | rs10071993 | 179.394 | 0 | FER |
| chr11:42185849-126756938 | 15451 | 84571090 | 1 | rs4375424 | rs10750356 | 36.99 | 0 | FEZ1 |
| chr11:21723471-131521797 | 20508 | 109798327 | 1 | rs11828478 | rs2512898 | 27.565 | 0 | FEZ1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr11:74545378-134940416 | 14496 | 60395039 | 3 | rs512780 | rs11224228 | 527.758 | 0 | FEZ1 |
| chr2:12056323-227979775 | 39094 | 215923453 | 1 | rs966391 | rs1922020 | 31.384 | 0 | FEZ2 |
| chr2:34870277-241929621 | 37755 | 207059345 | 3 | rs13422005 | rs10205276 | 46.946 | 0 | FEZ2 |
| chr2:18856-41136833 | 9721 | 41117978 | 3 | rs11901199 | rs10187704 | 191.638 | 0 | FEZ2 |
| chr19:31569338-53780966 | 3788 | 22211629 | 1 | rs2867544 | rs10407424 | 33.9 | 0 | FFAR1 |
| chr19:288246-59110628 | 11009 | 58822383 | 3 | rs10409452 | cnvi0009466 | 100.582 | 0 | FFAR1 |
| chr19:31569338-53780966 | 3788 | 22211629 | 1 | rs2867544 | rs10407424 | 33.9 | 0 | FFAR2 |
| chr19:288246-59110628 | 11009 | 58822383 | 3 | rs10409452 | cnvi0009466 | 100.582 | 0 | FFAR2 |
| chr20:236802-54845796 | 12646 | 54608995 | 3 | rs448294 | rs6064362 | 286.151 | 0 | FKBP1A |
| chr14:26898958-104436931 | 17396 | 77537974 | 1 | rs1245195 | rs11851097 | 57.233 | 0 | FKBP3 |
| chr14:19917123-65327288 | 10286 | 45410166 | 3 | rs2495197 | rs9323455 | 270.291 | 0 | FKBP3 |
| chr12:10113083-116370432 | 20594 | 106257350 | 1 | rs2012504 | rs7958254 | 35.157 | 0 | FLJ41278 |
| chr12:59512781-127744939 | 13469 | 68232159 | 3 | rs908394 | rs7966946 | 20.62 | 0 | FLJ41278 |
| chr12:10020267-129866293 | 23654 | 119846027 | 1 | rs1597097 | rs2170504 | 45.428 | 0 | FLJ41278 |
| chr12:39967134-84174413 | 8879 | 44207280 | 1 | rs11172661 | rs11116039 | 39.568 | 0 | FLJ41278 |
| chr12:50855195-133778796 | 17748 | 82923602 | 3 | rs4351895 | rs7975069 | 159.589 | 0 | FLJ41278 |
| chr3:13878889-149737330 | 24723 | 135858442 | 1 | rs12634112 | rs2007869 | 55.663 | 0 | FLNB |
| chr3:33409611-170735099 | 23775 | 137325489 | 1 | rs3915062 | rs11924032 | 26.867 | 0 | FLNB |
| chr3:179527-114630641 | 23879 | 114451115 | 3 | rs4684741 | rs1587972 | 207.852 | 0 | FLNB |
| chr19:31569338-53780966 | 3788 | 22211629 | 1 | rs2867544 | rs10407424 | 33.9 | 0 | FPR1 |
| chr19:43257015-55294329 | −7309 | 12037315 | 3 | rs7246152 | rs2569676 | 21.402 | 0 | FPR1 |
| chr19:288246-59110628 | 11009 | 58822383 | 3 | rs10409452 | cnvi0009466 | 100.582 | 0 | FPR1 |
| chr12:10113083-116370432 | 20594 | 106257350 | 1 | rs2012504 | rs7958254 | 35.157 | 0 | FRS2 |
| chr12:59512781-127744939 | 13469 | 68232159 | 3 | rs908394 | rs7966946 | 20.62 | 0 | FRS2 |
| chr12:10020267-129866293 | 23654 | 119846027 | 1 | rs1597097 | rs2170504 | 45.428 | 0 | FRS2 |
| chr12:39967134-84174413 | 8879 | 44207280 | 1 | rs11172661 | rs11116039 | 39.568 | 0 | FRS2 |
| chr12:69888884-69992465 | 15 | 103582 | 3 | rs221103 | rs710764 | 16.735 | 0 | FRS2 |
| chr12:50855195-133778796 | 17748 | 82923602 | 3 | rs4351895 | rs7975069 | 159.589 | 0 | FRS2 |
| chr7:60392-84158180 | 19095 | 84097789 | 3 | rs12670102 | rs2715048 | 208.308 | 0 | FSCN1 |
| chr2:12056323-227979775 | 39094 | 215923453 | 1 | rs966391 | rs1922020 | 31.384 | 0 | FSHR |
| chr2:34870277-241929621 | 37755 | 207059345 | 3 | rs13422005 | rs10205276 | 46.946 | 0 | FSHR |
| chr2:38101137-241482099 | 36812 | 203380963 | 1 | rs879321 | rs7576043 | 52.099 | 0 | FSHR |
| chr2:49646785-49758675 | 35 | 111891 | 1 | rs10172488 | rs6728261 | 127.406 | 265119 | FSHR |
| chr2:49639121-49752589 | 40 | 113469 | 1 | rs817060 | rs4971621 | 119.056 | 257455 | FSHR |
| chr2:41212010-82396211 | 9721 | 41184202 | 3 | rs12614285 | rs934310 | 396.396 | 0 | FSHR |
| chr15:91345348-91492877 | 34 | 147530 | 3 | rs16944840 | rs749938 | 0 | 0 | FURIN |
| chr15:51688996-102398060 | 11030 | 50709065 | 1 | rs2459396 | rs7181527 | 36.939 | 0 | FURIN |
| chr15:53775670-96810867 | 9973 | 43035198 | 1 | rs657495 | rs2589238 | 49.204 | 0 | FURIN |
| chr15:66108544-102427006 | 8615 | 36318463 | 3 | cnvi0007613 | rs11632620 | 159.164 | 0 | FURIN |
| chr9:1989033-107532317 | 18263 | 105543285 | 1 | rs7864828 | rs10820726 | 39.824 | 0 | FXN |
| chr9:2522475-140068342 | 25719 | 137545868 | 3 | rs10966757 | rs4074426 | 93.386 | 0 | FXN |
| chr9:33180228-132003792 | 14691 | 98823565 | 1 | rs7854765 | rs9408988 | 28.69 | 0 | FXN |
| chr9:46587-94335290 | 17484 | 94288704 | 3 | rs10814410 | rs9409606 | 762.393 | 0 | FXN |
| chr3:166503411-190576461 | 4854 | 24073051 | 1 | rs11925936 | rs1393054 | 31.414 | 0 | FXR1 |
| chr3:102240202-195550366 | 17318 | 93310165 | 1 | rs1620217 | rs11711870 | 41.031 | 0 | FXR1 |
| chr3:164955741-191742104 | 5741 | 26786364 | 1 | rs2218152 | rs9835019 | 52.438 | 0 | FXR1 |
| chr3:83075971-196935563 | 21465 | 113859687 | 1 | rs9872858 | rs34729751 | 44.35 | 0 | FXR1 |
| chr3:177912894-197551411 | 4129 | 19638518 | 3 | rs9290640 | rs1273562 | 185.507 | 0 | FXR1 |
| chr6:64844594-169078546 | 21567 | 104233953 | 1 | rs4710465 | rs601639 | 46.524 | 0 | FYN |
| chr6:66609532-147053632 | 15315 | 80444101 | 3 | rs9354335 | rs4896886 | 44.941 | 0 | FYN |
| chr6:73120320-165130872 | 18715 | 92010553 | 1 | rs9442780 | rs10946016 | 76.383 | 0 | FYN |
| chr6:66541198-162520133 | 19344 | 95978936 | 1 | rs2000382 | rs6901071 | 27.509 | 0 | FYN |
| chr6:94117546-165103679 | 15579 | 70986134 | 1 | rs3799792 | rs9347902 | 34.066 | 0 | FYN |
| chr6:67621368-147709180 | 16188 | 80087813 | 1 | rs6919455 | rs7739314 | 52.498 | 0 | FYN |
| chr6:100082983-170909002 | 16393 | 70826020 | 3 | rs594231 | rs12213906 | 261.313 | 0 | FYN |
| chr6:64844594-169078546 | 21567 | 104233953 | 1 | rs4710465 | rs601639 | 46.524 | 0 | GABRR1 |
| chr6:66609532-147053632 | 15315 | 80444101 | 3 | rs9354335 | rs4896886 | 44.941 | 0 | GABRR1 |
| chr6:73120320-165130872 | 18715 | 92010553 | 1 | rs9442780 | rs10946016 | 76.383 | 0 | GABRR1 |
| chr6:26922906-93578359 | 19746 | 66655454 | 1 | rs9348738 | rs9363009 | 27.061 | 0 | GABRR1 |
| chr6:66541198-162520133 | 19344 | 95978936 | 1 | rs2000382 | rs6901071 | 27.509 | 0 | GABRR1 |
| chr6:62697746-94090076 | 6391 | 31392331 | 1 | rs6455128 | rs3799807 | 108.85 | 0 | GABRR1 |
| chr6:67621368-147709180 | 16188 | 80087813 | 1 | rs6919455 | rs7739314 | 52.498 | 0 | GABRR1 |
| chr6:79198069-99893938 | 4062 | 20695870 | 3 | rs1321584 | rs4504482 | 200.961 | 0 | GABRR1 |
| chr6:64844594-169078546 | 21567 | 104233953 | 1 | rs4710465 | rs601639 | 46.524 | 0 | GABRR2 |
| chr6:66609532-147053632 | 15315 | 80444101 | 3 | rs9354335 | rs4896886 | 44.941 | 0 | GABRR2 |
| chr6:73120320-165130872 | 18715 | 92010553 | 1 | rs9442780 | rs10946016 | 76.383 | 0 | GABRR2 |
| chr6:26922906-93578359 | 19746 | 66655454 | 1 | rs9348738 | rs9363009 | 27.061 | 0 | GABRR2 |
| chr6:66541198-162520133 | 19344 | 95978936 | 1 | rs2000382 | rs6901071 | 27.509 | 0 | GABRR2 |
| chr6:62697746-94090076 | 6391 | 31392331 | 1 | rs6455128 | rs3799807 | 108.85 | 0 | GABRR2 |
| chr6:67621368-147709180 | 16188 | 80087813 | 1 | rs6919455 | rs7739314 | 52.498 | 0 | GABRR2 |
| chr6:79198069-99893938 | 4062 | 20695870 | 3 | rs1321584 | rs4504482 | 200.961 | 0 | GABRR2 |
| chr17:44458950-81047708 | −8195 | 36588759 | 1 | cnvi0016818 | rs35680231 | 35.591 | 0 | GALR2 |
| chr17:62662507-81047708 | −11496 | 18385202 | 3 | rs6504246 | rs35680231 | 56.048 | 0 | GALR2 |
| chr3:13878889-149737330 | 24723 | 135858442 | 1 | rs12634112 | rs2007869 | 55.663 | 0 | GAP43 |
| chr3:33409611-170735099 | 23775 | 137325489 | 1 | rs3915062 | rs11924032 | 26.867 | 0 | GAP43 |
| chr3:102240202-195550366 | 17318 | 93310165 | 1 | rs1620217 | rs11711870 | 41.031 | 0 | GAP43 |
| chr3:103140700-144883172 | 8539 | 41742473 | 1 | rs4314176 | rs6797159 | 44.122 | 0 | GAP43 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr3:83075971-196935657 | 21465 | 113859687 | 1 | rs9872858 | rs34729751 | 44.35 | 0 | GAP43 |
| chr3:114889454-177826047 | 12700 | 62936594 | 3 | rs6795297 | rs7628308 | 102.526 | 0 | GAP43 |
| chr12:6485661-6711147 | 48 | 225487 | 1 | rs3759324 | rs1639122 | 18.66 | 0 | GAPDH |
| chr12:6562293-6711147 | 27 | 148855 | 1 | rs2041385 | rs1639122 | 19.307 | 0 | GAPDH |
| chr12:207886-50770291 | 11565 | 50562406 | 3 | rs868249 | rs4477515 | 43.892 | 0 | GAPDH |
| chr4:31222833-180548076 | 24457 | 149325244 | 1 | rs7662351 | rs3849606 | 36.162 | 0 | GC |
| chr4:71849697-72861878 | 167 | 1012182 | 3 | rs6446977 | rs11722798 | 16.573 | 0 | GC |
| chr4:68173959-185767176 | 20235 | 117593218 | 1 | rs6552083 | rs4862428 | 61.893 | 0 | GC |
| chr4:22401728-188608857 | 28456 | 166207130 | 1 | rs4697297 | rs7687115 | 35.717 | 0 | GC |
| chr4:63726348-173015421 | 19817 | 109289074 | 1 | rs17082970 | rs2131002 | 30.251 | 0 | GC |
| chr4:29179713-117038307 | 15513 | 87858595 | 1 | rs1507441 | rs1068807 | 71.6 | 0 | GC |
| chr4:69590353-190872778 | 23145 | 121282426 | 3 | rs293433 | rs12646565 | 315.633 | 0 | GC |
| chr17:21685812-67308196 | 12365 | 45622385 | 1 | rs34864328 | rs17686852 | 50.018 | 0 | GFAP |
| chr17:26648492-58955084 | 5831 | 32306593 | 3 | rs1981512 | rs8068776 | 15.642 | 0 | GFAP |
| chr1:64114301-245591329 | 29842 | 181477029 | 1 | rs11208257 | rs1173850 | 37.504 | 0 | GFI1 |
| chr1:1005806-105612342 | 19173 | 104606537 | 3 | rs3934834 | rs1584633 | 44.152 | 0 | GFI1 |
| chr1:75098453-243531649 | 27360 | 168433197 | 1 | rs12117493 | rs10927002 | 32.113 | 0 | GFI1 |
| chr1:79710545-188898319 | 17303 | 109187775 | 1 | rs417181 | rs16829637 | 45.89 | 0 | GFI1 |
| chr1:2006108-109527861 | 22130 | 107521754 | 3 | rs2254669 | rs839879 | 162.269 | 0 | GFI1 |
| chr9:2522475-140068342 | 25719 | 137545868 | 3 | rs10966757 | rs4074426 | 93.386 | 0 | GFI1B |
| chr9:100158052-139077343 | 9815 | 38919292 | 3 | rs1020884 | rs4842126 | 470.601 | 0 | GFI1B |
| chr2:12056323-227969775 | 39094 | 215923453 | 1 | rs966391 | rs1922020 | 31.384 | 0 | GFPT1 |
| chr2:34870277-241929621 | 37755 | 207059345 | 3 | rs13422005 | rs10205276 | 46.946 | 0 | GFPT1 |
| chr2:38101137-241482099 | 36812 | 203380963 | 1 | rs879321 | rs7576043 | 52.099 | 0 | GFPT1 |
| chr2:41212010-82396211 | 9721 | 41184202 | 3 | rs12614285 | rs934310 | 396.396 | 0 | GFPT1 |
| chr17:44458950-81047708 | −8195 | 36588759 | 1 | cnvi0016818 | rs35680231 | 35.591 | 0 | GH1 |
| chr17:21685812-67308196 | 12365 | 45622385 | 1 | rs34864328 | rs17686852 | 50.018 | 0 | GH1 |
| chr17:61016209-66240093 | 890 | 5223885 | 1 | rs1588368 | rs11658645 | 37.309 | 0 | GH1 |
| chr17:59314257-66170047 | 1135 | 6855791 | 1 | rs758467 | rs4558468 | 71.379 | 0 | GH1 |
| chr17:59205829-62530143 | 453 | 3324315 | 3 | rs7222210 | rs9897203 | 107.455 | 0 | GH1 |
| chr17:21685812-67308196 | 12365 | 45622385 | 1 | rs34864328 | rs17686852 | 50.018 | 0 | GIT1 |
| chr17:26648492-58955084 | 5831 | 32306593 | 3 | rs1981512 | rs8068776 | 15.642 | 0 | GIT1 |
| chr12:10113083-116370432 | 20594 | 106257350 | 1 | rs2012504 | rs7958254 | 35.157 | 0 | GIT2 |
| chr12:59512781-127744939 | 13469 | 68232159 | 3 | rs908394 | rs7966946 | 20.62 | 0 | GIT2 |
| chr12:10020267-129866293 | 23654 | 119846027 | 1 | rs1597097 | rs2170504 | 45.428 | 0 | GIT2 |
| chr12:50855195-133778796 | 17748 | 82923602 | 3 | rs4351895 | rs7975069 | 159.589 | 0 | GIT2 |
| chr6:64844594-169078546 | 21567 | 104233953 | 1 | rs4710465 | rs601639 | 46.524 | 0 | GJA1 |
| chr6:66609532-147053632 | 15315 | 80444101 | 3 | rs9354335 | rs4896886 | 44.941 | 0 | GJA1 |
| chr6:73120320-165130983 | 18715 | 92010553 | 1 | rs9442780 | rs10946016 | 76.383 | 0 | GJA1 |
| chr6:66541198-162520133 | 19344 | 95978936 | 1 | rs2000382 | rs6901071 | 27.509 | 0 | GJA1 |
| chr6:94117546-165103679 | 15579 | 70986134 | 1 | rs3799792 | rs9347902 | 34.066 | 0 | GJA1 |
| chr6:67621368-147709180 | 16188 | 80087813 | 1 | rs6919455 | rs7739314 | 52.498 | 0 | GJA1 |
| chr6:100082983-170909002 | 16393 | 70826029 | 3 | rs594231 | rs12213906 | 261.313 | 0 | GJA1 |
| chr6:26922906-93578359 | 19746 | 66655454 | 1 | rs9348738 | rs9363009 | 27.061 | 0 | GLP1R |
| chr6:31289284-56929863 | 15402 | 25640580 | 3 | rs9265170 | cnvi0015437 | 25.647 | 0 | GLP1R |
| chr6:32968276-73449742 | 15442 | 40481467 | 3 | rs2395300 | rs4235869 | 415.87 | 0 | GLP1R |
| chr17:108420-26610769 | 5548 | 26502350 | 3 | rs12452527 | rs658592 | 82.699 | 0 | GLP2R |
| chr14:26898958-104436931 | 17396 | 77537974 | 1 | rs1245195 | rs11851097 | 57.233 | 0 | GMFB |
| chr14:19917123-65327288 | 10286 | 45410166 | 3 | rs2495197 | rs9323455 | 270.291 | 0 | GMFB |
| chr7:60392-84158180 | 19095 | 84097789 | 3 | rs12670102 | rs2715048 | 208.308 | 0 | GNA12 |
| chr19:266034-18061509 | 3100 | 17795476 | 3 | rs2312724 | rs7250332 | 19.51 | 0 | GNA15 |
| chr19:629303-4119012 | 709 | 3489710 | 1 | rs2283575 | rs350887 | 26.758 | 0 | GNA15 |
| chr19:288246-59110628 | 11009 | 58822383 | 3 | rs10409452 | cnvi0009466 | 100.582 | 0 | GNA15 |
| chr7:11855636-156148608 | 26852 | 144292973 | 1 | rs6947930 | rs6945016 | 36.446 | 0 | GNAI1 |
| chr7:78621315-155831817 | 13678 | 77210503 | 3 | rs1006818 | rs6969015 | 123.319 | 0 | GNAI1 |
| chr7:8872727-156383359 | 27773 | 147510633 | 1 | rs917038 | rs878717 | 32.336 | 0 | GNAI1 |
| chr7:8794418-119068130 | 23484 | 110273713 | 1 | rs2189621 | rs6977904 | 70.867 | 0 | GNAI1 |
| chr7:60392-84158180 | 19095 | 84097789 | 3 | rs12670102 | rs2715048 | 208.308 | 0 | GNAI1 |
| chr3:13878889-149737330 | 24723 | 135858442 | 1 | rs12634112 | rs2007869 | 55.663 | 0 | GNAI2 |
| chr3:33409611-170735099 | 23775 | 137325499 | 1 | rs3915062 | rs11924032 | 26.867 | 0 | GNAI2 |
| chr3:179527-114630641 | 23879 | 114451115 | 3 | rs4684741 | rs1587972 | 207.852 | 0 | GNAI2 |
| chr1:64114301-245591329 | 29842 | 181477029 | 1 | rs11208257 | rs1173850 | 37.504 | 0 | GNAI3 |
| chr1:75098453-243531649 | 27360 | 168433197 | 1 | rs12117493 | rs10927002 | 32.113 | 0 | GNAI3 |
| chr1:79710545-188898319 | 17303 | 109187775 | 1 | rs417181 | rs16829637 | 45.89 | 0 | GNAI3 |
| chr1:109645793-194560463 | 12025 | 84914671 | 3 | cnvi0008281 | rs10921616 | 63.121 | 0 | GNAI3 |
| chr16:50219449-89544756 | 10324 | 39325308 | 3 | rs6500298 | rs3803681 | 108.108 | 0 | GNAO1 |
| chr9:1989033-107532317 | 18263 | 105543285 | 1 | rs7864828 | rs10820726 | 39.824 | 0 | GNAQ |
| chr9:2522475-140068342 | 25719 | 137545868 | 3 | rs10966757 | rs4074426 | 93.386 | 0 | GNAQ |
| chr9:33180228-132003792 | 14691 | 98823565 | 1 | rs7854765 | rs9408988 | 28.69 | 0 | GNAQ |
| chr9:46587-94335290 | 17484 | 94288704 | 3 | rs10814410 | rs9409606 | 762.393 | 0 | GNAQ |
| chr20:7869025-62424661 | 11941 | 54555637 | 3 | rs2294306 | rs6010652 | 9.732 | 0 | GNAS |
| chr20:4591715-58420336 | 11753 | 53828622 | 1 | rs6139494 | rs1416388 | 40.922 | 0 | GNAS |
| chr20:54870769-62912463 | 2390 | 8041695 | 3 | rs6069696 | rs6062363 | 249.708 | 0 | GNAS |
| chr22:22998337-23649242 | 126 | 650906 | 1 | rs6003181 | rs131693 | 276.751 | 0 | GNAZ |
| chr22:16871137-51184393 | 9245 | 34313257 | 3 | rs131538 | rs7284680 | 209.79 | 0 | GNAZ |
| chr5:4872310-180709915 | 35876 | 175837606 | 3 | rs816467 | rs10071993 | 179.394 | 0 | GNB2L1 |
| chr10:7188484-134205354 | 26672 | 127016871 | 1 | rs1977295 | rs3923858 | 50.772 | 0 | GOT1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr10:58385643-124973104 | 13625 | 66587462 | 1 | rs7920235 | rs17663304 | 36.18 | 0 | GOT1 |
| chr10:57671424-133349223 | 16243 | 75677800 | 1 | rs11005106 | rs4301710 | 37.114 | 0 | GOT1 |
| chr10:55492162-117205017 | 13465 | 61712856 | 1 | rs6481032 | rs1933664 | 62.56 | 0 | GOT1 |
| chr10:53602190-135522754 | 19167 | 81920565 | 3 | rs12247820 | rs10909028 | 139.373 | 0 | GOT1 |
| chr17:108420-26610769 | 5548 | 26502263 | 3 | rs12452527 | rs658591 | 82.699 | 0 | GP1BA |
| chr4:31222833-180548076 | 24457 | 149325244 | 1 | rs7662351 | rs3849606 | 36.162 | 0 | GPM6A |
| chr4:163766726-189931630 | 5627 | 26164905 | 3 | rs10033012 | rs10018868 | 25.326 | 0 | GPM6A |
| chr4:68173959-185767176 | 20235 | 117593218 | 1 | rs6552083 | rs4862428 | 61.893 | 0 | GPM6A |
| chr4:22401728-188608857 | 28456 | 166207130 | 1 | rs4697297 | rs7687115 | 35.717 | 0 | GPM6A |
| chr4:162592024-189861553 | 6129 | 27269530 | 1 | rs5005966 | rs6853039 | 63.501 | 0 | GPM6A |
| chr4:69590353-190872778 | 23145 | 121282426 | 3 | rs293433 | rs12646565 | 315.633 | 0 | GPM6A |
| chr10:7188484-134205354 | 26672 | 127016871 | 1 | rs1977295 | rs3923858 | 50.772 | 0 | GPR26 |
| chr10:124668629-135157955 | 2949 | 10489327 | 3 | rs11248331 | rs10776672 | 23.553 | 0 | GPR26 |
| chr10:57671424-133349223 | 16243 | 75677800 | 1 | rs11005106 | rs4301710 | 37.114 | 0 | GPR26 |
| chr10:53602190-135522754 | 19167 | 81920565 | 3 | rs12247820 | rs10909028 | 139.373 | 0 | GPR26 |
| chr1:64114301-245591329 | 29842 | 181477029 | 1 | rs11208257 | rs1173850 | 37.504 | 0 | GPSM2 |
| chr1:75098453-243531649 | 27360 | 168433197 | 1 | rs12117493 | rs10927002 | 32.113 | 0 | GPSM2 |
| chr1:79710545-188898319 | 17303 | 109187775 | 1 | rs417181 | rs16829637 | 45.89 | 0 | GPSM2 |
| chr1:2006108-109527861 | 22130 | 107521754 | 3 | rs2254669 | rs839879 | 162.269 | 0 | GPSM2 |
| chr2:12056323-227979775 | 39094 | 215923453 | 1 | rs966391 | rs1922020 | 31.384 | 0 | GRB14 |
| chr2:34870277-241929621 | 37755 | 207059345 | 3 | rs13422005 | rs10205276 | 46.946 | 0 | GRB14 |
| chr2:38101137-241482009 | 36812 | 203380693 | 1 | rs879321 | rs7576403 | 52.099 | 0 | GRB14 |
| chr2:77041264-194763754 | 21140 | 117722491 | 1 | rs2102827 | rs16835406 | 94.091 | 0 | GRB14 |
| chr2:83383702-175194550 | 16291 | 91810849 | 3 | rs12469609 | rs11891208 | 154.4 | 0 | GRB14 |
| chr17:44458950-81047708 | −8195 | 36588759 | 1 | cnvi0016818 | rs35680231 | 35.591 | 0 | GRB2 |
| chr17:62662507-81047708 | −11496 | 18385202 | 3 | rs6504246 | rs35680231 | 56.048 | 0 | GRB2 |
| chr17:21685812-67308196 | 12365 | 45622385 | 1 | rs34864328 | rs17686852 | 50.018 | 0 | GRB7 |
| chr17:26648492-58955084 | 5831 | 32306593 | 3 | rs1981512 | rs8068776 | 15.642 | 0 | GRB7 |
| chr5:84830796-171903310 | 16642 | 87072515 | 1 | rs300657 | rs10042482 | 42.208 | 0 | GRIA1 |
| chr5:57343495-171903310 | 21683 | 114559816 | 1 | rs10940593 | rs10042482 | 61.169 | 0 | GRIA1 |
| chr5:4872310-180709915 | 35876 | 175837606 | 3 | rs816467 | rs10071993 | 179.394 | 0 | GRIA1 |
| chr4:31222833-180548076 | 24457 | 149325244 | 1 | rs7662351 | rs3849606 | 36.162 | 0 | GRIA2 |
| chr4:137206602-158430547 | 3577 | 21223946 | 3 | rs1597600 | rs12507865 | 83.533 | 0 | GRIA2 |
| chr4:68173959-185767176 | 20235 | 117593218 | 1 | rs6552083 | rs4862428 | 61.893 | 0 | GRIA2 |
| chr4:22401728-188608857 | 28456 | 166207130 | 1 | rs4697297 | rs7687115 | 35.717 | 0 | GRIA2 |
| chr4:63726348-173015421 | 19817 | 109289074 | 1 | rs17082970 | rs2131002 | 30.251 | 0 | GRIA2 |
| chr4:126374899-162380016 | 6166 | 36005118 | 1 | rs4834042 | rs17041092 | 33.404 | 0 | GRIA2 |
| chr4:155739051-165849854 | 1997 | 10110804 | 1 | rs7691720 | rs10005938 | 26.215 | 0 | GRIA2 |
| chr4:69590353-190872778 | 23145 | 121282426 | 3 | rs293433 | rs12646565 | 315.633 | 0 | GRIA2 |
| chr11:42185849-126756938 | 15451 | 84571090 | 1 | rs4375424 | rs10750356 | 36.99 | 0 | GRIA4 |
| chr11:84128537-120941583 | 7678 | 36813047 | 1 | rs488925 | rs4643089 | 29.271 | 0 | GRIA4 |
| chr11:21723471-131521797 | 20508 | 109798327 | 1 | rs11828478 | rs2512898 | 27.565 | 0 | GRIA4 |
| chr11:98062720-121890280 | 5422 | 23827561 | 1 | rs6589308 | rs1944465 | 29.075 | 0 | GRIA4 |
| chr11:23168804-106781292 | 16332 | 83612489 | 1 | rs11027007 | rs7103285 | 49.747 | 0 | GRIA4 |
| chr11:74545378-134940416 | 14496 | 60395039 | 3 | rs512780 | rs11224228 | 527.758 | 0 | GRIA4 |
| chr21:14601415-48084989 | 8249 | 33483575 | 3 | rs2775537 | rs2839378 | 12047.211 | 0 | GRIK1 |
| chr21:14601415-48084989 | 8249 | 33483575 | 3 | rs2775537 | rs2839378 | 41.154 | 0 | GRIK1 |
| chr21:30057145-31992864 | 372 | 1935720 | 1 | rs6516861 | rs1702405 | 41.668 | 0 | GRIK1 |
| chr21:14768343-48084989 | 8193 | 33316647 | 3 | rs2257224 | rs2839378 | 5021.076 | 0 | GRIK1 |
| chr21:14601415-48084989 | 8249 | 33483575 | 3 | rs2775537 | rs2839378 | 4787.438 | 0 | GRIK1 |
| chr21:14595264-48084989 | 8781 | 33489726 | 3 | rs2847443 | rs2839378 | 1871.363 | 0 | GRIK1 |
| chr21:10708231-47970581 | 8807 | 37262351 | 3 | rs4044122 | rs2255397 | 73.188 | 0 | GRIK1 |
| chr1:1005806-105612342 | 19173 | 104606537 | 3 | rs3934834 | rs1584633 | 44.152 | 0 | GRIK3 |
| chr1:2006108-109527861 | 22130 | 107521754 | 3 | rs2254669 | rs839879 | 162.269 | 0 | GRIK3 |
| chr9:139929435-140068342 | 13 | 138908 | 1 | rs12337910 | rs4074426 | 9.973 | 0 | GRIN1 |
| chr9:2522475-140068342 | 25719 | 137545868 | 3 | rs10966757 | rs4074426 | 93.386 | 0 | GRIN1 |
| chr9:139492789-140913833 | 196 | 1421045 | 1 | rs28485548 | cnvi0002661 | 28.211 | 0 | GRIN1 |
| chr9:139492789-140212642 | 109 | 719854 | 3 | rs28485548 | rs13295516 | 12.464 | 0 | GRIN1 |
| chr9:139926402-140277524 | 42 | 351123 | 1 | 200006 | rs7390551 | 31.315 | 0 | GRIN1 |
| chr9:140018138-140153851 | 12 | 135714 | 3 | rs4880094 | rs28457075 | 17.073 | 0 | GRIN1 |
| chr9:139725120-140176250 | 50 | 451131 | 1 | rs2811750 | rs28576426 | 24.435 | 0 | GRIN1 |
| chr9:140018138-140392494 | 38 | 374357 | 1 | rs4880094 | rs4962232 | 27.672 | 0 | GRIN1 |
| chr9:139821068-141105225 | 163 | 1284158 | 3 | rs3750512 | rs11559363 | 55.611 | 0 | GRIN1 |
| chr16:176743-50013967 | 8328 | 49837225 | 3 | rs2562164 | rs12597023 | 174.392 | 0 | GRIN2A |
| chr12:10113083-116370432 | 20594 | 106257350 | 1 | rs2012504 | rs7958254 | 35.157 | 0 | GRIN2B |
| chr12:8171838-32535863 | 5853 | 24364026 | 3 | rs11609309 | rs7963182 | 23.697 | 0 | GRIN2B |
| chr12:10020267-129866293 | 23654 | 119846027 | 1 | rs1597097 | rs2170504 | 45.428 | 0 | GRIN2B |
| chr12:207886-50770291 | 11565 | 50562406 | 3 | rs868249 | rs4477515 | 43.892 | 0 | GRIN2B |
| chr13:23742931-115064482 | 19829 | 91321552 | 1 | rs4770401 | rs7999630 | 44.074 | 0 | GRK1 |
| chr13:65193124-115053155 | 12025 | 49860032 | 3 | rs9598811 | rs7327124 | 78.057 | 0 | GRK1 |
| chr4:179131-68998153 | 13495 | 68819023 | 3 | rs7686948 | rs7687396 | 625.133 | 0 | GRK4 |
| chr6:64844594-169078546 | 21567 | 104233953 | 1 | rs4710465 | rs601639 | 46.524 | 0 | GRM1 |
| chr6:66609532-147053632 | 15315 | 80444101 | 3 | rs9354335 | rs4896886 | 44.941 | 0 | GRM1 |
| chr6:73120320-165130872 | 18715 | 92010553 | 1 | rs9442780 | rs10946016 | 76.383 | 0 | GRM1 |
| chr6:66541198-162520133 | 19344 | 95978936 | 1 | rs2000382 | rs6901071 | 27.509 | 0 | GRM1 |
| chr6:94117546-165103679 | 15579 | 70986134 | 1 | rs3799792 | rs9347902 | 34.066 | 0 | GRM1 |
| chr6:67621368-147709180 | 16188 | 80087813 | 1 | rs6919455 | rs7739314 | 52.498 | 0 | GRM1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr6:100082983-170909002 | 16393 | 70826020 | 3 | rs594231 | rs12213906 | 261.313 | 0 | GRM1 |
| chr3:13878889-149737330 | 24723 | 135858442 | 1 | rs12634112 | rs2007869 | 55.663 | 0 | GRM2 |
| chr3:33409611-170735099 | 23775 | 137325489 | 1 | rs3915062 | rs11924032 | 26.867 | 0 | GRM2 |
| chr3:179527-114630641 | 23879 | 114451115 | 3 | rs4684741 | rs1587972 | 207.852 | 0 | GRM2 |
| chr7:11855636-156148608 | 26852 | 144292973 | 1 | rs6947930 | rs6945016 | 36.446 | 0 | GRM3 |
| chr7:78621315-155831817 | 13678 | 77210503 | 3 | rs1006818 | rs6969015 | 123.319 | 0 | GRM3 |
| chr7:8872727-156383359 | 27773 | 147510633 | 1 | rs917038 | rs878717 | 32.336 | 0 | GRM3 |
| chr7:8794418-119068130 | 23484 | 110273713 | 1 | rs2189621 | rs6977904 | 70.867 | 0 | GRM3 |
| chr7:85117732-86026526 | 122 | 908795 | 1 | rs4728584 | rs10242995 | 65.094 | 246704 | GRM3 |
| chr7:84302877-110993169 | 5183 | 26690293 | 3 | rs4338048 | rs10254893 | 203.09 | 0 | GRM3 |
| chr6:26922906-93578359 | 19746 | 66655454 | 1 | rs9348738 | rs9363009 | 27.061 | 0 | GRM4 |
| chr6:31289284-56929863 | 15402 | 25640580 | 3 | rs9265170 | cnvi0015437 | 25.647 | 0 | GRM4 |
| chr6:32968276-73449742 | 15442 | 40481467 | 3 | rs2395300 | rs4235869 | 415.87 | 0 | GRM4 |
| chr11:42185849-126756938 | 15451 | 84571090 | 1 | rs4375424 | rs10750356 | 36.99 | 0 | GRM5 |
| chr11:81251505-103234729 | 4842 | 21983225 | 3 | rs7935238 | rs1913462 | 26.176 | 0 | GRM5 |
| chr11:84128537-120941583 | 7678 | 36813047 | 1 | rs488925 | rs4643089 | 29.271 | 0 | GRM5 |
| chr11:21723471-131521797 | 20508 | 109798327 | 1 | rs11828478 | rs2512898 | 27.565 | 0 | GRM5 |
| chr11:23168804-106781292 | 16332 | 83612489 | 1 | rs11027007 | rs7103285 | 49.747 | 0 | GRM5 |
| chr11:74545378-134940416 | 14496 | 60395039 | 3 | rs512780 | rs11224228 | 527.758 | 0 | GRM5 |
| chr5:161172541-179954615 | 4271 | 18782075 | 3 | rs4921415 | rs10059433 | 6.291 | 0 | GRM6 |
| chr5:4872310-180709915 | 35876 | 175837606 | 3 | rs816467 | rs10071993 | 179.394 | 0 | GRM6 |
| chr3:5824878-8781331 | 952 | 2956454 | 3 | rs2470628 | rs11916022 | 924.891 | 0 | GRM7 |
| chr3:179527-114630641 | 23879 | 114451115 | 3 | rs4684741 | rs1587972 | 207.852 | 0 | GRM7 |
| chr7:11855636-156148608 | 26852 | 144292973 | 1 | rs6947930 | rs6945016 | 36.446 | 0 | GRM8 |
| chr7:78621315-155831817 | 13678 | 77210503 | 3 | rs1006818 | rs6969015 | 123.319 | 0 | GRM8 |
| chr7:8872727-156383359 | 27773 | 147510633 | 1 | rs917038 | rs878717 | 32.336 | 0 | GRM8 |
| chr7:125676925-125780682 | 24 | 103758 | 1 | rs1419535 | rs10267757 | 26.358 | 297970 | GRM8 |
| chr7:120061880-143606234 | 4616 | 23544355 | 3 | rs12531689 | rs10247493 | 18.96 | 0 | GRM8 |
| chr19:31569338-53780966 | 3788 | 22211629 | 1 | rs2867544 | rs10407424 | 33.9 | 0 | GSK3A |
| chr19:288246-59110628 | 11009 | 58822383 | 3 | rs10409452 | cnvi0009466 | 100.582 | 0 | GSK3A |
| chr3:13878889-149737330 | 24723 | 135858442 | 1 | rs12634112 | rs2007869 | 55.663 | 0 | GSK3B |
| chr3:33409611-170735099 | 23775 | 137325489 | 1 | rs3915062 | rs11924032 | 26.867 | 0 | GSK3B |
| chr3:102240202-195550366 | 17318 | 93310165 | 1 | rs1620217 | rs11711870 | 41.031 | 0 | GSK3B |
| chr3:103140700-144803172 | 8539 | 41742473 | 1 | rs4314176 | rs6797159 | 44.122 | 0 | GSK3B |
| chr3:83075971-196935657 | 21465 | 113859687 | 1 | rs9872858 | rs34729751 | 44.35 | 0 | GSK3B |
| chr3:114889454-177826047 | 12700 | 62936594 | 3 | rs6795297 | rs7628308 | 102.526 | 0 | GSK3B |
| chr9:2522475-140068342 | 25719 | 137545868 | 3 | rs10966757 | rs4074426 | 93.386 | 0 | GSN |
| chr9:33180228-132003792 | 14691 | 98823565 | 1 | rs7854765 | rs9408988 | 28.69 | 0 | GSN |
| chr9:100158052-139047343 | 9815 | 38919292 | 3 | rs1020884 | rs4842126 | 470.601 | 0 | GSN |
| chr1:64114301-245591329 | 29842 | 181477029 | 1 | rs11208257 | rs1173850 | 37.504 | 0 | GSTM4 |
| chr1:75098453-243531649 | 27360 | 168433197 | 1 | rs12117493 | rs10927002 | 32.113 | 0 | GSTM4 |
| chr1:79710545-188898319 | 17303 | 109187775 | 1 | rs417181 | rs16829637 | 45.89 | 0 | GSTM4 |
| chr1:109645793-194560463 | 12025 | 84914671 | 3 | cnvi0008281 | rs10921616 | 63.121 | 0 | GSTM4 |
| chr9:1989033-107532317 | 18263 | 105543285 | 1 | rs7864828 | rs10820726 | 39.824 | 0 | HABP4 |
| chr9:2522475-140068342 | 25719 | 137545868 | 3 | rs10966757 | rs4074426 | 93.386 | 0 | HABP4 |
| chr9:99171631-99360461 | 19 | 188831 | 1 | rs10820564 | rs6477568 | 18.889 | 0 | HABP4 |
| chr9:33180228-132003792 | 14691 | 98823565 | 1 | rs7854765 | rs9408988 | 28.69 | 0 | HABP4 |
| chr9:94405452-99509624 | 947 | 5104173 | 3 | rs10992024 | rs10114863 | 116.934 | 0 | HABP4 |
| chr5:84830796-171903310 | 16642 | 87072515 | 1 | rs300657 | rs10042482 | 42.208 | 0 | HAND1 |
| chr5:153684038-153925210 | 100 | 241173 | 3 | rs6580069 | rs2253311 | 14.734 | 0 | HAND1 |
| chr5:57343495-171903310 | 21683 | 114559816 | 1 | rs10940593 | rs10042482 | 61.169 | 0 | HAND1 |
| chr5:4872310-180709915 | 35876 | 175837606 | 3 | rs816467 | rs10071993 | 179.394 | 0 | HAND1 |
| chr4:31222833-180548076 | 24457 | 149325244 | 1 | rs7662351 | rs3849606 | 36.162 | 0 | HAND2 |
| chr4:163766726-189931630 | 5627 | 26164905 | 3 | rs10033012 | rs10018868 | 25.326 | 0 | HAND2 |
| chr4:68173959-185767176 | 20235 | 117593218 | 1 | rs6552083 | rs4862428 | 61.893 | 0 | HAND2 |
| chr4:22401728-188608857 | 28456 | 166207130 | 1 | rs4697297 | rs7687115 | 35.717 | 0 | HAND2 |
| chr4:162592024-189861553 | 6129 | 27269530 | 1 | rs5005966 | rs6853039 | 63.501 | 0 | HAND2 |
| chr4:69590353-190872778 | 23145 | 121282426 | 3 | rs293433 | rs12646565 | 315.633 | 0 | HAND2 |
| chr5:84830796-171903310 | 16642 | 87072515 | 1 | rs300657 | rs10042482 | 42.208 | 0 | HARS |
| chr5:57343495-171903310 | 21683 | 114559816 | 1 | rs10940593 | rs10042482 | 61.169 | 0 | HARS |
| chr5:98442871-150317237 | 9828 | 51874367 | 1 | rs1447379 | rs7710790 | 38.687 | 0 | HARS |
| chr5:4872310-180709915 | 35876 | 175837606 | 3 | rs816467 | rs10071993 | 179.394 | 0 | HARS |
| chr1:64114301-245591329 | 29842 | 181477029 | 1 | rs11208257 | rs1173850 | 37.504 | 0 | HBXIP |
| chr1:75098453-243531649 | 27360 | 168433197 | 1 | rs12117493 | rs10927002 | 32.113 | 0 | HBXIP |
| chr1:79710545-188898319 | 17303 | 109187775 | 1 | rs417181 | rs16829637 | 45.89 | 0 | HBXIP |
| chr1:109645793-194560463 | 12025 | 84914671 | 3 | cnvi0008281 | rs10921616 | 63.121 | 0 | HBXIP |
| chr3:102240202-195550366 | 17318 | 93310165 | 1 | rs1620217 | rs11711870 | 41.031 | 0 | HES1 |
| chr3:192603329-196181269 | 617 | 3577941 | 3 | rs6805010 | rs7648887 | 385.598 | 0 | HES1 |
| chr3:193664994-193931852 | 58 | 266859 | 1 | rs1986907 | rs4613405 | 104.029 | 0 | HES1 |
| chr3:83075971-196935657 | 21465 | 113859687 | 1 | rs9872858 | rs34729751 | 44.35 | 0 | HES1 |
| chr3:177912894-197551411 | 4129 | 19638518 | 3 | rs9290640 | rs1273562 | 185.507 | 0 | HES1 |
| chr6:10123365-31221039 | -3135 | 21097275 | 1 | rs2181334 | rs4416711 | 318.459 | 0 | HLA-A |
| chr6:26922906-93578359 | 19746 | 66655454 | 1 | rs9348738 | rs9363009 | 27.061 | 0 | HLA-A |
| chr6:2681610-31453618 | 81 | 28772009 | 3 | rs1131896 | rs9267212 | 428.177 | 0 | HLA-A |
| chr6:3760708-31957364 | 8062 | 28196657 | 3 | rs2187825 | cnvi0006380 | 39.016 | 0 | HLA-A |
| chr6:19044000-31286381 | -6774 | 12242382 | 1 | rs6922929 | rs9265057 | 31.384 | 0 | HLA-A |
| chr6:2585208-31281876 | -2 | 28696669 | 1 | rs1634746 | rs1634747 | 31.615 | 0 | HLA-A |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr6:24697388-31341340 | −8293 | 6643953 | 1 | rs2092404 | rs9266515 | 38.794 | 0 | HLA-A |
| chr6:29177102-30253339 | 1364 | 1076238 | 1 | rs1883329 | rs1132547 | 42.696 | 0 | HLA-A |
| chr6:29812471-29937541 | 221 | 125071 | 1 | rs7452613 | rs11752303 | 122.513 | 0 | HLA-A |
| chr6:26430981-31878433 | −8001 | 5447453 | 1 | rs2893848 | rs519417 | 55.651 | 0 | HLA-A |
| chr6:2584569-31286381 | 8 | 28701813 | 1 | rs9391764 | rs9265057 | 34.598 | 0 | HLA-A |
| chr6:2681610-31453618 | 81 | 28772009 | 3 | rs1131896 | rs9267212 | 390.234 | 0 | HLA-A |
| chr6:29253756-32671521 | 2267 | 3417766 | 1 | rs9468508 | rs9275439 | 51.553 | 0 | HLA-A |
| chr6:19044000-31286381 | −6774 | 12242382 | 0 | rs6922929 | rs9265057 | 33.119 | 0 | HLA-A |
| chr6:181089-30430875 | 1806 | 30249787 | 3 | rs1535053 | rs35792611 | 80.394 | 0 | HLA-A |
| chr6:26922906-93578359 | 19746 | 66655454 | 1 | rs9348738 | rs9363009 | 27.061 | 0 | HLA-C |
| chr6:30792235-31321211 | 404 | 528977 | 1 | rs4713391 | rs2596501 | 72.355 | 0 | HLA-C |
| chr6:2681610-31453618 | 81 | 28772009 | 3 | rs1131896 | rs9267212 | 428.177 | 0 | HLA-C |
| chr6:3760708-31957364 | 8062 | 28196657 | 3 | rs2187825 | cnvi0006380 | 39.016 | 0 | HLA-C |
| chr6:19044000-31286381 | −6774 | 12242382 | 1 | rs6922929 | rs9265057 | 31.384 | 0 | HLA-C |
| chr6:2585208-31281876 | −2 | 28696669 | 1 | rs1634746 | rs1634747 | 31.615 | 0 | HLA-C |
| chr6:24697388-31341340 | −8293 | 6643953 | 1 | rs2092404 | rs9266515 | 38.794 | 0 | HLA-C |
| chr6:26430981-31878433 | −8001 | 5447453 | 1 | rs2893848 | rs519417 | 55.651 | 0 | HLA-C |
| chr6:2584569-31286381 | 8 | 28701813 | 1 | rs9391764 | rs9265057 | 34.598 | 0 | HLA-C |
| chr6:2681610-31453618 | 81 | 28772009 | 3 | rs1131896 | rs9267212 | 390.234 | 0 | HLA-C |
| chr6:29253756-32671521 | 2267 | 3417766 | 1 | rs9468508 | rs9275439 | 51.553 | 0 | HLA-C |
| chr6:19044000-31286381 | −6774 | 12242382 | 0 | rs6922929 | rs9265057 | 33.119 | 0 | HLA-C |
| chr6:30475431-32449411 | −7687 | 1973967 | 3 | cnvi0005997 | rs1964995 | 153.275 | 0 | HLA-C |
| chr6:26922906-93578359 | 19746 | 66655454 | 1 | rs9348738 | rs9363009 | 27.061 | 0 | HLA-DQA2 |
| chr6:32496748-33038766 | −7385 | 542019 | 1 | rs34955825 | rs2301220 | 35.189 | 0 | HLA-DQA2 |
| chr6:32496748-32895580 | −7661 | 398833 | 1 | rs34955825 | rs9501239 | 61.369 | 0 | HLA-DQA2 |
| chr6:32505531-32874796 | −7700 | 369266 | 1 | cnvi0006586 | rs9469310 | 29.88 | 0 | HLA-DQA2 |
| chr6:31281438-32874796 | −7311 | 1593359 | 1 | cnvi0006173 | rs9469310 | 36.913 | 0 | HLA-DQA2 |
| chr6:32496748-32895580 | −7661 | 398833 | 1 | rs34955825 | rs9501239 | 49.158 | 0 | HLA-DQA2 |
| chr6:32505531-32895580 | −7668 | 390050 | 1 | cnvi0006586 | rs9501239 | 48.21 | 0 | HLA-DQA2 |
| chr6:31289284-56929863 | 15402 | 25640580 | 3 | rs9265170 | cnvi0015437 | 25.647 | 0 | HLA-DQA2 |
| chr6:32524224-32814659 | −7820 | 290436 | 3 | rs28594633 | rs4711312 | 142.044 | 0 | HLA-DQA2 |
| chr13:19584477-81204088 | 13265 | 61619612 | 3 | rs1334954 | rs1176297 | 22.162 | 0 | HMGB1 |
| chr13:23742931-115064482 | 19829 | 91321552 | 1 | rs4770401 | rs7999630 | 44.074 | 0 | HMGB1 |
| chr13:19121741-63373781 | 10326 | 44252041 | 3 | rs9578050 | rs9539575 | 82.761 | 0 | HMGB1 |
| chr21:14601415-48084989 | 8249 | 33483575 | 3 | rs2775537 | rs2839378 | 12047.211 | 0 | HMGN1 |
| chr21:14601415-48084989 | 8249 | 33483575 | 3 | rs2775537 | rs2839378 | 41.154 | 0 | HMGN1 |
| chr21:14768343-48084989 | 8193 | 33316647 | 3 | rs2257224 | rs2839378 | 5021.076 | 0 | HMGN1 |
| chr21:14601415-48084989 | 8249 | 33483575 | 3 | rs2775537 | rs2839378 | 4787.438 | 0 | HMGN1 |
| chr21:14595264-48084989 | 8781 | 33489726 | 3 | rs2847443 | rs2839378 | 1871.363 | 0 | HMGN1 |
| chr21:10708231-47970581 | 8807 | 37262351 | 3 | rs4044122 | rs2255397 | 73.188 | 0 | HMGN1 |
| chr1:1005806-105612342 | 19173 | 104606537 | 3 | rs3934834 | rs1584633 | 44.152 | 0 | HMGN2 |
| chr1:2006108-109527861 | 22130 | 107521754 | 3 | rs2254669 | rs839879 | 162.269 | 0 | HMGN2 |
| chr5:84830796-171903310 | 16642 | 87072515 | 1 | rs300657 | rs10042482 | 42.208 | 0 | HMMR |
| chr5:161172541-179954615 | 4271 | 18782075 | 3 | rs4921415 | rs10059433 | 6.291 | 0 | HMMR |
| chr5:57343495-171903310 | 21683 | 114559816 | 1 | rs10940593 | rs10042482 | 61.169 | 0 | HMMR |
| chr5:4872310-180709915 | 35876 | 175837606 | 3 | rs816467 | rs10071993 | 179.394 | 0 | HMMR |
| chr16:2941320-7172068 | 1303 | 4230749 | 3 | rs1034709 | rs1600230 | 22.392 | 0 | HMOX2 |
| chr16:176743-50013967 | 8328 | 49837225 | 3 | rs2562164 | rs12597023 | 174.392 | 0 | HMOX2 |
| chr5:161172541-179954615 | 4271 | 18782075 | 3 | rs4921415 | rs10059433 | 6.291 | 0 | HMP19 |
| chr5:4872310-180709915 | 35876 | 175837606 | 3 | rs816467 | rs10071993 | 179.394 | 0 | HMP19 |
| chr5:78520731-78765405 | 35 | 244675 | 1 | rs4704546 | rs7710089 | 12.78 | 0 | HOMER1 |
| chr5:49952847-89853069 | 7268 | 39900223 | 3 | rs12188654 | rs42467 | 26.225 | 0 | HOMER1 |
| chr5:57343495-171903310 | 21683 | 114559816 | 1 | rs10940593 | rs10042482 | 61.169 | 0 | HOMER1 |
| chr5:78542290-79057477 | 95 | 515188 | 1 | rs10474578 | rs259126 | 38.26 | 0 | HOMER1 |
| chr5:4872310-180709915 | 35876 | 175837606 | 3 | rs816467 | rs10071993 | 179.394 | 0 | HOMER1 |
| chr15:51688996-102398060 | 11030 | 50709065 | 1 | rs2459396 | rs7181527 | 36.939 | 0 | HOMER2 |
| chr15:53775670-96810867 | 9973 | 43035198 | 1 | rs657495 | rs2589238 | 49.204 | 0 | HOMER2 |
| chr15:66108544-102427006 | 8615 | 36318463 | 3 | cnvi0007613 | rs11632620 | 159.164 | 0 | HOMER2 |
| chr19:18622443-22202166 | 372 | 3579724 | 3 | rs4808812 | rs10412244 | 11.197 | 0 | HOMER3 |
| chr19:288246-59110628 | 11009 | 58822383 | 3 | rs10409452 | cnvi0009466 | 100.582 | 0 | HOMER3 |
| chr18:1583633-58142042 | 11490 | 56558410 | 3 | rs9945988 | rs1560399 | 3.736 | 0 | HRH4 |
| chr18:10274-30780701 | 6393 | 30770428 | 3 | cnvi0008694 | rs271534 | 338.777 | 0 | HRH4 |
| chr14:80818058-105348552 | 5492 | 24530495 | 3 | rs6574553 | rs2028416 | 15.874 | 0 | HSP90AA1 |
| chr14:26898958-104436931 | 17396 | 77537974 | 1 | rs1245195 | rs11851097 | 57.233 | 0 | HSP90AA1 |
| chr14:65405722-103799039 | 8979 | 38393318 | 3 | rs11623705 | rs11628472 | 266.153 | 0 | HSP90AA1 |
| chr6:26922906-93578359 | 19746 | 66655454 | 1 | rs9348738 | rs9363009 | 27.061 | 0 | HSP90AB1 |
| chr6:31289284-56929863 | 15402 | 25640580 | 3 | rs9265170 | cnvi0015437 | 25.647 | 0 | HSP90AB1 |
| chr6:32968276-73449742 | 15442 | 40481467 | 3 | rs2395300 | rs4235869 | 415.87 | 0 | HSP90AB1 |
| chr6:26922906-93578359 | 19746 | 66655454 | 1 | rs9348738 | rs9363009 | 27.061 | 0 | HSPA1A |
| chr6:31289284-32512613 | 10001 | 1223330 | 3 | rs9265170 | rs35571839 | 45.035 | 0 | HSPA1A |
| chr6:3760708-31957364 | 8062 | 28196657 | 3 | rs2187825 | cnvi0006380 | 39.016 | 0 | HSPA1A |
| chr6:31281438-32449411 | −7879 | 1167974 | 1 | cnvi0006173 | rs1964995 | 24.023 | 0 | HSPA1A |
| chr6:31337633-32449411 | 1650 | 1111779 | 1 | rs9266433 | rs1964995 | 124.395 | 0 | HSPA1A |
| chr6:31281438-32354428 | −8033 | 1072991 | 1 | cnvi0006173 | rs4424066 | 37.329 | 0 | HSPA1A |
| chr6:31289284-31960770 | 9811 | 671487 | 3 | rs9265170 | cnvi0006385 | 29.628 | 0 | HSPA1A |
| chr6:31281438-32874796 | −7311 | 1593359 | 1 | cnvi0006173 | rs9469310 | 36.913 | 0 | HSPA1A |
| chr6:26430981-31878433 | −8001 | 5447453 | 1 | rs2893848 | rs519417 | 55.651 | 0 | HSPA1A |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr6:29253756-32671521 | 2267 | 3417766 | 1 | rs9468508 | rs9275439 | 51.553 | 0 | HSPA1A |
| chr6:31289284-56929863 | 15402 | 25640580 | 3 | rs9265170 | cnvi0015437 | 25.647 | 0 | HSPA1A |
| chr6:30475431-32449411 | −7687 | 1973981 | 3 | cnvi0005997 | rs1964995 | 153.275 | 0 | HSPA1A |
| chr6:26922906-93578359 | 19746 | 66655454 | 1 | rs9348738 | rs9363009 | 27.061 | 0 | HSPA1B |
| chr6:31289284-32512613 | 10001 | 1223330 | 3 | rs9265170 | rs35571839 | 45.035 | 0 | HSPA1B |
| chr6:3760708-31957364 | 8062 | 28196657 | 3 | rs2187825 | cnvi0006380 | 39.016 | 0 | HSPA1B |
| chr6:31281438-32449411 | −7879 | 1167974 | 1 | cnvi0006173 | rs1964995 | 24.023 | 0 | HSPA1B |
| chr6:31337633-32449411 | 1650 | 1111779 | 1 | rs9266433 | rs1964995 | 124.395 | 0 | HSPA1B |
| chr6:31281438-32354428 | −8033 | 1072991 | 1 | cnvi0006173 | rs4424066 | 37.329 | 0 | HSPA1B |
| chr6:31289284-31960770 | 9811 | 671487 | 3 | rs9265170 | cnvi0006385 | 29.628 | 0 | HSPA1B |
| chr6:31281438-32874796 | −7311 | 1593359 | 1 | cnvi0006173 | rs9469310 | 36.913 | 0 | HSPA1B |
| chr6:26430981-31878433 | −8001 | 5447453 | 1 | rs2893848 | rs519417 | 55.651 | 0 | HSPA1B |
| chr6:29253756-32671521 | 2267 | 3417766 | 1 | rs9468508 | rs9275439 | 51.553 | 0 | HSPA1B |
| chr6:31289284-56929863 | 15402 | 25640580 | 3 | rs9265170 | cnvi0015437 | 25.647 | 0 | HSPA1B |
| chr6:30475431-32449411 | −7687 | 1973981 | 3 | cnvi0005997 | rs1964995 | 153.275 | 0 | HSPA1B |
| chr5:84830796-171903310 | 16642 | 87072515 | 1 | rs300657 | rs10042482 | 42.208 | 0 | HSPA4 |
| chr5:57343495-171903310 | 21683 | 114559816 | 1 | rs10940593 | rs10042482 | 61.169 | 0 | HSPA4 |
| chr5:98442871-150317237 | 9828 | 51874367 | 1 | rs1447379 | rs7710790 | 38.687 | 0 | HSPA4 |
| chr5:4872310-180709915 | 35876 | 175837606 | 3 | rs816467 | rs10071993 | 179.394 | 0 | HSPA4 |
| chr7:11855636-156148608 | 26852 | 144292973 | 1 | rs6947930 | rs6945016 | 36.446 | 0 | HSPB1 |
| chr8:8872727-156383359 | 27773 | 147510633 | 1 | rs917038 | rs878717 | 32.336 | 0 | HSPB1 |
| chr7:8794418-119068130 | 23484 | 110273713 | 1 | rs2189621 | rs6977904 | 70.867 | 0 | HSPB1 |
| chr7:60392-84158180 | 19095 | 84097789 | 3 | rs12670102 | rs2715048 | 208.308 | 0 | HSPB1 |
| chr5:39526068-67275356 | 4441 | 27749289 | 1 | rs16869031 | rs999826 | 77.848 | 0 | HSPB3 |
| chr5:49952847-89853069 | 7268 | 39900223 | 3 | rs12188654 | rs42467 | 26.225 | 0 | HSPB3 |
| chr5:4872310-180709915 | 35876 | 175837606 | 3 | rs816467 | rs10071993 | 179.394 | 0 | HSPB3 |
| chr12:59512781-127744939 | 13469 | 68232159 | 3 | rs908394 | rs7966946 | 20.62 | 0 | HSPB8 |
| chr12:10020267-129866293 | 23654 | 119846027 | 1 | rs1597097 | rs2170504 | 45.428 | 0 | HSPB8 |
| chr12:112610714-133708729 | 5366 | 21098016 | 3 | rs11066188 | rs11147249 | 695.45 | 0 | HSPB8 |
| chr12:50855195-133778796 | 17748 | 82923602 | 3 | rs4351895 | rs7975069 | 159.589 | 0 | HSPB8 |
| chr19:288246-59110628 | 11009 | 58822383 | 3 | rs10409452 | cnvi0009466 | 100.582 | 0 | HSPBP1 |
| chr2:12056323-227979775 | 39094 | 215923453 | 1 | rs966391 | rs1922020 | 31.384 | 0 | HSPE1 |
| chr2:34870277-241929621 | 37755 | 207059345 | 3 | rs13422005 | rs10205276 | 46.946 | 0 | HSPE1 |
| chr2:38101137-241482099 | 36812 | 203380963 | 1 | rs879321 | rs7576043 | 52.099 | 0 | HSPE1 |
| chr2:185050218-212752193 | 4583 | 27701876 | 1 | rs1526196 | rs6727114 | 45.31 | 0 | HSPE1 |
| chr2:193255360-242529978 | 10289 | 49274619 | 3 | rs1351905 | cnvi0010399 | 93.244 | 0 | HSPE1 |
| chr13:19584477-81204088 | 13265 | 61619612 | 3 | rs1334954 | rs1176297 | 22.162 | 0 | HSPH1 |
| chr13:23742931-115064482 | 19829 | 91321552 | 1 | rs4770401 | rs7999630 | 44.074 | 0 | HSPH1 |
| chr13:19121741-63373781 | 10326 | 44252041 | 3 | rs9578050 | rs9539575 | 82.761 | 0 | HSPH1 |
| chr13:36707502-103656104 | 13622 | 66948603 | 1 | rs3827890 | rs1952590 | 38.726 | 0 | HTR2A |
| chr13:19584477-81204088 | 13265 | 61619612 | 3 | rs1334954 | rs1176297 | 22.162 | 0 | HTR2A |
| chr13:23742931-115064482 | 19829 | 91321552 | 1 | rs4770401 | rs7999630 | 44.074 | 0 | HTR2A |
| chr13:47300055-47409034 | 48 | 108980 | 1 | rs1539177 | rs6314 | 25.525 | 0 | HTR2A |
| chr13:19121741-63373781 | 10326 | 44252041 | 3 | rs9578050 | rs9539575 | 82.761 | 0 | HTR2A |
| chr2:231927569-232035793 | 10 | 108225 | 1 | rs3815844 | rs2032953 | 14.229 | 0 | HTR2B |
| chr2:34870277-241929621 | 37755 | 207059345 | 3 | rs13422005 | rs10205276 | 46.946 | 0 | HTR2B |
| chr2:38101137-241482099 | 36812 | 203380963 | 1 | rs879321 | rs7576043 | 52.099 | 0 | HTR2B |
| chr2:193255360-242529978 | 10289 | 49274619 | 3 | rs1351905 | cnvi0010399 | 93.244 | 0 | HTR2B |
| chr1:1005806-105612342 | 19173 | 104606537 | 3 | rs3934834 | rs1584633 | 44.152 | 0 | HTR6 |
| chr1:2006108-109527861 | 22130 | 107521754 | 3 | rs2254669 | rs839879 | 162.269 | 0 | HTR6 |
| chr8:30757798-142750969 | 20699 | 111993702 | 1 | rs10101203 | rs6421025 | 34.223 | 0 | IKBKB |
| chr8:41983076-50280013 | 418 | 8296938 | 1 | rs12544318 | rs12677656 | 39.988 | 0 | IKBKB |
| chr8:23218101-146274708 | 23020 | 123056608 | 1 | rs7010362 | rs7822726 | 38.828 | 0 | IKBKB |
| chr8:25304020-43159151 | 3371 | 17855132 | 3 | rs10503771 | cnvi0018779 | 263.504 | 0 | IKBKB |
| chr1:64114301-245591228 | 29842 | 181477029 | 1 | rs11208257 | rs1173850 | 37.504 | 0 | IKBKE |
| chr1:178626526-244159143 | 13064 | 65532618 | 3 | rs2761477 | rs479338 | 11.373 | 0 | IKBKE |
| chr1:75098453-243531649 | 27360 | 168433197 | 1 | rs12117493 | rs10927002 | 32.113 | 0 | IKBKE |
| chr1:188850774-235423607 | 10060 | 46572834 | 1 | rs16829466 | rs12409696 | 43.25 | 0 | IKBKE |
| chr1:191875752-235423607 | 9517 | 43547856 | 1 | rs9427811 | rs12409696 | 62.01 | 0 | IKBKE |
| chr1:189128124-227340790 | 7927 | 38212667 | 1 | rs7515205 | rs12752546 | 167.428 | 0 | IKBKE |
| chr1:174219398-247422297 | 15986 | 73202900 | 1 | rs16846809 | rs4642922 | 35.258 | 0 | IKBKE |
| chr1:197187605-226404457 | 6316 | 29216853 | 3 | rs10922187 | rs3008192 | 130.989 | 0 | IKBKE |
| chr16:176743-50013967 | 8328 | 49837225 | 3 | rs2562164 | rs12597023 | 174.392 | 0 | IL4R |
| chr3:234726-6328081 | 2293 | 6093356 | 3 | rs7632811 | rs1595039 | 106.207 | 0 | IL5RA |
| chr3:179527-114630641 | 23879 | 114451115 | 3 | rs4684741 | rs1587972 | 207.852 | 0 | IL5RA |
| chr3:48801929-49362892 | 29 | 560964 | 1 | rs6766238 | rs1865741 | 15.852 | 0 | IMPDH2 |
| chr3:13878889-149737330 | 24723 | 135858442 | 1 | rs12634112 | rs2007869 | 55.663 | 0 | IMPDH2 |
| chr3:33409611-170735099 | 23775 | 137325489 | 1 | rs3915062 | rs11924032 | 26.867 | 0 | IMPDH2 |
| chr3:179527-114630641 | 23879 | 114451115 | 3 | rs4684741 | rs1587972 | 207.852 | 0 | IMPDH2 |
| chr19:266034-18061509 | 3100 | 17795476 | 3 | rs2312724 | rs7250332 | 19.51 | 0 | INSR |
| chr19:288246-59110628 | 11009 | 58822383 | 3 | rs10409452 | cnvi0009466 | 100.582 | 0 | INSR |
| chr3:120658659-121614175 | 112 | 955517 | 1 | rs7618583 | rs1881998 | 31.134 | 0 | IQCB1 |
| chr3:13878889-149737330 | 24723 | 135858442 | 1 | rs12634112 | rs2007869 | 55.663 | 0 | IQCB1 |
| chr3:33409611-170735099 | 23775 | 137325489 | 1 | rs3915062 | rs11924032 | 26.867 | 0 | IQCB1 |
| chr3:102240202-195550366 | 17318 | 93310165 | 1 | rs1620217 | rs11711870 | 41.031 | 0 | IQCB1 |
| chr3:121453361-121631841 | 22 | 178481 | 1 | rs9841861 | rs1523519 | 24.376 | 0 | IQCB1 |
| chr3:121459589-121614175 | 21 | 154587 | 1 | rs12498138 | rs1881998 | 18.424 | 0 | IQCB1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr3:103140700-144883172 | 8539 | 41742473 | 1 | rs4314176 | rs6797159 | 44.122 | 0 | IQCB1 |
| chr3:83075971-196935657 | 21465 | 113859687 | 1 | rs9872858 | rs34729751 | 44.35 | 0 | IQCB1 |
| chr3:121526849-121670405 | 23 | 143557 | 1 | rs6770719 | rs9871743 | 13.308 | 0 | IQCB1 |
| chr3:121453361-121564989 | 15 | 111629 | 1 | rs9841861 | rs6767409 | 18.746 | 0 | IQCB1 |
| chr3:121526849-121648168 | 25 | 121320 | 1 | rs6770719 | rs1143672 | 14.896 | 0 | IQCB1 |
| chr3:114889454-177826047 | 12700 | 62936594 | 3 | rs6795297 | rs7628308 | 102.526 | 0 | IQCB1 |
| chr15:90962971-91108674 | 28 | 145704 | 3 | rs17176602 | rs8031453 | 41.934 | 0 | IQGAP1 |
| chr15:51688996-102398060 | 11030 | 50709065 | 1 | rs2459396 | rs7181527 | 36.939 | 0 | IQGAP1 |
| chr15:53775670-96810867 | 9973 | 43035198 | 1 | rs657495 | rs2589238 | 49.204 | 0 | IQGAP1 |
| chr15:66108544-102427006 | 8615 | 36318463 | 3 | cnvi0007613 | rs11632620 | 159.164 | 0 | IQGAP1 |
| chr5:49952847-89853069 | 7268 | 39900223 | 3 | rs12188654 | rs42467 | 26.225 | 0 | IQGAP2 |
| chr5:57343495-171903310 | 21683 | 114559816 | 1 | rs10940593 | rs10042482 | 61.169 | 0 | IQGAP2 |
| chr5:4872310-180709915 | 35876 | 175837606 | 3 | rs816467 | rs10071993 | 179.394 | 0 | IQGAP2 |
| chr2:12056323-227979775 | 39094 | 215923453 | 1 | rs966391 | rs1922020 | 31.384 | 0 | IRS1 |
| chr2:34870277-241929621 | 37755 | 207059345 | 3 | rs13422005 | rs10205276 | 46.946 | 0 | IRS1 |
| chr2:38101137-241482099 | 36812 | 203380963 | 1 | rs879321 | rs7576043 | 52.099 | 0 | IRS1 |
| chr2:193255360-242529978 | 10289 | 49274619 | 3 | rs1351905 | cnvi0010399 | 93.244 | 0 | IRS1 |
| chr10:7188484-134605354 | 26672 | 127016871 | 1 | rs1977295 | rs3923858 | 50.772 | 0 | ITGB1 |
| chr10:734229-69155636 | 14859 | 68421408 | 3 | rs1769236 | rs2394375 | 72.104 | 0 | ITGB1 |
| chr10:88874-53366180 | 12853 | 53277307 | 3 | cnvi0015449 | rs10998465 | 319.021 | 0 | ITGB1 |
| chr21:44839153-47856106 | 674 | 3016954 | 1 | rs2838302 | rs2236616 | 38.158 | 0 | ITGB2 |
| chr21:14601415-48084989 | 8249 | 33483575 | 3 | rs2775537 | rs2839378 | 12047.211 | 0 | ITGB2 |
| chr21:14601415-48084989 | 8249 | 33483575 | 3 | rs2775537 | rs2839378 | 41.154 | 0 | ITGB2 |
| chr21:14768343-48084989 | 8193 | 33316647 | 3 | rs2257224 | rs2839378 | 5021.076 | 0 | ITGB2 |
| chr21:14601415-48084989 | 8249 | 33483575 | 3 | rs2775537 | rs2839378 | 4787.438 | 0 | ITGB2 |
| chr21:14595264-48084989 | 8781 | 33489726 | 3 | rs2847443 | rs2839378 | 1871.363 | 0 | ITGB2 |
| chr21:10708231-47970581 | 8807 | 37262351 | 3 | rs4044122 | rs2255397 | 73.188 | 0 | ITGB2 |
| chr1:1005806-105612342 | 19173 | 104606537 | 3 | rs3934834 | rs1584633 | 44.152 | 0 | ITGB3BP |
| chr1:63914117-64047615 | 16 | 133499 | 1 | rs3009577 | rs10127824 | 22.702 | 0 | ITGB3BP |
| chr1:2006108-109527861 | 22130 | 107521754 | 3 | rs2254669 | rs839879 | 162.269 | 0 | ITGB3BP |
| chr17:73600891-73844748 | 34 | 243858 | 1 | rs1624922 | rs2290771 | 19.222 | 0 | ITGB4 |
| chr17:44458950-81047708 | −8195 | 36588759 | 1 | cnvi0016818 | rs35680231 | 35.591 | 0 | ITGB4 |
| chr17:62662507-81047708 | −11496 | 18385202 | 3 | rs6504246 | rs35680231 | 56.048 | 0 | ITGB4 |
| chr3:13878889-149737330 | 24723 | 135858442 | 1 | rs12634112 | rs2007869 | 55.663 | 0 | ITGB5 |
| chr3:33409611-170735099 | 23775 | 137325499 | 1 | rs3915062 | rs11924032 | 26.867 | 0 | ITGB5 |
| chr3:102240202-195550366 | 17318 | 93310165 | 1 | rs1620217 | rs11711870 | 41.031 | 0 | ITGB5 |
| chr3:103140700-144883172 | 8539 | 41742473 | 1 | rs4314176 | rs6797159 | 44.122 | 0 | ITGB5 |
| chr3:83075971-196935657 | 21465 | 113859687 | 1 | rs9872858 | rs34729751 | 44.35 | 0 | ITGB5 |
| chr3:114889454-177826047 | 12700 | 62936594 | 3 | rs6795297 | rs7628308 | 102.526 | 0 | ITGB5 |
| chr12:10113083-116370432 | 20594 | 106257350 | 1 | rs2012504 | rs7958254 | 35.157 | 0 | ITGB7 |
| chr12:10020267-129866293 | 23654 | 119846027 | 1 | rs1597097 | rs2170504 | 45.428 | 0 | ITGB7 |
| chr12:39967134-84174413 | 8879 | 44207280 | 1 | rs11172661 | rs11116039 | 39.568 | 0 | ITGB7 |
| chr12:50855195-133743796 | 17748 | 82923602 | 3 | rs4351891 | rs7975049 | 159.589 | 0 | ITGB7 |
| chr15:29325866-56044189 | 5303 | 26718324 | 3 | rs4779705 | rs2414433 | 21.732 | 0 | ITPKA |
| chr15:32939946-43104406 | 2544 | 10164461 | 3 | rs12594777 | rs13380301 | 32.942 | 0 | ITPKA |
| chr1:64114301-245591329 | 29842 | 181477029 | 1 | rs11208257 | rs1173850 | 37.504 | 0 | ITPKB |
| chr1:178626526-244159143 | 13064 | 65532618 | 3 | rs2761471 | rs479338 | 11.373 | 0 | ITPKB |
| chr1:75098453-243531649 | 27360 | 168433197 | 1 | rs12117493 | rs10927002 | 32.113 | 0 | ITPKB |
| chr1:188850774-235423607 | 10060 | 46572834 | 1 | rs16829466 | rs12409696 | 43.25 | 0 | ITPKB |
| chr1:191875752-235423607 | 9517 | 43547856 | 1 | rs9427811 | rs12409696 | 62.01 | 0 | ITPKB |
| chr1:189128124-227340790 | 7927 | 38212670 | 1 | rs7515205 | rs12752546 | 167.428 | 0 | ITPKB |
| chr1:174219398-247422297 | 15986 | 73202900 | 1 | rs16846809 | rs4642922 | 35.258 | 0 | ITPKB |
| chr1:226423572-227452700 | 215 | 1029129 | 1 | rs66605032 | rs1969230 | 24.875 | 0 | ITPKB |
| chr1:226536645-236803753 | 2600 | 10267109 | 3 | rs874583 | rs10925178 | 100.109 | 0 | ITPKB |
| chr3:3748218-4590681 | 268 | 842464 | 1 | rs901050 | rs6802929 | 33.083 | 0 | ITPR1 |
| chr3:234726-6328081 | 2293 | 6093356 | 3 | rs7632811 | rs1595039 | 106.207 | 0 | ITPR1 |
| chr3:179527-114630641 | 23879 | 114451115 | 3 | rs4684741 | rs1587972 | 207.852 | 0 | ITPR1 |
| chr6:26922906-93578359 | 19746 | 66655454 | 1 | rs9348738 | rs9363009 | 27.061 | 0 | ITPR3 |
| chr6:31289284-56929863 | 15402 | 25640580 | 3 | rs9265170 | cnvi0015437 | 25.647 | 0 | ITPR3 |
| chr6:32968276-73449742 | 15442 | 40481447 | 3 | rs2395300 | rs4235869 | 415.87 | 0 | ITPR3 |
| chr1:64114301-245591329 | 29842 | 181477029 | 1 | rs11208257 | rs1173850 | 37.504 | 0 | JAK1 |
| chr1:1005806-105612342 | 19173 | 104606537 | 3 | rs3934834 | rs1584633 | 44.152 | 0 | JAK1 |
| chr1:2006108-109527861 | 22130 | 107521754 | 3 | rs2254669 | rs839879 | 162.269 | 0 | JAK1 |
| chr21:14601415-48084989 | 8249 | 33483575 | 3 | rs2775537 | rs2839378 | 12047.211 | 0 | KCNE1 |
| chr21:14601415-48084989 | 8249 | 33483575 | 3 | rs2775537 | rs2839378 | 41.154 | 0 | KCNE1 |
| chr21:14768343-48084989 | 8193 | 33316647 | 3 | rs2257224 | rs2839378 | 5021.076 | 0 | KCNE1 |
| chr21:14601415-48084989 | 8249 | 33483575 | 3 | rs2775537 | rs2839378 | 4787.438 | 0 | KCNE1 |
| chr21:14595264-48084989 | 8781 | 33489726 | 3 | rs2847443 | rs2839378 | 1871.363 | 0 | KCNE1 |
| chr21:10708231-47970581 | 8807 | 37262351 | 3 | rs4044122 | rs2255397 | 73.188 | 0 | KCNE1 |
| chr2:12056323-227979775 | 39094 | 215923453 | 1 | rs966391 | rs1922020 | 31.384 | 0 | KCNE4 |
| chr2:34870277-241929621 | 37755 | 207059345 | 3 | rs13422005 | rs10205276 | 46.946 | 0 | KCNE4 |
| chr2:38101137-241482099 | 36812 | 203380963 | 1 | rs879321 | rs7576043 | 52.099 | 0 | KCNE4 |
| chr2:193255360-242529978 | 10289 | 49274619 | 3 | rs1351905 | cnvi0010399 | 93.244 | 0 | KCNE4 |
| chr7:11855636-156148608 | 26852 | 144292973 | 1 | rs6947930 | rs6945016 | 36.446 | 0 | KCNH2 |
| chr7:78621315-155831817 | 13678 | 77210503 | 3 | rs1006818 | rs6969015 | 123.319 | 0 | KCNH2 |
| chr7:8872727-156383359 | 27773 | 147510633 | 1 | rs917038 | rs878717 | 32.336 | 0 | KCNH2 |
| chr7:143807304-158827326 | 3603 | 15020023 | 3 | rs10252253 | rs2071624 | 54.584 | 0 | KCNH2 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr17:44458950-81047708 | −8195 | 36588759 | 1 | cnvi0016818 | rs35680231 | 35.591 | 0 | KCNJ2 |
| chr17:62662507-81047708 | −11496 | 18385202 | 3 | rs6504246 | rs35680231 | 56.048 | 0 | KCNJ2 |
| chr5:84830796-171903310 | 16642 | 87072515 | 1 | rs300657 | rs10042482 | 42.208 | 0 | KCNN2 |
| chr5:108979318-132114847 | 4575 | 23135530 | 1 | rs31595 | rs30514 | 35.063 | 0 | KCNN2 |
| chr5:57343495-171903310 | 21683 | 114559816 | 1 | rs10940593 | rs10042482 | 61.169 | 0 | KCNN2 |
| chr5:98442871-150317237 | 9828 | 51874367 | 1 | rs1447379 | rs7710790 | 38.687 | 0 | KCNN2 |
| chr5:80735161-125293366 | 8499 | 44558206 | 1 | rs1541830 | rs327816 | 52.167 | 0 | KCNN2 |
| chr5:4872310-180709915 | 35876 | 175837606 | 3 | rs816467 | rs10071993 | 179.394 | 0 | KCNN2 |
| chr19:31569338-53780966 | 3788 | 22211629 | 1 | rs2867544 | rs10407424 | 33.9 | 0 | KCNN4 |
| chr19:43257015-55294329 | −7309 | 12037315 | 3 | rs7246152 | rs2569676 | 21.402 | 0 | KCNN4 |
| chr19:288246-59110628 | 11009 | 58822383 | 3 | rs10409452 | cnvi0009466 | 100.582 | 0 | KCNN4 |
| chr20:61852629-62212928 | 57 | 360300 | 1 | rs6010873 | rs310672 | 29.152 | 0 | KCNQ2 |
| chr20:61867454-62198348 | 53 | 330895 | 1 | rs6011691 | rs438363 | 35.319 | 0 | KCNQ2 |
| chr20:7869025-62424661 | 11941 | 54555637 | 3 | rs2294306 | rs6010652 | 9.732 | 0 | KCNQ2 |
| chr20:54870769-62912463 | 2390 | 8041695 | 3 | rs6069696 | rs6062363 | 249.708 | 0 | KCNQ2 |
| chr8:30757798-142750969 | 20699 | 111993172 | 1 | rs10101203 | rs6421025 | 34.223 | 0 | KCNQ3 |
| chr8:60424884-145286483 | 17030 | 84861600 | 3 | rs1401422 | rs9720889 | 8.858 | 0 | KCNQ3 |
| chr8:130808973-134279601 | 923 | 3470692 | 3 | rs7823788 | rs2976574 | 37.758 | 0 | KCNQ3 |
| chr8:23218101-146274708 | 23020 | 123056608 | 1 | rs7010362 | rs7822726 | 38.828 | 0 | KCNQ3 |
| chr8:66822030-144791126 | 16557 | 77969097 | 3 | rs6472235 | rs10100154 | 251.068 | 0 | KCNQ3 |
| chr6:64844594-169078546 | 21567 | 104233953 | 1 | rs4710465 | rs601639 | 46.524 | 0 | KCNQ5 |
| chr6:66609532-147053632 | 15315 | 80444101 | 3 | rs9354335 | rs4896886 | 44.941 | 0 | KCNQ5 |
| chr6:73120320-165130872 | 18715 | 92010553 | 1 | rs9442780 | rs10946016 | 76.383 | 0 | KCNQ5 |
| chr6:26922906-93578359 | 19746 | 66655454 | 1 | rs9348738 | rs9363009 | 27.061 | 0 | KCNQ5 |
| chr6:66541198-162520133 | 19344 | 95978936 | 1 | rs2000382 | rs6901071 | 27.509 | 0 | KCNQ5 |
| chr6:62697746-94090076 | 6391 | 31392331 | 1 | rs6455128 | rs3799800 | 108.85 | 0 | KCNQ5 |
| chr6:67621368-147709180 | 16188 | 80087813 | 1 | rs6919455 | rs7739314 | 52.498 | 0 | KCNQ5 |
| chr6:73376868-73489110 | 34 | 112243 | 1 | rs12194741 | rs7740606 | 24.362 | 0 | KCNQ5 |
| chr6:32968276-73449742 | 15442 | 40481467 | 3 | rs2395300 | rs4235869 | 415.87 | 0 | KCNQ5 |
| chr6:73478625-75558759 | 448 | 2080251 | 3 | rs7775641 | rs9293982 | 54.62 | 0 | KCNQ5 |
| chr4:31222833-180548076 | 24457 | 149325244 | 1 | rs7662351 | rs3849606 | 36.162 | 0 | KDR |
| chr4:39472311-63464732 | 3456 | 23992422 | 3 | rs2687975 | rs4403080 | 120.672 | 0 | KDR |
| chr4:22401728-188608857 | 28456 | 166207130 | 1 | rs4697297 | rs7687115 | 35.717 | 0 | KDR |
| chr4:29179713-117038307 | 15513 | 87858595 | 1 | rs1507441 | rs1068807 | 71.6 | 0 | KDR |
| chr4:179131-68998153 | 13495 | 68819023 | 3 | rs7686948 | rs7687396 | 625.133 | 0 | KDR |
| chr1:1005806-105612342 | 19173 | 104606537 | 3 | rs3934834 | rs1584633 | 44.152 | 0 | KIAA0090 |
| chr1:2006108-109527861 | 22130 | 107521754 | 3 | rs2254669 | rs839879 | 162.269 | 0 | KIAA0090 |
| chr11:42185849-126756938 | 15451 | 84571090 | 1 | rs4375424 | rs10750356 | 36.99 | 0 | KIAA1377 |
| chr11:81251505-103237429 | 4842 | 21983225 | 3 | rs7935232 | rs1913462 | 26.176 | 0 | KIAA1377 |
| chr11:84128537-120941583 | 7678 | 36813047 | 1 | rs488925 | rs4643089 | 29.271 | 0 | KIAA1377 |
| chr11:21723471-131521797 | 20508 | 109798327 | 1 | rs11828478 | rs2512898 | 27.565 | 0 | KIAA1377 |
| chr11:98062720-121890280 | 5422 | 23827561 | 3 | rs6589308 | rs1944465 | 29.075 | 0 | KIAA1377 |
| chr11:23168804-106781292 | 16332 | 83612489 | 1 | rs11027007 | rs7103285 | 49.747 | 0 | KIAA1377 |
| chr11:74545378-134940416 | 14496 | 60395039 | 3 | rs512780 | rs11224228 | 527.758 | 0 | KIAA1377 |
| chr7:11855636-156148608 | 26852 | 144292973 | 1 | rs6947930 | rs6945016 | 36.446 | 0 | KIAA1549 |
| chr7:78621315-155831817 | 13678 | 77210503 | 3 | rs1006818 | rs6969015 | 123.319 | 0 | KIAA1549 |
| chr7:8872727-156383559 | 27773 | 147510623 | 1 | rs917038 | rs878717 | 32.336 | 0 | KIAA1549 |
| chr7:120061880-143606234 | 4616 | 23544355 | 3 | rs12531689 | rs10247493 | 18.96 | 0 | KIAA1549 |
| chr19:288246-59110628 | 11009 | 58822383 | 3 | rs10409452 | cnvi0009466 | 100.582 | 0 | KIAA1683 |
| chr5:84830796-171903310 | 16642 | 87072515 | 1 | rs300657 | rs10042482 | 42.208 | 0 | KIF3A |
| chr5:108979318-132114847 | 4575 | 23135530 | 1 | rs31595 | rs30514 | 35.063 | 0 | KIF3A |
| chr5:57343495-171903310 | 21683 | 114559816 | 1 | rs10940593 | rs10042482 | 61.169 | 0 | KIF3A |
| chr5:98442871-150317237 | 9828 | 51874367 | 1 | rs1447379 | rs7710790 | 38.687 | 0 | KIF3A |
| chr5:4872310-180709915 | 35876 | 175837606 | 3 | rs816467 | rs10071993 | 179.394 | 0 | KIF3A |
| chr4:31222833-180548076 | 24457 | 149325244 | 1 | rs7662351 | rs3849606 | 36.162 | 0 | KIT |
| chr4:39472311-63464732 | 3456 | 23992422 | 3 | rs2687975 | rs4403080 | 120.672 | 0 | KIT |
| chr4:22401728-188608857 | 28456 | 166207130 | 1 | rs4697297 | rs7687115 | 35.717 | 0 | KIT |
| chr4:29179713-117038307 | 15513 | 87858595 | 1 | rs1507441 | rs1068807 | 71.6 | 0 | KIT |
| chr4:179131-68998153 | 13495 | 68819023 | 3 | rs7686948 | rs7687396 | 625.133 | 0 | KIT |
| chr1:64114301-245591329 | 29842 | 181477029 | 1 | rs11208257 | rs1173850 | 37.504 | 0 | KLHL20 |
| chr1:75098453-243531649 | 27360 | 168433197 | 1 | rs12117493 | rs10927002 | 32.113 | 0 | KLHL20 |
| chr1:79710545-188898319 | 17303 | 109187775 | 1 | rs417181 | rs16829637 | 45.89 | 0 | KLHL20 |
| chr1:109645793-194560463 | 12025 | 84914671 | 3 | cnvi0008281 | rs10921616 | 63.121 | 0 | KLHL20 |
| chr5:84830796-171903310 | 16642 | 87072515 | 1 | rs300657 | rs10042482 | 42.208 | 0 | KLHL3 |
| chr5:57343495-171903310 | 21683 | 114559816 | 1 | rs10940593 | rs10042482 | 61.169 | 0 | KLHL3 |
| chr5:98442871-150317237 | 9828 | 51874367 | 1 | rs1447379 | rs7710790 | 38.687 | 0 | KLHL3 |
| chr5:4872310-180709915 | 35876 | 175837606 | 3 | rs816467 | rs10071993 | 179.394 | 0 | KLHL3 |
| chr19:31569338-53780966 | 3788 | 22211629 | 1 | rs2867544 | rs10407424 | 33.9 | 0 | KLK10 |
| chr19:43257015-55294329 | −7309 | 12037315 | 3 | rs7246152 | rs2569676 | 21.402 | 0 | KLK10 |
| chr19:288246-59110628 | 11009 | 58822383 | 3 | rs10409452 | cnvi0009466 | 100.582 | 0 | KLK10 |
| chr12:25264259-25401822 | 40 | 137564 | 1 | rs17387019 | rs4368021 | 16.172 | 0 | KRAS |
| chr12:10113083-116370432 | 20594 | 106257193 | 1 | rs2012504 | rs7958254 | 35.157 | 0 | KRAS |
| chr12:8171838-32535863 | 5853 | 24364026 | 3 | rs11609309 | rs7963182 | 23.697 | 0 | KRAS |
| chr12:10020267-129866293 | 23654 | 119846027 | 1 | rs1597097 | rs2170504 | 45.428 | 0 | KRAS |
| chr12:25264259-25397282 | 37 | 133024 | 1 | rs17387019 | rs17389103 | 24.756 | 0 | KRAS |
| chr12:207886-50770291 | 11565 | 50562406 | 3 | rs868249 | rs4477515 | 43.892 | 0 | KRAS |
| chr17:21685812-67308196 | 12365 | 45622385 | 1 | rs34864328 | rs17686852 | 50.018 | 0 | KRT10 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr17:38899411-39347296 | 80 | 447886 | 1 | rs7220877 | rs7214006 | 23.174 | 0 | KRT10 |
| chr17:26648492-58955084 | 5831 | 32306593 | 3 | rs1981512 | rs8068776 | 15.642 | 0 | KRT10 |
| chr12:10113083-116370432 | 20594 | 106257350 | 1 | rs2012504 | rs7958254 | 35.157 | 0 | KRT18 |
| chr12:10020267-129866293 | 23654 | 119846027 | 1 | rs1597097 | rs2170504 | 45.428 | 0 | KRT18 |
| chr12:39967134-84174413 | 8879 | 44207280 | 1 | rs11172661 | rs11116039 | 39.568 | 0 | KRT18 |
| chr12:50855195-133778796 | 17748 | 82923602 | 3 | rs4351895 | rs7975069 | 159.589 | 0 | KRT18 |
| chr6:64844594-169078546 | 21567 | 104233953 | 1 | rs4710465 | rs601639 | 46.524 | 0 | LAMA4 |
| chr6:66609532-147053632 | 15315 | 80444101 | 3 | rs9354335 | rs4896886 | 44.941 | 0 | LAMA4 |
| chr6:73120320-165130872 | 18715 | 92010553 | 1 | rs9442780 | rs10946016 | 76.383 | 0 | LAMA4 |
| chr6:66541198-162520133 | 19344 | 95978936 | 1 | rs2000382 | rs6901071 | 27.509 | 0 | LAMA4 |
| chr6:94117546-165103679 | 15579 | 70986134 | 1 | rs3799792 | rs9347902 | 34.066 | 0 | LAMA4 |
| chr6:67621368-147709180 | 16188 | 80087813 | 1 | rs6919455 | rs7739314 | 52.498 | 0 | LAMA4 |
| chr6:100082983-170909002 | 16393 | 70826020 | 3 | rs594231 | rs12213906 | 261.313 | 0 | LAMA4 |
| chr1:1005806-105612342 | 19173 | 104606537 | 3 | rs3934834 | rs1584633 | 44.152 | 0 | LCK |
| chr1:2006108-109527861 | 22130 | 107521754 | 3 | rs2254669 | rs839879 | 162.269 | 0 | LCK |
| chr22:16871137-51184393 | 9245 | 34313257 | 3 | rs131538 | rs7284680 | 209.79 | 0 | LGALS2 |
| chr1:64114301-245591329 | 29842 | 181477029 | 1 | rs11208257 | rs1173850 | 37.504 | 0 | LMNA |
| chr1:75098453-243531649 | 27360 | 168433197 | 1 | rs12117493 | rs10927002 | 32.113 | 0 | LMNA |
| chr1:79710545-188898319 | 17303 | 109187775 | 1 | rs417181 | rs16829637 | 45.89 | 0 | LMNA |
| chr1:109645793-194560463 | 12025 | 84914671 | 3 | cnvi0008281 | rs10921616 | 63.121 | 0 | LMNA |
| chr5:84830796-171903310 | 16642 | 87072515 | 1 | rs300657 | rs10042482 | 42.208 | 0 | LMNB1 |
| chr5:108979318-132114847 | 4575 | 23135530 | 1 | rs31595 | rs30514 | 35.063 | 0 | LMNB1 |
| chr5:57343495-171903310 | 21683 | 114559816 | 1 | rs10940593 | rs10042482 | 61.169 | 0 | LMNB1 |
| chr5:98442871-150317237 | 9828 | 51874367 | 1 | rs1447379 | rs7710790 | 38.687 | 0 | LMNB1 |
| chr5:4872310-180709915 | 35876 | 175837606 | 3 | rs816467 | rs10071993 | 179.394 | 0 | LMNB1 |
| chr8:60424884-145286483 | 17030 | 84861600 | 3 | rs1401422 | rs9720889 | 8.858 | 0 | LOC100133669 |
| chr8:23218101-146274708 | 23020 | 123056608 | 1 | rs7010362 | rs7822726 | 38.828 | 0 | LOC100133669 |
| chr8:66822030-144791126 | 16557 | 77969097 | 3 | rs6472235 | rs10100154 | 251.068 | 0 | LOC100133669 |
| chr6:64844594-169078546 | 21567 | 104233953 | 1 | rs4710465 | rs601639 | 46.524 | 0 | LOC154092 |
| chr6:66609532-147053632 | 15315 | 80444101 | 3 | rs9354335 | rs4896886 | 44.941 | 0 | LOC154092 |
| chr6:73120320-165130872 | 18715 | 92010553 | 1 | rs9442780 | rs10946016 | 76.383 | 0 | LOC154092 |
| chr6:66541198-162520133 | 19344 | 95978936 | 1 | rs2000382 | rs6901071 | 27.509 | 0 | LOC154092 |
| chr6:94117546-165103679 | 15579 | 70986134 | 1 | rs3799792 | rs9347902 | 34.066 | 0 | LOC154092 |
| chr6:67621368-147709180 | 16188 | 80087813 | 1 | rs6919455 | rs7739314 | 52.498 | 0 | LOC154092 |
| chr6:100082983-170909002 | 16393 | 70826020 | 3 | rs594231 | rs12213906 | 261.313 | 0 | LOC154092 |
| chr18:1583633-58142042 | 11490 | 56558410 | 3 | rs9945988 | rs1560399 | 3.736 | 0 | LOC339290 |
| chr18:10274-30780701 | 6393 | 30770428 | 3 | cnvi0008694 | rs271534 | 338.777 | 0 | LOC339290 |
| chr8:2365648-32608792 | 10334 | 30243145 | 3 | rs2100623 | rs3757934 | 31.188 | 0 | LOC340357 |
| chr8:11876689-15051158 | 1245 | 3174470 | 1 | rs10096955 | rs7840505 | 32.747 | 0 | LOC340357 |
| chr8:62041-25061807 | 9818 | 24999767 | 3 | rs4710857 | rs1510758 | 96.736 | 0 | LOC340357 |
| chr17:44458950-81047708 | −8195 | 36588759 | 1 | cnvi0016818 | rs35680231 | 35.591 | 0 | LOC400604 |
| chr17:21685812-67308196 | 12365 | 45622385 | 1 | rs34864328 | rs17686852 | 50.018 | 0 | LOC400604 |
| chr17:26648492-58955084 | 5831 | 32306593 | 3 | rs1981512 | rs8068776 | 15.642 | 0 | LOC400604 |
| chr4:163766726-189931630 | 5627 | 26164905 | 3 | rs10033012 | rs10018868 | 25.326 | 0 | LRP2BP |
| chr4:22401728-188608857 | 28456 | 166207130 | 1 | rs4697297 | rs7687115 | 35.717 | 0 | LRP2BP |
| chr4:162592024-189861553 | 6129 | 27269530 | 1 | rs5005966 | rs6853039 | 63.501 | 0 | LRP2BP |
| chr4:69590353-190827789 | 23145 | 121282426 | 3 | rs293433 | rs12646565 | 315.633 | 0 | LRP2BP |
| chr17:44458950-81047708 | −8195 | 36588759 | 1 | cnvi0016818 | rs35680231 | 35.591 | 0 | LRRC59 |
| chr17:21685812-67308196 | 12365 | 45622385 | 1 | rs34864328 | rs17686852 | 50.018 | 0 | LRRC59 |
| chr17:26648492-58955084 | 5831 | 32306593 | 3 | rs1981512 | rs8068776 | 15.642 | 0 | LRRC59 |
| chr6:26922906-93578454 | 19746 | 66655476 | 1 | rs9348738 | rs9363009 | 27.061 | 0 | LTA |
| chr6:31289284-32512613 | 10001 | 1223330 | 3 | rs9265170 | rs35571839 | 45.035 | 0 | LTA |
| chr6:3760708-31957364 | 8062 | 28196657 | 3 | rs2187825 | cnvi0006380 | 39.016 | 0 | LTA |
| chr6:31281438-32449411 | −7879 | 1167974 | 1 | cnvi0006173 | rs1964995 | 24.023 | 0 | LTA |
| chr6:31337633-32449411 | 1650 | 1111779 | 1 | rs9266433 | rs1964995 | 124.395 | 0 | LTA |
| chr6:31281438-32354428 | −8033 | 1072991 | 1 | cnvi0006173 | rs4424066 | 37.329 | 0 | LTA |
| chr6:31289284-31960770 | 9811 | 671487 | 3 | rs9265170 | cnvi0006385 | 29.628 | 0 | LTA |
| chr6:31281438-32874796 | −7311 | 1593359 | 1 | cnvi0006173 | rs9469310 | 36.913 | 0 | LTA |
| chr6:26430981-31878493 | −8001 | 5447453 | 1 | rs2893848 | rs519417 | 55.651 | 0 | LTA |
| chr6:29253756-32671521 | 2267 | 3417766 | 1 | rs9468508 | rs9275439 | 51.553 | 0 | LTA |
| chr6:31289284-56929863 | 15402 | 25640580 | 3 | rs9265170 | cnvi0015437 | 25.647 | 0 | LTA |
| chr6:30475431-32449411 | −7687 | 1973981 | 3 | cnvi0005997 | rs1964995 | 153.275 | 0 | LTA |
| chr14:22513116-32242747 | 1997 | 9729632 | 1 | rs4982546 | rs17098165 | 31.673 | 0 | LTB4R |
| chr14:22349686-25012116 | 755 | 2662430 | 1 | rs994827 | rs7142675 | 27.602 | 0 | LTB4R |
| chr14:19917123-65327288 | 10286 | 45410166 | 3 | rs2495197 | rs9323455 | 270.291 | 0 | LTB4R |
| chr3:13878889-149737330 | 24723 | 135858442 | 1 | rs12634112 | rs2007869 | 55.663 | 0 | LTF |
| chr3:33409611-170735099 | 23775 | 137325489 | 1 | rs3915062 | rs11924032 | 26.867 | 0 | LTF |
| chr3:179527-114630466 | 23879 | 114451115 | 3 | rs4684741 | rs1587972 | 207.852 | 0 | LTF |
| chr3:157117977-158675961 | 280 | 1557985 | 1 | rs1840673 | rs1112930 | 71.366 | 0 | LXN |
| chr3:145967173-173899890 | 4912 | 27932718 | 3 | rs9863647 | rs7618997 | 46.396 | 0 | LXN |
| chr3:33409611-170735099 | 23775 | 137325489 | 1 | rs3915062 | rs11924032 | 26.867 | 0 | LXN |
| chr3:102240202-195550366 | 17318 | 93310165 | 1 | rs1620217 | rs11711870 | 41.031 | 0 | LXN |
| chr3:83075971-196935657 | 21465 | 113859687 | 1 | rs9872858 | rs34729751 | 44.35 | 0 | LXN |
| chr3:114889454-177896047 | 12700 | 62936594 | 3 | rs6795297 | rs7628308 | 102.526 | 0 | LXN |
| chr4:179131-68998153 | 13495 | 68819023 | 3 | rs7686948 | rs7687396 | 625.133 | 0 | LYAR |
| chr8:56843930-57035027 | 38 | 191098 | 1 | rs10091244 | rs4386955 | 14.478 | 0 | LYN |
| chr8:30757798-142750969 | 20699 | 111993172 | 1 | rs10101203 | rs6421025 | 34.223 | 0 | LYN |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr8:56706994-56851419 | 31 | 144426 | 3 | rs2316972 | rs1126327 | 1.58 | 0 | LYN |
| chr8:23218101-146274708 | 23020 | 123056608 | 1 | rs7010362 | rs7822726 | 38.828 | 0 | LYN |
| chr8:43235525-66712108 | 3632 | 23476584 | 3 | rs10091311 | rs7001138 | 58.838 | 0 | LYN |
| chr1:64114301-245591329 | 29842 | 181477029 | 1 | rs11208257 | rs1173850 | 37.504 | 0 | LYST |
| chr1:178626526-244159143 | 13064 | 65532618 | 3 | rs2761477 | rs479338 | 11.373 | 0 | LYST |
| chr1:236039174-236265665 | 54 | 226492 | 4 | rs17714318 | rs16833290 | 11.648 | 0 | LYST |
| chr1:75098453-243531649 | 27360 | 168433197 | 1 | rs12117493 | rs10927002 | 32.113 | 0 | LYST |
| chr1:235832555-236429953 | 113 | 597399 | 1 | rs11810173 | rs1254188 | 31.543 | 0 | LYST |
| chr1:174219398-247422297 | 15986 | 73202900 | 1 | rs16846809 | rs4642922 | 35.258 | 0 | LYST |
| chr1:226536645-236803753 | 2600 | 10267109 | 3 | rs874583 | rs10925178 | 100.109 | 0 | LYST |
| chr6:26922906-93578359 | 19746 | 66655454 | 1 | rs9348738 | rs9363009 | 27.061 | 0 | MAD2L1BP |
| chr6:31289284-56929863 | 15402 | 25640580 | 3 | rs9265170 | cnvi0015437 | 25.647 | 0 | MAD2L1BP |
| chr6:32968276-73449742 | 15442 | 40481467 | 3 | rs2395300 | rs4235869 | 415.87 | 0 | MAD2L1BP |
| chr5:29325866-56044189 | 5303 | 26718324 | 3 | rs4779705 | rs2414433 | 21.732 | 0 | MAP1A |
| chr15:43614724-43836478 | 29 | 221755 | 1 | rs488756 | rs2251844 | 14.185 | 0 | MAP1A |
| chr15:43392075-66051345 | 4963 | 22659271 | 3 | rs8028608 | rs6494537 | 59.842 | 0 | MAP1A |
| chr20:13712393-55093901 | 8218 | 41381509 | 1 | rs6033810 | rs6999 | 41.237 | 0 | MAP1LC3A |
| chr20:7869025-62424661 | 11941 | 54555637 | 3 | rs2294306 | rs6010652 | 9.732 | 0 | MAP1LC3A |
| chr20:4591715-58420336 | 11753 | 53828622 | 1 | rs6139494 | rs1416388 | 40.922 | 0 | MAP1LC3A |
| chr20:236802-54845796 | 12646 | 54608995 | 3 | rs448294 | rs6064362 | 286.151 | 0 | MAP1LC3A |
| chr15:51688996-102398060 | 11030 | 50709065 | 1 | rs2459396 | rs7181527 | 36.939 | 0 | MAP2K1 |
| chr15:53775670-96810867 | 9973 | 43035198 | 1 | rs657495 | rs2589238 | 49.204 | 0 | MAP2K1 |
| chr15:66108544-102427006 | 8615 | 36318463 | 3 | cnvi0007613 | rs11632620 | 159.164 | 0 | MAP2K1 |
| chr17:108420-26610769 | 5548 | 26502350 | 3 | rs12452527 | rs658591 | 82.699 | 0 | MAP2K4 |
| chr15:51688996-102398060 | 11030 | 50709065 | 1 | rs2459396 | rs7181527 | 36.939 | 0 | MAP2K5 |
| chr15:67505066-68012403 | 39 | 507338 | 1 | rs7169664 | rs4502166 | 30.191 | 0 | MAP2K5 |
| chr15:53775670-96810867 | 9973 | 43035198 | 1 | rs657495 | rs2589238 | 49.204 | 0 | MAP2K5 |
| chr15:66108544-102427006 | 8615 | 36318463 | 3 | cnvi0007613 | rs11632620 | 159.164 | 0 | MAP2K5 |
| chr19:31569338-53780966 | 3788 | 22211629 | 1 | rs2867544 | rs10407424 | 33.9 | 0 | MAP3K10 |
| chr19:288246-59110628 | 11009 | 58822383 | 3 | rs10409452 | cnvi0009466 | 100.582 | 0 | MAP3K10 |
| chr17:44458950-81047708 | -8195 | 36588759 | 1 | cnvi0016818 | rs35680231 | 35.591 | 0 | MAP3K3 |
| chr17:21685812-67308196 | 12365 | 45622385 | 1 | rs34864328 | rs17686852 | 50.018 | 0 | MAP3K3 |
| chr17:61016209-66240093 | 890 | 5223885 | 1 | rs1588368 | rs11658645 | 37.309 | 0 | MAP3K3 |
| chr17:59314257-66170047 | 1135 | 6855791 | 1 | rs758467 | rs4558468 | 71.379 | 0 | MAP3K3 |
| chr17:59205829-62530143 | 453 | 3324315 | 3 | rs7222210 | rs9897203 | 107.455 | 0 | MAP3K3 |
| chr6:64844594-169078546 | 21567 | 104233953 | 1 | rs4710465 | rs601639 | 46.524 | 0 | MAP3K7 |
| chr6:66609532-147053632 | 15315 | 80444101 | 3 | rs9354335 | rs4896886 | 44.941 | 0 | MAP3K7 |
| chr6:73120320-165130872 | 18715 | 92010553 | 1 | rs9442780 | rs10946016 | 76.383 | 0 | MAP3K7 |
| chr6:26922906-93578359 | 19746 | 66655454 | 1 | rs9348738 | rs9363009 | 27.061 | 0 | MAP3K7 |
| chr6:66541198-162520133 | 19344 | 95978936 | 1 | rs2000382 | rs6901071 | 27.509 | 0 | MAP3K7 |
| chr6:62697746-94090076 | 6391 | 31392331 | 1 | rs6455128 | rs3799807 | 108.85 | 0 | MAP3K7 |
| chr6:67621368-147709180 | 16188 | 80087813 | 1 | rs6919455 | rs7739314 | 52.498 | 0 | MAP3K7 |
| chr6:79198069-99893938 | 4062 | 20695870 | 3 | rs1321584 | rs4504482 | 200.961 | 0 | MAP3K7 |
| chr10:7188484-134205354 | 26672 | 127016871 | 1 | rs1977295 | rs3923858 | 50.772 | 0 | MAP3K8 |
| chr10:734229-69155636 | 14859 | 68421408 | 3 | rs1769236 | rs2394375 | 72.104 | 0 | MAP3K8 |
| chr10:88874-53366180 | 12853 | 53277307 | 3 | cnvi0015449 | rs10998465 | 319.021 | 0 | MAP3K8 |
| chr3:13878889-149737330 | 24723 | 135858442 | 1 | rs12634112 | rs2007869 | 55.663 | 0 | MAP4 |
| chr3:33409611-170735099 | 23775 | 137325489 | 1 | rs3915062 | rs11924032 | 26.867 | 0 | MAP4 |
| chr3:179527-114630641 | 23879 | 114451115 | 3 | rs4684741 | rs15587972 | 207.852 | 0 | MAP4 |
| chr11:42185849-126756938 | 15451 | 84571090 | 1 | rs4375424 | rs10750356 | 36.99 | 0 | MAP6 |
| chr11:21723471-131521797 | 20508 | 109798321 | 1 | rs11828478 | rs2512898 | 27.565 | 0 | MAP6 |
| chr11:23168804-106781292 | 16332 | 83612489 | 1 | rs11027007 | rs7103285 | 49.747 | 0 | MAP6 |
| chr11:74545378-134940416 | 14496 | 60395039 | 3 | rs512780 | rs11224228 | 527.758 | 0 | MAP6 |
| chr22:16871137-51184393 | 9245 | 34313257 | 3 | rs131538 | rs7284680 | 209.79 | 0 | MAPK1 |
| chr6:26922906-93578359 | 19746 | 66655454 | 1 | rs9348738 | rs9363009 | 27.061 | 0 | MAPK14 |
| chr6:31289284-56929863 | 15402 | 25640580 | 3 | rs9265170 | cnvi0015437 | 25.647 | 0 | MAPK14 |
| chr6:32968276-73449742 | 15442 | 40481467 | 3 | rs2395300 | rs4235869 | 415.87 | 0 | MAPK14 |
| chr16:29441284-33923125 | 585 | 4481842 | 3 | rs7206789 | rs4043755 | 42.437 | 0 | MAPK3 |
| chr16:176743-50013961 | 8328 | 49837225 | 3 | rs2562164 | rs12597023 | 174.392 | 0 | MAPK3 |
| chr17:43657921-44354796 | 88 | 696876 | 3 | rs9898857 | rs2732700 | 21.196 | 0 | MAPT |
| chr17:43657921-44064851 | 65 | 406931 | 3 | rs9898857 | rs8079215 | 86.447 | 0 | MAPT |
| chr17:21685812-67308196 | 12365 | 45622385 | 1 | rs34864328 | rs17686852 | 50.018 | 0 | MAPT |
| chr17:26648492-58955084 | 5831 | 32306593 | 3 | rs1981512 | rs8068776 | 15.642 | 0 | MAPT |
| chr6:64844594-169078546 | 21567 | 104233953 | 1 | rs4710465 | rs601639 | 46.524 | 0 | MARCKS |
| chr6:66609532-147053632 | 15315 | 80444101 | 3 | rs9354335 | rs4896886 | 44.941 | 0 | MARCKS |
| chr6:73120320-165130872 | 18715 | 92010553 | 1 | rs9442780 | rs10946016 | 76.383 | 0 | MARCKS |
| chr6:66541198-162520133 | 19344 | 95978936 | 1 | rs2000382 | rs6901071 | 27.509 | 0 | MARCKS |
| chr6:94117546-165103679 | 15579 | 70986134 | 1 | rs3799792 | rs9347902 | 34.066 | 0 | MARCKS |
| chr6:67621368-147709180 | 16188 | 80087813 | 1 | rs6919455 | rs7739314 | 52.498 | 0 | MARCKS |
| chr6:100082983-170909002 | 16393 | 70826020 | 3 | rs594231 | rs12213906 | 261.313 | 0 | MARCKS |
| chr19:31569338-53780966 | 3788 | 22211629 | 1 | rs2867544 | rs10407424 | 33.9 | 0 | MARK4 |
| chr19:43257015-55294329 | -7309 | 12037315 | 3 | rs7246152 | rs2569676 | 21.402 | 0 | MARK4 |
| chr19:288246-59110628 | 11009 | 58822383 | 3 | rs10409452 | cnvi0009466 | 100.582 | 0 | MARK4 |
| chr18:25388300-75954881 | 11539 | 50566582 | 1 | rs11083228 | rs1876021 | 39.235 | 0 | MBP |
| chr18:62041997-76047493 | 3846 | 14005497 | 1 | rs1421538 | rs8085865 | 33.212 | 0 | MBP |
| chr18:44788908-78015180 | 8492 | 33226273 | 3 | rs9944807 | rs12960632 | 579.2 | 0 | MBP |
| chr18:25388300-75954881 | 11539 | 50566582 | 1 | rs11083228 | rs1876021 | 39.235 | 0 | MC4R |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr18:1583633-58142042 | 11490 | 56558410 | 3 | rs9945988 | rs1560399 | 3.736 | 0 | MC4R |
| chr18:46516210-68441007 | 5088 | 21924798 | 1 | rs7229153 | rs1282652 | 51.891 | 0 | MC4R |
| chr18:26550830-63713914 | 8241 | 37163085 | 1 | rs16945738 | rs2715304 | 17.922 | 0 | MC4R |
| chr18:26162481-67193217 | 9255 | 41030737 | 1 | rs12458903 | rs9961907 | 31.327 | 0 | MC4R |
| chr18:44788908-78015180 | 8492 | 33226273 | 3 | rs9944807 | rs12960632 | 579.2 | 0 | MC4R |
| chr5:84830796-171903310 | 16642 | 87072515 | 1 | rs300657 | rs10042482 | 42.208 | 0 | MCC |
| chr5:108979318-132114847 | 4575 | 23135530 | 1 | rs31595 | rs30514 | 35.063 | 0 | MCC |
| chr5:57343495-171903310 | 21683 | 114559816 | 1 | rs10940593 | rs10042482 | 61.169 | 0 | MCC |
| chr5:98442871-150317237 | 9828 | 51874367 | 1 | rs1447379 | rs7710790 | 38.687 | 0 | MCC |
| chr5:80735161-125293366 | 8499 | 44558206 | 1 | rs1541830 | rs327816 | 52.167 | 0 | MCC |
| chr5:4872310-180709915 | 35876 | 175837606 | 3 | rs816467 | rs10071993 | 179.394 | 0 | MCC |
| chr10:7188484-134205354 | 26672 | 127016871 | 1 | rs1977295 | rs3923858 | 50.772 | 0 | MGMT |
| chr10:124668629-135157955 | 2949 | 10489327 | 3 | rs11248331 | rs10776672 | 23.553 | 0 | MGMT |
| chr10:57671424-133349223 | 16243 | 75677800 | 1 | rs11005106 | rs4301710 | 37.114 | 0 | MGMT |
| chr10:53602190-135522754 | 19167 | 81920565 | 3 | rs12247820 | rs10909028 | 139.373 | 0 | MGMT |
| chr12:10113083-116370432 | 20594 | 106257350 | 1 | rs2012504 | rs7958254 | 35.157 | 0 | MIP |
| chr12:10020267-129866293 | 23654 | 119846027 | 1 | rs1597097 | rs2170504 | 45.428 | 0 | MIP |
| chr12:39967134-84174413 | 8879 | 44207280 | 1 | rs11172661 | rs11116039 | 39.568 | 0 | MIP |
| chr12:50855195-133778796 | 17748 | 82923602 | 3 | rs4351895 | rs7975069 | 159.589 | 0 | MIP |
| chr12:207886-50770291 | 11565 | 50562406 | 3 | rs868249 | rs4477515 | 43.892 | 0 | MLF2 |
| chr9:20322932-20430468 | 22 | 107537 | 1 | rs7048991 | rs6475430 | 13.942 | 0 | MLLT3 |
| chr9:1989033-107532317 | 18263 | 105543285 | 1 | rs7864828 | rs10820726 | 39.824 | 0 | MLLT3 |
| chr9:2522475-140068342 | 25719 | 137545868 | 3 | rs10966757 | rs4074426 | 93.386 | 0 | MLLT3 |
| chr9:12078499-29930098 | 5275 | 17851600 | 1 | rs4449884 | rs10813203 | 117.912 | 0 | MLLT3 |
| chr9:46587-94335290 | 17484 | 94288704 | 3 | rs10814410 | rs9409606 | 762.393 | 0 | MLLT3 |
| chr14:61278684-61530401 | 23 | 251718 | 1 | rs2020892 | rs4902024 | 17.437 | 0 | MNAT1 |
| chr14:26898958-104436931 | 17396 | 77537974 | 1 | rs1245195 | rs11851097 | 57.233 | 0 | MNAT1 |
| chr14:60826810-61530401 | 106 | 703592 | 1 | rs17097373 | rs4902024 | 40.432 | 0 | MNAT1 |
| chr14:19917123-65327288 | 10286 | 45410166 | 3 | rs2495197 | rs9323455 | 270.291 | 0 | MNAT1 |
| chr16:59854720-89273883 | 7609 | 29419164 | 3 | rs1373880 | rs8046156 | 31.884 | 0 | MPHOSPH6 |
| chr16:64107047-82920737 | 4544 | 18813691 | 1 | rs2319723 | rs918661 | 28.887 | 0 | MPHOSPH6 |
| chr16:50219449-89544756 | 10324 | 39325308 | 3 | rs6500298 | rs3803681 | 108.108 | 0 | MPHOSPH6 |
| chr6:26922906-93578359 | 19746 | 66655454 | 1 | rs9348738 | rs9363009 | 27.061 | 0 | MRPL14 |
| chr6:31289284-56929863 | 15402 | 25640580 | 3 | rs9265170 | cnvi0015437 | 25.647 | 0 | MRPL14 |
| chr6:32968276-73449742 | 15442 | 40481467 | 3 | rs2395300 | rs4235869 | 415.87 | 0 | MRPL14 |
| chr19:31569338-53780966 | 3788 | 22211629 | 1 | rs2867544 | rs10407424 | 33.9 | 0 | MRPS12 |
| chr19:288246-59110628 | 11009 | 58822383 | 3 | rs10409452 | cnvi0009466 | 100.582 | 0 | MRPS12 |
| chr10:7188484-134205354 | 26672 | 127016871 | 1 | rs1977295 | rs3923858 | 50.772 | 0 | MRPS16 |
| chr10:58385643-124973104 | 13625 | 66587462 | 1 | rs7920235 | rs17663304 | 36.18 | 0 | MRPS16 |
| chr10:57671424-133349223 | 16243 | 75677800 | 1 | rs11005106 | rs4301710 | 37.114 | 0 | MRPS16 |
| chr10:55492162-117205017 | 13465 | 61712856 | 1 | rs6481032 | rs1933664 | 62.56 | 0 | MRPS16 |
| chr10:53602190-135522754 | 19167 | 81920565 | 3 | rs12247820 | rs10909028 | 139.373 | 0 | MRPS16 |
| chr21:14601415-48084989 | 8249 | 33483575 | 3 | rs2775537 | rs2839378 | 12047.211 | 0 | MRPS6 |
| chr21:14601415-48084989 | 8249 | 33483575 | 3 | rs2775537 | rs2839378 | 41.154 | 0 | MRPS6 |
| chr21:14768343-48084989 | 8193 | 33316647 | 3 | rs2257224 | rs2839378 | 5021.076 | 0 | MRPS6 |
| chr21:14601415-48084989 | 8249 | 33483575 | 3 | rs2775537 | rs2839378 | 4787.438 | 0 | MRPS6 |
| chr21:14595264-48084989 | 8781 | 33489726 | 3 | rs2847443 | rs2839378 | 1871.363 | 0 | MRPS6 |
| chr21:10708231-47970581 | 8807 | 37262351 | 3 | rs4044122 | rs2255397 | 73.188 | 0 | MRPS6 |
| chr11:345515-17408630 | 4247 | 17063116 | 3 | rs11246094 | rs5215 | 30.474 | 0 | MRVI1 |
| chr11:10323478-10713432 | 111 | 389955 | 3 | rs4399321 | rs4910170 | 17.647 | 0 | MRVI1 |
| chr11:211482-66910026 | 13813 | 66699345 | 3 | rs2293168 | rs4375446 | 30.249 | 0 | MRVI1 |
| chr14:26898958-104436931 | 17396 | 77537974 | 1 | rs1245195 | rs11851097 | 57.233 | 0 | MTHFD1 |
| chr14:64926097-65063315 | 19 | 137219 | 1 | rs2281603 | rs10134770 | 14.377 | 0 | MTHFD1 |
| chr14:19917123-65327288 | 10286 | 45410166 | 3 | rs2495197 | rs9323455 | 270.291 | 0 | MTHFD1 |
| chr4:163766726-189931630 | 5627 | 26164905 | 3 | rs10033012 | rs10018868 | 25.326 | 0 | MTNR1A |
| chr4:22401728-188608857 | 28456 | 166207130 | 1 | rs4697297 | rs7687115 | 35.717 | 0 | MTNR1A |
| chr4:162592024-189861553 | 6129 | 27269530 | 1 | rs5005966 | rs6853039 | 63.501 | 0 | MTNR1A |
| chr4:69590353-190872778 | 23145 | 121282426 | 3 | rs293433 | rs12646565 | 315.633 | 0 | MTNR1A |
| chr11:42185849-126756938 | 15451 | 84571090 | 1 | rs4375424 | rs10750356 | 36.99 | 0 | MTNR1B |
| chr11:81251505-103234729 | 4842 | 21983225 | 3 | rs7935238 | rs1913294 | 26.176 | 0 | MTNR1B |
| chr11:84128537-120941583 | 7678 | 36813047 | 1 | rs488925 | rs4643089 | 29.271 | 0 | MTNR1B |
| chr11:21723471-131521797 | 20508 | 109798327 | 1 | rs11828478 | rs2512898 | 27.565 | 0 | MTNR1B |
| chr11:23168804-106781292 | 16332 | 83612489 | 1 | rs11027007 | rs7103285 | 49.747 | 0 | MTNR1B |
| chr11:74545378-134940416 | 14496 | 60395039 | 3 | rs512780 | rs11224228 | 527.758 | 0 | MTNR1B |
| chr21:14601415-48084989 | 8249 | 33483575 | 3 | rs2775537 | rs2839378 | 12047.211 | 0 | MX1 |
| chr21:14601415-48084989 | 8249 | 33483575 | 3 | rs2775537 | rs2839378 | 41.154 | 0 | MX1 |
| chr21:14768343-48084989 | 8193 | 33316647 | 3 | rs2257224 | rs2839378 | 5021.076 | 0 | MX1 |
| chr21:14601415-48084989 | 8249 | 33483575 | 3 | rs2775537 | rs2839378 | 4787.438 | 0 | MX1 |
| chr21:14595264-48084989 | 8781 | 33489726 | 3 | rs2847443 | rs2839378 | 1871.363 | 0 | MX1 |
| chr21:10708231-47970581 | 8807 | 37262351 | 3 | rs4044122 | rs2255397 | 73.188 | 0 | MX1 |
| chr8:30757798-142750969 | 20699 | 111993172 | 1 | rs10101203 | rs6421025 | 34.223 | 0 | MYC |
| chr8:60424884-145286483 | 17030 | 84861600 | 3 | rs1401422 | rs9720805 | 8.858 | 0 | MYC |
| chr8:23218101-146274708 | 23020 | 123056608 | 1 | rs7010362 | rs7822726 | 38.828 | 0 | MYC |
| chr8:66822030-144791126 | 16557 | 77969097 | 3 | rs6472235 | rs10100154 | 251.068 | 0 | MYC |
| chr12:10113083-116370432 | 20594 | 106257350 | 1 | rs2012504 | rs7958254 | 35.157 | 0 | MYF5 |
| chr12:59512781-127744939 | 13469 | 68232159 | 3 | rs908394 | rs7966946 | 20.62 | 0 | MYF5 |
| chr12:10020267-129866293 | 23654 | 119846027 | 1 | rs1597097 | rs2170504 | 45.428 | 0 | MYF5 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr12:39967134-84174413 | 8879 | 44207280 | 1 | rs11172661 | rs11116039 | 39.568 | 0 | MYF5 |
| chr12:50855195-133778796 | 17748 | 82923602 | 3 | rs4351895 | rs7975069 | 159.589 | 0 | MYF5 |
| chr12:10113083-116370432 | 20594 | 106257350 | 1 | rs2012504 | rs7958254 | 35.157 | 0 | MYF6 |
| chr12:59512781-127744939 | 13469 | 68232159 | 3 | rs908394 | rs7966946 | 20.62 | 0 | MYF6 |
| chr12:10020267-129866293 | 23654 | 119846027 | 1 | rs1597097 | rs2170504 | 45.428 | 0 | MYF6 |
| chr12:39967134-84174413 | 8879 | 44207280 | 1 | rs11172661 | rs11116039 | 39.568 | 0 | MYF6 |
| chr12:50855195-133778796 | 17748 | 82923602 | 3 | rs4351895 | rs7975069 | 159.589 | 0 | MYF6 |
| chr3:13878889-149737330 | 24723 | 135858442 | 1 | rs12634112 | rs2007869 | 55.663 | 0 | MYLK |
| chr3:33409611-170735099 | 23775 | 137325489 | 1 | rs3915062 | rs11924032 | 26.867 | 0 | MYLK |
| chr3:102240202-195550366 | 17318 | 93310165 | 1 | rs1620217 | rs11711870 | 41.031 | 0 | MYLK |
| chr3:103140700-144883172 | 8539 | 41742473 | 1 | rs4314176 | rs6797159 | 44.122 | 0 | MYLK |
| chr3:83075971-196935657 | 21465 | 113859687 | 1 | rs9872858 | rs34729751 | 44.35 | 0 | MYLK |
| chr3:114889454-177826047 | 12700 | 62936594 | 3 | rs6795297 | rs7628308 | 102.526 | 0 | MYLK |
| chr5:141659-19010008 | 4662 | 18868350 | 3 | rs11741126 | rs4642370 | 50.124 | 0 | MYO10 |
| chr5:4872310-180709915 | 35876 | 175837606 | 3 | rs816467 | rs10071993 | 179.394 | 0 | MYO10 |
| chr6:64844594-169078546 | 21567 | 104233953 | 1 | rs4710465 | rs601639 | 46.524 | 0 | MYO6 |
| chr6:66609532-147053632 | 15315 | 80444101 | 3 | rs9354335 | rs4896886 | 44.941 | 0 | MYO6 |
| chr6:73120320-165130872 | 18715 | 92010553 | 1 | rs9442780 | rs10946016 | 76.383 | 0 | MYO6 |
| chr6:26922906-93578359 | 19746 | 66655454 | 1 | rs9348738 | rs9363009 | 27.061 | 0 | MYO6 |
| chr6:66541198-162520133 | 19344 | 95978936 | 1 | rs2000382 | rs6901071 | 27.509 | 0 | MYO6 |
| chr6:62697746-94090076 | 6391 | 31392331 | 1 | rs6455128 | rs3799807 | 108.85 | 0 | MYO6 |
| chr6:67621368-147709180 | 16188 | 80087813 | 1 | rs6919455 | rs7739314 | 52.498 | 0 | MYO6 |
| chr6:75600804-78928379 | 602 | 3327576 | 3 | rs7743423 | rs1416055 | 49.19 | 0 | MYO6 |
| chr11:42185849-126756938 | 15451 | 84571090 | 1 | rs4375424 | rs10750356 | 36.99 | 0 | MYO7A |
| chr11:21723471-131521797 | 20508 | 109798327 | 1 | rs11828478 | rs2512898 | 27.565 | 0 | MYO7A |
| chr11:23168804-106781202 | 16332 | 83612489 | 1 | rs11027007 | rs7103235 | 49.747 | 0 | MYO7A |
| chr11:74545378-134940416 | 14496 | 60395039 | 3 | rs512780 | rs11224228 | 527.758 | 0 | MYO7A |
| chr19:266034-18061509 | 3100 | 17795476 | 3 | rs2312724 | rs7250332 | 19.51 | 0 | MYO9B |
| chr19:288246-59110628 | 11009 | 58822383 | 3 | rs10409452 | cnvi0009466 | 100.582 | 0 | MYO9B |
| chr1:64114301-245591329 | 29842 | 181477029 | 1 | rs11208257 | rs1173850 | 37.504 | 0 | MYOC |
| chr1:75098453-243531649 | 27360 | 168433197 | 1 | rs12117493 | rs10927002 | 32.113 | 0 | MYOC |
| chr1:79710545-188898319 | 17303 | 109187775 | 1 | rs417181 | rs16829637 | 45.89 | 0 | MYOC |
| chr1:109645793-194560463 | 12025 | 84914671 | 3 | cnvi0008281 | rs10921616 | 63.121 | 0 | MYOC |
| chr11:211482-66910826 | 13813 | 66699345 | 3 | rs2293168 | rs4375446 | 30.249 | 0 | MYOD1 |
| chr1:64114301-245591329 | 29842 | 181477029 | 1 | rs11208257 | rs1173850 | 37.504 | 0 | MYOG |
| chr1:178626526-244159143 | 13064 | 65532618 | 3 | rs2761477 | rs479338 | 11.373 | 0 | MYOG |
| chr1:75098453-243531649 | 27360 | 168433197 | 1 | rs12117493 | rs10927002 | 32.113 | 0 | MYOG |
| chr1:188850774-235423607 | 10060 | 46572834 | 1 | rs16829466 | rs12409696 | 43.25 | 0 | MYOG |
| chr1:191875752-235423607 | 9517 | 43547856 | 1 | rs9427811 | rs12409696 | 62.01 | 0 | MYOG |
| chr1:189128124-227340790 | 7927 | 38212667 | 1 | rs7515205 | rs12752546 | 167.428 | 0 | MYOG |
| chr1:174219398-247422297 | 15986 | 73202900 | 1 | rs16846809 | rs4642922 | 35.258 | 0 | MYOG |
| chr1:197187605-226404457 | 6316 | 29216853 | 3 | rs10922187 | rs3008192 | 130.989 | 0 | MYOG |
| chr5:84830796-171903310 | 16642 | 87072515 | 1 | rs300657 | rs10042482 | 42.208 | 0 | MYOT |
| chr5:57343495-171903310 | 21683 | 114559816 | 1 | rs10940593 | rs10042482 | 61.169 | 0 | MYOT |
| chr5:98442871-150317237 | 9828 | 51874367 | 1 | rs1447379 | rs7710790 | 38.687 | 0 | MYOT |
| chr5:4872310-180709915 | 35876 | 175837606 | 3 | rs816467 | rs10071993 | 179.394 | 0 | MYOT |
| chr2:18856-41136833 | 9721 | 41117978 | 3 | rs11901199 | rs10187704 | 191.638 | 0 | MYT1L |
| chr12:10113083-116370432 | 20594 | 106257350 | 1 | rs2012504 | rs7958254 | 35.157 | 0 | NACA |
| chr12:10020267-129866293 | 23654 | 119846027 | 1 | rs1597097 | rs2170504 | 45.428 | 0 | NACA |
| chr12:39967134-84174413 | 8879 | 44207280 | 1 | rs11172661 | rs11116039 | 39.568 | 0 | NACA |
| chr12:50855195-133778796 | 17748 | 82923602 | 3 | rs4351895 | rs7975069 | 159.589 | 0 | NACA |
| chr9:1989033-107532317 | 18263 | 105543285 | 1 | rs7864828 | rs10820726 | 39.824 | 0 | NANS |
| chr9:2522475-140068342 | 25719 | 137545868 | 3 | rs10966757 | rs4074426 | 93.386 | 0 | NANS |
| chr9:33180228-132003792 | 14691 | 98823565 | 1 | rs7854765 | rs9408988 | 28.69 | 0 | NANS |
| chr9:100158052-139077343 | 9815 | 38919292 | 3 | rs1020884 | rs4842126 | 470.601 | 0 | NANS |
| chr8:30757798-142750969 | 20699 | 111993172 | 1 | rs10101203 | rs6421025 | 34.223 | 0 | NCALD |
| chr8:60424884-145286483 | 17030 | 84861600 | 3 | rs1401422 | rs9720889 | 8.858 | 0 | NCALD |
| chr8:23218101-146274708 | 23020 | 123056608 | 1 | rs7010362 | rs7822726 | 38.828 | 0 | NCALD |
| chr8:76354446-113652365 | 6767 | 37297920 | 1 | rs830783 | rs16883889 | 127.023 | 0 | NCALD |
| chr8:66822030-144791126 | 16557 | 77969097 | 3 | rs6472235 | rs10100154 | 251.068 | 0 | NCALD |
| chr7:11855636-156148608 | 26852 | 144292973 | 1 | rs6947930 | rs6945016 | 36.446 | 0 | NCF1C |
| chr7:8872727-156383359 | 27773 | 147510633 | 1 | rs917038 | rs878717 | 32.336 | 0 | NCF1C |
| chr7:8794418-119068130 | 23484 | 110273713 | 1 | rs2189621 | rs6977904 | 70.867 | 0 | NCF1C |
| chr7:60392-84158180 | 19095 | 84097789 | 3 | rs12670102 | rs2715048 | 208.308 | 0 | NCF1C |
| chr3:13878889-149737330 | 24723 | 135858442 | 1 | rs12634112 | rs2007869 | 55.663 | 0 | NCK1 |
| chr3:33409611-170735099 | 23775 | 137325489 | 1 | rs3915062 | rs11924032 | 26.867 | 0 | NCK1 |
| chr3:102240202-195550366 | 17318 | 93310165 | 1 | rs1620217 | rs11711870 | 41.031 | 0 | NCK1 |
| chr3:103140700-144883172 | 8539 | 41742473 | 1 | rs4314176 | rs6797159 | 44.122 | 0 | NCK1 |
| chr3:83075971-196935657 | 21465 | 113859687 | 1 | rs9872858 | rs34729751 | 44.35 | 0 | NCK1 |
| chr3:114889454-177826047 | 12700 | 62936594 | 3 | rs6795297 | rs7628308 | 102.526 | 0 | NCK1 |
| chr2:34870277-241929621 | 37755 | 207059345 | 3 | rs13422005 | rs10205276 | 46.946 | 0 | NCL |
| chr2:38101137-241482099 | 36812 | 203380856 | 1 | rs879321 | rs7576043 | 52.099 | 0 | NCL |
| chr2:193255360-242529978 | 10289 | 49274619 | 3 | rs1351905 | cnvi0010399 | 93.244 | 0 | NCL |
| chr12:59512781-127744939 | 13469 | 68232159 | 3 | rs908394 | rs7966946 | 20.62 | 0 | NCOR2 |
| chr12:10020267-129866293 | 23654 | 119846027 | 1 | rs1597097 | rs2170504 | 45.428 | 0 | NCOR2 |
| chr12:112610714-133708729 | 5366 | 21098016 | 3 | rs11066188 | rs11147249 | 695.45 | 0 | NCOR2 |
| chr12:50855195-133778796 | 17748 | 82923602 | 3 | rs4351895 | rs7975069 | 159.589 | 0 | NCOR2 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr2:12056323-227979775 | 39094 | 215923453 | 1 | rs966391 | rs1922020 | 31.384 | 0 | NEUROD1 |
| chr2:34870277-241929621 | 37755 | 207059345 | 3 | rs13422005 | rs10205276 | 46.946 | 0 | NEUROD1 |
| chr2:38101137-241482099 | 36812 | 203380963 | 1 | rs879321 | rs7576043 | 52.099 | 0 | NEUROD1 |
| chr2:77041264-194763754 | 21140 | 117722491 | 1 | rs2102827 | rs16835406 | 94.091 | 0 | NEUROD1 |
| chr2:180138805-193144041 | 2298 | 13005237 | 3 | rs6746115 | rs2592243 | 132.36 | 0 | NEUROD1 |
| chr22:16871137-51184393 | 9245 | 34313257 | 3 | rs131538 | rs7284680 | 209.79 | 0 | NF2 |
| chr1:64114301-245591329 | 29842 | 181477029 | 1 | rs11208257 | rs1173850 | 37.504 | 0 | NFASC |
| chr1:178626526-244159143 | 13064 | 65532618 | 3 | rs2761477 | rs479338 | 11.373 | 0 | NFASC |
| chr1:75098453-243531649 | 27360 | 168433197 | 1 | rs12117493 | rs10253700 | 32.113 | 0 | NFASC |
| chr1:188850774-235423607 | 10060 | 46572834 | 1 | rs16829466 | rs12409696 | 43.25 | 0 | NFASC |
| chr1:191875752-235423607 | 9517 | 43547856 | 1 | rs9427811 | rs12409696 | 62.01 | 0 | NFASC |
| chr1:189128124-227340790 | 7927 | 38212667 | 1 | rs7515205 | rs12752546 | 167.428 | 0 | NFASC |
| chr1:174219398-247422297 | 15986 | 73202900 | 1 | rs16846809 | rs4642922 | 35.258 | 0 | NFASC |
| chr1:197187605-226404457 | 6316 | 29216853 | 3 | rs10922187 | rs3008192 | 130.989 | 0 | NFASC |
| chr18:44788908-78015180 | 8492 | 33226273 | 3 | rs9944807 | rs12960632 | 579.2 | 0 | NFATC1 |
| chr20:13712393-55093901 | 8218 | 41381509 | 1 | rs6033810 | rs6999 | 41.237 | 0 | NFATC2 |
| chr20:7869025-62424661 | 11941 | 54555637 | 3 | rs2294306 | rs6010652 | 9.732 | 0 | NFATC2 |
| chr20:4591715-58420336 | 11753 | 53828622 | 1 | rs6139494 | rs1416388 | 40.922 | 0 | NFATC2 |
| chr20:236802-54845796 | 12646 | 54608995 | 3 | rs448294 | rs6064362 | 286.151 | 0 | NFATC2 |
| chr10:7188484-134205354 | 26672 | 127016871 | 1 | rs1977295 | rs3923858 | 50.772 | 0 | NFKB2 |
| chr10:58385643-124973104 | 13625 | 66587462 | 1 | rs7920235 | rs17663304 | 36.18 | 0 | NFKB2 |
| chr10:57671424-133349223 | 16243 | 75677800 | 1 | rs11005106 | rs4301710 | 37.114 | 0 | NFKB2 |
| chr10:55492162-117205017 | 13465 | 61712856 | 1 | rs6481032 | rs1933664 | 62.56 | 0 | NFKB2 |
| chr10:53602190-135522754 | 19167 | 81920565 | 3 | rs12247820 | rs10909028 | 139.373 | 0 | NFKB2 |
| chr14:26018408-44486343 | 3682 | 18467936 | 3 | rs10138454 | rs9323093 | 17.669 | 0 | NFKBIA |
| chr14:35760062-35886959 | 27 | 126894 | 4 | rs17536892 | rs2415290 | 5.425 | 0 | NFKBIA |
| chr14:35433187-35884639 | 78 | 451453 | 3 | rs2273154 | rs1012919 | 170.85 | 0 | NFKBIA |
| chr14:26898958-104436931 | 17396 | 77537974 | 1 | rs1245195 | rs11851097 | 57.233 | 0 | NFKBIA |
| chr14:19917123-65327288 | 10286 | 45410166 | 3 | rs2495197 | rs9323455 | 270.291 | 0 | NFKBIA |
| chr19:31569338-53780966 | 3788 | 22211629 | 1 | rs2867544 | rs10407424 | 33.9 | 0 | NFKBIB |
| chr19:288246-59110628 | 11009 | 58822383 | 3 | rs10409452 | cnvi0009466 | 100.582 | 0 | NFKBIB |
| chr6:26922906-93578359 | 19746 | 66655454 | 1 | rs9348738 | rs9363009 | 27.061 | 0 | NFKBIE |
| chr6:31289284-56929863 | 15402 | 25640580 | 3 | rs9265170 | cnvi0015437 | 25.647 | 0 | NFKBIE |
| chr6:32968276-73449742 | 15442 | 40481467 | 3 | rs2395300 | rs4235869 | 415.87 | 0 | NFKBIE |
| chr14:26898958-104436931 | 17396 | 77537974 | 1 | rs1245195 | rs11851097 | 57.233 | 0 | NGB |
| chr14:65405722-103799039 | 8979 | 38393318 | 3 | rs11623705 | rs11628472 | 266.153 | 0 | NGB |
| chr22:16871137-51184393 | 9245 | 34313257 | 3 | rs131538 | rs7284680 | 209.79 | 0 | NHP2L1 |
| chr2:12056323-227979775 | 39094 | 215923453 | 1 | rs966391 | rs1922020 | 31.384 | 0 | NMI |
| chr2:34870277-241929621 | 37755 | 207059345 | 3 | rs13422005 | rs10205276 | 46.946 | 0 | NMI |
| chr2:38101137-241482099 | 36812 | 203380963 | 1 | rs879321 | rs7576043 | 52.099 | 0 | NMI |
| chr2:77041264-194763754 | 21140 | 117722491 | 1 | rs2102827 | rs16835406 | 94.091 | 0 | NMI |
| chr2:83383702-175194550 | 16291 | 91810849 | 3 | rs12469609 | rs11891208 | 154.4 | 0 | NMI |
| chr2:59512781-127744989 | 13469 | 68232159 | 3 | rs908394 | rs7966946 | 20.62 | 0 | NOS1 |
| chr2:10020267-129866293 | 23654 | 119846027 | 1 | rs1597097 | rs2170504 | 45.428 | 0 | NOS1 |
| chr2:112610714-133708729 | 5366 | 21098016 | 3 | rs11066188 | rs11147249 | 695.45 | 0 | NOS1 |
| chr2:50855195-133778796 | 17748 | 82923602 | 3 | rs4351895 | rs7975069 | 159.589 | 0 | NOS1 |
| chr2:110829655-110982530 | 15 | 152876 | 1 | rs163667 | rs13386516 | 42.435 | 0 | NPHP1 |
| chr2:12056323-227979775 | 39094 | 215923453 | 1 | rs966391 | rs1922020 | 31.384 | 0 | NPHP1 |
| chr2:34870277-241929621 | 37755 | 207059345 | 3 | rs13422005 | rs10205276 | 46.946 | 0 | NPHP1 |
| chr2:110829655-110982530 | 15 | 152876 | 3 | rs163667 | rs13386516 | 33.513 | 0 | NPHP1 |
| chr2:110829655-110929964 | 12 | 100310 | 3 | rs163667 | rs6747701 | 18.706 | 0 | NPHP1 |
| chr2:110829655-110934723 | 13 | 105069 | 1 | rs163667 | rs1154652 | 10.443 | 0 | NPHP1 |
| chr2:38101137-241482099 | 36812 | 203380963 | 1 | rs879321 | rs7576043 | 52.099 | 0 | NPHP1 |
| chr2:110871665-110983050 | 21 | 111386 | 1 | rs17842653 | rs10173717 | 83.324 | 0 | NPHP1 |
| chr2:110834186-111144295 | 30 | 310110 | 3 | rs163660 | rs2117529 | 40.53 | 0 | NPHP1 |
| chr2:110891433-111068787 | 18 | 177355 | 3 | rs1588327 | rs339216 | 20.575 | 0 | NPHP1 |
| chr2:77041264-194763754 | 21140 | 117722491 | 1 | rs2102827 | rs16835406 | 94.091 | 0 | NPHP1 |
| chr2:110857243-111068787 | 24 | 211545 | 3 | rs6716800 | rs339216 | 35.798 | 0 | NPHP1 |
| chr2:110732676-111068787 | 32 | 336112 | 3 | rs12467706 | rs339216 | 109.625 | 0 | NPHP1 |
| chr2:83383702-175194550 | 16291 | 91810849 | 3 | rs12469609 | rs11891208 | 154.4 | 0 | NPHP1 |
| chr4:31222833-180548076 | 24457 | 149325244 | 1 | rs7662351 | rs3849606 | 36.162 | 0 | NPY2R |
| chr4:137206602-158430547 | 3577 | 21223946 | 3 | rs1597600 | rs12507865 | 83.533 | 0 | NPY2R |
| chr4:68173959-185767176 | 20235 | 117593218 | 1 | rs6552083 | rs4862428 | 61.893 | 0 | NPY2R |
| chr4:22401728-188608583 | 28456 | 166207130 | 1 | rs4697297 | rs7687115 | 35.717 | 0 | NPY2R |
| chr4:63726348-173015421 | 19817 | 109289074 | 1 | rs17082970 | rs2131002 | 30.251 | 0 | NPY2R |
| chr4:126374899-162380016 | 6166 | 36005118 | 1 | rs4834042 | rs17041092 | 33.404 | 0 | NPY2R |
| chr4:155739051-165849854 | 1997 | 10110804 | 1 | rs7691720 | rs10005938 | 26.215 | 0 | NPY2R |
| chr4:69590353-190872778 | 23145 | 121282426 | 3 | rs293433 | rs12646565 | 315.633 | 0 | NPY2R |
| chr2:12056323-227979775 | 39094 | 215923453 | 1 | rs966391 | rs1922020 | 31.384 | 0 | NRBP1 |
| chr2:27260469-27667297 | 33 | 406829 | 1 | rs1124649 | rs4803 | 15.064 | 0 | NRBP1 |
| chr2:18856-41136833 | 9721 | 41117978 | 3 | rs11901199 | rs10187704 | 191.638 | 0 | NRBP1 |
| chr11:42185849-126756938 | 15451 | 84571090 | 1 | rs4375424 | rs10250356 | 36.99 | 0 | NRGN |
| chr11:21723471-131521797 | 20508 | 109798327 | 1 | rs11828478 | rs2512898 | 27.565 | 0 | NRGN |
| chr11:74545378-134940416 | 14496 | 60395039 | 3 | rs512780 | rs11224228 | 527.758 | 0 | NRGN |
| chr19:31569338-53780966 | 3788 | 22211629 | 1 | rs2867544 | rs10407424 | 33.9 | 0 | NUCB1 |
| chr19:43257015-55294329 | −7309 | 12037315 | 3 | rs7246152 | rs2569676 | 21.402 | 0 | NUCB1 |
| chr19:288246-59110628 | 11009 | 58822383 | 3 | rs10409452 | cnvi0009466 | 100.582 | 0 | NUCB1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr1:1005806-105612342 | 19173 | 104606537 | 3 | rs3934834 | rs1584633 | 44.152 | 0 | NUDC |
| chr1:2006108-109527861 | 22130 | 107521754 | 3 | rs2254669 | rs839879 | 162.269 | 0 | NUDC |
| chr1:64114301-245591329 | 29842 | 181477029 | 1 | rs11208257 | rs1173850 | 37.504 | 0 | OBSCN |
| chr1:178626526-244159143 | 13064 | 65532618 | 3 | rs2761477 | rs479338 | 11.373 | 0 | OBSCN |
| chr1:75098453-243531649 | 27360 | 168433197 | 1 | rs12117493 | rs10927002 | 32.113 | 0 | OBSCN |
| chr1:188850774-235423607 | 10060 | 46572834 | 1 | rs16829466 | rs12409696 | 43.25 | 0 | OBSCN |
| chr1:191875752-235423607 | 9517 | 43547856 | 1 | rs9427811 | rs12409696 | 62.01 | 0 | OBSCN |
| chr1:174219398-247422297 | 15986 | 73202900 | 1 | rs16846809 | rs4642922 | 35.258 | 0 | OBSCN |
| chr1:226536645-236803753 | 2600 | 10267109 | 3 | rs874583 | rs10925178 | 100.109 | 0 | OBSCN |
| chr3:179527-114630641 | 23879 | 114451115 | 3 | rs4684741 | rs1587972 | 207.852 | 0 | OGG1 |
| chr1:1005806-105612342 | 19173 | 104606537 | 3 | rs3934834 | rs1584633 | 44.152 | 0 | OPRD1 |
| chr1:2006108-109527861 | 22130 | 107521754 | 3 | rs2254669 | rs839879 | 162.269 | 0 | OPRD1 |
| chr8:30757798-142750969 | 20699 | 111993172 | 1 | rs10101203 | rs6421025 | 34.223 | 0 | OPRK1 |
| chr8:23218101-146274708 | 23020 | 123056608 | 1 | rs7010362 | rs7822726 | 38.828 | 0 | OPRK1 |
| chr8:53908875-54088142 | 47 | 179268 | 1 | rs360974 | rs2194910 | 15.819 | 50134 | OPRK1 |
| chr8:43235525-66712108 | 3632 | 23476584 | 3 | rs10091311 | rs7001138 | 58.838 | 0 | OPRK1 |
| chr6:64844594-169078546 | 21567 | 104233953 | 1 | rs4710465 | rs601639 | 46.524 | 0 | OPRM1 |
| chr6:151495387-165969396 | 3761 | 14474010 | 3 | rs9322304 | rs1022180 | 22.826 | 0 | OPRM1 |
| chr6:73120320-165130872 | 18715 | 92010553 | 1 | rs9442780 | rs10946016 | 76.383 | 0 | OPRM1 |
| chr6:66541198-162520133 | 19344 | 95978936 | 1 | rs2000382 | rs6901071 | 27.509 | 0 | OPRM1 |
| chr6:94117546-165103679 | 15579 | 70986134 | 1 | rs3799792 | rs9347902 | 34.066 | 0 | OPRM1 |
| chr6:100082983-170909002 | 16393 | 70826029 | 3 | rs594231 | rs12213906 | 261.313 | 0 | OPRM1 |
| chr3:152392877-152613883 | 31 | 221007 | 3 | rs9828639 | rs2872090 | 1.227 | 0 | P2RY1 |
| chr3:145967173-173899890 | 4912 | 27932718 | 3 | rs9863647 | rs7618997 | 46.396 | 0 | P2RY1 |
| chr3:33409611-170735099 | 23775 | 137325489 | 1 | rs3915062 | rs11924032 | 26.867 | 0 | P2RY1 |
| chr3:102240202-195550366 | 17318 | 93310165 | 1 | rs1620217 | rs11711870 | 41.031 | 0 | P2RY1 |
| chr3:83075971-196935657 | 21465 | 113859687 | 1 | rs9872858 | rs34729751 | 44.35 | 0 | P2RY1 |
| chr3:114889454-177826047 | 12700 | 62936594 | 3 | rs6795297 | rs7628308 | 102.526 | 0 | P2RY1 |
| chr12:10113083-116370432 | 20594 | 106257350 | 1 | rs2012504 | rs7958254 | 35.157 | 0 | PA2G4 |
| chr12:10020267-129866293 | 23654 | 119846027 | 1 | rs1597097 | rs2170504 | 45.428 | 0 | PA2G4 |
| chr12:39967134-84174413 | 8879 | 44207280 | 1 | rs11172661 | rs11116039 | 39.568 | 0 | PA2G4 |
| chr12:50855195-133778796 | 17748 | 82923602 | 3 | rs4351895 | rs7975069 | 159.589 | 0 | PA2G4 |
| chr1:1005806-105612342 | 19173 | 104606537 | 3 | rs3934834 | rs1584633 | 44.152 | 0 | PABPC4 |
| chr1:2006108-109527861 | 22130 | 107521754 | 3 | rs2254669 | rs839879 | 162.269 | 0 | PABPC4 |
| chr9:2522475-140068342 | 25719 | 137545868 | 3 | rs10966757 | rs4074426 | 93.386 | 0 | PAEP |
| chr9:100158052-139077343 | 9815 | 38919292 | 3 | rs1020884 | rs4842126 | 470.601 | 0 | PAEP |
| chr17:108420-26610769 | 5548 | 26502350 | 3 | rs12452527 | rs658591 | 82.699 | 0 | PAFAH1B1 |
| chr19:31569338-53780966 | 3788 | 22211629 | 1 | rs2867544 | rs10407424 | 33.9 | 0 | PAFAH1B3 |
| chr19:288246-59110628 | 11009 | 58822383 | 3 | rs10409452 | cnvi0009466 | 100.582 | 0 | PAFAH1B3 |
| chr5:84830796-171903310 | 16642 | 87072515 | 1 | rs300657 | rs10042482 | 42.208 | 0 | PAM |
| chr5:93678849-103794722 | 1632 | 10115874 | 3 | rs160270 | rs2963216 | 3.838 | 0 | PAM |
| chr5:57343495-171903310 | 21683 | 114559816 | 1 | rs10940593 | rs10042482 | 61.169 | 0 | PAM |
| chr5:98442871-150340710 | 9828 | 51874367 | 1 | rs1447379 | rs7710790 | 38.687 | 0 | PAM |
| chr5:84160703-104650005 | 3339 | 20489303 | 1 | rs6860783 | rs560688 | 92.914 | 0 | PAM |
| chr5:80735161-125293366 | 8499 | 44558206 | 1 | rs1541830 | rs327816 | 52.167 | 0 | PAM |
| chr5:4872310-180709915 | 35876 | 175837606 | 3 | rs816467 | rs10071993 | 179.394 | 0 | PAM |
| chr6:59854720-89273880 | 7609 | 29419164 | 3 | rs1373880 | rs8046156 | 31.884 | 0 | PARD6A |
| chr16:64107047-82920737 | 4544 | 18813691 | 1 | rs2319723 | rs918661 | 28.887 | 0 | PARD6A |
| chr16:67634786-67780829 | 11 | 146044 | 1 | cnvi0008013 | rs9925393 | 12.023 | 0 | PARD6A |
| chr16:50219449-89544756 | 10324 | 39325308 | 3 | rs6500298 | rs3803681 | 108.108 | 0 | PARD6A |
| chr20:13712393-55053901 | 8218 | 41381509 | 1 | rs6033810 | rs6999 | 41.237 | 0 | PARD6B |
| chr20:7869025-62424661 | 11941 | 54555637 | 3 | rs2294306 | rs6010652 | 9.732 | 0 | PARD6B |
| chr20:4591715-58420336 | 11753 | 53828622 | 1 | rs6139494 | rs1416388 | 40.922 | 0 | PARD6B |
| chr20:236802-54845796 | 12646 | 54608995 | 3 | rs448294 | rs6064362 | 286.151 | 0 | PARD6B |
| chr18:44788908-78015180 | 8492 | 33226273 | 3 | rs9944807 | rs12960632 | 579.2 | 0 | PARD6G |
| chr12:10113083-116370432 | 20594 | 106257350 | 1 | rs2012504 | rs7958254 | 35.157 | 0 | PAWR |
| chr12:59512781-127744939 | 13469 | 68232159 | 3 | rs908394 | rs7966946 | 20.62 | 0 | PAWR |
| chr12:10020267-129866293 | 23654 | 119846027 | 1 | rs1597097 | rs2170504 | 45.428 | 0 | PAWR |
| chr12:39967134-84174413 | 8879 | 44207280 | 1 | rs11172661 | rs11116039 | 39.568 | 0 | PAWR |
| chr12:79291372-80266372 | 130 | 975001 | 1 | rs1551847 | rs2698261 | 34.672 | 0 | PAWR |
| chr12:50855195-133778796 | 17748 | 82923602 | 3 | rs4351895 | rs7975069 | 159.589 | 0 | PAWR |
| chr2:12056323-227979775 | 39094 | 215923453 | 1 | rs966391 | rs1922020 | 31.384 | 0 | PCBP1 |
| chr2:34870277-241929621 | 37755 | 207059345 | 3 | rs13422005 | rs10205276 | 46.946 | 0 | PCBP1 |
| chr2:69979290-70389200 | 49 | 410611 | 3 | rs10177224 | rs11677137 | 16.309 | 0 | PCBP1 |
| chr2:38101137-241482099 | 36812 | 203380963 | 1 | rs879321 | rs7576043 | 52.099 | 0 | PCBP1 |
| chr2:41212010-82396211 | 9721 | 41184202 | 3 | rs12614285 | rs934310 | 396.396 | 0 | PCBP1 |
| chr21:44839153-47856106 | 674 | 3016954 | 1 | rs2838302 | rs2236616 | 38.158 | 0 | PCBP3 |
| chr21:14601415-48084989 | 8249 | 33483575 | 3 | rs2775537 | rs2839378 | 12047.211 | 0 | PCBP3 |
| chr21:14601415-48084989 | 8249 | 33483575 | 3 | rs2775537 | rs2839378 | 41.154 | 0 | PCBP3 |
| chr21:47091361-47226895 | 18 | 135535 | 1 | rs2838973 | rs2839002 | 14.709 | 0 | PCBP3 |
| chr21:14768343-48084989 | 8193 | 33316647 | 3 | rs2257224 | rs2839378 | 5021.076 | 0 | PCBP3 |
| chr21:14601415-48084989 | 8249 | 33483575 | 3 | rs2775537 | rs2839378 | 4787.438 | 0 | PCBP3 |
| chr21:14595264-48084989 | 8781 | 33489726 | 3 | rs2847443 | rs2839378 | 1871.363 | 0 | PCBP3 |
| chr21:46381900-48098560 | 448 | 1716661 | 1 | rs8132265 | cnvi0019195 | 712.68 | 0 | PCBP3 |
| chr21:10708231-47970581 | 8807 | 37262351 | 3 | rs4044122 | rs2255397 | 73.188 | 0 | PCBP3 |
| chr5:84830796-171903310 | 16642 | 87072515 | 1 | rs300657 | rs10042482 | 42.208 | 0 | PCDHA4 |
| chr5:57343495-171903310 | 21683 | 114559816 | 1 | rs10940593 | rs10042482 | 61.169 | 0 | PCDHA4 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr5:98442871-150317237 | 9828 | 51874367 | 1 | rs1447379 | rs7710790 | 38.687 | 0 | PCDHA4 |
| chr5:4872310-180709915 | 35876 | 175837606 | 3 | rs816467 | rs10071993 | 179.394 | 0 | PCDHA4 |
| chr6:64844594-169078546 | 21567 | 104233953 | 1 | rs4710465 | rs601639 | 46.524 | 0 | PCMT1 |
| chr6:73120320-165130872 | 18715 | 92010553 | 1 | rs9442780 | rs10946016 | 76.383 | 0 | PCMT1 |
| chr6:66541198-162520133 | 19344 | 95978936 | 1 | rs2000382 | rs6901071 | 27.509 | 0 | PCMT1 |
| chr6:94117546-165103679 | 15579 | 70986134 | 1 | rs3799792 | rs9347902 | 34.066 | 0 | PCMT1 |
| chr6:100082983-170909002 | 16393 | 70826020 | 3 | rs594231 | rs12213906 | 261.313 | 0 | PCMT1 |
| chr21:44839153-47856106 | 674 | 3016954 | 1 | rs2838302 | rs2236616 | 38.158 | 0 | PCNT |
| chr21:14601415-48084989 | 8249 | 33483575 | 3 | rs2775537 | rs2839378 | 12047.211 | 0 | PCNT |
| chr21:14601415-48084989 | 8249 | 33483575 | 3 | rs2775537 | rs2839378 | 41.154 | 0 | PCNT |
| chr21:14768343-48084989 | 8193 | 33316647 | 3 | rs2257224 | rs2839378 | 5021.076 | 0 | PCNT |
| chr21:14601415-48084989 | 8249 | 33483575 | 3 | rs2775537 | rs2839378 | 4787.438 | 0 | PCNT |
| chr21:14595264-48084989 | 8781 | 33489726 | 3 | rs2847443 | rs2839378 | 1871.363 | 0 | PCNT |
| chr21:46381900-48098560 | 448 | 1716661 | 1 | rs8132265 | cnvi0019195 | 712.68 | 0 | PCNT |
| chr21:10708231-47970581 | 8807 | 37262351 | 3 | rs4044122 | rs2255397 | 73.188 | 0 | PCNT |
| chr21:14601415-48084989 | 8249 | 33483575 | 3 | rs2775537 | rs2839378 | 12047.211 | 0 | PCP4 |
| chr21:14601415-48084989 | 8249 | 33483575 | 3 | rs2775537 | rs2839378 | 41.154 | 0 | PCP4 |
| chr21:14768343-48084989 | 8193 | 33316647 | 3 | rs2257224 | rs2839378 | 5021.076 | 0 | PCP4 |
| chr21:14601415-48084989 | 8249 | 33483575 | 3 | rs2775537 | rs2839378 | 4787.438 | 0 | PCP4 |
| chr21:14595264-48084989 | 8781 | 33489726 | 3 | rs2847443 | rs2839378 | 1871.363 | 0 | PCP4 |
| chr21:10708231-47970581 | 8807 | 37262351 | 3 | rs4044122 | rs2255397 | 73.188 | 0 | PCP4 |
| chr1:64114301-245591329 | 29842 | 181477029 | 1 | rs11208257 | rs1173850 | 37.504 | 0 | PDC |
| chr1:178626526-244159143 | 13064 | 65532618 | 3 | rs2761477 | rs479338 | 11.373 | 0 | PDC |
| chr1:75098453-243531649 | 27360 | 168433197 | 1 | rs12117493 | rs10927002 | 32.113 | 0 | PDC |
| chr1:79710545-188898319 | 17303 | 109187775 | 1 | rs417181 | rs16829637 | 45.89 | 0 | PDC |
| chr1:174219398-247422297 | 15986 | 73202900 | 1 | rs16846809 | rs4642922 | 35.258 | 0 | PDC |
| chr1:109645793-194560463 | 12025 | 84914671 | 3 | cnvi0008281 | rs10921616 | 63.121 | 0 | PDC |
| chr19:31569338-53780966 | 3788 | 22211629 | 1 | rs2867544 | rs10407424 | 33.9 | 0 | PDCD5 |
| chr19:288246-59110628 | 11009 | 58822383 | 3 | rs10409452 | cnvi0009466 | 100.582 | 0 | PDCD5 |
| chr9:2522475-140068342 | 25719 | 137545868 | 3 | rs10966715 | rs4074426 | 93.386 | 0 | PDCL |
| chr9:33180228-132003792 | 14691 | 98823565 | 1 | rs7854765 | rs9408988 | 28.69 | 0 | PDCL |
| chr9:100158052-139077343 | 9815 | 38919292 | 3 | rs1020884 | rs4842126 | 470.601 | 0 | PDCL |
| chr2:12056323-227979775 | 39094 | 215923453 | 1 | rs966391 | rs1922020 | 31.384 | 0 | PDE1A |
| chr2:34870277-241929621 | 37755 | 207059345 | 3 | rs13422005 | rs10205276 | 46.946 | 0 | PDE1A |
| chr2:38101137-241482099 | 36812 | 203380963 | 1 | rs879321 | rs7576043 | 52.099 | 0 | PDE1A |
| chr2:77041264-194763754 | 21140 | 117722491 | 1 | rs2102827 | rs16835406 | 94.091 | 0 | PDE1A |
| chr2:180138805-193144041 | 2298 | 13005237 | 3 | rs6746115 | rs2592243 | 132.36 | 0 | PDE1A |
| chr12:10113083-116370432 | 20594 | 106257350 | 1 | rs2012504 | rs7958254 | 35.157 | 0 | PDE1B |
| chr12:10020267-129866293 | 23654 | 119846027 | 1 | rs1597097 | rs2170504 | 45.428 | 0 | PDE1B |
| chr12:39967134-84174413 | 8879 | 44207280 | 1 | rs11172661 | rs11116039 | 39.568 | 0 | PDE1B |
| chr12:50855195-133778796 | 17748 | 82923602 | 3 | rs4351895 | rs7975069 | 159.589 | 0 | PDE1B |
| chr7:11855636-156148608 | 26852 | 144292973 | 1 | rs6947930 | rs6945016 | 36.446 | 0 | PDE1C |
| chr7:7724805-53845684 | 11772 | 46120880 | 3 | rs10263415 | rs6948633 | 42.007 | 0 | PDE1C |
| chr7:8872727-156383359 | 27773 | 147510633 | 1 | rs917038 | rs878717 | 32.336 | 0 | PDE1C |
| chr7:8794418-119068130 | 23484 | 110273713 | 1 | rs2189621 | rs6977904 | 70.867 | 0 | PDE1C |
| chr7:60392-84158180 | 19095 | 84097789 | 3 | rs12670102 | rs2715048 | 208.308 | 0 | PDE1C |
| chr1:64114301-245591329 | 29842 | 181477029 | 1 | rs11208257 | rs1173850 | 37.504 | 0 | PDE4DIP |
| chr1:75098453-243531649 | 27360 | 168433197 | 1 | rs12117493 | rs10927002 | 32.113 | 0 | PDE4DIP |
| chr1:121171208-145073750 | 112 | 23902543 | 3 | rs4844616 | rs634953 | 101.367 | 0 | PDE4DIP |
| chr1:79710545-188898319 | 17303 | 109187775 | 1 | rs417181 | rs16829637 | 45.89 | 0 | PDE4DIP |
| chr1:109645793-194560463 | 12025 | 84914671 | 3 | cnvi0008281 | rs10921616 | 63.121 | 0 | PDE4DIP |
| chr2:34870277-241929621 | 37755 | 207059345 | 3 | rs13422005 | rs10205276 | 46.946 | 0 | PDE6D |
| chr2:38101137-241482099 | 36812 | 203380963 | 1 | rs879321 | rs7576043 | 52.099 | 0 | PDE6D |
| chr2:193255360-242529978 | 10289 | 49274619 | 3 | rs1351905 | cnvi0010399 | 93.244 | 0 | PDE6D |
| chr17:44458950-81047708 | −8195 | 36588759 | 1 | cnvi0016818 | rs35680231 | 35.591 | 0 | PDE6G |
| chr17:62662507-81047708 | −11496 | 18385202 | 3 | rs6504246 | rs35680231 | 56.048 | 0 | PDE6G |
| chr16:176743-50013967 | 8328 | 49837225 | 3 | rs2562164 | rs12597023 | 174.392 | 0 | PDIA2 |
| chr5:161172541-179954615 | 4271 | 18782075 | 3 | rs4921415 | rs10059433 | 6.291 | 0 | PDLIM7 |
| chr5:4872310-180709915 | 35876 | 175837606 | 3 | rs816467 | rs10071993 | 179.394 | 0 | PDLIM7 |
| chr16:176743-50013967 | 8328 | 49837225 | 3 | rs2562164 | rs12597023 | 174.392 | 0 | PDPK1 |
| chr1:64114301-245591329 | 29842 | 181477029 | 1 | rs11208257 | rs1173850 | 37.504 | 0 | PEA15 |
| chr1:75098453-243531649 | 27360 | 168433197 | 1 | rs12117493 | rs10927002 | 32.113 | 0 | PEA15 |
| chr1:79710545-188898319 | 17303 | 109187775 | 1 | rs417181 | rs16829637 | 45.89 | 0 | PEA15 |
| chr1:109645793-194560463 | 12025 | 84914671 | 3 | cnvi0008281 | rs10921616 | 63.121 | 0 | PEA15 |
| chr5:39526068-67275356 | 4441 | 27749289 | 1 | rs16869031 | rs999826 | 77.848 | 0 | PELO |
| chr5:49952847-89853069 | 7268 | 39900223 | 3 | rs12188654 | rs42467 | 26.225 | 0 | PELO |
| chr5:4872310-180709915 | 35876 | 175837606 | 3 | rs816467 | rs10071993 | 179.394 | 0 | PELO |
| chr5:84830796-171903310 | 16642 | 87072515 | 1 | rs300657 | rs10042482 | 42.208 | 0 | PFDN1 |
| chr5:57343495-171903310 | 21683 | 114559816 | 1 | rs10940593 | rs10042482 | 61.169 | 0 | PFDN1 |
| chr5:98442871-150317237 | 9828 | 51874367 | 1 | rs1447379 | rs7710790 | 38.687 | 0 | PFDN1 |
| chr5:4872310-180709915 | 35876 | 175837606 | 3 | rs816467 | rs10071993 | 179.394 | 0 | PFDN1 |
| chr20:13712393-55093901 | 8218 | 41381509 | 1 | rs6033810 | rs6999 | 41.237 | 0 | PFDN4 |
| chr20:7869025-62424661 | 11941 | 54555637 | 3 | rs2294306 | rs6010652 | 9.732 | 0 | PFDN4 |
| chr20:4591715-58420336 | 11753 | 53828622 | 1 | rs6139494 | rs1416388 | 40.922 | 0 | PFDN4 |
| chr20:236802-54845796 | 12646 | 54608995 | 3 | rs448294 | rs6064362 | 286.151 | 0 | PFDN4 |
| chr12:10113083-116370432 | 20594 | 106257350 | 1 | rs2012504 | rs7958254 | 35.157 | 0 | PFDN5 |
| chr12:10020267-129866293 | 23654 | 119846027 | 1 | rs1597097 | rs2170504 | 45.428 | 0 | PFDN5 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr12:39967134-84174413 | 8879 | 44207280 | 1 | rs11172661 | rs11116039 | 39.568 | 0 | PFDN5 |
| chr12:50855195-133778796 | 17748 | 82923602 | 3 | rs4351895 | rs7975069 | 159.589 | 0 | PFDN5 |
| chr1:64114301-245591329 | 29842 | 181477029 | 1 | rs11208257 | rs1173850 | 37.504 | 0 | PFKFB2 |
| chr1:178626526-244159143 | 13064 | 65532618 | 3 | rs2761477 | rs479338 | 11.373 | 0 | PFKFB2 |
| chr1:75098453-243531449 | 27360 | 168433197 | 1 | rs12117493 | rs10927002 | 32.113 | 0 | PFKFB2 |
| chr1:188850774-235423607 | 10060 | 46572834 | 1 | rs16829466 | rs12409696 | 43.25 | 0 | PFKFB2 |
| chr1:191875752-235423607 | 9517 | 43547856 | 1 | rs9427811 | rs12409696 | 62.01 | 0 | PFKFB2 |
| chr1:189128124-227340790 | 7927 | 38212667 | 1 | rs7515205 | rs12752546 | 167.428 | 0 | PFKFB2 |
| chr1:174219398-247422297 | 15986 | 73202900 | 1 | rs16846809 | rs4642922 | 35.258 | 0 | PFKFB2 |
| chr1:197187605-226404457 | 6316 | 29216853 | 3 | rs10922187 | rs3008192 | 130.989 | 0 | PFKFB2 |
| chr17:108420-26610769 | 5548 | 26502350 | 3 | rs12452527 | rs658591 | 82.699 | 0 | PFN1 |
| chr1:64114301-245591329 | 29842 | 181477029 | 1 | rs11208257 | rs1173850 | 37.504 | 0 | PGM1 |
| chr1:1005806-105612342 | 19173 | 104606537 | 3 | rs3934834 | rs1584633 | 44.152 | 0 | PGM1 |
| chr1:2006108-109527861 | 22130 | 107521754 | 3 | rs2254669 | rs839879 | 162.269 | 0 | PGM1 |
| chr16:176743-50013967 | 8328 | 49837225 | 3 | rs2562164 | rs12597023 | 174.392 | 0 | PHKB |
| chr7:11855636-156148608 | 26852 | 144292973 | 1 | rs6947930 | rs6945016 | 36.446 | 0 | PHKG1 |
| chr8:8872727-156383359 | 27773 | 147510633 | 1 | rs917038 | rs878717 | 32.336 | 0 | PHKG1 |
| chr7:8794418-119068130 | 23484 | 110273713 | 1 | rs2189621 | rs6977904 | 70.867 | 0 | PHKG1 |
| chr7:56147898-56348924 | 35 | 201027 | 3 | cnvi0001044 | rs940494 | 33.6 | 0 | PHKG1 |
| chr7:60392-84158180 | 19095 | 84097789 | 3 | rs12670102 | rs2715048 | 208.308 | 0 | PHKG1 |
| chr16:29441284-33923125 | 585 | 4481842 | 3 | rs7206789 | rs4043755 | 42.437 | 0 | PHKG2 |
| chr16:176743-50013967 | 8328 | 49837225 | 3 | rs2562164 | rs12597023 | 174.392 | 0 | PHKG2 |
| chr19:266034-18061509 | 3100 | 17795476 | 3 | rs2312724 | rs7250332 | 19.51 | 0 | PIAS4 |
| chr19:629303-4119012 | 709 | 3489710 | 1 | rs2283575 | rs350887 | 26.758 | 0 | PIAS4 |
| chr19:288246-59110628 | 11009 | 58822383 | 3 | rs10409452 | cnvi0009466 | 100.582 | 0 | PIAS4 |
| chr22:16871137-51184393 | 9245 | 34313257 | 3 | rs131538 | rs7284680 | 209.79 | 0 | PICK1 |
| chr18:25388300-75954881 | 11539 | 50566582 | 1 | rs11083228 | rs1876021 | 39.235 | 0 | PIK3C3 |
| chr18:1583633-58142042 | 11490 | 56558410 | 3 | rs9945988 | rs1560399 | 3.736 | 0 | PIK3C3 |
| chr18:26550830-63713914 | 8241 | 37163085 | 1 | rs16945738 | rs2715304 | 17.922 | 0 | PIK3C3 |
| chr18:26162481-67193217 | 9255 | 41030737 | 1 | rs12458903 | rs9961907 | 31.327 | 0 | PIK3C3 |
| chr18:30929223-44720664 | 2910 | 13791442 | 3 | rs10775453 | rs9304343 | 535.348 | 0 | PIK3C3 |
| chr3:166503411-190576461 | 4854 | 24073051 | 1 | rs11925936 | rs1393054 | 31.414 | 0 | PIK3CA |
| chr3:102240202-195550366 | 17318 | 93310165 | 1 | rs1620217 | rs11711870 | 41.031 | 0 | PIK3CA |
| chr3:164955741-191742104 | 5741 | 26786364 | 1 | rs2218152 | rs9835019 | 52.438 | 0 | PIK3CA |
| chr3:83075971-196935657 | 21465 | 113859687 | 1 | rs9872858 | rs34729751 | 44.35 | 0 | PIK3CA |
| chr3:177912894-197551411 | 4129 | 19638518 | 3 | rs9290640 | rs12273562 | 185.507 | 0 | PIK3CA |
| chr7:11855636-156148608 | 26852 | 144292973 | 1 | rs6947930 | rs6945016 | 36.446 | 0 | PIK3CG |
| chr7:78621315-155831817 | 13678 | 77210503 | 3 | rs1006818 | rs6969015 | 123.319 | 0 | PIK3CG |
| chr7:8872727-156383359 | 27773 | 147510633 | 1 | rs917038 | rs878717 | 32.336 | 0 | PIK3CG |
| chr7:8794418-119068130 | 23484 | 110273713 | 1 | rs2189621 | rs6977904 | 70.867 | 0 | PIK3CG |
| chr7:84302877-110993169 | 5183 | 26690293 | 3 | rs4338048 | rs10254893 | 203.09 | 0 | PIK3CG |
| chr5:49952847-89853069 | 7268 | 39900223 | 3 | rs12188654 | rs42467 | 26.225 | 0 | PIK3R1 |
| chr5:57343495-171903310 | 21683 | 114559816 | 1 | rs10940593 | rs10042482 | 61.169 | 0 | PIK3R1 |
| chr5:4872310-180709915 | 35876 | 175837606 | 3 | rs816467 | rs10071993 | 179.394 | 0 | PIK3R1 |
| chr6:26922906-93578359 | 19746 | 66655454 | 1 | rs9348738 | rs9363009 | 27.061 | 0 | PLA2G7 |
| chr6:31289284-56929863 | 15402 | 25640580 | 3 | rs9265170 | cnvi0015437 | 25.647 | 0 | PLA2G7 |
| chr6:32968276-73449742 | 15442 | 40481467 | 3 | rs2395300 | rs4235869 | 415.87 | 0 | PLA2G7 |
| chr20:7869025-62424661 | 11941 | 54555637 | 3 | rs2294306 | rs6010652 | 9.732 | 0 | PLCB1 |
| chr20:4591715-58420336 | 11753 | 53828622 | 1 | rs61139494 | rs1416388 | 40.922 | 0 | PLCB1 |
| chr20:236802-54845796 | 12646 | 54608995 | 3 | rs448294 | rs6064362 | 286.151 | 0 | PLCB1 |
| chr15:29325866-56044189 | 5303 | 26718324 | 3 | rs4779705 | rs2414433 | 21.732 | 0 | PLCB2 |
| chr15:32939946-43104406 | 2544 | 10164461 | 3 | rs12594777 | rs13380301 | 32.942 | 0 | PLCB2 |
| chr11:42185849-126756938 | 15451 | 84571090 | 1 | rs4375424 | rs10750356 | 36.99 | 0 | PLCB3 |
| chr11:21723471-131521797 | 20508 | 109798327 | 1 | rs11828478 | rs2512898 | 27.565 | 0 | PLCB3 |
| chr11:23168804-106781292 | 16332 | 83612489 | 1 | rs11027007 | rs7103285 | 49.747 | 0 | PLCB3 |
| chr11:211482-66910826 | 13813 | 66699345 | 3 | rs2293168 | rs4375446 | 30.249 | 0 | PLCB3 |
| chr3:13878889-149737330 | 24723 | 135858442 | 1 | rs12634112 | rs2007869 | 55.663 | 0 | PLCD1 |
| chr3:33409611-170735099 | 23775 | 137325489 | 1 | rs3915062 | rs11924032 | 26.867 | 0 | PLCD1 |
| chr3:179527-114630641 | 23879 | 114451115 | 3 | rs4684741 | rs1587972 | 207.852 | 0 | PLCD1 |
| chr16:59854720-89273883 | 7609 | 29419164 | 3 | rs1373880 | rs8046156 | 31.884 | 0 | PLCG2 |
| chr16:64107047-82920737 | 4544 | 18813691 | 1 | rs2319723 | rs918661 | 28.887 | 0 | PLCG2 |
| chr16:50219449-89544756 | 10324 | 39325308 | 3 | rs6500298 | rs3803681 | 108.108 | 0 | PLCG2 |
| chr3:166503411-190576461 | 4854 | 24073051 | 1 | rs11925936 | rs1393054 | 31.414 | 0 | PLD1 |
| chr3:145967173-173869390 | 4912 | 27932718 | 3 | rs9863647 | rs7618997 | 46.396 | 0 | PLD1 |
| chr3:102240202-195550366 | 17318 | 93310165 | 1 | rs1620217 | rs11711870 | 41.031 | 0 | PLD1 |
| chr3:164955741-191742104 | 5741 | 26786364 | 1 | rs2218152 | rs9835019 | 52.438 | 0 | PLD1 |
| chr3:83075971-196935657 | 21465 | 113859687 | 1 | rs9872858 | rs34729751 | 44.35 | 0 | PLD1 |
| chr3:114889454-177826047 | 12700 | 62936594 | 3 | rs6795097 | rs7628308 | 102.526 | 0 | PLD1 |
| chr17:108420-26610769 | 5548 | 26502350 | 3 | rs12452527 | rs658591 | 82.699 | 0 | PLD2 |
| chr19:31569338-53780966 | 3788 | 22211629 | 1 | rs2867544 | rs10407424 | 33.9 | 0 | PLEKHA4 |
| chr19:43257015-55294329 | −7309 | 12037315 | 3 | rs7246152 | rs2569676 | 21.402 | 0 | PLEKHA4 |
| chr19:288246-59110628 | 11009 | 58822383 | 3 | rs10409452 | cnvi0009466 | 100.582 | 0 | PLEKHA4 |
| chr16:176743-50013967 | 8328 | 49837225 | 3 | rs2562164 | rs12597023 | 174.392 | 0 | PLK1 |
| chr11:42185849-126756938 | 15451 | 84571090 | 1 | rs4375424 | rs10750356 | 36.99 | 0 | POLA2 |
| chr11:21723471-131521797 | 20508 | 109798327 | 1 | rs11828478 | rs2512898 | 27.565 | 0 | POLA2 |
| chr11:23168804-106781292 | 16332 | 83612489 | 1 | rs11027007 | rs7103285 | 49.747 | 0 | POLA2 |
| chr11:211482-66910826 | 13813 | 66699345 | 3 | rs2293168 | rs4375446 | 30.249 | 0 | POLA2 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr8:30757798-142750969 | 20699 | 111993172 | 1 | rs10101203 | rs6421025 | 34.223 | 0 | POLB |
| chr8:41983076-50280013 | 418 | 8296938 | 1 | rs12544318 | rs12677656 | 39.988 | 0 | POLB |
| chr8:23218101-146274708 | 23020 | 123056608 | 1 | rs7010362 | rs7822726 | 38.828 | 0 | POLB |
| chr8:25304020-43159151 | 3371 | 17855132 | 3 | rs10503771 | cnvi0018779 | 263.504 | 0 | POLB |
| chr16:50219449-89544756 | 10324 | 39325308 | 3 | rs6500298 | rs3803681 | 108.108 | 0 | POLR2C |
| chr20:13712393-55093901 | 8218 | 41381509 | 1 | rs6033810 | rs6999 | 41.237 | 0 | POLR3F |
| chr20:7869025-62424661 | 11941 | 54555637 | 3 | rs2294306 | rs6010652 | 9.732 | 0 | POLR3F |
| chr20:4591715-58420336 | 11753 | 53828622 | 1 | rs6139494 | rs1416388 | 40.922 | 0 | POLR3F |
| chr20:18389203-18575485 | 42 | 186283 | 1 | rs4814744 | rs6045492 | 14.642 | 0 | POLR3F |
| chr20:236802-54845796 | 12646 | 54608995 | 3 | rs448294 | rs6064362 | 286.151 | 0 | POLR3F |
| chr22:43483242-51178090 | 2461 | 7694849 | 3 | rs8141749 | rs2285395 | 30.687 | 0 | PPARA |
| chr22:16871137-51184393 | 9245 | 34313257 | 3 | rs131538 | rs7284680 | 209.79 | 0 | PPARA |
| chr4:31222833-180548076 | 24457 | 149325244 | 1 | rs7662351 | rs3849606 | 36.162 | 0 | PPEF2 |
| chr4:68173959-185767176 | 20235 | 117593218 | 1 | rs6552083 | rs4862428 | 61.893 | 0 | PPEF2 |
| chr4:22401728-188608857 | 28456 | 166207130 | 1 | rs4697297 | rs7687115 | 35.717 | 0 | PPEF2 |
| chr4:63726348-173015421 | 19817 | 109289074 | 1 | rs17082970 | rs2131002 | 30.251 | 0 | PPEF2 |
| chr4:29179713-117038307 | 15513 | 87858595 | 1 | rs1507441 | rs1068807 | 71.6 | 0 | PPEF2 |
| chr4:69590353-190872778 | 23145 | 121282426 | 3 | rs293433 | rs12646565 | 315.633 | 0 | PPEF2 |
| chr1:1005806-105612342 | 19173 | 104606537 | 3 | rs3934834 | rs1584633 | 44.152 | 0 | PPIH |
| chr1:2006108-109527861 | 22130 | 107521754 | 3 | rs2254669 | rs839879 | 162.269 | 0 | PPIH |
| chr14:26898958-104436931 | 17396 | 77537974 | 1 | rs1245195 | rs11851097 | 57.233 | 0 | PPM1A |
| chr14:19917123-65327288 | 10286 | 45410166 | 3 | rs2495199 | rs9323455 | 270.291 | 0 | PPM1A |
| chr14:80818058-105348552 | 5492 | 24530495 | 3 | rs6574553 | rs2028416 | 15.874 | 0 | PPP1R13B |
| chr14:26898958-104436931 | 17396 | 77537974 | 1 | rs1245195 | rs11851097 | 57.233 | 0 | PPP1R13B |
| chr14:103847274-107188715 | 464 | 3341442 | 3 | rs8020912 | rs4280141 | 104.64 | 0 | PPP1R13B |
| chr19:31569338-53780966 | 3788 | 22211629 | 1 | rs2867544 | rs10407424 | 33.9 | 0 | PPP1R14A |
| chr19:288246-59110628 | 11009 | 58822383 | 3 | rs10409452 | cnvi0009466 | 100.582 | 0 | PPP1R14A |
| chr19:31569338-53780966 | 3788 | 22211629 | 1 | rs2867544 | rs10407424 | 33.9 | 0 | PPP2R1A |
| chr19:52365654-54612628 | 524 | 2246975 | 3 | rs4514789 | rs254262 | 59.657 | 0 | PPP2R1A |
| chr19:43257015-55294329 | −7309 | 12037315 | 3 | rs7246152 | rs2569676 | 21.402 | 0 | PPP2R1A |
| chr19:288246-59110628 | 11009 | 58822383 | 3 | rs10409452 | cnvi0009466 | 100.582 | 0 | PPP2R1A |
| chr4:31222833-180548076 | 24457 | 149325244 | 1 | rs7662351 | rs3849606 | 36.162 | 0 | PPP3CA |
| chr4:89603085-113991140 | 4018 | 24388056 | 3 | rs2972038 | rs2279892 | 28.405 | 0 | PPP3CA |
| chr4:68173959-185767176 | 20235 | 117593218 | 1 | rs6552083 | rs4862428 | 61.893 | 0 | PPP3CA |
| chr4:102178963-102407109 | 19 | 228147 | 1 | rs2850965 | rs1863575 | 20.006 | 0 | PPP3CA |
| chr4:22401728-188608857 | 28456 | 166207130 | 1 | rs4697297 | rs7687115 | 35.717 | 0 | PPP3CA |
| chr4:63726348-173015421 | 19817 | 109289074 | 1 | rs17082970 | rs2131002 | 30.251 | 0 | PPP3CA |
| chr4:29179713-117038307 | 15513 | 87858595 | 1 | rs1507441 | rs1068807 | 71.6 | 0 | PPP3CA |
| chr4:69590353-190872778 | 23145 | 121282426 | 3 | rs293433 | rs12646565 | 315.633 | 0 | PPP3CA |
| chr10:7188484-134205354 | 26672 | 127016871 | 1 | rs1977295 | rs3923858 | 50.772 | 0 | PPYR1 |
| chr10:734229-69155636 | 14859 | 68421408 | 3 | rs1769236 | rs2394375 | 72.104 | 0 | PPYR1 |
| chr10:46990728-47670202 | 87 | 679475 | 3 | rs7898282 | rs12774812 | 148.333 | 0 | PPYR1 |
| chr10:46928388-47703613 | 103 | 775326 | 3 | rs7915055 | rs4128664 | 211.228 | 0 | PPYR1 |
| chr10:47020220-47121726 | 9 | 101507 | 3 | rs4434936 | rs6599598 | 18.769 | 0 | PPYR1 |
| chr10:46565132-49372024 | 398 | 2806893 | 3 | cnvi0015902 | rs1111323 | 101.866 | 0 | PPYR1 |
| chr10:46961667-47703613 | 102 | 741947 | 3 | rs506372 | rs4128664 | 61.091 | 0 | PPYR1 |
| chr10:47020220-47121726 | 9 | 101507 | 3 | rs4434936 | rs6599598 | 15.584 | 0 | PPYR1 |
| chr10:46928388-52437780 | 1060 | 5509393 | 3 | rs7915055 | rs3001866 | 425.826 | 0 | PPYR1 |
| chr10:46691610-49246290 | 367 | 2554681 | 3 | rs2611445 | rs1058785 | 74.315 | 0 | PPYR1 |
| chr10:46961667-47748912 | 104 | 787246 | 3 | rs506372 | rs3013867 | 198.089 | 0 | PPYR1 |
| chr10:46928388-49059803 | 333 | 2131416 | 3 | rs7915055 | rs4926101 | 51.799 | 0 | PPYR1 |
| chr10:46961667-47670202 | 88 | 708536 | 3 | rs506372 | rs12774812 | 112.263 | 0 | PPYR1 |
| chr10:46961667-47748912 | 104 | 787246 | 3 | rs506372 | rs3013867 | 124.114 | 0 | PPYR1 |
| chr10:46961667-49059803 | 332 | 2098137 | 3 | rs506372 | rs4926101 | 252.089 | 0 | PPYR1 |
| chr10:47020220-47121726 | 102 | 728693 | 3 | rs4434936 | rs3013867 | 217.507 | 0 | PPYR1 |
| chr10:46928388-49059803 | 333 | 2131416 | 3 | rs7915055 | rs4926101 | 32.715 | 0 | PPYR1 |
| chr10:46961667-47748912 | 104 | 787246 | 3 | rs506372 | rs3013867 | 139.094 | 0 | PPYR1 |
| chr10:46961667-47748912 | 104 | 787246 | 3 | rs506372 | rs3013867 | 156.17 | 0 | PPYR1 |
| chr10:46769902-49047366 | 348 | 2277465 | 1 | cnvi0015917 | cnvi0022253 | 48.528 | 0 | PPYR1 |
| chr10:46928388-46988968 | 9 | 160581 | 3 | rs7915055 | rs28702886 | 7.159 | 0 | PPYR1 |
| chr10:46961667-47748912 | 104 | 787246 | 3 | rs506372 | rs3013867 | 97.267 | 0 | PPYR1 |
| chr10:46928388-47149117 | 13 | 220730 | 3 | rs7915055 | rs4979753 | 20.682 | 0 | PPYR1 |
| chr10:46961667-47121726 | 11 | 160060 | 3 | rs506372 | rs6599598 | 15.813 | 0 | PPYR1 |
| chr10:46961667-47748912 | 104 | 787246 | 3 | rs506372 | rs3013867 | 124.017 | 0 | PPYR1 |
| chr10:46961667-47088968 | 8 | 127302 | 3 | rs506372 | rs28702886 | 21.05 | 0 | PPYR1 |
| chr10:46928388-49201964 | 334 | 2273577 | 3 | rs7915055 | rs3013936 | 217.279 | 0 | PPYR1 |
| chr10:47041592-47164700 | 10 | 123109 | 3 | rs4593952 | cnvi0019847 | 26.227 | 0 | PPYR1 |
| chr10:47020220-47121726 | 9 | 101507 | 3 | rs4434936 | rs6599598 | 19.555 | 0 | PPYR1 |
| chr10:46928388-47121726 | 12 | 193339 | 3 | rs7915055 | rs6599598 | 17.084 | 0 | PPYR1 |
| chr10:46961667-47748912 | 104 | 787246 | 3 | rs506372 | rs3013867 | 72.604 | 0 | PPYR1 |
| chr10:46961667-47149117 | 12 | 187451 | 3 | rs506372 | rs4979753 | 25.412 | 0 | PPYR1 |
| chr10:46961667-47099529 | 9 | 137863 | 3 | rs506372 | rs4481963 | 14.479 | 0 | PPYR1 |
| chr10:46961667-47099529 | 9 | 137863 | 3 | rs506372 | rs4481963 | 5.516 | 0 | PPYR1 |
| chr10:46961667-47121726 | 11 | 160060 | 3 | rs506372 | rs6599598 | 17.522 | 0 | PPYR1 |
| chr10:46961667-47121726 | 11 | 160060 | 3 | rs506372 | rs6599598 | 8.359 | 0 | PPYR1 |
| chr10:46928388-47748912 | 105 | 820525 | 3 | rs7915055 | rs3013867 | 115.204 | 0 | PPYR1 |
| chr10:46961667-47121726 | 11 | 160060 | 3 | rs506372 | rs6599598 | 21.039 | 0 | PPYR1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr10:47020220-47121726 | 9 | 101507 | 3 | rs4434936 | rs6599598 | 11.163 | 0 | PPYR1 |
| chr10:46892172-47149117 | 15 | 256946 | 3 | cnvi0015924 | rs4979753 | 35.314 | 0 | PPYR1 |
| chr10:46961667-47121726 | 11 | 160060 | 3 | rs506372 | rs6599598 | 13.506 | 0 | PPYR1 |
| chr10:46961667-47121726 | 11 | 160060 | 3 | rs506372 | rs6599598 | 21.312 | 0 | PPYR1 |
| chr10:46961667-47121726 | 11 | 160060 | 3 | rs506372 | rs6599598 | 15.771 | 0 | PPYR1 |
| chr10:46990728-47748912 | 103 | 758185 | 3 | rs7898282 | rs3013867 | 14.294 | 0 | PPYR1 |
| chr10:46961667-47748912 | 104 | 787246 | 3 | rs506372 | rs3013867 | 164.218 | 0 | PPYR1 |
| chr10:46961667-47121726 | 11 | 160060 | 3 | rs506372 | rs6599598 | 12.386 | 0 | PPYR1 |
| chr10:46961667-47121726 | 11 | 160060 | 3 | rs506372 | rs6599598 | 11.748 | 0 | PPYR1 |
| chr10:46990728-47703613 | 101 | 712886 | 3 | rs7898282 | rs4128664 | 119.651 | 0 | PPYR1 |
| chr10:88874-53366180 | 12853 | 53277307 | 3 | cnvi0015449 | rs10998465 | 319.021 | 0 | PPYR1 |
| chr1:1005806-105612342 | 19173 | 104606537 | 3 | rs3934834 | rs1584633 | 44.152 | 0 | PRDX1 |
| chr1:2006108-109527861 | 22130 | 107521754 | 3 | rs2254669 | rs839879 | 162.269 | 0 | PRDX1 |
| chr11:42185849-126756938 | 15451 | 84571090 | 1 | rs4375424 | rs10750356 | 36.99 | 0 | PRG2 |
| chr11:21723471-131521797 | 20508 | 109798327 | 1 | rs11828478 | rs2512898 | 27.565 | 0 | PRG2 |
| chr11:23168804-106781292 | 16332 | 83612489 | 1 | rs11027007 | rs7103285 | 49.747 | 0 | PRG2 |
| chr11:211482-66910826 | 13813 | 66699345 | 3 | rs2293168 | rs4375446 | 30.249 | 0 | PRG2 |
| chr19:266034-18061509 | 3100 | 17795476 | 3 | rs2312724 | rs7250332 | 19.51 | 0 | PRKACA |
| chr19:288246-59110628 | 11009 | 58822383 | 3 | rs10409452 | cnvi0009466 | 100.582 | 0 | PRKACA |
| chr7:44458950-81047708 | −8195 | 36588759 | 1 | cnvi0016818 | rs35680231 | 35.591 | 0 | PRKCA |
| chr7:21685812-67308196 | 12365 | 45622385 | 1 | rs34864328 | rs17686852 | 50.018 | 0 | PRKCA |
| chr7:61016209-66240093 | 890 | 5223885 | 1 | rs1588368 | rs11658645 | 37.309 | 0 | PRKCA |
| chr7:59314257-66170047 | 1135 | 6855791 | 1 | rs758467 | rs4558468 | 71.379 | 0 | PRKCA |
| chr7:62662507-81047708 | −11496 | 18385202 | 3 | rs6504246 | rs35680231 | 56.048 | 0 | PRKCA |
| chr3:13878889-149737330 | 24723 | 135858442 | 1 | rs12634112 | rs2007869 | 55.663 | 0 | PRKCD |
| chr3:53033796-53274602 | 48 | 240807 | 3 | rs12635298 | rs2306569 | 0.826 | 0 | PRKCD |
| chr3:33409611-170735099 | 23775 | 137325489 | 1 | rs3915062 | rs11924032 | 26.867 | 0 | PRKCD |
| chr3:179527-114630641 | 23879 | 114451115 | 3 | rs4684741 | rs1587972 | 207.852 | 0 | PRKCD |
| chr19:53533161-54743217 | 317 | 1210057 | 3 | rs2870438 | rs17239607 | 11.393 | 0 | PRKCG |
| chr19:52365654-54612628 | 524 | 2246975 | 3 | rs4514789 | rs254262 | 59.657 | 0 | PRKCG |
| chr19:43257015-55294329 | −7309 | 12037315 | 3 | rs7246152 | rs2569676 | 21.402 | 0 | PRKCG |
| chr19:288246-59110628 | 11009 | 58822383 | 3 | rs10409452 | cnvi0009466 | 100.582 | 0 | PRKCG |
| chr3:166503411-190576461 | 4854 | 24073051 | 1 | rs11925936 | rs1393054 | 31.414 | 0 | PRKCI |
| chr3:145967173-173899890 | 4912 | 27932718 | 3 | rs9863647 | rs7618997 | 46.396 | 0 | PRKCI |
| chr3:33409611-170735099 | 23775 | 137325489 | 1 | rs3915062 | rs11924032 | 26.867 | 0 | PRKCI |
| chr3:102240202-195550366 | 17318 | 93310165 | 1 | rs1620217 | rs11711870 | 41.031 | 0 | PRKCI |
| chr3:164955741-191742104 | 5741 | 26786364 | 1 | rs2218152 | rs9835019 | 52.438 | 0 | PRKCI |
| chr3:83075971-196935657 | 21465 | 113859687 | 1 | rs9872858 | rs34729751 | 44.35 | 0 | PRKCI |
| chr3:114889454-177826047 | 12700 | 62936594 | 3 | rs6795297 | rs7628308 | 102.526 | 0 | PRKCI |
| chr1:1005806-105612342 | 19173 | 104606537 | 3 | rs3934834 | rs1584633 | 44.152 | 0 | PRKCZ |
| chr1:1229770-2378046 | 167 | 1148277 | 1 | rs6669227 | rs34241773 | 44.903 | 0 | PRKCZ |
| chr1:2113565-2379248 | 78 | 265684 | 1 | rs262688 | rs11581548 | 72.771 | 0 | PRKCZ |
| chr1:1911558-2218100 | 55 | 306543 | 1 | rs28645431 | rs12119470 | 41.757 | 0 | PRKCZ |
| chr1:1201632-2182470 | 109 | 980839 | 1 | rs12402622 | rs260512 | 27.748 | 0 | PRKCZ |
| chr1:1254841-3342804 | 386 | 2087964 | 1 | rs10907179 | rs870171 | 39.259 | 0 | PRKCZ |
| chr1:2006108-109527861 | 22130 | 107521754 | 3 | rs2254669 | rs839879 | 162.269 | 0 | PRKCZ |
| chr10:7188484-134205354 | 26672 | 127016871 | 1 | rs1977295 | rs3923858 | 50.772 | 0 | PRKG1 |
| chr10:734229-69155636 | 14859 | 68421408 | 3 | rs1769236 | rs2394375 | 72.104 | 0 | PRKG1 |
| chr10:53679060-53826682 | 70 | 147623 | 1 | rs1937683 | rs10824010 | 27.553 | 0 | PRKG1 |
| chr10:53602190-135522754 | 19167 | 81920565 | 3 | rs12247820 | rs10909028 | 139.373 | 0 | PRKG1 |
| chr10:88874-53366180 | 12853 | 53277307 | 3 | cnvi0015449 | rs10998465 | 319.021 | 0 | PRKG1 |
| chr10:7188484-134205354 | 26672 | 127016871 | 1 | rs1977295 | rs3923858 | 50.772 | 0 | PRLHR |
| chr10:58385643-124973104 | 13625 | 66587462 | 1 | rs7920235 | rs17663304 | 36.18 | 0 | PRLHR |
| chr10:57671424-133349223 | 16243 | 75677800 | 1 | rs11005106 | rs4301710 | 37.114 | 0 | PRLHR |
| chr10:53602190-135522754 | 19167 | 81920565 | 3 | rs12247820 | rs10909028 | 139.373 | 0 | PRLHR |
| chr19:31569338-53780966 | 3788 | 22211629 | 1 | rs2867544 | rs10407424 | 33.9 | 0 | PRMT1 |
| chr19:43257015-55294329 | −7309 | 12037315 | 3 | rs7246152 | rs2569676 | 21.402 | 0 | PRMT1 |
| chr19:288246-59110628 | 11009 | 58822383 | 3 | rs10409452 | cnvi0009466 | 100.582 | 0 | PRMT1 |
| chr7:44458950-81047708 | −8195 | 36588759 | 1 | cnvi0016818 | rs35680231 | 35.591 | 0 | PRPSAP1 |
| chr7:62662507-81047708 | −11496 | 18385202 | 3 | rs6504246 | rs35680231 | 56.048 | 0 | PRPSAP1 |
| chr9:1989033-107532317 | 18263 | 105543285 | 1 | rs7864828 | rs10820726 | 39.824 | 0 | PSAT1 |
| chr9:2522475-140068342 | 25719 | 137545868 | 3 | rs10966757 | rs4074426 | 93.386 | 0 | PSAT1 |
| chr9:33180228-132003792 | 14691 | 98823565 | 1 | rs7854765 | rs9408988 | 28.69 | 0 | PSAT1 |
| chr9:46587-94335290 | 17484 | 94288704 | 3 | rs10814410 | rs9409606 | 762.393 | 0 | PSAT1 |
| chr14:26898958-104436931 | 17396 | 77537974 | 1 | rs1245195 | rs11851097 | 57.233 | 0 | PSEN1 |
| chr14:65405722-103799039 | 8979 | 38393318 | 3 | rs11623705 | rs11628472 | 266.153 | 0 | PSEN1 |
| chr1:64114301-245591329 | 29842 | 181477029 | 1 | rs11208257 | rs1173850 | 37.504 | 0 | PSEN2 |
| chr1:178626526-244159143 | 13064 | 65532618 | 3 | rs2761477 | rs479338 | 11.373 | 0 | PSEN2 |
| chr1:75098453-243531649 | 27360 | 168433197 | 1 | rs12117493 | rs10927002 | 32.113 | 0 | PSEN2 |
| chr1:188850774-235423607 | 10060 | 46572834 | 1 | rs16829466 | rs12409696 | 43.25 | 0 | PSEN2 |
| chr1:191875752-235423607 | 9517 | 43547856 | 1 | rs9427811 | rs12409696 | 62.01 | 0 | PSEN2 |
| chr1:189128124-227340790 | 7927 | 38212667 | 1 | rs7515205 | rs12752546 | 167.428 | 0 | PSEN2 |
| chr1:174219398-247422297 | 15986 | 73202900 | 1 | rs16846809 | rs4642922 | 35.258 | 0 | PSEN2 |
| chr1:226423572-227452700 | 215 | 1029129 | 1 | rs6605032 | rs1969230 | 24.875 | 0 | PSEN2 |
| chr1:226536645-236803753 | 2600 | 10267109 | 3 | rs874583 | rs10925178 | 100.109 | 0 | PSEN2 |
| chr19:31569338-53780966 | 3788 | 22211629 | 1 | rs2867544 | rs10407424 | 33.9 | 0 | PSG9 |
| chr19:43257015-55294329 | −7309 | 12037315 | 3 | rs7246152 | rs2569676 | 21.402 | 0 | PSG9 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr19:43318068-43774853 | 60 | 456786 | 3 | rs10410612 | rs11672322 | 88.945 | 0 | PSG9 |
| chr19:43663086-43840088 | 54 | 177003 | 1 | rs12460930 | rs2159134 | 65.237 | 0 | PSG9 |
| chr19:43465816-43774853 | 41 | 309038 | 3 | rs17345014 | rs11672322 | 25.803 | 0 | PSG9 |
| chr19:288246-59110628 | 11009 | 58822383 | 3 | rs10409452 | cnvi0009466 | 100.582 | 0 | PSG9 |
| chr11:345515-17408630 | 4247 | 17063116 | 3 | rs11246094 | rs5215 | 30.474 | 0 | PSMA1 |
| chr11:211482-66910826 | 13813 | 66699345 | 3 | rs2293168 | rs4375446 | 30.249 | 0 | PSMA1 |
| chr7:11855636-156148608 | 26852 | 144292973 | 1 | rs6947930 | rs6945016 | 36.446 | 0 | PSMA2 |
| chr7:7724805-53845684 | 11772 | 46120880 | 3 | rs10263415 | rs6948633 | 42.007 | 0 | PSMA2 |
| chr7:8872727-156383359 | 27773 | 147510633 | 1 | rs917038 | rs878717 | 32.336 | 0 | PSMA2 |
| chr7:8794418-119068130 | 23484 | 110273713 | 1 | rs2189621 | rs6977904 | 70.867 | 0 | PSMA2 |
| chr7:60392-84158180 | 19095 | 84097789 | 3 | rs12670102 | rs2715048 | 208.308 | 0 | PSMA2 |
| chr14:80818058-105348552 | 5492 | 24530495 | 3 | rs6574553 | rs2028416 | 15.874 | 0 | PSMC1 |
| chr14:90716051-90836365 | 22 | 120315 | 1 | rs11159958 | rs11626241 | 15.241 | 0 | PSMC1 |
| chr14:26898958-104436931 | 17396 | 77537974 | 1 | rs1245195 | rs11851097 | 57.233 | 0 | PSMC1 |
| chr14:65405722-103799039 | 8979 | 38393318 | 3 | rs11623705 | rs11628472 | 266.153 | 0 | PSMC1 |
| chr2:231927569-232035793 | 10 | 108225 | 1 | rs3815844 | rs2032953 | 14.229 | 0 | PSMD1 |
| chr2:34870277-241929621 | 37755 | 207059345 | 3 | rs13422005 | rs10205276 | 46.946 | 0 | PSMD1 |
| chr2:38101137-241482099 | 36812 | 203380963 | 1 | rs879321 | rs7576043 | 52.099 | 0 | PSMD1 |
| chr2:193255360-242529978 | 10289 | 49274619 | 3 | rs1351905 | cnvi0010399 | 93.244 | 0 | PSMD1 |
| chr17:21685812-67308196 | 12365 | 45622385 | 1 | rs34864328 | rs17686852 | 50.018 | 0 | PSMD11 |
| chr17:26648492-58955084 | 5831 | 32306593 | 3 | rs1981512 | rs8068776 | 15.642 | 0 | PSMD11 |
| chr11:211482-66910826 | 13813 | 66699345 | 3 | rs2293168 | rs4375446 | 30.249 | 0 | PSMD13 |
| chr3:166503411-190576461 | 4854 | 24073051 | 1 | rs11925936 | rs1393054 | 31.414 | 0 | PSMD2 |
| chr3:102240202-195550366 | 17318 | 93310165 | 1 | rs1620217 | rs11711870 | 41.031 | 0 | PSMD2 |
| chr3:164955741-191742104 | 5741 | 26786364 | 1 | rs2218152 | rs9835019 | 52.438 | 0 | PSMD2 |
| chr3:83075971-196935657 | 21465 | 113859687 | 1 | rs9872858 | rs34729751 | 44.35 | 0 | PSMD2 |
| chr3:177912894-197551411 | 4129 | 19638518 | 3 | rs9290640 | rs1273562 | 185.507 | 0 | PSMD2 |
| chr3:13878889-149737330 | 24723 | 135858442 | 1 | rs12634112 | rs2007869 | 55.663 | 0 | PSMD6 |
| chr3:33409611-170735099 | 23775 | 137325489 | 1 | rs3915062 | rs11924032 | 26.867 | 0 | PSMD6 |
| chr3:179527-114630466 | 23879 | 114451115 | 3 | rs4684741 | rs1587972 | 207.852 | 0 | PSMD6 |
| chr14:22513116-32242747 | 1997 | 9729632 | 1 | rs4982546 | rs17098165 | 31.673 | 0 | PSME1 |
| chr14:22349686-25012115 | 755 | 2662430 | 1 | rs994827 | rs7142675 | 27.602 | 0 | PSME1 |
| chr14:19917123-65327288 | 10286 | 45410166 | 3 | rs2495197 | rs9323455 | 270.291 | 0 | PSME1 |
| chr13:20211434-20377448 | 13 | 166015 | 3 | rs11617480 | rs9508901 | 22.015 | 0 | PSPC1 |
| chr13:19584477-81204058 | 13265 | 61619612 | 3 | rs1334954 | rs1176297 | 22.162 | 0 | PSPC1 |
| chr13:20338643-20442879 | 14 | 104237 | 1 | rs4769903 | rs9552026 | 14.251 | 0 | PSPC1 |
| chr13:19771535-20664819 | 93 | 893285 | 1 | rs9511997 | rs9509033 | 30.263 | 0 | PSPC1 |
| chr13:19121741-63373781 | 10326 | 44252041 | 3 | rs9578050 | rs9539575 | 82.761 | 0 | PSPC1 |
| chr19:31569338-53780966 | 3788 | 22211629 | 1 | rs2867544 | rs10407424 | 33.9 | 0 | PTGIR |
| chr19:43257015-55294329 | −7309 | 12037315 | 3 | rs7246152 | rs2569676 | 21.402 | 0 | PTGIR |
| chr19:288246-59110628 | 11009 | 58822383 | 3 | rs10409452 | cnvi0009466 | 100.582 | 0 | PTGIR |
| chr6:26922906-93578359 | 19746 | 66655454 | 1 | rs9348738 | rs9363009 | 27.061 | 0 | PTP4A1 |
| chr6:62697746-94090076 | 6391 | 31392331 | 1 | rs6455128 | rs3799807 | 108.85 | 0 | PTP4A1 |
| chr6:62697746-67410283 | 787 | 4712538 | 1 | rs6455128 | rs9294717 | 74.311 | 0 | PTP4A1 |
| chr6:32968276-73449742 | 15442 | 40481467 | 3 | rs2395300 | rs4235869 | 415.87 | 0 | PTP4A1 |
| chr8:30757798-142750969 | 20699 | 111993172 | 1 | rs10101203 | rs6421025 | 34.223 | 0 | PTP4A3 |
| chr8:60424884-145286483 | 17030 | 84861600 | 3 | rs1401422 | rs9720889 | 8.858 | 0 | PTP4A3 |
| chr8:23218101-146274708 | 23020 | 123056608 | 1 | rs7010362 | rs7822726 | 38.828 | 0 | PTP4A3 |
| chr8:66822030-144791126 | 16557 | 77969097 | 3 | rs6472235 | rs10100154 | 251.068 | 0 | PTP4A3 |
| chr12:10113083-116370432 | 20594 | 106257350 | 1 | rs2012504 | rs7958254 | 35.157 | 0 | PTPN11 |
| chr12:59512781-127744939 | 13469 | 68232159 | 3 | rs908394 | rs7966946 | 20.62 | 0 | PTPN11 |
| chr12:10020267-129866293 | 23654 | 119846027 | 1 | rs1597097 | rs2170504 | 45.428 | 0 | PTPN11 |
| chr12:112610714-133708729 | 5366 | 21098016 | 3 | rs11066188 | rs11147249 | 695.45 | 0 | PTPN11 |
| chr12:50855195-133778796 | 17748 | 82923602 | 3 | rs4351895 | rs7975069 | 159.589 | 0 | PTPN11 |
| chr7:11855636-156148608 | 26852 | 144292973 | 1 | rs6947930 | rs6945016 | 36.446 | 0 | PTPN12 |
| chr7:8872727-156383359 | 27773 | 147510633 | 1 | rs917038 | rs878717 | 32.336 | 0 | PTPN12 |
| chr7:8794418-119068130 | 23484 | 110273713 | 1 | rs2189621 | rs6977904 | 70.867 | 0 | PTPN12 |
| chr7:60392-84158180 | 19095 | 84097789 | 3 | rs12670102 | rs2715048 | 208.308 | 0 | PTPN12 |
| chr2:207886-50770291 | 11565 | 50562406 | 3 | rs868249 | rs4477515 | 43.892 | 0 | PTPN6 |
| chr20:2882947-3055513 | 33 | 172567 | 1 | rs6138938 | rs4813627 | 15.318 | 0 | PTPRA |
| chr20:236802-54845796 | 12646 | 54608995 | 3 | rs448294 | rs6064362 | 286.151 | 0 | PTPRA |
| chr11:42185849-126756938 | 15451 | 84571090 | 1 | rs4375424 | rs10750356 | 36.99 | 0 | PTPRJ |
| chr11:21723471-131521797 | 20508 | 109798327 | 1 | rs11828478 | rs2512898 | 27.565 | 0 | PTPRJ |
| chr11:23168804-106781292 | 16332 | 83612489 | 1 | rs11027007 | rs7103285 | 49.747 | 0 | PTPRJ |
| chr11:211482-66910826 | 13813 | 66699345 | 3 | rs2293168 | rs4375446 | 30.249 | 0 | PTPRJ |
| chr19:266034-18061509 | 3100 | 17795476 | 3 | rs2312724 | rs7250332 | 19.51 | 0 | PTPRS |
| chr19:288246-59110628 | 11009 | 58822383 | 3 | rs10409452 | cnvi0009466 | 100.582 | 0 | PTPRS |
| chr1:1005806-105612342 | 19173 | 104606537 | 3 | rs3934834 | rs1584633 | 44.152 | 0 | PTPRU |
| chr1:2006108-109527861 | 22130 | 107521754 | 3 | rs2254669 | rs839879 | 162.269 | 0 | PTPRU |
| chr12:59512781-127744939 | 13469 | 68232159 | 3 | rs908394 | rs7966946 | 20.62 | 0 | PXN |
| chr12:10020267-129866293 | 23654 | 119846027 | 1 | rs1597097 | rs2170504 | 45.428 | 0 | PXN |
| chr12:112610714-133708729 | 5366 | 21098016 | 3 | rs11066188 | rs11147249 | 695.45 | 0 | PXN |
| chr12:50855195-133778796 | 17748 | 82923602 | 3 | rs4351895 | rs7975069 | 159.589 | 0 | PXN |
| chr14:26898958-104436931 | 17396 | 77537974 | 1 | rs1245195 | rs11851097 | 57.233 | 0 | PYGL |
| chr14:19917123-65327288 | 10286 | 45410166 | 3 | rs2495197 | rs9323455 | 270.291 | 0 | PYGL |
| chr11:42185849-126756938 | 15451 | 84571090 | 1 | rs4375424 | rs10750356 | 36.99 | 0 | PYGM |
| chr11:21723471-131521797 | 20508 | 109798327 | 1 | rs11828478 | rs2512898 | 27.565 | 0 | PYGM |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr11:23168804-106781292 | 16332 | 83612489 | 1 | rs11027007 | rs7103285 | 49.747 | 0 | PYGM |
| chr11:211482-66910826 | 13813 | 66699345 | 3 | rs2293168 | rs4375446 | 30.249 | 0 | PYGM |
| chr17:44458950-81047708 | −8195 | 36588759 | 1 | cnvi0016818 | rs35680231 | 35.591 | 0 | QRICH2 |
| chr17:62662507-81047708 | −11496 | 18385202 | 3 | rs6504246 | rs35680231 | 56.048 | 0 | QRICH2 |
| chr15:29325866-56044189 | 5303 | 26718324 | 3 | rs4779705 | rs2414433 | 21.732 | 0 | RAB27A |
| chr15:51688996-102398060 | 11030 | 50709065 | 1 | rs2459396 | rs7181527 | 36.939 | 0 | RAB27A |
| chr15:53775670-96810867 | 9973 | 43035198 | 1 | rs657495 | rs2589238 | 49.204 | 0 | RAB27A |
| chr15:43392075-66051345 | 4963 | 22659271 | 3 | rs8028608 | rs6494537 | 59.842 | 0 | RAB27A |
| chr1:1005806-105612342 | 19173 | 104606537 | 3 | rs3934834 | rs1584633 | 44.152 | 0 | RAB3B |
| chr1:2006108-109527861 | 22130 | 107521754 | 3 | rs2254669 | rs839879 | 162.269 | 0 | RAB3B |
| chr3:13878889-149737330 | 24723 | 135858442 | 1 | rs12634112 | rs2007869 | 55.663 | 0 | RAB5A |
| chr3:179527-114630641 | 23879 | 114451115 | 3 | rs4684741 | rs1587972 | 207.852 | 0 | RAB5A |
| chr15:51688996-102398060 | 11030 | 50709065 | 1 | rs2459396 | rs7181527 | 36.939 | 0 | RAB8B |
| chr15:53775670-96810867 | 9973 | 43035198 | 1 | rs657495 | rs2589238 | 49.204 | 0 | RAB8B |
| chr15:43392075-66051345 | 4963 | 22659271 | 3 | rs8028608 | rs6494537 | 59.842 | 0 | RAB8B |
| chr19:42462788-42637232 | 14 | 174445 | 1 | rs1075728 | rs3826705 | 19.764 | 0 | RABAC1 |
| chr19:31569338-53780966 | 3788 | 22211629 | 1 | rs2867544 | rs10407424 | 33.9 | 0 | RABAC1 |
| chr19:288246-59110628 | 11009 | 58822383 | 3 | rs10409452 | cnvi0009466 | 100.582 | 0 | RABAC1 |
| chr7:60392-84158180 | 19095 | 84097789 | 3 | rs12670102 | rs2715048 | 208.308 | 0 | RAC1 |
| chr12:10113083-116370432 | 20594 | 106257350 | 1 | rs2012504 | rs7958254 | 35.157 | 0 | RACGAP1 |
| chr12:10020267-129866293 | 23654 | 119846027 | 1 | rs1597097 | rs2170504 | 45.428 | 0 | RACGAP1 |
| chr12:39967134-84174413 | 8879 | 44207820 | 1 | rs11172661 | rs11116039 | 39.568 | 0 | RACGAP1 |
| chr12:207886-50770291 | 11565 | 50562406 | 3 | rs868249 | rs4477515 | 43.892 | 0 | RACGAP1 |
| chr3:179527-114630641 | 23879 | 114451115 | 3 | rs4684741 | rs1587972 | 207.852 | 0 | RAF1 |
| chr7:11855636-156148608 | 26852 | 144292973 | 1 | rs6947930 | rs6945016 | 36.446 | 0 | RALA |
| chr7:7724805-53845684 | 11772 | 46120880 | 3 | rs10263415 | rs6948633 | 42.007 | 0 | RALA |
| chr7:8872727-156383359 | 27773 | 147510633 | 1 | rs917038 | rs878717 | 32.336 | 0 | RALA |
| chr7:8794418-119068130 | 23484 | 110273713 | 1 | rs2189621 | rs6977904 | 70.867 | 0 | RALA |
| chr7:60392-84158180 | 19095 | 84097789 | 3 | rs12670102 | rs2715048 | 208.308 | 0 | RALA |
| chr2:12056323-227979775 | 39094 | 215923453 | 1 | rs966391 | rs1922020 | 31.384 | 0 | RALB |
| chr2:34870277-241929621 | 37755 | 207059345 | 3 | rs13422005 | rs10205276 | 46.946 | 0 | RALB |
| chr2:38101137-241482099 | 36812 | 203380963 | 1 | rs879321 | rs7576043 | 52.099 | 0 | RALB |
| chr2:77041264-194763754 | 21140 | 117722491 | 1 | rs2102827 | rs16835406 | 94.091 | 0 | RALB |
| chr2:83383702-175194550 | 16291 | 91810849 | 3 | rs12469609 | rs11891208 | 154.4 | 0 | RALB |
| chr22:19601238-20241160 | 201 | 639923 | 3 | rs8135473 | rs1567871 | 11.687 | 0 | RANBP1 |
| chr22:18907405-21465780 | 610 | 2558376 | 3 | rs9618419 | rs11703181 | 1799.961 | 0 | RANBP1 |
| chr22:18877787-21462353 | 613 | 2584567 | 1 | rs2543958 | rs140392 | 772.063 | 0 | RANBP1 |
| chr22:18877787-21462353 | 512 | 2584567 | 1 | rs2543958 | rs140392 | 1596.687 | 0 | RANBP1 |
| chr22:16871137-51184393 | 9245 | 34313257 | 3 | rs131538 | rs7284680 | 209.79 | 0 | RANBP1 |
| chr13:36707502-103656104 | 13622 | 66948603 | 1 | rs3827890 | rs1952590 | 38.726 | 0 | RAP2A |
| chr13:87746779-104646511 | 3908 | 16899733 | 3 | rs9301986 | rs17414312 | 27.724 | 0 | RAP2A |
| chr13:23742931-115064482 | 19829 | 91321552 | 1 | rs4770401 | rs7999630 | 44.074 | 0 | RAP2A |
| chr13:90018392-105190802 | 4136 | 15172411 | 1 | rs7335222 | rs11841281 | 42.954 | 0 | RAP2A |
| chr13:65193124-115053155 | 12025 | 49860032 | 3 | rs9598811 | rs7327124 | 78.057 | 0 | RAP2A |
| chr3:13878889-149737330 | 24723 | 135858442 | 1 | rs12634112 | rs2007869 | 55.663 | 0 | RASSF1 |
| chr3:33409611-170735099 | 23775 | 137325489 | 1 | rs3915062 | rs11924032 | 26.867 | 0 | RASSF1 |
| chr3:179527-114630641 | 23879 | 114451115 | 3 | rs4684741 | rs1587972 | 207.852 | 0 | RASSF1 |
| chr14:22513116-32242747 | 1997 | 9729632 | 1 | rs4982546 | rs17098165 | 31.673 | 0 | RBM23 |
| chr14:22513116-24480333 | 636 | 1967218 | 1 | rs4982546 | rs4982844 | 28.02 | 0 | RBM23 |
| chr14:22349686-25012115 | 755 | 2662430 | 1 | rs994827 | rs7142675 | 27.602 | 0 | RBM23 |
| chr14:19917123-65327288 | 10286 | 45410166 | 3 | rs2495197 | rs9323455 | 270.291 | 0 | RBM23 |
| chr3:13878889-149737330 | 24723 | 135858442 | 1 | rs12634112 | rs2007869 | 55.663 | 0 | RBM5 |
| chr3:33409611-170735099 | 23775 | 137325489 | 1 | rs3915062 | rs11924032 | 26.867 | 0 | RBM5 |
| chr3:50028385-50132131 | 12 | 103747 | 1 | rs4688758 | rs2624834 | 12.939 | 0 | RBM5 |
| chr3:179527-114630641 | 23879 | 114451115 | 3 | rs4684741 | rs1587972 | 207.852 | 0 | RBM5 |
| chr1:1005806-105612342 | 19173 | 104606537 | 3 | rs3934834 | rs1584633 | 44.152 | 0 | RCC1 |
| chr1:2006108-109527861 | 22130 | 107521754 | 3 | rs2254669 | rs839879 | 162.269 | 0 | RCC1 |
| chr1:1005806-105612342 | 19173 | 104606537 | 3 | rs3934834 | rs1584633 | 44.152 | 0 | RCC2 |
| chr1:2006108-109527861 | 22130 | 107521754 | 3 | rs2254669 | rs839879 | 162.269 | 0 | RCC2 |
| chr17:108420-26610769 | 5548 | 26502350 | 3 | rs12452527 | rs658591 | 82.699 | 0 | RCVRN |
| chr2:12056323-227979775 | 39094 | 215923453 | 1 | rs966391 | rs1922020 | 31.384 | 0 | REL |
| chr2:34870277-241929621 | 37755 | 207059345 | 3 | rs13422005 | rs10205276 | 46.946 | 0 | REL |
| chr2:38101137-241482099 | 36812 | 203380963 | 1 | rs879321 | rs7576043 | 52.099 | 0 | REL |
| chr2:41212010-82396210 | 9721 | 41184202 | 3 | rs12614285 | rs934310 | 396.396 | 0 | REL |
| chr11:42185849-126756938 | 15451 | 84571090 | 1 | rs4375424 | rs10750356 | 36.99 | 0 | RELA |
| chr11:21723471-131521797 | 20508 | 109798327 | 1 | rs11828478 | rs2512898 | 27.565 | 0 | RELA |
| chr11:23168804-106781292 | 16332 | 83612489 | 1 | rs11027007 | rs7103285 | 49.747 | 0 | RELA |
| chr11:211482-66910826 | 13813 | 66699345 | 3 | rs2293168 | rs4375446 | 30.249 | 0 | RELA |
| chr19:31569338-53780966 | 3788 | 22211629 | 1 | rs2867544 | rs10407424 | 33.9 | 0 | RELB |
| chr19:43257015-55294329 | −7309 | 12037315 | 3 | rs7246152 | rs2569676 | 21.402 | 0 | RELB |
| chr19:288246-59110628 | 11009 | 58822383 | 3 | rs10409452 | cnvi0009466 | 100.582 | 0 | RELB |
| chr2:59512781-127744939 | 13469 | 68232259 | 3 | rs908394 | rs7966946 | 20.62 | 0 | RFC5 |
| chr12:10020267-129866293 | 23654 | 119846027 | 1 | rs1597097 | rs2170504 | 45.428 | 0 | RFC5 |
| chr12:112610714-133708729 | 5366 | 21098016 | 3 | rs11066188 | rs11147249 | 695.45 | 0 | RFC5 |
| chr12:50855195-133778796 | 17748 | 82923602 | 3 | rs4351895 | rs7975069 | 159.589 | 0 | RFC5 |
| chr10:7188484-134205354 | 26672 | 127016871 | 1 | rs1977295 | rs3923858 | 50.772 | 0 | RGS10 |
| chr10:58385643-124973104 | 13625 | 66587462 | 1 | rs7920235 | rs17663304 | 36.18 | 0 | RGS10 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr10:57671424-133349223 | 16243 | 75677800 | 1 | rs11005106 | rs4301710 | 37.114 | 0 | RGS10 |
| chr10:53602190-135522754 | 19167 | 81920565 | 3 | rs12247820 | rs10909028 | 139.373 | 0 | RGS10 |
| chr4:179131-68998153 | 13495 | 68819023 | 3 | rs7686948 | rs7687396 | 625.133 | 0 | RGS12 |
| chr1:64114301-245591329 | 29842 | 181477029 | 1 | rs11208257 | rs1173850 | 37.504 | 0 | RGS13 |
| chr1:178626526-244159143 | 13064 | 65532618 | 3 | rs2761477 | rs479338 | 11.373 | 0 | RGS13 |
| chr1:75098453-243531649 | 27360 | 168433197 | 1 | rs12117493 | rs10927002 | 32.113 | 0 | RGS13 |
| chr1:188850774-235423607 | 10060 | 46572834 | 1 | rs16829466 | rs12409696 | 43.25 | 0 | RGS13 |
| chr1:191875752-235423607 | 9517 | 43547856 | 1 | rs9427811 | rs12409696 | 62.01 | 0 | RGS13 |
| chr1:189128124-227340790 | 7927 | 38212667 | 1 | rs7515205 | rs12752546 | 167.428 | 0 | RGS13 |
| chr1:174219398-247422297 | 15986 | 73202900 | 1 | rs16846809 | rs4642922 | 35.258 | 0 | RGS13 |
| chr1:109645793-194560463 | 12025 | 84914671 | 3 | cnvi0008281 | rs10921616 | 63.121 | 0 | RGS13 |
| chr5:161172541-179954615 | 4271 | 18782075 | 3 | rs4921415 | rs10059433 | 6.291 | 0 | RGS14 |
| chr5:4872310-180709915 | 35876 | 175837606 | 3 | rs816467 | rs10071993 | 179.394 | 0 | RGS14 |
| chr1:64114301-245591329 | 29842 | 181477029 | 1 | rs11208257 | rs1173850 | 37.504 | 0 | RGS16 |
| chr1:178626526-244159143 | 13064 | 65532618 | 3 | rs2761477 | rs479338 | 11.373 | 0 | RGS16 |
| chr1:75098453-243531649 | 27360 | 168433197 | 1 | rs12117493 | rs10927002 | 32.113 | 0 | RGS16 |
| chr1:79710545-188898319 | 17303 | 109187775 | 1 | rs417181 | rs16829637 | 45.89 | 0 | RGS16 |
| chr1:174219398-247422297 | 15986 | 73202900 | 1 | rs16846809 | rs4642922 | 35.258 | 0 | RGS16 |
| chr1:109645793-194560463 | 12025 | 84914671 | 3 | cnvi0008281 | rs10921616 | 63.121 | 0 | RGS16 |
| chr1:64114301-245591329 | 29842 | 181477029 | 1 | rs11208257 | rs1173850 | 37.504 | 0 | RGS18 |
| chr1:178626526-244159143 | 13064 | 65532618 | 3 | rs2761477 | rs479338 | 11.373 | 0 | RGS18 |
| chr1:75098453-243531649 | 27360 | 168433197 | 1 | rs12117493 | rs10927002 | 32.113 | 0 | RGS18 |
| chr1:191636974-191875752 | 41 | 238779 | 1 | rs12118448 | rs9427811 | 14.635 | 251840 | RGS18 |
| chr1:191772972-192059022 | 49 | 286051 | 1 | rs9427526 | rs10921078 | 19.199 | 68570 | RGS18 |
| chr1:188850774-235423607 | 10060 | 46572834 | 1 | rs16829466 | rs12409696 | 43.25 | 0 | RGS18 |
| chr1:191875752-235423607 | 9517 | 43547856 | 1 | rs9427811 | rs12409696 | 62.01 | 0 | RGS18 |
| chr1:189128124-227340790 | 7927 | 38212667 | 1 | rs7515205 | rs12752546 | 167.428 | 0 | RGS18 |
| chr1:174219398-247422297 | 15986 | 73202900 | 1 | rs16846809 | rs4642922 | 35.258 | 0 | RGS18 |
| chr1:191640296-191788524 | 25 | 148229 | 1 | rs10920990 | rs17402518 | 14.942 | 339068 | RGS18 |
| chr1:109645793-194560463 | 12025 | 84914671 | 3 | cnvi0008281 | rs10921616 | 63.121 | 0 | RGS18 |
| chr20:54870769-62912463 | 2390 | 8041695 | 3 | rs6069696 | rs6062363 | 249.708 | 0 | RGS19 |
| chr1:64114301-245591329 | 29842 | 181477029 | 1 | rs11208257 | rs1173850 | 37.504 | 0 | RGS2 |
| chr1:178626526-244159143 | 13064 | 65532618 | 3 | rs2761477 | rs479338 | 11.373 | 0 | RGS2 |
| chr1:75098453-243531649 | 27360 | 168433197 | 1 | rs12117493 | rs10927002 | 32.113 | 0 | RGS2 |
| chr1:188850774-235423607 | 10060 | 46572834 | 1 | rs16829466 | rs12409696 | 43.25 | 0 | RGS2 |
| chr1:191875752-235423607 | 9517 | 43547856 | 1 | rs9427811 | rs12409696 | 62.01 | 0 | RGS2 |
| chr1:189128124-227340790 | 7927 | 38212667 | 1 | rs7515205 | rs12752546 | 167.428 | 0 | RGS2 |
| chr1:174219398-247422297 | 15986 | 73202900 | 1 | rs16846809 | rs4642922 | 35.258 | 0 | RGS2 |
| chr1:109645793-194560463 | 12025 | 84914671 | 3 | cnvi0008281 | rs10921616 | 63.121 | 0 | RGS2 |
| chr1:64114301-245591329 | 29842 | 181477029 | 1 | rs11208257 | rs1173850 | 37.504 | 0 | RGS4 |
| chr1:75098453-243531649 | 27360 | 168433197 | 1 | rs12117493 | rs10927002 | 32.113 | 0 | RGS4 |
| chr1:79710545-188898319 | 17303 | 109187775 | 1 | rs417181 | rs16829637 | 45.89 | 0 | RGS4 |
| chr1:162920811-163351718 | 112 | 430908 | 1 | rs2343490 | rs3010344 | 311.918 | 0 | RGS4 |
| chr1:109645793-194560463 | 12025 | 84914671 | 3 | cnvi0008281 | rs10921616 | 63.121 | 0 | RGS4 |
| chr1:64114301-245591329 | 29842 | 181477029 | 1 | rs11208257 | rs1173850 | 37.504 | 0 | RGS5 |
| chr1:75098453-243531649 | 27360 | 168433197 | 1 | rs12117493 | rs10927002 | 32.113 | 0 | RGS5 |
| chr1:79710545-188898319 | 17303 | 109187775 | 1 | rs417181 | rs16829637 | 45.89 | 0 | RGS5 |
| chr1:162920811-163351718 | 112 | 430908 | 1 | rs2343490 | rs3010344 | 311.918 | 0 | RGS5 |
| chr1:109645793-194560463 | 12025 | 84914671 | 3 | cnvi0008281 | rs10921616 | 63.121 | 0 | RGS5 |
| chr1:64114301-245591329 | 29842 | 181477029 | 1 | rs11208257 | rs1173850 | 37.504 | 0 | RGS7 |
| chr1:178626526-244159143 | 13064 | 65532618 | 3 | rs2761477 | rs479338 | 11.373 | 0 | RGS7 |
| chr1:75098453-243531649 | 27360 | 168433197 | 1 | rs12117493 | rs10927002 | 32.113 | 0 | RGS7 |
| chr1:238655362-242087644 | 1078 | 3432283 | 3 | rs2392861 | rs4658565 | 806.215 | 0 | RGS7 |
| chr1:174219398-247422297 | 15986 | 73202900 | 1 | rs16846809 | rs4642922 | 35.258 | 0 | RGS7 |
| chr1:236848751-249226957 | 3293 | 12370570 | 3 | rs819666 | cnvi0018731 | 920.725 | 0 | RGS7 |
| chr3:13878889-149737330 | 24723 | 135858442 | 1 | rs12634112 | rs2007869 | 55.663 | 0 | RHO |
| chr3:33409611-170735099 | 23775 | 137325489 | 1 | rs3915062 | rs11924032 | 26.867 | 0 | RHO |
| chr3:102240202-195550366 | 17318 | 93310165 | 1 | rs1620217 | rs11711870 | 41.031 | 0 | RHO |
| chr3:103140700-144883172 | 8539 | 41742473 | 1 | rs4314176 | rs6797159 | 44.122 | 0 | RHO |
| chr3:83075971-196935657 | 21465 | 113859687 | 1 | rs9872858 | rs34729751 | 44.35 | 0 | RHO |
| chr3:114889454-177826047 | 12700 | 62936594 | 3 | rs6795297 | rs7628308 | 102.526 | 0 | RHO |
| chr3:13878889-149737330 | 24723 | 135858442 | 1 | rs12634112 | rs2007869 | 55.663 | 0 | RHOA |
| chr3:33409611-170735099 | 23775 | 137325489 | 1 | rs3915062 | rs11924032 | 26.867 | 0 | RHOA |
| chr3:179527-114630641 | 23879 | 114451115 | 3 | rs4874741 | rs1587972 | 207.852 | 0 | RHOA |
| chr4:31222833-180548076 | 24457 | 149325244 | 1 | rs7662351 | rs3849606 | 36.162 | 0 | RHOH |
| chr4:39472311-63464732 | 3456 | 23992422 | 3 | rs2687975 | rs4403080 | 120.672 | 0 | RHOH |
| chr4:22401728-188608857 | 28456 | 166207130 | 1 | rs4697297 | rs7687115 | 35.717 | 0 | RHOH |
| chr4:29179713-117038307 | 15513 | 87858595 | 1 | rs1507441 | rs1068807 | 71.6 | 0 | RHOH |
| chr4:179131-68998153 | 13495 | 68819023 | 3 | rs7686948 | rs7687396 | 625.133 | 0 | RHOH |
| chr11:211482-66910826 | 13813 | 66699345 | 3 | rs2293168 | rs4375446 | 30.249 | 0 | RIC8A |
| chr12:10113083-116370432 | 20594 | 106257350 | 1 | rs2012504 | rs7958254 | 35.157 | 0 | RIC8B |
| chr12:59512781-127744939 | 13469 | 68232159 | 3 | rs908394 | rs7966946 | 20.62 | 0 | RIC8B |
| chr12:10020267-129866293 | 23654 | 119846027 | 1 | rs1597097 | rs2170504 | 45.428 | 0 | RIC8B |
| chr12:50855195-133778796 | 17748 | 82923602 | 3 | rs4351895 | rs7975069 | 159.589 | 0 | RIC8B |
| chr2:12056323-227979775 | 39094 | 215923453 | 1 | rs966391 | rs1922020 | 31.384 | 0 | RIF1 |
| chr2:34870277-241929621 | 37755 | 207059345 | 3 | rs13422005 | rs10205276 | 46.946 | 0 | RIF1 |
| chr2:38101137-241482099 | 36812 | 203380963 | 1 | rs879321 | rs7576043 | 52.099 | 0 | RIF1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr2:77041264-194763754 | 21140 | 117722491 | 1 | rs2102827 | rs16835406 | 94.091 | 0 | RIF1 |
| chr2:83383702-175194550 | 16291 | 91810849 | 3 | rs12469609 | rs11891208 | 154.4 | 0 | RIF1 |
| chr18:1583633-58142042 | 11490 | 56558410 | 3 | rs9945988 | rs1560399 | 3.736 | 0 | RIOK3 |
| chr18:10274-30780701 | 6393 | 30770428 | 3 | cnvi0008694 | rs271534 | 338.777 | 0 | RIOK3 |
| chr6:2681610-31453618 | 81 | 28772009 | 3 | rs1131896 | rs9267212 | 428.177 | 0 | RIPK1 |
| chr6:1171596-29895228 | 43 | 28723633 | 0 | rs3128994 | rs9259831 | 53.123 | 0 | RIPK1 |
| chr6:1171596-29899147 | 47 | 28727552 | 0 | rs3128994 | rs2394704 | 80.695 | 0 | RIPK1 |
| chr6:1177990-29899147 | 39 | 28721158 | 0 | rs2428530 | rs2394704 | 44.381 | 0 | RIPK1 |
| chr6:1175965-29899147 | 43 | 28723183 | 0 | rs1611522 | rs2394704 | 52.089 | 0 | RIPK1 |
| chr6:2585208-31281876 | −2 | 28696669 | 1 | rs1634746 | rs1634747 | 31.615 | 0 | RIPK1 |
| chr6:1171596-29899147 | 47 | 28727552 | 0 | rs3128994 | rs2394704 | 63.572 | 0 | RIPK1 |
| chr6:2584569-31286381 | 8 | 28701813 | 1 | rs9391764 | rs9265057 | 34.598 | 0 | RIPK1 |
| chr6:2681610-31453618 | 81 | 28772009 | 3 | rs1131896 | rs9267212 | 390.234 | 0 | RIPK1 |
| chr6:1171596-29892436 | 39 | 28720841 | 1 | rs3128994 | rs9259806 | 31.699 | 0 | RIPK1 |
| chr6:1171596-29895228 | 43 | 28723633 | 0 | rs3128994 | rs9259831 | 43.568 | 0 | RIPK1 |
| chr6:181089-30430875 | 1806 | 30249787 | 3 | rs1535053 | rs35792611 | 80.394 | 0 | RIPK1 |
| chr8:89855372-90385087 | 98 | 529716 | 1 | rs10504865 | rs4458917 | 376.728 | 384888 | RIPK2 |
| chr8:30757798-142750969 | 20699 | 111993172 | 1 | rs10101203 | rs6421025 | 34.223 | 0 | RIPK2 |
| chr8:60424884-145286483 | 17030 | 84861600 | 3 | rs1401422 | rs9720889 | 8.858 | 0 | RIPK2 |
| chr8:23218101-146274708 | 23020 | 123056608 | 1 | rs7010362 | rs7822726 | 38.828 | 0 | RIPK2 |
| chr8:89499072-90708428 | 202 | 1209357 | 3 | rs7832310 | rs6981616 | 372.548 | 61547 | RIPK2 |
| chr8:76354446-113652745 | 6767 | 37297920 | 1 | rs830783 | rs16883889 | 127.023 | 0 | RIPK2 |
| chr8:66822030-144791126 | 16557 | 77969097 | 3 | rs6472235 | rs10100154 | 251.068 | 0 | RIPK2 |
| chr1:64114301-245591329 | 29842 | 181477029 | 1 | rs11208257 | rs1173850 | 37.504 | 0 | RIT1 |
| chr1:75098453-243531649 | 27360 | 168433197 | 1 | rs12117493 | rs10927002 | 32.113 | 0 | RIT1 |
| chr1:79710545-188898934 | 17303 | 109187775 | 1 | rs417181 | rs16829677 | 45.89 | 0 | RIT1 |
| chr1:109645793-194560463 | 12025 | 84914671 | 3 | cnvi0008281 | rs10921616 | 63.121 | 0 | RIT1 |
| chr18:25388300-75954881 | 11539 | 50566582 | 1 | rs11083228 | rs1876021 | 39.235 | 0 | RIT2 |
| chr18:1583633-58142042 | 11490 | 56558410 | 3 | rs9945988 | rs1560399 | 3.736 | 0 | RIT2 |
| chr18:40271967-40472219 | 29 | 200253 | 1 | rs1430916 | rs656134 | 18.041 | 0 | RIT2 |
| chr18:26550830-63713914 | 8241 | 37163085 | 1 | rs16945738 | rs2715304 | 17.922 | 0 | RIT2 |
| chr18:26162481-67193217 | 9255 | 41030737 | 1 | rs12458903 | rs9961907 | 31.327 | 0 | RIT2 |
| chr18:30929223-44720664 | 2910 | 13791442 | 3 | rs10775453 | rs9304343 | 535.348 | 0 | RIT2 |
| chr12:59512781-127744939 | 13469 | 68232159 | 3 | rs908394 | rs7966946 | 20.62 | 0 | RNF10 |
| chr12:10020267-129866293 | 23654 | 119846027 | 1 | rs1597097 | rs2170509 | 45.428 | 0 | RNF10 |
| chr12:112610714-133708729 | 5366 | 21098016 | 3 | rs11066188 | rs11147249 | 695.45 | 0 | RNF10 |
| chr12:50855195-133778796 | 17748 | 82923602 | 3 | rs4351895 | rs7975069 | 159.589 | 0 | RNF10 |
| chr1:51547424-51719315 | 12 | 171892 | 1 | rs11205809 | rs6701572 | 18.548 | 0 | RNF11 |
| chr1:1005806-105612342 | 19173 | 104606537 | 3 | rs3934834 | rs1584633 | 44.152 | 0 | RNF11 |
| chr1:2006108-109527861 | 22130 | 107521754 | 3 | rs2254669 | rs839879 | 162.269 | 0 | RNF11 |
| chr1:1005806-105612342 | 19173 | 104606537 | 3 | rs3934834 | rs1584633 | 44.152 | 0 | RPA2 |
| chr1:2006108-109527861 | 22130 | 107521754 | 3 | rs2254669 | rs839879 | 162.269 | 0 | RPA2 |
| chr9:2522475-140068342 | 25719 | 137545868 | 3 | rs10966757 | rs4074426 | 93.386 | 0 | RPL12 |
| chr9:33180228-132003792 | 14691 | 98823565 | 1 | rs7854765 | rs9408988 | 28.69 | 0 | RPL12 |
| chr9:100158052-139077343 | 9815 | 38919292 | 3 | rs1020884 | rs4842126 | 470.601 | 0 | RPL12 |
| chr2:12056323-227979775 | 39094 | 215923453 | 1 | rs966391 | rs1922020 | 31.384 | 0 | RPL37A |
| chr2:34870277-241929621 | 37755 | 207059345 | 3 | rs13422005 | rs10205276 | 46.946 | 0 | RPL37A |
| chr2:38101137-241482099 | 36812 | 203380963 | 1 | rs879321 | rs7576043 | 52.099 | 0 | RPL37A |
| chr2:193255360-242529978 | 10289 | 49274619 | 3 | rs1351905 | cnvi0010399 | 93.244 | 0 | RPL37A |
| chr11:345515-17408630 | 4247 | 17063116 | 3 | rs11246094 | rs5215 | 30.474 | 0 | RPLP2 |
| chr11:211482-66910826 | 13813 | 66699345 | 3 | rs2293168 | rs4375446 | 30.249 | 0 | RPLP2 |
| chr20:13712393-55093901 | 8218 | 41381509 | 1 | rs6033810 | rs6999 | 41.237 | 0 | RPN2 |
| chr20:7869025-62424661 | 11941 | 54555637 | 3 | rs2294306 | rs6010652 | 9.732 | 0 | RPN2 |
| chr20:4591715-58420336 | 11753 | 53828622 | 1 | rs6139494 | rs1416388 | 40.922 | 0 | RPN2 |
| chr20:236802-54845796 | 12646 | 54608995 | 3 | rs448294 | rs6064362 | 286.151 | 0 | RPN2 |
| chr5:84830796-171903310 | 16642 | 87072515 | 1 | rs300657 | rs10042482 | 42.208 | 0 | RPS14 |
| chr5:57343495-171903310 | 21683 | 114559816 | 1 | rs10940593 | rs10042482 | 61.169 | 0 | RPS14 |
| chr5:98442871-150317237 | 9828 | 51874367 | 1 | rs1447379 | rs7710790 | 38.687 | 0 | RPS14 |
| chr5:4872310-180709915 | 35876 | 175837606 | 3 | rs816467 | rs10071993 | 179.394 | 0 | RPS14 |
| chr16:59854720-89273883 | 7609 | 29419164 | 3 | rs1373880 | rs8046156 | 31.884 | 0 | RRAD |
| chr16:64107047-82920737 | 4544 | 18813691 | 1 | rs2319723 | rs918661 | 28.887 | 0 | RRAD |
| chr16:50219449-89544756 | 10324 | 39325308 | 3 | rs6500298 | rs3803681 | 108.108 | 0 | RRAD |
| chr11:3906740-4201641 | 55 | 294902 | 1 | rs11600857 | rs2044138 | 27.361 | 0 | RRM1 |
| chr11:345515-17408630 | 4247 | 17063116 | 3 | rs11246094 | rs5215 | 30.474 | 0 | RRM1 |
| chr11:211482-66910826 | 13813 | 66699345 | 3 | rs2293168 | rs4375446 | 30.249 | 0 | RRM1 |
| chr2:12056323-227979775 | 39094 | 215923453 | 1 | rs966391 | rs1922020 | 31.384 | 0 | RTN4 |
| chr2:34870277-241929621 | 37755 | 207059345 | 3 | rs13422005 | rs10205276 | 46.946 | 0 | RTN4 |
| chr2:38101137-241482099 | 36812 | 203380963 | 1 | rs879321 | rs7576043 | 52.099 | 0 | RTN4 |
| chr2:55031023-55437014 | 143 | 405992 | 1 | rs17345167 | rs17039586 | 453.996 | 0 | RTN4 |
| chr2:41212010-82396211 | 9721 | 41184202 | 3 | rs12614285 | rs934310 | 396.396 | 0 | RTN4 |
| chr19:31569338-53780966 | 3788 | 22211629 | 1 | rs2867544 | rs10407424 | 33.9 | 0 | RUVBL2 |
| chr19:43257015-55294329 | −7309 | 12037375 | 1 | rs7246152 | rs2569676 | 21.402 | 0 | RUVBL2 |
| chr19:288246-59110628 | 11009 | 58822383 | 3 | rs10409452 | cnvi0009466 | 100.582 | 0 | RUVBL2 |
| chr19:31569338-53780966 | 3788 | 22211629 | 1 | rs2867544 | rs10407424 | 33.9 | 0 | RYR1 |
| chr19:288246-59110628 | 11009 | 58822383 | 3 | rs10409452 | cnvi0009466 | 100.582 | 0 | RYR1 |
| chr1:237570457-237675464 | 37 | 105008 | 1 | rs4659495 | rs2618721 | 15.007 | 0 | RYR2 |
| chr1:64114301-245591329 | 29842 | 181477029 | 1 | rs11208257 | rs1173850 | 37.504 | 0 | RYR2 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr1:178626526-244159143 | 13064 | 65532618 | 3 | rs2761477 | rs479338 | 11.373 | 0 | RYR2 |
| chr1:75098453-243531649 | 27360 | 168433197 | 1 | rs12117493 | rs10927002 | 32.113 | 0 | RYR2 |
| chr1:174219398-247422297 | 15986 | 73202900 | 1 | rs16846809 | rs4642922 | 35.258 | 0 | RYR2 |
| chr1:237584925-237904870 | 86 | 319946 | 1 | rs4593814 | rs10925504 | 31.95 | 0 | RYR2 |
| chr1:236848751-249215320 | 3293 | 12370570 | 3 | rs819666 | cnvi0018731 | 920.725 | 0 | RYR2 |
| chr1:64114301-245591329 | 29842 | 181477029 | 1 | rs11208257 | rs1173850 | 37.504 | 0 | S100A6 |
| chr1:75098453-243531649 | 27360 | 168433197 | 1 | rs12117493 | rs10927002 | 32.113 | 0 | S100A6 |
| chr1:79710545-188898319 | 17303 | 109187775 | 1 | rs417181 | rs16829637 | 45.89 | 0 | S100A6 |
| chr1:109645793-194560463 | 12025 | 84914671 | 3 | cnvi0008281 | rs10921616 | 63.121 | 0 | S100A6 |
| chr1:64114301-245591329 | 29842 | 181477029 | 1 | rs11208257 | rs1173850 | 37.504 | 0 | S100A8 |
| chr1:75098453-243531649 | 27360 | 168433197 | 1 | rs12117493 | rs10927002 | 32.113 | 0 | S100A8 |
| chr1:79710545-188898319 | 17303 | 109187775 | 1 | rs417181 | rs16829637 | 45.89 | 0 | S100A8 |
| chr1:109645793-194560463 | 12025 | 84914671 | 3 | cnvi0008281 | rs10921616 | 63.121 | 0 | S100A8 |
| chr13:19584477-81204088 | 13265 | 61619612 | 3 | rs1334954 | rs1176297 | 22.162 | 0 | SACS |
| chr13:23742931-115064482 | 19829 | 91321552 | 1 | rs4770401 | rs7999630 | 44.074 | 0 | SACS |
| chr13:19121741-63373781 | 10326 | 44252041 | 3 | rs9578050 | rs9539575 | 82.761 | 0 | SACS |
| chr1:64114301-245591329 | 29842 | 181477029 | 1 | rs11208257 | rs1173850 | 37.504 | 0 | SARS |
| chr1:75098453-243531649 | 27360 | 168433197 | 1 | rs12117493 | rs10927002 | 32.113 | 0 | SARS |
| chr1:79710545-188898319 | 17303 | 109187775 | 1 | rs417181 | rs16829637 | 45.89 | 0 | SARS |
| chr1:109645793-194560463 | 12025 | 84914671 | 3 | cnvi0008281 | rs10921616 | 63.121 | 0 | SARS |
| chr12:10113083-116370432 | 20594 | 106257350 | 1 | rs2012504 | rs7958254 | 35.157 | 0 | SCN8A |
| chr12:10020267-129866293 | 23654 | 119846027 | 1 | rs1597097 | rs2170501 | 45.428 | 0 | SCN8A |
| chr12:39967134-84174413 | 8879 | 44207280 | 1 | rs11172661 | rs11116039 | 39.568 | 0 | SCN8A |
| chr12:50855195-133778796 | 17748 | 82923602 | 3 | rs4351895 | rs7975069 | 159.589 | 0 | SCN8A |
| chr2:12056323-227979775 | 39094 | 215923453 | 1 | rs966391 | rs1922020 | 31.384 | 0 | SCTR |
| chr2:34870277-241929621 | 37755 | 207059345 | 3 | rs13422005 | rs10205276 | 46.946 | 0 | SCTR |
| chr2:38101137-241482099 | 36812 | 203380963 | 1 | rs879321 | rs7576043 | 52.099 | 0 | SCTR |
| chr2:77041264-194763754 | 21140 | 117722491 | 1 | rs2102827 | rs16835406 | 94.091 | 0 | SCTR |
| chr2:83383702-175194550 | 16291 | 91810849 | 3 | rs12469609 | rs11891208 | 154.4 | 0 | SCTR |
| chr2:12056323-227979775 | 39094 | 215923453 | 1 | rs966391 | rs1922020 | 31.384 | 0 | SDC1 |
| chr2:18856-41136833 | 9721 | 41117978 | 3 | rs11901199 | rs10187704 | 191.638 | 0 | SDC1 |
| chr8:30757798-142750969 | 20699 | 111993172 | 1 | rs10101203 | rs6421025 | 34.223 | 0 | SDC2 |
| chr8:60424884-145286483 | 17030 | 84861600 | 3 | rs1401422 | rs9720889 | 8.858 | 0 | SDC2 |
| chr8:23218101-146274708 | 23020 | 123056608 | 1 | rs7010362 | rs7822726 | 38.828 | 0 | SDC2 |
| chr8:76354446-113652365 | 6767 | 37297920 | 1 | rs830783 | rs16883889 | 127.023 | 0 | SDC2 |
| chr8:66822030-144791126 | 16557 | 77969097 | 3 | rs6472235 | rs10100154 | 251.068 | 0 | SDC2 |
| chr1:1005806-105612342 | 19173 | 104606537 | 3 | rs3934834 | rs1584633 | 44.152 | 0 | SDC3 |
| chr1:2006108-109527861 | 22130 | 107521754 | 3 | rs2254669 | rs839879 | 162.269 | 0 | SDC3 |
| chr20:13712393-55093901 | 8218 | 41381509 | 1 | rs6033810 | rs6999 | 41.237 | 0 | SDC4 |
| chr20:7869025-62424661 | 11941 | 54555637 | 3 | rs2294306 | rs6010652 | 9.732 | 0 | SDC4 |
| chr20:4591715-58420336 | 11753 | 53828622 | 1 | rs6139494 | rs1416388 | 40.922 | 0 | SDC4 |
| chr20:236802-54845796 | 12646 | 54608995 | 3 | rs448294 | rs6064362 | 286.151 | 0 | SDC4 |
| chr8:30757798-142750969 | 20699 | 111993172 | 1 | rs10101203 | rs6421025 | 34.223 | 0 | SDCBP |
| chr8:23218101-146274708 | 23020 | 123056608 | 1 | rs7010362 | rs7822726 | 38.828 | 0 | SDCBP |
| chr8:43235525-66712108 | 3632 | 23476584 | 3 | rs10091311 | rs7001138 | 58.838 | 0 | SDCBP |
| chr20:236802-54845796 | 12646 | 54608995 | 3 | rs448294 | rs6064362 | 286.151 | 0 | SDCBP2 |
| chr2:12056323-227979775 | 39094 | 215923453 | 1 | rs966391 | rs1922020 | 31.384 | 0 | SDPR |
| chr2:34870277-241929621 | 37755 | 207059345 | 3 | rs13422005 | rs10205276 | 46.946 | 0 | SDPR |
| chr2:38101137-241482099 | 36812 | 203380963 | 1 | rs879321 | rs7576043 | 52.099 | 0 | SDPR |
| chr2:77041264-194763754 | 21140 | 117722491 | 1 | rs2102827 | rs16835406 | 94.091 | 0 | SDPR |
| chr2:185050218-212752193 | 4583 | 27701976 | 1 | rs1526196 | rs6727114 | 45.31 | 0 | SDPR |
| chr2:180138805-193144041 | 2298 | 13005237 | 3 | rs6746115 | rs2592243 | 132.36 | 0 | SDPR |
| chr1:64114301-245591329 | 29842 | 181477029 | 1 | rs11208257 | rs1173850 | 37.504 | 0 | SELE |
| chr1:169556446-171300348 | 340 | 1743903 | 1 | rs9332480 | rs7541160 | 32.81 | 0 | SELE |
| chr1:75098453-243531649 | 27360 | 168433197 | 1 | rs12117493 | rs10927002 | 32.113 | 0 | SELE |
| chr1:79710545-188898319 | 17303 | 109187775 | 1 | rs417181 | rs16829637 | 45.89 | 0 | SELE |
| chr1:109645793-194560463 | 12025 | 84914671 | 3 | cnvi0008281 | rs10921616 | 63.121 | 0 | SELE |
| chr1:64114301-245591329 | 29842 | 181477029 | 1 | rs11208257 | rs1173850 | 37.504 | 0 | SELENBP1 |
| chr1:75098453-243531649 | 27360 | 168433197 | 1 | rs12117493 | rs10927002 | 32.113 | 0 | SELENBP1 |
| chr1:79710545-188898319 | 17303 | 109187775 | 1 | rs417181 | rs16829637 | 45.89 | 0 | SELENBP1 |
| chr1:109645793-194560463 | 12025 | 84914671 | 3 | cnvi0008281 | rs10921616 | 63.121 | 0 | SELENBP1 |
| chr20:13712393-55093901 | 8218 | 41381509 | 1 | rs6033810 | rs6999 | 41.237 | 0 | SEMG1 |
| chr20:7869025-62424661 | 11941 | 54555637 | 3 | rs2294306 | rs6010652 | 9.732 | 0 | SEMG1 |
| chr20:4591715-58420336 | 11753 | 53828622 | 1 | rs6139494 | rs1416388 | 40.922 | 0 | SEMG1 |
| chr20:236802-54845796 | 12646 | 54608995 | 3 | rs448294 | rs6064362 | 286.151 | 0 | SEMG1 |
| chr20:13712393-55093901 | 8218 | 41381509 | 1 | rs6033810 | rs6999 | 41.237 | 0 | SEMG2 |
| chr20:7869025-62424661 | 11941 | 54555637 | 3 | rs2294306 | rs6010652 | 9.732 | 0 | SEMG2 |
| chr20:4591715-58420336 | 11753 | 53828622 | 1 | rs6139494 | rs1416388 | 40.922 | 0 | SEMG2 |
| chr20:236802-54845796 | 12646 | 54608995 | 3 | rs448294 | rs6064362 | 286.151 | 0 | SEMG2 |
| chr6:2681610-31453618 | 81 | 28772009 | 3 | rs1131896 | rs9267212 | 428.177 | 0 | SERPINB9 |
| chr6:1171596-29895228 | 43 | 28723633 | 0 | rs3128994 | rs9259831 | 53.123 | 0 | SERPINB9 |
| chr6:1171596-29899147 | 47 | 28727552 | 0 | rs3128994 | rs2394704 | 80.695 | 0 | SERPINB9 |
| chr6:1177990-29899147 | 39 | 28721158 | 0 | rs2428530 | rs2394704 | 44.381 | 0 | SERPINB9 |
| chr6:1175965-29899147 | 43 | 28723183 | 0 | rs1611522 | rs2394704 | 52.089 | 0 | SERPINB9 |
| chr6:2585208-31281876 | −2 | 28696669 | 1 | rs1634746 | rs1634747 | 31.615 | 0 | SERPINB9 |
| chr6:1171596-29899147 | 47 | 28727552 | 0 | rs3128994 | rs2394704 | 63.572 | 0 | SERPINB9 |
| chr6:2584569-31286381 | 8 | 28701813 | 1 | rs9391764 | rs9265057 | 34.598 | 0 | SERPINB9 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr6:2681610-31453618 | 81 | 28772009 | 3 | rs1131896 | rs9267212 | 390.234 | 0 | SERPINB9 |
| chr6:1171596-29892436 | 39 | 28720841 | 1 | rs3128994 | rs9259806 | 31.699 | 0 | SERPINB9 |
| chr6:1171596-29895228 | 43 | 28723633 | 0 | rs3128994 | rs9259831 | 43.568 | 0 | SERPINB9 |
| chr6:181089-30430875 | 1806 | 30249787 | 3 | rs1535053 | rs35792611 | 80.394 | 0 | SERPINB9 |
| chr9:2522475-140068342 | 25719 | 137545868 | 3 | rs10966757 | rs4074426 | 93.386 | 0 | SET |
| chr9:33180228-132003792 | 14691 | 98823565 | 1 | rs7854765 | rs9408988 | 28.69 | 0 | SET |
| chr9:100158052-139077343 | 9815 | 38919292 | 3 | rs1020884 | rs4842126 | 470.601 | 0 | SET |
| chr21:36927793-37647438 | 142 | 719646 | 3 | rs2205031 | rs9980084 | 187.28 | 0 | SETD4 |
| chr21:14601415-48084989 | 8249 | 33483575 | 3 | rs2775537 | rs2839378 | 12047.211 | 0 | SETD4 |
| chr21:14601415-48084989 | 8249 | 33483575 | 3 | rs2775537 | rs2839378 | 41.154 | 0 | SETD4 |
| chr21:14768343-48084989 | 8193 | 33316647 | 3 | rs2257224 | rs2839378 | 5021.076 | 0 | SETD4 |
| chr21:14601415-48084989 | 8249 | 33483575 | 3 | rs2775537 | rs2839378 | 4787.438 | 0 | SETD4 |
| chr21:14595264-48084989 | 8781 | 33489726 | 3 | rs2847443 | rs2839378 | 1871.363 | 0 | SETD4 |
| chr21:10708231-47970581 | 8807 | 37262351 | 3 | rs4044122 | rs2255397 | 73.188 | 0 | SETD4 |
| chr1:64114301-245591329 | 29842 | 181477029 | 1 | rs11208257 | rs1173850 | 37.504 | 0 | SETDB1 |
| chr1:75098453-243531649 | 27360 | 168433197 | 1 | rs12117493 | rs10927002 | 32.113 | 0 | SETDB1 |
| chr1:79710545-188898319 | 17303 | 109187775 | 1 | rs417181 | rs16829637 | 45.89 | 0 | SETDB1 |
| chr1:109645793-194560463 | 12025 | 84914671 | 3 | cnvi0008281 | rs10921616 | 63.121 | 0 | SETDB1 |
| chr2:12056323-227979775 | 39094 | 215923453 | 1 | rs966391 | rs1922020 | 31.384 | 0 | SF3B14 |
| chr2:18856-41136833 | 9721 | 41117978 | 3 | rs11901199 | rs10187704 | 191.638 | 0 | SF3B14 |
| chr3:13878889-149737330 | 24723 | 135858442 | 1 | rs12634112 | rs2007869 | 55.663 | 0 | SGOL1 |
| chr3:179527-114630641 | 23879 | 114451115 | 3 | rs4684741 | rs1587972 | 207.852 | 0 | SGOL1 |
| chr2:12056323-227979775 | 39094 | 215923453 | 1 | rs966391 | rs1922020 | 31.384 | 0 | SGOL2 |
| chr2:34870277-241929621 | 37755 | 207059345 | 3 | rs13422005 | rs10205276 | 46.946 | 0 | SGOL2 |
| chr2:38101137-241482099 | 36812 | 203380963 | 1 | rs879321 | rs7576043 | 52.099 | 0 | SGOL2 |
| chr2:185050218-212752193 | 4583 | 27701976 | 1 | rs1526196 | rs6727114 | 45.31 | 0 | SGOL2 |
| chr2:193255360-242529978 | 10289 | 49274619 | 3 | rs1351905 | cnvi0010399 | 93.244 | 0 | SGOL2 |
| chr12:10113083-116370432 | 20594 | 106257350 | 1 | rs2012504 | rs7958254 | 35.157 | 0 | SH2B3 |
| chr12:59512781-127744939 | 13469 | 68232159 | 3 | rs908394 | rs7966946 | 20.62 | 0 | SH2B3 |
| chr12:10020267-129866293 | 23654 | 119846027 | 1 | rs1597297 | rs2170504 | 45.428 | 0 | SH2B3 |
| chr12:50855195-133778796 | 17748 | 82923602 | 3 | rs4351895 | rs7975069 | 159.589 | 0 | SH2B3 |
| chr19:31569338-53780966 | 3788 | 22211629 | 1 | rs2867544 | rs10407424 | 33.9 | 0 | SHANK1 |
| chr19:43257015-55294329 | −7309 | 12037315 | 3 | rs7246152 | rs2569676 | 21.402 | 0 | SHANK1 |
| chr19:288246-59110628 | 11009 | 58822383 | 3 | rs10409452 | cnvi0009466 | 100.582 | 0 | SHANK1 |
| chr17:108420-26610769 | 5548 | 26502350 | 3 | rs12452527 | rs658591 | 82.699 | 0 | SHBG |
| chr1:64114301-245591329 | 29842 | 181477029 | 1 | rs11208257 | rs1173850 | 37.504 | 0 | SHC1 |
| chr1:154752736-154944156 | 62 | 191421 | 3 | rs10908440 | rs12076073 | 65.821 | 0 | SHC1 |
| chr1:75098453-243531649 | 27360 | 168433197 | 1 | rs12117493 | rs10927002 | 32.113 | 0 | SHC1 |
| chr1:79710545-188898319 | 17303 | 109187775 | 1 | rs417181 | rs16829637 | 45.89 | 0 | SHC1 |
| chr1:109645793-194560463 | 12025 | 84914671 | 3 | cnvi0008281 | rs10921616 | 63.121 | 0 | SHC1 |
| chr16:176743-50013967 | 8328 | 49837225 | 3 | rs2562164 | rs12597023 | 174.392 | 0 | SIAH1 |
| chr19:31569338-53780966 | 3788 | 22211629 | 1 | rs2867544 | rs10407424 | 33.9 | 0 | SIRT2 |
| chr19:288246-59110628 | 11009 | 58822383 | 3 | rs10409452 | cnvi0009466 | 100.582 | 0 | SIRT2 |
| chr9:1989033-107532317 | 18263 | 105543285 | 1 | rs7864828 | rs10820726 | 39.824 | 0 | SLC1A1 |
| chr9:2522475-140068342 | 25719 | 137545868 | 3 | rs10966757 | rs4074426 | 93.386 | 0 | SLC1A1 |
| chr9:46587-94335290 | 17484 | 94288704 | 3 | rs10814410 | rs9409606 | 762.393 | 0 | SLC1A1 |
| chr1:1005806-105612342 | 19173 | 104606537 | 3 | rs3934834 | rs1584633 | 44.152 | 0 | SLC2A1 |
| chr1:2006108-109527861 | 22130 | 107521754 | 3 | rs2254669 | rs839879 | 162.269 | 0 | SLC2A1 |
| chr5:141659-19010008 | 4662 | 18868350 | 3 | rs11741126 | rs4642370 | 50.124 | 0 | SLC6A3 |
| chr5:506051-4746181 | 1345 | 4240131 | 3 | rs6864158 | rs7716294 | 447.942 | 0 | SLC6A3 |
| chr1:1005806-105612342 | 19173 | 104606537 | 3 | rs3934834 | rs1584633 | 44.152 | 0 | SLC6A9 |
| chr1:2006108-109527861 | 22130 | 107521754 | 3 | rs2254669 | rs839879 | 162.269 | 0 | SLC6A9 |
| chr17:44458950-81047708 | −8195 | 36588759 | 1 | cnvi0016818 | rs35680231 | 35.591 | 0 | SLC9A3R1 |
| chr17:62662507-81047708 | −11496 | 18385202 | 3 | rs6504246 | rs35680231 | 56.048 | 0 | SLC9A3R1 |
| chr15:51688996-102398060 | 11030 | 50709065 | 1 | rs2459396 | rs7181527 | 36.939 | 0 | SMAD3 |
| chr15:53775670-96810867 | 9973 | 43035198 | 1 | rs657495 | rs2589238 | 49.204 | 0 | SMAD3 |
| chr15:66108544-102427006 | 8615 | 36318463 | 3 | cnvi0007613 | rs11632620 | 159.164 | 0 | SMAD3 |
| chr5:84830796-171903310 | 16642 | 87072515 | 1 | rs300657 | rs10042482 | 42.208 | 0 | SMAD5 |
| chr5:57343495-171903310 | 21683 | 114559816 | 1 | rs10940593 | rs10042482 | 61.169 | 0 | SMAD5 |
| chr5:98442871-150317237 | 9828 | 51874367 | 1 | rs1447379 | rs7710790 | 38.687 | 0 | SMAD5 |
| chr5:4872310-180709915 | 35876 | 175837606 | 3 | rs816467 | rs10071993 | 179.394 | 0 | SMAD5 |
| chr5:49952847-89853069 | 7268 | 39900223 | 3 | rs12188654 | rs42467 | 26.225 | 0 | SMN2 |
| chr5:57343495-171903310 | 21683 | 114559816 | 1 | rs10940593 | rs10042482 | 61.169 | 0 | SMN2 |
| chr5:69323596-70398523 | 189 | 1074928 | 1 | cnvi0017237 | cnvi0017343 | 91.012 | 0 | SMN2 |
| chr5:69268538-70308861 | 189 | 1040324 | 3 | cnvi0017230 | cnvi0023254 | 49.308 | 0 | SMN2 |
| chr5:69243138-69405204 | 46 | 162067 | 3 | cnvi0023208 | cnvi0023221 | 30.078 | 0 | SMN2 |
| chr5:69677532-70379466 | 127 | 701935 | 3 | cnvi0017312 | cnvi0023557 | 34.65 | 0 | SMN2 |
| chr5:69283377-70251701 | 177 | 968325 | 1 | cnvi0023548 | cnvi0021172 | 83.517 | 0 | SMN2 |
| chr5:69291141-70271505 | 180 | 980365 | 1 | cnvi0017232 | cnvi0021174 | 88.653 | 0 | SMN2 |
| chr5:69279340-70251701 | 179 | 972362 | 1 | cnvi0017231 | cnvi0021172 | 78.887 | 0 | SMN2 |
| chr5:69323596-70275720 | 177 | 952125 | 1 | cnvi0017237 | cnvi0017327 | 103.484 | 0 | SMN2 |
| chr5:69268538-70251701 | 181 | 983164 | 3 | cnvi0017230 | cnvi0021172 | 60.056 | 0 | SMN2 |
| chr5:69328641-70291250 | 177 | 962610 | 1 | cnvi0023210 | cnvi0017323 | 62.594 | 0 | SMN2 |
| chr5:69688350-70369397 | 124 | 681048 | 1 | cnvi0017249 | cnvi0018714 | 25.677 | 0 | SMN2 |
| chr5:69243138-70291250 | 191 | 1048113 | 1 | cnvi0023208 | cnvi0017323 | 65.988 | 0 | SMN2 |
| chr5:68835256-70379466 | 254 | 1544211 | 1 | cnvi0017190 | cnvi0023557 | 55.77 | 0 | SMN2 |
| chr5:69291141-70251701 | 176 | 960561 | 1 | cnvi0017232 | cnvi0021172 | 46.783 | 0 | SMN2 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr5:69283377-70275720 | 182 | 992344 | 1 | cnvi0023548 | cnvi0017327 | 79.66 | 0 | SMN2 |
| chr5:69243138-70488200 | 217 | 1245063 | 1 | cnvi0023208 | cnvi0021181 | 90.718 | 0 | SMN2 |
| chr5:68976129-70599000 | 267 | 1622872 | 3 | cnvi0017227 | cnvi0017334 | 64.229 | 0 | SMN2 |
| chr5:68835256-70450158 | 262 | 1614903 | 3 | cnvi0017190 | cnvi0017349 | 49.942 | 0 | SMN2 |
| chr5:69440806-70593467 | 185 | 1152662 | 1 | cnvi0017247 | cnvi0026040 | 53.84 | 0 | SMN2 |
| chr5:69688350-70379466 | 126 | 691117 | 3 | cnvi0017249 | cnvi0023557 | 32.967 | 0 | SMN2 |
| chr5:69174834-70636542 | 245 | 1461709 | 3 | cnvi0017202 | cnvi0017338 | 140.179 | 0 | SMN2 |
| chr5:68894461-70636542 | 283 | 1742082 | 3 | cnvi0017213 | cnvi0017338 | 68.289 | 0 | SMN2 |
| chr5:4872310-180709915 | 35876 | 175837606 | 3 | rs816467 | rs10071993 | 179.394 | 0 | SMN2 |
| chr16:59854720-89273883 | 7609 | 29419164 | 3 | rs1373880 | rs8046156 | 31.884 | 0 | SMPD3 |
| chr16:64107047-82920737 | 4544 | 18813691 | 1 | rs2319723 | rs918661 | 28.887 | 0 | SMPD3 |
| chr16:50219449-89544756 | 10324 | 39325308 | 3 | rs6500298 | rs3803681 | 108.108 | 0 | SMPD3 |
| chr15:29325866-56044189 | 5303 | 26718324 | 3 | rs4779705 | rs2414433 | 21.732 | 0 | SNAP23 |
| chr15:32939946-43104406 | 2544 | 10164443 | 3 | rs12594777 | rs13380301 | 32.942 | 0 | SNAP23 |
| chr20:7869025-62424661 | 11941 | 54555637 | 3 | rs2294306 | rs6010652 | 9.732 | 0 | SNAP25 |
| chr20:4591715-58420336 | 11753 | 53828622 | 1 | rs6139494 | rs1416388 | 40.922 | 0 | SNAP25 |
| chr20:236802-54845796 | 12646 | 54608995 | 3 | rs448294 | rs6064362 | 286.151 | 0 | SNAP25 |
| chr6:64844594-169208546 | 21567 | 104233953 | 1 | rs4710465 | rs601639 | 46.524 | 0 | SNAP91 |
| chr6:66609532-147053632 | 15315 | 80444101 | 3 | rs9354335 | rs4896886 | 44.941 | 0 | SNAP91 |
| chr6:73120320-165130872 | 18715 | 92010553 | 1 | rs9442780 | rs10946016 | 76.383 | 0 | SNAP91 |
| chr6:26922906-93578359 | 19746 | 66655454 | 1 | rs9348738 | rs9363009 | 27.061 | 0 | SNAP91 |
| chr6:66541198-162520133 | 19344 | 95978936 | 1 | rs2000382 | rs6901071 | 27.509 | 0 | SNAP91 |
| chr6:84250330-84391540 | 19 | 141211 | 1 | rs7741310 | rs1454130 | 14.57 | 0 | SNAP91 |
| chr6:62697746-94090076 | 6391 | 31392331 | 1 | rs6455128 | rs3799807 | 108.85 | 0 | SNAP91 |
| chr6:67621368-147709180 | 16188 | 80087813 | 1 | rs6919455 | rs7739314 | 52.498 | 0 | SNAP91 |
| chr6:79198069-99893938 | 4062 | 20695870 | 3 | rs1321584 | rs4504482 | 200.961 | 0 | SNAP91 |
| chr4:31222833-180548076 | 24457 | 149325244 | 1 | rs7662351 | rs3849606 | 36.162 | 0 | SNCA |
| chr4:89603085-113991140 | 4018 | 24388056 | 3 | rs2972038 | rs2279892 | 28.405 | 0 | SNCA |
| chr4:68173959-185767176 | 20235 | 117593218 | 1 | rs6552083 | rs4862428 | 61.893 | 0 | SNCA |
| chr4:22401728-188608857 | 28456 | 166207130 | 1 | rs4697297 | rs7687111 | 35.717 | 0 | SNCA |
| chr4:90618264-90784528 | 33 | 166265 | 1 | rs17286290 | rs2736994 | 16.242 | 0 | SNCA |
| chr4:63726348-173015421 | 19817 | 109289074 | 1 | rs17082970 | rs2131002 | 30.251 | 0 | SNCA |
| chr4:29179713-117038307 | 15513 | 87858595 | 1 | rs1507441 | rs1068807 | 71.6 | 0 | SNCA |
| chr4:69590353-190872778 | 23145 | 121282426 | 3 | rs293433 | rs12646565 | 315.633 | 0 | SNCA |
| chr20:13712393-55093901 | 8218 | 41381509 | 1 | rs6033810 | rs6999 | 41.237 | 0 | SNRPB2 |
| chr20:7869025-62424661 | 11941 | 54555637 | 3 | rs2294306 | rs6010652 | 9.732 | 0 | SNRPB2 |
| chr20:4591715-58420336 | 11753 | 53828622 | 1 | rs6139494 | rs1416388 | 40.922 | 0 | SNRPB2 |
| chr20:236802-54845796 | 12646 | 54608995 | 3 | rs448294 | rs6064362 | 286.151 | 0 | SNRPB2 |
| chr20:13712393-55093901 | 8218 | 41381509 | 1 | rs6033810 | rs6999 | 41.237 | 0 | SNTA1 |
| chr20:7869025-62424661 | 11941 | 54555637 | 3 | rs2294306 | rs6010652 | 9.732 | 0 | SNTA1 |
| chr20:4591715-58420336 | 11753 | 53828622 | 1 | rs6139494 | rs1416388 | 40.922 | 0 | SNTA1 |
| chr20:236802-54845796 | 12646 | 54608995 | 3 | rs448294 | rs6064362 | 286.151 | 0 | SNTA1 |
| chr15:20058438-32486479 | 2394 | 12486242 | 3 | rs12591240 | cnvi0018163 | 296.82 | 0 | SNURF |
| chr15:22267462-32461463 | 2232 | 10194002 | 3 | rs4123826 | rs286103 | 218.215 | 0 | SNURF |
| chr18:25388300-75954881 | 11539 | 50566582 | 1 | rs11083228 | rs1876021 | 39.235 | 0 | SOCS6 |
| chr18:64480206-70125971 | 1534 | 5645766 | 3 | rs10516001 | rs1347013 | 65.248 | 0 | SOCS6 |
| chr18:46516210-68441007 | 5088 | 21924798 | 1 | rs7229153 | rs1282652 | 51.891 | 0 | SOCS6 |
| chr18:65585580-69281510 | 1074 | 3695931 | 1 | rs11875790 | rs8090683 | 111.579 | 0 | SOCS6 |
| chr18:62041997-76047493 | 3846 | 14005497 | 1 | rs1421538 | rs8085865 | 33.212 | 0 | SOCS6 |
| chr18:44788908-78015180 | 8492 | 33226273 | 3 | rs9944807 | rs12960632 | 579.2 | 0 | SOCS6 |
| chr17:21685812-67308196 | 12365 | 45622385 | 1 | rs34864328 | rs17686852 | 50.018 | 0 | SOCS7 |
| chr17:26648492-58955084 | 5831 | 32306593 | 3 | rs1981512 | rs8068776 | 15.642 | 0 | SOCS7 |
| chr15:29325866-56044189 | 5303 | 26718324 | 3 | rs4779705 | rs2414433 | 21.732 | 0 | SORD |
| chr15:44763598-47394943 | 502 | 2631346 | 3 | rs7172106 | rs4095484 | 142.088 | 0 | SORD |
| chr15:43392075-66051345 | 4963 | 22659271 | 3 | rs8028608 | rs6494537 | 59.842 | 0 | SORD |
| chr6:10123365-31221039 | -3135 | 21097675 | 1 | rs2181334 | rs4416711 | 318.459 | 0 | SOX4 |
| chr6:2681610-31453618 | 81 | 28772009 | 3 | rs1131896 | rs9267212 | 428.177 | 0 | SOX4 |
| chr6:3760708-31957364 | 8062 | 28196657 | 3 | rs2187825 | cnvi0006380 | 39.016 | 0 | SOX4 |
| chr6:1171596-29895228 | 43 | 28723633 | 0 | rs3128994 | rs9259831 | 53.123 | 0 | SOX4 |
| chr6:19044000-31286381 | -6774 | 12242382 | 1 | rs6922929 | rs9265057 | 31.384 | 0 | SOX4 |
| chr6:1171596-29899147 | 47 | 28727552 | 0 | rs3128994 | rs2394704 | 80.695 | 0 | SOX4 |
| chr6:1177990-29899147 | 39 | 28721158 | 0 | rs2428530 | rs2394704 | 44.381 | 0 | SOX4 |
| chr6:1175965-29899147 | 43 | 28723183 | 0 | rs1611522 | rs2394704 | 52.089 | 0 | SOX4 |
| chr6:2585208-31281876 | -2 | 28696669 | 1 | rs1634746 | rs1634747 | 31.615 | 0 | SOX4 |
| chr6:1171596-29899147 | 47 | 28727552 | 0 | rs3128994 | rs2394704 | 63.572 | 0 | SOX4 |
| chr6:2584569-31286381 | 8 | 28701813 | 1 | rs9391764 | rs9265057 | 34.598 | 0 | SOX4 |
| chr6:2681610-31453618 | 81 | 28772009 | 3 | rs1131896 | rs9267212 | 390.234 | 0 | SOX4 |
| chr6:1171596-29892436 | 39 | 28720841 | 1 | rs3128994 | rs9259806 | 31.699 | 0 | SOX4 |
| chr6:1171596-29895228 | 43 | 28723633 | 0 | rs3128994 | rs9259831 | 43.568 | 0 | SOX4 |
| chr6:19044000-31286381 | -6774 | 12242382 | 0 | rs6922929 | rs9265057 | 33.119 | 0 | SOX4 |
| chr6:181089-30430875 | 1806 | 30249787 | 3 | rs1535053 | rs35792611 | 80.394 | 0 | SOX4 |
| chr8:30757798-142750969 | 20699 | 111993172 | 1 | rs10101203 | rs6421025 | 34.223 | 0 | SPAG1 |
| chr8:60424884-145286483 | 17030 | 84861600 | 3 | rs1401422 | rs9720889 | 8.858 | 0 | SPAG1 |
| chr8:23218101-146274708 | 23020 | 123056608 | 1 | rs7010362 | rs7822726 | 38.828 | 0 | SPAG1 |
| chr8:76354446-113652365 | 6767 | 37297920 | 1 | rs830783 | rs16883889 | 127.023 | 0 | SPAG1 |
| chr8:66822030-144791126 | 16557 | 77969097 | 3 | rs6472235 | rs10100154 | 251.068 | 0 | SPAG1 |
| chr16:88780175-89789898 | 143 | 1009724 | 1 | rs4782321 | rs6500437 | 27.339 | 0 | SPG7 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr4:31222833-180548076 | 24457 | 149325244 | 1 | rs7662351 | rs3849606 | 36.162 | 0 | SPP1 |
| chr4:68173959-185767176 | 20235 | 117593218 | 1 | rs6552083 | rs4862428 | 61.893 | 0 | SPP1 |
| chr4:22401728-188608857 | 28456 | 166207130 | 1 | rs4697297 | rs7687115 | 35.717 | 0 | SPP1 |
| chr4:63726348-173015421 | 19817 | 109289074 | 1 | rs17082970 | rs2131002 | 30.251 | 0 | SPP1 |
| chr4:29179713-117038307 | 15513 | 87858595 | 1 | rs1507441 | rs1068807 | 71.6 | 0 | SPP1 |
| chr4:69590353-190872778 | 23145 | 121282426 | 3 | rs293433 | rs12646565 | 315.633 | 0 | SPP1 |
| chr2:12056323-227979775 | 39094 | 215923453 | 1 | rs966391 | rs1922020 | 31.384 | 0 | SPTBN1 |
| chr2:34870277-241929621 | 37755 | 207059345 | 3 | rs13422005 | rs10205276 | 46.946 | 0 | SPTBN1 |
| chr2:38101137-241482099 | 36812 | 203380963 | 1 | rs879321 | rs7576043 | 52.099 | 0 | SPTBN1 |
| chr2:41212010-82396211 | 9721 | 41184202 | 3 | rs12614285 | rs934310 | 396.396 | 0 | SPTBN1 |
| chr5:161172541-179954615 | 4271 | 18782075 | 3 | rs4921415 | rs10059433 | 6.291 | 0 | SQSTM1 |
| chr5:4872310-180709915 | 35876 | 175837606 | 3 | rs816467 | rs10071993 | 179.394 | 0 | SQSTM1 |
| chr20:35942718-36175566 | 43 | 232849 | 3 | rs6104528 | rs4810841 | 2.708 | 0 | SRC |
| chr20:13712393-55093901 | 8218 | 41381509 | 1 | rs6033810 | rs6999 | 41.237 | 0 | SRC |
| chr20:7869025-62424661 | 11941 | 54555637 | 3 | rs2294306 | rs6010652 | 9.732 | 0 | SRC |
| chr20:4591715-58420336 | 11753 | 53828622 | 1 | rs6139494 | rs1416388 | 40.922 | 0 | SRC |
| chr20:236802-54845796 | 12646 | 54608995 | 3 | rs448294 | rs6064362 | 286.151 | 0 | SRC |
| chr3:179527-114630641 | 23879 | 114451115 | 3 | rs4684741 | rs1587972 | 207.852 | 0 | SRGAP3 |
| chr13:19584477-81204088 | 13265 | 61619612 | 3 | rs1334954 | rs1176297 | 22.162 | 0 | STARD13 |
| chr13:23742931-115064482 | 19829 | 91321552 | 1 | rs4770401 | rs7999630 | 44.074 | 0 | STARD13 |
| chr13:19121741-63373781 | 10326 | 44252041 | 3 | rs9578050 | rs9539575 | 82.761 | 0 | STARD13 |
| chr20:13712393-55093901 | 8218 | 41381509 | 1 | rs6033810 | rs6999 | 41.237 | 0 | STAU1 |
| chr20:7869025-62424661 | 11941 | 54555637 | 3 | rs2294306 | rs6010652 | 9.732 | 0 | STAU1 |
| chr20:4591715-58420336 | 11753 | 53828622 | 1 | rs6139494 | rs1416388 | 40.922 | 0 | STAU1 |
| chr20:236802-54845796 | 12646 | 54608995 | 3 | rs448294 | rs6064362 | 286.151 | 0 | STAU1 |
| chr5:161172541-179954615 | 4271 | 18782075 | 3 | rs4921415 | rs10059433 | 6.291 | 0 | STC2 |
| chr5:4872310-180709915 | 35876 | 175837606 | 3 | rs816467 | rs10071993 | 179.394 | 0 | STC2 |
| chr12:10113083-116370432 | 20594 | 106257350 | 1 | rs2012504 | rs7958254 | 35.157 | 0 | STRAP |
| chr12:8171838-32535863 | 5853 | 24364026 | 3 | rs11609309 | rs7963182 | 23.697 | 0 | STRAP |
| chr12:10020267-129866293 | 23654 | 119846027 | 1 | rs1597097 | rs2170504 | 45.428 | 0 | STRAP |
| chr12:207886-50770291 | 11565 | 50562406 | 3 | rs868249 | rs4477515 | 43.892 | 0 | STRAP |
| chr2:12056323-227979775 | 39094 | 215923453 | 1 | rs966391 | rs1922020 | 31.384 | 0 | STRN |
| chr2:34870277-241929621 | 37755 | 207059345 | 3 | rs13422005 | rs10205276 | 46.946 | 0 | STRN |
| chr2:18856-41136833 | 9721 | 41117978 | 3 | rs11901199 | rs10187704 | 191.638 | 0 | STRN |
| chr19:31569338-53780966 | 3788 | 22211629 | 1 | rs2867544 | rs10407424 | 33.9 | 0 | STRN4 |
| chr19:43257015-55294329 | −7309 | 12037315 | 3 | rs7246152 | rs2569676 | 21.402 | 0 | STRN4 |
| chr19:288246-59110628 | 11009 | 58822383 | 3 | rs10409452 | cnvi0009466 | 100.582 | 0 | STRN4 |
| chr1:1005806-105612342 | 19173 | 104606537 | 3 | rs3934834 | rs1584633 | 44.152 | 0 | STX12 |
| chr1:2006108-109527861 | 22130 | 107521754 | 3 | rs2254669 | rs839879 | 162.269 | 0 | STX12 |
| chr16:29441284-33923125 | 585 | 4481842 | 3 | rs7206789 | rs4043755 | 42.437 | 0 | STX4 |
| chr16:176743-50013967 | 8328 | 49837225 | 3 | rs2562164 | rs12597023 | 174.392 | 0 | STX4 |
| chr11:42185849-126756938 | 15451 | 84571090 | 1 | rs4375424 | rs10750356 | 36.99 | 0 | STX5 |
| chr11:21723471-131521797 | 20508 | 109798327 | 1 | rs11828478 | rs2512898 | 27.565 | 0 | STX5 |
| chr11:23168804-106781292 | 16332 | 83612489 | 1 | rs11027007 | rs7103285 | 49.747 | 0 | STX5 |
| chr11:211482-66910826 | 13813 | 66699345 | 3 | rs2293168 | rs4375446 | 30.249 | 0 | STX5 |
| chr9:2522475-140068342 | 25719 | 137545868 | 3 | rs10966757 | rs4074426 | 93.386 | 0 | STXBP1 |
| chr9:33180228-132003792 | 14691 | 98823565 | 1 | rs7854765 | rs9408988 | 28.69 | 0 | STXBP1 |
| chr9:100158052-139077343 | 9815 | 38919292 | 3 | rs1020884 | rs4842126 | 470.601 | 0 | STXBP1 |
| chr1:64114301-245591329 | 29842 | 181477029 | 1 | rs11208257 | rs1173850 | 37.504 | 0 | STXBP3 |
| chr1:75098453-243531649 | 27360 | 168433197 | 1 | rs12117493 | rs10927002 | 32.113 | 0 | STXBP3 |
| chr1:79710545-188898319 | 17303 | 109187775 | 1 | rs417181 | rs16829637 | 45.89 | 0 | STXBP3 |
| chr1:2006108-109527861 | 22130 | 107521754 | 3 | rs2254669 | rs839879 | 162.269 | 0 | STXBP3 |
| chr4:31222833-180548076 | 24457 | 149325244 | 1 | rs7662351 | rs3849606 | 36.162 | 0 | SULT1E1 |
| chr4:68173959-185767176 | 20235 | 117593218 | 1 | rs6552083 | rs4862428 | 61.893 | 0 | SULT1E1 |
| chr4:22401728-188608857 | 28456 | 166207130 | 1 | rs4697297 | rs7687115 | 35.717 | 0 | SULT1E1 |
| chr4:63726348-173015421 | 19817 | 109289074 | 1 | rs17082970 | rs2131002 | 30.251 | 0 | SULT1E1 |
| chr4:29179713-117038307 | 15513 | 87858595 | 1 | rs1507441 | rs1068807 | 71.6 | 0 | SULT1E1 |
| chr4:69590353-190872778 | 23145 | 121282426 | 3 | rs293433 | rs12646565 | 315.633 | 0 | SULT1E1 |
| chr6:64844594-169078546 | 21567 | 104233953 | 1 | rs4710465 | rs601639 | 46.524 | 0 | SUMO4 |
| chr6:73120320-165130872 | 18715 | 92010553 | 1 | rs9442780 | rs10946016 | 76.383 | 0 | SUMO4 |
| chr6:66541198-162520133 | 19344 | 95978936 | 1 | rs2000382 | rs6901071 | 27.509 | 0 | SUMO4 |
| chr6:94117546-165103679 | 15579 | 70986134 | 1 | rs3799792 | rs9347902 | 34.066 | 0 | SUMO4 |
| chr6:100082983-170909002 | 16393 | 70826020 | 3 | rs594231 | rs12213906 | 261.313 | 0 | SUMO4 |
| chr9:1989033-107532375 | 18263 | 105543285 | 1 | rs7864828 | rs10820726 | 39.824 | 0 | SYK |
| chr9:2522475-140068342 | 25719 | 137545868 | 3 | rs10966757 | rs4074426 | 93.386 | 0 | SYK |
| chr9:33180228-132003792 | 14691 | 98823565 | 1 | rs7854765 | rs9408988 | 28.69 | 0 | SYK |
| chr9:46587-94335290 | 17484 | 94288704 | 3 | rs10814410 | rs9409606 | 762.393 | 0 | SYK |
| chr12:10113083-116370432 | 20594 | 106257350 | 1 | rs2012504 | rs7958254 | 35.157 | 0 | SYT1 |
| chr12:59512781-127744939 | 13469 | 68232159 | 3 | rs908394 | rs7966946 | 20.62 | 0 | SYT1 |
| chr12:10020267-129866293 | 23654 | 119846027 | 1 | rs1597097 | rs2170504 | 45.428 | 0 | SYT1 |
| chr12:39967134-84174413 | 8879 | 44207280 | 1 | rs11172661 | rs11116039 | 39.568 | 0 | SYT1 |
| chr12:79291372-80266733 | 130 | 975001 | 1 | rs1551847 | rs2698261 | 34.672 | 0 | SYT1 |
| chr12:50855195-133778796 | 17748 | 82923602 | 3 | rs4351895 | rs7975069 | 159.589 | 0 | SYT1 |
| chr11:345515-17408630 | 4247 | 17063116 | 3 | rs11246094 | rs5215 | 30.474 | 0 | SYT9 |
| chr11:211482-66910826 | 13813 | 66699345 | 3 | rs2293168 | rs4375446 | 30.249 | 0 | SYT9 |
| chr2:12056323-227979775 | 39094 | 215923453 | 1 | rs966391 | rs1922020 | 31.384 | 0 | TANC1 |
| chr2:34870277-241929621 | 37755 | 207059345 | 3 | rs13422005 | rs10205276 | 46.946 | 0 | TANC1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr2:38101137-241482099 | 36812 | 203380963 | 1 | rs879321 | rs7576043 | 52.099 | 0 | TANC1 |
| chr2:77041264-194763754 | 21140 | 117722491 | 1 | rs2102827 | rs16835406 | 94.091 | 0 | TANC1 |
| chr2:83383702-175194550 | 16291 | 91810849 | 3 | rs12469609 | rs11891208 | 154.4 | 0 | TANC1 |
| chr2:12056323-227979775 | 39094 | 215923453 | 1 | rs966391 | rs1922020 | 31.384 | 0 | TANK |
| chr2:34870277-241929621 | 37755 | 207059345 | 3 | rs13422005 | rs10205276 | 46.946 | 0 | TANK |
| chr2:38101137-241482099 | 36812 | 203380963 | 1 | rs879321 | rs7576043 | 52.099 | 0 | TANK |
| chr2:77041264-194763754 | 21140 | 117722491 | 1 | rs2102827 | rs16835406 | 94.091 | 0 | TANK |
| chr2:83383702-175194550 | 16291 | 91810849 | 3 | rs12469609 | rs11891208 | 154.4 | 0 | TANK |
| chr16:29441284-33923125 | 585 | 4481842 | 3 | rs7206789 | rs4043755 | 42.437 | 0 | TAOK2 |
| chr16:176743-50013967 | 8328 | 49837225 | 3 | rs2562164 | rs12597023 | 174.392 | 0 | TAOK2 |
| chr5:49952847-89853069 | 7268 | 39900223 | 3 | rs12188654 | rs42467 | 26.225 | 0 | TBCA |
| chr5:57343495-171903310 | 21683 | 114559816 | 1 | rs10940593 | rs10042482 | 61.169 | 0 | TBCA |
| chr5:4872310-180709915 | 35876 | 175837606 | 3 | rs816467 | rs10071993 | 179.394 | 0 | TBCA |
| chr17:44458950-81047708 | −8195 | 36588759 | 1 | cnvi0016818 | rs35680231 | 35.591 | 0 | TBCD |
| chr17:62662507-81047708 | −11496 | 18385202 | 3 | rs6504246 | rs35680231 | 56.048 | 0 | TBCD |
| chr1:64114301-245591329 | 29842 | 181477029 | 1 | rs11208257 | rs1173850 | 37.504 | 0 | TBCE |
| chr1:178626526-244159143 | 13064 | 65532618 | 3 | rs2761477 | rs479338 | 11.373 | 0 | TBCE |
| chr1:75098453-243531649 | 27360 | 168433197 | 1 | rs12117493 | rs10927002 | 32.113 | 0 | TBCE |
| chr1:174219398-247422297 | 15986 | 73202900 | 1 | rs16846809 | rs4642922 | 35.258 | 0 | TBCE |
| chr1:226536645-236803753 | 2600 | 10267109 | 3 | rs874583 | rs10925178 | 100.109 | 0 | TBCE |
| chr12:10113083-116370432 | 20594 | 106257350 | 1 | rs2012504 | rs7958254 | 35.157 | 0 | TBK1 |
| chr12:59512781-127744893 | 13469 | 68232159 | 3 | rs908394 | rs7966946 | 20.62 | 0 | TBK1 |
| chr12:10020267-129866293 | 23654 | 119846027 | 1 | rs1597097 | rs2170504 | 45.428 | 0 | TBK1 |
| chr12:39967134-84174413 | 8879 | 44207280 | 1 | rs11172661 | rs11116039 | 39.568 | 0 | TBK1 |
| chr12:50855195-133778796 | 17748 | 82923602 | 3 | rs4351895 | rs7975069 | 159.589 | 0 | TBK1 |
| chr19:266034-18061509 | 3100 | 17795476 | 3 | rs2312724 | rs7250332 | 19.51 | 0 | TBXA2R |
| chr19:629303-4119012 | 709 | 3489710 | 1 | rs2283575 | rs350887 | 26.758 | 0 | TBXA2R |
| chr19:288246-59110628 | 11009 | 58822383 | 3 | rs10409452 | cnvi0009466 | 100.582 | 0 | TBXA2R |
| chr19:1130986-2128054 | 143 | 997069 | 1 | rs10413074 | rs1017084 | 25.799 | 0 | TCF3 |
| chr19:859214-1650134 | 121 | 790921 | 1 | rs1683564 | rs1860661 | 36.427 | 0 | TCF3 |
| chr19:266034-18061509 | 3100 | 17795476 | 3 | rs2312724 | rs7250332 | 19.51 | 0 | TCF3 |
| chr19:629303-4119012 | 709 | 3489710 | 1 | rs2283575 | rs350887 | 26.758 | 0 | TCF3 |
| chr19:1351916-1716865 | 58 | 364950 | 1 | rs11670805 | rs11878765 | 31.586 | 0 | TCF3 |
| chr19:288246-59110628 | 11009 | 58822383 | 3 | rs10409452 | cnvi0009466 | 100.582 | 0 | TCF3 |
| chr18:25388300-75954881 | 11539 | 50566582 | 1 | rs11083228 | rs1876021 | 39.235 | 0 | TCF4 |
| chr18:1583633-58142042 | 11490 | 56558410 | 3 | rs9945988 | rs1560399 | 3.736 | 0 | TCF4 |
| chr18:46516210-68441007 | 5088 | 21924798 | 1 | rs7229153 | rs1282652 | 51.891 | 0 | TCF4 |
| chr18:26550830-63713914 | 8241 | 37163085 | 1 | rs16945738 | rs2715304 | 17.922 | 0 | TCF4 |
| chr18:26162481-67193217 | 9255 | 41030737 | 1 | rs12458903 | rs9961907 | 31.327 | 0 | TCF4 |
| chr18:44788908-78015180 | 8492 | 33226273 | 3 | rs9944807 | rs12960632 | 579.2 | 0 | TCF4 |
| chr6:64844594-169078546 | 21567 | 104233953 | 1 | rs4710465 | rs601639 | 46.524 | 0 | TCP1 |
| chr6:151495387-165969396 | 3761 | 14474010 | 3 | rs9322304 | rs1022180 | 22.826 | 0 | TCP1 |
| chr6:73120320-165133612 | 18715 | 92010553 | 1 | rs9442780 | rs10946016 | 76.383 | 0 | TCP1 |
| chr6:66541198-162520133 | 19344 | 95978936 | 1 | rs2000382 | rs6901071 | 27.509 | 0 | TCP1 |
| chr6:94117546-165103679 | 15579 | 70986134 | 1 | rs3799792 | rs9347902 | 34.066 | 0 | TCP1 |
| chr6:100082983-170909002 | 16393 | 70826020 | 3 | rs594231 | rs12213906 | 261.313 | 0 | TCP1 |
| chr3:13878889-149733703 | 24723 | 135858402 | 1 | rs12634112 | rs2007890 | 55.663 | 0 | TDGF1 |
| chr3:33409611-170735099 | 23775 | 137325489 | 1 | rs3915062 | rs11924032 | 26.867 | 0 | TDGF1 |
| chr3:179527-114630641 | 23879 | 114451115 | 3 | rs4684741 | rs1587972 | 207.852 | 0 | TDGF1 |
| chr6:26922906-93578359 | 19746 | 66655454 | 1 | rs9348738 | rs9363009 | 27.061 | 0 | TEAD3 |
| chr6:31289284-56929863 | 15402 | 25640580 | 3 | rs9265170 | cnvi0015437 | 25.647 | 0 | TEAD3 |
| chr6:32968276-73449742 | 15442 | 40481467 | 3 | rs2395300 | rs4235869 | 415.87 | 0 | TEAD3 |
| chr14:19917123-65327288 | 10286 | 45410166 | 3 | rs2495197 | rs9323455 | 270.291 | 0 | TEP1 |
| chr5:141659-19010008 | 4662 | 18868350 | 3 | rs11741126 | rs4642370 | 50.124 | 0 | TERT |
| chr5:830376-1276121 | 128 | 445746 | 3 | rs12657470 | cnvi0012572 | 5.026 | 0 | TERT |
| chr5:506051-4746181 | 1345 | 4240131 | 3 | rs6864158 | rs7716294 | 447.942 | 0 | TERT |
| chr10:7188484-134205354 | 26672 | 127016871 | 1 | rs1977295 | rs3923858 | 50.772 | 0 | TFAM |
| chr10:734229-69155636 | 14859 | 68421408 | 3 | rs1769236 | rs2394375 | 72.104 | 0 | TFAM |
| chr10:58385643-124973104 | 13625 | 66587462 | 1 | rs7920235 | rs17663304 | 36.18 | 0 | TFAM |
| chr10:57671424-133349223 | 16243 | 75677800 | 1 | rs11005106 | rs4301710 | 37.114 | 0 | TFAM |
| chr10:55492162-117205017 | 13465 | 61712856 | 1 | rs6481032 | rs1933664 | 62.56 | 0 | TFAM |
| chr10:53602190-135522754 | 19167 | 81920565 | 3 | rs12247820 | rs10909028 | 139.373 | 0 | TFAM |
| chr2:12056323-227979775 | 39094 | 215923453 | 1 | rs966391 | rs1922020 | 31.384 | 0 | TGFA |
| chr2:34870277-241929621 | 37755 | 207059345 | 3 | rs13422005 | rs10205276 | 46.946 | 0 | TGFA |
| chr2:38101137-241482099 | 36812 | 203380963 | 1 | rs879321 | rs7576043 | 52.099 | 0 | TGFA |
| chr2:41212010-82396211 | 9721 | 41184202 | 3 | rs12614285 | rs934310 | 396.396 | 0 | TGFA |
| chr20:13712393-55093901 | 8218 | 41381509 | 1 | rs6033810 | rs6999 | 41.237 | 0 | TGM2 |
| chr20:7869025-62424661 | 11941 | 54555637 | 3 | rs2294306 | rs6010652 | 9.732 | 0 | TGM2 |
| chr20:4591715-58420336 | 11753 | 53828622 | 1 | rs6139494 | rs1416388 | 40.922 | 0 | TGM2 |
| chr20:236802-54845796 | 12646 | 54608995 | 3 | rs448294 | rs6064362 | 286.151 | 0 | TGM2 |
| chr21:14601415-48084989 | 8249 | 33483575 | 3 | rs2775537 | rs2839378 | 12047.211 | 0 | TIAM1 |
| chr21:14601415-48084989 | 8249 | 33483575 | 3 | rs2775537 | rs2839378 | 41.154 | 0 | TIAM1 |
| chr21:14768343-48084989 | 8193 | 33316647 | 3 | rs2257224 | rs2839378 | 5021.076 | 0 | TIAM1 |
| chr21:14601415-48084989 | 8249 | 33483575 | 3 | rs2775537 | rs2839378 | 4787.438 | 0 | TIAM1 |
| chr21:14595264-48084989 | 8781 | 33489726 | 3 | rs2847443 | rs2839378 | 1871.363 | 0 | TIAM1 |
| chr21:10708231-47970581 | 8807 | 37262351 | 3 | rs4044122 | rs2255397 | 73.188 | 0 | TIAM1 |
| chr15:29325866-56044189 | 5303 | 26718324 | 3 | rs4779705 | rs2414433 | 21.732 | 0 | TJP1 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr15:29659013-30239328 | 126 | 580316 | 1 | rs4779618 | rs12905328 | 41.602 | 0 | TJP1 |
| chr15:20058438-32544679 | 2394 | 12486242 | 3 | rs12591240 | cnvi0018163 | 296.82 | 0 | TJP1 |
| chr15:22267462-32461463 | 2232 | 10194002 | 3 | rs4123826 | rs286103 | 218.215 | 0 | TJP1 |
| chr17:75730493-79302149 | 880 | 3571657 | 3 | rs7210773 | rs2864474 | 14.319 | 0 | TK1 |
| chr17:44458950-81047708 | −8195 | 36588759 | 1 | cnvi0016818 | rs35680231 | 35.591 | 0 | TK1 |
| chr17:62662507-81047708 | −11496 | 18385202 | 3 | rs6504246 | rs35680231 | 56.048 | 0 | TK1 |
| chr4:31222833-180548076 | 24457 | 149325244 | 1 | rs7662351 | rs3849606 | 36.162 | 0 | TLR10 |
| chr4:22401728-188608857 | 28456 | 166207130 | 1 | rs4697297 | rs7687115 | 35.717 | 0 | TLR10 |
| chr4:29179713-117038307 | 15513 | 87858595 | 1 | rs1507441 | rs1068807 | 71.6 | 0 | TLR10 |
| chr4:179131-68998153 | 13495 | 68819023 | 3 | rs7686948 | rs7687396 | 625.133 | 0 | TLR10 |
| chr3:13878889-149737330 | 24723 | 135858442 | 1 | rs12634112 | rs2007869 | 55.663 | 0 | TM4SF1 |
| chr3:145967173-173899890 | 4912 | 27932718 | 3 | rs9863647 | rs7618997 | 46.396 | 0 | TM4SF1 |
| chr3:33409611-170735099 | 23775 | 137325489 | 1 | rs3915062 | rs11924032 | 26.867 | 0 | TM4SF1 |
| chr3:102240202-195550366 | 17318 | 93310165 | 1 | rs1620217 | rs11711870 | 41.031 | 0 | TM4SF1 |
| chr3:83075971-196935657 | 21465 | 113859687 | 1 | rs9872858 | rs34729751 | 44.35 | 0 | TM4SF1 |
| chr3:114889454-177826047 | 12700 | 62936594 | 3 | rs6795297 | rs7628308 | 102.526 | 0 | TM4SF1 |
| chr1:1005806-105612342 | 19173 | 104606537 | 3 | rs3934834 | rs1584633 | 44.152 | 0 | TNFRSF14 |
| chr1:1254841-3342804 | 386 | 2087964 | 1 | rs10907179 | rs870171 | 39.259 | 0 | TNFRSF14 |
| chr1:2006108-109527861 | 22130 | 107521754 | 3 | rs2254669 | rs839879 | 162.269 | 0 | TNFRSF14 |
| chr12:207886-50770291 | 11565 | 50562406 | 3 | rs868249 | rs4477515 | 43.892 | 0 | TNFRSF1A |
| chr1:1005806-105612342 | 19173 | 104606537 | 3 | rs3934834 | rs1584633 | 44.152 | 0 | TNFRSF1B |
| chr1:2006108-109527861 | 22130 | 107521754 | 3 | rs2254669 | rs839879 | 162.269 | 0 | TNFRSF1B |
| chr3:166503411-190576461 | 4854 | 24073051 | 1 | rs11925936 | rs1393054 | 31.414 | 0 | TNIK |
| chr3:145967173-173899890 | 4912 | 27932718 | 3 | rs9863647 | rs7618997 | 46.396 | 0 | TNIK |
| chr3:102240202-195550366 | 17318 | 93310165 | 1 | rs1620217 | rs11711870 | 41.031 | 0 | TNIK |
| chr3:164955741-191742104 | 5741 | 26786364 | 1 | rs2218152 | rs9835019 | 52.438 | 0 | TNIK |
| chr3:83075971-196935657 | 21465 | 113859687 | 1 | rs9872858 | rs34729751 | 44.35 | 0 | TNIK |
| chr3:114889454-177826047 | 12700 | 62936594 | 3 | rs6795297 | rs7628308 | 102.526 | 0 | TNIK |
| chr4:179131-68998153 | 13495 | 68819023 | 3 | rs7686948 | rs7687396 | 625.133 | 0 | TNIP2 |
| chr11:345515-17408630 | 4247 | 17063146 | 3 | rs11246094 | rs5215 | 30.474 | 0 | TNNI2 |
| chr11:211482-66910826 | 13813 | 66699345 | 3 | rs2293168 | rs4375446 | 30.249 | 0 | TNNI2 |
| chr19:288246-59110628 | 11009 | 58822383 | 3 | rs10409452 | cnvi0009466 | 100.582 | 0 | TNNI3 |
| chr1:64114301-245591329 | 29842 | 181477029 | 1 | rs11208257 | rs1173850 | 37.504 | 0 | TNNT2 |
| chr1:178626526-244159143 | 13064 | 65532618 | 3 | rs2761477 | rs479338 | 11.373 | 0 | TNNT2 |
| chr1:75098453-243531649 | 27360 | 168433197 | 1 | rs12117493 | rs10927002 | 32.113 | 0 | TNNT2 |
| chr1:188850774-235423607 | 10060 | 46572834 | 1 | rs16829466 | rs12409696 | 43.25 | 0 | TNNT2 |
| chr1:191875752-235423607 | 9517 | 43547856 | 1 | rs9427811 | rs12409696 | 62.01 | 0 | TNNT2 |
| chr1:189128124-227340790 | 7927 | 38212667 | 1 | rs7515205 | rs12752546 | 167.428 | 0 | TNNT2 |
| chr1:174219398-247422297 | 15986 | 73202900 | 1 | rs16846809 | rs4642922 | 35.258 | 0 | TNNT2 |
| chr1:197187605-226404457 | 6316 | 29216853 | 3 | rs10922187 | rs3008192 | 130.989 | 0 | TNNT2 |
| chr1:64114301-245591329 | 29842 | 181477029 | 1 | rs11208257 | rs1173850 | 37.504 | 0 | TOMM20 |
| chr1:178626526-244159143 | 13064 | 65532618 | 3 | rs2761477 | rs479338 | 11.373 | 0 | TOMM20 |
| chr1:75098453-243531649 | 27360 | 168433197 | 1 | rs12117493 | rs10927002 | 32.113 | 0 | TOMM20 |
| chr1:188850774-235423607 | 10060 | 46572834 | 1 | rs16829466 | rs12409696 | 43.25 | 0 | TOMM20 |
| chr1:191875752-235423607 | 9517 | 43547856 | 1 | rs9427811 | rs12409696 | 62.01 | 0 | TOMM20 |
| chr1:174219398-247422297 | 15986 | 73202900 | 1 | rs16846809 | rs4642922 | 35.258 | 0 | TOMM20 |
| chr1:226536645-236803753 | 2600 | 10267019 | 3 | rs874583 | rs10925178 | 100.109 | 0 | TOMM20 |
| chr17:38388040-38909192 | 55 | 521153 | 3 | rs9916782 | rs2109217 | 3.141 | 0 | TOP2A |
| chr7:21685812-67308196 | 12365 | 45622385 | 1 | rs34864328 | rs17686852 | 50.018 | 0 | TOP2A |
| chr17:26648492-58955084 | 5831 | 32306593 | 3 | rs1981512 | rs8068776 | 15.642 | 0 | TOP2A |
| chr17:108420-26610769 | 5548 | 26502350 | 3 | rs12452527 | rs658591 | 82.699 | 0 | TP53 |
| chr12:207886-50770291 | 11565 | 50562406 | 3 | rs868249 | rs4477515 | 43.892 | 0 | TPI1 |
| chr16:59854720-89273883 | 7609 | 29419164 | 3 | rs1373880 | rs8046156 | 31.884 | 0 | TRADD |
| chr16:64107047-82920737 | 4544 | 18813691 | 1 | rs2319723 | rs918661 | 28.887 | 0 | TRADD |
| chr16:50219449-89544756 | 10324 | 39325308 | 3 | rs6500298 | rs3803681 | 108.108 | 0 | TRADD |
| chr9:2522475-140068342 | 25719 | 137545868 | 3 | rs10966757 | rs4074426 | 93.386 | 0 | TRAF1 |
| chr9:33180228-132003792 | 14691 | 98823565 | 1 | rs7854765 | rs9408988 | 28.69 | 0 | TRAF1 |
| chr9:100158052-139077343 | 9815 | 38919292 | 3 | rs1020884 | rs4842126 | 470.601 | 0 | TRAF1 |
| chr9:2522475-140068342 | 25719 | 137545868 | 3 | rs10966757 | rs4074426 | 93.386 | 0 | TRAF2 |
| chr9:139492789-140913833 | 196 | 1421045 | 1 | rs28485548 | cnvi0002661 | 28.211 | 0 | TRAF2 |
| chr9:139492789-140212642 | 109 | 719854 | 3 | rs28485548 | rs13295516 | 12.464 | 0 | TRAF2 |
| chr9:139725120-140176250 | 50 | 451131 | 1 | rs2811750 | rs28576426 | 24.435 | 0 | TRAF2 |
| chr11:24610019-42414566 | 3388 | 17804548 | 3 | rs1858156 | rs7127426 | 27.914 | 0 | TRAF6 |
| chr11:21723471-131521797 | 20508 | 109798327 | 1 | rs11828478 | rs2512898 | 27.565 | 0 | TRAF6 |
| chr11:23168804-106781292 | 16332 | 83612489 | 1 | rs11027007 | rs7103285 | 49.747 | 0 | TRAF6 |
| chr11:211482-66910826 | 13813 | 66699345 | 3 | rs2293168 | rs4375446 | 30.249 | 0 | TRAF6 |
| chr4:31222833-180548076 | 24457 | 149325244 | 1 | rs7662351 | rs3849606 | 36.162 | 0 | TRIM2 |
| chr4:137206602-158430547 | 3577 | 21223946 | 3 | rs1597600 | rs12507865 | 83.533 | 0 | TRIM2 |
| chr4:68173959-185767176 | 20235 | 117593218 | 1 | rs6552083 | rs4862428 | 61.893 | 0 | TRIM2 |
| chr4:22401728-188608857 | 28456 | 166207130 | 1 | rs4697297 | rs7687115 | 35.717 | 0 | TRIM2 |
| chr4:63726348-173015421 | 19817 | 109289074 | 1 | rs17082970 | rs2131002 | 30.251 | 0 | TRIM2 |
| chr4:126374899-162830016 | 6166 | 36005118 | 1 | rs4834042 | rs17041092 | 33.404 | 0 | TRIM2 |
| chr4:69590353-190872778 | 23145 | 121282426 | 3 | rs293433 | rs12646565 | 315.633 | 0 | TRIM2 |
| chr11:42185849-126756938 | 15451 | 84571090 | 1 | rs4375424 | rs10750356 | 36.99 | 0 | TRIM29 |
| chr11:84128537-120941583 | 7678 | 36813047 | 1 | rs488925 | rs4643089 | 29.271 | 0 | TRIM29 |
| chr11:21723471-131521797 | 20508 | 109798327 | 1 | rs11828478 | rs2512898 | 27.565 | 0 | TRIM29 |
| chr11:98062720-121890280 | 5422 | 23827561 | 1 | rs6589308 | rs1944465 | 29.075 | 0 | TRIM29 |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr11:74545378-134940416 | 14496 | 60395039 | 3 | rs512780 | rs11224228 | 527.758 | 0 | TRIM29 |
| chr5:141659-19010008 | 4662 | 18868350 | 3 | rs11741126 | rs4642370 | 50.124 | 0 | TRIO |
| chr5:13798559-14174106 | 121 | 375548 | 3 | rs795544 | rs32571 | 239.534 | 0 | TRIO |
| chr5:4872310-180709915 | 35876 | 175837606 | 3 | rs816467 | rs10071993 | 179.394 | 0 | TRIO |
| chr11:42185849-126756938 | 15451 | 84571090 | 1 | rs4375424 | rs10750356 | 36.99 | 0 | TRMT112 |
| chr11:21723471-131521797 | 20508 | 109798327 | 1 | rs11828478 | rs2512898 | 27.565 | 0 | TRMT112 |
| chr11:23168804-106781292 | 16332 | 83612489 | 1 | rs11027007 | rs7103285 | 49.747 | 0 | TRMT112 |
| chr11:211482-66910826 | 13813 | 66699345 | 3 | rs2293168 | rs4375446 | 30.249 | 0 | TRMT112 |
| chr3:13878889-149737330 | 24723 | 135858442 | 1 | rs12634112 | rs2007869 | 55.663 | 0 | TRPC1 |
| chr3:33409611-170735099 | 23775 | 137325489 | 1 | rs3915062 | rs11924032 | 26.867 | 0 | TRPC1 |
| chr3:102240202-195550366 | 17318 | 93310165 | 1 | rs1620217 | rs11711870 | 41.031 | 0 | TRPC1 |
| chr3:103140700-144883172 | 8539 | 41742473 | 1 | rs4314176 | rs6797159 | 44.122 | 0 | TRPC1 |
| chr3:83075971-196935657 | 21465 | 113859687 | 1 | rs9872858 | rs34729751 | 44.35 | 0 | TRPC1 |
| chr3:114889454-177826047 | 12700 | 62936594 | 3 | rs6795297 | rs7628308 | 102.526 | 0 | TRPC1 |
| chr4:31222833-180548076 | 24457 | 149325244 | 1 | rs7662351 | rs3849606 | 36.162 | 0 | TRPC3 |
| chr4:117433230-126039335 | 1532 | 8606106 | 3 | rs11734105 | rs3956574 | 31.166 | 0 | TRPC3 |
| chr4:68173959-185767176 | 20235 | 117593218 | 1 | rs6552083 | rs4862428 | 61.893 | 0 | TRPC3 |
| chr4:22401728-188608857 | 28456 | 166207130 | 1 | rs4697297 | rs7687115 | 35.717 | 0 | TRPC3 |
| chr4:63726348-173015421 | 19817 | 109289074 | 1 | rs17082970 | rs2131002 | 30.251 | 0 | TRPC3 |
| chr4:69590353-190872778 | 23145 | 121282426 | 3 | rs293433 | rs12646565 | 315.633 | 0 | TRPC3 |
| chr13:36707502-103656104 | 13622 | 66948603 | 1 | rs3827890 | rs1952590 | 38.726 | 0 | TRPC4 |
| chr13:19584477-81204088 | 13265 | 61619612 | 3 | rs1334954 | rs1176297 | 22.162 | 0 | TRPC4 |
| chr13:23742931-115064482 | 19829 | 91321552 | 1 | rs4770401 | rs7999630 | 44.074 | 0 | TRPC4 |
| chr13:19121741-63373781 | 10326 | 44252041 | 3 | rs9578050 | rs9539575 | 82.761 | 0 | TRPC4 |
| chr17:108420-26610769 | 5548 | 26502350 | 3 | rs12452527 | rs658591 | 82.699 | 0 | TRPV1 |
| chr12:10113083-116370432 | 20594 | 106257350 | 1 | rs2012504 | rs7958254 | 35.157 | 0 | TRPV4 |
| chr12:59512781-127744939 | 13469 | 68232159 | 3 | rs908394 | rs7966946 | 20.62 | 0 | TRPV4 |
| chr12:10020267-129866293 | 23654 | 119846027 | 1 | rs1597097 | rs2170504 | 45.428 | 0 | TRPV4 |
| chr12:50855195-133778796 | 17748 | 82923602 | 3 | rs4351895 | rs7975069 | 159.589 | 0 | TRPV4 |
| chr7:11855636-156148608 | 26852 | 144292973 | 1 | rs6947930 | rs6945016 | 36.446 | 0 | TRPV6 |
| chr7:78621315-155831817 | 13678 | 77210503 | 3 | rs1006818 | rs6969015 | 123.319 | 0 | TRPV6 |
| chr7:8872727-156383359 | 27773 | 147510633 | 1 | rs917038 | rs878717 | 32.336 | 0 | TRPV6 |
| chr7:120061880-143606234 | 4616 | 23544355 | 3 | rs12531689 | rs10247493 | 18.96 | 0 | TRPV6 |
| chr7:11855636-156148608 | 26852 | 144292973 | 1 | rs6947930 | rs6945016 | 36.446 | 0 | TSC22D4 |
| chr7:78621315-155831817 | 13678 | 77210503 | 3 | rs1006818 | rs6969015 | 123.319 | 0 | TSC22D4 |
| chr7:8872727-156383359 | 27773 | 147510633 | 1 | rs917038 | rs878717 | 32.336 | 0 | TSC22D4 |
| chr7:8794418-119068130 | 23484 | 110273713 | 1 | rs2189621 | rs6977904 | 70.867 | 0 | TSC22D4 |
| chr7:84302877-110993169 | 5183 | 26690293 | 3 | rs4338048 | rs10254893 | 203.09 | 0 | TSC22D4 |
| chr14:80818058-105348552 | 5492 | 24530495 | 3 | rs6574553 | rs2028416 | 15.874 | 0 | TSHR |
| chr14:26898958-104436931 | 17396 | 77537974 | 1 | rs1245195 | rs11851097 | 57.233 | 0 | TSHR |
| chr14:65405722-103799039 | 8979 | 38393318 | 3 | rs11623705 | rs11628472 | 266.153 | 0 | TSHR |
| chr6:26922906-93578359 | 19746 | 66655454 | 1 | rs9348738 | rs9363009 | 27.061 | 0 | TTBK1 |
| chr6:31289284-56929863 | 15402 | 25640590 | 3 | rs6515170 | cnvi0015437 | 25.647 | 0 | TTBK1 |
| chr6:32968276-73449742 | 15442 | 40481467 | 3 | rs2395300 | rs4235869 | 415.87 | 0 | TTBK1 |
| chr5:84830796-171903310 | 16642 | 87072515 | 1 | rs300657 | rs10042482 | 42.208 | 0 | TTC1 |
| chr5:57343495-171903310 | 21683 | 114559816 | 1 | rs10940593 | rs10042482 | 61.169 | 0 | TTC1 |
| chr5:4872310-180709915 | 35876 | 175837606 | 3 | rs816467 | rs10071993 | 179.394 | 0 | TTC1 |
| chr6:64844594-169078546 | 21567 | 104233953 | 1 | rs4710465 | rs601639 | 46.524 | 0 | TTK |
| chr6:66609532-147053632 | 15315 | 80444101 | 3 | rs9354335 | rs4896886 | 44.941 | 0 | TTK |
| chr6:73120320-165130872 | 18715 | 92010553 | 1 | rs9442780 | rs10946016 | 76.383 | 0 | TTK |
| chr6:26922906-93578359 | 19746 | 66655454 | 1 | rs9348738 | rs9363009 | 27.061 | 0 | TTK |
| chr6:66541198-162520133 | 19344 | 95978936 | 1 | rs2000382 | rs6901071 | 27.509 | 0 | TTK |
| chr6:62697746-94090076 | 6391 | 31392331 | 1 | rs6455128 | rs3799807 | 108.85 | 0 | TTK |
| chr6:67621368-147709180 | 16188 | 80087813 | 1 | rs6919455 | rs7739314 | 52.498 | 0 | TTK |
| chr6:79198069-99893938 | 4062 | 20695870 | 3 | rs1321584 | rs4504482 | 200.961 | 0 | TTK |
| chr2:12056323-227979775 | 39094 | 215923453 | 1 | rs966391 | rs1922020 | 31.384 | 0 | TTN |
| chr2:34870277-241929621 | 37755 | 207059345 | 3 | rs13422005 | rs10205276 | 46.946 | 0 | TTN |
| chr2:38101137-241482099 | 36812 | 203380963 | 1 | rs879321 | rs7576043 | 52.099 | 0 | TTN |
| chr2:77041264-194763754 | 21140 | 117722491 | 1 | rs2102827 | rs16835406 | 94.091 | 0 | TTN |
| chr2:175243501-180024167 | 926 | 4780667 | 3 | rs2305292 | rs17454311 | 283.917 | 0 | TTN |
| chr11:345515-17408630 | 4247 | 17063116 | 3 | rs11246094 | rs5215 | 30.474 | 0 | TUB |
| chr11:211482-66910826 | 13813 | 66699345 | 3 | rs2293168 | rs4375446 | 30.249 | 0 | TUB |
| chr12:10113083-116370432 | 20594 | 106257350 | 1 | rs2012504 | rs7958254 | 35.157 | 0 | TUBA1A |
| chr12:10020267-129866293 | 23654 | 119846027 | 1 | rs1597097 | rs2170504 | 45.428 | 0 | TUBA1A |
| chr12:39967134-84174413 | 8879 | 44207280 | 1 | rs11172661 | rs11116039 | 39.568 | 0 | TUBA1A |
| chr12:207886-50770291 | 11565 | 50562406 | 3 | rs868249 | rs4477515 | 43.892 | 0 | TUBA1A |
| chr12:10113083-116370432 | 20594 | 106257350 | 1 | rs2012504 | rs7958254 | 35.157 | 0 | TUBA1B |
| chr12:10020267-129866293 | 23654 | 119846027 | 1 | rs1597097 | rs2170504 | 45.428 | 0 | TUBA1B |
| chr12:39967134-84174413 | 8879 | 44207280 | 1 | rs11172661 | rs11116039 | 39.568 | 0 | TUBA1B |
| chr12:207886-50770291 | 11565 | 50562406 | 3 | rs868249 | rs4477515 | 43.892 | 0 | TUBA1B |
| chr22:16871137-51184393 | 9245 | 34313257 | 3 | rs131538 | rs7284680 | 209.79 | 0 | TUBA8 |
| chr6:10123365-31021039 | -3135 | 21097675 | 1 | rs2181334 | rs4416711 | 318.459 | 0 | TUBB |
| chr6:26922906-93578359 | 19746 | 66655454 | 1 | rs9348738 | rs9363009 | 27.061 | 0 | TUBB |
| chr6:2681610-31453618 | 81 | 28772009 | 3 | rs1131896 | rs9267212 | 428.177 | 0 | TUBB |
| chr6:3760708-31957364 | 8062 | 28196657 | 3 | rs2187825 | cnvi0006380 | 39.016 | 0 | TUBB |
| chr6:19044000-31286381 | -6774 | 12242382 | 1 | rs6922929 | rs9265057 | 31.384 | 0 | TUBB |
| chr6:2585208-31281876 | -2 | 28696669 | 1 | rs1634746 | rs1634747 | 31.615 | 0 | TUBB |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr6:24697388-31341340 | −8293 | 6643953 | 1 | rs2092404 | rs9266515 | 38.794 | 0 | TUBB |
| chr6:26430981-31878433 | −8001 | 5447453 | 1 | rs2893848 | rs519417 | 55.651 | 0 | TUBB |
| chr6:2584569-31286381 | 8 | 28701813 | 1 | rs9391764 | rs9265057 | 34.598 | 0 | TUBB |
| chr6:2681610-31453618 | 81 | 28772009 | 3 | rs1131896 | rs9267212 | 390.234 | 0 | TUBB |
| chr6:29253756-32671521 | 2267 | 3417766 | 1 | rs9468508 | rs9275439 | 51.553 | 0 | TUBB |
| chr6:19044000-31286381 | −6774 | 12242382 | 0 | rs6922929 | rs9265057 | 33.119 | 0 | TUBB |
| chr6:30475431-32449411 | −7687 | 1973981 | 3 | cnvi0005997 | rs1964995 | 153.275 | 0 | TUBB |
| chr17:21685812-67308196 | 12365 | 45622385 | 1 | rs34864328 | rs17686852 | 50.018 | 0 | TUBG1 |
| chr17:26648492-58955084 | 5831 | 32306593 | 3 | rs1981512 | rs8068776 | 15.642 | 0 | TUBG1 |
| chr9:2522475-140068342 | 25719 | 137545868 | 3 | rs10966757 | rs4074426 | 93.386 | 0 | TXN |
| chr9:33180228-132003792 | 14691 | 98823565 | 1 | rs7854765 | rs9408988 | 28.69 | 0 | TXN |
| chr9:100158052-139077343 | 9815 | 38919292 | 3 | rs1020884 | rs4842126 | 470.601 | 0 | TXN |
| chr18:10274-30780701 | 6393 | 30770428 | 3 | cnvi0008694 | rs271534 | 338.777 | 0 | TYMS |
| chr8:30757798-142750969 | 20699 | 111993172 | 1 | rs10101203 | rs6421025 | 34.223 | 0 | UBE2V2 |
| chr8:49046707-49170958 | 16 | 124252 | 1 | rs4433176 | rs4552930 | 12.646 | 72253 | UBE2V2 |
| chr8:41983076-50280013 | 418 | 8296938 | 1 | rs12544318 | rs12677656 | 39.988 | 0 | UBE2V2 |
| chr8:23218101-146274708 | 23020 | 123056608 | 1 | rs7010362 | rs7822726 | 38.828 | 0 | UBE2V2 |
| chr8:43235525-66712108 | 3632 | 23476694 | 3 | rs10091311 | rs7001138 | 58.838 | 0 | UBE2V2 |
| chr1:64114301-245591329 | 29842 | 181477029 | 1 | rs11208257 | rs1173850 | 37.504 | 0 | UBQLN4 |
| chr1:75098453-243531649 | 27360 | 168433197 | 1 | rs12117493 | rs10927002 | 32.113 | 0 | UBQLN4 |
| chr1:79710545-188898319 | 17303 | 109187775 | 1 | rs417181 | rs16829637 | 45.89 | 0 | UBQLN4 |
| chr1:109645793-194560463 | 12025 | 84914671 | 3 | cnvi0008281 | rs10921616 | 63.121 | 0 | UBQLN4 |
| chr4:31222833-180548076 | 24457 | 149325244 | 1 | rs7662351 | rs3849606 | 36.162 | 0 | UCHL1 |
| chr4:39472311-63464732 | 3456 | 23992422 | 3 | rs2687975 | rs4403080 | 120.672 | 0 | UCHL1 |
| chr4:22401728-188608857 | 28456 | 166207130 | 1 | rs4697297 | rs7687115 | 35.717 | 0 | UCHL1 |
| chr4:29179713-117038307 | 15513 | 87858595 | 1 | rs1507441 | rs1068807 | 71.6 | 0 | UCHL1 |
| chr4:179131-68998153 | 13495 | 68819023 | 3 | rs7686948 | rs7687396 | 625.133 | 0 | UCHL1 |
| chr12:131894274-133778796 | 308 | 1884523 | 1 | rs10848373 | rs7975069 | 29.931 | 0 | ULK1 |
| chr12:131564183-133161346 | 306 | 1597164 | 1 | rs2141189 | rs11208 | 31.414 | 0 | ULK1 |
| chr12:112610714-133768729 | 5366 | 21098016 | 3 | rs11066188 | rs11147249 | 695.49 | 0 | ULK1 |
| chr12:132378017-133778796 | 190 | 1400780 | 1 | rs11246867 | rs7975069 | 39.951 | 0 | ULK1 |
| chr12:50855195-133778796 | 17748 | 82923602 | 3 | rs4351895 | rs7975069 | 159.589 | 0 | ULK1 |
| chr16:176743-50013967 | 8328 | 49837225 | 3 | rs2562164 | rs12597023 | 174.392 | 0 | USP7 |
| chr19:266034-18061509 | 3100 | 17795476 | 3 | rs2312724 | rs7250332 | 19.51 | 0 | VAV1 |
| chr19:6812891-7000401 | 66 | 187511 | 3 | rs2174759 | rs11665875 | 138.272 | 0 | VAV1 |
| chr19:288246-59110628 | 11009 | 58822383 | 3 | rs10409452 | cnvi0009466 | 100.582 | 0 | VAV1 |
| chr10:7188484-134205354 | 26672 | 127016871 | 1 | rs1977295 | rs3923858 | 50.772 | 0 | VCL |
| chr10:58385643-124973104 | 13625 | 66587462 | 1 | rs7920235 | rs17663304 | 36.18 | 0 | VCL |
| chr10:57671424-133349223 | 16243 | 75677800 | 1 | rs11005106 | rs4301710 | 37.114 | 0 | VCL |
| chr10:55492162-117205017 | 13465 | 61712856 | 1 | rs6481032 | rs1933664 | 62.56 | 0 | VCL |
| chr10:53602190-135522754 | 19167 | 81920565 | 3 | rs12247820 | rs10909028 | 139.373 | 0 | VCL |
| chr5:84830796-171903310 | 16642 | 87072515 | 1 | rs300657 | rs10042482 | 42.208 | 0 | VDAC1 |
| chr5:57343495-171903310 | 21683 | 114559816 | 1 | rs10940593 | rs10042482 | 61.169 | 0 | VDAC1 |
| chr5:98442871-150317237 | 9828 | 51874367 | 1 | rs1447379 | rs7710790 | 38.687 | 0 | VDAC1 |
| chr5:4872310-180709915 | 35876 | 175837606 | 3 | rs816467 | rs10071993 | 179.394 | 0 | VDAC1 |
| chr3:179527-114630641 | 23879 | 114451115 | 3 | rs4684741 | rs1587972 | 207.852 | 0 | VHL |
| chr10:7188484-134205354 | 26672 | 127016871 | 1 | rs1977295 | rs3923858 | 50.772 | 0 | VIM |
| chr10:734229-69155636 | 14859 | 68421408 | 3 | rs1769236 | rs2394375 | 72.104 | 0 | VIM |
| chr10:88874-53366180 | 12853 | 53277307 | 3 | cnvi0015449 | rs10998465 | 319.021 | 0 | VIM |
| chr3:13878889-149737330 | 24723 | 135858442 | 1 | rs12634112 | rs2007869 | 55.663 | 0 | VIPR1 |
| chr3:33409611-170735099 | 23775 | 137325489 | 1 | rs3915062 | rs11924032 | 26.867 | 0 | VIPR1 |
| chr3:179527-114630641 | 23879 | 114451115 | 3 | rs4684741 | rs1587972 | 207.852 | 0 | VIPR1 |
| chr17:21685812-67308196 | 12365 | 45622385 | 1 | rs34864328 | rs17686852 | 50.018 | 0 | VTN |
| chr17:26648492-58955084 | 5831 | 32306593 | 3 | rs1981512 | rs8068776 | 15.642 | 0 | VTN |
| chr19:31569338-53780966 | 3788 | 22211629 | 1 | rs2867544 | rs10407424 | 33.9 | 0 | WDR62 |
| chr19:288246-59110628 | 11009 | 58822383 | 3 | rs10409452 | cnvi0009466 | 100.582 | 0 | WDR62 |
| chr7:11855636-156148608 | 26852 | 144292973 | 1 | rs6947930 | rs6945016 | 36.446 | 0 | WDR91 |
| chr7:78621315-155831817 | 13678 | 77210503 | 3 | rs1006818 | rs6969015 | 123.319 | 0 | WDR91 |
| chr7:8872727-156383359 | 27773 | 147510633 | 1 | rs917038 | rs878717 | 32.336 | 0 | WDR91 |
| chr7:134696740-135170448 | 89 | 473709 | 1 | rs4329203 | rs2696888 | 28.6 | 0 | WDR91 |
| chr7:120061880-143606234 | 4616 | 23544355 | 3 | rs12531689 | rs10247493 | 18.96 | 0 | WDR91 |
| chr5:84830796-171903310 | 16642 | 87072515 | 1 | rs300657 | rs10042482 | 42.208 | 0 | WWC1 |
| chr5:161172541-179954615 | 4271 | 18782075 | 3 | rs4921415 | rs10059433 | 6.291 | 0 | WWC1 |
| chr5:57343495-171903310 | 21683 | 114559816 | 1 | rs10940593 | rs10042482 | 61.169 | 0 | WWC1 |
| chr5:4872310-180709915 | 35876 | 175837606 | 3 | rs816467 | rs10071993 | 179.394 | 0 | WWC1 |
| chr20:13712393-55093901 | 8218 | 41381509 | 1 | rs6033810 | rs6999 | 41.237 | 0 | YWHAB |
| chr20:7869025-62424661 | 11941 | 54555637 | 3 | rs2294306 | rs6010652 | 9.732 | 0 | YWHAB |
| chr20:4591715-58420336 | 11753 | 53828622 | 1 | rs6139494 | rs1416388 | 40.922 | 0 | YWHAB |
| chr20:236802-54845796 | 12646 | 54608995 | 3 | rs448294 | rs6064362 | 286.151 | 0 | YWHAB |
| chr17:108420-26610769 | 5548 | 26502350 | 3 | rs12452527 | rs658591 | 82.699 | 0 | YWHAE |
| chr7:11855636-156148608 | 26852 | 144292973 | 1 | rs6947930 | rs6945016 | 36.446 | 0 | YWHAG |
| chr7:8872727-156383359 | 27773 | 147510633 | 1 | rs917038 | rs878717 | 32.336 | 0 | YWHAG |
| chr7:8794418-119068130 | 23484 | 110273713 | 1 | rs2189621 | rs6977904 | 70.867 | 0 | YWHAG |
| chr7:60392-84158180 | 19095 | 84097789 | 3 | rs12670102 | rs2715048 | 208.308 | 0 | YWHAG |
| chr2:18856-41136833 | 9721 | 41117978 | 3 | rs11901199 | rs10187704 | 191.638 | 0 | YWHAQ |
| chr8:30757798-142750969 | 20699 | 111993172 | 1 | rs10101203 | rs6421025 | 34.223 | 0 | YWHAZ |
| chr8:60424884-145286483 | 17030 | 84861600 | 3 | rs1401422 | rs9720889 | 8.858 | 0 | YWHAZ |

TABLE 3-continued

| Chr:Start-Stop(hg19) | NumSNP | Length | State, CN | StartSNP | EndSNP | Confidence | Distance From Gene | mGluR Gene |
|---|---|---|---|---|---|---|---|---|
| chr8:23218101-146274708 | 23020 | 123056608 | 1 | rs7010362 | rs7822726 | 38.828 | 0 | YWHAZ |
| chr8:76354446-113652365 | 6767 | 37297920 | 1 | rs830783 | rs16883889 | 127.023 | 0 | YWHAZ |
| chr8:66822030-144791126 | 16557 | 77969097 | 3 | rs6472235 | rs10100154 | 251.068 | 0 | YWHAZ |
| chr2:12056323-227979775 | 39094 | 215923453 | 1 | rs966391 | rs1922020 | 31.384 | 0 | ZAP70 |
| chr2:34870277-241929621 | 37755 | 207059345 | 3 | rs13422005 | rs10205276 | 46.946 | 0 | ZAP70 |
| chr2:38101137-241482099 | 36812 | 203380963 | 1 | rs879321 | rs7576043 | 52.099 | 0 | ZAP70 |
| chr2:77041264-194763754 | 21140 | 117722491 | 1 | rs2102827 | rs16835406 | 94.091 | 0 | ZAP70 |
| chr2:83383702-175194550 | 16291 | 91810849 | 3 | rs12469609 | rs11891208 | 154.4 | 0 | ZAP70 |
| chr18:25388300-75954881 | 11539 | 50566582 | 1 | rs11083228 | rs1876021 | 39.235 | 0 | ZNF24 |
| chr18:1583633-58142042 | 11490 | 56558410 | 3 | rs9945988 | rs1560399 | 3.736 | 0 | ZNF24 |
| chr18:32722154-33260373 | 96 | 538220 | 3 | rs13512 | rs508284 | 245.257 | 0 | ZNF24 |
| chr18:26550830-63713914 | 8241 | 37163085 | 1 | rs16945738 | rs2715304 | 17.922 | 0 | ZNF24 |
| chr18:26162481-67193217 | 9255 | 41030737 | 1 | rs12458903 | rs9961907 | 31.327 | 0 | ZNF24 |
| chr18:30929223-44720664 | 2910 | 13791442 | 3 | rs10775453 | rs9304343 | 535.348 | 0 | ZNF24 |

What is claimed is:

1. A method for treating anxiety disorder in a subject comprising:
    (a) isolating a sample comprising nucleic acid from a subject,
    (b) detecting at least one copy number variation (CNV) in at least one an mGluR network gene of the subject that has anxiety disorder, and
    (c) administering an effective amount of fasoracetam to the subject with the at least one CNV in an mGluR network gene, and
    (d) assessing said patient for a reduction in one or more anxiety symptoms.

2. The method of claim 1, wherein the CNV is a duplication or deletion.

3. The method of claim 1, wherein fasoracetam is fasoracetam monohydrate.

4. The method of claim 1, wherein fasoracetam is administered at a dose of 100-400 mg twice daily.

5. The method of claim 4, wherein the fasoracetam is administered at a dose of 200-400 mg twice daily.

6. The method of claim 1, wherein the subject has a CNV in at least 2 mGluR network genes.

7. The method of claim 1, wherein the subject does not have a CNV in any of GRM1, GRM2, GRM3, GRM4, GRM5, GRM6, GRM7, or GRM8.

8. The method of claim 1, wherein the anxiety disorder is one or more of generalized anxiety disorder, phobia, social anxiety disorder, social phobia, panic disorder, panic attack, post-traumatic stress disorders, separation anxiety disorder, selective mutism, agoraphobia, or an anxiety disorder induced by a substance/medication or due to another medical condition.

9. The method of claim 1, wherein the subject is a pediatric or adolescent subject.

10. The method of claim 9, wherein the pediatric or adolescent subject is between the ages of 12 and 18.

11. The method of claim 1, wherein the subject has experienced symptoms of anxiety for at least six months.

12. The method of claim 1, wherein anxiety symptoms are reduced in the subject following at least 4 weeks of treatment with the fasoracetam.

13. The method of claim 1, wherein symptoms are assessed by a clinician using the Pediatric Anxiety Rating Scale, and/or the clinical global impression scores.

14. The method of claim 1, wherein the subject has at least one CNV in a Tier 1 mGluR network gene.

15. The method of claim 1, wherein the subject has at least one CNV in a Tier 2 mGluR network gene.

16. The method of claim 1, wherein the subject has at least one CNV in a Tier I and/or Tier 2 mGluR gene but does not have a CNV in a Tier 3 mGluR network gene.

* * * * *